United States Patent
Jackson et al.

(10) Patent No.: US 11,384,064 B2
(45) Date of Patent: Jul. 12, 2022

(54) CHEMOKINE RECEPTOR MODULATORS AND USES THEREOF

(71) Applicant: RAPT THERAPEUTICS, INC., South San Francisco, CA (US)

(72) Inventors: Jeffrey J. Jackson, San Bruno, CA (US); John Michael Ketcham, San Mateo, CA (US); Akinori Okano, San Mateo, CA (US); Maureen Kay Reilly, San Francisco, CA (US); Omar Robles-Resendiz, Redwood City, CA (US); Jacob Bradley Schwarz, San Ramon, CA (US); Parcharee Tivitmahaisoon, San Francisco, CA (US); David Juergen Wustrow, Los Gatos, CA (US); Ashkaan Younai, Daly City, CA (US); Mikhail Zibinsky, Redwood City, CA (US)

(73) Assignee: RAPT Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/859,896

(22) Filed: Apr. 27, 2020

(65) Prior Publication Data
US 2020/0325117 A1    Oct. 15, 2020

Related U.S. Application Data

(62) Division of application No. 16/256,987, filed on Jan. 24, 2019, now Pat. No. 10,683,280.

(60) Provisional application No. 62/784,161, filed on Dec. 21, 2018, provisional application No. 62/772,027, filed on Nov. 27, 2018, provisional application No. 62/622,771, filed on Jan. 26, 2018.

(51) Int. Cl.
| | |
|---|---|
| *C07D 401/14* | (2006.01) |
| *C07D 495/04* | (2006.01) |
| *A61P 17/00* | (2006.01) |
| *A61P 11/06* | (2006.01) |
| *A61P 35/00* | (2006.01) |
| *A61P 29/00* | (2006.01) |

(52) U.S. Cl.
CPC ............ *C07D 401/14* (2013.01); *A61P 11/06* (2018.01); *A61P 17/00* (2018.01); *A61P 29/00* (2018.01); *A61P 35/00* (2018.01); *C07D 495/04* (2013.01)

(58) Field of Classification Search
CPC .................................................. C07D 401/14
See application file for complete search history.

(56) References Cited

U.S. PATENT DOCUMENTS

| | | |
|---|---|---|
| 10,683,280 B2 | 6/2020 | Jackson et al. |
| 2012/0015932 A1 | 1/2012 | Hobbs et al. |
| 2019/0134031 A1 | 5/2019 | Cutler et al. |

FOREIGN PATENT DOCUMENTS

| | | |
|---|---|---|
| EP | 2 000 469 A2 | 12/2008 |
| EP | 2 000 469 A9 | 12/2008 |
| WO | WO-03/077907 A1 | 9/2003 |
| WO | WO-2008/146914 A1 | 12/2008 |
| WO | WO-2011/112662 A1 | 9/2011 |
| WO | WO-2013/082429 A1 | 6/2013 |
| WO | WO-2013/082490 A1 | 6/2013 |
| WO | WO-2018/022992 A1 | 2/2018 |

OTHER PUBLICATIONS

Solari et al. European Journal of Pharmacology, vol. 763, Part B, p. 169-177. (Year: 2015).*
Comerford, I. et al. (Feb. 2011). "Mini-review series: focus on chemokines," *Immunol Cell Biol* 89(2):183-184.
Gadhe, C.G. et al. (Feb. 2015, e-published Dec. 4, 2014). "Insights into the binding modes of CC chemokine receptor 4 (CCR4) inhibitors: a combined approach involving homology modelling, docking, and molecular dynamics simulation studies," *Mol Biosyst* 11(2):618-634.
Horuk, R. (May 1994). "Molecular properties of the chemokine receptor family," *Trends Pharmacol Sci* 15(5):159-165.
International Search Report dated May 28, 2019, for PCT Application No. PCT/US2019/015023, filed Jan. 24, 2019, 5 pages.
Le, Y. et al. (Apr. 2004). "Chemokines and Chemokine Receptors: Their Manifold Roles in Homeostatis and Disease," *Cellular & Molec Immuno* 1(2):95-104.
Ness, T.L. et al. (Dec. 1, 2006). "CCR4 is a key modulator of innate immune responses," *J Immunol* 777(11):7531-7539.
Power, C.A. et al. (Aug. 18, 1995). "Molecular cloning and functional expression of a novel CC chemokine receptor cDNA from a human basophilic cell line," *J Biol Chem* 270(33):9495-19500.
Teicher, B.A. (Oct. 2006). "Tumor models for efficacy determination," *Mol Cancer Ther* 5(10):2435-2443.
Xu, L. et al. (Mar. 21, 2014). "Design, Synthesis and SAR Study of Novel Trisubstituted Pyrimidine Amide Derivatives as CCR4 Antagonists," *Molecules* 19(3):3539-3551.

* cited by examiner

*Primary Examiner* — Erich A Leeser
(74) *Attorney, Agent, or Firm* — Irina E. Britva; Mintz, Levin, Cohn, Ferris, Glovsky and Popeo, P.C.

(57) ABSTRACT

Disclosed herein, inter alia, are compounds and methods of use thereof for the modulation of certain chemokine receptor activity.

28 Claims, 3 Drawing Sheets

CHEMOKINE RECEPTOR MODULATORS AND USES THEREOF

CROSS-REFERENCES TO RELATED APPLICATIONS

This application claims priority to U.S. Provisional Application No. 62/622,771 filed Jan. 26, 2018, U.S. Provisional Application No. 62/772,027 filed Nov. 27, 2018, and U.S. Provisional Application No. 62/784,161 filed Dec. 21, 2018.

BACKGROUND

The successful operation of the host defense system is the result of several processes that work together to eliminate foreign pathogens. Coordinated innate and acquired immune responses are required, and many secreted and cell-associated factors have been identified as important mediators coordinating and regulating these two arms of host defense. Chemokines are a family of cytokines that act as chemoattractants to guide leukocyte migration. They are secreted by a wide variety of cells and can be functionally divided into two groups, hemostatic chemokines and inflammatory chemokines. Hemostatic chemokines are constitutively produced in certain tissues and control cells of the immune system during processes of immune surveillance, such as directing lymphocytes to the lymph nodes to allow them to screen for invasion of pathogens. Inflammatory chemokines are released from cells in response to a pathological event (e.g., pro-inflammatory stimuli such as IL-1 or viruses). They function primarily as chemoattractants as part of the inflammatory response and serve to guide cells of both the innate and adaptive immune systems to the site of inflammation. The C—C chemokine receptor type 4 (CCR4), plays a role in the progression of a number of inflammation-related and other disorders. The identification of compounds that modulate CCR4 function is an ongoing challenge. Disclosed herein, inter alia, are solutions to these and other problems in the art.

BRIEF SUMMARY

In an aspect provided herein, is a compound having structural Formula (I):

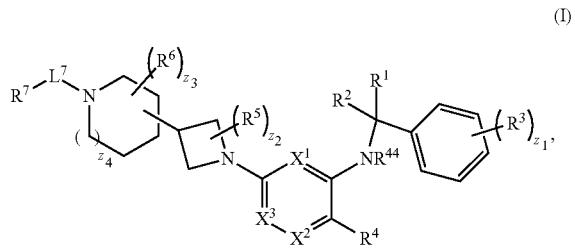

or a pharmaceutically acceptable salt thereof. $X^1$ is $CR^8$ or N. $X^2$ is $CR^9$ or N. $X^3$ is $CR^{10}$ or N. The symbols n1, n2, n3, n4, n5, n6, n7, n8, n9, n10, and n44 are independently an integer from 0 to 4. The symbol z3 is an integer from 0 to 11. The symbols m1, m2, m3, m4, m5, m6, m7, m8, m9, m10, v1, v2, v3, v4, v5, v6, v7, v8, v9, v10, and v44 are independently 1 or 2. The symbol z1 is an integer from 0 to 5. The symbol z2 is an integer from 0 to 4. The symbol z4 is an integer from 0 to 2. $L^7$ is a bond, —O—, —S—, $-NR^{7.2B}-$, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, $-CX^{1.1}_3$, $-CHX^{1.1}_2$, $-CH_2X^{1.1}$, —CN, $-N_3$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, $-OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-CX^{2.1}_3$, $-CHX^{2.1}_2$, $-CH_2X^{2.1}$, —CN, $-N_3$, $-SO_{n2}R^{2A}$, $-SO_{v2}NR^{2B}R^{2C}$, $-NNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, $-OCH_2X^{2.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently halogen, $-CX^{3.1}_3$, $-CHX^{3.1}_2$, $-CH_2X^{3.1}$, —CN, $-N_3$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ is hydrogen, halogen, $-CX^{4.1}_3$, $-CHX^{4.1}_2$, $-CH_2X^{4.1}$, —CN, $-N_3$, $-SO_{n4}R^{4A}$, $-SO_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}_3$, $-OCHX^{4.1}_2$, $-OCH_2X^{4.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; when $X^2$ is $CR^9$, then $R^4$ and $R^9$ may optionally be joined to form a substituted or unsubstituted cycloalkyl, substituted or unsubstituted heterocycloalkyl, substituted or unsubstituted aryl, or substituted or unsubstituted heteroaryl. $R^5$ is independently halogen, oxo, $-CX^{5.1}_3$, $-CHX^{5.1}_2$, $-CH_2X^5$, —CN, $-N_3$, $-SO_{n5}R^{5A}$, $-SO_{v5}NR^{5B}R^{5C}$, $-NHNR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}_3$, $-OCHX^{5.1}_2$, $-OCH_2X^{5.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is independently halogen, oxo, $-CX^{6.1}_3$, $-CHX^{6.1}_2$, $-CH_2X^{6.1}$, —CN, $-N_3$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, —C(O)

$-OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}_3$, $-OCHX^{6.1}_2$, $-OCH_2X^{6.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^7$ is hydrogen, halogen, $-CX^{7.1}_3$, $-CHX^{7.1}_2$, $-CH_2X^{7.1}$, $-CN$, $-N_3$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}_3$, $-OCHX^{7.1}_2$, $-OCH_2X^{7.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^7$ is hydrogen, halogen, $-CX^{8.1}_3$, $-CHX^{8.1}_2$, $-CH_2X^{8.1}$, $-CN$, $-N_3$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}_3$, $-OCHX^{8.1}_2$, $-OCH_2X^{8.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}_3$, $-CHX^{9.1}_2$, $-CH_2X^{9.1}$, $-CN$, $-N_3$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}_3$, $-OCHX^{9.1}_2$, $-OCH_2X^{9.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; when $X^2$ is $CR^9$, then $R^4$ and $R^9$ may optionally be joined to form a substituted or unsubstituted cycloalkyl, substituted or unsubstituted heterocycloalkyl, substituted or unsubstituted aryl, or substituted or unsubstituted heteroaryl; or when $X^2$ is $CR^9$ and $X^3$ is $CR^{10}$, then $R^9$ and $R^{10}$ may optionally be joined to form a substituted or unsubstituted cycloalkyl, substituted or unsubstituted heterocycloalkyl, or unsubstituted aryl, or substituted or unsubstituted heteroaryl. $R^{10}$ is hydrogen, halogen, $-CX^{10.1}_3$, $-CHX^{10.1}_2$, $-CH_2X^{10.1}$, $-CN$, $-N_3$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}_3$, $-OCHX^{10.1}_2$, $-OCH_2X^{10.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or when $X^2$ is $CR^9$ and $X^3$ is $CR^{10}$, then $R^9$ and $R^{10}$ may optionally be joined to form a substituted or unsubstituted cycloalkyl, substituted or unsubstituted heterocycloalkyl, or unsubstituted aryl, or substituted or unsubstituted heteroaryl. $R^{44}$ is hydrogen, $-CX^{44.1}_3$, $-CHX^{44.1}_2$, $-CH_2X^{44.1}$, $-SO_{n44}R^{44A}$, $-SO_{v44}NR^{44B}R^{44C}$, $-C(O)R^{44D}$, $-C(O)OR^{44D}$, $-C(O)NR^{44B}R^{44C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{7.2B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{44A}$, $R^{44B}$, $R^{44C}$ and $R^{44D}$ are independently hydrogen, halogen, $-CF_3$, $-CCl_3$, $-CBr_3$, $-CI_3$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{44B}$ and $R^{44C}$ substituents bonded to the same nitrogen atom may optionally be joined to form a substituted or unsubstituted heterocycloalkyl or substituted or unsubstituted heteroaryl. $X^{1.1}$, $X^{2.1}$, $X^{3.1}$, $X^{4.1}$, $X^{5.1}$, $X^{6.1}$, $X^{7.1}$, $X^{8.1}$, $X^{9.1}$, $X^{10.1}$, and $X^{44.1}$ are independently $-Cl$, $-Br$, $-I$ or $-F$. At least one of $X^1$, $X^2$ and $X^3$ is N.

In an aspect is provided a pharmaceutical composition, including a compound as described herein, including embodiments, and a pharmaceutically acceptable excipient.

In an aspect is provided a method of inhibiting C—C chemokine receptor type 4 (CCR4), the method including contacting CCR4 with a compound as described herein, including embodiments, or a pharmaceutically acceptable salt thereof.

In an aspect, is provided a method of treating or preventing a disease or disorder mediated by CCR4, including administering to a subject in need thereof a therapeutically effective amount of a compound as described herein, including embodiments, or a pharmaceutically acceptable salt thereof.

In another aspect, provided herein is a kit including a compound described herein (e.g., a CCR4 inhibitor) or pharmaceutical composition thereof. The kit may be in the form of a physical structure housing various components, as described below, and may be utilized, for example, in practicing the methods described herein.

DETAILED DESCRIPTION

Figure 1:
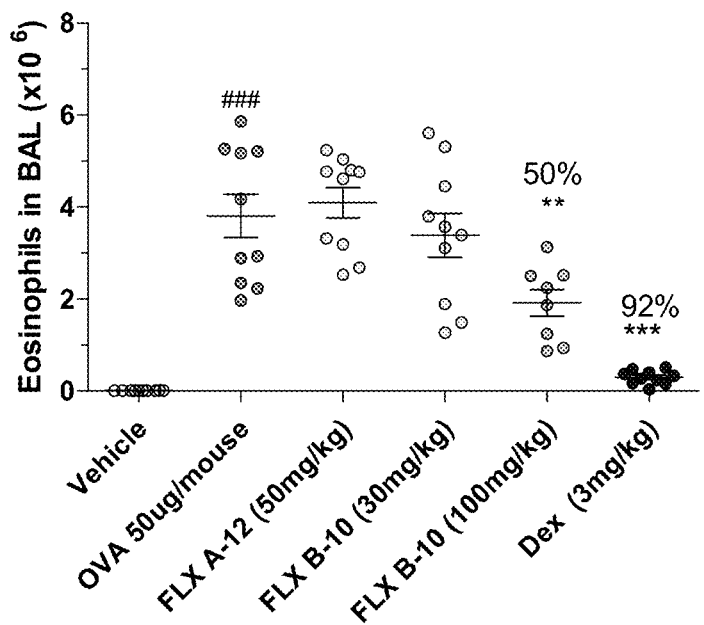
FIG. 1 depicts a graph of eosinophil cell counts in bronchoalveolar lavage fluid.

Provided herein are, for example, compounds and compositions for inhibition of C—C chemokine receptor type 4, and pharmaceutical compositions including the same. Also provided herein are, for example, methods of treating or preventing a disease, disorder or condition, or a symptom thereof, for example a disease, disorder or condition, or a symptom thereof, mediated by modulation (e.g., inhibition) of CCR4.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH$_2$—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ∼∼∼ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

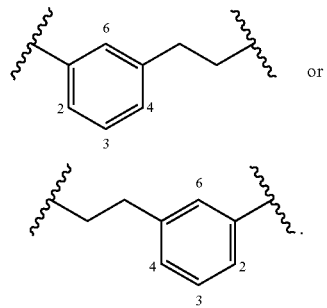

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$—C alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R"', and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —OCH $Br_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{3A}$, $R^{3B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present invention contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of a compound to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

A "CCR4 inhibitor" refers to a compound (e.g., a compound described herein) capable of reducing the activity of CCR4 (e.g., by binding to CCR4) when compared to a control, such as absence of the compound or a compound with known inactivity.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. In embodiments, the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences, with or without N-terminus methionine residues; immunologically tagged proteins; and the like.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway (e.g., MAP kinase pathway).

As defined herein, the term "activation", "activate", "activating" and the like in reference to a target-inhibitor interaction means positively affecting (e.g. increasing) the activity or function of the target (e.g., protein) relative to the activity or function of the target (e.g., protein) in the absence of the inhibitor. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein relative to a control (e.g., in the absence of the agonist). The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist. In embodiments, an agonist is a molecule that interacts with a target to cause or promote an increase in the activation of the target. In embodiments, activators are molecules that increase, activate, facilitate, enhance activation, sensitize, or up-regulate, e.g., a gene, protein, ligand, receptor, or cell.

As defined herein, the term "inhibition," "inhibit," "inhibiting," and the like, in reference to a target-inhibitor interaction means negatively affecting (e.g. decreasing) the activity or function of the target (e.g., protein) relative to the activity or function of the target (e.g., protein) in the absence of the inhibitor. In embodiments inhibition means negatively affecting (e.g. decreasing) the concentration or levels of the target (e.g., protein) relative to the concentration or level of the target (e.g., protein) in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a target (e.g., protein). In embodiments, inhibition refers to a reduction of activity of a target (e.g., protein) resulting from a direct interaction (e.g. an inhibitor binds to the target (e.g., protein)). In embodiments, inhibition refers to a reduction of activity of a target (e.g., protein) from an indirect interaction (e.g. an inhibitor binds to a protein that activates the target (e.g., protein), thereby preventing target (e.g., protein) activation).

The terms "inhibitor," "repressor" or "antagonist" or "downregulator" interchangeably refer to a substance capable of detectably decreasing the expression or activity of a given gene or protein relative to a control (e.g., in the absence of the inhibitor). The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist. An antagonist prevents, reduces, inhibits, or neutralizes the activity of an agonist, and an antagonist can also prevent, inhibit, or reduce constitutive activity of a target, e.g., a target receptor, even where there is no identified agonist. In embodiments, inhibitors are molecules that decrease, block, prevent, delay activation, inactivate, desensitize, or down-regulate, e.g., a gene, protein, ligand, receptor, or cell. An inhibitor may also be defined as a molecule that reduces, blocks, or inactivates a constitutive activity. An "antagonist" is a molecule that opposes the action(s) of an agonist.

The terms "C—C chemokine receptor type 4" and "CCR4" refer to a protein (including homologs, isoforms, and functional fragments thereof) that is a high affinity receptor for the C—C-type chemokines (e.g., CCL2 (MCP-1), CCL4 (MIP-1), CCL5 (RANTES), CCL17 (TARC), and CCL22 (MDC)). It is referred to by a number of different names in the scientific literature, including "CC—CKR-4", "C—C CKR-4", "K5-5", "CD194", "CMKBR4", "ChemR13", "HGCN", and "14099". The term includes any recombinant or naturally-occurring form of CCR4 and/or variants thereof that maintain CCR4 activity (e.g. within at least 30%, 40%, 50%, 60%, 70%, 80%, 90%, 95%, or 100% activity compared to wildtype CCR4). The term includes any mutant form of CCR4 variants (e.g., frameshift mutations) thereof that maintain CCR4 activity (e.g. within at least 30%, 40%, 50%, 60%, 70%, 80%, 90%, 95%, or 100% activity compared to wildtype CCR4). In embodiments, the CCR4 protein encoded by the CCR4 gene has the amino acid sequence set forth in or corresponding to Entrez 1233, UniProt P51679, or RefSeq (protein) NP_005499.1. In embodiments, the CCR4 gene has the nucleic acid sequence set forth in RefSeq (mRNA) NM_005508. In embodiments, the amino acid sequence or nucleic acid sequence is the sequence known at the time of filing of the present application. In embodiments, the sequence corresponds to GI5031627. In embodiments, the sequence corresponds to NP_005499.1. In embodiments, the sequence corresponds to NM_005508.4. In embodiments, the sequence corresponds to GI48762930. In embodiments, the CCR4 is a human CCR4, such as a human cancer causing CCR4. Though frequently found on dendritic cells, macrophages, NK cells, platelets, and basophils, CCR4 is predominantly associated with T cells. It plays a role in the progression of multiple inflammation-related disorders, and, as described herein, has also been implicated in a number of other conditions. The genomic sequence of CCR4 is present on chromosome 3 (NC_000003.12), and the CCR4 gene is conserved in a number of species, including chimpanzee, Rhesus monkey, dog, cow, mouse, rat, chicken, and zebrafish. The CCR4 polypeptide comprises 360 amino acid residues (NP_005499.1), and, like other chemokine receptors, CCR4 is a G protein-coupled receptor that may be found on the surface of leukocytes (see, for example, Horuk (1994) Trends Pharm. Sci. 15:159-165).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including MDS, AML, ALL, ATLL and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, pelvic inflammatory disease, reperfusion injury, ischemia reperfusion injury, stroke, sarcoidosis, transplant rejection, interstitial cystitis, atherosclerosis, scleroderma, and atopic dermatitis. Such conditions are frequently inextricably intertwined with other diseases, disorders and conditions. A non-limiting list of inflammatory-related diseases, disorders and conditions which may, for example, be caused by inflammatory cytokines, include, arthritis, kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (IBD), allergic contact dermatitis and other eczemas, systemic sclerosis, transplantation and multiple sclerosis. Some of the aforementioned diseases, disorders and conditions for which a compound (e.g., CCR4 inhibitor) described herein may be particularly efficacious (due to, for example, limitations of current therapies) are described in more detail hereafter. Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

As used herein, the term "cancer" refers to all types of cancer, neoplasm or malignant tumors found in mammals (e.g. humans), including leukemia, lymphoma, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, the treating or treatment is no prophylactic treatment.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease symptoms in a patient. As indicated above, the prevention may be complete (no detectable symptoms) or partial, such that fewer symptoms are observed than would likely occur absent treatment. In embodiments, prevent refers to slowing the progression of the disease, disorder or condition or inhibiting progression thereof to a harmful or otherwise undesired state.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). The therapeutically effective amount can be ascertained by measuring relevant physiological effects, and it can be adjusted in connection with the dosing regimen and diagnostic analysis of the subject's condition, and the like. By way of example, measurement of the serum level of a CCR4 inhibitor (or, e.g., a metabolite thereof) at a particular time post-administration may be indicative of whether a therapeutically effective amount has been administered.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan. Adjusting the dose to achieve maximal therapeutic window efficacy or toxicity in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent, chemotherapeutic, or treatment for a neurodegenerative disease). In embodiments, the administering does not include administration of any active agent other than the recited active agent. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles. In embodiments, the administering does not include administration of any active agent other than the recited active agent.

By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). The compositions of the present invention can be delivered transdermally, by a topical route, or formulated as applicator sticks, solutions, suspensions, emulsions, gels, creams, ointments, pastes, jellies, paints, powders, and aerosols.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer (e.g. colon cancer), cardiovascular disease, metabolic disease, immune or inflammatory disease or disorder.

In some embodiments, co-administration includes administering one active agent within 0.5, 1, 2, 4, 6, 8, 10, 12, 16, 20, 24 hours, 2 days, 4 days, 1 week or 1 month of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer (e.g. colon cancer), cardiovascular disease, metabolic disease, immune or inflammatory disease or disorder.

"Cardiovascular agent" is used in accordance with its plain ordinary meaning and refers to a composition (e.g. compound, drug, antagonist, inhibitor, modulator) used in any way to treat conditions of the heart or the circulatory or vascular system relative to a control. In some embodiments, a cardiovascular agent is an agent identified herein having utility in methods of treating cardiovascular disease or disorder. In some embodiments, a cardiovascular agent is an agent approved by the FDA or similar regulatory agency of a country other than the USA, for treating cardiovascular disease or disorder.

"Anti-inflammatory agent" is used in accordance with its plain ordinary meaning and refers to a composition (e.g. compound, drug, antagonist, inhibitor, modulator) used in any way to reduce inflammation or swelling relative to a control (e.g., the absence of the agent). In some embodiments, an anti-inflammatory agent is an agent identified herein having utility in methods of treating an inflammatory disease or disorder. In some embodiments, an anti-inflammatory agent is an agent approved by the FDA or similar regulatory agency of a country other than the USA, for reducing swelling and inflammation.

The compounds described herein can be administered to treat an immune or inflammatory disease or disorder, a cardiovascular or metabolic disease or disorder and/or cancer. In this regard, the compounds disclosed herein may be administered either alone to treat such diseases or disorders or may be co-administered with another therapeutic agent to treat such diseases or disorders.

The compounds disclosed herein may be co-administered with a cytokine or agonist or antagonist of cytokine function, (including agents which act on cytokine signaling pathways such as modulators of the SOCS system) including alpha-, beta-, and gamma-interferons; insulin-like growth factor type I (IGF-1); interleukins (IL) including IL1 to 17, and interleukin antagonists or inhibitors such as analcinra; tumour necrosis factor alpha (TNF-.alpha.) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

The compounds disclosed herein may be co-administered with an anti-inflammatory agent, such as thalidomide or a derivative thereof, a retinoid, dithranol or calcipotriol, a non-steroidal anti-inflammatory agent (hereinafter NSAID) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The compounds disclosed herein may be co-administered with a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bis antrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixmab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bis antrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin Al (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER$^2$, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™) panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER$^2$, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

The compounds disclosed herein may be co-administered with an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin); (ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride; (iii) an agent which inhibits cancer cell invasion (for example a metalloproteinase inhibitor like marimastat or an inhibitor of urokinase plasminogen activator receptor function); (iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazoli-n-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazoli-n-4-amine (CI 1033)), an inhibitor of the platelet-derived growth factor family, or an inhibitor of the hepatocyte growth factor family; (v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin.alpha.v.beta.3 function or an angiostatin); (vi) a vascular damaging agent such as combretastatin A4, or a compound disclosed in WO 99/02166, WO 00/40529, WO 00/41669, WO 01/92224, WO 02/04434 or WO 02/08213; (vii) an agent used in antisense therapy, for example one directed to one of the targets listed above, such as ISIS 2503, an anti-ras antisense; (viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In embodiments, the compounds disclosed herein can be co-administered with an antibody, such as a monoclonal antibody targeting B-Lymphocytes (such as CD20 (rituximab), MRA-aIL16R and T-Lymphocytes, CTLA4-Ig, HuMax I1-15) or antibody modulating Ig function such as anti-IgE (for example omalizumab).

In embodiments, treatment of cancer includes administration of an effective amount of at least two of the following: a CCR4 inhibitor (e.g., compound described herein), an inhibitor of the PD-L1/PD-1 pathway, an inhibitor of CTLA-4, an agonistic antibody of CD137 (4-1BB). In some embodiments, the method may include the use of two or more combinations.

In embodiments, treatment of cancer includes an effective amount of at least two or more of the following: a CCR4 inhibitor (e.g., compound described herein) and any combination of agent that may be an immune modulator such as, but not limited to, those listed in Table 1, or described herein (e.g., an anti-cancer agent). These immune modulators can be depleting antibodies, neutralizing antibodies, blocking antibodies, agonistic antibodies, small molecule modulators (inhibitors or stimulators) or small molecule analogs.

TABLE 1

| Target or Therapy | Examples of Agents | Regulatory Mechanism |
|---|---|---|
| TIM-3 | TSR-022, MGB453 | Checkpoint-receptor |
| LAG-3 | BMS-986016, IMP321 | Checkpoint-receptor |
| B7-H3 | MGA271, MGD-009 | Checkpoint-receptor |
| TIGIT | RG-6058 | Checkpoint-receptor |
| BTLA | | Checkpoint-receptor |
| CD28 | AMG 557, | Checkpoint-receptor |
| CD40 | SEA-CD40, dacetuzumab, CP-870,893, Chi Lob 7/4, lucatumumab | Checkpoint-receptor |
| CD80 | galiximab | Checkpoint-receptor |
| GITR | INCAGN1876, TRX518, | Checkpoint-receptor |
| ICOS | MEDI-570 | Checkpoint-receptor |
| OX40 (CD134) | MEDI-6469, INCAGN1949, huMab OX40L, | Checkpoint-receptor |
| NKG2A | monalizumab | Checkpoint-receptor |
| TGF-beta | Galunisertib, luspatercept, YH-14618, dalantercept, BG-00011, trabedersen, isth-0036 ace-083, | Cytokines |
| IL2 | NKTR-214, recombinant IL2, aldesleukin | Cytokines |
| IL12 | EGEN-001, NHS-IL12 | Cytokines |
| IL7 | Recombinant IL-7, | Cytokines |
| IL15 | NIZ-985, ALT-803, | Cytokines |
| IL21 | Recombinant IL-21, anti-CD20.IL21, | Cytokines |
| IL13 | Tralokinumab, dupilumab | |
| CSF1R | cabiralizumab | Cytokine |
| PI3K delta | INCB50465, idealisib, TGR-1202, AMG319, | Kinase |
| PI3K gamma | IPI-549 | Kinase |
| DNMT (DNA methyl transferase inhibitor) | Azacytidine, decitabine, guadecitabine, | Epigenetic Regulator |

TABLE 1-continued

| Target or Therapy | Examples of Agents | Regulatory Mechanism |
|---|---|---|
| HDAC (histone deacetylase) | Vorinostat, Panobinostat, belinostat, entinostat, mocetinostat, givinostat, chidamide, quisinostat, abexinostat, chr-3996, ar-42, | Epigenetic Regulator |
| Brd4 | INCN54329, INCB57643, birabresib, apabetalone, alvocidib, PLX-51107, FT-1101, RG-6146, AZD-8186, CPI-0610, JQ1 | Transcription regulator |
| HMT (histone methyl transferases) | | Epigenetic Regulator |
| LSD1 | INCB59872, IMG-7289, RG-6016, CC-90011, GSK-2879552, ORY-2001, 4SC-202, ORY-3001, | Epigenetic Regulator |
| TNFa | Recombinant TNFa, MEDI-1873, FPA-154, LKZ-145 | Cytokine |
| IL1 | Recombinant IL1 | Cytokine |
| IFNa | Recombinant interferon alpha-n1, Recombinant interferon alpha-2b, Recombinant interferon alpha-n3 | Cytokine |
| IFNb | Recombinant IFN beta-1a, | Cytokine |
| IFNg | actimmune | Cytokine |
| STING | Cyclic di-nucleotides | Signaling Molecule |
| TLR | Poly I:C, IMO-2055, TMX-101, imiquimod, CpG, MGN1703, glucopyranosyl lipid A, CBLB502, BCG, HILTONOL, AMPLIGEN, MOTOLIMOD, DUK-CPG-001, AS15 | Pathogen Recognition Receptor |
| IL10 | Recombinant IL-10 | Cytokine |
| CCR2 | CCX140, CCX872, BMS-813160, CENICRIVIROC, CNTX-6970. PF-4136309, plozalizumab, INCB-9471, PF-04634817 | Chemokine |
| CCR5 | Maraviroc, PRO-140, BMS-813160, NIFEVIROC, OHR-118 | Chemokine |
| CXCR4 | Ulocuplumab, plerixafor, x4p-001, usl-311, ly-2510924, APH-0812, BL-8040, BURIXAFOR, BALIXAFORTIDE, PTX-9908, GMI-1359, F-50067 | Chemokine |
| LFA1 | | Adhesion Molecule |
| MICA/B | IPH-4301 | Immune Receptor Ligand |
| VISTA | CA-170 | Checkpoint-Ligand |
| Adenosine | ISTRADEFYLLINE, TOZADENANT, PBF-509, PBF-999, CPI-444 | Nucleoside |
| CD39 | OREG-103. Anti-CD39 antibodies, | Ecto-enzyme |
| CD73 | Oleclumab, PBF-1662, anti-CD73 antibodies | Ecto-Enzyme |
| PD1 | Pembrolizumab, nivolumab, INCSHR1210, CT-011, AMP224 | Checkpoint-receptor |
| PD-L1 | Atezolizumab, avelumab | Checkpoint-Ligand |
| PD-L2 | | Checkpoint-Ligand |
| CTLA4 | Tremelimumab | Checkpoint-receptor |
| CD137 | Urelumab, utomilumab, BMS-663513, PF-05082566 | |
| AXL | BGB-324, BPI-9016M, S-49076 | Kinase |
| MERTK | BGB-324, BPI-9016M, S-49076 | Kinase |
| TYRO | BGB-324, BPI-9016M, S-49076 | |
| BTK | ibrutinib | Kinase |
| ITK | ibrutinib | Kinase |
| LCK | | Kinase |
| TET2 | | Enzyme |
| Arginase | Cb-1158 | Endo/ecto enzyme |
| GCN2 | | Kinase |
| B7-H4 | MDX-1140, AMP-110 | Checkpoint-receptor |
| HIF1alpha | PT2385 | Transcription Factor |
| LIGHT (TNFSF14) | | TNF Superfamily |
| FLT3 | CDX-301, FLX925, quizartinib, gilteritinib, PKC412, midostaurin, crenolanib | Kinase |
| CD158 | Lirlumab, IPH-2101 | |
| CD47 | Anti-CD47, TTI-621, NI-1701, SRF-231, Effi-DEM, RCT-1938 | |
| IDO | Epacadostat, F287, BMS983205, GDC-0919, indoximod | |
| RORgamma | | |

In a further embodiment, the compounds described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho $^{177}$Lu, $^{186}$Re, $^{188}$Re, $^{211}$At, and $^{212}$Bi, optionally conjugated to antibodies directed against tumor antigens.

In addition, a CCR4 inhibitor (e.g., compound described herein) may be combined with the therapeutic administration of immune cells, sometimes referred to as adoptive cell transfer. These cells may be cells from the patient, a genetically related or unrelated donor, they may be genetically modified (e.g. CAR-T cells, NK cells, etc), cell lines, genetically modified cell lines and live or dead versions of the above. CCR4 inhibitors may also be combined with vaccines of any kind (e.g. protein/peptide, viral, bacterial, cellular vaccines) to stimulate immune responses to cancer.

In embodiments, treatment is administration of an effective amount of a CCR4 inhibitor (e.g., compound described herein) in combination with an inhibitor of the PD-L1/PD-1 pathway, an inhibitor of CTLA-4, an agonistic antibody of CD137 (4-1B) or in combination with another immune modulator as listed in Table 1.

In embodiments, treatment is therapeutic administration of an effective amount of a CCR4 inhibitor (e.g., compound described herein) in combination with an inhibitor of the PD-L1/PD-1 pathway, an inhibitor of CTLA-4, an agonistic antibody of CD137 (4-1BB) or in combination with another immune modulator as listed in Table 1. In embodiments, treatment starts when tumors reach a size of about 40-70 mm$^3$.

The CCR4 inhibitors disclosed herein (e.g., compounds described herein) can be administered by any acceptable route, such oral, intraadiposal, intraarterial, intraarticular, intracranial, intradermal, intralesional, intramusculay, intranasal, intraocularal, intrapericardial, intraperitoneal, intrapleural, intraprostatical, intrarectal, intrathecal, intratracheal, intratumoral, intraumbilical, intravaginal, intravenousl, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The immune modulators disclosed herein can be administered by any acceptable route, such oral, intraadiposal, intraarterial, intraarticular, intracranial, intradermal, intralesional, intramusculay, intranasal, intraocularal, intrapericardial, intraperitoneal, intrapleural, intraprostatical, intrarectal, intrathecal, intratracheal, intratumoral, intraumbilical, intravaginal, intravenousl, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

The CCR4 inhibitors disclosed herein (e.g., compound described herein) may be administered once daily until study reached endpoint. The immune modulator disclosed herein may be administered at least three times but in some studies four or more times depending on the length of the study and/or the design of the study.

The methods disclosed herein may be used in combination with additional cancer therapy. In some embodiments, the distinct cancer therapy comprises surgery, radiotherapy, chemotherapy, toxin therapy, immunotherapy, cryotherapy or gene therapy. In some embodiments, the cancer is a chemotherapy-resistant or radio-resistant cancer.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule. In some embodiments, a CCR4 associated disease modulator is a compound that reduces the severity of one or more symptoms of a disease associated with CCR4 (e.g. cancer, inflammatory disease, autoimmune disease, or infectious disease). A CCR4 modulator is a compound that increases or decreases the activity or function or level of activity or level of function of CCR4. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an activator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule. In embodiments, the terms "modulate", "modulation" and the like refer to the ability of a molecule (e.g., an activator or an inhibitor) to increase or decrease the function or activity of CCR4, either directly or indirectly, relative to the absence of the molecule.

The term "associated" or "associated with" or "mediated by" in the context of a substance or substance activity or function associated with a disease (e.g. a protein associated disease, a cancer associated with CCR4 activity, CCR4 associated cancer, CCR4 associated disease (e.g., cancer, inflammatory disease, autoimmune disease, or infectious disease)) or a disease mediated by a substance, substance activity, or substance function, means that the disease (e.g. cancer, inflammatory disease, autoimmune disease, or infectious disease) is caused by (in whole or in part), or a symptom of the disease is caused by (in whole or in part) the substance or substance activity or function. For example, a cancer associated with CCR4 activity or function may be a cancer that results (entirely or partially) from aberrant CCR4 function (e.g., enzyme activity, protein-protein interaction, signaling pathway) or a cancer wherein a particular symptom of the disease is caused (entirely or partially) by aberrant CCR4 activity or function. As used herein, what is described as being associated with a disease, if a causative agent, could be a target for treatment of the disease. For example, a cancer associated with CCR4 activity or function or a CCR4 associated disease (e.g., cancer, inflammatory disease, autoimmune disease, or infectious disease), may be treated with a compound described herein (e.g., CCR4 modulator or CCR4 inhibitor), in the instance where increased CCR4 activity or function (e.g. signaling pathway activity) causes the disease (e.g., cancer, inflammatory disease, autoimmune disease, or infectious disease). For example, an inflammatory disease associated with CCR4 activity or function or a CCR4 associated inflammatory disease, may be treated with an CCR4 modulator or CCR4 inhibitor, in the instance where increased CCR4 activity or function (e.g. signaling pathway activity) causes the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a CCR4 with a compound as described herein may reduce the level of a product of the CCR4 catalyzed reaction or the level of a downstream derivative of the product or binding may reduce the interactions between the CCR4 or a reaction product and downstream effectors or signaling pathway components (e.g., MAP kinase pathway), resulting in changes in cell growth, proliferation, or survival.

As used herein, the terms "CCR4 inhibitor", "CCR4 antagonist", "C—C chemokine receptor type 4 inhibitor", "C—C chemokine receptor type 4 antagonist" and all other related art-accepted terms, many of which are set forth below, refer to a compound capable of detectably decreasing the expression or activity, either directly or indirectly, the CCR4 receptor in an in vitro assay, an in vivo model, and/or other means indicative of therapeutic efficacy. The terms may also refer to a compound that exhibits at least some therapeutic benefit (e.g., as determined via an objective parameter such as a serum concentration or subjective parameter, such as a subject's feeling of well-being) in a human subject.

The phrase "in a sufficient amount to effect a change" means that there is a detectable difference between a level of an indicator measured before (e.g., a baseline level or in the presence of a control) and after administration of a particular therapy. Indicators include any objective parameter (e.g., serum concentration) or subjective parameter (e.g., a subject's feeling of well-being).

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component will make up greater than about 90%, or greater than about 95% of the total content of the composition (percentage in a weight per weight basis).

The terms "specifically binds" and "selectively binds," when referring to a binder/target, ligand/receptor, antibody/antigen, or other binding pair, indicate a binding reaction which is determinative of the presence of the target (e.g., protein) in a heterogeneous population of components (e.g., proteins and other biologics). Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant thereof, with an affinity that is at least two-fold greater, at least 10-times greater, at least 20-times greater, or at least 100-times greater than the affinity with any other target, or binding composition derived therefrom. In embodiments, the antibody will have an affinity that is greater than about $10^9$ liters/mol, as determined by, e.g., Scatchard analysis (Munsen, et al. (1980) Analyt. Biochem. 107:220-239).

The terms "nucleic acid," "nucleic acid molecule," "polynucleotide" and the like are used interchangeably herein to refer to a polymeric form of nucleotides of any length (e.g., either deoxyribonucleotides or ribonucleotides) or analogs thereof. Non-limiting examples of polynucleotides include linear and circular nucleic acids, messenger RNA (mRNA), complementary DNA (cDNA), recombinant polynucleotides, vectors, probes, primers and the like.

As used herein, the terms "variants" and "homologs" are used interchangeably to refer to amino acid or nucleic acid sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring amino acid and nucleic acid sequences encoded thereby and their isoforms, as well as splice variants of a protein or gene. The terms also encompass nucleic acid sequences that vary in one or more bases from a naturally-occurring nucleic acid sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced; for example, the change is generated in the laboratory by human intervention ("hand of man"). Therefore, non-naturally occurring variants and homologs may also refer to those that differ from the naturally occurring sequences by one or more conservative substitutions and/or tags and/or conjugates.

II. Compounds

In an aspect provided herein, is a compound having structural Formula (I):

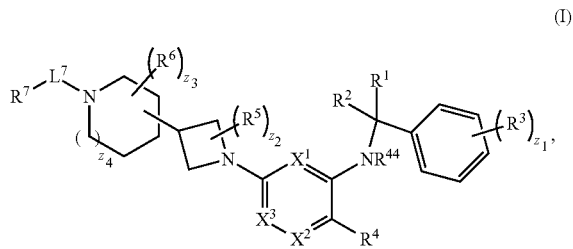

or a pharmaceutically acceptable salt thereof. $X^1$ is $CR^8$ or N. $X^2$ is $CR^9$ or N. $X^3$ is $CR^{10}$ or N. The symbols n1, n2, n3, n4, n5, n6, n7, n8, n9, n10, and n44 are independently an integer from 0 to 4. The symbols m1, m2, m3, m4, m5, m6, m7, m8, m9, m10, v1, v2, v3, v4, v5, v6, v7, v8, v9, v10, and v44 are independently 1 or 2. The symbol z1 is an integer from 0 to 5. The symbol z2 is an integer from 0 to 5. The symbol z3 is an integer from 0 to 11. The symbol z4 is an integer from 0 to 2. $L^7$ is a bond, —O—, —S—, —NR$^{7.2B}$—, —C(O)—, —C(O)O—, —S(O)—, —S(O)$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^1$ is hydrogen, halogen, $-CX^{1.1}{}_3$, $-CHX^{1.1}{}_2$, $-CH_2X^{1.1}$, $-CN$, $-N_3$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}{}_3$, $-OCHX^{1.1}{}_2$, $-OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-CX^{2.1}{}_3$, $-CHX^{2.1}{}_2$, $-CH_2X^{2.1}$, $-CN$, $-N_3$, $-SO_{n2}R^{2A}$, $-SO_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}{}_3$, $-OCHX^{2.1}{}_2$, $-OCH_2X^{2.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently halogen, $-CX^{3.1}{}_3$, $-CHX^{3.1}{}_2$, $-CH_2X^{3.1}$, $-CN$, $-N_3$, $-SO_{n3}R^{3A}$, $-SO_{v3}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m3}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}{}_3$, $-OCHX^{3.1}{}_2$, $-OCH_2X^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^4$ is hydrogen, halogen, $-CX^{4.1}{}_3$, $-CHX^{4.1}{}_2$, $-CH_2X^{4.1}$, $-CN$, $-N_3$, $-SO_{n4}R^{4A}$, $-SO_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}{}_3$, $-OCHX^{4.1}{}_2$, $-OCH_2X^{4.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; when $X^2$ is $CR^9$, then $R^4$ and $R^9$ may optionally be joined to form a substituted or unsubstituted cycloalkyl, substituted or unsubstituted heterocycloalkyl, or unsubstituted aryl, or substituted or unsubstituted heteroaryl. $R^5$ is independently halogen, oxo, $-CX^{5.1}{}_3$, $-CHX^{5.1}{}_2$, $-CH_2X^{5.1}$, $-CN$, $-N_3$, $-SO_{n5}R^{5A}$, $-SO_{v5}NR^{5B}R^{5C}$, $-NHR^{5B}R^{5C}$, $-ONR^{5B}R^{5C}$, $-NHC(O)NHNR^{5B}R^{5C}$, $-NHC(O)NR^{5B}R^{5C}$, $-N(O)_{m5}$, $-NR^{5B}R^{5C}$, $-C(O)R^{5D}$, $-C(O)OR^{5D}$, $-C(O)NR^{5B}R^{5C}$, $-OR^{5A}$, $-NR^{5B}SO_2R^{5A}$, $-NR^{5B}C(O)R^{5D}$, $-NR^{5B}C(O)OR^{5D}$, $-NR^{5B}OR^{5D}$, $-OCX^{5.1}{}_3$, $-OCHX^{5.1}{}_2$, $-OCH_2X^{5.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is independently halogen, oxo, $-CX^{6.1}{}_3$, $-CHX^{6.1}{}_2$, $-CH_2X^{6.1}$, $-CN$, $-N_3$, $-SO_{n6}R^{6A}$, $-SO_{v6}NR^{6B}R^{6C}$, $-NHNR^{6B}R^{6C}$, $-ONR^{6B}R^{6C}$, $-NHC(O)NHNR^{6B}R^{6C}$, $-NHC(O)NR^{6B}R^{6C}$, $-N(O)_{m6}$, $-NR^{6B}R^{6C}$, $-C(O)R^{6D}$, $-C(O)OR^{6D}$, $-C(O)NR^{6B}R^{6C}$, $-OR^{6A}$, $-NR^{6B}SO_2R^{6A}$, $-NR^{6B}C(O)R^{6D}$, $-NR^{6B}C(O)OR^{6D}$, $-NR^{6B}OR^{6D}$, $-OCX^{6.1}{}_3$, $-OCHX^{6.1}{}_2$, $-OCH_2X^{6.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^7$ is hydrogen, halogen, $-CX^{7.1}{}_3$, $-CHX^{7.1}{}_2$, $-CH_2X^{7.1}$, $-CN$, $-N_3$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{1C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}{}_3$, $-OCHX^{7.1}{}_2$, $-OCH_2X^{7.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^8$ is hydrogen, halogen, $-CX^{8.1}{}_3$, $-CHX^{8.1}{}_2$, $-CH_2X^{8.1}$, $-CN$, $-N_3$, $-SO_8R^{8A}$, $-SO_{v8}NR^{8B}R^{8C}$, $-NHNR^{8B}R^{8C}$, $-ONR^{8B}R^{8C}$, $-NHC(O)NHNR^{8B}R^{1C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, $-OCH_2X^{8.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^9$ is hydrogen, halogen, $-CX^{9.1}{}_3$, $-CHX^{9.1}{}_2$, $-CH_2X^{9.1}$, $-CN$, $-N_3$, $-SO_9R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}{}_3$, $-OCHX^{9.1}{}_2$, $-OCH_2X^{9.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; when $X^2$ is $CR^9$ and $X^3$ is $CR^{10}$, then $R^9$ and $R^{10}$ may optionally be joined to form a substituted or unsubstituted cycloalkyl, substituted or unsubstituted heterocycloalkyl, or aryl, or substituted or unsubstituted heteroaryl. $R^{10}$ is hydrogen, halogen, $-CX^{10.1}{}_3$, $-CHX^{10.1}{}_2$, $-CH_2X^{10.1}$, $-CN$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, $-OCH_2X^{10.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or when $X^2$ is $CR^9$ and $X^3$ is $CR^{10}$, then $R^9$ and $R^{10}$ may optionally be joined to form a substituted or unsubstituted cycloalkyl, substituted or unsubstituted heterocycloalkyl, or unsubstituted aryl, or substituted or unsubstituted heteroaryl. $R^{44}$ is hydrogen, $-CX^{44.1}{}_3$, $-CHX^{44.1}{}_2$, $-CH_2X^{44.1}$, $-SO_{n44}R^{44A}$, $-SO_{v44}NR^{44B}R^{44C}$, $-C(O)R^{44D}$, $-C(O)OR^{44D}$, $-C(O)NR^{44B}R^{44C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{72B}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{44A}$, $R^{44B}$, $R^{44}$ and $R^{44D}$ are independently hydrogen, halogen, —$CF_3$, —$CCl_3$, —$CBr_3$, —$C_3$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$, $R^{3C}$, $R^{4B}$, $R^{4C}$, $R^{5B}$, $R^{5C}$, $R^{6B}$, $R^{6C}$, $R^{7B}$, $R^{7C}$, $R^{8B}$, $R^{8C}$, $R^{9B}$, $R^{9C}$, $R^{10B}$, $R^{10C}$, $R^{44B}$, and $R^{44C}$ substituents bonded to the same nitrogen atom may optionally be joined to form a substituted or unsubstituted heterocycloalkyl or substituted or unsubstituted heteroaryl. $X^{11}$, $X^{2.1}$, $X^{3.1}$, $X^{4.1}$, $X^{5.1}$, $X^{6.1}$, $X^7$, $X^{8.1}$, $X^{9.1}$, $X^{10}$, and $X^{44.1}$ are independently —Cl, —Br, —I or —F, wherein at least one of $X^1$, $X^2$ and $X^3$ is N.

In embodiments, $X^1$ is $CR^8$. In embodiments, $X^2$ is $CR^9$. In embodiments, $X^3$ is $CR^{10}$. In embodiments, $X^1$ is N. In embodiments, $X^2$ is N. In embodiments, $X^3$ is N. In embodiments, at least one of $X^1$, $X^2$ and $X^3$ is N.

In embodiments, $R^1$ is halogen, —$CX^{1.1}_3$, —$CHX^{1.1}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, —$OCH_2X^{1.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is hydrogen.

In embodiments, $R^1$ is hydrogen, halogen, —$CX^{1.1}_3$, —$CHX^{1.1}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, —$OCH_2X^{1.1}$, $R^{11}$-substituted or unsubstituted alkyl (e.g., $C_1$-$C_8$ alkyl, $C_1$-$C_6$ alkyl, or $C_1$-$C_4$ alkyl), $R^{11}$-substituted or unsubstituted heteroalkyl (e.g., 2 to 8 membered heteroalkyl, 2 to 6 membered heteroalkyl, or 2 to 4 membered heteroalkyl), $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11}$-substituted or unsubstituted aryl (e.g., $C_6$-$C_{10}$ aryl, $C_{10}$ aryl, or phenyl), or $R^{11}$-substituted or unsubstituted heteroaryl (e.g., 5 to 10 membered heteroaryl, 5 to 9 membered heteroaryl, or 5 to 6 membered heteroaryl).

In embodiments, $R^1$ is $R^{11}$-substituted or unsubstituted alkyl (e.g., $C_1$-$C_8$ alkyl, $C_1$-$C_6$ alkyl, or $C_1$-$C_4$ alkyl). In embodiments, $R^1$ is $R^{11}$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl).

In embodiments, $R^1$ is $R^{11}$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^{11}$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl).

In embodiments, $R^1$ is $R^{11}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^{11}$-substituted cycloalkyl (e.g., $C_3$-$C_8$ cycloalkyl, $C_3$-$C_6$ cycloalkyl, or $C_5$-$C_6$ cycloalkyl). In embodiments, $R^1$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^1$ is $R^{11}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{11}$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^1$ is $R^{11}$-substituted or unsubstituted aryl (e.g., $C_6$-$C_{10}$ aryl, $C_{10}$ aryl, or phenyl). In embodiments, $R^1$ is $R^{11}$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl).

In embodiments, $R^1$ is $R^{11}$-substituted or unsubstituted heteroaryl (e.g., 5 to 10 membered heteroaryl, 5 to 9 membered heteroaryl, or 5 to 6 membered heteroaryl). In embodiments, $R^1$ is $R^{11}$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

In embodiments, $R^1$ is $R^{11}$-substituted or unsubstituted alkyl (e.g., $C_1$-$C_8$ alkyl, $C_1$-$C_6$ alkyl, or $C_1$-$C_4$ alkyl). In embodiments, $R^1$ is $R^{11}$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl). In embodiments, $R^1$ is hydrogen.

In embodiments, $R^1$ is $R^{11}$-substituted or unsubstituted methyl. In embodiments, $R^1$ is $R^{11}$-substituted or unsubstituted $C_2$ alkyl. In embodiments, $R^1$ is $R^{11}$-substituted or unsubstituted $C_3$ alkyl. In embodiments, $R^1$ is $R^{11}$-substituted or unsubstituted $C_4$ alkyl. In embodiments, $R^1$ is $R^{11}$-substituted or unsubstituted $C_5$ alkyl. In embodiments, $R^1$ is $R^{11}$-substituted or unsubstituted $C_6$ alkyl. In embodiments, $R^1$ is $R^{11}$-substituted or unsubstituted $C_7$ alkyl. In embodiments, $R^1$ is $R^{11}$-substituted or unsubstituted $C_8$ alkyl. In embodiments, $R^1$ is $R^{11}$-substituted methyl. In embodiments, $R^1$ is $R^{11}$-substituted $C_2$ alkyl. In embodiments, $R^1$ is $R^{11}$-substituted $C_3$ alkyl. In embodiments, $R^1$ is $R^{11}$-substituted $C_4$ alkyl. In embodiments, $R^1$ is $R^{11}$-substituted CS alkyl. In embodiments, $R^1$ is $R^{11}$-substituted $C_6$ alkyl. In embodiments, $R^1$ is $R^{11}$-substituted $C_7$ alkyl. In embodiments, $R^1$ is $R^{11}$-substituted $C_8$ alkyl. In embodiments, $R^1$ is an unsubstituted methyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted CS alkyl. In embodiments, $R^1$ is an unsubstituted $C_6$ alkyl. In embodiments, R is an unsubstituted $C_7$ alkyl. In embodiments, $R^1$ is an unsubstituted $C_8$ alkyl.

In embodiments, $R^2$ is halogen, —$CX^{2.1}_3$, —$CHX^{2.1}_2$, —$CH_2X^{2.1}$, —CN, —$N_3$, —$SO_{n2}R^{2A}$, —$SO_{v2}NR^{2B}R^{2C}$, —$NHNR^{2B}R^{2C}$, —$ONR^{2B}R^{2C}$, —$NHC(O)NHNR^{2B}R^{2C}$, —$NHC(O)NR^{2B}R^{2C}$, —$N(O)_{m2}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —OCX$^{2.1}_3$, —OCHX$^{2.1}_2$, —OCH$_2$X$^{2.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^2$ is hydrogen.

In embodiments, R$^2$ is hydrogen, halogen, —CX$^{2.1}_3$, —CHX$^{2.1}_2$, —CH$_2$X$^{2.1}$, —CN, —N$_3$, —SO$_{n2}$R$^{2A}$, —SO$_2$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m2}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2B}$, —OCHX$^{2.1}_2$, —OCH$_2$X$^{2.1}$, R$^{14}$-substituted or unsubstituted alkyl (e.g., C$_1$-C$_8$ alkyl, C$_1$-C$_6$ alkyl, or C$_1$-C$_4$ alkyl), R$^{14}$-substituted or unsubstituted heteroalkyl (e.g., 2 to 8 membered heteroalkyl, 2 to 6 membered heteroalkyl, or 2 to 4 membered heteroalkyl), R$^{14}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{14}$-substituted or unsubstituted heterocycloalkyl (e.g., 3 to 8 membered heterocycloalkyl, 3 to 6 membered heterocycloalkyl, or 5 to 6 membered heterocycloalkyl), R$^{14}$-substituted or unsubstituted aryl (e.g., C$_6$-C$_{10}$ aryl, C$_{10}$ aryl, or phenyl), or R$^{14}$-substituted or unsubstituted heteroaryl (e.g., 5 to 10 membered heteroaryl, 5 to 9 membered heteroaryl, or 5 to 6 membered heteroaryl).

In embodiments, R$^2$ is R$^{14}$-substituted or unsubstituted alkyl (e.g., C$_1$-C$_8$ alkyl, C$_1$-C$_6$ alkyl, or C$_1$-C$_4$ alkyl). In embodiments, R$^2$ is R$^{14}$-substituted alkyl (e.g., C$_1$-C$_8$ alkyl, C$_1$-C$_6$ alkyl, or C$_1$-C$_4$ alkyl). In embodiments, R$^2$ is an unsubstituted alkyl (e.g., C$_1$-C$_8$ alkyl, C$_1$-C$_6$ alkyl, or C$_1$-C$_4$ alkyl). In embodiments, R$^2$ is an unsubstituted ethyl. In embodiments, R$^2$ is an unsubstituted C$_3$ alkyl. In embodiments, R$^2$ is an unsubstituted C$_4$ alkyl.

In embodiments, R$^2$ is R$^{14}$-substituted or unsubstituted heteroalkyl (e.g., 2 to 8 membered heteroalkyl, 2 to 6 membered heteroalkyl, or 2 to 4 membered heteroalkyl). In embodiments, R$^2$ is R$^{14}$-substituted heteroalkyl (e.g., 2 to 8 membered heteroalkyl, 2 to 6 membered heteroalkyl, or 2 to 4 membered heteroalkyl). In embodiments, R$^2$ is an unsubstituted heteroalkyl (e.g., 2 to 8 membered heteroalkyl, 2 to 6 membered heteroalkyl, or 2 to 4 membered heteroalkyl).

In embodiments, R$^2$ is R$^{14}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^2$ is R$^{14}$-substituted cycloalkyl (e.g., C$_3$-C$_8$ cycloalkyl, C$_3$-C$_6$ cycloalkyl, or C$_5$-C$_6$ cycloalkyl). In embodiments, R$^2$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, R$^2$ is R$^{14}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^2$ is R$^{14}$-substituted heterocycloalkyl (e.g., 3 to 8 membered heterocycloalkyl, 3 to 6 membered heterocycloalkyl, or 5 to 6 membered heterocycloalkyl). In embodiments, R$^2$ is an unsubstituted heterocycloalkyl (e.g., 3 to 8 membered heterocycloalkyl, 3 to 6 membered heterocycloalkyl, or 5 to 6 membered heterocycloalkyl).

In embodiments, R$^2$ is R$^{14}$-substituted or unsubstituted aryl (e.g., C$_6$-C$_{10}$ aryl, C$_{10}$ aryl, or phenyl). In embodiments, R$^2$ is R$^{14}$-substituted aryl (e.g., C$_6$-C$_{10}$ aryl, C$_{10}$ aryl, or phenyl). In embodiments, R$^2$ is an unsubstituted aryl (e.g., C$_6$-C$_{10}$ aryl, C$_{10}$ aryl, or phenyl).

In embodiments, R$^2$ is R$^{14}$-substituted or unsubstituted heteroaryl (e.g., 5 to 10 membered heteroaryl, 5 to 9 membered heteroaryl, or 5 to 6 membered heteroaryl). In embodiments, R$^2$ is R$^{14}$-substituted heteroaryl (e.g., 5 to 10 membered heteroaryl, 5 to 9 membered heteroaryl, or 5 to 6 membered heteroaryl). In embodiments, R$^2$ is an unsubstituted heteroaryl (e.g., 5 to 10 membered heteroaryl, 5 to 9 membered heteroaryl, or 5 to 6 membered heteroaryl).

In embodiments, R$^2$ is R$^{14}$-substituted or unsubstituted alkyl (e.g., C$_1$-C$_8$ alkyl, C$_1$-C$_6$ alkyl, or C$_1$-C$_4$ alkyl). In embodiments, R$^2$ is R$^{14}$-substituted alkyl (e.g., C$_1$-C$_8$ alkyl, C$_1$-C$_6$ alkyl, or C$_1$-C$_4$ alkyl). In embodiments, R$^2$ is an unsubstituted alkyl (e.g., C$_1$-C$_8$ alkyl, C$_1$-C$_6$ alkyl, or C$_1$-C$_4$ alkyl). In embodiments, R$^2$ is hydrogen.

In embodiments, R$^2$ is R$^{14}$-substituted or unsubstituted methyl. In embodiments, R$^2$ is R$^{14}$-substituted or unsubstituted C$_2$ alkyl. In embodiments, R$^2$ is R$^{14}$-substituted or unsubstituted C$_3$ alkyl. In embodiments, R$^2$ is R$^{14}$-substituted or unsubstituted C$_4$ alkyl. In embodiments, R$^2$ is R$^{14}$-substituted or unsubstituted C$_5$ alkyl. In embodiments, R$^2$ is R$^{14}$-substituted or unsubstituted C$_6$ alkyl. In embodiments, R$^2$ is R$^{14}$-substituted or unsubstituted C$_7$ alkyl. In embodiments, R$^2$ is R$^{14}$-substituted or unsubstituted C$_8$ alkyl. In embodiments, R$^2$ is R$^{14}$-substituted methyl. In embodiments, R$^2$ is R$^{14}$-substituted C$_2$ alkyl. In embodiments, R$^2$ is R$^{14}$-substituted C$_3$ alkyl. In embodiments, R$^2$ is R$^{14}$-substituted C$_4$ alkyl. In embodiments, R$^2$ is R$^{14}$-substituted CS alkyl. In embodiments, R$^2$ is R$^{14}$-substituted C$_6$ alkyl. In embodiments, R$^2$ is R$^{14}$-substituted C$_7$ alkyl. In embodiments, R$^2$ is R$^{14}$-substituted C$_8$ alkyl. In embodiments, R$^2$ is an unsubstituted methyl. In embodiments, R$^2$ is an unsubstituted C$_2$ alkyl. In embodiments, R$^2$ is an unsubstituted C$_3$ alkyl. In embodiments, R$^2$ is an unsubstituted C$_4$ alkyl. In embodiments, R$^2$ is an unsubstituted CS alkyl. In embodiments, R$^2$ is an unsubstituted C$_6$ alkyl. In embodiments, R$^2$ is an unsubstituted C$_7$ alkyl. In embodiments, R$^2$ is an unsubstituted C$_8$ alkyl.

In embodiments, R$^1$ and R$^2$ are independently hydrogen, substituted or unsubstituted alkyl or substituted or unsubstituted heteroalkyl. In embodiments, R$^1$ is substituted or unsubstituted alkyl. R$^2$ is substituted or unsubstituted alkyl. In embodiments, R$^1$ is —CH$_3$. In embodiments, R$^2$ is —CH$_3$. In embodiments, R$^1$ is hydrogen. In embodiments, R$^2$ is hydrogen.

In embodiments, R$^3$ is independently halogen, —CX$^{3.1}_3$, —CHX$^{3.1}_2$, —CH$_2$X$^{3.1}$, —CN, —N$_3$, —SO$_{n3}$R$^{3A}$, —SO$_{v3}$NR$^{3B}$R$^{3C}$, —N—NR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^{3.1}_3$, —OCHX$^{3.1}_2$, —OCH$_2$X$^{3.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, R$^3$ is independently halogen, —CX$^{3.1}_3$, —CHX$^{3.1}_2$, —CH$_2$X$^{3.1}$, —CN, —N$_3$, —SO$_{n3}$R$^{3A}$, —SO$_{v3}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m3}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^{3.1}_3$, —OCHX$^{3.1}_2$, —OCH$_2$X$^{3.1}$, R$^{17}$-substituted or unsubstituted alkyl (e.g., C$_1$-C$_8$ alkyl, C$_1$-C$_6$ alkyl, or C$_1$-C$_4$ alkyl), R$^{17}$-substituted or unsubstituted heteroalkyl (e.g., 2 to 8 membered heteroalkyl, 2 to 6 membered heteroalkyl, or 2 to 4 membered heteroalkyl), R$^{17}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{17}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17}$-substituted or unsubstituted aryl (e.g., $C_6$-$C_{10}$ aryl, $C_{10}$ aryl, or phenyl), or $R^{17}$-substituted or unsubstituted heteroaryl (e.g., 5 to 10 membered heteroaryl, 5 to 9 membered heteroaryl, or 5 to 6 membered heteroaryl).

In embodiments, $R^3$ is independently $R^{17}$-substituted or unsubstituted alkyl (e.g., $C_1$-$C_8$ alkyl, $C_1$-$C_6$ alkyl, or $C_1$-$C_4$ alkyl). In embodiments, $R^3$ is independently $R^{17}$-substituted alkyl (e.g., $C_1$-$C_8$ alkyl, $C_1$-$C_6$ alkyl, or $C_1$-$C_4$ alkyl). In embodiments, $R^3$ is independently an unsubstituted alkyl (e.g., $C_1$-$C_8$ alkyl, $C_1$-$C_6$ alkyl, or $C_1$-$C_4$ alkyl).

In embodiments, $R^3$ is independently $R^{17}$-substituted or unsubstituted heteroalkyl (e.g., 2 to 8 membered heteroalkyl, 2 to 6 membered heteroalkyl, or 2 to 4 membered heteroalkyl). In embodiments, $R^3$ is independently $R^{17}$-substituted heteroalkyl (e.g., 2 to 8 membered heteroalkyl, 2 to 6 membered heteroalkyl, or 2 to 4 membered heteroalkyl). In embodiments, $R^3$ is independently an unsubstituted heteroalkyl (e.g., 2 to 8 membered heteroalkyl, 2 to 6 membered heteroalkyl, or 2 to 4 membered heteroalkyl).

In embodiments, $R^3$ is independently $R^{17}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is independently $R^{17}$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is independently an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^3$ is independently $R^{17}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is independently $R^{17}$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is independently an unsubstituted heterocycloalkyl (e.g., 3 to 8 membered heterocycloalkyl, 3 to 6 membered heterocycloalkyl, or 5 to 6 membered heterocycloalkyl).

In embodiments, $R^3$ is independently $R^{17}$-substituted or unsubstituted aryl (e.g., $C_6$-$C_{10}$ aryl, $C_{10}$ aryl, or phenyl). In embodiments, $R^3$ is independently $R^{17}$-substituted aryl (e.g., $C_6$-$C_{10}$ aryl, $C_{10}$ aryl, or phenyl). In embodiments, $R^3$ is independently an unsubstituted aryl (e.g., $C_6$-$C_{10}$ aryl, $C_{10}$ aryl, or phenyl).

In embodiments, $R^3$ is independently $R^{17}$-substituted or unsubstituted heteroaryl (e.g., 5 to 10 membered heteroaryl, 5 to 9 membered heteroaryl, or 5 to 6 membered heteroaryl). In embodiments, $R^3$ is independently $R^{17}$-substituted heteroaryl (e.g., 5 to 10 membered heteroaryl, 5 to 9 membered heteroaryl, or 5 to 6 membered heteroaryl). In embodiments, $R^3$ is independently an unsubstituted heteroaryl (e.g., 5 to 10 membered heteroaryl, 5 to 9 membered heteroaryl, or 5 to 6 membered heteroaryl).

In embodiments, $R^3$ is independently halogen, —$CF_3$, —$CHF_2$, —$CH_2F$, —CN, —$N_3$, —$SO_2R^{3.4}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. It is understood that when z3 is 0, $R^3$ is hydrogen. In embodiments, $R^3$ is independently —Cl. In embodiments, $R^3$ is independently —F. In embodiments, $R^3$ is independently —Br. In embodiments, $R^3$ is independently —I. In embodiments, $R^3$ is independently —$SO_2CH_3$. In embodiments, $R^3$ is independently —$SO_2CH_2CH_3$. In embodiments, $R^3$ is independently —$SO_2C_1$.

In embodiments, the definition of $R^3$ is assumed by (independently assigned to) $R^{3.1}$, $R^{3.2}$, $R^{3.3}$, $R^{3.4}$, $R^{3.5}$. The substituents $R^{3.1}$, $R^{3.2}$, $R^{3.3}$, $R^{3.4}$, and $R^{3.5}$ are each $R^3$ at a fixed position on the attached ring. In embodiments, $R^{3.2}$ is a substituent of $R^3$ or hydrogen. In embodiments, $R^{3.3}$ is a substituent of $R^3$ or hydrogen.

In embodiments, $R^{3.2}$ is halogen, —$CX^{3.2}_3$, —$CHX^{3.2}_2$, —$CH_2X^{3.2}$, —CN, —$N_3$, —$SO_{n3.2}R^{3.2A}$, —$SO_{v3.2}NR^{3.2B}R^{3.2C}$, —N—$NR^{3.2B}R^{3.2C}$, —$ONR^{3.2B}R^{3.2C}$, —NHC(O)NHN$R^{3.2B}R^{3.2C}$, —NHC(O)NR$^{3.2B}R^{3.2C}$, —N(O)$_{m3.2}$, —$NR^{3.2B}R^{3.2C}$, —C(O)$R^{3.2D}$, —C(O)O$R^{3.2D}$, —C(O)NR$^{3.2B}R^{3.2C}$, —OR$^{3.2A}$, —NR$^{3.2B}SO_2R^{3.2A}$, —NR$^{3.2B}C(O)R^{3.2D}$, —NR$^{3.2B}C(O)$OR$^{3.2D}$, —NR$^{3.2B}$OR$^{3.2D}$, —OCX$^{3.2}_3$, —OCHX$^{3.2}_2$, —OCH$_2X^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^{3.2}$ is halogen. In embodiments, $R^{3.2}$ is hydrogen. In embodiments, $R^{3.2}$ is halogen. In embodiments, $R^{3.2}$ is chlorine. In embodiments, $R^{3.2}$ and $R^{3.3}$ are independently halogen. In embodiments, $R^{3.2}$ and $R^{3.3}$ are independently chlorine. In embodiments, $R^{3.2}$ and $R^{3.3}$ are independently fluorine. In embodiments, $R^{3.2}$ and $R^{3.3}$ are independently bromine.

In embodiments, $R^{3.2}$ is hydrogen, halogen, —$CX^{3.2}_3$, —$CHX^{3.2}_2$, —$CH_2X^{3.2}$, —CN, —$N_3$, —$SO_{n3.2}R^{3.2A}$, —$SO_{v3.2}NR^{3.2B}R^{3.2C}$, —NHNR$^{3.2B}R^{3.2C}$, —ONR$^{3.2B}R^{3.2C}$, —NHC(O)NHNR$^{3.2B}R^{3.2C}$, —NHC(O)NR$^{3.2B}R^{3.2C}$, —N(O)$_{m3.2}$, —NR$^{3.2B}R^{3.2C}$, —C(O)R$^{3.2D}$, —C(O)OR$^{3.2D}$, —C(O)NR$^{3.2B}R^{3.2C}$, —OR$^{3.2A}$, —NR$^{3.2B}SO_2R^{3.2A}$, —NR$^{3.2B}C(O)R^{3.2D}$, —NR$^{3.2B}C(O)$OR$^{3.2D}$, —NR$^{3.2B}$OR$^{3.2D}$, —OCX$^{3.2}_3$, —OCHX$^{3.2}_2$, —OCH$_2X^{3.2}$, $R^{17.2}$-substituted or unsubstituted alkyl (e.g., $C_1$-$C_8$ alkyl, $C_1$-$C_6$ alkyl, or $C_1$-$C_4$ alkyl), $R^{17.2}$-substituted or unsubstituted heteroalkyl (e.g., 2 to 8 membered heteroalkyl, 2 to 6 membered heteroalkyl, or 2 to 4 membered heteroalkyl), $R^{17.2}$-substituted or unsubstituted cycloalkyl (e.g., $C_3$-$C_8$ cycloalkyl, $C_3$-$C_6$ cycloalkyl, or C—$C_6$ cycloalkyl), $R^{17.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.2}$-substituted or unsubstituted aryl (e.g., $C_6$-$C_{10}$ aryl, $C_{10}$ aryl, or phenyl), or $R^{17.2}$-substituted or unsubstituted heteroaryl (e.g., 5 to 10 membered heteroaryl, 5 to 9 membered heteroaryl, or 5 to 6 membered heteroaryl).

In embodiments, $R^{3.2}$ is $R^{17.2}$-substituted or unsubstituted alkyl (e.g., $C_1$-$C_8$ alkyl, $C_1$-$C_6$ alkyl, or $C_1$-$C_4$ alkyl). In embodiments, $R^{3.2}$ is $R^{17.2}$-substituted alkyl (e.g., $C_1$-$C_8$ alkyl, $C_1$-$C_6$ alkyl, or $C_1$-$C_4$ alkyl). In embodiments, $R^{3.2}$ is an unsubstituted alkyl (e.g., $C_1$-$C_8$ alkyl, $C_1$-$C_6$ alkyl, or $C_1$-$C_4$ alkyl).

In embodiments, $R^{3.2}$ is $R^{17.2}$-substituted or unsubstituted heteroalkyl (e.g., 2 to 8 membered heteroalkyl, 2 to 6 membered heteroalkyl, or 2 to 4 membered heteroalkyl). In embodiments, $R^{3.2}$ is $R^{17.2}$-substituted heteroalkyl (e.g., 2 to 8 membered heteroalkyl, 2 to 6 membered heteroalkyl, or 2 to 4 membered heteroalkyl). In embodiments, $R^{3.2}$ is an unsubstituted heteroalkyl (e.g., 2 to 8 membered heteroalkyl, 2 to 6 membered heteroalkyl, or 2 to 4 membered heteroalkyl).

In embodiments, $R^{3.2}$ is $R^{17.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3.2}$ is $R^{17.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3.2}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{3.2}$ is $R^{17.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.2}$ is $R^{17.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{3.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{3.2}$ is $R^{17.2}$-substituted or unsubstituted aryl (e.g., $C_6$-$C_{10}$ aryl, $C_{10}$ aryl, or phenyl). In embodiments, $R^{3.2}$ is $R^{17.2}$-substituted aryl (e.g., $C_6$-$C_{10}$ aryl, $C_{10}$ aryl, or phenyl). In embodiments, $R^{3.2}$ is an unsubstituted aryl (e.g., $C_6$-$C_{10}$ aryl, $C_{10}$ aryl, or phenyl).

In embodiments, $R^{3.2}$ is $R^{17.2}$-substituted or unsubstituted heteroaryl (e.g., 5 to 10 membered heteroaryl, 5 to 9 membered heteroaryl, or 5 to 6 membered heteroaryl). In embodiments, $R^{3.2}$ is $R^{17.2}$-substituted heteroaryl (e.g., 5 to 10 membered heteroaryl, 5 to 9 membered heteroaryl, or 5 to 6 membered heteroaryl). In embodiments, $R^{3.2}$ is an unsubstituted heteroaryl (e.g., 5 to 10 membered heteroaryl, 5 to 9 membered heteroaryl, or 5 to 6 membered heteroaryl).

In embodiments, $R^{3.2}$ is independently halogen, —$CF_3$, —$CHF_2$, —$CH_2F$, —CN, —$N_3$, —$SO_2R^{3.2A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. It is understood that when z3 is 0, $R^{3.2}$ is hydrogen. In embodiments, $R^{3.2}$ is independently —Cl. In embodiments, $R^{3.2}$ is independently —F. In embodiments, $R^{3.2}$ is independently —Br. In embodiments, $R^{3.2}$ is independently —I. In embodiments, $R^{3.2}$ is independently —$SO_2CH_3$. In embodiments, $R^{3.2}$ is independently —$SO_2CH_2CH_3$. In embodiments, $R^{3.2}$ is independently —$SO_2Cl$.

In embodiments, $R^{3.3}$ is, halogen, —$CX^{3.3}_3$, —$CHX^{3.3}_2$, —$CH_2X^{3.3}$, —CN, —$N_3$, —$SO_{n3.3}R^{3.3A}$, —$SO_{v3.3}NR^{3.3B}R^{3.3C}$, —N—$NR^{3.3B}R^{3.3C}$, —$ONR^{3.3B}R^{3.3C}$, —NHC(O)NHNR$^{3.3B}R^{3.3C}$, —NHC(O)NR$^{3.3B}R^{3.3C}$, —N(O)$_{m3.3}$, —$NR^{3.3B}R^{3.3C}$, —C(O)$R^{3.3D}$, —C(O)O$R^{3.3D}$, —C(O)NR$^{3.3B}R^{3.3C}$, —OR$^{3.3A}$, —$NR^{3.3B}SO_2R^{3.3A}$, —NR$^{3.3B}$C(O)R$^{3.3D}$, —NR$^{3.3B}$C(O)OR$^{3.3D}$, —NR$^{3.3B}$OR$^{3.3D}$, —OCX$^{3.3}_3$, —OCHX$^{3.3}_2$, —OCH$_2$X$^{3.3}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^{3.3}$ is halogen. In embodiments, $R^{3.3}$ is hydrogen. In embodiments, $R^{3.3}$ is halogen. In embodiments, $R^{3.3}$ is chlorine.

In embodiments, $R^{3.3}$ is hydrogen, halogen, —$CX^{3.3}_3$, —CHX$^{3.3}_2$, —CH$_2$X$^{3.3}$, —CN, —$N_3$, —SO$_{n3.3}$R$^{3.3A}$, —SO$_{v3.3}$NR$^{3.3B}$R$^{3.3C}$, —NHNR$^{3.3B}$R$^{3.3C}$, —ONR$^{3.3B}$R$^{3.3C}$, —NHC(O)NHNR$^{3.3B}$R$^{3.3C}$, —NHC(O)NR$^{3.3B}$R$^{3.3C}$, —N(O)$_{m3.3}$, —NR$^{3.3B}$R$^{3.3C}$, —C(O)R$^{3.3D}$, —C(O)OR$^{3.3D}$, —C(O)NR$^{3.3B}$R$^{3.3C}$, —OR$^{3.3A}$, —NR$^{3.3B}$SO$_2$R$^{3.3A}$, —NR$^{3.3B}$C(O)R$^{3.3D}$, —NR$^{3.3B}$C(O)OR$^{3.3D}$, —NR$^{3.3B}$OR$^{3.3D}$, —OCX$^{3.3}_3$, —OCHX$^{3.3}_2$, —OCH$_2$X$^{3.3}$, $R^{17.3}$-substituted or unsubstituted alkyl (e.g., $C_1$-$C_8$ alkyl, $C_1$-$C_6$ alkyl, or $C_1$-$C_4$ alkyl), $R^{17.3}$-substituted or unsubstituted heteroalkyl (e.g., 2 to 8 membered heteroalkyl, 2 to 6 membered heteroalkyl, or 2 to 4 membered heteroalkyl), $R^{17.3}$-substituted or unsubstituted cycloalkyl (e.g., $C_3$-$C_8$ cycloalkyl, $C_3$-$C_6$ cycloalkyl, or C—$C_6$ cycloalkyl), $R^{17.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.3}$-substituted or unsubstituted aryl (e.g., $C_6$-$C_{10}$ aryl, $C_{10}$ aryl, or phenyl), or $R^{17.3}$-substituted or unsubstituted heteroaryl (e.g., 5 to 10 membered heteroaryl, 5 to 9 membered heteroaryl, or 5 to 6 membered heteroaryl).

In embodiments, $R^{3.3}$ is $R^{17.3}$-substituted or unsubstituted alkyl (e.g., $C_1$-$C_8$ alkyl, $C_1$-$C_6$ alkyl, or $C_1$-$C_4$ alkyl). In embodiments, $R^{3.3}$ is $R^{17.3}$-substituted alkyl (e.g., $C_1$-$C_8$ alkyl, C—$C_6$ alkyl, or $C_1$-$C_4$ alkyl). In embodiments, $R^{3.3}$ is an unsubstituted alkyl (e.g., $C_1$-$C_8$ alkyl, C—$C_6$ alkyl, or $C_1$-$C_4$ alkyl).

In embodiments, $R^{3.3}$ is $R^{17.3}$-substituted or unsubstituted heteroalkyl (e.g., 2 to 8 membered heteroalkyl, 2 to 6 membered heteroalkyl, or 2 to 4 membered heteroalkyl). In embodiments, $R^{3.3}$ is $R^{17.3}$-substituted heteroalkyl (e.g., 2 to 8 membered heteroalkyl, 2 to 6 membered heteroalkyl, or 2 to 4 membered heteroalkyl). In embodiments, $R^{3.3}$ is an unsubstituted heteroalkyl (e.g., 2 to 8 membered heteroalkyl, 2 to 6 membered heteroalkyl, or 2 to 4 membered heteroalkyl).

In embodiments, $R^{3.3}$ is $R^{17.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{3.3}$ is $R^{17.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3.3}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{3.3}$ is $R^{17.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{3.3}$ is $R^{17.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{3.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{3.3}$ is $R^{17.3}$-substituted or unsubstituted aryl (e.g., $C_6$-$C_{10}$ aryl, $C_{10}$ aryl, or phenyl). In embodiments, $R^{3.3}$ is $R^{17.3}$-substituted aryl (e.g., $C_6$-$C_{10}$ aryl, $C_{10}$ aryl, or phenyl). In embodiments, $R^{3.3}$ is an unsubstituted aryl (e.g., $C_6$-$C_{10}$ aryl, $C_{10}$ aryl, or phenyl).

In embodiments, $R^{3.3}$ is $R^{17.3}$-substituted or unsubstituted heteroaryl (e.g., 5 to 10 membered heteroaryl, 5 to 9 membered heteroaryl, or 5 to 6 membered heteroaryl). In embodiments, $R^{3.3}$ is $R^{17.3}$-substituted heteroaryl (e.g., 5 to 10 membered heteroaryl, 5 to 9 membered heteroaryl, or 5 to 6 membered heteroaryl). In embodiments, $R^{3.3}$ is an unsubstituted heteroaryl (e.g., 5 to 10 membered heteroaryl, 5 to 9 membered heteroaryl, or 5 to 6 membered heteroaryl).

In embodiments, $R^{3.3}$ is independently halogen, —$CF_3$, —$CHF_2$, —$CH_2F$, —CN, —$N_3$, —$SO_2R^{3.3A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. It is understood that when z3 is 0, $R^{3.3}$ is hydrogen. In embodiments, $R^{3.3}$ is independently —Cl. In embodiments, $R^{3.3}$ is independently —F. In embodiments, $R^{3.3}$ is independently —Br. In embodiments, $R^{3.3}$ is independently —I. In embodiments, $R^{3.3}$ is independently —$SO_2CH_3$. In embodiments, $R^{3.3}$ is independently —$SO_2CH_2CH_3$. In embodiments, $R^{3.3}$ is independently —$SO_2Cl$.

In embodiments, $R^4$ is halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —N—$NR^{4B}R^{4C}$, —$ONR^{4B}R^{4C}$, —NHC(O)NHNR$^{4B}R^{4C}$, —NHC(O)$NR^{4B}R^{4C}$, —$N(O)_{m4}$, —$NR^{4B}R^{4C}$, —C(O)$R^{4D}$, —C(O)$OR^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, —$OCH_2X^{4.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^4$ is hydrogen.

In embodiments, $R^4$ is halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —$NHNR^{4B}R^{4C}$, —$ONR^{4B}R^{4C}$, —NHC(O)NHNR$^{4B}R^{4C}$, —NHC(O)$NR^{4B}R^{4C}$, —$N(O)_{m4}$, —$NR^{4B}R^{4C}$, —C(O)$R^{4D}$, —C(O)$OR^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, —$OCH_2X^{4.1}$, $R^{20}$-substituted or unsubstituted alkyl (e.g., $C_1$-$C_8$ alkyl, $C_1$-$C_6$ alkyl, or $C_1$-$C_4$ alkyl), $R^{20}$-substituted or unsubstituted heteroalkyl (e.g., 2 to 8 membered heteroalkyl, 2 to 6 membered heteroalkyl, or 2 to 4 membered heteroalkyl), $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl). In embodiments, $R^4$ is —CN. In embodiments, $R^4$ is —C(O)$NH_2$. In embodiments, $R^4$ is —$CF_3$. In embodiments, $R^4$ is —$CH_3$.

In embodiments, $R^4$ is $R^{20}$-substituted or unsubstituted alkyl (e.g., $C_1$-$C_8$ alkyl, $C_1$-$C_6$ alkyl, or $C_1$-$C_4$ alkyl). In embodiments, $R^4$ is $R^{20}$-substituted alkyl (e.g., $C_1$-$C_8$ alkyl, $C_1$-$C_6$ alkyl, or $C_1$-$C_4$ alkyl). In embodiments, $R^4$ is an unsubstituted alkyl (e.g., $C_1$-$C_8$ alkyl, $C_1$-$C_6$ alkyl, or $C_1$-$C_4$ alkyl). In embodiments, $R^4$ is an unsubstituted ethyl. In embodiments, $R^4$ is an unsubstituted $C_3$ alkyl. In embodiments, $R^4$ is an unsubstituted $C_4$ alkyl.

In embodiments, $R^4$ is $R^{20}$-substituted or unsubstituted heteroalkyl (e.g., 2 to 8 membered heteroalkyl, 2 to 6 membered heteroalkyl, or 2 to 4 membered heteroalkyl). In embodiments, $R^4$ is $R^{20}$-substituted heteroalkyl (e.g., 2 to 8 membered heteroalkyl, 2 to 6 membered heteroalkyl, or 2 to 4 membered heteroalkyl). In embodiments, $R^4$ is an unsubstituted heteroalkyl (e.g., 2 to 8 membered heteroalkyl, 2 to 6 membered heteroalkyl, or 2 to 4 membered heteroalkyl).

In embodiments, $R^4$ is $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ is $R^{20}$-substituted cycloalkyl (e.g., $C_3$-$C_8$ cycloalkyl, $C_3$-$C_6$ cycloalkyl, or $C_5$-$C_6$ cycloalkyl). In embodiments, $R^4$ is an unsubstituted cycloalkyl (e.g., $C_3$-$C_8$ cycloalkyl, $C_3$-$C_6$ cycloalkyl, or C—$C_6$ cycloalkyl).

In embodiments, $R^4$ is $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ is $R^{20}$-substituted heterocycloalkyl (e.g., 3 to 8 membered heterocycloalkyl, 3 to 6 membered heterocycloalkyl, or 5 to 6 membered heterocycloalkyl). In embodiments, $R^4$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^4$ is $R^{20}$-substituted or unsubstituted aryl (e.g., $C_6$-$C_{10}$ aryl, $C_{10}$ aryl, or phenyl). In embodiments, $R^4$ is $R^{20}$-substituted aryl (e.g., $C_6$-$C_{10}$ aryl, $C_{10}$ aryl, or phenyl). In embodiments, $R^4$ is an unsubstituted aryl (e.g., $C_6$-$C_{10}$ aryl, $C_{10}$ aryl, or phenyl).

In embodiments, $R^4$ is $R^{20}$-substituted or unsubstituted heteroaryl (e.g., 5 to 10 membered heteroaryl, 5 to 9 membered heteroaryl, or 5 to 6 membered heteroaryl). In embodiments, $R^4$ is $R^{20}$-substituted heteroaryl (e.g., 5 to 10 membered heteroaryl, 5 to 9 membered heteroaryl, or 5 to 6 membered heteroaryl). In embodiments, $R^4$ is an unsubstituted heteroaryl (e.g., 5 to 10 membered heteroaryl, 5 to 9 membered heteroaryl, or 5 to 6 membered heteroaryl).

In embodiments, $R^4$ is hydrogen, —CN, halogen, —$CF_3$, —COOH, —$COOCH_2CH_3$,

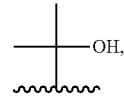

—$CH_3$. In embodiments, $R^4$ is hydrogen. In embodiments, $R^4$ is —CN. In embodiments, $R^4$ is halogen. In embodiments, $R^4$ is —F. In embodiments, $R^4$ is —Cl. In embodiments, $R^4$ is —Br. In embodiments, $R^4$ is —I. In embodiments, $R^4$ is —$CF_3$. In embodiments, $R^4$ is —COOH. In embodiments, $R^4$ is —$COOCH_2CH_3$. In embodiments, $R^4$ is —$CH_3$. In embodiments, $R^4$ is —$CHCH_2CH_2OH$. In embodiments, $R^4$ is

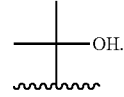

In embodiments, $R^4$ is substituted or unsubstituted $C_1$-$C_4$ alkyl. In embodiments, $R^4$ is substituted $C_1$-$C_4$ alkyl. In embodiments, $R^4$ is unsubstituted $C_1$-$C_4$ alkyl.

In embodiments, $R^4$ is halogen, —$CF_3$, —$CHF_2$, —$CH_2F$, —CN, —$N_3$, —$SO_2CH_3$, —C(O)$R^{4D}$, —C(O)$OR^{4D}$, substituted or unsubstituted alkyl, substituted or unsubstituted heteroalkyl. In embodiments, $R^4$ is halogen, —$CF_3$, —$CHF_2$, —$CH_2F$, —CN, —$N_3$, —$SO_2CH_3$, —C(O)$R^{4D}$, —C(O)$OR^{4D}$, substituted or unsubstituted alkyl, substituted or unsubstituted heteroalkyl.

In embodiments, $R^4$ is $R^{20}$-substituted or unsubstituted alkyl (e.g., $C_1$-$C_8$ alkyl, $C_1$-$C_6$ alkyl, or $C_1$-$C_4$ alkyl). In embodiments, $R^4$ is $R^{20}$-substituted alkyl (e.g., $C_1$-$C_8$ alkyl, $C_1$-$C_6$ alkyl, or $C_1$-$C_4$ alkyl). In embodiments, $R^4$ is an unsubstituted alkyl (e.g., $C_1$-$C_8$ alkyl, $C_1$-$C_6$ alkyl, or $C_1$-$C_4$ alkyl).

In embodiments, $R^4$ is $R^{20}$-substituted or unsubstituted methyl. In embodiments, $R^4$ is $R^{20}$-substituted or unsubstituted $C_2$ alkyl. In embodiments, $R^4$ is $R^{20}$-substituted or unsubstituted $C_3$ alkyl. In embodiments, $R^4$ is $R^{20}$-substituted or unsubstituted $C_4$ alkyl. In embodiments, $R^4$ is $R^{20}$-substituted or unsubstituted CS alkyl. In embodiments, $R^4$ is $R^{20}$-substituted or unsubstituted $C_6$ alkyl. In embodiments, $R^4$ is $R^{20}$-substituted or unsubstituted $C_7$ alkyl. In embodiments, $R^4$ is $R^{20}$-substituted or unsubstituted $C_8$ alkyl. In embodiments, $R^4$ is $R^{20}$-substituted methyl. In embodiments, $R^4$ is $R^{20}$-substituted $C_2$ alkyl. In embodiments, $R^4$ is $R^{20}$-substituted $C_3$ alkyl. In embodiments, $R^4$ is $R^{20}$-substituted $C_4$ alkyl. In embodiments, $R^4$ is $R^{20}$-substituted $C_5$ alkyl. In embodiments, $R^4$ is $R^{20}$-substituted $C_6$ alkyl. In embodiments, $R^4$ is $R^{20}$-substituted $C_7$ alkyl. In embodiments, $R^4$ is $R^{20}$-substituted $C_8$ alkyl. In embodiments, $R^4$ is an unsubstituted methyl. In embodiments, $R^4$ is an unsubstituted $C_2$ alkyl. In embodiments, $R^4$ is an unsubstituted $C_3$ alkyl. In embodiments, $R^4$ is an unsubstituted $C_4$ alkyl. In embodiments, $R^4$ is an unsubstituted CS alkyl. In embodiments, $R^4$ is an unsubstituted $C_6$ alkyl. In embodiments, $R^4$ is an unsubstituted $C_7$ alkyl. In embodiments, $R^4$ is an unsubstituted $C_8$ alkyl.

In embodiments, $R^4$ is hydrogen, —$CX^{4.1}_3$, —CN, —C(O)$NR^{4B}R^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^4$ is hydrogen, halogen, —$CX^{4.1}_3$, —$CHX^{4.1}_2$, —$CH_2X^{4.1}$, —CN, —$NR^{4B}R^{4C}$, —C(O)$R^{4D}$, —C(O)$OR^{4D}$, —C(O)$NR^{4B}R^{4C}$, —$OR^{4A}$, —$NR^{4B}$C(O)$R^{4D}$, —$NR^{4B}$C(O)$OR^{4D}$, —$OCX^{4.1}_3$, —$OCHX^{4.1}_2$, —$OCH_2X^{4.1}$, substituted or unsubstituted alkyl, or substituted or unsubstituted heteroalkyl. In embodiments, $R^4$ is hydrogen, halogen, —$CX^{4.1}_3$, —$CHX^{4.1}_2$, —$CH_2X^{4.1}$, —CN, —C(O)$OR^{4D}$, —C(O)$NR^{4B}R^{4C}$, substituted or unsubstituted $C_1$-$C_4$ alkyl, or substituted or unsubstituted 2 to 4 membered heteroalkyl. In embodiments, $R^4$ is —Cl, —Br, —F, —CN, —COOH, —C(O)$OCH_2CH_3$, —C($CH_3$)$_2$OH, —C(O)$NH_2$, —$CF_3$ or —$CH_3$. In embodiments, $R^4$ is hydrogen. In embodiments, $R^4$ is halogen. In embodiments, $R^4$ is —$CX^{4.1}_3$. In embodiments, $R^4$ is —$CHX^{4.1}_2$. In embodiments, $R^4$ is —$CH_2X^{4.1}$. In embodiments, $R^4$ is —CN. In embodiments, $R^4$ is —$NR^{4B}R^{4C}$. In embodiments, $R^4$ is —C(O)$R^{4D}$. In embodiments, $R^4$ is —C(O)$OR^{4D}$. In embodiments, $R^4$ is —C(O)$NR^{4B}R^{4C}$. In embodiments, $R^4$ is —$OR^{4A}$. In embodiments, $R^4$ is —$NR^{4B}$C(O)$R^{4D}$. In embodiments, $R^4$ is —$NR^{4B}$C(O)$OR^{4D}$. In embodiments, $R^4$ is —$OCX^{4.1}_3$. In embodiments, $R^4$ is —$OCHX^{4.1}_2$. In embodiments, $R^4$ is —$OCH_2X^{4.1}$. In embodiments, $R^4$ is substituted or unsubstituted alkyl. In embodiments, $R^4$ is substituted or unsubstituted heteroalkyl. In embodiments, $R^4$ is —Cl. In embodiments, $R^4$ is —Br. In embodiments, $R^4$ is —F. In embodiments, $R^4$ is —CN. In embodiments, $R^4$ is —COOH. In embodiments, $R^4$ is —C(O)$OCH_2CH_3$. In embodiments, $R^4$ is —C($CH_3$)$_2$OH. In embodiments, $R^4$ is —C(O)$NH_2$. In embodiments, $R^4$ is —$CF_3$. In embodiments, $R^4$ is —$CH_3$.

In embodiments, $R^5$ is independently halogen, oxo, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)RD, —C(O)$OR^{5D}$, —C(O)$NR^{5B}R^{5C}$, —$OR^{5A}$, —$NR^{5B}SO_2R^{5A}$, —$NR^{5B}$C(O)$R^{5D}$, —$NR^{5B}$C(O)$OR^{5D}$, —$NR^{5B}OR^{5D}$, —$OCX^{5.1}_3$, —$OCHX^{5.1}_2$, —$OCH_2X^{5.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^5$ is independently halogen, —$CX^{5.1}_3$, —$CHX^{5.1}_2$, —$CH_2X^{5.1}$, —CN, —$N_3$, —$SO_{n5}R^{5A}$, —$SO_{v5}NR^{5B}R^{5C}$, —$NHNR^{5B}R^{5C}$, —$ONR^{5B}R^{5C}$, —NHC(O)$NHNR^{5B}R^{5C}$, —NHC(O)$NR^{5B}R^{5C}$, —N(O)$_{m5}$, —$NR^{5B}R^{5C}$, —C(O)RD, —C(O)$OR^{5D}$, —C(O)$NR^{5B}R^{5C}$, —$OR^{5A}$, —$NR^{5B}SO_2R^{5A}$, —$NR^{5B}$C(O)$R^{5D}$, —$NR^{5B}$C(O)$OR^{5D}$, —$NR^{5B}OR^{5D}$, —$OCX^{5.1}_3$, —$OCHX^{5.1}_2$, —$OCH_2X^{5.1}$, $R^{23}$-substituted or unsubstituted alkyl (e.g., $C_1$-$C_8$ alkyl, $C_1$-$C_6$ alkyl, or $C_1$-$C_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., $C_6$-$C_{10}$ aryl, $C_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl).

In embodiments, $R^5$ is independently $R^{23}$-substituted or unsubstituted alkyl (e.g., $C_1$-$C_8$ alkyl, $C_1$-$C_6$ alkyl, or $C_1$-$C_4$ alkyl). In embodiments, $R^5$ is independently $R^{23}$-substituted alkyl (e.g., $C_1$-$C_8$ alkyl, $C_1$-$C_6$ alkyl, or $C_1$-$C_4$ alkyl). In embodiments, $R^5$ is independently an unsubstituted alkyl (e.g., $C_1$-$C_8$ alkyl, $C_1$-$C_6$ alkyl, or $C_1$-$C_4$ alkyl).

In embodiments, $R^5$ is independently $R^{23}$-substituted or unsubstituted heteroalkyl (e.g., 2 to 8 membered heteroalkyl, 2 to 6 membered heteroalkyl, or 2 to 4 membered heteroalkyl). In embodiments, $R^5$ is independently $R^{23}$-substituted heteroalkyl (e.g., 2 to 8 membered heteroalkyl, 2 to 6 membered heteroalkyl, or 2 to 4 membered heteroalkyl). In embodiments, $R^5$ is independently an unsubstituted heteroalkyl (e.g., 2 to 8 membered heteroalkyl, 2 to 6 membered heteroalkyl, or 2 to 4 membered heteroalkyl).

In embodiments, $R^5$ is independently $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^5$ is independently $R^{23}$-substituted cycloalkyl (e.g., $C_3$-$C_8$ cycloalkyl, $C_3$-$C_6$ cycloalkyl, or $C_5$-$C_6$ cycloalkyl). In embodiments, $R^5$ is independently an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^5$ is independently $R^{23}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is independently $R^{23}$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is independently an unsubstituted heterocycloalkyl (e.g., 3 to 8 membered heterocycloalkyl, 3 to 6 membered heterocycloalkyl, or 5 to 6 membered heterocycloalkyl).

In embodiments, $R^5$ is independently $R^{23}$-substituted or unsubstituted aryl (e.g., $C_6$-$C_{10}$ aryl, $C_{10}$ aryl, or phenyl). In embodiments, $R^5$ is independently $R^{23}$-substituted aryl (e.g., $C_6$-$C_{10}$ aryl, $C_{10}$ aryl, or phenyl). In embodiments, $R^5$ is independently an unsubstituted aryl (e.g., $C_6$-$C_{10}$ aryl, $C_{10}$ aryl, or phenyl).

In embodiments, $R^5$ is independently $R^{23}$-substituted or unsubstituted heteroaryl (e.g., 5 to 10 membered heteroaryl, 5 to 9 membered heteroaryl, or 5 to 6 membered heteroaryl). In embodiments, $R^5$ is independently $R^{23}$-substituted heteroaryl (e.g., 5 to 10 membered heteroaryl, 5 to 9 membered heteroaryl, or 5 to 6 membered heteroaryl). In embodiments, $R^5$ is independently an unsubstituted heteroaryl (e.g., 5 to 10 membered heteroaryl, 5 to 9 membered heteroaryl, or 5 to 6 membered heteroaryl).

In embodiments, $R^6$ is independently halogen, oxo, —$CX^{6.1}_3$, —$CHX^{6.1}_2$, —$CH_2X^{6.1}$, —CN, —$N_3$, —$SO_{n6}R^{6A}$, —$SO_{v6}NR^{6B}R^{6C}$, —N—$R^{6B}R^{6C}$, —$ONR^{6B}R^{6C}$, —NHC(O)$NHNR^{6B}R^{6C}$, —NHC(O)$NR^{6B}R^{6C}$, —N(O)$_{m6}$, —$NR^{6B}R^{6C}$, —C(O)$R^{6D}$, —C(O)$OR^{6D}$, —C(O)$NR^{6B}R^{6C}$, —$OR^{6A}$, —$NR^{6B}SO_2R^{6A}$, —$NR^{6B}$C(O)$R^{6D}$, —$NR^{6B}$C(O)$OR^{6D}$, —$NR^{6B}OR^{6D}$, —$OCX^{6.1}_3$, —$OCHX^{6.1}_2$, —$OCH_2X^{6.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments $R^6$ is —COOH.

In embodiments, $R^6$ is independently halogen, —$CX^{6.1}_3$, —$CHX^{6.1}_2$, —$CH_2X^{6.1}$, —CN, —$N_3$, —$SO_{n6}R^{6A}$, —$SO_{v6}NR^{6B}R^{6C}$, —$NHNR^{6B}R^{6C}$, —$ONR^{6B}R^{6C}$, —NHC(O)NHNR$^{6B}$R$^{6C}$, —NHC(O)NR$^{6B}$R$^{6C}$, —N(O)$_{m6}$, —NR$^{6B}$R$^{6C}$, —C(O)R$^{6D}$, —C(O)OR$^{6D}$, —C(O)NR$^{6B}$R$^{6C}$, —OR$^{6A}$, —NR$^{6B}$SO$_2$R$^{6A}$, —NR$^{6B}$C(O)R$^{6D}$, —NR$^{6B}$C(O)OR$^{6D}$, —NR$^{6B}$OR$^{6D}$, —OCX$^{6.1}_3$, —OCHX$^{6.1}_2$, —OCH$_2$X$^{6.1}$, R$^{26}$-substituted or unsubstituted alkyl (e.g., $C_1$-$C_8$ alkyl, $C_1$-$C_6$ alkyl, or $C_1$-$C_4$ alkyl), R$^{26}$-substituted or unsubstituted heteroalkyl (e.g., 2 to 8 membered heteroalkyl, 2 to 6 membered heteroalkyl, or 2 to 4 membered heteroalkyl), R$^{26}$-substituted or unsubstituted cycloalkyl (e.g., $C_3$-$C_8$ cycloalkyl, $C_3$-$C_6$ cycloalkyl, or $C_5$-$C_6$ cycloalkyl), R$^{26}$-substituted or unsubstituted heterocycloalkyl (e.g., 3 to 8 membered heterocycloalkyl, 3 to 6 membered heterocycloalkyl, or 5 to 6 membered heterocycloalkyl), R$^{26}$-substituted or unsubstituted aryl (e.g., $C_6$-$C_{10}$ aryl, $C_{10}$ aryl, or phenyl), or R$^{26}$-substituted or unsubstituted heteroaryl (e.g., 5 to 10 membered heteroaryl, 5 to 9 membered heteroaryl, or 5 to 6 membered heteroaryl).

In embodiments, $R^6$ is R$^{26}$-substituted or unsubstituted alkyl. In embodiments, $R^6$ is unsubstituted phenyl. In embodiments, $R^6$ is —F. In embodiments, $R^6$ is —OH. In embodiments, $R^6$ is —$CH_2OH$. In embodiments, $R^6$ is —$(CH_2)_2OH$. In embodiments, $R^6$ is —$(CH_2)_3OH$. In embodiments, $R^6$ is —$C(CH_3)_2OH$. In embodiments, $R^6$ is —$CH_2SO_2NH_2$. In embodiments, $R^6$ is —$(CH_2)_2SO_2NH_2$. In embodiments, $R^6$ is —$CH_2C(O)NH_2$. In embodiments, $R^6$ is —$(CH_2)_2C(O)NH_2$. In embodiments, $R^6$ is —$(CH_2)_3C(O)NH_2$. In embodiments, $R^6$ is —$CH_2NHSO_2CF_3$. In embodiments, $R^6$ is —$(CH_2)_2NHSO_2CF_3$. In embodiments, $R^6$ is —$(CH_2)_3NHSO_2CF_3$. In embodiments, $R^6$ is —$CH_2NHSO_2CH_3$. In embodiments, $R^6$ is —$(CH_2)_2NHSO_2CH_3$. In embodiments, $R^6$ is —$(CH_2)_3NHSO_2CH_3$. In embodiments, $R^6$ is —$CH_2SO_2CH_3$. In embodiments, $R^6$ is —$(CH_2)_2SO_2CH_3$. In embodiments, $R^6$ is —$CH_2SO_2NH_2$. In embodiments, $R^6$ is —$(CH_2)_2SO_2NH_2$.

In embodiments, $R^6$ is independently R$^{26}$-substituted or unsubstituted alkyl (e.g., $C_1$-$C_8$ alkyl, $C_1$-$C_6$ alkyl, or $C_1$-$C_4$ alkyl). In embodiments, $R^6$ is independently R$^{26}$-substituted alkyl (e.g., $C_1$-$C_8$ alkyl, $C_1$-$C_6$ alkyl, or $C_1$-$C_4$ alkyl). In embodiments, $R^6$ is independently an unsubstituted alkyl (e.g., $C_1$-$C_8$ alkyl, $C_1$-$C_6$ alkyl, or $C_1$-$C_4$ alkyl).

In embodiments, $R^6$ is independently R$^{26}$-substituted or unsubstituted heteroalkyl (e.g., 2 to 8 membered heteroalkyl, 2 to 6 membered heteroalkyl, or 2 to 4 membered heteroalkyl). In embodiments, $R^6$ is independently R$^{26}$-substituted heteroalkyl (e.g., 2 to 8 membered heteroalkyl, 2 to 6 membered heteroalkyl, or 2 to 4 membered heteroalkyl). In embodiments, $R^6$ is independently an unsubstituted heteroalkyl (e.g., 2 to 8 membered heteroalkyl, 2 to 6 membered heteroalkyl, or 2 to 4 membered heteroalkyl).

In embodiments, $R^6$ is independently R$^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently R$^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^6$ is independently an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^6$ is independently R$^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^6$ is independently R$^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^6$ is independently an unsubstituted heterocycloalkyl (e.g., 3 to 8 membered heterocycloalkyl, 3 to 6 membered heterocycloalkyl, or 5 to 6 membered heterocycloalkyl).

In embodiments, $R^6$ is independently R$^{26}$-substituted or unsubstituted aryl (e.g., $C_6$-$C_{10}$ aryl, $C_{10}$ aryl, or phenyl). In embodiments, $R^6$ is independently R$^{26}$-substituted aryl (e.g., $C_6$-$C_{10}$ aryl, $C_{10}$ aryl, or phenyl). In embodiments, $R^6$ is independently an unsubstituted aryl (e.g., $C_6$-$C_{10}$ aryl, $C_{10}$ aryl, or phenyl).

In embodiments, $R^6$ is independently R$^{26}$-substituted or unsubstituted heteroaryl (e.g., 5 to 10 membered heteroaryl, 5 to 9 membered heteroaryl, or 5 to 6 membered heteroaryl). In embodiments, $R^6$ is independently R$^{26}$-substituted heteroaryl (e.g., 5 to 10 membered heteroaryl, 5 to 9 membered heteroaryl, or 5 to 6 membered heteroaryl). In embodiments, $R^6$ is independently an unsubstituted heteroaryl (e.g., 5 to 10 membered heteroaryl, 5 to 9 membered heteroaryl, or 5 to 6 membered heteroaryl).

In embodiments, $R^7$ is halogen, —$CX^{7.1}_3$, —$CHX^{7.1}_2$, —$CH_2X^{7.1}$, —CN, —$N_3$, —$SO_{n7}R^{7A}$, —$SO_{v7}NR^{7B}R^{7C}$, —NR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7B}$C(O)R$^{7D}$, —NR$^{7B}$C(O)OR$^{7D}$, —NR$^{7B}$OR$^{7D}$, —OCX$^{7.1}_3$, —OCHX$^{7.1}_2$, —OCH$_2$X$^{7.1}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^7$ is halogen. In embodiments, $R^7$ is —$CX^{7.1}_3$. In embodiments, $R^7$ is —$CHX^{7.1}_2$. In embodiments, $R^7$ is —$CH_2X^{7.1}$. In embodiments, $R^7$ is —CN. In embodiments, $R^7$ is —$N_3$. In embodiments, $R^7$ is —$SO_{n7}R^{7A}$. In embodiments, $R^7$ is —$SO_{v7}NR^{7B}R^{7C}$. In embodiments, $R^7$ is —N—NR$^{7B}$R$^{7C}$. In embodiments, $R^7$ is —ONR$^{7B}$R$^{7C}$. In embodiments, $R^7$ is —NHC(O)NHNR$^{7B}$R$^{7C}$. In embodiments, $R^7$ is —NHC(O)NR$^{7B}$R$^{7C}$. In embodiments, $R^7$ is —N(O)$_{m7}$. In embodiments, $R^7$ is —NR$^{7B}$R$^{7C}$. In embodiments, $R^7$ is —C(O)R$^{7D}$. In embodiments, $R^7$ is —C(O)OR$^{7D}$. In embodiments, $R^7$ is —C(O)NR$^{7B}$R$^{7C}$. In embodiments, $R^7$ is —OR$^{7A}$. In embodiments, $R^7$ is —NR$^{7B}$SO$_2$R$^{7A}$. In embodiments, $R^7$ is —NR$^{7B}$C(O)R$^{7D}$. In embodiments, $R^7$ is —NR$^{B}$C(O)OR$^{7D}$. In embodiments, $R^7$ is —NR$^{7B}$OR$^{7D}$. In embodiments, $R^7$ is —OCX$^{7.1}_3$. In embodiments, $R^7$ is —OCHX$^{7.1}_2$. In embodiments, $R^7$ is —OCH$_2$X$^{7.1}$. In embodiments, $R^7$ is —$CF_3$. In embodiments, $R^7$ is —$CHF_2$. In embodiments, $R^7$ is —$CH_2F$. In embodiments, $R^7$ is —$SO_2CH_3$. In embodiments, $R^7$ is —$SO_2NH_2$. In embodiments, $R^7$ is —$NHNH_2$. In embodiments, $R^7$ is —$ONH_2$. In embodiments, $R^7$ is —$NHC(O)NHNH_2$. In embodiments, $R^7$ is —$NHC(O)NH_2$. In embodiments, $R^7$ is —$N(O)_2$. In embodiments, $R^7$ is —$NH_2$. In embodiments, $R^7$ is —C(O)OH. In embodiments, $R^7$ is —C(O)OCH$_3$. In embodiments, $R^7$ is —C(O)NH$_2$. In embodiments, $R^7$ is —OCH$_3$. In embodiments, $R^7$ is —NHSO$_2$CH$_3$. In embodiments, $R^7$ is —NHC(O)CH$_3$. In embodiments, $R^7$ is —NHC(O)OH. In embodiments, $R^7$ is —NHOH. In embodiments, $R^7$ is —OCF$_3$. In embodiments, $R^7$ is —OCHF$_2$. In embodiments, $R^7$ is —OCH$_2$F. In embodiments, $R^7$ is hydrogen. In embodiments, $R^7$ is —C(O)OH. In embodiments, $R^7$ is —OH. In embodiments, $R^7$ is —NH$_2$. In embodiments, $R^7$ is —C(O)NH$_2$.

In embodiments, $R^7$ is halogen, $-CX^{7.1}_3$, $-CHX^{7.1}_2$, $-CH_2X^{7.1}$, $-CN$, $-N_3$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}_3$, $-OCHX^{7.1}_2$, $-OCH_2X^{7.1}$, $R^{29}$-substituted or unsubstituted alkyl (e.g., $C_1$-$C_5$ alkyl, $C_1$-$C_6$ alkyl, or $C_1$-$C_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., $C_6$-$C_{10}$ aryl, $C_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl).

In embodiments, $R^7$ is $-(CH_2)_3COOH$. In embodiments, $R^7$ is $-(CH_2)_2COOH$. In embodiments, $R^7$ is $-(CH_2)COOH$. In embodiments, $R^7$ is $-(CH_2)_2CONH_2$. In embodiments, $R^7$ is $-(CH_2)_3CONH_2$. In embodiments, $R^7$ is $-(CH_2)_{30}H$. In embodiments, $R^7$ is substituted cyclobutyl. In embodiments, $R^7$ is $-(CH_2)_2SO_2CH_3$. In embodiments, $R^7$ is $-CH_2CH(CH_3)OH$. In embodiments, $R^7$ is $-(CH_2)_2OH$. In embodiments, $R^7$ is $-(CH_2)_{40}H$. In embodiments, $R^7$ is $-(CH_2)OH$. In embodiments, $R^7$ is $-(CH_2)_2NHSO_2CH_3$. In embodiments, $R^7$ is $-(CH_2)_2NHSO_2CH_2CH_3$. In embodiments, $R^7$ is $-(CH_2)_2NHSO_2(CH_2)_2CH_3$. In embodiments, $R^7$ is $-(CH_2)_2NHSO_2CH(CH_3)_2$. In embodiments, $R^7$ is $-(CH_2)_2NHC(O)OCH_3$. In embodiments, $R^7$ is $-(CH_2)_3SO_2CH_3$. In embodiments, $R^7$ is $-(CH_2)_2NHC(O)CH_3$. In embodiments, $R^7$ is $-(CH_2)_2NHC(O)H$. In embodiments, $R^7$ is $-CH_2C(O)OCH_3$. In embodiments, $R^7$ is $-CH_2C(O)OCH_2CH_3$. In embodiments, $R^7$ is $-(CH_2)_3SO_2NH_2$. In embodiments, $R^7$ is $-(CH_2)_2SO_2NH_2$. In embodiments, $R^7$ is $-(CH_2)_3SO_2NH_2$. In embodiments, $R^7$ is $-(CH_2)_2NHC(O)CH_2CH_3$. In embodiments, $R^7$ is $-(CH_2)_2NHC(O)CH(CH_3)_2$.

In embodiments, $R^7$ is hydrogen. In embodiments, $R^7$ is $R^{29}$-substituted or unsubstituted alkyl. In embodiments, $R^7$ is substituted or unsubstituted phenyl. In embodiments, $R^7$ is $-(CH_2)_2OH$. In embodiments, $R^7$ is $-CH_2C(CH_3)_2OH$. In embodiments, $R^7$ is $-(CH_2)_{30}H$. In embodiments, $R^7$ is $-(CH_2)_2CH(CH_3)_2OH$. In embodiments, $R^7$ is $-(CH_2)_2SO_2NH_2$. In embodiments, $R^7$ is $-(CH_2)_3SO_2NH_2$. In embodiments, $R^7$ is $-(CH_2)_2CONH_2$. In embodiments, $R^7$ is $-(CH_2)_3CONH_2$. In embodiments, $R^7$ is $-(CH_2)_3CON(H)Me$. In embodiments, $R^7$ is $-(CH_2)_3CON(Me)_2$. In embodiments, $R^7$ is $-(CH_2)_2SO_2Me$. In embodiments, $R^7$ is $-(CH_2)_3SO_2Me$. In embodiments, $R^7$ is $-CH_2CH(OH)Me$. In embodiments, $R^7$ is $-CH_2CO_2H$. In embodiments, $R^7$ is $-(CH_2)_2CO_2H$. In embodiments, $R^7$ is $-CH(CH_3)CH_2CO_2H$. In embodiments, $R^7$ is $-(CH_2)_3CO_2H$. In embodiments, $R^7$ is $-(CH_2)_2SO_2NHCH_3$. In embodiments, $R^7$ is $-(CH_2)_2SO_2N(CH_3)_2$. In embodiments, $R^7$ is $-(CH_2)_2SO_2-(N-morpholinyl)$. In embodiments, $R^7$ is $-(CH_2)_2NHCOCH_3$. In embodiments, $R^7$ is $-(CH_2)_2NHC(O)OCH_3$. In embodiments, $R^7$ is $-(CH_2)_3NHCOCH_3$. In embodiments, $R^7$ is $-(CH_2)_2NHCOCH(CH_3)_2$. In embodiments, $R^7$ is $-(CH_2)_2NHSO_2CH_3$. In embodiments, $R^7$ is $-(CH_2)_2NHSO_2CF_3$. In embodiments, $R^7$ is $-(CH_2)_2NHSO_2NHCH(CH_3)_2$. In embodiments, $R^7$ is $-CH_2CH(CH_3)CH_2OH$ (R and S). In embodiments, $R^7$ is $-CH(CH_3)(CH_2)_2OH$. In embodiments, $R^7$ is $-CH_2-(2\text{-imidazoyl})$. In embodiments, $R^7$ is $-CH_2-(4\text{-imidazoyl})$. In embodiments, $R^7$ is $-CH_2-(3\text{-pyrazoyl})$. In embodiments, $R^7$ is 4-tetrahydropyranyl. In embodiments, $R^7$ is 3-oxetanyl. In embodiments, $R^7$ is $-(CH_2)_2NHCO_2Me$. In embodiments, $R^7$ is $-(CH_2)_3NHCO_2Me$.

In embodiments, $R^7$ is hydrogen. In embodiments, $R^7$ is $-OH$. In embodiments, $R^7$ is $-COOH$. In embodiments, $R^7$ is a substituted pyrrolidinyl (e.g., oxo-substituted pyrrolidinyl). In embodiments, $R^7$ is oxo. In embodiments, $R^7$ is $-SO_2NH_2$. In embodiments, $R^7$ is $-NH_2$. In embodiments, $R^7$ is $-CH_3$. In embodiments, $R^7$ is $-CH_2CH_3$. In embodiments, $R^7$ is $-NHCOCH_3$. In embodiments, $R^7$ is $-CONHCH_3$. In embodiments, $R^7$ is $-NHSO_2CH_3$. In embodiments, $R^7$ is $-NR^{7B}SO_2R^{7A}$. In embodiments, $R^7$ is $-NHSO_2CH_3$. In embodiments, $R^7$ is $-NHSO_2CH_2CH_3$. In embodiments, $R^7$ is $-NHSO_2(C_1\text{-}C_6\text{ alkyl})$. In embodiments, $R^7$ is $-COCH(CH_3)_2$.

In embodiments, $R^7$ is $-CH_2OH$.

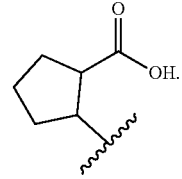 [SMILES: *C1CCCC1C(=O)O]

In embodiments, $R^7$ is

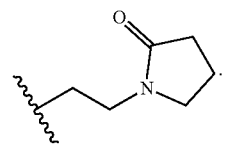 [SMILES: *CCN1CCCC1=O]

In embodiments, $R^7$ is

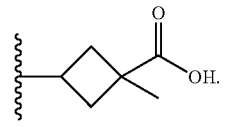 [SMILES: *C1CC(C)(C(=O)O)C1]

In embodiments, $R^7$ is

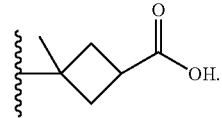 [SMILES: *C1(C)CC(C(=O)O)C1]

In embodiments, $R^7$ is

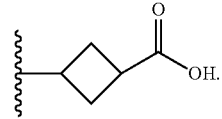 [SMILES: *C1CC(C(=O)O)C1]

In embodiments, $R^7$ is

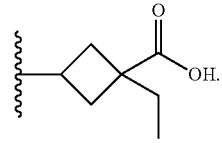 [SMILES: *C1CC(CC)(C(=O)O)C1]

In embodiments, R⁷ is hydrogen, substituted or unsubstituted alkyl, substituted or unsubstituted phenyl, —C(O)OH, —C(O)OCH₃, —C(O)OCH₂CH₃, —CH₂C(O)OH, —NHC(O)OH, —NHC(O)OCH₃, —NHC(O)OCH₂CH₃, —CH₂C(O)OH, —CH₂C(O)OCH₃, —CH₂C(O)OCH₂CH₃, —SO₂CH₃, —SO₂CH₂CH₃, —SO₂CH(CH₃)₂, —NHSO₂CH₃, —NHSO₂CH₂CH₃, —NHSO₂CH(CH₃)₂, —SO₂NH₂, —SO₂NHCH₃, —(CH₂)₂OH, —CH₂C(CH₃)₂OH, —(CH₂)₃OH, —(CH₂)₂CH(CH₃)₂OH, —(CH₂)₂SO₂NH₂, —(CH₂)₃SO₂NH₂, —(CH₂)₂CONH₂, —(CH₂)₃CONH₂ —(CH₂)₃CON(H)Me, —(CH₂)₃CON(Me)₂, —(CH₂)₂SO₂Me, —(CH₂)₃SO₂Me, —CH₂CH(OH)Me, —CH₂CO₂H, —(CH₂)₂CO₂H, —CH(CH₃)CH₂CO₂H, —(CH₂)₃CO₂H, —(CH₂)₂SO₂NHCH₃, —(CH₂)₂SO₂N(CH₃)₂, —(CH₂)₂SO₂—(N-morpholinyl), —(CH₂)₂NHCOCH₃, —(CH₂)₃NHCOCH₃, —(CH₂)₂NHCOCH(CH₃)₂, —(CH₂)₂NHSO₂CH₃, —(CH₂)₂NHSO₂CF₃, —(CH₂)₂NHSO₂NHCH(CH₃)₂, —CH₂CH(CH₃)CH₂OH (R and S), —CH(CH₃)(CH₂)₂OH, —CH₂—(2-imidazoyl), —CH₂—(4-imidazoyl), —CH₂—(3-pyrazoyl), 4-tetrahydropyranyl, 3-oxetanyl, —(CH₂)₂NHCO₂Me, —(CH₂)₃NHCO₂Me, —CH₂OH,

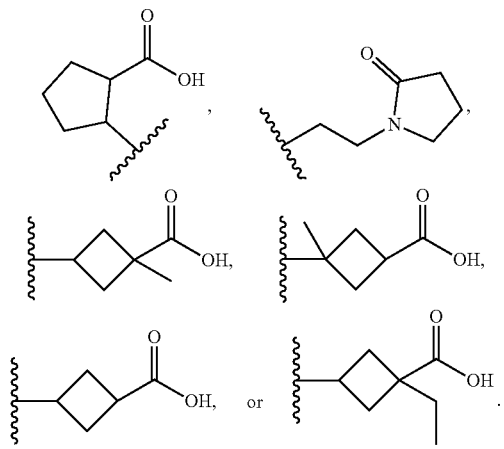

In embodiments, R⁷ is substituted or unsubstituted aziridinyl, oxiranyl, thiiranyl, azetidinyl, oxetanyl, thietanyl, pyrrolidinyl, pyrrolyl, imidazolyl, imidazolinyl, pyrazolinyl, tetrahydrofuranyl, thiolanyl, piperidinyl, piperazinyl, pyranyl, morpholinyl, 1,4-dioxanyl, tetrahydropyranyl, thianyl, or dithianyl. In embodiments, R⁷ is substituted or unsubstituted phenyl, thiofuranyl, imidazolyl, pyrazolyl, triazolyl, tetrazolyl, furanyl, oxazolyl, isooxazolyl, oxadiazolyl, oxatriazolyl, thienyl, thiazolyl, isothiazolyl, pyridinyl, pyrazinyl, pyrimidinyl, pyridazinyl, or triazinyl (e.g., 1,3,5-triazinyl, 1,2,3-triazinyl, or 1,2,4-triazinyl). In embodiments, R⁷ is substituted or unsubstituted indolyl, benzimidazolyl, indazolyl, benzotriazolyl, pyrrolopyrimidinyl, purinyl, indolizinyl, pyrrolopyriazinyl, pyrrolopyrimidinyl, imidazopyridazinyl, imidazopyridinyl, imidazopyrimidinyl, cinnolinyl, quinazolinyl, quinoxalinyl, phthalazinyl, pyridopyrazinyl, pteridinyl, pyrazolopyridinyl, quinolinyl, isoquinolinyl, naphthyridinyl, or carbazolyl.

In embodiments, R⁷ is substituted aziridinyl. In embodiments, R⁷ is substituted oxiranyl. In embodiments, R⁷ is substituted thiiranyl. In embodiments, R⁷ is substituted azetidinyl. In embodiments, R⁷ is substituted oxetanyl. In embodiments, R⁷ is substituted thietanyl. In embodiments, R⁷ is substituted pyrrolidinyl. In embodiments, R⁷ is substituted pyrrolyl. In embodiments, R⁷ is substituted imidazolyl. In embodiments, R⁷ is substituted imidazolinyl. In embodiments, R⁷ is substituted pyrazolinyl. In embodiments, R⁷ is substituted tetrahydrofuranyl. In embodiments, R⁷ is substituted thiolanyl. In embodiments, R⁷ is substituted piperidinyl. In embodiments, R⁷ is substituted piperazinyl. In embodiments, R⁷ is substituted pyranyl. In embodiments, R⁷ is substituted morpholinyl. In embodiments, R⁷ is substituted 1,4-dioxanyl. In embodiments, R⁷ is substituted tetrahydropyranyl. In embodiments, R⁷ is substituted thianyl. In embodiments, R⁷ is substituted or dithianyl.

In embodiments, R⁷ is substituted phenyl. In embodiments, R⁷ is substituted thiofuranyl. In embodiments, R⁷ is substituted imidazolyl. In embodiments, R⁷ is substituted pyrazolyl. In embodiments, R⁷ is substituted triazolyl. In embodiments, R⁷ is substituted tetrazolyl. In embodiments, R⁷ is substituted furanyl. In embodiments, R⁷ is substituted oxazolyl. In embodiments, R⁷ is substituted isooxazolyl. In embodiments, R⁷ is substituted oxadiazolyl. In embodiments, R⁷ is substituted oxatriazolyl. In embodiments, R⁷ is substituted thienyl. In embodiments, R⁷ is substituted thiazolyl. In embodiments, R⁷ is substituted isothiazolyl. In embodiments, R⁷ is substituted pyridinyl. In embodiments, R⁷ is substituted pyrazinyl. In embodiments, R⁷ is substituted pyrimidinyl. In embodiments, R⁷ is substituted pyridazinyl. In embodiments, R⁷ is substituted or triazinyl (e.g., 1,3,5-triazinyl, 1,2,3-triazinyl, or 1,2,4-triazinyl).

In embodiments, R⁷ is substituted indolyl. In embodiments, R⁷ is substituted benzimidazolyl. In embodiments, R⁷ is substituted indazolyl. In embodiments, R⁷ is substituted benzotriazolyl. In embodiments, R⁷ is substituted pyrrolopyrimidinyl. In embodiments, R⁷ is substituted purinyl. In embodiments, R⁷ is substituted indolizinyl. In embodiments, R⁷ is substituted pyrrolopyriazinyl. In embodiments, R⁷ is substituted pyrrolopyrimidinyl. In embodiments, R⁷ is substituted imidazopyridazinyl. In embodiments, R⁷ is substituted imidazopyridinyl. In embodiments, R⁷ is substituted imidazopyrimidinyl. In embodiments, R⁷ is substituted cinnolinyl. In embodiments, R⁷ is substituted quinazolinyl. In embodiments, R⁷ is substituted quinoxalinyl. In embodiments, R⁷ is substituted phthalazinyl. In embodiments, R⁷ is substituted pyridopyrazinyl. In embodiments, R⁷ is substituted pteridinyl. In embodiments, R⁷ is substituted pyrazolopyridinyl. In embodiments, R⁷ is substituted quinolinyl. In embodiments, R⁷ is substituted isoquinolinyl. In embodiments, R⁷ is substituted naphthyridinyl. In embodiments, R⁷ is substituted carbazolyl.

In embodiments, R⁷ is an unsubstituted aziridinyl. In embodiments, R⁷ is an unsubstituted oxiranyl. In embodiments, R⁷ is an unsubstituted thiiranyl. In embodiments, R⁷ is an unsubstituted azetidinyl. In embodiments, R⁷ is an unsubstituted oxetanyl. In embodiments, R⁷ is an unsubstituted thietanyl. In embodiments, R⁷ is an unsubstituted pyrrolidinyl. In embodiments, R⁷ is an unsubstituted pyrrolyl. In embodiments, R⁷ is an unsubstituted imidazolyl. In embodiments, R⁷ is an unsubstituted imidazolinyl. In embodiments, R⁷ is an unsubstituted pyrazolinyl. In embodiments, R⁷ is an unsubstituted tetrahydrofuranyl. In embodiments, R⁷ is an unsubstituted thiolanyl. In embodiments, R⁷ is an unsubstituted piperidinyl. In embodiments, R⁷ is an unsubstituted piperazinyl. In embodiments, R⁷ is an unsubstituted pyranyl. In embodiments, R⁷ is an unsubstituted morpholinyl. In embodiments, R⁷ is an unsubstituted 1,4-dioxanyl. In embodiments, R⁷ is an unsubstituted tetrahydropyranyl. In embodiments, R⁷ is an unsubstituted thianyl. In embodiments, R⁷ is an unsubstituted dithianyl.

In embodiments, $R^7$ is an unsubstituted phenyl. In embodiments, $R^7$ is an unsubstituted thiofuranyl. In embodiments, $R^7$ is an unsubstituted imidazolyl. In embodiments, $R^7$ is an unsubstituted pyrazolyl. In embodiments, $R^7$ is an unsubstituted triazolyl. In embodiments, $R^7$ is an unsubstituted tetrazolyl. In embodiments, $R^7$ is an unsubstituted furanyl. In embodiments, $R^7$ is an unsubstituted oxazolyl. In embodiments, $R^7$ is an unsubstituted isooxazolyl. In embodiments, $R^7$ is an unsubstituted oxadiazolyl. In embodiments, $R^7$ is an unsubstituted oxatriazolyl. In embodiments, $R^7$ is an unsubstituted thienyl. In embodiments, $R^7$ is an unsubstituted thiazolyl. In embodiments, $R^7$ is an unsubstituted isothiazolyl. In embodiments, $R^7$ is an unsubstituted pyridinyl. In embodiments, $R^7$ is an unsubstituted pyrazinyl. In embodiments, $R^7$ is an unsubstituted pyrimidinyl. In embodiments, $R^7$ is an unsubstituted pyridazinyl. In embodiments, $R^7$ is an unsubstituted triazinyl (e.g. 1,3,5-triazinyl, 1,2,3-triazinyl, or 1,2,4-triazinyl).

In embodiments, $R^7$ is an unsubstituted indolyl. In embodiments, $R^7$ is an unsubstituted benzimidazolyl. In embodiments, $R^7$ is an unsubstituted indazolyl. In embodiments, $R^7$ is an unsubstituted benzotriazolyl. In embodiments, $R^7$ is an unsubstituted pyrrolopyrimidinyl. In embodiments, $R^7$ is an unsubstituted purinyl. In embodiments, $R^7$ is an unsubstituted indolizinyl. In embodiments, $R^7$ is an unsubstituted pyrrolopyriazinyl. In embodiments, $R^7$ is an unsubstituted pyrrolopyrimidinyl. In embodiments, $R^7$ is an unsubstituted imidazopyridazinyl. In embodiments, $R^7$ is an unsubstituted imidazopyridinyl. In embodiments, $R^7$ is an unsubstituted imidazopyrimidinyl. In embodiments, $R^7$ is an unsubstituted cinnolinyl. In embodiments, $R^7$ is an unsubstituted quinazolinyl. In embodiments, $R^7$ is an unsubstituted quinoxalinyl. In embodiments, $R^7$ is an unsubstituted phthalazinyl. In embodiments, $R^7$ is an unsubstituted pyridopyrazinyl. In embodiments, $R^7$ is an unsubstituted pteridinyl. In embodiments, $R^7$ is an unsubstituted pyrazolopyridinyl. In embodiments, $R^7$ is an unsubstituted quinolinyl. In embodiments, $R^7$ is an unsubstituted isoquinolinyl. In embodiments, $R^7$ is an unsubstituted naphthyridinyl. In embodiments, $R^7$ is an unsubstituted carbazolyl.

In embodiments, $R^7$ is hydrogen, halogen, $-SO_{n7}R^{7A}$, $-SO_{v7}NR^{7B}R^{7C}$, $-NHC(O)NR^{7B}R^{7C}$, $-NR^{7B}R^{1C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^7$ is $-OR^{7A}$, $-C(O)R^{7D}$, $-C(O)OR^{7D}$, $-C(O)NR^{7B}R^{7C}$, $-SO_{n7}R^{7A}$, $-SO_{v7}NR^{7B}R^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^7$ is hydrogen, substituted or unsubstituted alkyl, phenyl, $-C(O)OH$, $-C(O)OCH_3$, $-C(O)OCH_2CH_3$, $-CH_2C(O)OH$, $-NHC(O)OH$, $-NHC(O)OCH_3$, $-NHC(O)OCH_2CH_3$, $-CH_2C(O)OH$, $-CH_2C(O)OCH_3$, $-CH_2C(O)OCH_2CH_3$, $-SO_2CH_3$, $-SO_2CH_2CH_3$, $-SO_2CH(CH_3)_2$, $-NHSO_2CH_3$, $-NHSO_2CH_2CH_3$, $-NHSO_2CH(CH_3)_2$, $-SO_2NH_2$, $-SO_2NHCH_3$, $-F$, $-OH$, $-CH_2OH$, $-(CH_2)_2OH$, $-(CH_2)_3OH$, $-C(CH_3)_2OH$, $-CH_2SO_2NH_2$, $-(CH_2)_2SO_2NH_2$, $-CH_2C(O)NH_2$, $-(CH_2)_2C(O)NH_2$, $-(CH_2)_3C(O)NH_2$, $-CH_2NHSO_2CF_3$, $-(CH_2)_2NHSO_2CF_3$, $-(CH_2)_3NHSO_2CF_3$, $-CH_2NHSO_2CH_3$, $-(CH_2)_2NHSO_2CH_3$, $-(CH_2)_3NHSO_2CH_3$, $-CH_2SO_2CH_3$, $-(CH_2)_2SO_2CH_3$, $-CH_2SO_2NH_2$ or $-(CH_2)_2SO_2NH_2$.

In embodiments, $R^7$ is hydrogen. In embodiments, $R^7$ is substituted or unsubstituted alkyl. In embodiments, $R^7$ is substituted or unsubstituted phenyl. In embodiments, $R^7$ is $-C(O)OH$. In embodiments, $R^7$ is $-C(O)OCH_3$. In embodiments, $R^7$ is $-C(O)OCH_2CH_3$. In embodiments, $R^7$ is $-CH_2C(O)OH$. In embodiments, $R^7$ is $-NHC(O)OH$. In embodiments, $R^7$ is $-NHC(O)OCH_3$. In embodiments, $R^7$ is $-NHC(O)OCH_2CH_3$. In embodiments, $R^7$ is $-CH_2C(O)OH$. In embodiments, $R^7$ is $-CH_2C(O)OCH_3$. In embodiments, $R^7$ is $-CH_2C(O)OCH_2CH_3$. In embodiments, $R^7$ is $-SO_2CH_3$. In embodiments, $R^7$ is $-SO_2CH_2CH_3$. In embodiments, $R^7$ is $-SO_2CH(CH_3)_2$. In embodiments, $R^7$ is $-NHSO_2CH_3$. In embodiments, $R^7$ is $-NHSO_2CH_2CH_3$. In embodiments, $R^7$ is $-NHSO_2CH(CH_3)_2$. In embodiments, $R^7$ is $-SO_2NH_2$. In embodiments, $R^7$ is $-SO_2NHCH_3$. In embodiments, $R^7$ is $-F$. In embodiments, $R^7$ is $-OH$. In embodiments, $R^7$ is $-CH_2OH$. In embodiments, $R^7$ is $-(CH_2)_2OH$. In embodiments, $R^7$ is $-(CH_2)_3OH$. In embodiments, $R^7$ is $-C(CH_3)_2OH$. In embodiments, $R^7$ is $-CH_2SO_2NH_2$. In embodiments, $R^7$ is $-(CH_2)_2SO_2NH_2$. In embodiments, $R^7$ is $-CH_2C(O)NH_2$. In embodiments, $R^7$ is $-(CH_2)_2C(O)NH_2$. In embodiments, $R^7$ is $-(CH_2)_3C(O)NH_2$. In embodiments, $R^7$ is $-CH_2NHSO_2CF_3$. In embodiments, $R^7$ is $-(CH_2)_2NHSO_2CF_3$. In embodiments, $R^7$ is $-(CH_2)_3NHSO_2CF_3$. In embodiments, $R^7$ is $-CH_2NHSO_2CH_3$. In embodiments, $R^7$ is $-(CH_2)_2NHSO_2CH_3$. In embodiments, $R^7$ is $-(CH_2)_3NHSO_2CH_3$. In embodiments, $R^7$ is $-CH_2SO_2CH_3$. In embodiments, $R^7$ is $-(CH_2)_2SO_2CH_3$. In embodiments, $R^7$ is $-CH_2SO_2NH_2$. In embodiments, $R^7$ is $-(CH_2)_2SO_2NH_2$.

In embodiments, $R^7$ is hydrogen, substituted or unsubstituted alkyl, phenyl, $-C(O)OH$, $-C(O)OCH_3$, $-C(O)OCH_2CH_3$, $-CH_2C(O)OH$, $-NHC(O)OH$, $-NHC(O)OCH_3$, $-NHC(O)OCH_2CH_3$, $-CH_2C(O)OH$, $-CH_2C(O)OCH_3$, $-CH_2C(O)OCH_2CH_3$, $-SO_2CH_3$, $-SO_2CH_2CH_3$, $-SO_2CH(CH_3)_2$, $-NHSO_2CH_3$, $-NHSO_2CH_2CH_3$, $-NHSO_2CH(CH_3)_2$, $-SO_2NH_2$, $-SO_2NHCH_3$, $-(CH_2)_2OH$, $-CH_2C(CH_3)_2OH$, $-(CH_2)_3OH$, $-(CH_2)_2CH(CH_3)_2OH$, $-(CH_2)_2SO_2NH_2$, $-(CH_2)_3SO_2NH_2$, $-(CH_2)_2CONH_2$, $-(CH_2)_3CONH_2$, $-(CH_2)_3CON(H)Me$, $-(CH_2)_3CON(Me)_2$, $-(CH_2)_2SO_2Me$, $-(CH_2)_3SO_2Me$, $-CH_2CH(OH)Me$, $-CH_2CO_2H$, $-(CH_2)_2CO_2H$, $-CH(CH_3)CH_2CO_2H$, $-(CH_2)_3CO_2H$, $-(CH_2)_2SO_2NHCH_3$, $-(CH_2)_2SO_2N(CH_3)_2$, $-(CH_2)_2SO_2-(N-morpholinyl)$, $-(CH_2)_2NHCOCH_3$, $-(CH_2)_3NHCOCH_3$, $-(CH_2)_2NHCOCH(CH_3)_2$, $-(CH_2)_2NHSO_2CH_3$, $-(CH_2)_2NHSO_2CF_3$, $-(CH_2)_2NHSO_2NHCH(CH_3)_2$, $-CH_2CH(CH_3)CH_2OH$ (R and S), $-CH(CH_3)(CH_2)_2OH$, $-CH_2-(2$-imidazoyl$)$, $-CH_2-(4$-imidazoyl$)$, $-CH_2-(3$-pyrazoyl$)$, 4-tetrahydropyranyl, 3-oxetanyl, $-(CH_2)_2NHCO_2Me$, or $-(CH_2)_3NHCO_2Me$. In embodiments, $R^7$ is hydrogen. In embodiments, $R^7$ is substituted or unsubstituted alkyl. In embodiments, $R^7$ is substituted or unsubstituted phenyl. In embodiments, $R^7$ is $-C(O)OH$. In embodiments, $R^7$ is $-C(O)OCH_3$. In embodiments, $R^7$ is $-C(O)OCH_2CH_3$. In embodiments, $R^7$ is $-CH_2C(O)OH$. In embodiments, $R^7$ is $-NHC(O)OH$. In embodiments, $R^7$ is $-NHC(O)OCH_3$. In embodiments, $R^7$ is $-NHC(O)OCH_2CH_3$. In embodiments, $R^7$ is $-CH_2C(O)OH$. In embodiments, $R^7$ is $-CH_2C(O)OCH_3$. In embodiments, $R^7$ is $-CH_2C(O)OCH_2CH_3$. In embodiments, $R^7$ is $-SO_2CH_3$. In embodiments, $R^7$ is $-SO_2CH_2CH_3$. In embodiments, $R^7$ is $-SO_2CH(CH_3)_2$. In embodiments, $R^7$ is $-NHSO_2CH_3$. In embodiments, $R^7$ is $-NHSO_2CH_2CH_3$.

In embodiments, $R^7$ is —NHSO$_2$CH(CH$_3$)$_2$. In embodiments, $R^7$ is —SO$_2$NH$_2$. In embodiments, $R^7$ is —SO$_2$NHCH$_3$. In embodiments, $R^7$ is —(CH$_2$)$_2$OH. In embodiments, $R^7$ is —CH$_2$C(CH$_3$)$_2$OH. In embodiments, $R^7$ is —(CH$_2$)$_3$OH. In embodiments, $R^7$ is —(CH$_2$)$_2$CH(CH$_3$)$_2$OH. In embodiments, $R^7$ is —(CH$_2$)$_2$SO$_2$NH$_2$. In embodiments, $R^7$ is —(CH$_2$)$_3$SO$_2$NH$_2$. In embodiments, $R^7$ is —(CH$_2$)$_2$CONH$_2$. In embodiments, $R^7$ is —(CH$_2$)$_3$CONH$_2$—(CH$_2$)$_3$CON(H)Me. In embodiments, $R^7$ is —(CH$_2$)$_3$CON(Me)$_2$. In embodiments, $R^7$ is —(CH$_2$)$_2$SO$_2$Me. In embodiments, $R^7$ is —(CH$_2$)$_3$SO$_2$Me. In embodiments, $R^7$ is —CH$_2$CH(OH)Me. In embodiments, $R^7$ is —CH$_2$CO$_2$H. In embodiments, $R^7$ is —(CH$_2$)$_2$CO$_2$H. In embodiments, $R^7$ is —CH(CH$_3$)CH$_2$CO$_2$H. In embodiments, $R^7$ is —(CH$_2$)$_3$CO$_2$H. In embodiments, $R^7$ is —(CH$_2$)$_2$SO$_2$NHCH$_3$. In embodiments, $R^7$ is —(CH$_2$)$_2$SO$_2$N(CH$_3$)$_2$. In embodiments, $R^7$ is —(CH$_2$)$_2$SO$_2$—(N-morpholinyl). In embodiments, $R^7$ is —(CH$_2$)$_2$NHCOCH$_3$. In embodiments, $R^7$ is —(CH$_2$)$_3$NHCOCH$_3$. In embodiments, $R^7$ is —(CH$_2$)$_2$NHCOCH(CH$_3$)$_2$. In embodiments, $R^7$ is —(CH$_2$)$_2$NHSO$_2$CH$_3$. In embodiments, $R^7$ is —(CH$_2$)$_2$NHSO$_2$CF$_3$. In embodiments, $R^7$ is —(CH$_2$)$_2$NHSO$_2$NHCH(CH$_3$)$_2$. In embodiments, $R^7$ is —CH$_2$CH(CH$_3$)CH$_2$OH (R and S). In embodiments, $R^7$ is —CH(CH$_3$)(CH$_2$)$_2$OH. In embodiments, $R^7$ is —CH$_2$—(2-imidazoyl). In embodiments, $R^7$ is —CH$_2$—(4-imidazoyl). In embodiments, $R^7$ is —CH$_2$—(3-pyrazoyl). In embodiments, $R^7$ is 4-tetrahydropyranyl. In embodiments, $R^7$ is 3-oxetanyl. In embodiments, $R^7$ is —(CH$_2$)$_2$NHCO$_2$Me. In embodiments, $R^7$ is —(CH$_2$)$_3$NHCO$_2$Me.

In embodiments, $R^7$ is $R^{29}$-substituted or unsubstituted $C_1$-$C_6$ alkyl. In embodiments, $R^7$ is $R^{29}$-substituted $C_1$-$C_6$ alkyl. In embodiments, $R^7$ is unsubstituted $C_1$-$C_6$ alkyl. In embodiments, $R^7$ is $R^{29}$-substituted or unsubstituted $C_2$-$C_6$ alkyl. In embodiments, $R^7$ is $R^{29}$-substituted $C_2$-$C_6$ alkyl. In embodiments, $R^7$ is unsubstituted $C_2$-$C_6$ alkyl. In embodiments, $R^7$ is $R^{29}$-substituted or unsubstituted $C_1$ alkyl. In embodiments, $R^7$ is $R^{29}$-substituted $C_1$ alkyl. In embodiments, $R^7$ is unsubstituted $C_1$ alkyl. In embodiments, $R^7$ is $R^{29}$-substituted or unsubstituted $C_2$ alkyl. In embodiments, $R^7$ is $R^{29}$-substituted $C_2$ alkyl. In embodiments, $R^7$ is unsubstituted $C_2$ alkyl. In embodiments, $R^7$ is $R^{29}$-substituted or unsubstituted $C_3$ alkyl. In embodiments, $R^7$ is $R^{29}$-substituted $C_3$ alkyl. In embodiments, $R^7$ is unsubstituted $C_3$ alkyl. In embodiments, $R^7$ is $R^{29}$-substituted or unsubstituted $C_4$ alkyl. In embodiments, $R^7$ is $R^{29}$-substituted $C_4$ alkyl. In embodiments, $R^7$ is unsubstituted $C_4$ alkyl. In embodiments, $R^7$ is $R^{29}$-substituted or unsubstituted CS alkyl. In embodiments, $R^7$ is $R^{29}$-substituted CS alkyl. In embodiments, $R^7$ is unsubstituted CS alkyl. In embodiments, $R^7$ is $R^{29}$-substituted or unsubstituted $C_6$ alkyl. In embodiments, $R^7$ is $R^{29}$-substituted $C_6$ alkyl. In embodiments, $R^7$ is unsubstituted $C_6$ alkyl.

In embodiments, $R^7$ is $R^{29}$-substituted or unsubstituted 2 to 8 membered heteroalkyl. In embodiments, $R^7$ is $R^{29}$-substituted 2 to 8 membered heteroalkyl. In embodiments, $R^7$ is unsubstituted 2 to 8 membered heteroalkyl. In embodiments, $R^7$ is $R^{29}$-substituted or unsubstituted 2 membered heteroalkyl. In embodiments, $R^7$ is $R^{29}$-substituted 2 membered heteroalkyl. In embodiments, $R^7$ is unsubstituted 2 membered heteroalkyl. In embodiments, $R^7$ is $R^{29}$-substituted or unsubstituted 3 membered heteroalkyl. In embodiments, $R^7$ is $R^{29}$-substituted 3 membered heteroalkyl. In embodiments, $R^7$ is unsubstituted 3 membered heteroalkyl. In embodiments, $R^7$ is $R^{29}$-substituted or unsubstituted 4 membered heteroalkyl. In embodiments, $R^7$ is $R^{29}$-substituted 4 membered heteroalkyl. In embodiments, $R^7$ is unsubstituted 4 membered heteroalkyl. In embodiments, $R^7$ is $R^{29}$-substituted or unsubstituted 5 membered heteroalkyl. In embodiments, $R^7$ is $R^{29}$-substituted 5 membered heteroalkyl. In embodiments, $R^7$ is unsubstituted 5 membered heteroalkyl. In embodiments, $R^7$ is $R^{29}$-substituted or unsubstituted 6 membered heteroalkyl. In embodiments, $R^7$ is $R^{29}$-substituted 6 membered heteroalkyl. In embodiments, $R^7$ is unsubstituted 6 membered heteroalkyl. In embodiments, $R^7$ is $R^{29}$-substituted or unsubstituted 7 membered heteroalkyl. In embodiments, $R^7$ is $R^{29}$-substituted 7 membered heteroalkyl. In embodiments, $R^7$ is unsubstituted 7 membered heteroalkyl.

In embodiments, $R^7$ is $R^{29}$-substituted or unsubstituted $C_4$-$C_6$ cycloalkyl. In embodiments, $R^7$ is $R^{29}$-substituted $C_4$-$C_6$ cycloalkyl. In embodiments, $R^7$ is $R^{29}$-substituted $C_4$-$C_6$ cycloalkyl. In embodiments, $R^7$ is $R^{29}$-substituted or unsubstituted $C_4$ cycloalkyl. In embodiments, $R^7$ is $R^{29}$-substituted $C_4$ cycloalkyl. In embodiments, $R^7$ is $R^{29}$-substituted $C_4$ cycloalkyl. In embodiments, $R^7$ is $R^{29}$-substituted or unsubstituted $C_5$ cycloalkyl. In embodiments, $R^7$ is $R^{29}$-substituted $C_5$ cycloalkyl. In embodiments, $R^7$ is $R^{29}$-substituted $C_5$ cycloalkyl.

In embodiments, $R^7$ is $R^{29}$-substituted or unsubstituted 5 to 6 membered heterocycloalkyl. In embodiments, $R^7$ is $R^{29}$-substituted 5 to 6 membered heterocycloalkyl. In embodiments, $R^7$ is unsubstituted 5 to 6 membered heterocycloalkyl. In embodiments, $R^7$ is $R^{29}$-substituted or unsubstituted 5 membered heterocycloalkyl. In embodiments, $R^7$ is $R^{29}$-substituted 5 membered heterocycloalkyl. In embodiments, $R^7$ is unsubstituted 5 membered heterocycloalkyl. In embodiments, $R^7$ is $R^{29}$-substituted or unsubstituted 6 membered heterocycloalkyl. In embodiments, $R^7$ is $R^{29}$-substituted 6 membered heterocycloalkyl. In embodiments, $R^7$ is unsubstituted 6 membered heterocycloalkyl.

In embodiments, $R^7$ is $R^{29}$-substituted or unsubstituted phenyl. In embodiments, $R^7$ is $R^{29}$-substituted phenyl. In embodiments, $R^7$ is unsubstituted phenyl.

In embodiments, $R^7$ is $R^{29}$-substituted or unsubstituted 5 to 6 membered heteroaryl. In embodiments, $R^7$ is $R^{29}$-substituted 5 to 6 membered heteroaryl. In embodiments, $R^7$ is unsubstituted 5 to 6 membered heteroaryl. In embodiments, $R^7$ is $R^{29}$-substituted or unsubstituted 5 membered heteroaryl. In embodiments, $R^7$ is $R^{29}$-substituted 5 membered heteroaryl. In embodiments, $R^7$ is unsubstituted 5 membered heteroaryl. In embodiments, $R^7$ is $R^{29}$-substituted or unsubstituted 6 membered heteroaryl. In embodiments, $R^7$ is $R^{29}$-substituted 6 membered heteroaryl. In embodiments, $R^7$ is unsubstituted 6 membered heteroaryl.

In embodiments, $R^7$ is oxo. In embodiments, $R^7$ is —CF$_3$. In embodiments, $R^7$ is —CHF$_2$. In embodiments, $R^7$ is —CH$_2$F. In embodiments, $R^7$ is —SO$_2$CH$_3$. In embodiments, $R^7$ is —SO$_2$NH$_2$. In embodiments, $R^7$ is —NHC(O)NH$_2$. In embodiments, $R^7$ is —NH$_2$. In embodiments, $R^7$ is —C(O)OH. In embodiments, $R^7$ is —C(O)OCH$_3$. In embodiments, $R^7$ is —C(O)NH$_2$. In embodiments, $R^7$ is —OCH$_3$. In embodiments, $R^7$ is —NHSO$_2$CH$_3$. In embodiments, $R^7$ is —NHC(O)CH$_3$. In embodiments, $R^7$ is —NHC(O)OH. In embodiments, $R^7$ is —OCF$_3$. In embodiments, $R^7$ is —OCHF$_2$. In embodiments, $R^7$ is —OCH$_2$F. In embodiments, $R^7$ is hydrogen. In embodiments, $R^7$ is —OH. In embodiments, $R^7$ is —C(O)OCH$_2$CH$_3$. In embodiments, $R^7$ is —SO$_2$CH$_2$CH$_3$. In embodiments, $R^7$ is —SO$_2$CH$_2$CH$_2$CH$_3$. In embodiments, $R^7$ is —SO$_2$CH(CH$_3$)$_2$. In embodiments, $R^7$ is —C(O)NHCH$_3$. In embodiments, $R^7$ is —C(O)N(CH$_3$)$_2$. In embodiments, $R^7$ is —NHC(O)OCH$_3$. In embodiments, $R^7$ is —NHC(O)OCH$_2$CH$_3$. In embodiments, $R^7$ is —NHC(O)

OCH₂CH₂CH₃. In embodiments, R⁷ is —NHC(O)OCH(CH₃)₂. In embodiments, R⁷ is —NHC(O)CH₃. In embodiments, R⁷ is —NHC(O)CH₂CH₃. In embodiments, R⁷ is —NHC(O)CH₂CH₂CH₃. In embodiments, R⁷ is —NHC(O)CH(CH₃)₂.

In embodiments, R²⁹ is oxo. In embodiments, R²⁹ is —CF₃. In embodiments, R²⁹ is —CHF₂. In embodiments, R²⁹ is —CH₂F. In embodiments, R²⁹ is —SO₂CH₃. In embodiments, R²⁹ is —SO₂NH₂. In embodiments, R²⁹ is —NHC(O)NH₂. In embodiments, R²⁹ is —NH₂. In embodiments, R²⁹ is —C(O)OH. In embodiments, R²⁹ is —C(O)OCH₃. In embodiments, R²⁹ is —C(O)NH₂. In embodiments, R²⁹ is —OCH₃. In embodiments, R²⁹ is —NHSO₂CH₃. In embodiments, R²⁹ is —NHC(O)CH₃. In embodiments, R²⁹ is —NHC(O)OH. In embodiments, R²⁹ is —OCF₃. In embodiments, R²⁹ is —OCHF₂. In embodiments, R²⁹ is —OCH₂F. In embodiments, R²⁹ is hydrogen. In embodiments, R²⁹ is —OH. In embodiments, R²⁹ is —C(O)OCH₂CH₃. In embodiments, R²⁹ is —SO₂CH₂CH₃. In embodiments, R²⁹ is —SO₂CH₂CH₂CH₃. In embodiments, R²⁹ is —SO₂CH(CH₃)₂. In embodiments, R²⁹ is —C(O)NHCH₃. In embodiments, R²⁹ is —C(O)N(CH₃)₂. In embodiments, R²⁹ is —NHC(O)OCH₃. In embodiments, R²⁹ is —NHC(O)OCH₂CH₃. In embodiments, R²⁹ is —NHC(O)OCH₂CH₂CH₃. In embodiments, R²⁹ is —NHC(O)OCH(CH₃)₂. In embodiments, R²⁹ is —NHC(O)CH₃. In embodiments, R²⁹ is —NHC(O)CH₂CH₃. In embodiments, R²⁹ is —NHC(O)CH₂CH₂CH₃. In embodiments, R²⁹ is —NHC(O)CH(CH₃)₂.

In embodiments, R²⁹ is R³⁰-substituted or unsubstituted C₁-C₆ alkyl. In embodiments, R²⁹ is R³⁰-substituted C—C₆ alkyl. In embodiments, R²⁹ is unsubstituted C₁-C₆ alkyl. In embodiments, R²⁹ is R³⁰-substituted or unsubstituted C₂-C₆ alkyl. In embodiments, R²⁹ is R³⁰-substituted C₂-C₆ alkyl. In embodiments, R²⁹ is unsubstituted C₂-C₆ alkyl. In embodiments, R²⁹ is R³⁰-substituted or unsubstituted C₁ alkyl. In embodiments, R²⁹ is R³⁰-substituted C₁ alkyl. In embodiments, R²⁹ is unsubstituted C₁ alkyl. In embodiments, R²⁹ is R³⁰-substituted or unsubstituted C₂ alkyl. In embodiments, R²⁹ is R³⁰-substituted C₂ alkyl. In embodiments, R²⁹ is unsubstituted C₂ alkyl. In embodiments, R²⁹ is R³⁰-substituted or unsubstituted C₃ alkyl. In embodiments, R²⁹ is R³⁰-substituted C₃ alkyl. In embodiments, R²⁹ is unsubstituted C₃ alkyl. In embodiments, R²⁹ is R³⁰-substituted or unsubstituted C₄ alkyl. In embodiments, R²⁹ is R³⁰-substituted C₄ alkyl. In embodiments, R²⁹ is unsubstituted C₄ alkyl. In embodiments, R²⁹ is R³⁰-substituted or unsubstituted CS alkyl. In embodiments, R²⁹ is R³⁰-substituted CS alkyl. In embodiments, R²⁹ is unsubstituted CS alkyl. In embodiments, R²⁹ is R³⁰-substituted or unsubstituted C₆ alkyl. In embodiments, R²⁹ is R³⁰-substituted C₆ alkyl. In embodiments, R²⁹ is unsubstituted C₆ alkyl.

In embodiments, R²⁹ is R³⁰-substituted or unsubstituted 2 to 8 membered heteroalkyl. In embodiments, R²⁹ is R³⁰-substituted 2 to 8 membered heteroalkyl. In embodiments, R²⁹ is unsubstituted 2 to 8 membered heteroalkyl. In embodiments, R²⁹ is R³⁰-substituted or unsubstituted 2 membered heteroalkyl. In embodiments, R²⁹ is R³⁰-substituted 2 membered heteroalkyl. In embodiments, R²⁹ is unsubstituted 2 membered heteroalkyl. In embodiments, R²⁹ is R³⁰-substituted or unsubstituted 3 membered heteroalkyl. In embodiments, R²⁹ is R³⁰-substituted 3 membered heteroalkyl. In embodiments, R²⁹ is unsubstituted 3 membered heteroalkyl. In embodiments, R²⁹ is R³⁰-substituted or unsubstituted 4 membered heteroalkyl. In embodiments, R²⁹ is R³⁰-substituted 4 membered heteroalkyl. In embodiments, R²⁹ is unsubstituted 4 membered heteroalkyl. In embodiments, R²⁹ is R³⁰-substituted or unsubstituted 5 membered heteroalkyl. In embodiments, R²⁹ is R³⁰-substituted 5 membered heteroalkyl. In embodiments, R²⁹ is unsubstituted 5 membered heteroalkyl. In embodiments, R²⁹ is R³⁰-substituted or unsubstituted 6 membered heteroalkyl. In embodiments, R²⁹ is R³⁰-substituted 6 membered heteroalkyl. In embodiments, R²⁹ is unsubstituted 6 membered heteroalkyl. In embodiments, R²⁹ is R³⁰-substituted or unsubstituted 7 membered heteroalkyl. In embodiments, R²⁹ is R³⁰-substituted 7 membered heteroalkyl. In embodiments, R²⁹ is unsubstituted 7 membered heteroalkyl.

In embodiments, R²⁹ is R³⁰-substituted or unsubstituted C₄-C₆ cycloalkyl. In embodiments, R²⁹ is R³⁰-substituted C₄-C₆ cycloalkyl. In embodiments, R²⁹ is R³⁰-substituted C₄-C₆ cycloalkyl. In embodiments, R²⁹ is R³⁰-substituted or unsubstituted C₄ cycloalkyl. In embodiments, R²⁹ is R³⁰-substituted C₄ cycloalkyl. In embodiments, R²⁹ is R³⁰-substituted C₄ cycloalkyl. In embodiments, R²⁹ is R³⁰-substituted or unsubstituted C₅ cycloalkyl. In embodiments, R²⁹ is R³⁰-substituted C₅ cycloalkyl. In embodiments, R²⁹ is R³⁰-substituted C₅ cycloalkyl.

In embodiments, R²⁹ is R³⁰-substituted or unsubstituted 5 to 6 membered heterocycloalkyl. In embodiments, R²⁹ is R³⁰-substituted 5 to 6 membered heterocycloalkyl. In embodiments, R²⁹ is unsubstituted 5 to 6 membered heterocycloalkyl. In embodiments, R²⁹ is R³⁰-substituted or unsubstituted 5 membered heterocycloalkyl. In embodiments, R²⁹ is R³⁰-substituted 5 membered heterocycloalkyl. In embodiments, R²⁹ is unsubstituted 5 membered heterocycloalkyl. In embodiments, R²⁹ is R³⁰-substituted or unsubstituted 6 membered heterocycloalkyl. In embodiments, R²⁹ is R³⁰-substituted 6 membered heterocycloalkyl. In embodiments, R²⁹ is unsubstituted 6 membered heterocycloalkyl.

In embodiments, R²⁹ is R³⁰-substituted or unsubstituted phenyl. In embodiments, R²⁹ is R³⁰-substituted phenyl. In embodiments, R²⁹ is unsubstituted phenyl.

In embodiments, R²⁹ is R³⁰-substituted or unsubstituted 5 to 6 membered heteroaryl. In embodiments, R²⁹ is R³⁰-substituted 5 to 6 membered heteroaryl. In embodiments, R²⁹ is unsubstituted 5 to 6 membered heteroaryl. In embodiments, R²⁹ is R³⁰-substituted or unsubstituted 5 membered heteroaryl. In embodiments, R²⁹ is R³⁰-substituted 5 membered heteroaryl. In embodiments, R²⁹ is unsubstituted 5 membered heteroaryl. In embodiments, R²⁹ is R³⁰-substituted or unsubstituted 6 membered heteroaryl. In embodiments, R²⁹ is R³⁰-substituted 6 membered heteroaryl. In embodiments, R²⁹ is unsubstituted 6 membered heteroaryl.

In embodiments, R⁷ is

[structure: cyclobutane with C(=O)OH substituent]

In embodiments, R⁷ is

[structure: CH with OH substituent]

In embodiments, R⁷ is
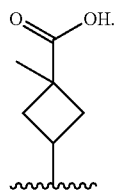
In embodiments, R⁷ is
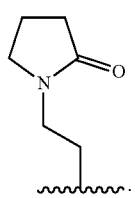 [SMILES: *CCN1CCCC1=O]
In embodiments, R⁷ is
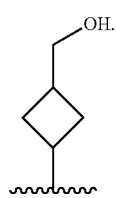 [SMILES: *C1CC(CO)C1]
In embodiments, R⁷ is
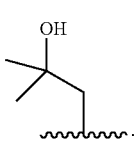 [SMILES: *CC(C)(C)O]
In embodiments, R⁷ is
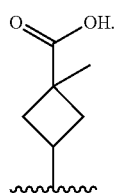 [SMILES: *C1CC(C)(C(=O)O)C1]
In embodiments, R⁷ is
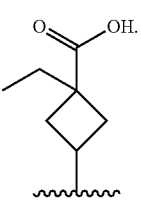 [SMILES: *C1CC(CC)(C(=O)O)C1]
In embodiments, R⁷ is
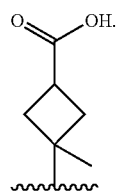 [SMILES: *C1(C)CC(C(=O)O)C1]
In embodiments, R⁷ is
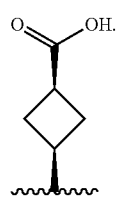 [SMILES: *[C@H]1C[C@@H](C(=O)O)C1]
In embodiments, R⁷ is
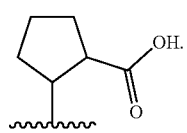 [SMILES: *C1CCCC1C(=O)O]
In embodiments, R⁷ is
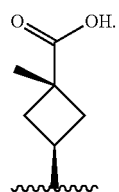 [SMILES: *[C@H]1C[C@](C)(C(=O)O)C1]
In embodiments, R⁷ is
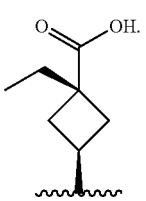 [SMILES: *[C@H]1C[C@](CC)(C(=O)O)C1]
In embodiments, R⁷ is
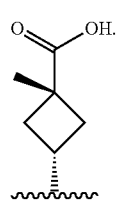 [SMILES: *[C@H]1C[C@@](C)(C(=O)O)C1]

In embodiments, $R^7$ is
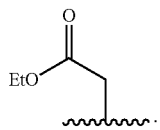
In embodiments, $R^7$ is
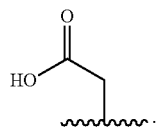
In embodiments, $R^7$ is
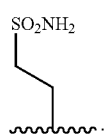
In embodiments, $R^7$ is
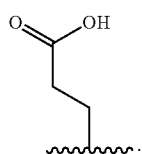 [SMILES: *CCC(=O)O]
In embodiments, $R^7$ is,
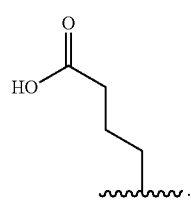
In embodiments, $R^7$ is
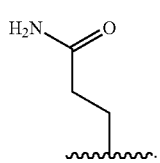
In embodiments, $R^7$ is
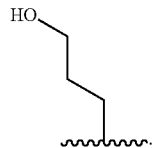
In embodiments, $R^7$ is
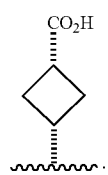 [SMILES: *[C@H]1C[C@@H](C(=O)O)C1]
In embodiments, $R^7$ is
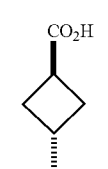
In embodiments, $R^7$ is
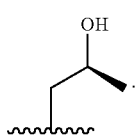
In embodiments, $R^7$ is
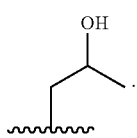
In embodiments, $R^7$ is
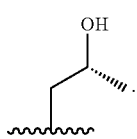

In embodiments, $R^7$ is,
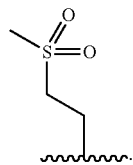 [SMILES: *CCS(C)(=O)=O]
In embodiments, $R^7$ is
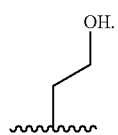
In embodiments, $R^7$ is
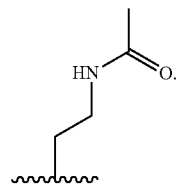 [SMILES: *CCNC(C)=O]
In embodiments, $R^7$ is,
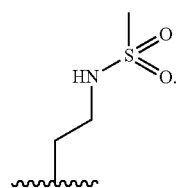 [SMILES: *CCNS(C)(=O)=O]
In embodiments, $R^7$ is
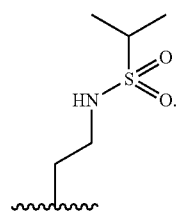 [SMILES: *CCNS(=O)(=O)C(C)C]
In embodiments, $R^7$ is
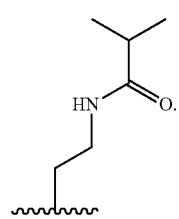 [SMILES: *CCNC(=O)C(C)C]
In embodiments, $R^7$ is
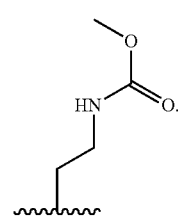 [SMILES: *CCNC(=O)OC]
In embodiments, $R^7$ is
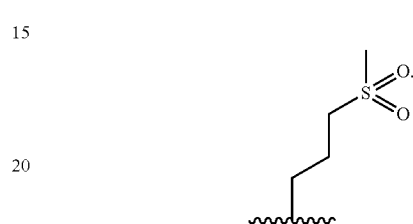
In embodiments, $R^7$ is,
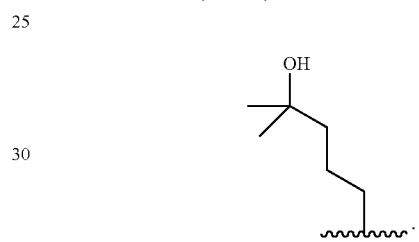
In embodiments, $R^7$ is
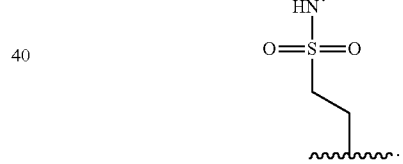
In embodiments, $R^7$ is,
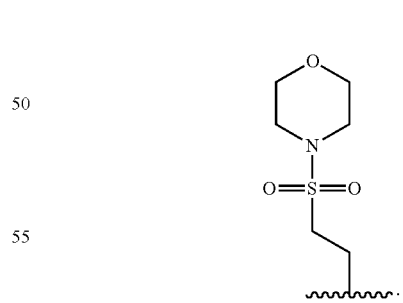
In embodiments, $R^7$ is
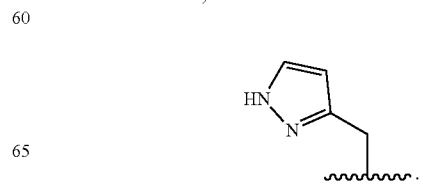

In embodiments, $R^7$ is
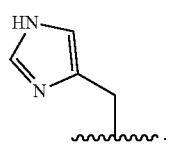 [SMILES: *Cc1c[nH]cn1]
In embodiments, $R^7$ is
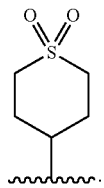
In embodiments, $R^7$ is
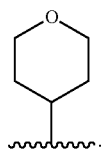
In embodiments, $R^7$ is
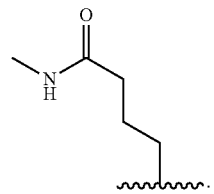 [SMILES: *CCCC(=O)NC]
In embodiments, $R^7$ is
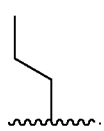
In embodiments, $R^7$ is
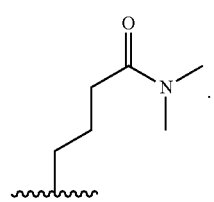 [SMILES: *CCCC(=O)N(C)C]
In embodiments, $R^7$ is
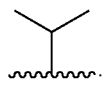 [SMILES: *C(C)C]
In embodiments, $R^7$ is,
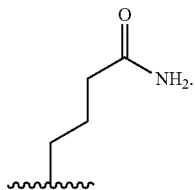 [SMILES: *CCCC(N)=O]
In embodiments, $R^7$ is
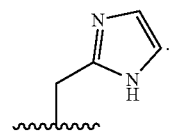 [SMILES: *Cc1ncc[nH]1]
In embodiments, $R^7$ is
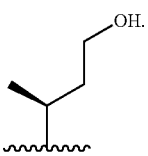 [SMILES: *[C@@H](C)CCO]
In embodiments, $R^7$ is
In embodiments, $R^7$ is
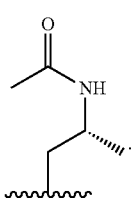
In embodiments, $R^7$ is,
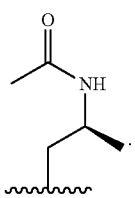 [SMILES: *C[C@H](C)NC(C)=O]

In embodiments, $R^7$ is

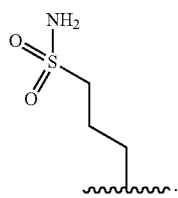

In embodiments, $R^7$ is

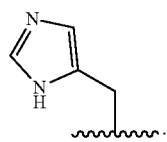 [SMILES: *Cc1cnc[nH]1]

In embodiments, $R^7$ is oxo. In embodiments, $R^7$ is —$CH_3$. In embodiments, $R^7$ is —COOH. In embodiments, $R^7$ is —NHC(O)$NH_2$. In embodiments, $R^7$ is —OH. In embodiments, $R^7$ is —$NH_2$. In embodiments, $R^7$ is —$CONH_2$. In embodiments, $R^7$ is —NHC(O)OH. In embodiments, $R^7$ is —$SO_2CH_3$. In embodiments, $R^7$ is —$NHSO_2CH_3$. In embodiments, $R^7$ is —$SO_2CH_2CH_3$. In embodiments, $R^7$ is —$SO_2R^{29}$. In embodiments, $R^7$ is —$SO_2CH(CH_3)_2$. In embodiments, $R^7$ is —COOEt. In embodiments, $R^7$ is —$NHCOCH_3$. In embodiments, $R^7$ is —$NHSO_2CH(CH_3)_2$. In embodiments, $R^7$ is —$NHCOCH(CH_3)_2$. In embodiments, $R^7$ is —$NHCOOCH_3$. In embodiments, $R^7$ is —$SO_2NHCH_3$. In embodiments, $R^7$ is —$CONHCH_3$. In embodiments, $R^7$ is —$CON(CH_3)_2$. In embodiments, $R^7$ is —$SO_2NH_2$. In embodiments, $R^7$ is unsubstituted morpholinyl. In embodiments, $R^7$ is unsubstituted imidazolyl. In embodiments, $R^7$ is unsubstituted thianyl. In embodiments, $R^7$ is unsubstituted tetrahydropyranyl. In embodiments, $R^7$ is unsubstituted pyrazolyl. In embodiments, $R^7$ is unsubstituted pyrrolidinyl. In embodiments, $R^7$ is $R^{29}$-substituted morpholinyl. In embodiments, $R^7$ is $R^{29}$-substituted imidazolyl. In embodiments, $R^7$ is $R^{29}$-substituted thianyl. In embodiments, $R^7$ is $R^{29}$-substituted tetrahydropyranyl. In embodiments, $R^7$ is $R^{29}$-substituted pyrazolyl. In embodiments, $R^7$ is $R^{29}$-substituted pyrrolidinyl. In embodiments, $R^7$ is —$CH_3$. In embodiments, $R^7$ is unsubstituted methyl. In embodiments, $R^7$ is unsubstituted ethyl. In embodiments, $R^7$ is unsubstituted propyl. In embodiments, $R^7$ is unsubstituted n-propyl. In embodiments, $R^7$ is unsubstituted isopropyl. In embodiments, $R^7$ is unsubstituted butyl. In embodiments, $R^7$ is unsubstituted n-butyl. In embodiments, $R^7$ is unsubstituted isobutyl. In embodiments, $R^7$ is unsubstituted tert-butyl. In embodiments, $R^7$ is unsubstituted pentyl. In embodiments, $R^7$ is unsubstituted n-pentyl. In embodiments, $R^7$ is unsubstituted hexyl. In embodiments, $R^7$ is unsubstituted heptyl. In embodiments, $R^7$ is $R^{29}$-substituted methyl. In embodiments, $R^7$ is $R^{29}$-substituted ethyl. In embodiments, $R^7$ is $R^{29}$-substituted propyl. In embodiments, $R^7$ is $R^{29}$-substituted n-propyl. In embodiments, $R^7$ is $R^{29}$-substituted isopropyl. In embodiments, $R^7$ is $R^{29}$-substituted butyl. In embodiments, $R^7$ is $R^{29}$-substituted n-butyl. In embodiments, $R^7$ is $R^{29}$-substituted isobutyl. In embodiments, $R^7$ is $R^{29}$-substituted tert-butyl. In embodiments, $R^7$ is $R^{29}$-substituted pentyl. In embodiments, $R^7$ is $R^{29}$-substituted n-pentyl. In embodiments, $R^7$ is $R^{29}$-substituted hexyl. In embodiments, $R^7$ is $R^{29}$-substituted heptyl.

In embodiments, $R^7$ is hydrogen, $R^{29}$-substituted or unsubstituted alkyl, phenyl, —F, —OH, $CH_2OH$, —$(CH_2)_2OH$, —$(CH_2)_{30}H$, —$C(CH_3)_2OH$, —$CH_2SO_2NH_2$, —$(CH_2)_2SO_2NH_2$, —$CH_2C(O)NH_2$, —$(CH_2)_2C(O)NH_2$, —$(CH_2)_3C(O)NH_2$, —$CH_2NHSO_2CF_3$, —$(CH_2)_2NHSO_2CF_3$, —$(CH_2)_3NHSO_2CF_3$, —$CH_2NHSO_2CH_3$, —$(CH_2)_2NHSO_2CH_3$, —$(CH_2)_3NHSO_2CH_3$, —$CH_2SO_2CH_3$, —$(CH_2)_2SO_2CH_3$, —$CH_2SO_2NH_2$, or —$(CH_2)_2SO_2NH_2$.

In embodiments, $R^7$ is $R^{29}$-substituted or unsubstituted alkyl (e.g., $C_1$-$C_8$ alkyl, $C_1$-$C_6$ alkyl, or $C_1$-$C_4$ alkyl). In embodiments, $R^7$ is $R^{29}$-substituted alkyl (e.g., $C_1$-$C_8$ alkyl, $C_1$-$C_6$ alkyl, or $C_1$-$C_4$ alkyl). In embodiments, $R^7$ is an unsubstituted alkyl (e.g., $C_1$-$C_8$ alkyl, $C_1$-$C_6$ alkyl, or $C_1$-$C_4$ alkyl). In embodiments, $R^7$ is an unsubstituted $C_1$-$C_4$ alkyl. In embodiments, $R^7$ is an unsubstituted $C_1$-$C_3$ alkyl. In embodiments, $R^7$ is an unsubstituted $C_1$-$C_2$ alkyl. In embodiments, $R^7$ is an unsubstituted $C_4$ alkyl. In embodiments, $R^7$ is an unsubstituted $C_3$ alkyl. In embodiments, $R^7$ is a $R^{29}$-substituted alkyl (e.g., $C_1$-$C_8$ alkyl, $C_1$-$C_6$ alkyl, or $C_1$-$C_4$ alkyl). In embodiments, $R^7$ is a $R^{29}$-substituted $C_1$-$C_4$ alkyl. In embodiments, $R^7$ is a $R^{29}$-substituted C—$C_3$ alkyl. In embodiments, $R^7$ is a $R^{29}$-substituted $C_1$-$C_2$ alkyl. In embodiments, $R^7$ is a $R^{29}$-substituted $C_4$ alkyl. In embodiments, $R^7$ is a $R^{29}$-substituted $C_3$ alkyl.

In embodiments, $R^7$ is $R^{29}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{29}$-substituted heteroalkyl (e.g., 2 to 8 membered heteroalkyl, 2 to 6 membered heteroalkyl, or 2 to 4 membered heteroalkyl). In embodiments, $R^7$ is an unsubstituted heteroalkyl (e.g., 2 to 8 membered heteroalkyl, 2 to 6 membered heteroalkyl, or 2 to 4 membered heteroalkyl).

In embodiments, $R^7$ is $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^{29}$-substituted cycloalkyl (e.g., $C_3$-$C_8$ cycloalkyl, $C_3$-$C_6$ cycloalkyl, or $C_5$-$C_6$ cycloalkyl). In embodiments, $R^7$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is an unsubstituted $C_3$-$C_6$ cycloalkyl. In embodiments, $R^7$ is an unsubstituted $C_3$-$C_5$ cycloalkyl. In embodiments, $R^7$ is an unsubstituted $C_3$-$C_4$ cycloalkyl. In embodiments, $R^7$ is an unsubstituted $C_4$ cycloalkyl. In embodiments, $R^7$ is a $R^{29}$-substituted $C_3$-$C_6$ cycloalkyl. In embodiments, $R^7$ is a $R^{29}$-substituted $C_3$-$C_5$ cycloalkyl. In embodiments, $R^7$ is a $R^{29}$-substituted $C_3$-$C_4$ cycloalkyl. In embodiments, $R^7$ is a $R^{29}$-substituted $C_4$ cycloalkyl.

In embodiments, $R^7$ is $R^{29}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{29}$-substituted heterocycloalkyl (e.g., 3 to 8 membered heterocycloalkyl, 3 to 6 membered heterocycloalkyl, or 5 to 6 membered heterocycloalkyl). In embodiments, $R^7$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{29}$-substituted 5 to 6 membered heterocycloalkyl. In embodiments, $R^7$ is $R^{29}$-substituted 5 membered heterocycloalkyl. In embodiments, $R^7$ is $R^{29}$-substituted 6 membered heterocycloalkyl.

In embodiments, $R^7$ is $R^{29}$-substituted or unsubstituted aryl (e.g., $C_6$-$C_{10}$ aryl, $C_{10}$ aryl, or phenyl). In embodiments, $R^7$ is $R^{29}$-substituted aryl (e.g., $C_6$-$C_{10}$ aryl, $C_{10}$ aryl, or phenyl). In embodiments, $R^7$ is an unsubstituted aryl (e.g., $C_6$-$C_{10}$ aryl, $C_{10}$ aryl, or phenyl).

In embodiments, $R^7$ is $R^{29}$-substituted or unsubstituted heteroaryl (e.g., 5 to 10 membered heteroaryl, 5 to 9 membered heteroaryl, or 5 to 6 membered heteroaryl). In embodiments, $R^7$ is $R^{29}$-substituted heteroaryl (e.g., 5 to 10 membered heteroaryl, 5 to 9 membered heteroaryl, or 5 to 6 membered heteroaryl). In embodiments, $R^7$ is an unsubstituted heteroaryl (e.g., 5 to 10 membered heteroaryl, 5 to 9 membered heteroaryl, or 5 to 6 membered heteroaryl).

In embodiments, $R^8$ is halogen, $-CX^{8.1}{}_3$, $-CHX^{8.1}{}_2$, $-CH_2X^{8.1}$, $-CN$, $-N_3$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, $-OCH_2X^{8.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^8$ is hydrogen.

In embodiments, $R^8$ is halogen, $-CX^{8.1}{}_3$, $-CHX^{8.1}{}_2$, $-CH_2X^{8.1}$, $-CN$, $-N_3$, $-SO_{n8}R^{8A}$, $-SO_{v8}NR^{8B}R^{8C}$, $-NHNR^{8B}R^{8C}$, $-ONR^{8B}R^{8C}$, $-NHC(O)NHNR^{8B}R^{8C}$, $-NHC(O)NR^{8B}R^{8C}$, $-N(O)_{m8}$, $-NR^{8B}R^{8C}$, $-C(O)R^{8D}$, $-C(O)OR^{8D}$, $-C(O)NR^{8B}R^{8C}$, $-OR^{8A}$, $-NR^{8B}SO_2R^{8A}$, $-NR^{8B}C(O)R^{8D}$, $-NR^{8B}C(O)OR^{8D}$, $-NR^{8B}OR^{8D}$, $-OCX^{8.1}{}_3$, $-OCHX^{8.1}{}_2$, $-OCH_2X^{8.1}$, $R^{32}$-substituted or unsubstituted alkyl (e.g., $C_1$-$C_8$ alkyl, $C_1$-$C_6$ alkyl, or $C_1$-$C_4$ alkyl), $R^{32}$-substituted or unsubstituted heteroalkyl (e.g., 2 to 8 membered heteroalkyl, 2 to 6 membered heteroalkyl, or 2 to 4 membered heteroalkyl), $R^{32}$-substituted or unsubstituted cycloalkyl (e.g., $C_3$—C cycloalkyl, $C_3$-$C_6$ cycloalkyl, or $C_5$-$C_6$ cycloalkyl), $R^{32}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32}$-substituted or unsubstituted aryl (e.g., $C_6$-$C_{10}$ aryl, $C_{10}$ aryl, or phenyl), or $R^{32}$-substituted or unsubstituted heteroaryl (e.g., 5 to 10 membered heteroaryl, 5 to 9 membered heteroaryl, or 5 to 6 membered heteroaryl).

In embodiments, $R^8$ is $R^{32}$-substituted or unsubstituted alkyl (e.g., $C_1$-$C_8$ alkyl, $C_1$-$C_6$ alkyl, or $C_1$-$C_4$ alkyl). In embodiments, $R^8$ is $R^{32}$-substituted alkyl (e.g., $C_1$-$C_8$ alkyl, $C_1$-$C_6$ alkyl, or $C_1$-$C_4$ alkyl). In embodiments, $R^8$ is an unsubstituted alkyl (e.g., $C_1$-$C_8$ alkyl, $C_1$-$C_6$ alkyl, or $C_1$-$C_4$ alkyl).

In embodiments, $R^8$ is $R^{32}$-substituted or unsubstituted heteroalkyl (e.g., 2 to 8 membered heteroalkyl, 2 to 6 membered heteroalkyl, or 2 to 4 membered heteroalkyl). In embodiments, $R^8$ is $R^{32}$-substituted heteroalkyl (e.g., 2 to 8 membered heteroalkyl, 2 to 6 membered heteroalkyl, or 2 to 4 membered heteroalkyl). In embodiments, $R^8$ is an unsubstituted heteroalkyl (e.g., 2 to 8 membered heteroalkyl, 2 to 6 membered heteroalkyl, or 2 to 4 membered heteroalkyl).

In embodiments, $R^8$ is $R^{32}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^8$ is $R^{32}$-substituted cycloalkyl (e.g., $C_3$-$C_8$ cycloalkyl, $C_3$-$C_6$ cycloalkyl, or $C_5$-$C_6$ cycloalkyl). In embodiments, $R^8$ is an unsubstituted cycloalkyl (e.g., $C_3$-$C_8$ cycloalkyl, $C_3$-$C_6$ cycloalkyl, or C—$C_6$ cycloalkyl).

In embodiments, $R^8$ is $R^{32}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^8$ is $R^{32}$-substituted heterocycloalkyl (e.g., 3 to 8 membered heterocycloalkyl, 3 to 6 membered heterocycloalkyl, or 5 to 6 membered heterocycloalkyl). In embodiments, $R^8$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^8$ is $R^{32}$-substituted or unsubstituted aryl (e.g., $C_6$-$C_{10}$ aryl, $C_{10}$ aryl, or phenyl). In embodiments, $R^8$ is $R^{32}$-substituted aryl (e.g., $C_6$-$C_{10}$ aryl, $C_{10}$ aryl, or phenyl). In embodiments, $R^8$ is an unsubstituted aryl (e.g., $C_6$-$C_{10}$ aryl, $C_{10}$ aryl, or phenyl).

In embodiments, $R^8$ is $R^{32}$-substituted or unsubstituted heteroaryl (e.g., 5 to 10 membered heteroaryl, 5 to 9 membered heteroaryl, or 5 to 6 membered heteroaryl). In embodiments, $R^8$ is $R^{32}$-substituted heteroaryl (e.g., 5 to 10 membered heteroaryl, 5 to 9 membered heteroaryl, or 5 to 6 membered heteroaryl). In embodiments, $R^8$ is an unsubstituted heteroaryl (e.g., 5 to 10 membered heteroaryl, 5 to 9 membered heteroaryl, or 5 to 6 membered heteroaryl).

In embodiments, $R^9$ is halogen, $-CX^{9.1}{}_3$, $-CHX^{9.1}{}_2$, $-CH_2X^{9.1}$, $-CN$, $-N_3$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}{}_3$, $-OCHX^9 12$, $-OCH_2X^{9.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is hydrogen.

In embodiments, $R^9$ is halogen, $-CX^{9.1}{}_3$, $-CHX^{9.1}{}_2$, $-CH_2X^{9.1}$, $-CN$, $-N_3$, $-SO_{n9}R^{9A}$, $-SO_{v9}NR^{9B}R^{9C}$, $-NHNR^{9B}R^{9C}$, $-ONR^{9B}R^{9C}$, $-NHC(O)NHNR^{9B}R^{9C}$, $-NHC(O)NR^{9B}R^{9C}$, $-N(O)_{m9}$, $-NR^{9B}R^{9C}$, $-C(O)R^{9D}$, $-C(O)OR^{9D}$, $-C(O)NR^{9B}R^{9C}$, $-OR^{9A}$, $-NR^{9B}SO_2R^{9A}$, $-NR^{9B}C(O)R^{9D}$, $-NR^{9B}C(O)OR^{9D}$, $-NR^{9B}OR^{9D}$, $-OCX^{9.1}{}_3$, $-OCHX^{9.1}{}_2$, $-OCH_2X^{9.1}$, $R^{35}$-substituted or unsubstituted alkyl (e.g., $C_1$-$C_8$ alkyl, $C_1$-$C_6$ alkyl, or $C_1$-$C_4$ alkyl), $R^{35}$-substituted or unsubstituted heteroalkyl (e.g., 2 to 8 membered heteroalkyl, 2 to 6 membered heteroalkyl, or 2 to 4 membered heteroalkyl), $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted or unsubstituted aryl (e.g., $C_6$-$C_{10}$ aryl, $C_{10}$ aryl, or phenyl), or $R^{35}$-substituted or unsubstituted heteroaryl (e.g., 5 to 10 membered heteroaryl, 5 to 9 membered heteroaryl, or 5 to 6 membered heteroaryl).

In embodiments, $R^9$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{35}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl).

In embodiments, $R^9$ is $R^{35}$-substituted or unsubstituted heteroalkyl (e.g., 2 to 8 membered heteroalkyl, 2 to 6 membered heteroalkyl, or 2 to 4 membered heteroalkyl). In embodiments, $R^9$ is $R^{35}$-substituted heteroalkyl (e.g., 2 to 8 membered heteroalkyl, 2 to 6 membered heteroalkyl, or 2 to 4 membered heteroalkyl). In embodiments, $R^9$ is an unsubstituted heteroalkyl (e.g., 2 to 8 membered heteroalkyl, 2 to 6 membered heteroalkyl, or 2 to 4 membered heteroalkyl).

In embodiments, $R^9$ is $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ is $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ is $R^{35}$-substituted or unsubstituted aryl (e.g., $C_6$-$C_{10}$ aryl, $C_{10}$ aryl, or phenyl). In embodiments, $R^9$ is $R^{35}$-substituted aryl (e.g., $C_6$-$C_{10}$ aryl, $C_{10}$ aryl, or phenyl). In embodiments, $R^9$ is an unsubstituted aryl (e.g., $C_6$-$C_{10}$ aryl, $C_{10}$ aryl, or phenyl).

In embodiments, $R^9$ is $R^{35}$-substituted or unsubstituted heteroaryl (e.g., 5 to 10 membered heteroaryl, 5 to 9 membered heteroaryl, or 5 to 6 membered heteroaryl). In embodiments, $R^9$ is $R^{35}$-substituted heteroaryl (e.g., 5 to 10 membered heteroaryl, 5 to 9 membered heteroaryl, or 5 to 6 membered heteroaryl). In embodiments, $R^9$ is an unsubstituted heteroaryl (e.g., 5 to 10 membered heteroaryl, 5 to 9 membered heteroaryl, or 5 to 6 membered heteroaryl).

In embodiments, $R^9$ is hydrogen, —CN, halogen, —CF$_3$, —COOH, —COOCH$_2$CH$_3$,

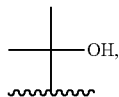
—OH,

—CH$_3$. In embodiments, $R^9$ is hydrogen. In embodiments, $R^9$ is —CN. In embodiments, $R^9$ is halogen. In embodiments, $R^9$ is —F. In embodiments, $R^9$ is —Cl. In embodiments, $R^9$ is —Br. In embodiments, $R^9$ is —I. In embodiments, $R^9$ is —CF$_3$. In embodiments, $R^9$ is —COOH. In embodiments, $R^9$ is —COOCH$_2$CH$_3$. In embodiments, $R^9$ is —CH$_3$. In embodiments, $R^9$ is —CHCH$_2$CH$_2$OH. In embodiments, $R^9$ is

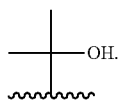 [SMILES: *C(C)(C)O]
—OH.

In embodiments, $R^9$ is substituted or unsubstituted $C_1$-$C_4$ alkyl. In embodiments, $R^9$ is substituted $C_1$-$C_4$ alkyl. In embodiments, $R^9$ is unsubstituted $C_1$-$C_4$ alkyl.

In embodiments, $R^9$ is halogen, —CF$_3$, —CHF$_2$, —CH$_2$F, —CN, —N$_3$, —SO$_2$CH$_3$, —C(O)$R^{9D}$, —C(O)O$R^{9D}$, substituted or unsubstituted alkyl, substituted or unsubstituted heteroalkyl. In embodiments, $R^9$ is halogen, —CF$_3$, —CHF$_2$, —CH$_2$F, —CN, —N$_3$, —SO$_2$CH$_3$, —C(O)$R^{9D}$, —C(O)O$R^{9D}$, substituted or unsubstituted alkyl, substituted or unsubstituted heteroalkyl.

In embodiments, $R^9$ is $R^{35}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{35}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl).

In embodiments, $R^9$ is $R^{35}$-substituted or unsubstituted methyl. In embodiments, $R^9$ is $R^{35}$-substituted or unsubstituted $C_2$ alkyl. In embodiments, $R^9$ is $R^{35}$-substituted or unsubstituted $C_3$ alkyl. In embodiments, $R^9$ is $R^{35}$-substituted or unsubstituted $C_4$ alkyl. In embodiments, $R^9$ is $R^{35}$-substituted or unsubstituted $C_5$ alkyl. In embodiments, $R^9$ is $R^{35}$-substituted or unsubstituted $C_6$ alkyl. In embodiments, $R^9$ is $R^{35}$-substituted or unsubstituted $C_7$ alkyl. In embodiments, $R^9$ is $R^{35}$-substituted or unsubstituted $C_8$ alkyl. In embodiments, $R^9$ is $R^{35}$-substituted methyl. In embodiments, $R^9$ is $R^{35}$-substituted $C_2$ alkyl. In embodiments, $R^9$ is $R^{35}$-substituted $C_3$ alkyl. In embodiments, $R^9$ is $R^{35}$-substituted $C_4$ alkyl. In embodiments, $R^9$ is $R^{35}$-substituted $C_5$ alkyl. In embodiments, $R^9$ is $R^{35}$-substituted $C_6$ alkyl. In embodiments, $R^9$ is $R^{35}$-substituted $C_7$ alkyl. In embodiments, $R^9$ is $R^{35}$-substituted $C_8$ alkyl. In embodiments, $R^9$ is an unsubstituted methyl. In embodiments, $R^9$ is an unsubstituted $C_2$ alkyl. In embodiments, $R^9$ is an unsubstituted $C_3$ alkyl. In embodiments, $R^9$ is an unsubstituted $C_4$ alkyl. In embodiments, $R^9$ is an unsubstituted $C_5$ alkyl. In embodiments, $R^9$ is an unsubstituted $C_6$ alkyl. In embodiments, $R^9$ is an unsubstituted $C_7$ alkyl. In embodiments, $R^9$ is an unsubstituted $C_8$ alkyl.

In embodiments, $X^2$ is $CR^9$; and $R^9$ is hydrogen, —$CX^{9.1}_3$, —$CHX^{9.1}_2$, —$CH_2X^{9.1}$, —CN, or substituted or unsubstituted $C_1$-$C_4$ alkyl. In embodiments, $X^2$ is $CR^9$; and $R^9$ is hydrogen. In embodiments, $X^2$ is $CR^9$; and $R^9$ is —$CX^{9.1}_3$. In embodiments, $X^2$ is $CR^9$; and $R^9$ is —$CHX^{9.1}_2$. In embodiments, $X^2$ is $CR^9$; and $R^9$ is —$CH_2X^{9.1}$. In embodiments, $X^2$ is $CR^9$; and $R^9$ is —CN. In embodiments, $X^2$ is $CR^9$; and $R^9$ is substituted or unsubstituted $C_1$-$C_4$ alkyl. In embodiments, $R^9$ is hydrogen, —CF$_3$, or unsubstituted methyl.

In embodiments, $R^4$ and $R^9$ may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^4$ and $R^9$ may optionally be joined to form a substituted or unsubstituted $C_5$-$C_7$ cycloalkyl. In embodiments, $R^4$ and $R^9$ may optionally be joined to form a substituted $C_5$-$C_7$ cycloalkyl. In embodiments, $R^4$ and $R^9$ may optionally be joined to form an unsubstituted $C_5$-$C_7$ cycloalkyl.

In embodiments, $R^4$ and $R^9$ may optionally be joined to form a substituted or unsubstituted 5 to 7 membered heterocycloalkyl. In embodiments, $R^4$ and $R^9$ may optionally be joined to form a substituted 5 to 7 membered heterocycloalkyl. In embodiments, $R^4$ and $R^9$ may optionally be joined to form an unsubstituted 5 to 7 membered heterocycloalkyl.

In embodiments, $R^4$ and $R^9$ may optionally be joined to form a substituted or unsubstituted phenyl. In embodiments, $R^4$ and $R^9$ may optionally be joined to form a substituted phenyl. In embodiments, $R^4$ and $R^9$ may optionally be joined to form an unsubstituted phenyl.

In embodiments, $R^4$ and $R^9$ may optionally be joined to form a substituted or unsubstituted 5 to 7 membered heteroaryl. In embodiments, $R^4$ and $R^9$ may optionally be joined to form a substituted 5 to 7 membered heteroaryl. In embodiments, $R^4$ and $R^9$ may optionally be joined to form an unsubstituted 5 to 7 membered heteroaryl. In embodiments, $R^4$ and $R^9$ may optionally be joined to forma substituted or unsubstituted 5 to 6 membered heteroaryl. In embodiments, $R^4$ and $R^9$ may optionally be joined to form a substituted 5 to 6 membered heteroaryl. In embodiments, $R^4$ and $R^9$ may optionally be joined to form an unsubstituted 5 to 6 membered heteroaryl.

In embodiments, $R^4$ and $R^9$ may optionally be joined to form a $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl). In embodiments, $R^4$ and $R^9$ may optionally be joined to form an unsubstituted phenyl. In embodiments, $R^4$ and $R^9$ may optionally be joined to form an unsubstituted $C_5$ cycloalkyl. In embodiments, $R^4$ and $R^9$ may optionally be joined to form an unsubstituted $C_6$ cycloalkyl. In embodiments, $R^4$ and $R^9$ may optionally be joined to form an unsubstituted thienyl.

In embodiments, $R^4$ and $R^9$ may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ and $R^9$ may optionally be joined to form a substituted cycloalkyl (e.g., $C_3$-$C_8$ cycloalkyl, $C_3$-$C_6$ cycloalkyl, or $C_5$-$C_6$ cycloalkyl). In embodiments, $R^4$ and $R^9$ may optionally be joined to form a $R^2$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^4$ and $R^9$ may optionally be joined to form a $R^{20}$-substituted cycloalkyl (e.g., $C_3$-$C_8$ cycloalkyl, $C_3$-$C_6$ cycloalkyl, or $C_5$-$C_6$ cycloalkyl). In embodiments, $R^4$ and $R^9$ may optionally be joined to form an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^4$ and $R^9$ may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ and $R^9$ may optionally be joined to form a substituted heterocycloalkyl (e.g., 3 to 8 membered heterocycloalkyl, 3 to 6 membered heterocycloalkyl, or 5 to 6 membered heterocycloalkyl). In embodiments, $R^4$ and $R^9$ may optionally be joined to form a $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^4$ and $R^9$ may optionally be joined to form a $R^{20}$-substituted heterocycloalkyl (e.g., 3 to 8 membered heterocycloalkyl, 3 to 6 membered heterocycloalkyl, or 5 to 6 membered heterocycloalkyl). In embodiments, $R^4$ and $R^9$ may optionally be joined to form an unsubstituted heterocycloalkyl (e.g., 3 to 8 membered heterocycloalkyl, 3 to 6 membered heterocycloalkyl, or 5 to 6 membered heterocycloalkyl).

In embodiments, $R^4$ and $R^9$ may optionally be joined to form a substituted or unsubstituted aryl (e.g., $C_6$-$C_{10}$ aryl, $C_{10}$ aryl, or phenyl). In embodiments, $R^4$ and $R^9$ may optionally be joined to form a substituted aryl (e.g., $C_6$-$C_{10}$ aryl, $C_{10}$ aryl, or phenyl). In embodiments, $R^4$ and $R^9$ may optionally be joined to form a $R^{20}$-substituted or unsubstituted aryl (e.g., $C_6$-$C_{10}$ aryl, $C_{10}$ aryl, or phenyl). In embodiments, $R^4$ and $R^9$ may optionally be joined to form a $R^{20}$-substituted aryl (e.g., $C_6$-$C_{10}$ aryl, $C_{10}$ aryl, or phenyl). In embodiments, $R^4$ and $R^9$ may optionally be joined to form an unsubstituted aryl (e.g., $C_6$-$C_{10}$ aryl, $C_{10}$ aryl, or phenyl).

In embodiments, $R^4$ and $R^9$ may optionally be joined to form a substituted or unsubstituted heteroaryl (e.g., 5 to 10 membered heteroaryl, 5 to 9 membered heteroaryl, or 5 to 6 membered heteroaryl). In embodiments, $R^4$ and $R^9$ may optionally be joined to form a substituted heteroaryl (e.g., 5 to 10 membered heteroaryl, 5 to 9 membered heteroaryl, or 5 to 6 membered heteroaryl). In embodiments, $R^4$ and $R^9$ may optionally be joined to form a $R^{20}$-substituted or unsubstituted heteroaryl (e.g., 5 to 10 membered heteroaryl, 5 to 9 membered heteroaryl, or 5 to 6 membered heteroaryl). In embodiments, $R^4$ and $R^9$ may optionally be joined to form a $R^{20}$-substituted heteroaryl (e.g., 5 to 10 membered heteroaryl, 5 to 9 membered heteroaryl, or 5 to 6 membered heteroaryl). In embodiments, $R^4$ and $R^9$ may optionally be joined to form an unsubstituted heteroaryl (e.g., 5 to 10 membered heteroaryl, 5 to 9 membered heteroaryl, or 5 to 6 membered heteroaryl).

In embodiments, $X^2$ is $CR^9$; and $R^4$ and $R^9$ are joined to form a substituted or unsubstituted cycloalkyl, substituted or unsubstituted heterocycloalkyl, substituted or unsubstituted aryl, or substituted or unsubstituted heteroaryl. In embodiments, $R^4$ and $R^9$ are joined to form a substituted or unsubstituted $C_5$-$C_7$ cycloalkyl, substituted or unsubstituted 5 to 7 membered heterocycloalkyl, substituted or unsubstituted phenyl, or substituted or unsubstituted 5 to 6 membered heteroaryl. In embodiments, $R^4$ and $R^9$ are joined to form an unsubstituted $C_5$-$C_7$ cycloalkyl, unsubstituted 5 to 7 membered heterocycloalkyl, unsubstituted phenyl, or unsubstituted 5 to 6 membered heteroaryl. In embodiments, $R^4$ and $R^9$ are joined to form an unsubstituted $C_5$ cycloalkyl, unsubstituted thienyl, or unsubstituted phenyl.

In embodiments, Ring A is a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, Ring A is a substituted or unsubstituted $C_5$-$C_7$ cycloalkyl. In embodiments, Ring A is a substituted $C_5$-$C_7$ cycloalkyl. In embodiments, Ring A is an unsubstituted $C_5$-$C_7$ cycloalkyl.

In embodiments, Ring A is a substituted or unsubstituted 5 to 7 membered heterocycloalkyl. In embodiments, Ring A is a substituted 5 to 7 membered heterocycloalkyl. In embodiments, Ring A is an unsubstituted 5 to 7 membered heterocycloalkyl.

In embodiments, Ring A is a substituted or unsubstituted phenyl. In embodiments, Ring A is a substituted phenyl. In embodiments, Ring A is an unsubstituted phenyl.

In embodiments, Ring A is a substituted or unsubstituted 5 to 7 membered heteroaryl. In embodiments, Ring A is a substituted 5 to 7 membered heteroaryl. In embodiments, Ring A is an unsubstituted 5 to 7 membered heteroaryl. In embodiments, Ring A is a substituted or unsubstituted 5 to 6 membered heteroaryl. In embodiments, Ring A is a substituted 5 to 6 membered heteroaryl. In embodiments, Ring A is an unsubstituted 5 to 6 membered heteroaryl.

In embodiments, Ring A is a $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20}$-substituted or unsubstituted aryl (e.g., $C_6$-$C_{10}$ aryl, $C_{10}$ aryl, or phenyl), or $R^{20}$-substituted or unsubstituted heteroaryl (e.g., 5 to 10 membered heteroaryl, 5 to 9 membered heteroaryl, or 5 to 6 membered heteroaryl).

In embodiments, Ring A is an unsubstituted phenyl. In embodiments, Ring A is an unsubstituted $C_5$ cycloalkyl. In embodiments, Ring A is an unsubstituted $C_6$ cycloalkyl. In embodiments, Ring A is an unsubstituted thienyl.

In embodiments, Ring A is a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, Ring A is a substituted cycloalkyl (e.g., $C_3$-$C_8$ cycloalkyl, $C_3$-$C_6$ cycloalkyl, or $C_5$-$C_6$ cycloalkyl). In embodiments, Ring A is a $R^2$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, Ring A is a $R^{20}$-substituted cycloalkyl (e.g., $C_3$-$C_8$ cycloalkyl, $C_3$-$C_6$ cycloalkyl, or $C_5$-$C_6$ cycloalkyl). In embodiments, Ring A is an unsubstituted cycloalkyl (e.g., $C_3$-$C_8$ cycloalkyl, $C_3$-$C_6$ cycloalkyl, or $C_5$-$C_6$ cycloalkyl).

In embodiments, Ring A is a substituted or unsubstituted heterocycloalkyl (e.g., 3 to 8 membered heterocycloalkyl, 3 to 6 membered heterocycloalkyl, or 5 to 6 membered heterocycloalkyl). In embodiments, Ring A is a substituted heterocycloalkyl (e.g., 3 to 8 membered heterocycloalkyl, 3 to 6 membered heterocycloalkyl, or 5 to 6 membered heterocycloalkyl). In embodiments, Ring A is a $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, Ring A is a $R^{20}$-substituted heterocycloalkyl (e.g., 3 to 8 membered heterocycloalkyl, 3 to 6 membered heterocycloalkyl, or 5 to 6 membered heterocycloalkyl). In embodiments, Ring A is an unsubstituted heterocycloalkyl (e.g., 3 to 8 membered heterocycloalkyl, 3 to 6 membered heterocycloalkyl, or 5 to 6 membered heterocycloalkyl).

In embodiments, Ring A is a substituted or unsubstituted aryl (e.g., $C_6$-$C_{10}$ aryl, $C_{10}$ aryl, or phenyl). In embodiments, Ring A is a substituted aryl (e.g., $C_6$-$C_{10}$ aryl, $C_{10}$ aryl, or phenyl). In embodiments, Ring A is a $R^2$-substituted or unsubstituted aryl (e.g., $C_6$-$C_{10}$ aryl, $C_{10}$ aryl, or phenyl). In embodiments, Ring A is a $R^2$-substituted aryl (e.g., $C_6$-$C_{10}$ aryl, $C_{10}$ aryl, or phenyl). In embodiments, Ring A is an unsubstituted aryl (e.g., $C_6$-$C_{10}$ aryl, $C_{10}$ aryl, or phenyl).

In embodiments, Ring A is a substituted or unsubstituted heteroaryl (e.g., 5 to 10 membered heteroaryl, 5 to 9 membered heteroaryl, or 5 to 6 membered heteroaryl). In embodiments, Ring A is a substituted heteroaryl (e.g., 5 to 10 membered heteroaryl, 5 to 9 membered heteroaryl, or 5 to 6 membered heteroaryl). In embodiments, Ring A is a $R^{20}$-substituted or unsubstituted heteroaryl (e.g., 5 to 10 membered heteroaryl, 5 to 9 membered heteroaryl, or 5 to 6 membered heteroaryl). In embodiments, Ring A is a $R^2$-substituted heteroaryl (e.g., 5 to 10 membered heteroaryl, 5 to 9 membered heteroaryl, or 5 to 6 membered heteroaryl). In embodiments, Ring A is an unsubstituted heteroaryl (e.g., 5 to 10 membered heteroaryl, 5 to 9 membered heteroaryl, or 5 to 6 membered heteroaryl).

In embodiments, Ring A is substituted (e.g., $R^{20}$-substituted) or unsubstituted aziridinyl, oxiranyl, thiiranyl, azetidinyl, oxetanyl, thietanyl, pyrrolidinyl, pyrrolyl, imidazolyl, imidazolinyl, pyrazolinyl, tetrahydrofuranyl, thiolanyl, piperidinyl, piperazinyl, pyranyl, morpholinyl, 1,4-dioxanyl, tetrahydro-2H-pyranyl, thianyl, or dithianyl. In embodiments, Ring A is substituted (e.g., $R^{20}$-substituted) or unsubstituted phenyl, thiofuranyl, imidazolyl, pyrazolyl, triazolyl, tetrazolyl, furanyl, oxazolyl, isooxazolyl, oxadiazolyl, oxatriazolyl, thienyl, thiazolyl, isothiazolyl, pyridinyl, pyrazinyl, pyrimidinyl, pyridazinyl, or triazinyl (e.g., 1,3,5-triazinyl, 1,2,3-triazinyl, or 1,2,4-triazinyl). In embodiments, Ring A is substituted (e.g., $R^{20}$-substituted) or unsubstituted indolyl, benzimidazolyl, indazolyl, benzotriazolyl, pyrrolopyrimidinyl, purinyl, indolizinyl, pyrrolopyriazinyl, pyrrolopyrimidinyl, imidazopyridazinyl, imidazopyridinyl, imidazopyrimidinyl, cinnolinyl, quinazolinyl, quinoxalinyl, phthalazinyl, pyridopyrazinyl, pteridinyl, pyrazolopyridinyl, quinolinyl, isoquinolinyl, naphthyridinyl, or carbazolyl.

In embodiments, $R^9$ and $R^{10}$ may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^9$ and $R^{10}$ may optionally be joined to form a substituted or unsubstituted $C_5$-$C_7$ cycloalkyl. In embodiments, $R^9$ and $R^{10}$ may optionally be joined to form a substituted $C_5$-$C_7$ cycloalkyl. In embodiments, $R^9$ and $R^{10}$ may optionally be joined to form an unsubstituted $C_5$-$C_7$ cycloalkyl.

In embodiments, $R^9$ and $R^{10}$ may optionally be joined to form a substituted or unsubstituted 5 to 7 membered heterocycloalkyl. In embodiments, $R^9$ and $R^{10}$ may optionally be joined to form a substituted 5 to 7 membered heterocycloalkyl. In embodiments, $R^9$ and $R^{10}$ may optionally be joined to form an unsubstituted 5 to 7 membered heterocycloalkyl.

In embodiments, $R^9$ and $R^{10}$ may optionally be joined to form a substituted or unsubstituted phenyl. In embodiments, $R^9$ and $R^{10}$ may optionally be joined to form a substituted phenyl. In embodiments, $R^9$ and $R^{10}$ may optionally be joined to form an unsubstituted phenyl.

In embodiments, $R^9$ and $R^{10}$ may optionally be joined to form a substituted or unsubstituted 5 to 7 membered heteroaryl. In embodiments, $R^9$ and $R^{10}$ may optionally be joined to form a substituted 5 to 7 membered heteroaryl. In embodiments, $R^9$ and $R^{10}$ may optionally be joined to form an unsubstituted 5 to 7 membered heteroaryl. In embodiments, $R^9$ and $R^{10}$ may optionally be joined to form a substituted or unsubstituted 5 to 6 membered heteroaryl. In embodiments, $R^9$ and $R^{10}$ may optionally be joined to form a substituted 5 to 6 membered heteroaryl. In embodiments, $R^9$ and $R^{10}$ may optionally be joined to form an unsubstituted 5 to 6 membered heteroaryl.

In embodiments, $R^9$ and $R^{10}$ may optionally be joined to form a $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35}$-substituted or unsubstituted aryl (e.g., $C_6$-$C_{10}$ aryl, $C_{10}$ aryl, or phenyl), or $R^{35}$-substituted or unsubstituted heteroaryl (e.g., 5 to 10 membered heteroaryl, 5 to 9 membered heteroaryl, or 5 to 6 membered heteroaryl). In embodiments, $R^9$ and $R^{10}$ may optionally be joined to form an unsubstituted phenyl. In embodiments, $R^9$ and $R^{10}$ may optionally be joined to form an unsubstituted $C_5$ cycloalkyl. In embodiments, $R^9$ and $R^{10}$ may optionally be joined to form an unsubstituted $C_6$ cycloalkyl. In embodiments, $R^9$ and $R^{10}$ may optionally be joined to form an unsubstituted thienyl.

In embodiments, $R^9$ and $R^{10}$ may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ and $R^{10}$ may optionally be joined to form a substituted cycloalkyl (e.g., $C_3$-$C_8$ cycloalkyl, $C_3$-$C_6$ cycloalkyl, or $C_5$-$C_6$ cycloalkyl). In embodiments, $R^9$ and $R^{10}$ may optionally be joined to form a $R^{35}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ and $R^{10}$ may optionally be joined to form a $R^{35}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ and $R^{10}$ may optionally be joined to form an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^9$ and $R^{10}$ may optionally be joined to forma substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ and $R^{10}$ may optionally be joined to form a substituted heterocycloalkyl (e.g., 3 to 8 membered heterocycloalkyl, 3 to 6 membered heterocycloalkyl, or 5 to 6 membered heterocycloalkyl). In embodiments, $R^9$ and $R^{10}$ may optionally be joined to form a $R^{35}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ and $R^{10}$ may optionally be joined to form a $R^{35}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ and R" may optionally be joined to form an unsubstituted heterocycloalkyl (e.g., 3 to 8 membered heterocycloalkyl, 3 to 6 membered heterocycloalkyl, or 5 to 6 membered heterocycloalkyl).

In embodiments, $R^9$ and $R^{10}$ may optionally be joined to forma substituted or unsubstituted aryl (e.g., $C_6$-$C_{10}$ aryl, $C_{10}$ aryl, or phenyl). In embodiments, $R^9$ and $R^{10}$ may optionally be joined to form a substituted aryl (e.g., $C_6$-$C_{10}$ aryl, $C_{10}$ aryl, or phenyl). In embodiments, $R^9$ and $R^{10}$ may optionally be joined to form a $R^{35}$-substituted or unsubstituted aryl (e.g., $C_6$-$C_{10}$ aryl, $C_{10}$ aryl, or phenyl). In embodiments, $R^9$ and $R^{10}$ may optionally be joined to form a $R^{35}$-substituted aryl (e.g., $C_6$-$C_{10}$ aryl, $C_{10}$ aryl, or phenyl). In embodiments, $R^9$ and $R^{10}$ may optionally be joined to form an unsubstituted aryl (e.g., $C_6$-$C_{10}$ aryl, $C_{10}$ aryl, or phenyl).

In embodiments, $R^9$ and $R^{10}$ may optionally be joined to forma substituted or unsubstituted heteroaryl (e.g., 5 to 10 membered heteroaryl, 5 to 9 membered heteroaryl, or 5 to 6 membered heteroaryl). In embodiments, $R^9$ and $R^{10}$ may optionally be joined to form a substituted heteroaryl (e.g., 5 to 10 membered heteroaryl, 5 to 9 membered heteroaryl, or 5 to 6 membered heteroaryl). In embodiments, $R^9$ and $R^{10}$ may optionally be joined to form a $R^{35}$-substituted or unsubstituted heteroaryl (e.g., 5 to 10 membered heteroaryl, 5 to 9 membered heteroaryl, or 5 to 6 membered heteroaryl). In embodiments, $R^9$ and $R^{10}$ may optionally be joined to form a $R^{35}$-substituted heteroaryl (e.g., 5 to 10 membered heteroaryl, 5 to 9 membered heteroaryl, or 5 to 6 membered heteroaryl). In embodiments, $R^9$ and $R^{10}$ may optionally be joined to form an unsubstituted heteroaryl (e.g., 5 to 10 membered heteroaryl, 5 to 9 membered heteroaryl, or 5 to 6 membered heteroaryl).

In embodiments, $R^{10}$ is halogen, $-CX^{10.1}{}_3$, $-CHX^{10.1}{}_2$, $-CH_2X^{10.1}$, $-CN$, $-N_3$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, $-OCH_2X^{10.1}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is hydrogen.

In embodiments, $R^1$ is halogen, $-CX^{10.1}{}_3$, $-CHX^{10.1}{}_2$, $-CH_2X^{10.1}$, $-CN$, $-N_3$, $-SO_{n10}R^{10A}$, $-SO_{v10}NR^{10B}R^{10C}$, $-NHNR^{10B}R^{10C}$, $-ONR^{10B}R^{10C}$, $-NHC(O)NHNR^{10B}R^{10C}$, $-NHC(O)NR^{10B}R^{10C}$, $-N(O)_{m10}$, $-NR^{10B}R^{10C}$, $-C(O)R^{10D}$, $-C(O)OR^{10D}$, $-C(O)NR^{10B}R^{10C}$, $-OR^{10A}$, $-NR^{10B}SO_2R^{10A}$, $-NR^{10B}C(O)R^{10D}$, $-NR^{10B}C(O)OR^{10D}$, $-NR^{10B}OR^{10D}$, $-OCX^{10.1}{}_3$, $-OCHX^{10.1}{}_2$, $-OCH_2X^{10.1}$, $R^{38}$-substituted or unsubstituted alkyl (e.g., $C_1$-$C_8$ alkyl, $C_1$-$C_6$ alkyl, or $C_1$-$C_4$ alkyl), $R^{38}$-substituted or unsubstituted heteroalkyl (e.g., 2 to 8 membered heteroalkyl, 2 to 6 membered heteroalkyl, or 2 to 4 membered heteroalkyl), $R^3$-substituted or unsubstituted cycloalkyl (e.g., $C_3$-$C_8$ cycloalkyl, $C_3$-$C_6$ cycloalkyl, or C—$C_6$ cycloalkyl), $R^{38}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38}$-substituted or unsubstituted aryl (e.g., $C_6$-$C_{10}$ aryl, $C_{10}$ aryl, or phenyl), or $R^{38}$-substituted or unsubstituted heteroaryl (e.g., 5 to 10 membered heteroaryl, 5 to 9 membered heteroaryl, or 5 to 6 membered heteroaryl).

In embodiments, $R^{10}$ is $R^{38}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R^{38}$-substituted alkyl (e.g., $C_1$-$C_8$ alkyl, $C_1$-$C_6$ alkyl, or $C_1$-$C_4$ alkyl). In embodiments, $R^{10}$ is an unsubstituted alkyl (e.g., $C_1$-$C_8$ alkyl, $C_1$-$C_6$ alkyl, or $C_1$-$C_4$ alkyl).

In embodiments, $R^{10}$ is $R^{38}$-substituted or unsubstituted heteroalkyl (e.g., 2 to 8 membered heteroalkyl, 2 to 6 membered heteroalkyl, or 2 to 4 membered heteroalkyl). In embodiments, $R^{10}$ is $R^{38}$-substituted heteroalkyl (e.g., 2 to 8 membered heteroalkyl, 2 to 6 membered heteroalkyl, or 2 to 4 membered heteroalkyl). In embodiments, $R^{10}$ is an unsubstituted heteroalkyl (e.g., 2 to 8 membered heteroalkyl, 2 to 6 membered heteroalkyl, or 2 to 4 membered heteroalkyl).

In embodiments, $R^{10}$ is $R^{38}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{38}$-substituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{10}$ is $R^{38}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{38}$-substituted heterocycloalkyl (e.g., 3 to 8 membered heterocycloalkyl, 3 to 6 membered heterocycloalkyl, or 5 to 6 membered heterocycloalkyl). In embodiments, $R^{10}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{10}$ is $R^{38}$-substituted or unsubstituted aryl (e.g., $C_6$-$C_{10}$ aryl, $C_{10}$ aryl, or phenyl). In embodiments, $R^{10}$ is $R^{38}$-substituted aryl (e.g., $C_6$-$C_{10}$ aryl, $C_{10}$ aryl, or phenyl). In embodiments, $R^{10}$ is an unsubstituted aryl (e.g., $C_6$-$C_{10}$ aryl, $C_{10}$ aryl, or phenyl).

In embodiments, $R^{10}$ is $R^{38}$-substituted or unsubstituted heteroaryl (e.g., 5 to 10 membered heteroaryl, 5 to 9 membered heteroaryl, or 5 to 6 membered heteroaryl). In embodiments, $R^{10}$ is $R^{38}$-substituted heteroaryl (e.g., 5 to 10 membered heteroaryl, 5 to 9 membered heteroaryl, or 5 to 6 membered heteroaryl). In embodiments, $R^{10}$ is an unsubstituted heteroaryl (e.g., 5 to 10 membered heteroaryl, 5 to 9 membered heteroaryl, or 5 to 6 membered heteroaryl).

In embodiments, $R^{10}$ is hydrogen, —CN, halogen, —CF$_3$, —COOH, —COOCH$_2$CH$_3$,

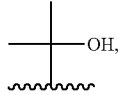

—CH$_3$. In embodiments, $R^{10}$ is hydrogen. In embodiments, $R^{10}$ is —CN. In embodiments, $R^{10}$ is halogen. In embodiments, $R^{10}$ is —F. In embodiments, $R^{10}$ is —Cl. In embodiments, $R^{10}$ is —Br. In embodiments, $R^{10}$ is —I. In embodiments, $R^{10}$ is —CF$_3$. In embodiments, $R^{10}$ is —COOH. In embodiments, $R^{10}$ is —COOCH$_2$CH$_3$. In embodiments, $R^{10}$ is —CH$_3$. In embodiments, $R^{10}$ is —CHCH$_2$CH$_2$OH. In embodiments, $R^{10}$ is

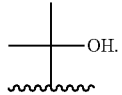

In embodiments, $R^{10}$ is substituted or unsubstituted C$_1$-C$_4$ alkyl. In embodiments, $R^{10}$ is substituted C$_1$-C$_4$ alkyl. In embodiments, $R^{10}$ is unsubstituted C$_1$-C$_4$ alkyl.

In embodiments, $R^{10}$ is halogen, —CF$_3$, —CHF$_2$, —CH$_2$F, —CN, —N$_3$, —SO$_2$CH$_3$, —C(O)R$^{10D}$, —C(O)OR$^{10D}$, substituted or unsubstituted alkyl, substituted or unsubstituted heteroalkyl. In embodiments, $R^{10}$ is halogen, —CF$_3$, —CHF$_2$, —CH$_2$F, —CN, —N$_3$, —SO$_2$CH$_3$, —C(O)R$^{10D}$, —C(O)OR$^{10D}$, substituted or unsubstituted alkyl, substituted or unsubstituted heteroalkyl.

In embodiments, $R^{10}$ is $R^{38}$-substituted or unsubstituted alkyl (e.g., C$_1$-C$_8$ alkyl, C$_1$-C$_6$ alkyl, or C$_1$-C$_4$ alkyl). In embodiments, $R^{10}$ is $R^{38}$-substituted alkyl (e.g., C$_1$-C$_8$ alkyl, C$_1$-C$_6$ alkyl, or C$_1$-C$_4$ alkyl). In embodiments, $R^{10}$ is an unsubstituted alkyl (e.g., C$_1$-C$_8$ alkyl, C$_1$-C$_6$ alkyl, or C$_1$-C$_4$ alkyl).

In embodiments, $R^{10}$ is $R^{38}$-substituted or unsubstituted methyl. In embodiments, $R^{10}$ is $R^{38}$-substituted or unsubstituted C$_2$ alkyl. In embodiments, $R^{10}$ is $R^{38}$-substituted or unsubstituted C$_3$ alkyl. In embodiments, $R^{10}$ is $R^{38}$-substituted or unsubstituted C$_4$ alkyl. In embodiments, $R^{10}$ is $R^{38}$-substituted or unsubstituted C$_5$ alkyl. In embodiments, $R^{10}$ is $R^{38}$-substituted or unsubstituted C$_6$ alkyl. In embodiments, $R^{10}$ is $R^{38}$-substituted or unsubstituted C$_7$ alkyl. In embodiments, $R^{10}$ is $R^{38}$-substituted or unsubstituted C$_8$ alkyl. In embodiments, $R^{10}$ is $R^{38}$-substituted methyl. In embodiments, $R^{10}$ is $R^{38}$-substituted C$_2$ alkyl. In embodiments, $R^{10}$ is $R^{38}$-substituted C$_3$ alkyl. In embodiments, $R^{10}$ is $R^{38}$-substituted C$_4$ alkyl. In embodiments, $R^{10}$ is $R^{38}$-substituted C$_5$ alkyl. In embodiments, $R^{10}$ is $R^{38}$-substituted C$_6$ alkyl. In embodiments, $R^{10}$ is $R^{38}$-substituted C$_7$ alkyl. In embodiments, $R^{10}$ is $R^{38}$-substituted C$_8$ alkyl. In embodiments, $R^{10}$ is an unsubstituted methyl. In embodiments, $R^{10}$ is an unsubstituted C$_2$ alkyl. In embodiments, $R^{10}$ is an unsubstituted C$_3$ alkyl. In embodiments, $R^{10}$ is an unsubstituted C$_4$ alkyl. In embodiments, $R^{10}$ is an unsubstituted C$_5$ alkyl. In embodiments, $R^{10}$ is an unsubstituted C$_6$ alkyl. In embodiments, $R^{10}$ is an unsubstituted C$_7$ alkyl. In embodiments, $R^{10}$ is an unsubstituted C$_8$ alkyl.

In embodiments, $X^3$ is CR$^{10}$; and $R^{10}$ is hydrogen, —CX$^{10.1}_3$, —CHX$^{10.1}_2$, —CH$_2$X$^{10.1}$, —CN, or substituted or unsubstituted C$_1$-C$_4$ alkyl. In embodiments, $X^3$ is CR$^{10}$; and $R^{10}$ is hydrogen. In embodiments, $X^3$ is CR$^{10}$; and $R^{10}$ is —CX$^{10.1}_3$. In embodiments, $X^3$ is CR$^{10}$; and $R^{10}$ is —CHX$^{1012}$. In embodiments, $X^3$ is CR$^{10}$; and $R^{10}$ is —CH$_2$X$^{10.1}$. In embodiments, $X^3$ is CR$^{10}$; and $R^{10}$ is —CN. In embodiments, $X^3$ is CR$^{10}$; and $R^{10}$ is substituted or unsubstituted C$_1$-C$_4$ alkyl. In embodiments, $R^{10}$ is hydrogen or —CN.

In embodiments, $L^7$ is a bond, —O—, —S—, —NR$^{7.2B}$, —C(O)—, —C(O)O—, —S(O)—, —S(O)$_2$—, substituted or unsubstituted alkylene (e.g., C$_1$-C$_8$ alkylene, C$_1$-C$_6$ alkylene, or C$_1$-C$_4$ alkylene), substituted or unsubstituted heteroalkylene (e.g., 2 to 8 membered heteroalkylene, 2 to 6 membered heteroalkylene, or 2 to 4 membered heteroalkylene), substituted or unsubstituted cycloalkylene (e.g., C$_3$-C$_8$ cycloalkylene, C$_3$-C$_6$ cycloalkylene, or C—C$_6$ cycloalkylene), substituted or unsubstituted heterocycloalkylene (e.g., 3 to 8 membered heterocycloalkylene, 3 to 6 membered heterocycloalkylene, or 5 to 6 membered heterocycloalkylene), substituted or unsubstituted arylene (e.g., C$_6$-C$_{10}$ arylene, C$_{10}$ arylene, or phenylene), or substituted or unsubstituted heteroarylene (e.g., 5 to 10 membered heteroarylene, 5 to 9 membered heteroarylene, or 5 to 6 membered heteroarylene).

In embodiments, $L^7$ is a bond, —O—, —S—, —NR$^{7.2B}$, —C(O)—, —C(O)O—, —S(O)—, —S(O)$_2$—, R$^{41}$-substituted or unsubstituted alkylene (e.g., C$_1$-C$_8$ alkylene, C$_1$-C$_6$ alkylene, or C$_1$-C$_4$ alkylene), R$^{41}$-substituted or unsubstituted heteroalkylene (e.g., 2 to 8 membered heteroalkylene, 2 to 6 membered heteroalkylene, or 2 to 4 membered heteroalkylene), R$^{41}$-substituted or unsubstituted cycloalkylene (e.g., C$_3$-C$_8$ cycloalkylene, C$_3$-C$_6$ cycloalkylene, or C—C$_6$ cycloalkylene), R$^{41}$-substituted or unsubstituted heterocycloalkylene (e.g., 3 to 8 membered heterocycloalkylene, 3 to 6 membered heterocycloalkylene, or 5 to 6 membered heterocycloalkylene), R$^{41}$-substituted or unsubstituted arylene (e.g., C$_6$-C$_{10}$ arylene, C$_{10}$ arylene, or phenylene), or R$^{41}$-substituted or unsubstituted heteroarylene (e.g., 5 to 10 membered heteroarylene, 5 to 9 membered heteroarylene, or 5 to 6 membered heteroarylene). In embodiments, $L^7$ is a bond. In embodiments, $L^7$ is a bond, —O—, —S—, —NH—, —C(O)—, —C(O)O—, —S(O)—, —S(O)$_2$—, R$^{41}$-substituted or unsubstituted alkylene (e.g., C$_1$-C$_8$ alkylene, C$_1$-C$_6$ alkylene, or C$_1$-C$_4$ alkylene), R$^{41}$-substituted or unsubstituted heteroalkylene (e.g., 2 to 8 membered heteroalkylene, 2 to 6 membered heteroalkylene, or 2 to 4 membered heteroalkylene), or R$^{41}$-substituted or unsubstituted cycloalkylene (e.g., C$_3$-C$_8$ cycloalkylene, C$_3$-C$_6$ cycloalkylene, or C$_5$-C$_6$ cycloalkylene).

In embodiments, $L^7$ is R$^{41}$-substituted or unsubstituted alkylene (e.g., C$_1$-C$_8$ alkylene, C$_1$-C$_6$ alkylene, or C$_1$-C$_4$ alkylene). In embodiments, $L^7$ is R$^{41}$-substituted alkylene (e.g., C$_1$-C$_8$ alkylene, C$_1$-C$_6$ alkylene, or C$_1$-C$_4$ alkylene). In embodiments, $L^7$ is an unsubstituted alkylene (e.g., C$_1$-C$_8$ alkylene, C$_1$-C$_6$ alkylene, or C$_1$-C$_4$ alkylene). In embodiments, $L^7$ is L$^{41}$-substituted or unsubstituted methylene. In embodiments, $L^7$ is L$^{41}$-substituted or unsubstituted C$_2$ alkylene. In embodiments, $L^7$ is L$^{41}$-substituted or unsubstituted C$_3$ alkylene. In embodiments, $L^7$ is L$^{41}$-substituted or unsubstituted C$_4$ alkylene. In embodiments, $L^7$ is L$^{41}$-substituted or unsubstituted C$_5$ alkylene. In embodiments, $L^7$ is L$^{41}$-substituted or unsubstituted C$_6$ alkylene. In embodiments, $L^7$ is L$^{41}$-substituted or unsubstituted C$_7$ alkylene. In embodiments, $L^7$ is L$^{41}$-substituted or unsubstituted C$_8$ alkylene. In embodiments, $L^7$ is L$^{41}$-substituted methylene. In embodiments, $L^7$ is L$^{41}$-substituted C$_2$ alkylene. In embodiments, $L^7$ is L$^{41}$-substituted C$_3$ alkylene.

In embodiments, $L^7$ is $L^{41}$-substituted $C_4$ alkylene. In embodiments, $L^7$ is $L^{41}$-substituted $C_5$ alkylene. In embodiments, $L^7$ is $L^{41}$-substituted $C_6$ alkylene. In embodiments, $L^7$ is $L^{41}$-substituted $C_7$ alkylene. In embodiments, $L^7$ is $L^{41}$-substituted $C_8$ alkylene. In embodiments, $L^7$ is an unsubstituted methylene. In embodiments, $L^7$ is an unsubstituted $C_2$ alkylene. In embodiments, $L^7$ is an unsubstituted $C_3$ alkylene. In embodiments, $L^7$ is an unsubstituted $C_4$ alkylene. In embodiments, $L^7$ is an unsubstituted $C_5$ alkylene. In embodiments, $L^7$ is an unsubstituted $C_6$ alkylene. In embodiments, $L^7$ is an unsubstituted $C_7$ alkylene. In embodiments, $L^7$ is an unsubstituted $C_8$ alkylene.

In embodiments, $L^7$ is $R^{41}$-substituted or unsubstituted heteroalkylene (e.g., 2 to 8 membered heteroalkylene, 2 to 6 membered heteroalkylene, or 2 to 4 membered heteroalkylene). In embodiments, $L^7$ is $R^{41}$-substituted heteroalkylene (e.g., 2 to 8 membered heteroalkylene, 2 to 6 membered heteroalkylene, or 2 to 4 membered heteroalkylene). In embodiments, $L^7$ is an unsubstituted heteroalkylene (e.g., 2 to 8 membered heteroalkylene, 2 to 6 membered heteroalkylene, or 2 to 4 membered heteroalkylene).

In embodiments, $L^7$ is $R^{41}$-substituted or unsubstituted cycloalkylene (e.g., $C_3$-$C_8$ cycloalkylene, $C_3$-$C_6$ cycloalkylene, or $C_5$-$C_6$ cycloalkylene). In embodiments, $L^7$ is $R^{41}$-substituted cycloalkylene (e.g., $C_3$-$C_8$ cycloalkylene, $C_3$-$C_6$ cycloalkylene, or $C_5$-$C_6$ cycloalkylene). In embodiments, $L^7$ is an unsubstituted cycloalkylene (e.g., $C_3$-$C_8$ cycloalkylene, $C_3$-$C_6$ cycloalkylene, or $C_5$-$C_6$ cycloalkylene). In embodiments, $L^7$ is $R^{41}$-substituted or unsubstituted $C_3$-$C_8$ cycloalkylene. In embodiments, $L^7$ is $R^{41}$-substituted or unsubstituted $C_4$-$C_8$ cycloalkylene. In embodiments, $L^7$ is $R^{41}$-substituted or unsubstituted $C_4$-$C_6$ cycloalkylene. In embodiments, $L^7$ is $R^{41}$-substituted or unsubstituted $C_4$ cycloalkylene. In embodiments, $L^7$ is $R^{41}$-substituted or unsubstituted $C_5$ cycloalkylene. In embodiments, $L^7$ is $R^{41}$-substituted or unsubstituted $C_6$ cycloalkylene. In embodiments, $L^7$ is $R^{41}$-substituted $C_3$-$C_8$ cycloalkylene. In embodiments, $L^7$ is $R^{41}$-substituted $C_4$-$C_8$ cycloalkylene. In embodiments, $L^7$ is $R^{41}$-substituted $C_4$-$C_6$ cycloalkylene. In embodiments, $L^7$ is $R^{41}$-substituted $C_4$ cycloalkylene. In embodiments, $L^7$ is $R^{41}$-substituted $C_5$ cycloalkylene. In embodiments, $L^7$ is $R^{41}$-substituted $C_6$ cycloalkylene. In embodiments, $L^7$ is unsubstituted $C_3$-$C_8$ cycloalkylene. In embodiments, $L^7$ is unsubstituted $C_4$-$C_8$ cycloalkylene. In embodiments, $L^7$ is unsubstituted $C_4$-$C_6$ cycloalkylene. In embodiments, $L^7$ is unsubstituted $C_4$ cycloalkylene. In embodiments, $L^7$ is unsubstituted $C_5$ cycloalkylene. In embodiments, $L^7$ is unsubstituted $C_6$ cycloalkylene.

In embodiments, $L^7$ is $R^{41}$-substituted or unsubstituted heterocycloalkylene (e.g., 3 to 8 membered heterocycloalkylene, 3 to 6 membered heterocycloalkylene, or 5 to 6 membered heterocycloalkylene). In embodiments, $L^7$ is $R^{41}$-substituted heterocycloalkylene (e.g., 3 to 8 membered heterocycloalkylene, 3 to 6 membered heterocycloalkylene, or 5 to 6 membered heterocycloalkylene). In embodiments, $L^7$ is an unsubstituted heterocycloalkylene (e.g., 3 to 8 membered heterocycloalkylene, 3 to 6 membered heterocycloalkylene, or 5 to 6 membered heterocycloalkylene).

In embodiments, $L^7$ is $R^{41}$-substituted or unsubstituted arylene (e.g., $C_6$-$C_{10}$ arylene, $C_{10}$ arylene, or phenylene). In embodiments, $L^7$ is $R^{41}$-substituted arylene (e.g., $C_6$-$C_{10}$ arylene, $C_{10}$ arylene, or phenylene). In embodiments, $L^7$ is an unsubstituted arylene (e.g., $C_6$-$C_{10}$ arylene, $C_{10}$ arylene, or phenylene).

In embodiments, $L^7$ is $R^{41}$-substituted or unsubstituted heteroarylene (e.g., 5 to 10 membered heteroarylene, 5 to 9 membered heteroarylene, or 5 to 6 membered heteroarylene). In embodiments, $L^7$ is $R^{41}$-substituted heteroarylene (e.g., 5 to 10 membered heteroarylene, 5 to 9 membered heteroarylene, or 5 to 6 membered heteroarylene). In embodiments, $L^7$ is an unsubstituted heteroarylene (e.g., 5 to 10 membered heteroarylene, 5 to 9 membered heteroarylene, or 5 to 6 membered heteroarylene).

In embodiments, $L^7$ is a bond, substituted or unsubstituted alkylene, or substituted or unsubstituted cycloalkylene. In embodiments, $L^7$ is a substituted or unsubstituted $C_4$-$C_6$ cycloalkylene. In embodiments, $L^7$ is an unsubstituted $C_4$-$C_6$ cycloalkylene. In embodiments, $L^7$ is a substituted or unsubstituted cyclobutylene. In embodiments, $L^7$ is a substituted or unsubstituted alkylene. In embodiments, $L^7$ is a substituted or unsubstituted $C_1$-$C_6$ alkylene. In embodiments, $L^7$ is a bond.

In embodiments, $L^7$ is $R^{41}$-substituted or unsubstituted $C_1$-$C_6$ alkylene. In embodiments, $L^7$ is $R^{41}$-substituted $C_1$-$C_6$ alkylene. In embodiments, $L^7$ is unsubstituted $C_1$-$C_6$ alkylene. In embodiments, $L^7$ is $R^{41}$-substituted or unsubstituted $C_2$-$C_6$ alkylene. In embodiments, $L^7$ is $R^{41}$-substituted $C_2$-$C_6$ alkylene. In embodiments, $L^7$ is unsubstituted $C_2$-$C_6$ alkylene. In embodiments, $L^7$ is $R^{41}$-substituted or unsubstituted $C_1$ alkylene. In embodiments, $L^7$ is $R^{41}$-substituted $C_1$ alkylene. In embodiments, $L^7$ is unsubstituted $C_1$ alkylene. In embodiments, $L^7$ is $R^{41}$-substituted or unsubstituted $C_2$ alkylene. In embodiments, $L^7$ is $R^{41}$-substituted $C_2$ alkylene. In embodiments, $L^7$ is unsubstituted $C_2$ alkylene. In embodiments, $L^7$ is $R^{41}$-substituted or unsubstituted $C_3$ alkylene. In embodiments, $L^7$ is $R^{41}$-substituted $C_3$ alkylene. In embodiments, $L^7$ is unsubstituted $C_3$ alkylene. In embodiments, $L^7$ is $R^{41}$-substituted or unsubstituted $C_4$ alkylene. In embodiments, $L^7$ is $R^{41}$-substituted $C_4$ alkylene. In embodiments, $L^7$ is unsubstituted $C_4$ alkylene. In embodiments, $L^7$ is $R^{41}$-substituted or unsubstituted $C_5$ alkylene. In embodiments, $L^7$ is $R^{41}$-substituted $C_5$ alkylene. In embodiments, $L^7$ is unsubstituted $C_5$ alkylene. In embodiments, $L^7$ is $R^{41}$-substituted or unsubstituted $C_6$ alkylene. In embodiments, $L^7$ is $R^{41}$-substituted $C_6$ alkylene. In embodiments, $L^7$ is unsubstituted $C_6$ alkylene.

In embodiments, $L^7$ is $R^{41}$-substituted or unsubstituted 2 to 8 membered heteroalkylene. In embodiments, $L^7$ is $R^{41}$-substituted 2 to 8 membered heteroalkylene. In embodiments, $L^7$ is unsubstituted 2 to 8 membered heteroalkylene. In embodiments, $L^7$ is $R^{41}$-substituted or unsubstituted 2 membered heteroalkylene. In embodiments, $L^7$ is $R^{41}$-substituted 2 membered heteroalkylene. In embodiments, $L^7$ is unsubstituted 2 membered heteroalkylene. In embodiments, $L^7$ is $R^{41}$-substituted or unsubstituted 3 membered heteroalkylene. In embodiments, $L^7$ is $R^{41}$-substituted 3 membered heteroalkylene. In embodiments, $L^7$ is unsubstituted 3 membered heteroalkylene. In embodiments, $L^7$ is $R^{41}$-substituted or unsubstituted 4 membered heteroalkylene. In embodiments, $L^7$ is $R^{41}$-substituted 4 membered heteroalkylene. In embodiments, $L^7$ is unsubstituted 4 membered heteroalkylene. In embodiments, $L^7$ is $R^{41}$-substituted or unsubstituted 5 membered heteroalkylene. In embodiments, $L^7$ is $R^{41}$-substituted 5 membered heteroalkylene. In embodiments, $L^7$ is unsubstituted 5 membered heteroalkylene. In embodiments, $L^7$ is $R^{41}$-substituted or unsubstituted 6 membered heteroalkylene. In embodiments, $L^7$ is $R^{41}$-substituted 6 membered heteroalkylene. In embodiments, $L^7$ is unsubstituted 6 membered heteroalkylene. In embodiments, $L^7$ is $R^{41}$-substituted or unsubstituted 7 membered heteroalkylene. In embodiments, $L^7$ is $R^{41}$-substituted 7 membered heteroalkylene. In embodiments, $L^7$ is unsubstituted 7 membered heteroalkylene.

In embodiments, $L^7$ is $R^{41}$-substituted or unsubstituted $C_4$-$C_6$ cycloalkylene. In embodiments, $L^7$ is $R^{41}$-substituted $C_4$-$C_6$ cycloalkylene. In embodiments, $L^7$ is $R^{41}$-substituted $C_4$-$C_6$ cycloalkylene. In embodiments, $L^7$ is $R^{41}$-substituted or unsubstituted $C_4$ cycloalkylene. In embodiments, $L^7$ is $R^{41}$-substituted $C_4$ cycloalkylene. In embodiments, $L^7$ is $R^{41}$-substituted $C_4$ cycloalkylene. In embodiments, $L^7$ is $R^{41}$-substituted or unsubstituted $C_5$ cycloalkylene. In embodiments, $L^7$ is $R^{41}$-substituted $C_5$ cycloalkylene. In embodiments, $L^7$ is $R^{41}$-substituted $C_5$ cycloalkylene.

In embodiments, $L^7$ is $R^{41}$-substituted or unsubstituted 5 to 6 membered heterocycloalkylene. In embodiments, $L^7$ is $R^{41}$-substituted 5 to 6 membered heterocycloalkylene. In embodiments, $L^7$ is unsubstituted 5 to 6 membered heterocycloalkylene. In embodiments, $L^7$ is $R^{41}$-substituted or unsubstituted 5 membered heterocycloalkylene. In embodiments, $L^7$ is $R^{41}$-substituted 5 membered heterocycloalkylene. In embodiments, $L^7$ is unsubstituted 5 membered heterocycloalkylene. In embodiments, $L^7$ is $R^{41}$-substituted or unsubstituted 6 membered heterocycloalkylene. In embodiments, $L^7$ is $R^{41}$-substituted 6 membered heterocycloalkylene. In embodiments, $L^7$ is unsubstituted 6 membered heterocycloalkylene.

In embodiments, $L^7$ is $R^{41}$-substituted or unsubstituted phenylene. In embodiments, $L^7$ is $R^{41}$-substituted phenylene. In embodiments, $L^7$ is unsubstituted phenylene.

In embodiments, $L^7$ is $R^{41}$-substituted or unsubstituted 5 to 6 membered heteroarylene. In embodiments, $L^7$ is $R^{41}$-substituted 5 to 6 membered heteroarylene. In embodiments, $L^7$ is unsubstituted 5 to 6 membered heteroarylene. In embodiments, $L^7$ is $R^{41}$-substituted or unsubstituted 5 membered heteroarylene. In embodiments, $L^7$ is $R^{41}$-substituted 5 membered heteroarylene. In embodiments, $L^7$ is unsubstituted 5 membered heteroarylene. In embodiments, $L^7$ is $R^{41}$-substituted or unsubstituted 6 membered heteroarylene. In embodiments, $L^7$ is $R^{41}$-substituted 6 membered heteroarylene. In embodiments, $L^7$ is unsubstituted 6 membered heteroarylene.

In embodiments, $L^7$ is

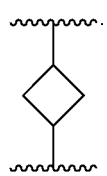 [SMILES: *C1CC(*)C1]

In embodiments, $L^7$ is —$CH_2CH_2$—. In embodiments, $L^7$ is

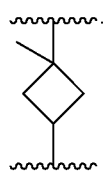 [SMILES: *C1CC(*)(C)C1]

In embodiments, $L^7$ is

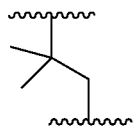

In embodiments, $L^7$ is

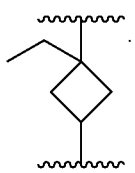 [SMILES: *C1CC(*)(CC)C1]

In embodiments, $L^7$ is

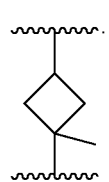 [SMILES: *C1CC(*)(C)C1]

In embodiments, $L^7$ is

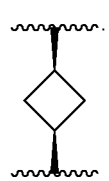 [SMILES: *[C@H]1C[C@@H](*)C1]

In embodiments, $L^7$ is

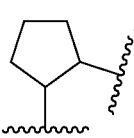

In embodiments, $L^7$ is

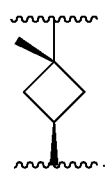 [SMILES: *[C@H]1C[C@@](*)(C)C1]

In embodiments, $L^7$ is

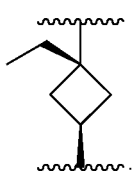 [SMILES: *[C@H]1C[C@@](*)(CC)C1]

In embodiments, L⁷ is

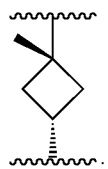

In embodiments, L⁷ is —CH₂—. In embodiments, L⁷ is —CH₂CH₂CH₂—. In embodiments, L⁷ is

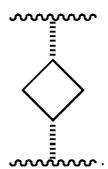

In embodiments, L⁷ is,

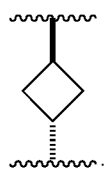

In embodiments, L⁷ is

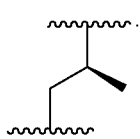 [SMILES: *C[C@@H](*)C]

In embodiments, L⁷ is

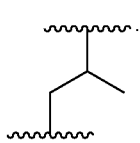

In embodiments, L⁷ is

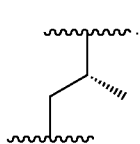 [SMILES: *C[C@H](*)C]

In embodiments, L⁷ is

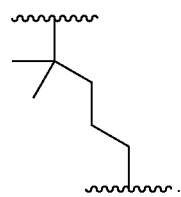 [SMILES: *CCCC(*)(C)C]

In embodiments, L⁷ is

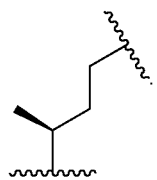 [SMILES: *CC[C@@H](*)C]

In embodiments, L⁷ is

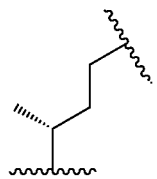

In embodiments, L⁷ is

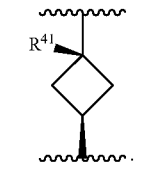

In embodiments, L⁷ is unsubstituted methylene. In embodiments, L⁷ is unsubstituted ethylene. In embodiments, L⁷ is unsubstituted propylene. In embodiments, L⁷ is unsubstituted n-propylene. In embodiments, L⁷ is unsubstituted isopropylene. In embodiments, L⁷ is unsubstituted butylene. In embodiments, L⁷ is unsubstituted n-butylene. In embodiments, L⁷ is unsubstituted isobutylene. In embodiments, L⁷ is unsubstituted tert-butylene. In embodiments, L⁷ is unsubstituted pentylene. In embodiments, L⁷ is unsubstituted n-pentylene. In embodiments, L⁷ is unsubstituted hexylene. In embodiments, L⁷ is unsubstituted heptylene. In embodiments, L⁷ is substituted methylene. In embodiments, L⁷ is substituted ethylene. In embodiments, L⁷ is substituted propylene. In embodiments, L⁷ is substituted n-propylene. In embodiments, L⁷ is substituted isopropylene. In embodiments, L⁷ is substituted butylene. In embodiments, L⁷ is substituted n-butylene. In embodiments, L⁷ is substituted isobutylene. In embodiments, L⁷ is substituted tert-butylene. In embodiments, L⁷ is substituted pentylene. In embodiments, L⁷ is substituted n-pentylene. In embodiments, L⁷ is substituted hexylene. In embodiments, L⁷ is substituted heptylene.

In embodiments, -L⁷-R⁷ is carboxylic acid substituted cyclobutyl, carboxylic acid substituted cyclopentyl, or hydroxyl substituted ethyl; all optionally further substituted with substituted or unsubstituted alkyl (e.g., $C_1$-$C_8$ alkyl, $C_1$-$C_6$ alkyl, or $C_1$-$C_4$ alkyl).

In embodiments, -L⁷-R⁷ is

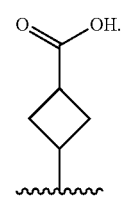 [SMILES: *C1CC(C(=O)O)C1]

In embodiments, -L⁷-R⁷ is
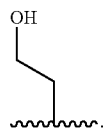
In embodiments, -L⁷-R⁷ is
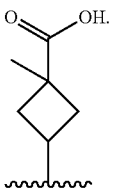
In embodiments, -L⁷-R⁷ is
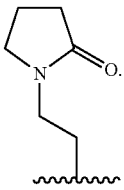 [SMILES: *CCN1CCCC1=O]
In embodiments, -L⁷-R⁷ is
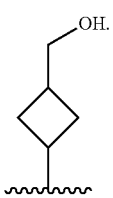 [SMILES: *C1CC(CO)C1]
In embodiments, -L⁷-R⁷ is
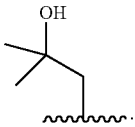 [SMILES: *CC(C)(C)O]
In embodiments, -L⁷-R⁷ is
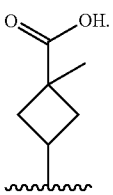 [SMILES: *C1CC(C)(C(=O)O)C1]
In embodiments, -L⁷-R⁷ is
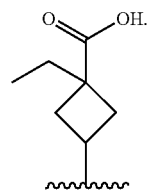
In embodiments, -L⁷-R⁷ is
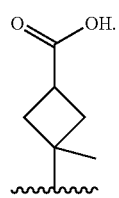 [SMILES: *C1(C)CC(C(=O)O)C1]
In embodiments, -L⁷-R⁷ is
In embodiments, -L⁷-R⁷ is
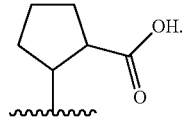 [SMILES: *C1CCCC1C(=O)O]
In embodiments, -L⁷-R⁷ is
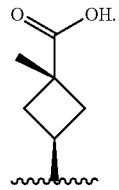 [SMILES: *[C@H]1C[C@](C)(C(=O)O)C1]
In embodiments, -L⁷-R⁷ is
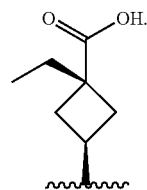

In embodiments, -L⁷-R⁷ is
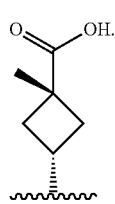 [SMILES: *[C@H]1C[C@@](C)(C(=O)O)C1]
In embodiments, -L⁷-R⁷ is
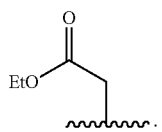
In embodiments, -L⁷-R⁷ is
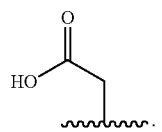
In embodiments, -L⁷-R⁷ is
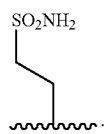
In embodiments, -L⁷-R⁷ is
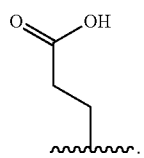
In embodiments, -L⁷-R⁷ is,
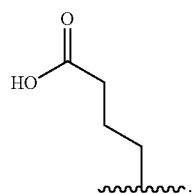
In embodiments, -L⁷-R⁷ is
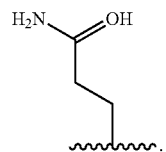
In embodiments, -L⁷-R⁷ is
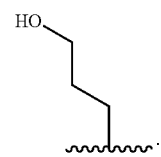
In embodiments, -L⁷-R⁷ is
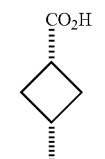
In embodiments, -L⁷-R⁷ is
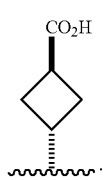
In embodiments, -L⁷-R⁷ is
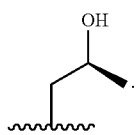 [SMILES: *C[C@H](C)O]
In embodiments, -L⁷-R⁷ is
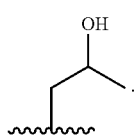
In embodiments, -L⁷-R⁷ is
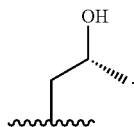

In embodiments, -L⁷-R⁷ is,
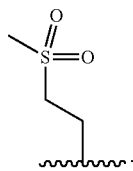 [SMILES: *CCS(C)(=O)=O]
In embodiments, -L⁷-R⁷ is
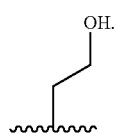
In embodiments, -L⁷-R⁷ is
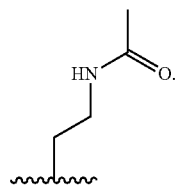 [SMILES: *CCNC(C)=O]
In embodiments, -L⁷-R⁷ is,
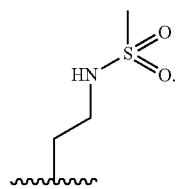 [SMILES: *CCNS(C)(=O)=O]
In embodiments, -L⁷-R⁷ is
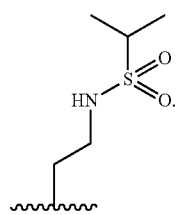 [SMILES: *CCNS(=O)(=O)C(C)C]
In embodiments, -L⁷-R⁷ is
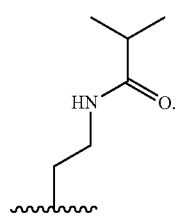 [SMILES: *CCNC(=O)C(C)C]
In embodiments, -L⁷-R⁷ is
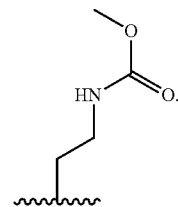
In embodiments, -L⁷-R⁷ is
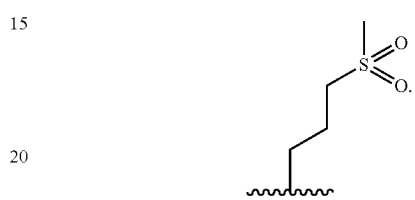
In embodiments, -L⁷-R⁷ is,
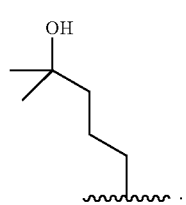 [SMILES: *CCCC(C)(C)O]
In embodiments, -L⁷-R⁷ is
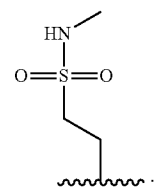 [SMILES: *CCS(=O)(=O)NC]
In embodiments, -L⁷-R⁷ is,
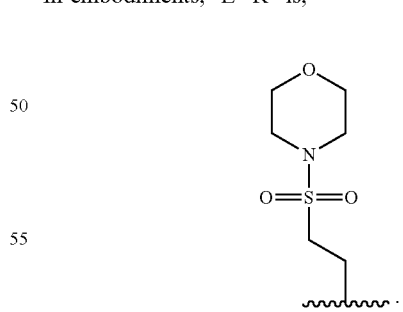
In embodiments, -L⁷-R⁷ is
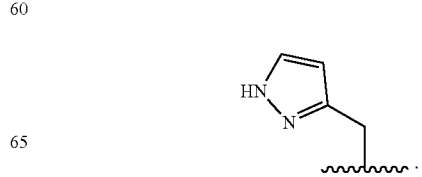

In embodiments, -L⁷-R⁷ is
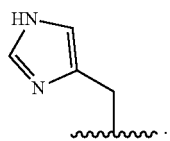
In embodiments, -L⁷-R⁷ is
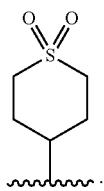
In embodiments, -L⁷-R⁷ is
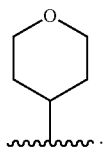
In embodiments, -L⁷-R⁷ is
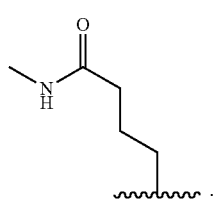 [SMILES: *CCCC(=O)NC]
In embodiments, -L⁷-R⁷ is
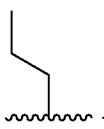
In embodiments, -L⁷-R⁷ is
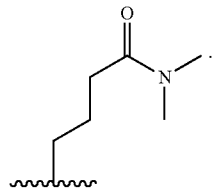 [SMILES: *CCCC(=O)N(C)C]
In embodiments, -L⁷-R⁷ is
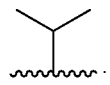
In embodiments, -L⁷-R⁷ is,
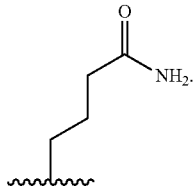 [SMILES: *CCCC(N)=O]
In embodiments, -L⁷-R⁷ is
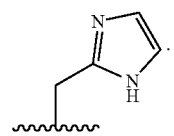
In embodiments, -L⁷-R⁷ is
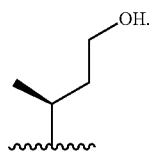
In embodiments, -L⁷-R⁷ is
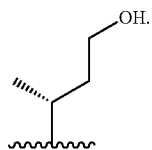 [SMILES: *[C@H](C)CCO]
In embodiments, -L⁷-R⁷ is
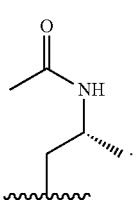 [SMILES: *C[C@@H](C)NC(C)=O]
In embodiments, -L⁷-R⁷ is
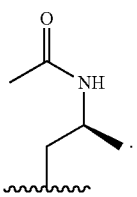 [SMILES: *C[C@H](C)NC(C)=O]

In embodiments, -L⁷-R⁷ is

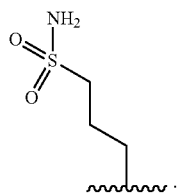 [SMILES: *CCCS(N)(=O)=O]

In embodiments, -L⁷-R⁷ is

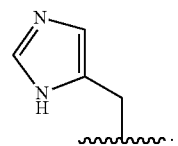 [SMILES: *Cc1cnc[nH]1]

In embodiments, $R^{1A}$ is hydrogen, halogen, —CF$_3$, —CCl$_3$, —CBr$_3$, —CI$_3$, —COOH, —CONH$_2$, $R^{11A}$-substituted or unsubstituted alkyl (e.g., C$_1$-C$_8$ alkyl, C$_1$-C$_6$ alkyl, or C$_1$-C$_4$ alkyl), $R^{11A}$-substituted or unsubstituted heteroalkyl (e.g., 2 to 8 membered heteroalkyl, 2 to 6 membered heteroalkyl, or 2 to 4 membered heteroalkyl), $R^{11A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{11A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11A}$-substituted or unsubstituted aryl (e.g., C$_6$-C$_{10}$ aryl, C$_{10}$ aryl, or phenyl), or $R^{11A}$-substituted or unsubstituted heteroaryl (e.g., 5 to 10 membered heteroaryl, 5 to 9 membered heteroaryl, or 5 to 6 membered heteroaryl).

In embodiments, $R^{2A}$ is hydrogen, halogen, —CF$_3$, —CCl$_3$, —CBr$_3$, —CI$_3$, —COOH, —CONH$_2$, $R^{14A}$-substituted or unsubstituted alkyl (e.g., C$_1$-C$_8$ alkyl, C$_1$-C$_6$ alkyl, or C$_1$-C$_4$ alkyl), $R^{14A}$-substituted or unsubstituted heteroalkyl (e.g., 2 to 8 membered heteroalkyl, 2 to 6 membered heteroalkyl, or 2 to 4 membered heteroalkyl), $R^{14A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{14A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14A}$-substituted or unsubstituted aryl (e.g., C$_6$-C$_{10}$ aryl, C$_{10}$ aryl, or phenyl), or $R^{14A}$-substituted or unsubstituted heteroaryl (e.g., 5 to 10 membered heteroaryl, 5 to 9 membered heteroaryl, or 5 to 6 membered heteroaryl).

In embodiments, $R^{3A}$ is hydrogen, halogen, —CF$_3$, —CCl$_3$, —CBr$_3$, —CI$_3$, —COOH, —CONH$_2$, $R^{17A}$-substituted or unsubstituted alkyl (e.g., C$_1$-C$_8$ alkyl, C$_1$-C$_6$ alkyl, or C$_1$-C$_4$ alkyl), $R^{17A}$-substituted or unsubstituted heteroalkyl (e.g., 2 to 8 membered heteroalkyl, 2 to 6 membered heteroalkyl, or 2 to 4 membered heteroalkyl), $R^{17A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{17A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17A}$-substituted or unsubstituted aryl (e.g., C$_6$-C$_{10}$ aryl, C$_{10}$ aryl, or phenyl), or $R^{17A}$-substituted or unsubstituted heteroaryl (e.g., 5 to 10 membered heteroaryl, 5 to 9 membered heteroaryl, or 5 to 6 membered heteroaryl).

In embodiments, $R^{3.2A}$, is hydrogen, halogen, —CF$_3$, —CCl$_3$, —CBr$_3$, —CI$_3$, —COOH, —CONH$_2$, $R^{17.2A}$-substituted or unsubstituted alkyl (e.g., C$_1$-C$_8$ alkyl, C$_1$-C$_6$ alkyl, or C$_1$-C$_4$ alkyl), $R^{17.2A}$-substituted or unsubstituted heteroalkyl (e.g., 2 to 8 membered heteroalkyl, 2 to 6 membered heteroalkyl, or 2 to 4 membered heteroalkyl), $R^{17.2A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{17.2A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.2A}$-substituted or unsubstituted aryl (e.g., C$_6$-C$_{10}$ aryl, C$_{10}$ aryl, or phenyl), or $R^{17.2A}$-substituted or unsubstituted heteroaryl (e.g., 5 to 10 membered heteroaryl, 5 to 9 membered heteroaryl, or 5 to 6 membered heteroaryl).

In embodiments, $R^{3.3A}$ is hydrogen, halogen, —CF$_3$, —CCl$_3$, —CBr$_3$, —CI$_3$, —COOH, —CONH$_2$, $R^{17.3A}$-substituted or unsubstituted alkyl (e.g., C$_1$-C$_8$ alkyl, C$_1$-C$_6$ alkyl, or C$_1$-C$_4$ alkyl), $R^{17.3A}$-substituted or unsubstituted heteroalkyl (e.g., 2 to 8 membered heteroalkyl, 2 to 6 membered heteroalkyl, or 2 to 4 membered heteroalkyl), $R^{17.3A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{17.3A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.3A}$-substituted or unsubstituted aryl (e.g., C$_6$-C$_{10}$ aryl, C$_{10}$ aryl, or phenyl), or $R^{17.3A}$-substituted or unsubstituted heteroaryl (e.g., 5 to 10 membered heteroaryl, 5 to 9 membered heteroaryl, or 5 to 6 membered heteroaryl).

In embodiments, $R^{4A}$ is hydrogen, halogen, —CF$_3$, —CCl$_3$, —CBr$_3$, —CI$_3$, —COOH, —CONH$_2$, $R^{20A}$-substituted or unsubstituted alkyl (e.g., C$_1$-C$_8$ alkyl, C$_1$-C$_6$ alkyl, or C$_1$-C$_4$ alkyl), $R^{20A}$-substituted or unsubstituted heteroalkyl (e.g., 2 to 8 membered heteroalkyl, 2 to 6 membered heteroalkyl, or 2 to 4 membered heteroalkyl), $R^{20A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{20A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20A}$-substituted or unsubstituted aryl (e.g., C$_6$-C$_{10}$ aryl, C$_{10}$ aryl, or phenyl), or $R^{20A}$-substituted or unsubstituted heteroaryl (e.g., 5 to 10 membered heteroaryl, 5 to 9 membered heteroaryl, or 5 to 6 membered heteroaryl).

In embodiments, $R^{5A}$ is hydrogen, halogen, —CF$_3$, —CCl$_3$, —CBr$_3$, —CI$_3$, —COOH, —CONH$_2$, $R^{23A}$-substituted or unsubstituted alkyl (e.g., C$_1$-C$_8$ alkyl, C$_1$-C$_6$ alkyl, or C$_1$-C$_4$ alkyl), $R^{23A}$-substituted or unsubstituted heteroalkyl (e.g., 2 to 8 membered heteroalkyl, 2 to 6 membered heteroalkyl, or 2 to 4 membered heteroalkyl), $R^{23A}$-substituted or unsubstituted cycloalkyl (e.g., C$_3$-C$_8$ cycloalkyl, C$_3$-C$_6$ cycloalkyl, or C$_5$-C$_6$ cycloalkyl), $R^{23A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23A}$-substituted or unsubstituted aryl (e.g., C$_6$-C$_{10}$ aryl, C$_{10}$ aryl, or phenyl), or $R^{23A}$-substituted or unsubstituted heteroaryl (e.g., 5 to 10 membered heteroaryl, 5 to 9 membered heteroaryl, or 5 to 6 membered heteroaryl).

In embodiments, $R^{6A}$ is hydrogen, halogen, —CF$_3$, —CCl$_3$, —CBr$_3$, —CI$_3$, —COOH, —CONH$_2$, $R^{26A}$-substituted or unsubstituted alkyl (e.g., C$_1$-C$_8$ alkyl, C$_1$-C$_6$ alkyl, or C$_1$-C$_4$ alkyl), $R^{26A}$-substituted or unsubstituted heteroalkyl (e.g., 2 to 8 membered heteroalkyl, 2 to 6 membered heteroalkyl, or 2 to 4 membered heteroalkyl), $R^{26A}$-substituted or unsubstituted cycloalkyl (e.g., C$_3$-C$_8$ cycloalkyl, $C_3$-$C_6$ cycloalkyl, or $C_5$-$C_6$ cycloalkyl), $R^{26A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26A}$-substituted or unsubstituted aryl (e.g., $C_6$-$C_{10}$ aryl, $C_{10}$ aryl, or phenyl), or $R^{26A}$-substituted or unsubstituted heteroaryl (e.g., 5 to 10 membered heteroaryl, 5 to 9 membered heteroaryl, or 5 to 6 membered heteroaryl).

In embodiments, $R^{7A}$ is hydrogen, halogen, —$CF_3$, —$CCl_3$, —$CBr_3$, —$CI_3$, —COOH, —$CONH_2$, $R^{29A}$-substituted or unsubstituted alkyl (e.g., $C_1$-$C_8$ alkyl, $C_1$-$C_6$ alkyl, or $C_1$-$C_4$ alkyl), $R^{29A}$-substituted or unsubstituted heteroalkyl (e.g., 2 to 8 membered heteroalkyl, 2 to 6 membered heteroalkyl, or 2 to 4 membered heteroalkyl), $R^{29A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29A}$-substituted or unsubstituted aryl (e.g., $C_6$-$C_{10}$ aryl, $C_{10}$ aryl, or phenyl), or $R^{29A}$-substituted or unsubstituted heteroaryl (e.g., 5 to 10 membered heteroaryl, 5 to 9 membered heteroaryl, or 5 to 6 membered heteroaryl).

In embodiments, $R^{8A}$ is hydrogen, halogen, —$CF_3$, —$CCl_3$, —$CBr_3$, —$CI_3$, —COOH, —$CONH_2$, $R^{32A}$-substituted or unsubstituted alkyl (e.g., $C_1$-$C_8$ alkyl, $C_1$-$C_6$ alkyl, or $C_1$-$C_4$ alkyl), $R^{32A}$-substituted or unsubstituted heteroalkyl (e.g., 2 to 8 membered heteroalkyl, 2 to 6 membered heteroalkyl, or 2 to 4 membered heteroalkyl), $R^{32A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32A}$-substituted or unsubstituted aryl (e.g., $C_6$-$C_{10}$ aryl, $C_{10}$ aryl, or phenyl), or $R^{32A}$-substituted or unsubstituted heteroaryl (e.g., 5 to 10 membered heteroaryl, 5 to 9 membered heteroaryl, or 5 to 6 membered heteroaryl).

In embodiments, $R^{9A}$ is hydrogen, halogen, —$CF_3$, —$CCl_3$, —$CBr_3$, —$CI_3$, —COOH, —$CONH_2$, $R^{35A}$-substituted or unsubstituted alkyl (e.g., $C_1$-$C_8$ alkyl, $C_1$-$C_6$ alkyl, or $C_1$-$C_4$ alkyl), $R^{35A}$-substituted or unsubstituted heteroalkyl (e.g., 2 to 8 membered heteroalkyl, 2 to 6 membered heteroalkyl, or 2 to 4 membered heteroalkyl), $R^{35A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35A}$-substituted or unsubstituted aryl (e.g., $C_6$-$C_{10}$ aryl, $C_{10}$ aryl, or phenyl), or $R^{35A}$-substituted or unsubstituted heteroaryl (e.g., 5 to 10 membered heteroaryl, 5 to 9 membered heteroaryl, or 5 to 6 membered heteroaryl).

In embodiments, $R^{10A}$, is hydrogen, halogen, —$CF_3$, —$CCl_3$, —$CBr_3$, —$CI_3$, —COOH, —$CONH_2$, $R^{38A}$-substituted or unsubstituted alkyl (e.g., $C_1$-$C_8$ alkyl, $C_1$-$C_6$ alkyl, or $C_1$-$C_4$ alkyl), $R^{38A}$-substituted or unsubstituted heteroalkyl (e.g., 2 to 8 membered heteroalkyl, 2 to 6 membered heteroalkyl, or 2 to 4 membered heteroalkyl), $R^{38A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38A}$-substituted or unsubstituted aryl (e.g., $C_6$-$C_{10}$ aryl, $C_{10}$ aryl, or phenyl), or $R^{38A}$-substituted or unsubstituted heteroaryl (e.g., 5 to 10 membered heteroaryl, 5 to 9 membered heteroaryl, or 5 to 6 membered heteroaryl).

In embodiments, $R^{44A}$ is hydrogen, halogen, —$CF_3$, —$CCl_3$, —$CBr_3$, —$CI_3$, —COOH, —$CONH_2$, $R^{45A}$-substituted or unsubstituted alkyl (e.g., $C_1$-$C_8$ alkyl, $C_1$-$C_6$ alkyl, or $C_1$-$C_4$ alkyl), $R^{45A}$-substituted or unsubstituted heteroalkyl (e.g., 2 to 8 membered heteroalkyl, 2 to 6 membered heteroalkyl, or 2 to 4 membered heteroalkyl), $R^{45A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45A}$-substituted or unsubstituted aryl (e.g., $C_6$-$C_{10}$ aryl, $C_{10}$ aryl, or phenyl), or $R^{45A}$-substituted or unsubstituted heteroaryl (e.g., 5 to 10 membered heteroaryl, 5 to 9 membered heteroaryl, or 5 to 6 membered heteroaryl).

In embodiments, RB is hydrogen, halogen, —$CF_3$, —$CCl_3$, —$CBr_3$, —$CI_3$, —COOH, —$CONH_2$, $R^{11B}$-substituted or unsubstituted alkyl (e.g., $C_1$-$C_8$ alkyl, $C_1$-$C_6$ alkyl, or $C_1$-$C_4$ alkyl), $R^{11B}$-substituted or unsubstituted heteroalkyl (e.g., 2 to 8 membered heteroalkyl, 2 to 6 membered heteroalkyl, or 2 to 4 membered heteroalkyl), $R^{11B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11B}$-substituted or unsubstituted aryl (e.g., $C_6$-$C_{10}$ aryl, $C_{10}$ aryl, or phenyl), or $R^{11B}$-substituted or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$ substituents bonded to the same nitrogen atom may optionally be joined to form a $R^{11B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{11B}$-substituted or unsubstituted heteroaryl (e.g., 5 to 10 membered heteroaryl, 5 to 9 membered heteroaryl, or 5 to 6 membered heteroaryl).

In embodiments, $R^{2B}$ is hydrogen, halogen, —$CF_3$, —$CCl_3$, —$CBr_3$, —$CI_3$, —COOH, —$CONH_2$, $R^{14B}$-substituted or unsubstituted alkyl (e.g., $C_1$-$C_8$ alkyl, $C_1$-$C_6$ alkyl, or $C_1$-$C_4$ alkyl), $R^{14B}$-substituted or unsubstituted heteroalkyl (e.g., 2 to 8 membered heteroalkyl, 2 to 6 membered heteroalkyl, or 2 to 4 membered heteroalkyl), $R^{14B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14B}$-substituted or unsubstituted aryl (e.g., $C_6$-$C_{10}$ aryl, $C_{10}$ aryl, or phenyl), or $R^{14B}$-substituted or unsubstituted heteroaryl (e.g., 5 to 10 membered heteroaryl, 5 to 9 membered heteroaryl, or 5 to 6 membered heteroaryl). In embodiments, $R^{2B}$ and $R^{2C}$ substituents bonded to the same nitrogen atom may optionally be joined to form a $R^{14B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{14B}$-substituted or unsubstituted heteroaryl (e.g., 5 to 10 membered heteroaryl, 5 to 9 membered heteroaryl, or 5 to 6 membered heteroaryl).

In embodiments, $R^{3B}$ is hydrogen, halogen, —$CF_3$, —$CCl_3$, —$CBr_3$, —$CI_3$, —COOH, —$CONH_2$, $R^{17B}$-substituted or unsubstituted alkyl (e.g., $C_1$-$C_8$ alkyl, $C_1$-$C_6$ alkyl, or $C_1$-$C_4$ alkyl), $R^{17B}$-substituted or unsubstituted heteroalkyl (e.g., 2 to 8 membered heteroalkyl, 2 to 6 membered heteroalkyl, or 2 to 4 membered heteroalkyl), $R^{17B}$-substituted or unsubstituted cycloalkyl (e.g., $C_3$-$C_8$ cycloalkyl, $C_3$-$C_6$ cycloalkyl, or C—$C_6$ cycloalkyl), $R^{17B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17B}$-substituted or unsubstituted aryl (e.g., $C_6$-$C_{10}$ aryl, $C_{10}$ aryl, or phenyl), or $R^{17B}$-substituted or unsubstituted heteroaryl (e.g., 5 to 10 membered heteroaryl, 5 to 9 membered heteroaryl, or 5 to 6 membered heteroaryl). In embodiments, $R^{3B}$ and $R^{3C}$ substituents bonded to the same nitrogen atom may optionally be joined to form a $R^{17B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{17B}$-substituted or unsubstituted heteroaryl (e.g., 5 to 10 membered heteroaryl, 5 to 9 membered heteroaryl, or 5 to 6 membered heteroaryl).

In embodiments, $R^{3.2B}$ is hydrogen, halogen, —$CF_3$, —$CCl_3$, —$CBr_3$, —$CI_3$, —COOH, —$CONH_2$, $R^{17.2B}$-substituted or unsubstituted alkyl (e.g., $C_1$-$C_8$ alkyl, $C_1$-$C_6$ alkyl, or $C_1$-$C_4$ alkyl), $R^{17.2B}$-substituted or unsubstituted heteroalkyl (e.g., 2 to 8 membered heteroalkyl, 2 to 6 membered heteroalkyl, or 2 to 4 membered heteroalkyl), $R^{17.2B}$-substituted or unsubstituted cycloalkyl (e.g., $C_3$-$C_8$ cycloalkyl, $C_3$-$C_6$ cycloalkyl, or C—$C_6$ cycloalkyl), $R^{17.2B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.2B}$-substituted or unsubstituted aryl (e.g., $C_6$-$C_{10}$ aryl, $C_{10}$ aryl, or phenyl), or $R^{17.2B}$-substituted or unsubstituted heteroaryl (e.g., 5 to 10 membered heteroaryl, 5 to 9 membered heteroaryl, or 5 to 6 membered heteroaryl). In embodiments, $R^{3.2B}$ and $R^{3.2C}$ substituents bonded to the same nitrogen atom may optionally be joined to form a $R^{17.2B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{17.2B}$-substituted or unsubstituted heteroaryl (e.g., 5 to 10 membered heteroaryl, 5 to 9 membered heteroaryl, or 5 to 6 membered heteroaryl).

In embodiments, $R^{3.3B}$ is hydrogen, halogen, —$CF_3$, —$CCl_3$, —$CBr_3$, —$CI_3$, —COOH, —$CONH_2$, $R^{17.3B}$-substituted or unsubstituted alkyl (e.g., $C_1$-$C_8$ alkyl, $C_1$-$C_6$ alkyl, or $C_1$-$C_4$ alkyl), $R^{17.3B}$-substituted or unsubstituted heteroalkyl (e.g., 2 to 8 membered heteroalkyl, 2 to 6 membered heteroalkyl, or 2 to 4 membered heteroalkyl), $R^{17.3B}$-substituted or unsubstituted cycloalkyl (e.g., $C_3$-$C_8$ cycloalkyl, $C_3$-$C_6$ cycloalkyl, or C—$C_6$ cycloalkyl), $R^{17.3B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.3B}$-substituted or unsubstituted aryl (e.g., $C_6$-$C_{10}$ aryl, $C_{10}$ aryl, or phenyl), or $R^{17.3B}$-substituted or unsubstituted heteroaryl (e.g., 5 to 10 membered heteroaryl, 5 to 9 membered heteroaryl, or 5 to 6 membered heteroaryl). In embodiments, $R^{3.3B}$ and $R^{3.3C}$ substituents bonded to the same nitrogen atom may optionally be joined to form a $R^{17.3B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{17.3B}$-substituted or unsubstituted heteroaryl (e.g., 5 to 10 membered heteroaryl, 5 to 9 membered heteroaryl, or 5 to 6 membered heteroaryl).

In embodiments, $R^{4B}$ is hydrogen, halogen, —$CF_3$, —$CCl_3$, —$CBr_3$, —$CI_3$, —COOH, —$CONH_2$, $R^{20B}$-substituted or unsubstituted alkyl (e.g., $C_1$-$C_8$ alkyl, $C_1$-$C_6$ alkyl, or $C_1$-$C_4$ alkyl), $R^{20B}$-substituted or unsubstituted heteroalkyl (e.g., 2 to 8 membered heteroalkyl, 2 to 6 membered heteroalkyl, or 2 to 4 membered heteroalkyl), $R^{20B}$-substituted or unsubstituted cycloalkyl (e.g., $C_3$-$C_8$ cycloalkyl, $C_3$-$C_6$ cycloalkyl, or C—$C_6$ cycloalkyl), $R^{20B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20B}$-substituted or unsubstituted aryl (e.g., $C_6$-$C_{10}$ aryl, $C_{10}$ aryl, or phenyl), or $R^{20B}$-substituted or unsubstituted heteroaryl (e.g., 5 to 10 membered heteroaryl, 5 to 9 membered heteroaryl, or 5 to 6 membered heteroaryl). In embodiments, $R^{4B}$ and $R^{4C}$ substituents bonded to the same nitrogen atom may optionally be joined to form a $R^{20B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{20B}$-substituted or unsubstituted heteroaryl (e.g., 5 to 10 membered heteroaryl, 5 to 9 membered heteroaryl, or 5 to 6 membered heteroaryl).

In embodiments, $R^{5B}$ is hydrogen, halogen, —$CF_3$, —$CCl_3$, —$CBr_3$, —$CI_3$, —COOH, —$CONH_2$, $R^{23B}$-substituted or unsubstituted alkyl (e.g., $C_1$-$C_8$ alkyl, $C_1$-$C_6$ alkyl, or $C_1$-$C_4$ alkyl), $R^{23B}$-substituted or unsubstituted heteroalkyl (e.g., 2 to 8 membered heteroalkyl, 2 to 6 membered heteroalkyl, or 2 to 4 membered heteroalkyl), $R^{23B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23B}$-substituted or unsubstituted aryl (e.g., $C_6$-$C_{10}$ aryl, $C_{10}$ aryl, or phenyl), or $R^{23B}$-substituted or unsubstituted heteroaryl (e.g., 5 to 10 membered heteroaryl, 5 to 9 membered heteroaryl, or 5 to 6 membered heteroaryl). In embodiments, $R^{5B}$ and $R^{5C}$ substituents bonded to the same nitrogen atom may optionally be joined to form a $R^{23B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{23B}$-substituted or unsubstituted heteroaryl (e.g., 5 to 10 membered heteroaryl, 5 to 9 membered heteroaryl, or 5 to 6 membered heteroaryl).

In embodiments, $R^{6B}$ is hydrogen, halogen, —$CF_3$, —$CCl_3$, —$CBr_3$, —$CI_3$, —COOH, —$CONH_2$, $R^{26B}$-substituted or unsubstituted alkyl (e.g., $C_1$-$C_8$ alkyl, $C_1$-$C_6$ alkyl, or $C_1$-$C_4$ alkyl), $R^{26B}$-substituted or unsubstituted heteroalkyl (e.g., 2 to 8 membered heteroalkyl, 2 to 6 membered heteroalkyl, or 2 to 4 membered heteroalkyl), $R^{26B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26B}$-substituted or unsubstituted aryl (e.g., $C_6$-$C_{10}$ aryl, $C_{10}$ aryl, or phenyl), or $R^{26B}$-substituted or unsubstituted heteroaryl (e.g., 5 to 10 membered heteroaryl, 5 to 9 membered heteroaryl, or 5 to 6 membered heteroaryl). In embodiments, $R^{6B}$ and $R^{6C}$ substituents bonded to the same nitrogen atom may optionally be joined to form a $R^{26B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{26B}$-substituted or unsubstituted heteroaryl (e.g., 5 to 10 membered heteroaryl, 5 to 9 membered heteroaryl, or 5 to 6 membered heteroaryl).

In embodiments, $R^{7B}$ is hydrogen, halogen, —$CF_3$, —$CCl_3$, —$CBr_3$, —$CI_3$, —COOH, —$CONH_2$, $R^{29B}$-substituted or unsubstituted alkyl (e.g., $C_1$-$C_8$ alkyl, $C_1$-$C_6$ alkyl, or $C_1$-$C_4$ alkyl), $R^{29B}$-substituted or unsubstituted heteroalkyl (e.g., 2 to 8 membered heteroalkyl, 2 to 6 membered heteroalkyl, or 2 to 4 membered heteroalkyl), $R^{29B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29B}$-substituted or unsubstituted aryl (e.g., $C_6$-$C_{10}$ aryl, $C_{10}$ aryl, or phenyl), or $R^{29B}$-substituted or unsubstituted heteroaryl (e.g., 5 to 10 membered heteroaryl, 5 to 9 membered heteroaryl, or 5 to 6 membered heteroaryl). In embodiments, $R^{7B}$ and $R^{7C}$ substituents bonded to the same nitrogen atom may optionally be joined to form a $R^{29B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{29B}$-substituted or unsubstituted heteroaryl (e.g., 5 to 10 membered heteroaryl, 5 to 9 membered heteroaryl, or 5 to 6 membered heteroaryl).

In embodiments, $R^{8B}$ is hydrogen, halogen, —$CF_3$, —$CCl_3$, —$CBr_3$, —$CI_3$, —COOH, —$CONH_2$, $R^{32B}$-substituted or unsubstituted alkyl (e.g., $C_1$-$C_8$ alkyl, $C_1$-$C_6$ alkyl, or $C_1$-$C_4$ alkyl), $R^{32B}$-substituted or unsubstituted heteroalkyl (e.g., 2 to 8 membered heteroalkyl, 2 to 6 membered heteroalkyl, or 2 to 4 membered heteroalkyl), $R^{32B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{32B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32B}$-substituted or unsubstituted aryl (e.g., $C_6$-$C_{10}$ aryl, $C_{10}$ aryl, or phenyl), or $R^{32B}$-substituted or unsubstituted heteroaryl (e.g., 5 to 10 membered heteroaryl, 5 to 9 membered heteroaryl, or 5 to 6 membered heteroaryl). In embodiments, $R^{8B}$ and $R^{8C}$ substituents bonded to the same nitrogen atom may optionally be joined to form a $R^{32B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{32B}$-substituted or unsubstituted heteroaryl (e.g., 5 to 10 membered heteroaryl, 5 to 9 membered heteroaryl, or 5 to 6 membered heteroaryl).

In embodiments, $R^{9B}$ is hydrogen, halogen, —$CF_3$, —$CCl_3$, —$CBr_3$, —$CI_3$, —COOH, —$CONH_2$, $R^{35B}$-substituted or unsubstituted alkyl (e.g., $C_1$-$C_8$ alkyl, $C_1$-$C_6$ alkyl, or $C_1$-$C_4$ alkyl), $R^{35B}$-substituted or unsubstituted heteroalkyl (e.g., 2 to 8 membered heteroalkyl, 2 to 6 membered heteroalkyl, or 2 to 4 membered heteroalkyl), $R^{35B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35B}$-substituted or unsubstituted aryl (e.g., $C_6$-$C_{10}$ aryl, $C_{10}$ aryl, or phenyl), or $R^{35B}$-substituted or unsubstituted heteroaryl (e.g., 5 to 10 membered heteroaryl, 5 to 9 membered heteroaryl, or 5 to 6 membered heteroaryl). In embodiments, $R^{9B}$ and $R^{9C}$ substituents bonded to the same nitrogen atom may optionally be joined to form a $R^{35B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{35B}$-substituted or unsubstituted heteroaryl (e.g., 5 to 10 membered heteroaryl, 5 to 9 membered heteroaryl, or 5 to 6 membered heteroaryl).

In embodiments, $R^{10B}$ is hydrogen, halogen, —$CF_3$, —$CCl_3$, —$CBr_3$, —$CI_3$, —COOH, —$CONH_2$, $R^{38B}$-substituted or unsubstituted alkyl (e.g., $C_1$-$C_8$ alkyl, $C_1$-$C_6$ alkyl, or $C_1$-$C_4$ alkyl), $R^{38B}$-substituted or unsubstituted heteroalkyl (e.g., 2 to 8 membered heteroalkyl, 2 to 6 membered heteroalkyl, or 2 to 4 membered heteroalkyl), $R^{38B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38B}$-substituted or unsubstituted aryl (e.g., $C_6$-$C_{10}$ aryl, $C_{10}$ aryl, or phenyl), or $R^{38B}$-substituted or unsubstituted heteroaryl (e.g., 5 to 10 membered heteroaryl, 5 to 9 membered heteroaryl, or 5 to 6 membered heteroaryl). In embodiments, $R^{10B}$ and $R^{10C}$ substituents bonded to the same nitrogen atom may optionally be joined to form a $R^{38B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{38B}$-substituted or unsubstituted heteroaryl (e.g., 5 to 10 membered heteroaryl, 5 to 9 membered heteroaryl, or 5 to 6 membered heteroaryl).

In embodiments, $R^{44B}$ is hydrogen, halogen, —$CF_3$, —$CCl_3$, —$CBr_3$, —$CI_3$, —COOH, —$CONH_2$, $R^{45B}$-substituted or unsubstituted alkyl (e.g., $C_1$-$C_8$ alkyl, $C_1$-$C_6$ alkyl, or $C_1$-$C_4$ alkyl), $R^{45B}$-substituted or unsubstituted heteroalkyl (e.g., 2 to 8 membered heteroalkyl, 2 to 6 membered heteroalkyl, or 2 to 4 membered heteroalkyl), $R^{45B}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45B}$-substituted or unsubstituted aryl (e.g., $C_6$-$C_{10}$ aryl, $C_{10}$ aryl, or phenyl), or $R^{45B}$-substituted or unsubstituted heteroaryl (e.g., 5 to 10 membered heteroaryl, 5 to 9 membered heteroaryl, or 5 to 6 membered heteroaryl). In embodiments, $R^{44B}$ and $R^{44C}$ substituents bonded to the same nitrogen atom may optionally be joined to form a $R^{45B}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{45B}$-substituted or unsubstituted heteroaryl (e.g., 5 to 10 membered heteroaryl, 5 to 9 membered heteroaryl, or 5 to 6 membered heteroaryl).

In embodiments, $R^{1C}$ is hydrogen, halogen, —$CF_3$, —$CCl_3$, —$CBr_3$, —$CI_3$, —COOH, —$CONH_2$, $R^{11C}$-substituted or unsubstituted alkyl (e.g., $C_1$-$C_8$ alkyl, $C_1$-$C_6$ alkyl, or $C_1$-$C_4$ alkyl), $R^{11C}$-substituted or unsubstituted heteroalkyl (e.g., 2 to 8 membered heteroalkyl, 2 to 6 membered heteroalkyl, or 2 to 4 membered heteroalkyl), $R^{11C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11C}$-substituted or unsubstituted aryl (e.g., $C_6$-$C_{10}$ aryl, $C_{10}$ aryl, or phenyl), or $R^{11C}$-substituted or unsubstituted heteroaryl (e.g., 5 to 10 membered heteroaryl, 5 to 9 membered heteroaryl, or 5 to 6 membered heteroaryl). In embodiments, $R^{1B}$ and $R^{1C}$ substituents bonded to the same nitrogen atom may optionally be joined to form a $R^{11C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{11C}$-substituted or unsubstituted heteroaryl (e.g., 5 to 10 membered heteroaryl, 5 to 9 membered heteroaryl, or 5 to 6 membered heteroaryl).

In embodiments, $R^{2C}$ is hydrogen, halogen, —$CF_3$, —$CCl_3$, —$CBr_3$, —$CI_3$, —COOH, —$CONH_2$, $R^{14C}$-substituted or unsubstituted alkyl (e.g., $C_1$-$C_8$ alkyl, $C_1$-$C_6$ alkyl, or C—$C_4$ alkyl), $R^{14C}$-substituted or unsubstituted heteroalkyl (e.g., 2 to 8 membered heteroalkyl, 2 to 6 membered heteroalkyl, or 2 to 4 membered heteroalkyl), $R^{14C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14C}$-substituted or unsubstituted aryl (e.g., $C_6$-$C_{10}$ aryl, $C_{10}$ aryl, or phenyl), or $R^{14C}$-substituted or unsubstituted heteroaryl (e.g., 5 to 10 membered heteroaryl, 5 to 9 membered heteroaryl, or 5 to 6 membered heteroaryl). In embodiments, $R^{2B}$ and $R^{2C}$ substituents bonded to the same nitrogen atom may optionally be joined to form a $R^{14C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{14C}$-substituted or unsubstituted heteroaryl (e.g., 5 to 10 membered heteroaryl, 5 to 9 membered heteroaryl, or 5 to 6 membered heteroaryl).

In embodiments, $R^{3C}$ is hydrogen, halogen, —$CF_3$, —$CCl_3$, —$CBr_3$, —$CI_3$, —COOH, —$CONH_2$, $R^{17C}$-substituted or unsubstituted alkyl (e.g., $C_1$-$C_8$ alkyl, $C_1$-$C_6$ alkyl, or $C_1$-$C_4$ alkyl), $R^{17C}$-substituted or unsubstituted heteroalkyl (e.g., 2 to 8 membered heteroalkyl, 2 to 6 membered heteroalkyl, or 2 to 4 membered heteroalkyl), $R^{17C}$-substituted or unsubstituted cycloalkyl (e.g., $C_3$-$C_8$ cycloalkyl, $C_3$-$C_6$ cycloalkyl, or C—$C_6$ cycloalkyl), $R^{17C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17C}$-substituted or unsubstituted aryl (e.g., $C_6$-$C_{10}$ aryl, $C_{10}$ aryl, or phenyl), or $R^{17C}$-substituted or unsubstituted heteroaryl (e.g., 5 to 10 membered heteroaryl, 5 to 9 membered heteroaryl, or 5 to 6 membered heteroaryl). In embodiments, $R^{3B}$ and $R^{3C}$ substituents bonded to the same nitrogen atom may optionally be joined to form a $R^{17C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{17C}$-substituted or unsubstituted heteroaryl (e.g., 5 to 10 membered heteroaryl, 5 to 9 membered heteroaryl, or 5 to 6 membered heteroaryl).

In embodiments, $R^{3.2C}$, is hydrogen, halogen, —$CF_3$, —$CCl_3$, —$CBr_3$, —$CI_3$, —COOH, —$CONH_2$, $R^{17.2C}$-substituted or unsubstituted alkyl (e.g., $C_1$-$C_8$ alkyl, $C_1$-$C_6$ alkyl, or C—$C_4$ alkyl), $R^{17.2C}$-substituted or unsubstituted heteroalkyl (e.g., 2 to 8 membered heteroalkyl, 2 to 6 membered heteroalkyl, or 2 to 4 membered heteroalkyl), $R^{17.2C}$-substituted or unsubstituted cycloalkyl (e.g., $C_3$-$C_8$ cycloalkyl, $C_3$-$C_6$ cycloalkyl, or C—$C_6$ cycloalkyl), $R^{17.2C}$-substituted or unsubstituted heterocycloalkyl (e.g., 3 to 6 membered heterocycloalkyl, 3 to 6 membered heterocycloalkyl, or 5 to 6 membered heterocycloalkyl), $R^{17.2C}$-substituted or unsubstituted aryl (e.g., $C_6$-$C_{10}$ aryl, $C_{10}$ aryl, or phenyl), or $R^{17.2C}$-substituted or unsubstituted heteroaryl (e.g., 5 to 10 membered heteroaryl, 5 to 9 membered heteroaryl, or 5 to 6 membered heteroaryl). In embodiments, $R^{3.2B}$ and $R^{3.2C}$ substituents bonded to the same nitrogen atom may optionally be joined to form a $R^{17.2C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{17.2C}$-substituted or unsubstituted heteroaryl (e.g., 5 to 10 membered heteroaryl, 5 to 9 membered heteroaryl, or 5 to 6 membered heteroaryl).

In embodiments, $R^{3.3C}$ is hydrogen, halogen, —$CF_3$, —$CCl_3$, —$CBr_3$, —$CI_3$, —COOH, —$CONH_2$, $R^{17.3C}$-substituted or unsubstituted alkyl (e.g., $C_1$-$C_8$ alkyl, $C_1$-$C_6$ alkyl, or $C_1$-$C_4$ alkyl), $R^{17.3C}$-substituted or unsubstituted heteroalkyl (e.g., 2 to 8 membered heteroalkyl, 2 to 6 membered heteroalkyl, or 2 to 4 membered heteroalkyl), $R^{17.3C}$-substituted or unsubstituted cycloalkyl (e.g., $C_3$-$C_8$ cycloalkyl, $C_3$-$C_6$ cycloalkyl, or C—$C_6$ cycloalkyl), $R^{17.3C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.3C}$-substituted or unsubstituted aryl (e.g., $C_6$-$C_{10}$ aryl, $C_{10}$ aryl, or phenyl), or $R^{17.3C}$-substituted or unsubstituted heteroaryl (e.g., 5 to 10 membered heteroaryl, 5 to 9 membered heteroaryl, or 5 to 6 membered heteroaryl). In embodiments, $R^{3.3B}$ and $R^{3.3C}$ substituents bonded to the same nitrogen atom may optionally be joined to form a $R^{17.3C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{17.3C}$-substituted or unsubstituted heteroaryl (e.g., 5 to 10 membered heteroaryl, 5 to 9 membered heteroaryl, or 5 to 6 membered heteroaryl).

In embodiments, $R^{4C}$ is hydrogen, halogen, —$CF_3$, —$CCl_3$, —$CBr_3$, —$CI_3$, —COOH, —$CONH_2$, $R^{20C}$-substituted or unsubstituted alkyl (e.g., $C_1$-$C_8$ alkyl, $C_1$-$C_6$ alkyl, or $C_1$-$C_4$ alkyl), $R^{20C}$-substituted or unsubstituted heteroalkyl (e.g., 2 to 8 membered heteroalkyl, 2 to 6 membered heteroalkyl, or 2 to 4 membered heteroalkyl), $R^{20C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{20C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20C}$-substituted or unsubstituted aryl (e.g., $C_6$-$C_{10}$ aryl, $C_{10}$ aryl, or phenyl), or $R^{20C}$-substituted or unsubstituted heteroaryl (e.g., 5 to 10 membered heteroaryl, 5 to 9 membered heteroaryl, or 5 to 6 membered heteroaryl). In embodiments, $R^{4B}$ and $R^{4C}$ substituents bonded to the same nitrogen atom may optionally be joined to form a $R^{20C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{20C}$-substituted or unsubstituted heteroaryl (e.g., 5 to 10 membered heteroaryl, 5 to 9 membered heteroaryl, or 5 to 6 membered heteroaryl).

In embodiments, $R^{5C}$ is hydrogen, halogen, —$CF_3$, —$CCl_3$, —$CBr_3$, —$CI_3$, —COOH, —$CONH_2$, $R^{23C}$-substituted or unsubstituted alkyl (e.g., $C_1$-$C_8$ alkyl, $C_1$-$C_6$ alkyl, or $C_1$-$C_4$ alkyl), $R^{23C}$-substituted or unsubstituted heteroalkyl (e.g., 2 to 8 membered heteroalkyl, 2 to 6 membered heteroalkyl, or 2 to 4 membered heteroalkyl), $R^{23C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23C}$-substituted or unsubstituted aryl (e.g., $C_6$-$C_{10}$ aryl, $C_{10}$ aryl, or phenyl), or $R^{23C}$-substituted or unsubstituted heteroaryl (e.g., 5 to 10 membered heteroaryl, 5 to 9 membered heteroaryl, or 5 to 6 membered heteroaryl). In embodiments, $R^{5B}$ and $R^{5C}$ substituents bonded to the same nitrogen atom may optionally be joined to form a $R^{23C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{23C}$-substituted or unsubstituted heteroaryl (e.g., 5 to 10 membered heteroaryl, 5 to 9 membered heteroaryl, or 5 to 6 membered heteroaryl).

In embodiments, $R^{6C}$ is hydrogen, halogen, —$CF_3$, —$CCl_3$, —$CBr_3$, —$CI_3$, —COOH, —$CONH_2$, $R^{26C}$-substituted or unsubstituted alkyl (e.g., $C_1$-$C_8$ alkyl, $C_1$-$C_6$ alkyl, or $C_1$-$C_4$ alkyl), $R^{26C}$-substituted or unsubstituted heteroalkyl (e.g., 2 to 8 membered heteroalkyl, 2 to 6 membered heteroalkyl, or 2 to 4 membered heteroalkyl), $R^{26C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26C}$-substituted or unsubstituted aryl (e.g., $C_6$-$C_{10}$ aryl, $C_{10}$ aryl, or phenyl), or $R^{26C}$-substituted or unsubstituted heteroaryl (e.g., 5 to 10 membered heteroaryl, 5 to 9 membered heteroaryl, or 5 to 6 membered heteroaryl). In embodiments, $R^{6B}$ and $R^{6C}$ substituents bonded to the same nitrogen atom may optionally be joined to form a $R^{26C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{26C}$-substituted or unsubstituted heteroaryl (e.g., 5 to 10 membered heteroaryl, 5 to 9 membered heteroaryl, or 5 to 6 membered heteroaryl).

In embodiments, $R^{7C}$ is hydrogen, halogen, —$CF_3$, —$CCl_3$, —$CBr_3$, —$CI_3$, —COOH, —$CONH_2$, $R^{29C}$-substituted or unsubstituted alkyl (e.g., $C_1$-$C_8$ alkyl, $C_1$-$C_6$ alkyl, or $C_1$-$C_4$ alkyl), $R^{29C}$-substituted or unsubstituted heteroalkyl (e.g., 2 to 8 membered heteroalkyl, 2 to 6 membered heteroalkyl, or 2 to 4 membered heteroalkyl), $R^{29C}$-substituted or unsubstituted cycloalkyl (e.g., $C_3$-$C_8$ cycloalkyl, $C_3$-$C_6$ cycloalkyl, or C—$C_6$ cycloalkyl), $R^{29C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29C}$-substituted or unsubstituted aryl (e.g., $C_6$-$C_{10}$ aryl, $C_{10}$ aryl, or phenyl), or $R^{29C}$-substituted or unsubstituted heteroaryl (e.g., 5 to 10 membered heteroaryl, 5 to 9 membered heteroaryl, or 5 to 6 membered heteroaryl). In embodiments, $R^{7B}$ and $R^{7C}$ substituents bonded to the same nitrogen atom may optionally be joined to form a $R^{29C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{29C}$-substituted or unsubstituted heteroaryl (e.g., 5 to 10 membered heteroaryl, 5 to 9 membered heteroaryl, or 5 to 6 membered heteroaryl).

In embodiments, $R^{8C}$ is hydrogen, halogen, —$CF_3$, —$CCl_3$, —$CBr_3$, —$CI_3$, —COOH, —$CONH_2$, $R^{32C}$-substituted or unsubstituted alkyl (e.g., $C_1$-$C_8$ alkyl, $C_1$-$C_6$ alkyl, or $C_1$-$C_4$ alkyl), $R^{32C}$-substituted or unsubstituted heteroalkyl (e.g., 2 to 8 membered heteroalkyl, 2 to 6 membered heteroalkyl, or 2 to 4 membered heteroalkyl), $R^{32C}$-substituted or unsubstituted cycloalkyl (e.g., $C_3$-$C_8$ cycloalkyl, $C_3$-$C_6$ cycloalkyl, or C—$C_6$ cycloalkyl), $R^{32C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32C}$-substituted or unsubstituted aryl (e.g., $C_6$-$C_{10}$ aryl, $C_{10}$ aryl, or phenyl), or $R^{32C}$-substituted or unsubstituted heteroaryl (e.g., 5 to 10 membered heteroaryl, 5 to 9 membered heteroaryl, or 5 to 6 membered heteroaryl). In embodiments, $R^{8B}$ and $R^{8C}$ substituents bonded to the same nitrogen atom may optionally be joined to form a $R^{32C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{32C}$-substituted or unsubstituted heteroaryl (e.g., 5 to 10 membered heteroaryl, 5 to 9 membered heteroaryl, or 5 to 6 membered heteroaryl).

In embodiments, $R^{9C}$ is hydrogen, halogen, —$CF_3$, —$CCl_3$, —$CBr_3$, —$CI_3$, —COOH, —$CONH_2$, $R^{35C}$-substituted or unsubstituted alkyl (e.g., $C_1$-$C_5$ alkyl, $C_1$-$C_6$ alkyl, or $C_1$-$C_4$ alkyl), $R^{35C}$-substituted or unsubstituted heteroalkyl (e.g., 2 to 8 membered heteroalkyl, 2 to 6 membered heteroalkyl, or 2 to 4 membered heteroalkyl), $R^{3C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{3C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35C}$-substituted or unsubstituted aryl (e.g., $C_6$-$C_{10}$ aryl, $C_{10}$ aryl, or phenyl), or $R^{35C}$-substituted or unsubstituted heteroaryl (e.g., 5 to 10 membered heteroaryl, 5 to 9 membered heteroaryl, or 5 to 6 membered heteroaryl). In embodiments, $R^{9B}$ and $R^{9C}$ substituents bonded to the same nitrogen atom may optionally be joined to form a $R^{35C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{35C}$-substituted or unsubstituted heteroaryl (e.g., 5 to 10 membered heteroaryl, 5 to 9 membered heteroaryl, or 5 to 6 membered heteroaryl).

In embodiments, $R^{10C}$ is hydrogen, halogen, —$CF_3$, —$CCl_3$, —$CBr_3$, —$CI_3$, —COOH, —$CONH_2$, $R^{38C}$-substituted or unsubstituted alkyl (e.g., $C_1$-$C_8$ alkyl, $C_1$-$C_6$ alkyl, or $C_1$-$C_4$ alkyl), $R^{38C}$-substituted or unsubstituted heteroalkyl (e.g., 2 to 8 membered heteroalkyl, 2 to 6 membered heteroalkyl, or 2 to 4 membered heteroalkyl), $R^{38C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38C}$-substituted or unsubstituted aryl (e.g., $C_6$-$C_{10}$ aryl, $C_{10}$ aryl, or phenyl), or $R^{38C}$-substituted or unsubstituted heteroaryl (e.g., 5 to 10 membered heteroaryl, 5 to 9 membered heteroaryl, or 5 to 6 membered heteroaryl). In embodiments, $R^{10B}$ and $R^{10C}$ substituents bonded to the same nitrogen atom may optionally be joined to form a $R^{38C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{38C}$-substituted or unsubstituted heteroaryl (e.g., 5 to 10 membered heteroaryl, 5 to 9 membered heteroaryl, or 5 to 6 membered heteroaryl).

In embodiments, $R^{44C}$ is hydrogen, halogen, —$CF_3$, —$CCl_3$, —$CBr_3$, —$CI_3$, —COOH, —$CONH_2$, $R^{45C}$-substituted or unsubstituted alkyl (e.g., $C_1$-$C_8$ alkyl, $C_1$-$C_6$ alkyl, or $C_1$-$C_4$ alkyl), $R^{45C}$-substituted or unsubstituted heteroalkyl (e.g., 2 to 8 membered heteroalkyl, 2 to 6 membered heteroalkyl, or 2 to 4 membered heteroalkyl), $R^{45C}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45C}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45C}$-substituted or unsubstituted aryl (e.g., $C_6$-$C_{10}$ aryl, $C_{10}$ aryl, or phenyl), or $R^{45C}$-substituted or unsubstituted heteroaryl (e.g., 5 to 10 membered heteroaryl, 5 to 9 membered heteroaryl, or 5 to 6 membered heteroaryl). In embodiments, $R^{44B}$ and $R^{44C}$ substituents bonded to the same nitrogen atom may optionally be joined to form a $R^{45C}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{45C}$-substituted or unsubstituted heteroaryl (e.g., 5 to 10 membered heteroaryl, 5 to 9 membered heteroaryl, or 5 to 6 membered heteroaryl).

In embodiments, RD is hydrogen, halogen, —$CF_3$, —$CCl_3$, —$CBr_3$, —$CI_3$, —COOH, —$CONH_2$, $R^{11D}$-substituted or unsubstituted alkyl (e.g., $C_1$-$C_8$ alkyl, $C_1$-$C_6$ alkyl, or $C_1$-$C_4$ alkyl), $R^{11D}$-substituted or unsubstituted heteroalkyl (e.g., 2 to 8 membered heteroalkyl, 2 to 6 membered heteroalkyl, or 2 to 4 membered heteroalkyl), $R^{11D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{11D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{11D}$-substituted or unsubstituted aryl (e.g., $C_6$-$C_{10}$ aryl, $C_{10}$ aryl, or phenyl), or $R^{11D}$- substituted or unsubstituted heteroaryl (e.g., 5 to 10 membered heteroaryl, 5 to 9 membered heteroaryl, or 5 to 6 membered heteroaryl).

In embodiments, $R^{2D}$ is hydrogen, halogen, —$CF_3$, —$CCl_3$, —$CBr_3$, —$CI_3$, —COOH, —$CONH_2$, $R^{14D}$-substituted or unsubstituted alkyl (e.g., $C_1$-$C_8$ alkyl, $C_1$-$C_6$ alkyl, or I-$C_4$ alkyl), $R^{14D}$-substituted or unsubstituted heteroalkyl (e.g., 2 to 8 membered heteroalkyl, 2 to 6 membered heteroalkyl, or 2 to 4 membered heteroalkyl), $R^{14D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{14D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{14D}$-substituted or unsubstituted aryl (e.g., $C_6$-$C_{10}$ aryl, $C_{10}$ aryl, or phenyl), or $R^{14D}$-substituted or unsubstituted heteroaryl (e.g., 5 to 10 membered heteroaryl, 5 to 9 membered heteroaryl, or 5 to 6 membered heteroaryl).

In embodiments, $R^{3D}$ is hydrogen, halogen, —$CF_3$, —$CCl_3$, —$CBr_3$, —$CI_3$, —COOH, —$CONH_2$, $R^{17D}$-substituted or unsubstituted alkyl (e.g., $C_1$-$C_8$ alkyl, $C_1$-$C_6$ alkyl, or $C_1$-$C_4$ alkyl), $R^{17D}$-substituted or unsubstituted heteroalkyl (e.g., 2 to 8 membered heteroalkyl, 2 to 6 membered heteroalkyl, or 2 to 4 membered heteroalkyl), $R^{17D}$-substituted or unsubstituted cycloalkyl (e.g., $C_3$-$C_8$ cycloalkyl, $C_3$-$C_6$ cycloalkyl, or C—$C_6$ cycloalkyl), $R^{17D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17D}$-substituted or unsubstituted aryl (e.g., $C_6$-$C_{10}$ aryl, $C_{10}$ aryl, or phenyl), or $R^{17D}$-substituted or unsubstituted heteroaryl (e.g., 5 to 10 membered heteroaryl, 5 to 9 membered heteroaryl, or 5 to 6 membered heteroaryl).

In embodiments, $R^{3.2D}$ is hydrogen, halogen, —$CF_3$, —$CCl_3$, —$CBr_3$, —$CI_3$, —COOH, —$CONH_2$, $R^{17.2D}$-substituted or unsubstituted alkyl (e.g., $C_1$-$C_8$ alkyl, $C_1$-$C_6$ alkyl, or $C_1$-$C_4$ alkyl), $R^{17.2D}$-substituted or unsubstituted heteroalkyl (e.g., 2 to 8 membered heteroalkyl, 2 to 6 membered heteroalkyl, or 2 to 4 membered heteroalkyl), $R^{17.2D}$-substituted or unsubstituted cycloalkyl (e.g., $C_3$-$C_8$ cycloalkyl, $C_3$-$C_6$ cycloalkyl, or C—$C_6$ cycloalkyl), $R^{17.2D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.2D}$-substituted or unsubstituted aryl (e.g., $C_6$-$C_{10}$ aryl, $C_{10}$ aryl, or phenyl), or $R^{17.2D}$-substituted or unsubstituted heteroaryl (e.g., 5 to 10 membered heteroaryl, 5 to 9 membered heteroaryl, or 5 to 6 membered heteroaryl).

In embodiments, $R^{3.3D}$ is hydrogen, halogen, —$CF_3$, —$CCl_3$, —$CBr_3$, —$CI_3$, —COOH, —$CONH_2$, $R^{17.3D}$-substituted or unsubstituted alkyl (e.g., $C_1$-$C_8$ alkyl, $C_1$-$C_6$ alkyl, or $C_1$-$C_4$ alkyl), $R^{17.3D}$-substituted or unsubstituted heteroalkyl (e.g., 2 to 8 membered heteroalkyl, 2 to 6 membered heteroalkyl, or 2 to 4 membered heteroalkyl), $R^{17.3D}$-substituted or unsubstituted cycloalkyl (e.g., $C_3$-$C_8$ cycloalkyl, $C_3$-$C_6$ cycloalkyl, or C—$C_6$ cycloalkyl), $R^{17.3D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17.3D}$-substituted or unsubstituted aryl (e.g., $C_6$-$C_{10}$ aryl, $C_{10}$ aryl, or phenyl), or $R^{17.3D}$-substituted or unsubstituted heteroaryl (e.g., 5 to 10 membered heteroaryl, 5 to 9 membered heteroaryl, or 5 to 6 membered heteroaryl).

In embodiments, $R^{4D}$ is hydrogen, halogen, —$CF_3$, —$CCl_3$, —$CBr_3$, —$CI_3$, —COOH, —$CONH_2$, $R^{20D}$-substituted or unsubstituted alkyl (e.g., $C_1$-$C_8$ alkyl, $C_1$-$C_6$ alkyl, or $C_1$-$C_4$ alkyl), $R^{20D}$-substituted or unsubstituted heteroalkyl (e.g., 2 to 8 membered heteroalkyl, 2 to 6 membered heteroalkyl, or 2 to 4 membered heteroalkyl), $R^{20D}$-substituted or unsubstituted cycloalkyl (e.g., $C_3$-$C_8$ cycloalkyl, $C_3$-$C_6$ cycloalkyl, or C—$C_6$ cycloalkyl), $R^{20D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{20D}$-substituted or unsubstituted aryl (e.g., $C_6$-$C_{10}$ aryl, $C_{10}$ aryl, or phenyl), or $R^{20D}$-substituted or unsubstituted heteroaryl (e.g., 5 to 10 membered heteroaryl, 5 to 9 membered heteroaryl, or 5 to 6 membered heteroaryl).

In embodiments, $R^{4D}$ is $R^{20D}$-substituted or unsubstituted alkyl (e.g., $C_1$-$C_8$ alkyl, $C_1$-$C_6$ alkyl, or $C_1$-$C_4$ alkyl). In embodiments, $R^{4D}$ is $R^{20D}$-substituted alkyl (e.g., $C_1$-$C_8$ alkyl, $C_1$-$C_6$ alkyl, or $C_1$-$C_4$ alkyl). In embodiments, $R^{4D}$ is an unsubstituted alkyl (e.g., $C_1$-$C_8$ alkyl, $C_1$-$C_6$ alkyl, or $C_1$-$C_4$ alkyl).

In embodiments, $R^{4D}$ is $R^{20D}$-substituted or unsubstituted methyl. In embodiments, $R^{4D}$ is $R^{20D}$-substituted or unsubstituted $C_2$ alkyl. In embodiments, $R^{4D}$ is $R^{20D}$-substituted or unsubstituted $C_3$ alkyl. In embodiments, $R^{4D}$ is $R^{20D}$-substituted or unsubstituted $C_4$ alkyl. In embodiments, $R^{4D}$ is $R^{20D}$-substituted or unsubstituted $C_5$ alkyl. In embodiments, $R^{4D}$ is $R^{20D}$-substituted or unsubstituted $C_6$ alkyl. In embodiments, $R^{4D}$ is $R^{20D}$-substituted or unsubstituted $C_7$ alkyl. In embodiments, $R^{4D}$ is $R^{20D}$-substituted or unsubstituted $C_8$ alkyl. In embodiments, $R^{4D}$ is $R^{20D}$-substituted methyl. In embodiments, $R^{4D}$ is $R^{20D}$-substituted $C_2$ alkyl. In embodiments, $R^{4D}$ is $R^{20D}$-substituted $C_3$ alkyl. In embodiments, $R^{4D}$ is $R^{20D}$-substituted $C_4$ alkyl. In embodiments, $R^{4D}$ is $R^{20D}$-substituted $C_5$ alkyl. In embodiments, $R^{4D}$ is $R^{20D}$-substituted $C_6$ alkyl. In embodiments, $R^{4D}$ is $R^{20D}$-substituted $C_7$ alkyl. In embodiments, $R^{4D}$ is $R^{20D}$-substituted $C_8$ alkyl. In embodiments, $R^{4D}$ is an unsubstituted methyl. In embodiments, $R^{4D}$ is an unsubstituted $C_2$ alkyl. In embodiments, $R^{4D}$ is an unsubstituted $C_3$ alkyl. In embodiments, $R^{4D}$ is an unsubstituted $C_4$ alkyl. In embodiments, $R^{4D}$ is an unsubstituted $C_5$ alkyl. In embodiments, $R^{4D}$ is an unsubstituted $C_6$ alkyl. In embodiments, $R^{4D}$ is an unsubstituted $C_7$ alkyl. In embodiments, $R^{4D}$ is an unsubstituted $C_8$ alkyl.

In embodiments, $R^{5D}$ is hydrogen, halogen, —$CF_3$, —$CCl_3$, —$CBr_3$, —$CI_3$, —COOH, —$CONH_2$, $R^{23D}$-substituted or unsubstituted alkyl (e.g., $C_1$-$C_8$ alkyl, $C_1$-$C_6$ alkyl, or $C_1$-$C_4$ alkyl), $R^{23D}$-substituted or unsubstituted heteroalkyl (e.g., 2 to 8 membered heteroalkyl, 2 to 6 membered heteroalkyl, or 2 to 4 membered heteroalkyl), $R^{23D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23D}$-substituted or unsubstituted aryl (e.g., $C_6$-$C_{10}$ aryl, $C_{10}$ aryl, or phenyl), or $R^{23D}$-substituted or unsubstituted heteroaryl (e.g., 5 to 10 membered heteroaryl, 5 to 9 membered heteroaryl, or 5 to 6 membered heteroaryl).

In embodiments, $R^{6D}$ is hydrogen, halogen, —$CF_3$, —$CCl_3$, —$CBr_3$, —$CI_3$, —COOH, —$CONH_2$, $R^{26D}$-substituted or unsubstituted alkyl (e.g., $C_1$-$C_8$ alkyl, $C_1$-$C_6$ alkyl, or $C_1$-$C_4$ alkyl), $R^{26D}$-substituted or unsubstituted heteroalkyl (e.g., 2 to 8 membered heteroalkyl, 2 to 6 membered heteroalkyl, or 2 to 4 membered heteroalkyl), $R^{26D}$-substituted or unsubstituted cycloalkyl (e.g., $C_3$-$C_8$ cycloalkyl, $C_3$-$C_6$ cycloalkyl, or C—$C_6$ cycloalkyl), $R^{26D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26D}$-substituted or unsubstituted aryl (e.g., $C_6$-$C_{10}$ aryl, $C_{10}$ aryl, or phenyl), or $R^{26D}$-substituted or unsubstituted heteroaryl (e.g., 5 to 10 membered heteroaryl, 5 to 9 membered heteroaryl, or 5 to 6 membered heteroaryl).

In embodiments, $R^{7D}$ is hydrogen, halogen, —$CF_3$, —$CCl_3$, —$CBr_3$, —$CI_3$, —COOH, —$CONH_2$, $R^{29D}$-substituted or unsubstituted alkyl (e.g., $C_1$-$C_8$ alkyl, $C_1$-$C_6$ alkyl, or $C_1$-$C_4$ alkyl), $R^{29D}$-substituted or unsubstituted heteroalkyl (e.g., 2 to 8 membered heteroalkyl, 2 to 6 membered heteroalkyl, or 2 to 4 membered heteroalkyl), $R^{29D}$-substituted or unsubstituted cycloalkyl (e.g., $C_3$-$C_8$ cycloalkyl, $C_3$-$C_6$ cycloalkyl, or C—$C_6$ cycloalkyl), $R^{29D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29D}$-substituted or unsubstituted aryl (e.g., $C_6$-$C_{10}$ aryl, $C_{10}$ aryl, or phenyl), or $R^{29D}$-substituted or unsubstituted heteroaryl (e.g., 5 to 10 membered heteroaryl, 5 to 9 membered heteroaryl, or 5 to 6 membered heteroaryl). In embodiments, $R^{7D}$ is hydrogen. In embodiments, $R^{7D}$ is —$NH_2$. In embodiments, $R^{7D}$ is —$CH_3$. In embodiments, $R^{7D}$ is unsubstituted $C_1$-$C_3$ alkyl.

In embodiments, $R^{8D}$ is hydrogen, halogen, —$CF_3$, —$CCl_3$, —$CBr_3$, —$CI_3$, —COOH, —$CONH_2$, $R^{32D}$-substituted or unsubstituted alkyl (e.g., $C_1$-$C_8$ alkyl, $C_1$-$C_6$ alkyl, or $C_1$-$C_4$ alkyl), $R^{32D}$-substituted or unsubstituted heteroalkyl (e.g., 2 to 8 membered heteroalkyl, 2 to 6 membered heteroalkyl, or 2 to 4 membered heteroalkyl), $R^{32D}$-substituted or unsubstituted cycloalkyl (e.g., $C_3$-$C_8$ cycloalkyl, $C_3$-$C_6$ cycloalkyl, or C—$C_6$ cycloalkyl), $R^{32D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{32D}$-substituted or unsubstituted aryl (e.g., $C_6$-$C_{10}$ aryl, $C_{10}$ aryl, or phenyl), or $R^{32D}$-substituted or unsubstituted heteroaryl (e.g., 5 to 10 membered heteroaryl, 5 to 9 membered heteroaryl, or 5 to 6 membered heteroaryl).

In embodiments, $R^{9D}$ is hydrogen, halogen, —$CF_3$, —$CCl_3$, —$CBr_3$, —$CI_3$, —COOH, —$CONH_2$, $R^{35D}$-substituted or unsubstituted alkyl (e.g., $C_1$-$C_8$ alkyl, $C_1$-$C_6$ alkyl, or $C_1$-$C_4$ alkyl), $R^{35D}$-substituted or unsubstituted heteroalkyl (e.g., 2 to 8 membered heteroalkyl, 2 to 6 membered heteroalkyl, or 2 to 4 membered heteroalkyl), $R^{35D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{35D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{35D}$-substituted or unsubstituted aryl (e.g., $C_6$-$C_{10}$ aryl, $C_{10}$ aryl, or phenyl), or $R^{35D}$-substituted or unsubstituted heteroaryl (e.g., 5 to 10 membered heteroaryl, 5 to 9 membered heteroaryl, or 5 to 6 membered heteroaryl).

In embodiments, $R^{10D}$ is hydrogen, halogen, —$CF_3$, —$CCl_3$, —$CBr_3$, —$CI_3$, —COOH, —$CONH_2$, $R^{38D}$-substituted or unsubstituted alkyl (e.g., $C_1$-$C_8$ alkyl, $C_1$-$C_6$ alkyl, or $C_1$-$C_4$ alkyl), $R^{38D}$-substituted or unsubstituted heteroalkyl (e.g., 2 to 8 membered heteroalkyl, 2 to 6 membered heteroalkyl, or 2 to 4 membered heteroalkyl), $R^{38D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{38D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{38D}$-substituted or unsubstituted aryl (e.g., $C_6$-$C_{10}$ aryl, $C_{10}$ aryl, or phenyl), or $R^{38D}$-substituted or unsubstituted heteroaryl (e.g., 5 to 10 membered heteroaryl, 5 to 9 membered heteroaryl, or 5 to 6 membered heteroaryl).

In embodiments, $R^{44D}$ is hydrogen, halogen, —$CF_3$, —$CCl_3$, —$CBr_3$, —$CI_3$, —COOH, —$CONH_2$, $R^{45D}$-substituted or unsubstituted alkyl (e.g., $C_1$-$C_8$ alkyl, $C_1$-$C_6$ alkyl, or $C_1$-$C_4$ alkyl), $R^{45D}$-substituted or unsubstituted heteroalkyl (e.g., 2 to 8 membered heteroalkyl, 2 to 6 membered heteroalkyl, or 2 to 4 membered heteroalkyl), $R^{45D}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45D}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45D}$-substituted or unsubstituted aryl (e.g., $C_6$-$C_{10}$ aryl, $C_{10}$ aryl, or phenyl), or $R^{45D}$-substituted or unsubstituted heteroaryl (e.g., 5 to 10 membered heteroaryl, 5 to 9 membered heteroaryl, or 5 to 6 membered heteroaryl).

In embodiments, $R^{72B}$ is hydrogen, halogen, —$CF_3$, —$CCl_3$, —$CBr_3$, —$CI_3$, —COOH, —$CONH_2$, $R^{41.2B}$-substituted or unsubstituted alkyl (e.g., $C_1$-$C_8$ alkyl, $C_1$-$C_6$ alkyl, or $C_1$-$C_4$ alkyl), $R^{41.2B}$-substituted or unsubstituted heteroalkyl (e.g., 2 to 8 membered heteroalkyl, 2 to 6 membered heteroalkyl, or 2 to 4 membered heteroalkyl), $R^{41.2B}$-substituted or unsubstituted cycloalkyl (e.g., $C_3$-$C_8$ cycloalkyl, $C_3$-$C_6$ cycloalkyl, or C—$C_6$ cycloalkyl), $R^{41.2B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{41.2B}$-substituted or unsubstituted aryl (e.g., $C_6$-$C_{10}$ aryl, $C_{10}$ aryl, or phenyl), or $R^{41.2B}$-substituted or unsubstituted heteroaryl (e.g., 5 to 10 membered heteroaryl, 5 to 9 membered heteroaryl, or 5 to 6 membered heteroaryl). In embodiments, $R^{7.2B}$ is hydrogen.

$R^{11}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2C_1$, —$OCH_2Br$, —$OCH_2I$, —$OCH_2F$, $R^{12}$-substituted or unsubstituted alkyl (e.g., $C_1$-$C_8$ alkyl, $C_1$-$C_6$ alkyl, or $C_1$-$C_4$ alkyl), $R^{12}$-substituted or unsubstituted heteroalkyl (e.g., 2 to 8 membered heteroalkyl, 2 to 6 membered heteroalkyl, or 2 to 4 membered heteroalkyl), $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{12}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12}$-substituted or unsubstituted aryl (e.g., $C_6$-$C_{10}$ aryl, $C_{10}$ aryl, or phenyl), or $R^{12}$-substituted or unsubstituted heteroaryl (e.g., 5 to 10 membered heteroaryl, 5 to 9 membered heteroaryl, or 5 to 6 membered heteroaryl).

In embodiments, $R^{11}$ is $R^{12}$-substituted or unsubstituted alkyl (e.g., $C_1$-$C_8$ alkyl, $C_1$-$C_6$ alkyl, or $C_1$-$C_4$ alkyl). In embodiments, $R^{11}$ is $R^{12}$-substituted alkyl (e.g., $C_1$-$C_8$ alkyl, $C_1$-$C_6$ alkyl, or $C_1$-$C_4$ alkyl). In embodiments, $R^{11}$ is an unsubstituted alkyl (e.g., $C_1$-$C_8$ alkyl, $C_1$-$C_6$ alkyl, or $C_1$-$C_4$ alkyl).

In embodiments, $R^{11}$ is $R^{12}$-substituted or unsubstituted heteroalkyl (e.g., 2 to 8 membered heteroalkyl, 2 to 6 membered heteroalkyl, or 2 to 4 membered heteroalkyl). In embodiments, $R^{11}$ is $R^{12}$-substituted heteroalkyl (e.g., 2 to 8 membered heteroalkyl, 2 to 6 membered heteroalkyl, or 2 to 4 membered heteroalkyl). In embodiments, $R^{11}$ is an unsubstituted heteroalkyl (e.g., 2 to 8 membered heteroalkyl, 2 to 6 membered heteroalkyl, or 2 to 4 membered heteroalkyl).

In embodiments, $R^{11}$ is $R^{12}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{11}$ is $R^{12}$-substituted cycloalkyl (e.g., $C_3$-$C_8$ cycloalkyl, $C_3$-$C_6$ cycloalkyl, or $C_5$-$C_6$ cycloalkyl). In embodiments, $R^{11}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{11}$ is $R^{12}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{11}$ is $R^{12}$-substituted heterocycloalkyl (e.g., 3 to 8 membered heterocycloalkyl, 3 to 6 membered heterocycloalkyl, or 5 to 6 membered heterocycloalkyl). In embodiments, $R^{11}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{11}$ is $R^{12}$-substituted or unsubstituted aryl (e.g., $C_6$-$C_{10}$ aryl, $C_{10}$ aryl, or phenyl). In embodiments, $R^{11}$ is $R^{12}$-substituted aryl (e.g., $C_6$-$C_{10}$ aryl, $C_{10}$ aryl, or phenyl). In embodiments, $R^{11}$ is an unsubstituted aryl (e.g., $C_6$-$C_{10}$ aryl, $C_{10}$ aryl, or phenyl).

In embodiments, $R^{11}$ is $R^{12}$-substituted or unsubstituted heteroaryl (e.g., 5 to 10 membered heteroaryl, 5 to 9 membered heteroaryl, or 5 to 6 membered heteroaryl). In embodiments, $R^{11}$ is $R^{12}$-substituted heteroaryl (e.g., 5 to 10 membered heteroaryl, 5 to 9 membered heteroaryl, or 5 to 6 membered heteroaryl). In embodiments, $R^{11}$ is an unsubstituted heteroaryl (e.g., 5 to 10 membered heteroaryl, 5 to 9 membered heteroaryl, or 5 to 6 membered heteroaryl).

$R^{12}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{13}$-substituted or unsubstituted alkyl (e.g., $C_1$-$C_8$ alkyl, $C_1$-$C_6$ alkyl, or $C_1$-$C_4$ alkyl), $R^{13}$-substituted or unsubstituted heteroalkyl (e.g., 2 to 8 membered heteroalkyl, 2 to 6 membered heteroalkyl, or 2 to 4 membered heteroalkyl), $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{13}$-substituted or unsubstituted heterocycloalkyl (e.g., 3 to 8 membered heterocycloalkyl, 3 to 6 membered heterocycloalkyl, or 5 to 6 membered heterocycloalkyl), $R^{13}$-substituted or unsubstituted aryl (e.g., $C_6$-$C_{10}$ aryl, $C_{10}$ aryl, or phenyl), or $R^{13}$-substituted or unsubstituted heteroaryl (e.g., 5 to 10 membered heteroaryl, 5 to 9 membered heteroaryl, or 5 to 6 membered heteroaryl).

In embodiments, $R^{12}$ is $R^{13}$-substituted or unsubstituted alkyl (e.g., $C_1$-$C_8$ alkyl, $C_1$-$C_6$ alkyl, or $C_1$-$C_4$ alkyl). In embodiments, $R^{12}$ is $R^{13}$-substituted alkyl (e.g., $C_1$-$C_8$ alkyl, $C_1$-$C_6$ alkyl, or $C_1$-$C_4$ alkyl). In embodiments, $R^{12}$ is an unsubstituted alkyl (e.g., $C_1$-$C_8$ alkyl, $C_1$-$C_6$ alkyl, or $C_1$-$C_4$ alkyl).

In embodiments, $R^{12}$ is $R^{13}$-substituted or unsubstituted heteroalkyl (e.g., 2 to 8 membered heteroalkyl, 2 to 6 membered heteroalkyl, or 2 to 4 membered heteroalkyl). In embodiments, $R^{12}$ is $R^{13}$-substituted heteroalkyl (e.g., 2 to 8 membered heteroalkyl, 2 to 6 membered heteroalkyl, or 2 to 4 membered heteroalkyl). In embodiments, $R^{12}$ is an unsubstituted heteroalkyl (e.g., 2 to 8 membered heteroalkyl, 2 to 6 membered heteroalkyl, or 2 to 4 membered heteroalkyl).

In embodiments, $R^{12}$ is $R^{13}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{12}$ is $R^{13}$-substituted cycloalkyl (e.g., $C_3$-$C_8$ cycloalkyl, $C_3$-$C_6$ cycloalkyl, or $C_5$-$C_6$ cycloalkyl). In embodiments, $R^{12}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{12}$ is $R^{13}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{12}$ is $R^{13}$-substituted heterocycloalkyl (e.g., 3 to 8 membered heterocycloalkyl, 3 to 6 membered heterocycloalkyl, or 5 to 6 membered heterocycloalkyl). In embodiments, $R^{12}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{12}$ is $R^{13}$-substituted or unsubstituted aryl (e.g., $C_6$-$C_{10}$ aryl, $C_{10}$ aryl, or phenyl). In embodiments, $R^{12}$ is $R^{13}$-substituted aryl (e.g., $C_6$-$C_{10}$ aryl, $C_{10}$ aryl, or phenyl). In embodiments, $R^{12}$ is an unsubstituted aryl (e.g., $C_6$-$C_{10}$ aryl, $C_{10}$ aryl, or phenyl).

In embodiments, $R^{12}$ is $R^{13}$-substituted or unsubstituted heteroaryl (e.g., 5 to 10 membered heteroaryl, 5 to 9 membered heteroaryl, or 5 to 6 membered heteroaryl). In embodiments, $R^{12}$ is $R^{13}$-substituted heteroaryl (e.g., 5 to 10 membered heteroaryl, 5 to 9 membered heteroaryl, or 5 to 6 membered heteroaryl). In embodiments, $R^{12}$ is an unsubstituted heteroaryl (e.g., 5 to 10 membered heteroaryl, 5 to 9 membered heteroaryl, or 5 to 6 membered heteroaryl).

$R^{14}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2C_1$, —$OCH_2Br$, —$OCH_2I$, —$OCH_2F$, $R^{15}$-substituted or unsubstituted alkyl (e.g., $C_1$-$C_8$ alkyl, $C_1$-$C_6$ alkyl, or $C_1$-$C_4$ alkyl), $R^{15}$-substituted or unsubstituted heteroalkyl (e.g., 2 to 8 membered heteroalkyl, 2 to 6 membered heteroalkyl, or 2 to 4 membered heteroalkyl), $R^{15}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{15}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15}$-substituted or unsubstituted aryl (e.g., $C_6$-$C_{10}$ aryl, $C_{10}$ aryl, or phenyl), or $R^{15}$-substituted or unsubstituted heteroaryl (e.g., 5 to 10 membered heteroaryl, 5 to 9 membered heteroaryl, or 5 to 6 membered heteroaryl).

In embodiments, $R^{14}$ is $R^{15}$-substituted or unsubstituted alkyl (e.g., $C_1$-$C_8$ alkyl, $C_1$-$C_6$ alkyl, or $C_1$-$C_4$ alkyl). In embodiments, $R^{14}$ is $R^{15}$-substituted alkyl (e.g., $C_1$-$C_8$ alkyl, $C_1$-$C_6$ alkyl, or $C_1$-$C_4$ alkyl). In embodiments, $R^{14}$ is an unsubstituted alkyl (e.g., $C_1$-$C_8$ alkyl, $C_1$-$C_6$ alkyl, or $C_1$-$C_4$ alkyl).

In embodiments, $R^{14}$ is $R^{15}$-substituted or unsubstituted heteroalkyl (e.g., 2 to 8 membered heteroalkyl, 2 to 6 membered heteroalkyl, or 2 to 4 membered heteroalkyl). In embodiments, $R^{14}$ is $R^{15}$-substituted heteroalkyl (e.g., 2 to 8 membered heteroalkyl, 2 to 6 membered heteroalkyl, or 2 to 4 membered heteroalkyl). In embodiments, $R^{14}$ is an unsubstituted heteroalkyl (e.g., 2 to 8 membered heteroalkyl, 2 to 6 membered heteroalkyl, or 2 to 4 membered heteroalkyl).

In embodiments, $R^{14}$ is $R^{15}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is $R^{15}$-substituted cycloalkyl (e.g., $C_3$-$C_8$ cycloalkyl, $C_3$-$C_6$ cycloalkyl, or $C_5$-$C_6$ cycloalkyl). In embodiments, $R^{14}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{14}$ is $R^{15}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{14}$ is $R^{15}$-substituted heterocycloalkyl (e.g., 3 to 8 membered heterocycloalkyl, 3 to 6 membered heterocycloalkyl, or 5 to 6 membered heterocycloalkyl). In embodiments, $R^{14}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{14}$ is $R^{15}$-substituted or unsubstituted aryl (e.g., $C_6$-$C_{10}$ aryl, $C_{10}$ aryl, or phenyl). In embodiments, $R^{14}$ is $R^{15}$-substituted aryl (e.g., $C_6$-$C_{10}$ aryl, $C_{10}$ aryl, or phenyl). In embodiments, $R^{14}$ is an unsubstituted aryl (e.g., $C_6$-$C_{10}$ aryl, $C_{10}$ aryl, or phenyl).

In embodiments, $R^{14}$ is $R^{15}$-substituted or unsubstituted heteroaryl (e.g., 5 to 10 membered heteroaryl, 5 to 9 membered heteroaryl, or 5 to 6 membered heteroaryl). In embodiments, $R^{14}$ is $R^{15}$-substituted heteroaryl (e.g., 5 to 10 membered heteroaryl, 5 to 9 membered heteroaryl, or 5 to 6 membered heteroaryl). In embodiments, $R^{14}$ is an unsubstituted heteroaryl (e.g., 5 to 10 membered heteroaryl, 5 to 9 membered heteroaryl, or 5 to 6 membered heteroaryl).

$R^{15}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{16}$-substituted or unsubstituted alkyl (e.g., $C_1$-$C_8$ alkyl, $C_1$-$C_6$ alkyl, or $C_1$-$C_4$ alkyl), $R^{16}$-substituted or unsubstituted heteroalkyl (e.g., 2 to 8 membered heteroalkyl, 2 to 6 membered heteroalkyl, or 2 to 4 membered heteroalkyl), $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16}$-substituted or unsubstituted aryl (e.g., $C_6$-$C_{10}$ aryl, $C_{10}$ aryl, or phenyl), or $R^{16}$-substituted or unsubstituted heteroaryl (e.g., 5 to 10 membered heteroaryl, 5 to 9 membered heteroaryl, or 5 to 6 membered heteroaryl).

In embodiments, $R^{15}$ is $R^{16}$-substituted or unsubstituted alkyl (e.g., $C_1$-$C_8$ alkyl, $C_1$-$C_6$ alkyl, or $C_1$-$C_4$ alkyl). In embodiments, $R^{15}$ is $R^{16}$-substituted alkyl (e.g., $C_1$-$C_8$ alkyl, $C_1$-$C_6$ alkyl, or $C_1$-$C_4$ alkyl). In embodiments, $R^{15}$ is an unsubstituted alkyl (e.g., $C_1$-$C_8$ alkyl, $C_1$-$C_6$ alkyl, or $C_1$-$C_4$ alkyl).

In embodiments, $R^{15}$ is $R^{16}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is $R^{16}$-substituted heteroalkyl (e.g., 2 to 8 membered heteroalkyl, 2 to 6 membered heteroalkyl, or 2 to 4 membered heteroalkyl). In embodiments, $R^{15}$ is an unsubstituted heteroalkyl (e.g., 2 to 8 membered heteroalkyl, 2 to 6 membered heteroalkyl, or 2 to 4 membered heteroalkyl).

In embodiments, $R^{15}$ is $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is $R^{16}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{15}$ is $R^{16}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is $R^{16}$-substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{15}$ is $R^{16}$-substituted or unsubstituted aryl (e.g., $C_6$-$C_{10}$ aryl, $C_{10}$ aryl, or phenyl). In embodiments, $R^{15}$ is $R^{16}$-substituted aryl (e.g., $C_6$-$C_{10}$ aryl, $C_{10}$ aryl, or phenyl). In embodiments, $R^{15}$ is an unsubstituted aryl (e.g., $C_6$-$C_{10}$ aryl, $C_{10}$ aryl, or phenyl).

In embodiments, $R^{15}$ is $R^{16}$-substituted or unsubstituted heteroaryl (e.g., 5 to 10 membered heteroaryl, 5 to 9 membered heteroaryl, or 5 to 6 membered heteroaryl). In embodiments, $R^{15}$ is $R^{16}$-substituted heteroaryl (e.g., 5 to 10 membered heteroaryl, 5 to 9 membered heteroaryl, or 5 to 6 membered heteroaryl). In embodiments, $R^{15}$ is an unsubstituted heteroaryl (e.g., 5 to 10 membered heteroaryl, 5 to 9 membered heteroaryl, or 5 to 6 membered heteroaryl).

$R^{17}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{18}$-substituted or unsubstituted alkyl (e.g., $C_1$-$C_8$ alkyl, $C_1$-$C_6$ alkyl, or $C_1$-$C_4$ alkyl), $R^{18}$-substituted or unsubstituted heteroalkyl (e.g., 2 to 8 membered heteroalkyl, 2 to 6 membered heteroalkyl, or 2 to 4 membered heteroalkyl), $R^{18}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{18}$-substituted or unsubstituted heterocycloalkyl (e.g., 3 to 8 membered heterocycloalkyl, 3 to 6 membered heterocycloalkyl, or 5 to 6 membered heterocycloalkyl), $R^{18}$-substituted or unsubstituted aryl (e.g., $C_6$-$C_{10}$ aryl, $C_{10}$ aryl, or phenyl), or $R^{18}$-substituted or unsubstituted heteroaryl (e.g., 5 to 10 membered heteroaryl, 5 to 9 membered heteroaryl, or 5 to 6 membered heteroaryl).

In embodiments, $R^{17}$ is $R^{18}$-substituted or unsubstituted alkyl (e.g., $C_1$-$C_8$ alkyl, $C_1$-$C_6$ alkyl, or $C_1$-$C_4$ alkyl). In embodiments, $R^{17}$ is $R^{18}$-substituted alkyl (e.g., $C_1$-$C_8$ alkyl, $C_1$-$C_6$ alkyl, or $C_1$-$C_4$ alkyl). In embodiments, $R^{17}$ is an unsubstituted alkyl (e.g., $C_1$-$C_8$ alkyl, $C_1$-$C_6$ alkyl, or $C_1$-$C_4$ alkyl).

In embodiments, $R^{17}$ is $R^{18}$-substituted or unsubstituted heteroalkyl (e.g., 2 to 8 membered heteroalkyl, 2 to 6 membered heteroalkyl, or 2 to 4 membered heteroalkyl). In embodiments, $R^{17}$ is $R^{18}$-substituted heteroalkyl (e.g., 2 to 8 membered heteroalkyl, 2 to 6 membered heteroalkyl, or 2 to 4 membered heteroalkyl). In embodiments, $R^{17}$ is an unsubstituted heteroalkyl (e.g., 2 to 8 membered heteroalkyl, 2 to 6 membered heteroalkyl, or 2 to 4 membered heteroalkyl).

In embodiments, $R^{17}$ is $R^{18}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is $R^{18}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17}$ is an unsubstituted cycloalkyl (e.g., $C_3$-$C_8$ cycloalkyl, $C_3$-$C_6$ cycloalkyl, or $C$—$C_6$ cycloalkyl).

In embodiments, $R^{17}$ is $R^{18}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17}$ is $R^{18}$-substituted heterocycloalkyl (e.g., 3 to 8 membered heterocycloalkyl, 3 to 6 membered heterocycloalkyl, or 5 to 6 membered heterocycloalkyl). In embodiments, $R^{17}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{17}$ is $R^{18}$-substituted or unsubstituted aryl (e.g., $C_6$-$C_{10}$ aryl, $C_{10}$ aryl, or phenyl). In embodiments, $R^{17}$ is $R^{18}$-substituted aryl (e.g., $C_6$-$C_{10}$ aryl, $C_{10}$ aryl, or phenyl). In embodiments, $R^{17}$ is an unsubstituted aryl (e.g., $C_6$-$C_{10}$ aryl, $C_{10}$ aryl, or phenyl).

In embodiments, $R^{17}$ is $R^{18}$-substituted or unsubstituted heteroaryl (e.g., 5 to 10 membered heteroaryl, 5 to 9 membered heteroaryl, or 5 to 6 membered heteroaryl). In embodiments, $R^{17}$ is $R^{18}$-substituted heteroaryl (e.g., 5 to 10 membered heteroaryl, 5 to 9 membered heteroaryl, or 5 to 6 membered heteroaryl). In embodiments, $R^{17}$ is an unsubstituted heteroaryl (e.g., 5 to 10 membered heteroaryl, 5 to 9 membered heteroaryl, or 5 to 6 membered heteroaryl).

$R^{18}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{19}$-substituted or unsubstituted alkyl (e.g., $C_1$-$C_8$ alkyl, $C_1$-$C_6$ alkyl, or $C_1$-$C_4$ alkyl), $R^{19}$-substituted or unsubstituted heteroalkyl (e.g., 2 to 8 membered heteroalkyl, 2 to 6 membered heteroalkyl, or 2 to 4 membered heteroalkyl), $R^{19}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19}$-substituted or unsubstituted aryl (e.g., $C_6$-$C_{10}$ aryl, $C_{10}$ aryl, or phenyl), or $R^{19}$-substituted or unsubstituted heteroaryl (e.g., 5 to 10 membered heteroaryl, 5 to 9 membered heteroaryl, or 5 to 6 membered heteroaryl).

In embodiments, $R^{18}$ is $R^{19}$-substituted or unsubstituted alkyl (e.g., $C_1$-$C_8$ alkyl, $C_1$-$C_6$ alkyl, or $C_1$-$C_4$ alkyl). In embodiments, $R^{18}$ is $R^{19}$-substituted alkyl (e.g., $C_1$-$C_8$ alkyl, $C_1$-$C_6$ alkyl, or $C_1$-$C_4$ alkyl). In embodiments, $R^{18}$ is an unsubstituted alkyl (e.g., $C_1$-$C_8$ alkyl, $C_1$-$C_6$ alkyl, or $C_1$-$C_4$ alkyl).

In embodiments, $R^{18}$ is $R^{19}$-substituted or unsubstituted heteroalkyl (e.g., 2 to 8 membered heteroalkyl, 2 to 6 membered heteroalkyl, or 2 to 4 membered heteroalkyl). In embodiments, $R^{18}$ is $R^{19}$-substituted heteroalkyl (e.g., 2 to 8 membered heteroalkyl, 2 to 6 membered heteroalkyl, or 2 to 4 membered heteroalkyl). In embodiments, $R^{18}$ is an unsubstituted heteroalkyl (e.g., 2 to 8 membered heteroalkyl, 2 to 6 membered heteroalkyl, or 2 to 4 membered heteroalkyl).

In embodiments, $R^{18}$ is $R^{19}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is $R^{19}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{18}$ is $R^{19}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18}$ is $R^{19}$-substituted heterocycloalkyl (e.g., 3 to 8 membered heterocycloalkyl, 3 to 6 membered heterocycloalkyl, or 5 to 6 membered heterocycloalkyl). In embodiments, $R^{18}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{18}$ is $R^{19}$-substituted or unsubstituted aryl (e.g., $C_6$-$C_{10}$ aryl, $C_{10}$ aryl, or phenyl). In embodiments, $R^{18}$ is $R^{19}$-substituted aryl (e.g., $C_6$-$C_{10}$ aryl, $C_{10}$ aryl, or phenyl). In embodiments, $R^{18}$ is an unsubstituted aryl (e.g., $C_6$-$C_{10}$ aryl, $C_{10}$ aryl, or phenyl).

In embodiments, $R^{18}$ is $R^{19}$-substituted or unsubstituted heteroaryl (e.g., 5 to 10 membered heteroaryl, 5 to 9 membered heteroaryl, or 5 to 6 membered heteroaryl). In embodiments, $R^{18}$ is $R^{19}$-substituted heteroaryl (e.g., 5 to 10 membered heteroaryl, 5 to 9 membered heteroaryl, or 5 to 6 membered heteroaryl). In embodiments, $R^{18}$ is an unsubstituted heteroaryl (e.g., 5 to 10 membered heteroaryl, 5 to 9 membered heteroaryl, or 5 to 6 membered heteroaryl).

$R^{17.2}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2C_1$, —$OCH_2Br$, —$OCH_2I$, —$OCH_2F$, $R^{18.2}$-substituted or unsubstituted alkyl (e.g., $C_1$-$C_8$ alkyl, $C_1$-$C_6$ alkyl, or $C_1$-$C_4$ alkyl), $R^{18.2}$-substituted or unsubstituted heteroalkyl (e.g., 2 to 8 membered heteroalkyl, 2 to 6 membered heteroalkyl, or 2 to 4 membered heteroalkyl), $R^{18.2}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{18.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{12}$-substituted or unsubstituted aryl (e.g., $C_6$-$C_{10}$ aryl, $C_{10}$ aryl, or phenyl), or $R^{18.2}$-substituted or unsubstituted heteroaryl (e.g., 5 to 10 membered heteroaryl, 5 to 9 membered heteroaryl, or 5 to 6 membered heteroaryl).

In embodiments, $R^{17.2}$ is $R^{18.2}$-substituted or unsubstituted alkyl (e.g., $C_1$-$C_8$ alkyl, $C_1$-$C_6$ alkyl, or $C_1$-$C_4$ alkyl). In embodiments, $R^{17.2}$ is $R^{18.2}$-substituted alkyl (e.g., $C_1$-$C_8$ alkyl, $C_1$-$C_6$ alkyl, or $C_1$-$C_4$ alkyl). In embodiments, $R^{17.2}$ is an unsubstituted alkyl (e.g., $C_1$-$C_8$ alkyl, $C_1$-$C_6$ alkyl, or $C_1$-$C_4$ alkyl).

In embodiments, $R^{17.2}$ is $R^{18.2}$-substituted or unsubstituted heteroalkyl (e.g., 2 to 8 membered heteroalkyl, 2 to 6 membered heteroalkyl, or 2 to 4 membered heteroalkyl). In embodiments, $R^{17.2}$ is $R^{18.2}$-substituted heteroalkyl (e.g., 2 to 8 membered heteroalkyl, 2 to 6 membered heteroalkyl, or 2 to 4 membered heteroalkyl). In embodiments, $R^{17.2}$ is an unsubstituted heteroalkyl (e.g., 2 to 8 membered heteroalkyl, 2 to 6 membered heteroalkyl, or 2 to 4 membered heteroalkyl).

In embodiments, $R^{17.2}$ is $R^{18.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17.2}$ is $R^{18.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17.2}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{17.2}$ is $R^{18.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17.2}$ is $R^{18.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{17.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{17.2}$ is $R^{18.2}$-substituted or unsubstituted aryl (e.g., $C_6$-$C_{10}$ aryl, $C_{10}$ aryl, or phenyl). In embodiments, $R^{17.2}$ is $R^{18.2}$-substituted aryl (e.g., $C_6$-$C_{10}$ aryl, $C_{10}$ aryl, or phenyl). In embodiments, $R^{17.2}$ is an unsubstituted aryl (e.g., $C_6$-$C_{10}$ aryl, $C_{10}$ aryl, or phenyl).

In embodiments, $R^{17.2}$ is $R^{18.2}$-substituted or unsubstituted heteroaryl (e.g., 5 to 10 membered heteroaryl, 5 to 9 membered heteroaryl, or 5 to 6 membered heteroaryl). In embodiments, $R^{17.2}$ is $R^{18.2}$-substituted heteroaryl (e.g., 5 to 10 membered heteroaryl, 5 to 9 membered heteroaryl, or 5 to 6 membered heteroaryl). In embodiments, $R^{17.2}$ is an unsubstituted heteroaryl (e.g., 5 to 10 membered heteroaryl, 5 to 9 membered heteroaryl, or 5 to 6 membered heteroaryl).

$R^{18.2}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{19.2}$-substituted or unsubstituted alkyl (e.g., $C_1$-$C_8$ alkyl, $C_1$-$C_6$ alkyl, or $C_1$-$C_4$ alkyl), $R^{19.2}$-substituted or unsubstituted heteroalkyl (e.g., 2 to 8 membered heteroalkyl, 2 to 6 membered heteroalkyl, or 2 to 4 membered heteroalkyl), $R^{19.2}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19.2}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19.2}$-substituted or unsubstituted aryl (e.g., $C_6$-$C_{10}$ aryl, $C_{10}$ aryl, or phenyl), or $R^{19.2}$-substituted or unsubstituted heteroaryl (e.g., 5 to 10 membered heteroaryl, 5 to 9 membered heteroaryl, or 5 to 6 membered heteroaryl).

In embodiments, $R^{18.2}$ is $R^{19.2}$-substituted or unsubstituted alkyl (e.g., $C_1$-$C_8$ alkyl, $C_1$-$C_6$ alkyl, or $C_1$-$C_4$ alkyl). In embodiments, $R^{18.2}$ is $R^{19.2}$-substituted alkyl (e.g., $C_1$-$C_8$ alkyl, $C_1$-$C_6$ alkyl, or $C_1$-$C_4$ alkyl). In embodiments, $R^{18.2}$ is an unsubstituted alkyl (e.g., $C_1$-$C_8$ alkyl, $C_1$-$C_6$ alkyl, or $C_1$-$C_4$ alkyl).

In embodiments, $R^{18.2}$ is $R^{19.2}$-substituted or unsubstituted heteroalkyl (e.g., 2 to 8 membered heteroalkyl, 2 to 6 membered heteroalkyl, or 2 to 4 membered heteroalkyl). In embodiments, $R^{18.2}$ is $R^{19.2}$-substituted heteroalkyl (e.g., 2 to 8 membered heteroalkyl, 2 to 6 membered heteroalkyl, or 2 to 4 membered heteroalkyl). In embodiments, $R^{18.2}$ is an unsubstituted heteroalkyl (e.g., 2 to 8 membered heteroalkyl, 2 to 6 membered heteroalkyl, or 2 to 4 membered heteroalkyl).

In embodiments, $R^{18.2}$ is $R^{19.2}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18.2}$ is $R^{19.2}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18.2}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{18.2}$ is $R^{19.2}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18.2}$ is $R^{19.2}$-substituted heterocycloalkyl (e.g., 3 to 8 membered heterocycloalkyl, 3 to 6 membered heterocycloalkyl, or 5 to 6 membered heterocycloalkyl). In embodiments, $R^{18.2}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{18.2}$ is $R^{19.2}$-substituted or unsubstituted aryl (e.g., $C_6$-$C_{10}$ aryl, $C_{10}$ aryl, or phenyl). In embodiments, $R^{18.2}$ is $R^{19.2}$-substituted aryl (e.g., $C_6$-$C_{10}$ aryl, $C_{10}$ aryl, or phenyl). In embodiments, $R^2$ is an unsubstituted aryl (e.g., $C_6$-$C_{10}$ aryl, $C_{10}$ aryl, or phenyl).

In embodiments, $R^{18.2}$ is $R^{19.2}$-substituted or unsubstituted heteroaryl (e.g., 5 to 10 membered heteroaryl, 5 to 9 membered heteroaryl, or 5 to 6 membered heteroaryl). In embodiments, $R^{18.2}$ is $R^{19.2}$-substituted heteroaryl (e.g., 5 to 10 membered heteroaryl, 5 to 9 membered heteroaryl, or 5 to 6 membered heteroaryl). In embodiments, $R^{18.2}$ is an unsubstituted heteroaryl (e.g., 5 to 10 membered heteroaryl, 5 to 9 membered heteroaryl, or 5 to 6 membered heteroaryl).

$R^{17.3}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C$_1$, —OCH$_2$Br, —OCH$_2$I, —OCH$_2$F, $R^{18.3}$-substituted or unsubstituted alkyl (e.g., $C_1$-$C_8$ alkyl, $C_1$-$C_6$ alkyl, or $C_1$-$C_4$ alkyl), $R^{18.3}$-substituted or unsubstituted heteroalkyl (e.g., 2 to 8 membered heteroalkyl, 2 to 6 membered heteroalkyl, or 2 to 4 membered heteroalkyl), $R^{18.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{18.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{18.3}$-substituted or unsubstituted aryl (e.g., $C_6$-$C_{10}$ aryl, $C_{10}$ aryl, or phenyl), or $R^{18.3}$-substituted or unsubstituted heteroaryl (e.g., 5 to 10 membered heteroaryl, 5 to 9 membered heteroaryl, or 5 to 6 membered heteroaryl).

In embodiments, $R^{17.3}$ is $R^{18.3}$-substituted or unsubstituted alkyl (e.g., $C_1$-$C_8$ alkyl, $C_1$-$C_6$ alkyl, or $C_1$-$C_4$ alkyl). In embodiments, $R^{17.3}$ is $R^{18.3}$-substituted alkyl (e.g., $C_1$-$C_8$ alkyl, $C_1$-$C_6$ alkyl, or $C_1$-$C_4$ alkyl). In embodiments, $R^{17.3}$ is an unsubstituted alkyl (e.g., $C_1$-$C_5$ alkyl, $C_1$-$C_6$ alkyl, or $C_1$-$C_4$ alkyl).

In embodiments, $R^{17.3}$ is $R^{18.3}$-substituted or unsubstituted heteroalkyl (e.g., 2 to 8 membered heteroalkyl, 2 to 6 membered heteroalkyl, or 2 to 4 membered heteroalkyl). In embodiments, $R^{17.3}$ is $R^{18.3}$-substituted heteroalkyl (e.g., 2 to 8 membered heteroalkyl, 2 to 6 membered heteroalkyl, or 2 to 4 membered heteroalkyl). In embodiments, $R^{17.3}$ is an unsubstituted heteroalkyl (e.g., 2 to 8 membered heteroalkyl, 2 to 6 membered heteroalkyl, or 2 to 4 membered heteroalkyl).

In embodiments, $R^{17.3}$ is $R^{18.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{17.3}$ is $R^{18.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{17.3}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{17.3}$ is $R^{18.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{17.3}$ is $R^{18.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{17.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{17.3}$ is $R^{18.3}$-substituted or unsubstituted aryl (e.g., $C_6$-$C_{10}$ aryl, $C_{10}$ aryl, or phenyl). In embodiments, $R^{17.3}$ is $R^{18.3}$-substituted aryl (e.g., $C_6$-$C_{10}$ aryl, $C_{10}$ aryl, or phenyl). In embodiments, $R^{17.3}$ is an unsubstituted aryl (e.g., $C_6$-$C_{10}$ aryl, $C_{10}$ aryl, or phenyl).

In embodiments, $R^{17.3}$ is $R^{18.3}$-substituted or unsubstituted heteroaryl (e.g., 5 to 10 membered heteroaryl, 5 to 9 membered heteroaryl, or 5 to 6 membered heteroaryl). In embodiments, $R^{17.3}$ is $R^{18.3}$-substituted heteroaryl (e.g., 5 to 10 membered heteroaryl, 5 to 9 membered heteroaryl, or 5 to 6 membered heteroaryl). In embodiments, $R^{17.3}$ is an unsubstituted heteroaryl (e.g., 5 to 10 membered heteroaryl, 5 to 9 membered heteroaryl, or 5 to 6 membered heteroaryl).

$R^{18.3}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{19.3}$-substituted or unsubstituted alkyl (e.g., $C_1$-$C_8$ alkyl, $C_1$-$C_6$ alkyl, or $C_1$-$C_4$ alkyl), $R^{19.3}$-substituted or unsubstituted heteroalkyl (e.g., 2 to 8 membered heteroalkyl, 2 to 6 membered heteroalkyl, or 2 to 4 membered heteroalkyl), $R^{19.3}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{19.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{19.3}$-substituted or unsubstituted aryl (e.g., $C_6$-$C_{10}$ aryl, $C_{10}$ aryl, or phenyl), or $R^{19.3}$-substituted or unsubstituted heteroaryl (e.g., 5 to 10 membered heteroaryl, 5 to 9 membered heteroaryl, or 5 to 6 membered heteroaryl).

In embodiments, $R^{18.3}$ is $R^{19.3}$-substituted or unsubstituted alkyl (e.g., $C_1$-$C_8$ alkyl, $C_1$-$C_6$ alkyl, or $C_1$-$C_4$ alkyl). In embodiments, $R^{18.3}$ is $R^{19.3}$-substituted alkyl (e.g., $C_1$-$C_8$ alkyl, $C_1$-$C_6$ alkyl, or $C_1$-$C_4$ alkyl). In embodiments, $R^{18.3}$ is an unsubstituted alkyl (e.g., $C_1$-$C_8$ alkyl, $C_1$-$C_6$ alkyl, or $C_1$-$C_4$ alkyl).

In embodiments, $R^{18.3}$ is $R^{19.3}$-substituted or unsubstituted heteroalkyl (e.g., 2 to 8 membered heteroalkyl, 2 to 6 membered heteroalkyl, or 2 to 4 membered heteroalkyl). In embodiments, $R^{18.3}$ is $R^{19.3}$-substituted heteroalkyl (e.g., 2 to 8 membered heteroalkyl, 2 to 6 membered heteroalkyl, or 2 to 4 membered heteroalkyl). In embodiments, $R^{18.3}$ is an unsubstituted heteroalkyl (e.g., 2 to 8 membered heteroalkyl, 2 to 6 membered heteroalkyl, or 2 to 4 membered heteroalkyl).

In embodiments, $R^{18.3}$ is $R^{19.3}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{18.3}$ is $R^{19.3}$-substituted cycloalkyl (e.g., $C_3$-$C_8$ cycloalkyl, $C_3$-$C_6$ cycloalkyl, or $C_5$-$C_6$ cycloalkyl). In embodiments, $R^{18.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{18.3}$ is $R^{19.3}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{18.3}$ is $R^{19.3}$-substituted heterocycloalkyl (e.g., 3 to 8 membered heterocycloalkyl, 3 to 6 membered heterocycloalkyl, or 5 to 6 membered heterocycloalkyl). In embodiments, $R^{18.3}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{18.3}$ is $R^{19.3}$-substituted or unsubstituted aryl (e.g., $C_6$-$C_{10}$ aryl, $C_{10}$ aryl, or phenyl). In embodiments, $R^{18.3}$ is $R^{19.3}$-substituted aryl (e.g., $C_6$-$C_{10}$ aryl, $C_{10}$ aryl, or phenyl). In embodiments, $R^{18.3}$ is an unsubstituted aryl (e.g., $C_6$-$C_{10}$ aryl, $C_{10}$ aryl, or phenyl).

In embodiments, $R^{18.3}$ is $R^{19.3}$-substituted or unsubstituted heteroaryl (e.g., 5 to 10 membered heteroaryl, 5 to 9 membered heteroaryl, or 5 to 6 membered heteroaryl). In embodiments, $R^{18.3}$ is $R^{19.3}$-substituted heteroaryl (e.g., 5 to 10 membered heteroaryl, 5 to 9 membered heteroaryl, or 5 to 6 membered heteroaryl). In embodiments, $R^{18.3}$ is an unsubstituted heteroaryl (e.g., 5 to 10 membered heteroaryl, 5 to 9 membered heteroaryl, or 5 to 6 membered heteroaryl).

$R^{20}$ is independently oxo, halogen, $-CCl_3$, $-CBr_3$, $-CF_3$, $-C_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2C_1$, $-OCH_2Br$, $-OCH_2I$, $-OCH_2F$, $R^{21}$-substituted or unsubstituted alkyl (e.g., $C_1$-$C_8$ alkyl, $C_1$-$C_6$ alkyl, or $C_1$-$C_4$ alkyl), $R^2$-substituted or unsubstituted heteroalkyl (e.g., 2 to 8 membered heteroalkyl, 2 to 6 membered heteroalkyl, or 2 to 4 membered heteroalkyl), $R^2$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl).

In embodiments, $R^{20}$ is $R^{21}$-substituted or unsubstituted alkyl (e.g., $C_1$-$C_8$ alkyl, $C_1$-$C_6$ alkyl, or $C_1$-$C_4$ alkyl). In embodiments, $R^{20}$ is $R^{21}$-substituted alkyl (e.g., $C_1$-$C_8$ alkyl, $C_1$-$C_6$ alkyl, or $C_1$-$C_4$ alkyl). In embodiments, $R^{20}$ is an unsubstituted alkyl (e.g., $C_1$-$C_8$ alkyl, $C_1$-$C_6$ alkyl, or $C_1$-$C_4$ alkyl).

In embodiments, $R^{20}$ is $R^{21}$-substituted or unsubstituted heteroalkyl (e.g., 2 to 8 membered heteroalkyl, 2 to 6 membered heteroalkyl, or 2 to 4 membered heteroalkyl). In embodiments, $R^{20}$ is $R^{21}$-substituted heteroalkyl (e.g., 2 to 8 membered heteroalkyl, 2 to 6 membered heteroalkyl, or 2 to 4 membered heteroalkyl). In embodiments, $R^{20}$ is an unsubstituted heteroalkyl (e.g., 2 to 8 membered heteroalkyl, 2 to 6 membered heteroalkyl, or 2 to 4 membered heteroalkyl).

In embodiments, $R^{20}$ is $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, $R^{20}$ is an unsubstituted cycloalkyl (e.g., $C_3$-$C_8$ cycloalkyl, $C_3$-$C_6$ cycloalkyl, or $C$-$C_6$ cycloalkyl).

In embodiments, $R^{20}$ is $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{20}$ is $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^{20}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{20}$ is $R^{21}$-substituted or unsubstituted aryl (e.g., $C_6$-$C_{10}$ aryl, $C_{10}$ aryl, or phenyl). In embodiments, $R^{20}$ is $R^{21}$-substituted aryl (e.g., $C_6$-$C_{10}$ aryl, $C_{10}$ aryl, or phenyl). In embodiments, $R^{20}$ is an unsubstituted aryl (e.g., $C_6$-$C_{10}$ aryl, $C_{10}$ aryl, or phenyl).

In embodiments, $R^{20}$ is $R^{21}$-substituted or unsubstituted heteroaryl (e.g., 5 to 10 membered heteroaryl, 5 to 9 membered heteroaryl, or 5 to 6 membered heteroaryl). In embodiments, $R^{20}$ is $R^{21}$-substituted heteroaryl (e.g., 5 to 10 membered heteroaryl, 5 to 9 membered heteroaryl, or 5 to 6 membered heteroaryl). In embodiments, $R^{20}$ is an unsubstituted heteroaryl (e.g., 5 to 10 membered heteroaryl, 5 to 9 membered heteroaryl, or 5 to 6 membered heteroaryl).

$R^{21}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl).

In embodiments, $R^{21}$ is $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21}$ is $R^{22}$-substituted alkyl (e.g., $C_1$-$C_8$ alkyl, $C_1$-$C_6$ alkyl, or $C_1$-$C_4$ alkyl). In embodiments, $R^{21}$ is an unsubstituted alkyl (e.g., $C_1$-$C_8$ alkyl, $C_1$-$C_6$ alkyl, or $C_1$-$C_4$ alkyl).

In embodiments, $R^{21}$ is $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21}$ is $R^{22}$-substituted heteroalkyl (e.g., 2 to 8 membered heteroalkyl, 2 to 6 membered heteroalkyl, or 2 to 4 membered heteroalkyl). In embodiments, $R^{21}$ is an unsubstituted heteroalkyl (e.g., 2 to 8 membered heteroalkyl, 2 to 6 membered heteroalkyl, or 2 to 4 membered heteroalkyl).

In embodiments, $R^{21}$ is $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is $R^{22}$-substituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{21}$ is $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21}$ is $R^{22}$-substituted heterocycloalkyl (e.g., 3 to 8 membered heterocycloalkyl, 3 to 6 membered heterocycloalkyl, or 5 to 6 membered heterocycloalkyl). In embodiments, $R^{21}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{21}$ is $R^{22}$-substituted or unsubstituted aryl (e.g., $C_6$-$C_{10}$ aryl, $C_{10}$ aryl, or phenyl). In embodiments, $R^{21}$ is $R^{22}$-substituted aryl (e.g., $C_6$-$C_{10}$ aryl, $C_{10}$ aryl, or phenyl). In embodiments, $R^{21}$ is an unsubstituted aryl (e.g., $C_6$-$C_{10}$ aryl, $C_{10}$ aryl, or phenyl).

In embodiments, $R^{21}$ is $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is $R^{22}$-substituted heteroaryl (e.g., 5 to 10 membered heteroaryl, 5 to 9 membered heteroaryl, or 5 to 6 membered heteroaryl). In embodiments, $R^{21}$ is an unsubstituted heteroaryl (e.g., 5 to 10 membered heteroaryl, 5 to 9 membered heteroaryl, or 5 to 6 membered heteroaryl).

$R^{23}$ is independently oxo, halogen, —CCl$_3$, —CBr$_3$, —CF$_3$, —C$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{24}$-substituted or unsubstituted alkyl (e.g., $C_1$-$C_8$ alkyl, $C_1$-$C_6$ alkyl, or $C_1$-$C_4$ alkyl), $R^{24}$-substituted or unsubstituted heteroalkyl (e.g., 2 to 8 membered heteroalkyl, 2 to 6 membered heteroalkyl, or 2 to 4 membered heteroalkyl), $R^{24}$-substituted or unsubstituted cycloalkyl (e.g., $C_3$-$C_8$ cycloalkyl, $C_3$-$C_6$ cycloalkyl, or C—$C_6$ cycloalkyl), $R^{24}$-substituted or unsubstituted heterocycloalkyl (e.g., 3 to 8 membered heterocycloalkyl, 3 to 6 membered heterocycloalkyl, or 5 to 6 membered heterocycloalkyl), $R^{24}$-substituted or unsubstituted aryl (e.g., $C_6$-$C_{10}$ aryl, $C_{10}$ aryl, or phenyl), or $R^{24}$-substituted or unsubstituted heteroaryl (e.g., 5 to 10 membered heteroaryl, 5 to 9 membered heteroaryl, or 5 to 6 membered heteroaryl).

In embodiments, $R^{23}$ is $R^{24}$-substituted or unsubstituted alkyl (e.g., $C_1$-$C_8$ alkyl, $C_1$-$C_6$ alkyl, or $C_1$-$C_4$ alkyl). In embodiments, $R^{23}$ is $R^{24}$-substituted alkyl (e.g., $C_1$-$C_8$ alkyl, $C_1$-$C_6$ alkyl, or $C_1$-$C_4$ alkyl). In embodiments, $R^{23}$ is an unsubstituted alkyl (e.g., $C_1$-$C_8$ alkyl, $C_1$-$C_6$ alkyl, or $C_1$-$C_4$ alkyl).

In embodiments, $R^{23}$ is $R^{24}$-substituted or unsubstituted heteroalkyl (e.g., 2 to 8 membered heteroalkyl, 2 to 6 membered heteroalkyl, or 2 to 4 membered heteroalkyl). In embodiments, $R^{23}$ is $R^{24}$-substituted heteroalkyl (e.g., 2 to 8 membered heteroalkyl, 2 to 6 membered heteroalkyl, or 2 to 4 membered heteroalkyl). In embodiments, $R^{23}$ is an unsubstituted heteroalkyl (e.g., 2 to 8 membered heteroalkyl, 2 to 6 membered heteroalkyl, or 2 to 4 membered heteroalkyl).

In embodiments, $R^{23}$ is $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{23}$ is $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23}$ is $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^{23}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23}$ is $R^{24}$-substituted or unsubstituted aryl (e.g., $C_6$-$C_{10}$ aryl, $C_{10}$ aryl, or phenyl). In embodiments, $R^{23}$ is $R^{24}$-substituted aryl (e.g., $C_6$-$C_{10}$ aryl, $C_{10}$ aryl, or phenyl). In embodiments, $R^{23}$ is an unsubstituted aryl (e.g., $C_6$-$C_{10}$ aryl, $C_{10}$ aryl, or phenyl).

In embodiments, $R^{23}$ is $R^{24}$-substituted or unsubstituted heteroaryl (e.g., 5 to 10 membered heteroaryl, 5 to 9 membered heteroaryl, or 5 to 6 membered heteroaryl). In embodiments, $R^{23}$ is $R^{24}$-substituted heteroaryl (e.g., 5 to 10 membered heteroaryl, 5 to 9 membered heteroaryl, or 5 to 6 membered heteroaryl). In embodiments, $R^{23}$ is an unsubstituted heteroaryl (e.g., 5 to 10 membered heteroaryl, 5 to 9 membered heteroaryl, or 5 to 6 membered heteroaryl).

$R^{24}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{25}$-substituted or unsubstituted alkyl (e.g., $C_1$-$C_5$ alkyl, $C_1$-$C_6$ alkyl, or $C_1$-$C_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl).

In embodiments, $R^{24}$ is $R^{25}$-substituted or unsubstituted alkyl (e.g., $C_1$-$C_8$ alkyl, $C_1$-$C_6$ alkyl, or $C_1$-$C_4$ alkyl). In embodiments, $R^{24}$ is $R^{25}$-substituted alkyl (e.g., $C_1$-$C_8$ alkyl, $C_1$-$C_6$ alkyl, or $C_1$-$C_4$ alkyl). In embodiments, $R^{24}$ is an unsubstituted alkyl (e.g., $C_1$-$C_8$ alkyl, $C_1$-$C_6$ alkyl, or $C_1$-$C_4$ alkyl).

In embodiments, $R^{24}$ is $R^{25}$-substituted or unsubstituted heteroalkyl (e.g., 2 to 8 membered heteroalkyl, 2 to 6 membered heteroalkyl, or 2 to 4 membered heteroalkyl). In embodiments, $R^{24}$ is $R^{25}$-substituted heteroalkyl (e.g., 2 to 8 membered heteroalkyl, 2 to 6 membered heteroalkyl, or 2 to 4 membered heteroalkyl). In embodiments, $R^{24}$ is an unsubstituted heteroalkyl (e.g., 2 to 8 membered heteroalkyl, 2 to 6 membered heteroalkyl, or 2 to 4 membered heteroalkyl).

In embodiments, $R^{24}$ is $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is $R^{25}$-substituted cycloalkyl (e.g., $C_3$-$C_8$ cycloalkyl, $C_3$-$C_6$ cycloalkyl, or $C_5$-$C_6$ cycloalkyl). In embodiments, $R^{24}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{24}$ is $R^{25}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{24}$ is $R^{25}$-substituted heterocycloalkyl (e.g., 3 to 8 membered heterocycloalkyl, 3 to 6 membered heterocycloalkyl, or 5 to 6 membered heterocycloalkyl). In embodiments, $R^{24}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{24}$ is $R^{25}$-substituted or unsubstituted aryl (e.g., $C_6$-$C_{10}$ aryl, $C_{10}$ aryl, or phenyl). In embodiments, $R^{24}$ is $R^{25}$-substituted aryl (e.g., $C_6$-$C_{10}$ aryl, $C_{10}$ aryl, or phenyl). In embodiments, $R^{24}$ is an unsubstituted aryl (e.g., $C_6$-$C_{10}$ aryl, $C_{10}$ aryl, or phenyl).

In embodiments, $R^{24}$ is $R^{25}$-substituted or unsubstituted heteroaryl (e.g., 5 to 10 membered heteroaryl, 5 to 9 membered heteroaryl, or 5 to 6 membered heteroaryl). In embodiments, $R^{24}$ is $R^{25}$-substituted heteroaryl (e.g., 5 to 10 membered heteroaryl, 5 to 9 membered heteroaryl, or 5 to 6 membered heteroaryl). In embodiments, $R^{24}$ is an unsubstituted heteroaryl (e.g., 5 to 10 membered heteroaryl, 5 to 9 membered heteroaryl, or 5 to 6 membered heteroaryl).

$R^{26}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2C_1$, —$OCH_2Br$, —$OCH_2I$, —$OCH_2F$, $R^{27}$-substituted or unsubstituted alkyl (e.g., $C_1$-$C_5$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl).

In embodiments, $R^{26}$ is $R^{27}$-substituted or unsubstituted alkyl (e.g., $C_1$-$C_8$ alkyl, $C_1$-$C_6$ alkyl, or $C_1$-$C_4$ alkyl). In embodiments, $R^{26}$ is $R^{27}$-substituted alkyl (e.g., $C_1$-$C_8$ alkyl, $C_1$-$C_6$ alkyl, or $C_1$-$C_4$ alkyl). In embodiments, $R^{26}$ is an unsubstituted alkyl (e.g., $C_1$-$C_8$ alkyl, $C_1$-$C_6$ alkyl, or $C_1$-$C_4$ alkyl).

In embodiments, $R^{26}$ is $R^{27}$-substituted or unsubstituted heteroalkyl (e.g., 2 to 8 membered heteroalkyl, 2 to 6 membered heteroalkyl, or 2 to 4 membered heteroalkyl). In embodiments, $R^{26}$ is $R^{27}$-substituted heteroalkyl (e.g., 2 to 8 membered heteroalkyl, 2 to 6 membered heteroalkyl, or 2 to 4 membered heteroalkyl). In embodiments, $R^{26}$ is an unsubstituted heteroalkyl (e.g., 2 to 8 membered heteroalkyl, 2 to 6 membered heteroalkyl, or 2 to 4 membered heteroalkyl).

In embodiments, $R^{26}$ is $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is $R^{27}$-substituted cycloalkyl (e.g., $C_3$-$C_8$ cycloalkyl, $C_3$-$C_6$ cycloalkyl, or $C_5$-$C_6$ cycloalkyl). In embodiments, $R^{26}$ is an unsubstituted cycloalkyl (e.g., $C_3$-$C_8$ cycloalkyl, $C_3$-$C_6$ cycloalkyl, or $C$—$C_6$ cycloalkyl).

In embodiments, $R^{26}$ is $R^{27}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{26}$ is $R^{27}$-substituted heterocycloalkyl (e.g., 3 to 8 membered heterocycloalkyl, 3 to 6 membered heterocycloalkyl, or 5 to 6 membered heterocycloalkyl). In embodiments, $R^{26}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{26}$ is $R^{27}$-substituted or unsubstituted aryl (e.g., $C_6$-$C_{10}$ aryl, $C_{10}$ aryl, or phenyl). In embodiments, $R^{26}$ is $R^{27}$-substituted aryl (e.g., $C_6$-$C_{10}$ aryl, $C_{10}$ aryl, or phenyl). In embodiments, $R^{26}$ is an unsubstituted aryl (e.g., $C_6$-$C_{10}$ aryl, $C_{10}$ aryl, or phenyl).

In embodiments, $R^{26}$ is $R^{27}$-substituted or unsubstituted heteroaryl (e.g., 5 to 10 membered heteroaryl, 5 to 9 membered heteroaryl, or 5 to 6 membered heteroaryl). In embodiments, $R^{26}$ is $R^{27}$-substituted heteroaryl (e.g., 5 to 10 membered heteroaryl, 5 to 9 membered heteroaryl, or 5 to 6 membered heteroaryl). In embodiments, $R^{26}$ is an unsubstituted heteroaryl (e.g., 5 to 10 membered heteroaryl, 5 to 9 membered heteroaryl, or 5 to 6 membered heteroaryl).

$R^{27}$ is independently oxo, halogen, —CCl$_3$, —CBr$_3$, —CF$_3$, —C$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C$_1$, —OCH$_2$Br, —OCH$_2$I, —OCH$_2$F, $R^{28}$-substituted or unsubstituted alkyl (e.g., C$_1$-C$_5$ alkyl, C$_1$-C$_6$ alkyl, or C$_1$-C$_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., C$_3$-C$_8$ cycloalkyl, C$_3$-C$_6$ cycloalkyl, or C—C$_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., C$_6$-C$_{10}$ aryl, C$_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl).

In embodiments, $R^{27}$ is $R^{28}$-substituted or unsubstituted alkyl (e.g., C$_1$-C$_8$ alkyl, C$_1$-C$_6$ alkyl, or C$_1$-C$_4$ alkyl). In embodiments, $R^{27}$ is $R^{28}$-substituted alkyl (e.g., C$_1$-C$_8$ alkyl, C$_1$-C$_6$ alkyl, or C$_1$-C$_4$ alkyl). In embodiments, $R^{27}$ is an unsubstituted alkyl (e.g., C$_1$-C$_8$ alkyl, C$_1$-C$_6$ alkyl, or C$_1$-C$_4$ alkyl).

In embodiments, $R^{27}$ is $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^{27}$ is $R^{28}$-substituted heteroalkyl (e.g., 2 to 8 membered heteroalkyl, 2 to 6 membered heteroalkyl, or 2 to 4 membered heteroalkyl). In embodiments, $R^{27}$ is an unsubstituted heteroalkyl (e.g., 2 to 8 membered heteroalkyl, 2 to 6 membered heteroalkyl, or 2 to 4 membered heteroalkyl).

In embodiments, $R^{27}$ is $R^{28}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^{27}$ is $R^{28}$-substituted cycloalkyl (e.g., C$_3$-C$_8$ cycloalkyl, C$_3$-C$_6$ cycloalkyl, or C$_5$-C$_6$ cycloalkyl). In embodiments, $R^{27}$ is an unsubstituted cycloalkyl (e.g., C$_3$-C$_8$ cycloalkyl, C$_3$-C$_6$ cycloalkyl, or C$_5$-C$_6$ cycloalkyl).

In embodiments, $R^{27}$ is $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{27}$ is $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^{27}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{27}$ is $R^{28}$-substituted or unsubstituted aryl (e.g., C$_6$-C$_{10}$ aryl, C$_{10}$ aryl, or phenyl). In embodiments, $R^{27}$ is $R^{28}$-substituted aryl (e.g., C$_6$-C$_{10}$ aryl, C$_{10}$ aryl, or phenyl). In embodiments, $R^{27}$ is an unsubstituted aryl (e.g., C$_6$-C$_{10}$ aryl, C$_{10}$ aryl, or phenyl).

In embodiments, $R^{27}$ is $R^{28}$-substituted or unsubstituted heteroaryl (e.g., 5 to 10 membered heteroaryl, 5 to 9 membered heteroaryl, or 5 to 6 membered heteroaryl). In embodiments, $R^{27}$ is $R^{28}$-substituted heteroaryl (e.g., 5 to 10 membered heteroaryl, 5 to 9 membered heteroaryl, or 5 to 6 membered heteroaryl). In embodiments, $R^{27}$ is an unsubstituted heteroaryl (e.g., 5 to 10 membered heteroaryl, 5 to 9 membered heteroaryl, or 5 to 6 membered heteroaryl).

$R^{29}$ is independently oxo, halogen, —CCl$_3$, —CBr$_3$, —CF$_3$, —C$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C$_1$, —OCH$_2$Br, —OCH$_2$I, —OCH$_2$F, $R^{30}$-substituted or unsubstituted alkyl (e.g., C$_1$-C$_8$ alkyl, C$_1$-C$_6$ alkyl, or C$_1$-C$_4$ alkyl), $R^{30}$-substituted or unsubstituted heteroalkyl (e.g., 2 to 8 membered heteroalkyl, 2 to 6 membered heteroalkyl, or 2 to 4 membered heteroalkyl), $R^{30}$-substituted or unsubstituted cycloalkyl (e.g., C$_3$-C$_8$ cycloalkyl, C$_3$-C$_6$ cycloalkyl, or C—C$_6$ cycloalkyl), $R^{30}$-substituted or unsubstituted heterocycloalkyl (e.g., 3 to 8 membered heterocycloalkyl, 3 to 6 membered heterocycloalkyl, or 5 to 6 membered heterocycloalkyl), $R^{30}$-substituted or unsubstituted aryl (e.g., C$_6$-C$_{10}$ aryl, C$_{10}$ aryl, or phenyl), or $R^{30}$-substituted or unsubstituted heteroaryl (e.g., 5 to 10 membered heteroaryl, 5 to 9 membered heteroaryl, or 5 to 6 membered heteroaryl).

In embodiments, $R^{29}$ is oxo. In embodiments, $R^{29}$ is —CH$_3$. In embodiments, $R^{29}$ is —COOH. In embodiments, $R^{29}$ is —NHC(O)NH$_2$. In embodiments, $R^{29}$ is —OH. In embodiments, $R^{29}$ is —NH$_2$. In embodiments, $R^{29}$ is —CONH$_2$. In embodiments, $R^{29}$ is —NHC(O)OH. In embodiments, $R^{29}$ is —SO$_2$CH$_3$. In embodiments, $R^{29}$ is —NHSO$_2$CH$_3$. In embodiments, $R^{29}$ is —SO$_2$CH$_2$CH$_3$. In embodiments, $R^{29}$ is —SO$_2$R$^{30}$. In embodiments, $R^{29}$ is —SO$_2$CH(CH$_3$)$_2$. In embodiments, $R^{29}$ is —COOEt. In embodiments, $R^{29}$ is —NHCOCH$_3$. In embodiments, $R^{29}$ is —NHSO$_2$CH(CH$_3$)$_2$. In embodiments, $R^{29}$ is —NHCOCH(CH$_3$)$_2$. In embodiments, $R^{29}$ is —NHCOOCH$_3$. In embodiments, $R^{29}$ is —SO$_2$NHCH$_3$. In embodiments, $R^{29}$ is —CONHCH$_3$. In embodiments, $R^{29}$ is —CON(CH$_3$)$_2$. In embodiments, $R^{29}$ is —S$_2$NH$_2$.

In embodiments, $R^{29}$ is —(CH$_2$)$_3$COOH. In embodiments, $R^{29}$ is —(CH$_2$)$_2$COOH. In embodiments, $R^{29}$ is —(CH$_2$)COOH. In embodiments, $R^{29}$ is —(CH$_2$)$_2$CONH$_2$. In embodiments, $R^{29}$ is —(CH$_2$)$_3$CONH$_2$. In embodiments, $R^{29}$ is —(CH$_2$)$_3$OH. In embodiments, $R^{29}$ is substituted cyclobutyl. In embodiments, $R^{29}$ is —(CH$_2$)$_2$SO$_2$CH$_3$. In embodiments, $R^{29}$ is —CH$_2$CH(CH$_3$)OH. In embodiments, $R^{29}$ is —(CH$_2$)$_2$OH. In embodiments, $R^{29}$ is —(CH$_2$)$_4$OH. In embodiments, $R^{29}$ is —(CH$_2$)OH. In embodiments, $R^{29}$ is —(CH$_2$)$_2$NHSO$_2$CH$_3$. In embodiments, $R^{29}$ is —(CH$_2$)$_2$NHS$_2$CH$_2$CH$_3$. In embodiments, $R^{29}$ is —(CH$_2$)$_2$NHSO$_2$(CH$_2$)$_2$CH$_3$. In embodiments, $R^{29}$ is —(CH$_2$)$_2$NHSO$_2$CH(CH$_3$)$_2$. In embodiments, $R^{29}$ is —(CH$_2$)$_2$NHC(O)OCH$_3$. In embodiments, $R^{29}$ is —(CH$_2$)$_3$SO$_2$CH$_3$. In embodiments, $R^{29}$ is —(CH$_2$)$_2$NHC(O)CH$_3$. In embodiments, $R^{29}$ is —(CH$_2$)$_2$NHC(O)H. In embodiments, $R^{29}$ is —CH$_2$C(O)OCH$_3$. In embodiments, $R^{29}$ is —CH$_2$C(O)OCH$_2$CH$_3$. In embodiments, $R^{29}$ is —(CH$_2$)$_3$SO$_2$NH$_2$. In embodiments, $R^{29}$ is —(CH$_2$)$_2$SO$_2$NH$_2$. In embodiments, $R^{29}$ is —(CH$_2$)$_1$SO$_2$NH$_2$. In embodiments, $R^{29}$ is —(CH$_2$)$_2$NHC(O)CH$_2$CH$_3$. In embodiments, $R^{29}$ is —(CH$_2$)$_2$NHC(O)CH(CH$_3$)$_2$.

In embodiments, $R^{29}$ is hydrogen. In embodiments, $R^{29}$ is $R^{30}$-substituted or unsubstituted alkyl. In embodiments, $R^{29}$ is substituted or unsubstituted phenyl. In embodiments, $R^{29}$ is —(CH$_2$)$_2$OH. In embodiments, $R^{29}$ is —CH$_2$C(CH$_3$)$_2$OH. In embodiments, $R^{29}$ is —(CH$_2$)$_3$OH. In embodiments, $R^{29}$ is —(CH$_2$)$_2$CH(CH$_3$)$_2$OH. In embodiments, $R^{29}$ is —(CH$_2$)$_2$SO$_2$NH$_2$. In embodiments, $R^{29}$ is —(CH$_2$)$_3$SO$_2$NH$_2$. In embodiments, $R^{29}$ is —(CH$_2$)$_2$CONH$_2$. In embodiments, $R^{29}$ is —(CH$_2$)$_3$CONH$_2$. In embodiments, $R^{29}$ is —(CH$_2$)$_3$CON(H)Me. In embodiments, $R^{29}$ is —(CH$_2$)$_3$ $CON(Me)_2$. In embodiments, $R^{29}$ is $-(CH_2)_2SO_2Me$. In embodiments, $R^{29}$ is $-(CH_2)_3SO_2Me$. In embodiments, $R^{29}$ is $-CH_2CH(OH)Me$. In embodiments, $R^{29}$ is $-CH_2CO_2H$. In embodiments, $R^{29}$ is $-(CH_2)_2CO_2H$. In embodiments, $R^{29}$ is $-CH(CH_3)CH_2CO_2H$. In embodiments, $R^{29}$ is $-(CH_2)_3CO_2H$. In embodiments, $R^{29}$ is $-(CH_2)_2SO_2NHCH_3$. In embodiments, $R^{29}$ is $-(CH_2)_2SO_2N(CH_3)_2$. In embodiments, $R^{29}$ is $-(CH_2)_2SO_2-(N\text{-morpholinyl})$. In embodiments, $R^{29}$ is $-(CH_2)_2NHCOCH_3$. In embodiments, $R^{29}$ is $-(CH_2)_2NHC(O)OCH_3$. In embodiments, $R^{29}$ is $-(CH_2)_3NHCOCH_3$. In embodiments, $R^{29}$ is $-(CH_2)_2NHCOCH(CH_3)_2$. In embodiments, $R^{29}$ is $-(CH_2)_2NHSO_2CH_3$. In embodiments, $R^{29}$ is $-(CH_2)_2NHSO_2CF_3$. In embodiments, $R^{29}$ is $-(CH_2)_2NHSO_2NHCH(CH_3)_2$. In embodiments, $R^{29}$ is $-CH_2CH(CH_3)CH_2OH$ (R and S). In embodiments, $R^{29}$ is $-CH(CH_3)(CH_2)_2OH$. In embodiments, $R^{29}$ is $-CH_2-(2\text{-imidazoyl})$. In embodiments, $R^{29}$ is $-CH_2-(4\text{-imidazoyl})$. In embodiments, $R^{29}$ is $-CH_2-(3\text{-pyrazoyl})$. In embodiments, $R^{29}$ is 4-tetrahydropyranyl. In embodiments, $R^{29}$ is 3-oxetanyl. In embodiments, $R^{29}$ is $-(CH_2)_2NHCO_2Me$. In embodiments, $R^{29}$ is $-(CH_2)_3NHCO_2Me$.

In embodiments, $R^{29}$ is $-OH$. In embodiments, $R^{29}$ is $-COOH$. In embodiments, $R^{29}$ is a substituted pyrrolidinyl (e.g., oxo-substituted pyrrolidinyl). In embodiments, $R^{29}$ is oxo. In embodiments, $R^{29}$ is $-SO_2NH_2$. In embodiments, $R^{29}$ is $-NH_2$. In embodiments, $R^{29}$ is $-CH_3$. In embodiments, $R^{29}$ is $-CH_2CH_3$. In embodiments, $R^{29}$ is $-NHCOCH_3$. In embodiments, $R^{29}$ is $-CONHCH_3$. In embodiments, $R^{29}$ is $-NHSO_2CH_3$. In embodiments, $R^{29}$ is $-NHSO_2CH_3$. In embodiments, $R^{29}$ is $-NHSO_2CH_2CH_3$. In embodiments, $R^{29}$ is $-NHSO_2(C_1\text{-}C_6 \text{ alkyl})$. In embodiments, $R^{29}$ is $-COCH(CH_3)_2$.

In embodiments, $R^{29}$ is unsubstituted morpholinyl. In embodiments, $R^{29}$ is unsubstituted imidazolyl. In embodiments, $R^{29}$ is unsubstituted thianyl. In embodiments, $R^{29}$ is unsubstituted tetrahydropyranyl. In embodiments, $R^{29}$ is unsubstituted pyrazolyl. In embodiments, $R^{29}$ is unsubstituted pyrrolidinyl. In embodiments, $R^{29}$ is $R^{30}$-substituted morpholinyl. In embodiments, $R^{29}$ is $R^{30}$-substituted imidazolyl. In embodiments, $R^{29}$ is $R^{30}$-substituted thianyl. In embodiments, $R^{29}$ is $R^{30}$-substituted tetrahydropyranyl. In embodiments, $R^{29}$ is $R^{30}$-substituted pyrazolyl. In embodiments, $R^{29}$ is $R^{30}$-substituted pyrrolidinyl. In embodiments, $R^{29}$ is $-CH_3$.

In embodiments, $R^{29}$ is $R^{30}$-substituted or unsubstituted alkyl (e.g., $C_1$-$C_8$ alkyl, $C_1$-$C_6$ alkyl, or $C_1$-$C_4$ alkyl). In embodiments, $R^{29}$ is $R^{30}$-substituted alkyl (e.g., $C_1$-$C_8$ alkyl, $C_1$-$C_6$ alkyl, or $C_1$-$C_4$ alkyl). In embodiments, $R^{29}$ is an unsubstituted alkyl (e.g., $C_1$-$C_8$ alkyl, $C_1$-$C_6$ alkyl, or $C_1$-$C_4$ alkyl).

In embodiments, $R^{29}$ is $R^{30}$-substituted or unsubstituted heteroalkyl (e.g., 2 to 8 membered heteroalkyl, 2 to 6 membered heteroalkyl, or 2 to 4 membered heteroalkyl). In embodiments, $R^{29}$ is $R^{30}$-substituted heteroalkyl (e.g., 2 to 8 membered heteroalkyl, 2 to 6 membered heteroalkyl, or 2 to 4 membered heteroalkyl). In embodiments, $R^{29}$ is an unsubstituted heteroalkyl (e.g., 2 to 8 membered heteroalkyl, 2 to 6 membered heteroalkyl, or 2 to 4 membered heteroalkyl).

In embodiments, $R^{29}$ is $R^{30}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{29}$ is $R^{30}$-substituted cycloalkyl (e.g., $C_3$-$C_8$ cycloalkyl, $C_3$-$C_6$ cycloalkyl, or $C_5$-$C_6$ cycloalkyl). In embodiments, $R^{29}$ is an unsubstituted cycloalkyl (e.g., $C_3$-$C_8$ cycloalkyl, $C_3$-$C_6$ cycloalkyl, or $C$—$C_6$ cycloalkyl).

In embodiments, $R^{29}$ is $R^{30}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{29}$ is $R^{30}$-substituted heterocycloalkyl (e.g., 3 to 8 membered heterocycloalkyl, 3 to 6 membered heterocycloalkyl, or 5 to 6 membered heterocycloalkyl). In embodiments, $R^{29}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{29}$ is $R^{30}$-substituted or unsubstituted aryl (e.g., $C_6$-$C_{10}$ aryl, $C_{10}$ aryl, or phenyl). In embodiments, $R^{29}$ is $R^{30}$-substituted aryl (e.g., $C_6$-$C_{10}$ aryl, $C_{10}$ aryl, or phenyl). In embodiments, $R^{29}$ is an unsubstituted aryl (e.g., $C_6$-$C_{10}$ aryl, $C_{10}$ aryl, or phenyl).

In embodiments, $R^{29}$ is $R^{30}$-substituted or unsubstituted heteroaryl (e.g., 5 to 10 membered heteroaryl, 5 to 9 membered heteroaryl, or 5 to 6 membered heteroaryl). In embodiments, $R^{29}$ is $R^{30}$-substituted heteroaryl (e.g., 5 to 10 membered heteroaryl, 5 to 9 membered heteroaryl, or 5 to 6 membered heteroaryl). In embodiments, $R^{29}$ is an unsubstituted heteroaryl (e.g., 5 to 10 membered heteroaryl, 5 to 9 membered heteroaryl, or 5 to 6 membered heteroaryl).

$R^{30}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{31}$-substituted or unsubstituted alkyl (e.g., $C_1$-$C_8$ alkyl, $C_1$-$C_6$ alkyl, or $C_1$-$C_4$ alkyl), $R^{31}$-substituted or unsubstituted heteroalkyl (e.g., 2 to 8 membered heteroalkyl, 2 to 6 membered heteroalkyl, or 2 to 4 membered heteroalkyl), $R^{31}$-substituted or unsubstituted cycloalkyl (e.g., $C_3$-$C_8$ cycloalkyl, $C_3$-$C_6$ cycloalkyl, or $C$—$C_6$ cycloalkyl), $R^{31}$-substituted or unsubstituted heterocycloalkyl (e.g., 3 to 8 membered heterocycloalkyl, 3 to 6 membered heterocycloalkyl, or 5 to 6 membered heterocycloalkyl), $R^{31}$-substituted or unsubstituted aryl (e.g., $C_6$-$C_{10}$ aryl, $C_{10}$ aryl, or phenyl), or $R^{31}$-substituted or unsubstituted heteroaryl (e.g., 5 to 10 membered heteroaryl, 5 to 9 membered heteroaryl, or 5 to 6 membered heteroaryl). In embodiments, $R^{30}$ is oxo. In embodiments, $R^{30}$ is $-CH_3$. In embodiments, $R^{30}$ is $-COOH$. In embodiments, $R^{30}$ is $-NHC(O)NH_2$. In embodiments, $R^{30}$ is $-OH$. In embodiments, $R^{30}$ is $-NH_2$. In embodiments, $R^{30}$ is $-CONH_2$. In embodiments, $R^{30}$ is $-NHC(O)OH$. In embodiments, $R^{30}$ is $-SO_2CH_3$. In embodiments, $R^{30}$ is $-NHSO_2CH_3$. In embodiments, $R^{30}$ is $-SO_2CH_2CH_3$. In embodiments, $R^{30}$ is $-SO_2R^{31}$. In embodiments, $R^{30}$ is $-SO_2CH(CH_3)_2$. In embodiments, $R^3$ is $-COOEt$. In embodiments, $R^{30}$ is $-NHCOCH_3$. In embodiments, $R^{30}$ is $-NHSO_2CH(CH_3)_2$. In embodiments, $R^{30}$ is $-NHCOCH(CH_3)_2$. In embodiments, $R^{30}$ is $-NHCOOCH_3$. In embodiments, $R^{30}$ is $-SO_2NHCH_3$. In embodiments, $R^{30}$ is $-CONHCH_3$. In embodiments, $R^{30}$ is $-CON(CH_3)_2$. In embodiments, $R^{30}$ is $-SO_2NH_2$. In embodiments, $R^{30}$ is $-CH_3$.

In embodiments, $R^{30}$ is $R^{31}$-substituted or unsubstituted alkyl (e.g., $C_1$-$C_8$ alkyl, $C_1$-$C_6$ alkyl, or $C_1$-$C_4$ alkyl). In embodiments, $R^{30}$ is $R^{31}$-substituted alkyl (e.g., $C_1$-$C_8$ alkyl, $C_1$-$C_6$ alkyl, or $C_1$-$C_4$ alkyl). In embodiments, $R^{30}$ is an unsubstituted alkyl (e.g., $C_1$-$C_8$ alkyl, $C_1$-$C_6$ alkyl, or $C_1$-$C_4$ alkyl).

In embodiments, $R^{30}$ is $R^{31}$-substituted or unsubstituted heteroalkyl (e.g., 2 to 8 membered heteroalkyl, 2 to 6 membered heteroalkyl, or 2 to 4 membered heteroalkyl). In embodiments, $R^{30}$ is $R^{31}$-substituted heteroalkyl (e.g., 2 to 8 membered heteroalkyl, 2 to 6 membered heteroalkyl, or 2 to 4 membered heteroalkyl). In embodiments, $R^{30}$ is an unsubstituted heteroalkyl (e.g., 2 to 8 membered heteroalkyl, 2 to 6 membered heteroalkyl, or 2 to 4 membered heteroalkyl).

In embodiments, $R^{30}$ is $R^{31}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{30}$ is $R^{31}$-substituted cycloalkyl (e.g., $C_3$-$C_8$ cycloalkyl, $C_3$-$C_6$ cycloalkyl, or $C_5$-$C_6$ cycloalkyl). In embodiments, $R^{30}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{30}$ is $R^{31}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{30}$ is $R^{31}$-substituted heterocycloalkyl (e.g., 3 to 8 membered heterocycloalkyl, 3 to 6 membered heterocycloalkyl, or 5 to 6 membered heterocycloalkyl). In embodiments, $R^{30}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{30}$ is $R^{31}$-substituted or unsubstituted aryl (e.g., $C_6$-$C_{10}$ aryl, $C_{10}$ aryl, or phenyl). In embodiments, $R^{30}$ is $R^{31}$-substituted aryl (e.g., $C_6$-$C_{10}$ aryl, $C_{10}$ aryl, or phenyl). In embodiments, $R^{30}$ is an unsubstituted aryl (e.g., $C_6$-$C_{10}$ aryl, $C_{10}$ aryl, or phenyl).

In embodiments, $R^{30}$ is $R^{31}$-substituted or unsubstituted heteroaryl (e.g., 5 to 10 membered heteroaryl, 5 to 9 membered heteroaryl, or 5 to 6 membered heteroaryl). In embodiments, $R^{30}$ is $R^{31}$-substituted heteroaryl (e.g., 5 to 10 membered heteroaryl, 5 to 9 membered heteroaryl, or 5 to 6 membered heteroaryl). In embodiments, $R^{30}$ is an unsubstituted heteroaryl (e.g., 5 to 10 membered heteroaryl, 5 to 9 membered heteroaryl, or 5 to 6 membered heteroaryl).

$R^{32}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{33}$-substituted or unsubstituted alkyl (e.g., $C_1$-$C_8$ alkyl, $C_1$-$C_6$ alkyl, or $C_1$-$C_4$ alkyl), $R^{33}$-substituted or unsubstituted heteroalkyl (e.g., 2 to 8 membered heteroalkyl, 2 to 6 membered heteroalkyl, or 2 to 4 membered heteroalkyl), $R^{3.3}$-substituted or unsubstituted cycloalkyl (e.g., $C_3$-$C_8$ cycloalkyl, $C_3$-$C_6$ cycloalkyl, or C—$C_6$ cycloalkyl), $R^{3.3}$-substituted or unsubstituted heterocycloalkyl (e.g., 3 to 8 membered heterocycloalkyl, 3 to 6 membered heterocycloalkyl, or 5 to 6 membered heterocycloalkyl), $R^{3.3}$-substituted or unsubstituted aryl (e.g., $C_6$-$C_{10}$ aryl, $C_{10}$ aryl, or phenyl), or $R^{3.3}$-substituted or unsubstituted heteroaryl (e.g., 5 to 10 membered heteroaryl, 5 to 9 membered heteroaryl, or 5 to 6 membered heteroaryl).

In embodiments, $R^{32}$ is $R^{33}$-substituted or unsubstituted alkyl (e.g., $C_1$-$C_8$ alkyl, $C_1$-$C_6$ alkyl, or $C_1$-$C_4$ alkyl). In embodiments, $R^{32}$ is $R^{33}$-substituted alkyl (e.g., $C_1$-$C_8$ alkyl, $C_1$-$C_6$ alkyl, or $C_1$-$C_4$ alkyl). In embodiments, $R^{32}$ is an unsubstituted alkyl (e.g., $C_1$-$C_8$ alkyl, $C_1$-$C_6$ alkyl, or $C_1$-$C_4$ alkyl).

In embodiments, $R^{32}$ is $R^{33}$-substituted or unsubstituted heteroalkyl (e.g., 2 to 8 membered heteroalkyl, 2 to 6 membered heteroalkyl, or 2 to 4 membered heteroalkyl). In embodiments, $R^{32}$ is $R^{33}$-substituted heteroalkyl (e.g., 2 to 8 membered heteroalkyl, 2 to 6 membered heteroalkyl, or 2 to 4 membered heteroalkyl). In embodiments, $R^{32}$ is an unsubstituted heteroalkyl (e.g., 2 to 8 membered heteroalkyl, 2 to 6 membered heteroalkyl, or 2 to 4 membered heteroalkyl).

In embodiments, $R^{32}$ is $R^{33}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{32}$ is $R^{33}$-substituted cycloalkyl (e.g., $C_3$-$C_8$ cycloalkyl, $C_3$-$C_6$ cycloalkyl, or $C_5$-$C_6$ cycloalkyl). In embodiments, $R^{32}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{32}$ is $R^{33}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{32}$ is $R^{33}$-substituted heterocycloalkyl (e.g., 3 to 8 membered heterocycloalkyl, 3 to 6 membered heterocycloalkyl, or 5 to 6 membered heterocycloalkyl). In embodiments, $R^{32}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{32}$ is $R^{33}$-substituted or unsubstituted aryl (e.g., $C_6$-$C_{10}$ aryl, $C_{10}$ aryl, or phenyl). In embodiments, $R^{32}$ is $R^{33}$-substituted aryl (e.g., $C_6$-$C_{10}$ aryl, $C_{10}$ aryl, or phenyl). In embodiments, $R^{32}$ is an unsubstituted aryl (e.g., $C_6$-$C_{10}$ aryl, $C_{10}$ aryl, or phenyl).

In embodiments, $R^{32}$ is $R^{33}$-substituted or unsubstituted heteroaryl (e.g., 5 to 10 membered heteroaryl, 5 to 9 membered heteroaryl, or 5 to 6 membered heteroaryl). In embodiments, $R^{32}$ is $R^{33}$-substituted heteroaryl (e.g., 5 to 10 membered heteroaryl, 5 to 9 membered heteroaryl, or 5 to 6 membered heteroaryl). In embodiments, $R^{32}$ is an unsubstituted heteroaryl (e.g., 5 to 10 membered heteroaryl, 5 to 9 membered heteroaryl, or 5 to 6 membered heteroaryl).

$R^{33}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{34}$-substituted or unsubstituted alkyl (e.g., $C_1$-$C_8$ alkyl, $C_1$-$C_6$ alkyl, or $C_1$-$C_4$ alkyl), $R^{34}$-substituted or unsubstituted heteroalkyl (e.g., 2 to 8 membered heteroalkyl, 2 to 6 membered heteroalkyl, or 2 to 4 membered heteroalkyl), $R^{34}$-substituted or unsubstituted cycloalkyl (e.g., $C_3$-$C_8$ cycloalkyl, $C_3$-$C_6$ cycloalkyl, or C—$C_6$ cycloalkyl), $R^{34}$-substituted or unsubstituted heterocycloalkyl (e.g., 3 to 8 membered heterocycloalkyl, 3 to 6 membered heterocycloalkyl, or 5 to 6 membered heterocycloalkyl), $R^{34}$-substituted or unsubstituted aryl (e.g., $C_6$-$C_{10}$ aryl, $C_{10}$ aryl, or phenyl), or $R^{34}$-substituted or unsubstituted heteroaryl (e.g., 5 to 10 membered heteroaryl, 5 to 9 membered heteroaryl, or 5 to 6 membered heteroaryl).

In embodiments, $R^{33}$ is $R^{34}$-substituted or unsubstituted alkyl (e.g., $C_1$-$C_8$ alkyl, $C_1$-$C_6$ alkyl, or $C_1$-$C_4$ alkyl). In embodiments, $R^{33}$ is $R^{34}$-substituted alkyl (e.g., $C_1$-$C_8$ alkyl, $C_1$-$C_6$ alkyl, or $C_1$-$C_4$ alkyl). In embodiments, $R^{33}$ is an unsubstituted alkyl (e.g., $C_1$-$C_8$ alkyl, $C_1$-$C_6$ alkyl, or $C_1$-$C_4$ alkyl).

In embodiments, $R^{33}$ is $R^{34}$-substituted or unsubstituted heteroalkyl (e.g., 2 to 8 membered heteroalkyl, 2 to 6 membered heteroalkyl, or 2 to 4 membered heteroalkyl). In embodiments, $R^{33}$ is $R^{34}$-substituted heteroalkyl (e.g., 2 to 8 membered heteroalkyl, 2 to 6 membered heteroalkyl, or 2 to 4 membered heteroalkyl). In embodiments, $R^{3.3}$ is an unsubstituted heteroalkyl (e.g., 2 to 8 membered heteroalkyl, 2 to 6 membered heteroalkyl, or 2 to 4 membered heteroalkyl).

In embodiments, $R^{33}$ is $R^{34}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{33}$ is $R^{34}$-substituted cycloalkyl (e.g., $C_3$-$C_8$ cycloalkyl, $C_3$-$C_6$ cycloalkyl, or $C_5$-$C_6$ cycloalkyl). In embodiments, $R^{3.3}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{33}$ is $R^{34}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{33}$ is $R^{34}$-substituted heterocycloalkyl (e.g., 3 to 8 membered heterocycloalkyl, 3 to 6 membered heterocycloalkyl, or 5 to 6 membered heterocycloalkyl). In embodiments, $R^{33}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{33}$ is $R^{34}$-substituted or unsubstituted aryl (e.g., $C_6$-$C_0$ aryl, $C_{10}$ aryl, or phenyl). In embodiments, $R^{33}$ is $R^{34}$-substituted aryl (e.g., $C_6$-$C_{10}$ aryl, $C_{10}$ aryl, or phenyl). In embodiments, $R^{33}$ is an unsubstituted aryl (e.g., $C_6$-$C_{10}$ aryl, $C_{10}$ aryl, or phenyl).

In embodiments, $R^{33}$ is $R^{34}$-substituted or unsubstituted heteroaryl (e.g., 5 to 10 membered heteroaryl, 5 to 9 membered heteroaryl, or 5 to 6 membered heteroaryl). In embodiments, $R^{33}$ is $R^{34}$-substituted heteroaryl (e.g., 5 to 10 membered heteroaryl, 5 to 9 membered heteroaryl, or 5 to 6 membered heteroaryl). In embodiments, $R^{3.3}$ is an unsubstituted heteroaryl (e.g., 5 to 10 membered heteroaryl, 5 to 9 membered heteroaryl, or 5 to 6 membered heteroaryl).

$R^{35}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{36}$-substituted or unsubstituted alkyl (e.g., $C_1$-$C_5$ alkyl, $C_1$-$C_6$ alkyl, or $C_1$-$C_4$ alkyl), $R^{36}$-substituted or unsubstituted heteroalkyl (e.g., 2 to 8 membered heteroalkyl, 2 to 6 membered heteroalkyl, or 2 to 4 membered heteroalkyl), $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{36}$-substituted or unsubstituted heterocycloalkyl (e.g., 3 to 8 membered heterocycloalkyl, 3 to 6 membered heterocycloalkyl, or 5 to 6 membered heterocycloalkyl), $R^{36}$-substituted or unsubstituted aryl (e.g., $C_6$-$C_{10}$ aryl, $C_{10}$ aryl, or phenyl), or $R^{36}$-substituted or unsubstituted heteroaryl (e.g., 5 to 10 membered heteroaryl, 5 to 9 membered heteroaryl, or 5 to 6 membered heteroaryl).

In embodiments, $R^{35}$ is $R^{36}$-substituted or unsubstituted alkyl (e.g., $C_1$-$C_8$ alkyl, $C_1$-$C_6$ alkyl, or $C_1$-$C_4$ alkyl). In embodiments, $R^{35}$ is $R^{36}$-substituted alkyl (e.g., $C_1$-$C_8$ alkyl, $C_1$-$C_6$ alkyl, or $C_1$-$C_4$ alkyl). In embodiments, $R^{35}$ is an unsubstituted alkyl (e.g., $C_1$-$C_8$ alkyl, $C_1$-$C_6$ alkyl, or $C_1$-$C_4$ alkyl).

In embodiments, $R^{35}$ is $R^{36}$-substituted or unsubstituted heteroalkyl (e.g., 2 to 8 membered heteroalkyl, 2 to 6 membered heteroalkyl, or 2 to 4 membered heteroalkyl). In embodiments, $R^{35}$ is $R^{36}$-substituted heteroalkyl (e.g., 2 to 8 membered heteroalkyl, 2 to 6 membered heteroalkyl, or 2 to 4 membered heteroalkyl). In embodiments, $R^{35}$ is an unsubstituted heteroalkyl (e.g., 2 to 8 membered heteroalkyl, 2 to 6 membered heteroalkyl, or 2 to 4 membered heteroalkyl).

In embodiments, $R^{35}$ is $R^{36}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{35}$ is $R^{36}$-substituted cycloalkyl (e.g., $C_3$-$C_8$ cycloalkyl, $C_3$-$C_6$ cycloalkyl, or $C_5$-$C_6$ cycloalkyl). In embodiments, $R^{35}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{35}$ is $R^{36}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{35}$ is $R^{36}$-substituted heterocycloalkyl (e.g., 3 to 8 membered heterocycloalkyl, 3 to 6 membered heterocycloalkyl, or 5 to 6 membered heterocycloalkyl). In embodiments, $R^{35}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{35}$ is $R^{36}$-substituted or unsubstituted aryl (e.g., $C_6$-$C_{10}$ aryl, $C_{10}$ aryl, or phenyl). In embodiments, $R^{35}$ is $R^{36}$-substituted aryl (e.g., $C_6$-$C_{10}$ aryl, $C_{10}$ aryl, or phenyl). In embodiments, $R^{35}$ is an unsubstituted aryl (e.g., $C_6$-$C_{10}$ aryl, $C_{10}$ aryl, or phenyl).

In embodiments, $R^{35}$ is $R^{36}$-substituted or unsubstituted heteroaryl (e.g., 5 to 10 membered heteroaryl, 5 to 9 membered heteroaryl, or 5 to 6 membered heteroaryl). In embodiments, $R^{35}$ is $R^{36}$-substituted heteroaryl (e.g., 5 to 10 membered heteroaryl, 5 to 9 membered heteroaryl, or 5 to 6 membered heteroaryl). In embodiments, $R^{35}$ is an unsubstituted heteroaryl (e.g., 5 to 10 membered heteroaryl, 5 to 9 membered heteroaryl, or 5 to 6 membered heteroaryl).

$R^{36}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{37}$-substituted or unsubstituted alkyl (e.g., $C_1$-$C_8$ alkyl, $C_1$-$C_6$ alkyl, or $C_1$-$C_4$ alkyl), $R^{37}$-substituted or unsubstituted heteroalkyl (e.g., 2 to 8 membered heteroalkyl, 2 to 6 membered heteroalkyl, or 2 to 4 membered heteroalkyl), $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{37}$-substituted or unsubstituted heterocycloalkyl (e.g., 3 to 8 membered heterocycloalkyl, 3 to 6 membered heterocycloalkyl, or 5 to 6 membered heterocycloalkyl), $R^{37}$-substituted or unsubstituted aryl (e.g., $C_6$-$C_{10}$ aryl, $C_{10}$ aryl, or phenyl), or $R^{37}$-substituted or unsubstituted heteroaryl (e.g., 5 to 10 membered heteroaryl, 5 to 9 membered heteroaryl, or 5 to 6 membered heteroaryl).

In embodiments, $R^{36}$ is $R^{37}$-substituted or unsubstituted alkyl (e.g., $C_1$-$C_8$ alkyl, $C_1$-$C_6$ alkyl, or $C_1$-$C_4$ alkyl). In embodiments, $R^{36}$ is $R^{37}$-substituted alkyl (e.g., $C_1$-$C_8$ alkyl, $C_1$-$C_6$ alkyl, or $C_1$-$C_4$ alkyl). In embodiments, $R^{36}$ is an unsubstituted alkyl (e.g., $C_1$-$C_8$ alkyl, $C_1$-$C_6$ alkyl, or $C_1$-$C_4$ alkyl).

In embodiments, $R^{36}$ is $R^{37}$-substituted or unsubstituted heteroalkyl (e.g., 2 to 8 membered heteroalkyl, 2 to 6 membered heteroalkyl, or 2 to 4 membered heteroalkyl). In embodiments, $R^{36}$ is $R^{37}$-substituted heteroalkyl (e.g., 2 to 8 membered heteroalkyl, 2 to 6 membered heteroalkyl, or 2 to 4 membered heteroalkyl). In embodiments, $R^{36}$ is an unsubstituted heteroalkyl (e.g., 2 to 8 membered heteroalkyl, 2 to 6 membered heteroalkyl, or 2 to 4 membered heteroalkyl).

In embodiments, $R^{36}$ is $R^{37}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{36}$ is $R^{37}$-substituted cycloalkyl (e.g., $C_3$-$C_8$ cycloalkyl, $C_3$-$C_6$ cycloalkyl, or $C_5$-$C_6$ cycloalkyl). In embodiments, $R^{36}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{36}$ is $R^{37}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{36}$ is $R^{37}$-substituted heterocycloalkyl (e.g., 3 to 8 membered heterocycloalkyl, 3 to 6 membered heterocycloalkyl, or 5 to 6 membered heterocycloalkyl). In embodiments, $R^{36}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{36}$ is $R^{37}$-substituted or unsubstituted aryl (e.g., $C_6$-$C_{10}$ aryl, $C_{10}$ aryl, or phenyl). In embodiments, $R^{36}$ is $R^{37}$-substituted aryl (e.g., $C_6$-$C_{10}$ aryl, $C_{10}$ aryl, or phenyl). In embodiments, $R^{36}$ is an unsubstituted aryl (e.g., $C_6$-$C_{10}$ aryl, $C_{10}$ aryl, or phenyl).

In embodiments, $R^{36}$ is $R^{37}$-substituted or unsubstituted heteroaryl (e.g., 5 to 10 membered heteroaryl, 5 to 9 membered heteroaryl, or 5 to 6 membered heteroaryl). In embodiments, $R^{36}$ is $R^{37}$-substituted heteroaryl (e.g., 5 to 10 membered heteroaryl, 5 to 9 membered heteroaryl, or 5 to 6 membered heteroaryl). In embodiments, $R^{36}$ is an unsubstituted heteroaryl (e.g., 5 to 10 membered heteroaryl, 5 to 9 membered heteroaryl, or 5 to 6 membered heteroaryl).

$R^{38}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{39}$-substituted or unsubstituted alkyl (e.g., $C_1$-$C_5$ alkyl, $C_1$-$C_6$ alkyl, or $C_1$-$C_4$ alkyl), $R^{39}$-substituted or unsubstituted heteroalkyl (e.g., 2 to 8 membered heteroalkyl, 2 to 6 membered heteroalkyl, or 2 to 4 membered heteroalkyl), $R^{39}$-substituted or unsubstituted cycloalkyl (e.g., $C_3$-$C_8$ cycloalkyl, $C_3$-$C_6$ cycloalkyl, or C—$C_6$ cycloalkyl), $R^{39}$-substituted or unsubstituted heterocycloalkyl (e.g., 3 to 8 membered heterocycloalkyl, 3 to 6 membered heterocycloalkyl, or 5 to 6 membered heterocycloalkyl), $R^{39}$-substituted or unsubstituted aryl (e.g., $C_6$-$C_{10}$ aryl, $C_{10}$ aryl, or phenyl), or $R^{39}$-substituted or unsubstituted heteroaryl (e.g., 5 to 10 membered heteroaryl, 5 to 9 membered heteroaryl, or 5 to 6 membered heteroaryl).

In embodiments, $R^{38}$ is $R^{39}$-substituted or unsubstituted alkyl (e.g., $C_1$-$C_8$ alkyl, $C_1$-$C_6$ alkyl, or $C_1$-$C_4$ alkyl). In embodiments, $R^3$ is $R^{39}$-substituted alkyl (e.g., $C_1$-$C_8$ alkyl, $C_1$-$C_6$ alkyl, or $C_1$-$C_4$ alkyl). In embodiments, $R^{38}$ is an unsubstituted alkyl (e.g., $C_1$-$C_8$ alkyl, $C_1$-$C_6$ alkyl, or $C_1$-$C_4$ alkyl).

In embodiments, $R^{38}$ is $R^{39}$-substituted or unsubstituted heteroalkyl (e.g., 2 to 8 membered heteroalkyl, 2 to 6 membered heteroalkyl, or 2 to 4 membered heteroalkyl). In embodiments, $R^{38}$ is $R^{39}$-substituted heteroalkyl (e.g., 2 to 8 membered heteroalkyl, 2 to 6 membered heteroalkyl, or 2 to 4 membered heteroalkyl). In embodiments, $R^{38}$ is an unsubstituted heteroalkyl (e.g., 2 to 8 membered heteroalkyl, 2 to 6 membered heteroalkyl, or 2 to 4 membered heteroalkyl).

In embodiments, $R^{38}$ is $R^{39}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{39}$-substituted cycloalkyl (e.g., $C_3$-$C_8$ cycloalkyl, $C_3$-$C_6$ cycloalkyl, or $C_5$-$C_6$ cycloalkyl). In embodiments, $R^{38}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{38}$ is $R^{39}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{38}$ is $R^{39}$-substituted heterocycloalkyl (e.g., 3 to 8 membered heterocycloalkyl, 3 to 6 membered heterocycloalkyl, or 5 to 6 membered heterocycloalkyl). In embodiments, $R^{38}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{38}$ is $R^{39}$-substituted or unsubstituted aryl (e.g., $C_6$-$C_{10}$ aryl, $C_{10}$ aryl, or phenyl). In embodiments, $R^{38}$ is $R^{39}$-substituted aryl (e.g., $C_6$-$C_{10}$ aryl, $C_{10}$ aryl, or phenyl). In embodiments, $R^{38}$ is an unsubstituted aryl (e.g., $C_6$-$C_{10}$ aryl, $C_{10}$ aryl, or phenyl).

In embodiments, $R^{38}$ is $R^{39}$-substituted or unsubstituted heteroaryl (e.g., 5 to 10 membered heteroaryl, 5 to 9 membered heteroaryl, or 5 to 6 membered heteroaryl). In embodiments, $R^{38}$ is $R^{39}$-substituted heteroaryl (e.g., 5 to 10 membered heteroaryl, 5 to 9 membered heteroaryl, or 5 to 6 membered heteroaryl). In embodiments, $R^{38}$ is an unsubstituted heteroaryl (e.g., 5 to 10 membered heteroaryl, 5 to 9 membered heteroaryl, or 5 to 6 membered heteroaryl).

$R^{39}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{40}$-substituted or unsubstituted alkyl (e.g., $C_1$-$C_5$ alkyl, $C_1$-$C_6$ alkyl, or $C_1$-$C_4$ alkyl), $R^{40}$-substituted or unsubstituted heteroalkyl (e.g., 2 to 8 membered heteroalkyl, 2 to 6 membered heteroalkyl, or 2 to 4 membered heteroalkyl), $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{40}$-substituted or unsubstituted heterocycloalkyl (e.g., 3 to 8 membered heterocycloalkyl, 3 to 6 membered heterocycloalkyl, or 5 to 6 membered heterocycloalkyl), $R^{40}$-substituted or unsubstituted aryl (e.g., $C_6$-$C_{10}$ aryl, $C_{10}$ aryl, or phenyl), or $R^{40}$-substituted or unsubstituted heteroaryl (e.g., 5 to 10 membered heteroaryl, 5 to 9 membered heteroaryl, or 5 to 6 membered heteroaryl).

In embodiments, $R^{39}$ is $R^{40}$-substituted or unsubstituted alkyl (e.g., $C_1$-$C_8$ alkyl, $C_1$-$C_6$ alkyl, or $C_1$-$C_4$ alkyl). In embodiments, $R^{39}$ is $R^{40}$-substituted alkyl (e.g., $C_1$-$C_8$ alkyl, $C_1$-$C_6$ alkyl, or $C_1$-$C_4$ alkyl). In embodiments, $R^{39}$ is an unsubstituted alkyl (e.g., $C_1$-$C_8$ alkyl, $C_1$-$C_6$ alkyl, or $C_1$-$C_4$ alkyl).

In embodiments, $R^{39}$ is $R^{40}$-substituted or unsubstituted heteroalkyl (e.g., 2 to 8 membered heteroalkyl, 2 to 6 membered heteroalkyl, or 2 to 4 membered heteroalkyl). In embodiments, $R^{39}$ is $R^{40}$-substituted heteroalkyl (e.g., 2 to 8 membered heteroalkyl, 2 to 6 membered heteroalkyl, or 2 to 4 membered heteroalkyl). In embodiments, $R^{39}$ is an unsubstituted heteroalkyl (e.g., 2 to 8 membered heteroalkyl, 2 to 6 membered heteroalkyl, or 2 to 4 membered heteroalkyl).

In embodiments, $R^{39}$ is $R^{40}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{39}$ is $R^{40}$-substituted cycloalkyl (e.g., $C_3$-$C_8$ cycloalkyl, $C_3$-$C_6$ cycloalkyl, or $C_5$-$C_6$ cycloalkyl). In embodiments, $R^{39}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{39}$ is $R^{40}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{39}$ is $R^{40}$-substituted heterocycloalkyl (e.g., 3 to 8 membered heterocycloalkyl, 3 to 6 membered heterocycloalkyl, or 5 to 6 membered heterocycloalkyl). In embodiments, $R^{39}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{39}$ is $R^{40}$-substituted or unsubstituted aryl (e.g., $C_6$-$C_{10}$ aryl, $C_{10}$ aryl, or phenyl). In embodiments, $R^{39}$ is $R^{40}$-substituted aryl (e.g., $C_6$-$C_{10}$ aryl, $C_{10}$ aryl, or phenyl). In embodiments, $R^{39}$ is an unsubstituted aryl (e.g., $C_6$-$C_{10}$ aryl, $C_{10}$ aryl, or phenyl).

In embodiments, $R^{39}$ is $R^{40}$-substituted or unsubstituted heteroaryl (e.g., 5 to 10 membered heteroaryl, 5 to 9 membered heteroaryl, or 5 to 6 membered heteroaryl). In embodiments, $R^{39}$ is $R^{40}$-substituted heteroaryl (e.g., 5 to 10 membered heteroaryl, 5 to 9 membered heteroaryl, or 5 to 6 membered heteroaryl). In embodiments, $R^{39}$ is an unsubstituted heteroaryl (e.g., 5 to 10 membered heteroaryl, 5 to 9 membered heteroaryl, or 5 to 6 membered heteroaryl).

$R^{41}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{42}$-substituted or unsubstituted alkyl (e.g., $C_1$-$C_8$ alkyl, $C_1$-$C_6$ alkyl, or $C_1$-$C_4$ alkyl), $R^{42}$-substituted or unsubstituted heteroalkyl (e.g., 2 to 8 membered heteroalkyl, 2 to 6 membered heteroalkyl, or 2 to 4 membered heteroalkyl), $R^{42}$-substituted or unsubstituted cycloalkyl (e.g., $C_3$-$C_8$ cycloalkyl, $C_3$-$C_6$ cycloalkyl, or C—$C_6$ cycloalkyl), $R^{42}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42}$-substituted or unsubstituted aryl (e.g., $C_6$-$C_{10}$ aryl, $C_{10}$ aryl, or phenyl), or $R^{42}$-substituted or unsubstituted heteroaryl (e.g., 5 to 10 membered heteroaryl, 5 to 9 membered heteroaryl, or 5 to 6 membered heteroaryl).

In embodiments, $R^{41}$ is $R^{42}$-substituted or unsubstituted alkyl (e.g., $C_1$-$C_8$ alkyl, $C_1$-$C_6$ alkyl, or $C_1$-$C_4$ alkyl). In embodiments, $R^{41}$ is $R^{42}$-substituted alkyl (e.g., $C_1$-$C_8$ alkyl, $C_1$-$C_6$ alkyl, or $C_1$-$C_4$ alkyl). In embodiments, $R^{41}$ is an unsubstituted alkyl (e.g., $C_1$-$C_8$ alkyl, $C_1$-$C_6$ alkyl, or $C_1$-$C_4$ alkyl).

In embodiments, $R^{41}$ is $R^{42}$-substituted or unsubstituted heteroalkyl (e.g., 2 to 8 membered heteroalkyl, 2 to 6 membered heteroalkyl, or 2 to 4 membered heteroalkyl). In embodiments, $R^{41}$ is $R^{42}$-substituted heteroalkyl (e.g., 2 to 8 membered heteroalkyl, 2 to 6 membered heteroalkyl, or 2 to 4 membered heteroalkyl). In embodiments, $R^{41}$ is an unsubstituted heteroalkyl (e.g., 2 to 8 membered heteroalkyl, 2 to 6 membered heteroalkyl, or 2 to 4 membered heteroalkyl).

In embodiments, $R^{41}$ is $R^{42}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{41}$ is $R^{42}$-substituted cycloalkyl (e.g., $C_3$-$C_8$ cycloalkyl, $C_3$-$C_6$ cycloalkyl, or $C_5$-$C_6$ cycloalkyl). In embodiments, $R^{41}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{41}$ is $R^{42}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{41}$ is $R^{42}$-substituted heterocycloalkyl (e.g., 3 to 8 membered heterocycloalkyl, 3 to 6 membered heterocycloalkyl, or 5 to 6 membered heterocycloalkyl). In embodiments, $R^{41}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{41}$ is $R^{42}$-substituted or unsubstituted aryl (e.g., $C_6$-$C_{10}$ aryl, $C_{10}$ aryl, or phenyl). In embodiments, $R^{41}$ is $R^{42}$-substituted aryl (e.g., $C_6$-$C_{10}$ aryl, $C_{10}$ aryl, or phenyl). In embodiments, $R^{41}$ is an unsubstituted aryl (e.g., $C_6$-$C_{10}$ aryl, $C_{10}$ aryl, or phenyl).

In embodiments, $R^{41}$ is $R^{42}$-substituted or unsubstituted heteroaryl (e.g., 5 to 10 membered heteroaryl, 5 to 9 membered heteroaryl, or 5 to 6 membered heteroaryl). In embodiments, $R^{41}$ is $R^{42}$-substituted heteroaryl (e.g., 5 to 10 membered heteroaryl, 5 to 9 membered heteroaryl, or 5 to 6 membered heteroaryl). In embodiments, $R^{41}$ is an unsubstituted heteroaryl (e.g., 5 to 10 membered heteroaryl, 5 to 9 membered heteroaryl, or 5 to 6 membered heteroaryl).

In embodiments, $R^{41}$ is oxo. In embodiments, $R^{41}$ is $R^{42}$-substituted or unsubstituted $C_1$-$C_8$ alkyl. In embodiments, $R^{41}$ is $R^{42}$-substituted or unsubstituted $C_1$-$C_6$ alkyl. In embodiments, $R^{41}$ is $R^{42}$-substituted or unsubstituted $C_1$-$C_4$ alkyl. In embodiments, $R^{41}$ is $R^{42}$-substituted or unsubstituted $C_1$-$C_2$ alkyl. In embodiments, $R^{41}$ is $R^{42}$-substituted $C_1$-$C_8$ alkyl. In embodiments, $R^{41}$ is $R^{42}$-substituted $C_1$-$C_6$ alkyl. In embodiments, $R^{41}$ is $R^{42}$-substituted C—$C_4$ alkyl. In embodiments, $R^{41}$ is $R^{42}$-substituted $C_1$-$C_2$ alkyl. In embodiments, $R^{41}$ is unsubstituted $C_1$-$C_8$ alkyl. In embodiments, $R^{41}$ is unsubstituted $C_1$-$C_6$ alkyl. In embodiments, $R^{41}$ is unsubstituted $C_1$-$C_4$ alkyl. In embodiments, $R^{41}$ is unsubstituted $C_1$-$C_2$ alkyl. In embodiments, $R^{41}$ is unsubstituted methyl. In embodiments, $R^{41}$ is unsubstituted ethyl.

$R^{42}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2C_1$, —$OCH_2Br$, —$OCH_2I$, —$OCH_2F$, $R^{43}$-substituted or unsubstituted alkyl (e.g., $C_1$-$C_8$ alkyl, $C_1$-$C_6$ alkyl, or $C_1$-$C_4$ alkyl), $R^{43}$-substituted or unsubstituted heteroalkyl (e.g., 2 to 8 membered heteroalkyl, 2 to 6 membered heteroalkyl, or 2 to 4 membered heteroalkyl), $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{43}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43}$-substituted or unsubstituted aryl (e.g., $C_6$-$C_{10}$ aryl, $C_{10}$ aryl, or phenyl), or $R^{43}$-substituted or unsubstituted heteroaryl (e.g., 5 to 10 membered heteroaryl, 5 to 9 membered heteroaryl, or 5 to 6 membered heteroaryl).

In embodiments, $R^{42}$ is $R^{43}$-substituted or unsubstituted alkyl (e.g., $C_1$-$C_8$ alkyl, $C_1$-$C_6$ alkyl, or $C_1$-$C_4$ alkyl). In embodiments, $R^{42}$ is $R^{43}$-substituted alkyl (e.g., $C_1$-$C_8$ alkyl, $C_1$-$C_6$ alkyl, or $C_1$-$C_4$ alkyl). In embodiments, $R^{42}$ is an unsubstituted alkyl (e.g., $C_1$-$C_8$ alkyl, $C_1$-$C_6$ alkyl, or $C_1$-$C_4$ alkyl).

In embodiments, $R^{42}$ is $R^{43}$-substituted or unsubstituted heteroalkyl (e.g., 2 to 8 membered heteroalkyl, 2 to 6 membered heteroalkyl, or 2 to 4 membered heteroalkyl). In embodiments, $R^{42}$ is $R^{43}$-substituted heteroalkyl (e.g., 2 to 8 membered heteroalkyl, 2 to 6 membered heteroalkyl, or 2 to 4 membered heteroalkyl). In embodiments, $R^{42}$ is an unsubstituted heteroalkyl (e.g., 2 to 8 membered heteroalkyl, 2 to 6 membered heteroalkyl, or 2 to 4 membered heteroalkyl).

In embodiments, $R^{42}$ is $R^{43}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{42}$ is $R^{43}$-substituted cycloalkyl (e.g., $C_3$-$C_8$ cycloalkyl, $C_3$-$C_6$ cycloalkyl, or $C_5$-$C_6$ cycloalkyl). In embodiments, $R^{42}$ is an unsubstituted cycloalkyl (e.g., $C_3$-$C_8$ cycloalkyl, $C_3$-$C_6$ cycloalkyl, or $C$—$C_6$ cycloalkyl).

In embodiments, $R^{42}$ is $R^{43}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{42}$ is $R^{43}$-substituted heterocycloalkyl (e.g., 3 to 8 membered heterocycloalkyl, 3 to 6 membered heterocycloalkyl, or 5 to 6 membered heterocycloalkyl). In embodiments, $R^{42}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{42}$ is $R^{43}$-substituted or unsubstituted aryl (e.g., $C_6$-$C_{10}$ aryl, $C_{10}$ aryl, or phenyl). In embodiments, $R^{42}$ is $R^{43}$-substituted aryl (e.g., $C_6$-$C_{10}$ aryl, $C_{10}$ aryl, or phenyl). In embodiments, $R^{42}$ is an unsubstituted aryl (e.g., $C_6$-$C_{10}$ aryl, $C_{10}$ aryl, or phenyl).

In embodiments, $R^{42}$ is $R^{43}$-substituted or unsubstituted heteroaryl (e.g., 5 to 10 membered heteroaryl, 5 to 9 membered heteroaryl, or 5 to 6 membered heteroaryl). In embodiments, $R^{42}$ is $R^{43}$-substituted heteroaryl (e.g., 5 to 10 membered heteroaryl, 5 to 9 membered heteroaryl, or 5 to 6 membered heteroaryl). In embodiments, $R^{42}$ is an unsubstituted heteroaryl (e.g., 5 to 10 membered heteroaryl, 5 to 9 membered heteroaryl, or 5 to 6 membered heteroaryl).

In embodiments, $R^{44}$ is hydrogen, —$CX^{44.1}_3$, —$CHX^{44.1}_2$, —$CH_2X^{44.1}$, —$SO_{n44}R^{44A}$, —$SO_{v44}NR^{44B}R^{44C}$, —$C(O)R^{44D}$, —$C(O)OR^{44D}$, —$C(O)NR^{44B}R^{44C}$, $R^{45}$-substituted or unsubstituted alkyl (e.g., $C_1$-$C_8$ alkyl, $C_1$-$C_6$ alkyl, or $C_1$-$C_4$ alkyl), $R^{45}$-substituted or unsubstituted heteroalkyl (e.g., 2 to 8 membered heteroalkyl, 2 to 6 membered heteroalkyl, or 2 to 4 membered heteroalkyl), $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{45}$-substituted or unsubstituted heterocycloalkyl (e.g., 3 to 8 membered heterocycloalkyl, 3 to 6 membered heterocycloalkyl, or 5 to 6 membered heterocycloalkyl), $R^{45}$-substituted or unsubstituted aryl (e.g., $C_6$-$C_{10}$ aryl, $C_{10}$ aryl, or phenyl), or $R^{45}$-substituted or unsubstituted heteroaryl (e.g., 5 to 10 membered heteroaryl, 5 to 9 membered heteroaryl, or 5 to 6 membered heteroaryl). In embodiments, $R^{44}$ is —CN. In embodiments, $R^{44}$ is —C(O)NH$_2$. In embodiments, $R^{44}$ is —CF$_3$. In embodiments, $R^{44}$ is —CH$_3$. In embodiments, $R^{44}$ is hydrogen.

In embodiments, $R^{44}$ is $R^{45}$-substituted or unsubstituted alkyl (e.g., $C_1$-$C_8$ alkyl, $C_1$-$C_6$ alkyl, or $C_1$-$C_4$ alkyl). In embodiments, $R^{44}$ is $R^{45}$-substituted alkyl (e.g., $C_1$-$C_8$ alkyl, $C_1$-$C_6$ alkyl, or $C_1$-$C_4$ alkyl). In embodiments, $R^{44}$ is an unsubstituted alkyl (e.g., $C_1$-$C_8$ alkyl, $C_1$-$C_6$ alkyl, or $C_1$-$C_4$ alkyl). In embodiments, $R^{44}$ is an unsubstituted ethyl. In embodiments, $R^{44}$ is an unsubstituted $C_3$ alkyl. In embodiments, $R^{44}$ is an unsubstituted $C_4$ alkyl.

In embodiments, $R^{44}$ is $R^{45}$-substituted or unsubstituted heteroalkyl (e.g., 2 to 8 membered heteroalkyl, 2 to 6 membered heteroalkyl, or 2 to 4 membered heteroalkyl). In embodiments, $R^{44}$ is $R^{45}$-substituted heteroalkyl (e.g., 2 to 8 membered heteroalkyl, 2 to 6 membered heteroalkyl, or 2 to 4 membered heteroalkyl). In embodiments, $R^{44}$ is an unsubstituted heteroalkyl (e.g., 2 to 8 membered heteroalkyl, 2 to 6 membered heteroalkyl, or 2 to 4 membered heteroalkyl).

In embodiments, $R^{44}$ is $R^{45}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{44}$ is $R^{45}$-substituted cycloalkyl (e.g., $C_3$-$C_8$ cycloalkyl, $C_3$-$C_6$ cycloalkyl, or $C_5$-$C_6$ cycloalkyl). In embodiments, $R^{44}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{44}$ is $R^{45}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{44}$ is $R^{45}$-substituted heterocycloalkyl (e.g., 3 to 8 membered heterocycloalkyl, 3 to 6 membered heterocycloalkyl, or 5 to 6 membered heterocycloalkyl). In embodiments, $R^{44}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{44}$ is $R^{45}$-substituted or unsubstituted aryl (e.g., $C_6$-$C_{10}$ aryl, $C_{10}$ aryl, or phenyl). In embodiments, $R^{44}$ is $R^{45}$-substituted aryl (e.g., $C_6$-$C_{10}$ aryl, $C_{10}$ aryl, or phenyl). In embodiments, $R^{44}$ is an unsubstituted aryl (e.g., $C_6$-$C_{10}$ aryl, $C_{10}$ aryl, or phenyl).

In embodiments, $R^{44}$ is $R^{45}$-substituted or unsubstituted heteroaryl (e.g., 5 to 10 membered heteroaryl, 5 to 9 membered heteroaryl, or 5 to 6 membered heteroaryl). In embodiments, $R^{44}$ is $R^{45}$-substituted heteroaryl (e.g., 5 to 10 membered heteroaryl, 5 to 9 membered heteroaryl, or 5 to 6 membered heteroaryl). In embodiments, $R^{44}$ is an unsubstituted heteroaryl (e.g., 5 to 10 membered heteroaryl, 5 to 9 membered heteroaryl, or 5 to 6 membered heteroaryl).

$R^{45}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C$_1$, —OCH$_2$Br, —OCH$_2$I, —OCH$_2$F, —N$_3$, $R^{46}$-substituted or unsubstituted alkyl (e.g., $C_1$-$C_5$ alkyl, $C_1$-$C_6$ alkyl, or $C_1$-$C_4$ alkyl), $R^{46}$-substituted or unsubstituted heteroalkyl (e.g., 2 to 8 membered heteroalkyl, 2 to 6 membered heteroalkyl, or 2 to 4 membered heteroalkyl), $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{46}$-substituted or unsubstituted heterocycloalkyl (e.g., 3 to 8 membered heterocycloalkyl, 3 to 6 membered heterocycloalkyl, or 5 to 6 membered heterocycloalkyl), $R^{46}$-substituted or unsubstituted aryl (e.g., $C_6$-$C_{10}$ aryl, $C_{10}$ aryl, or phenyl), or $R^{46}$-substituted or unsubstituted heteroaryl (e.g., 5 to 10 membered heteroaryl, 5 to 9 membered heteroaryl, or 5 to 6 membered heteroaryl).

In embodiments, $R^{45}$ is $R^{46}$-substituted or unsubstituted alkyl (e.g., $C_1$-$C_8$ alkyl, $C_1$-$C_6$ alkyl, or $C_1$-$C_4$ alkyl). In embodiments, $R^{45}$ is $R^{46}$-substituted alkyl (e.g., $C_1$-$C_8$ alkyl, $C_1$-$C_6$ alkyl, or $C_1$-$C_4$ alkyl). In embodiments, $R^{45}$ is an unsubstituted alkyl (e.g., $C_1$-$C_8$ alkyl, $C_1$-$C_6$ alkyl, or $C_1$-$C_4$ alkyl).

In embodiments, $R^{45}$ is $R^{46}$-substituted or unsubstituted heteroalkyl (e.g., 2 to 8 membered heteroalkyl, 2 to 6 membered heteroalkyl, or 2 to 4 membered heteroalkyl). In embodiments, $R^{45}$ is $R^{46}$-substituted heteroalkyl (e.g., 2 to 8 membered heteroalkyl, 2 to 6 membered heteroalkyl, or 2 to 4 membered heteroalkyl). In embodiments, $R^{45}$ is an unsubstituted heteroalkyl (e.g., 2 to 8 membered heteroalkyl, 2 to 6 membered heteroalkyl, or 2 to 4 membered heteroalkyl).

In embodiments, $R^{45}$ is $R^{46}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{45}$ is $R^{46}$-substituted cycloalkyl (e.g., $C_3$-$C_8$ cycloalkyl, $C_3$-$C_6$ cycloalkyl, or $C_5$-$C_6$ cycloalkyl). In embodiments, $R^{45}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{45}$ is $R^{46}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{45}$ is $R^{46}$-substituted heterocycloalkyl (e.g., 3 to 8 membered heterocycloalkyl, 3 to 6 membered heterocycloalkyl, or 5 to 6 membered heterocycloalkyl). In embodiments, $R^{45}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{45}$ is $R^{46}$-substituted or unsubstituted aryl (e.g., $C_6$-$C_0$ aryl, $C_{10}$ aryl, or phenyl). In embodiments, $R^{45}$ is $R^{46}$-substituted aryl (e.g., $C_6$-$C_{10}$ aryl, $C_{10}$ aryl, or phenyl). In embodiments, $R^{45}$ is an unsubstituted aryl (e.g., $C_6$-$C_{10}$ aryl, $C_{10}$ aryl, or phenyl).

In embodiments, $R^{45}$ is $R^{46}$-substituted or unsubstituted heteroaryl (e.g., 5 to 10 membered heteroaryl, 5 to 9 membered heteroaryl, or 5 to 6 membered heteroaryl). In embodiments, $R^{45}$ is $R^{46}$-substituted heteroaryl (e.g., 5 to 10 membered heteroaryl, 5 to 9 membered heteroaryl, or 5 to 6 membered heteroaryl). In embodiments, $R^{45}$ is an unsubstituted heteroaryl (e.g., 5 to 10 membered heteroaryl, 5 to 9 membered heteroaryl, or 5 to 6 membered heteroaryl).

$R^{46}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2C_1$, —$OCH_2Br$, —$OCH_2I$, —$OCH_2F$, —$N_3$, $R^{47}$-substituted or unsubstituted alkyl (e.g., $C_1$-$C_8$ alkyl, $C_1$-$C_6$ alkyl, or $C_1$-$C_4$ alkyl), $R^4$-substituted or unsubstituted heteroalkyl (e.g., 2 to 8 membered heteroalkyl, 2 to 6 membered heteroalkyl, or 2 to 4 membered heteroalkyl), $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{47}$-substituted or unsubstituted heterocycloalkyl (e.g., 3 to 8 membered heterocycloalkyl, 3 to 6 membered heterocycloalkyl, or 5 to 6 membered heterocycloalkyl), $R^4$-substituted or unsubstituted aryl (e.g., $C_6$-$C_{10}$ aryl, $C_{10}$ aryl, or phenyl), or $R^4$-substituted or unsubstituted heteroaryl (e.g., 5 to 10 membered heteroaryl, 5 to 9 membered heteroaryl, or 5 to 6 membered heteroaryl).

In embodiments, $R^{46}$ is $R^{47}$-substituted or unsubstituted alkyl (e.g., $C_1$-$C_8$ alkyl, $C_1$-$C_6$ alkyl, or $C_1$-$C_4$ alkyl). In embodiments, $R^{46}$ is $R^{47}$-substituted alkyl (e.g., $C_1$-$C_8$ alkyl, $C_1$-$C_6$ alkyl, or $C_1$-$C_4$ alkyl). In embodiments, $R^{46}$ is an unsubstituted alkyl (e.g., $C_1$-$C_8$ alkyl, $C_1$-$C_6$ alkyl, or $C_1$-$C_4$ alkyl).

In embodiments, $R^{46}$ is $R^{47}$-substituted or unsubstituted heteroalkyl (e.g., 2 to 8 membered heteroalkyl, 2 to 6 membered heteroalkyl, or 2 to 4 membered heteroalkyl). In embodiments, $R^{46}$ is $R^{47}$-substituted heteroalkyl (e.g., 2 to 8 membered heteroalkyl, 2 to 6 membered heteroalkyl, or 2 to 4 membered heteroalkyl). In embodiments, $R^{46}$ is an unsubstituted heteroalkyl (e.g., 2 to 8 membered heteroalkyl, 2 to 6 membered heteroalkyl, or 2 to 4 membered heteroalkyl).

In embodiments, $R^{46}$ is $R^{47}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{46}$ is $R^{47}$-substituted cycloalkyl (e.g., $C_3$-$C_8$ cycloalkyl, $C_3$-$C_6$ cycloalkyl, or $C_5$-$C_6$ cycloalkyl). In embodiments, $R^{46}$ is an unsubstituted cycloalkyl (e.g., $C_3$-$C_8$ cycloalkyl, $C_3$-$C_6$ cycloalkyl, or C—$C_6$ cycloalkyl).

In embodiments, $R^{46}$ is $R^{47}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{46}$ is $R^{47}$-substituted heterocycloalkyl (e.g., 3 to 8 membered heterocycloalkyl, 3 to 6 membered heterocycloalkyl, or 5 to 6 membered heterocycloalkyl). In embodiments, $R^{46}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{46}$ is $R^{47}$-substituted or unsubstituted aryl (e.g., $C_6$-$C_{10}$ aryl, $C_{10}$ aryl, or phenyl). In embodiments, $R^{46}$ is $R^{47}$-substituted aryl (e.g., $C_6$-$C_{10}$ aryl, $C_{10}$ aryl, or phenyl). In embodiments, $R^{46}$ is an unsubstituted aryl (e.g., $C_6$-$C_{10}$ aryl, $C_{10}$ aryl, or phenyl).

In embodiments, $R^{46}$ is $R^{47}$-substituted or unsubstituted heteroaryl (e.g., 5 to 10 membered heteroaryl, 5 to 9 membered heteroaryl, or 5 to 6 membered heteroaryl). In embodiments, $R^{46}$ is $R^{47}$-substituted heteroaryl (e.g., 5 to 10 membered heteroaryl, 5 to 9 membered heteroaryl, or 5 to 6 membered heteroaryl). In embodiments, $R^{46}$ is an unsubstituted heteroaryl (e.g., 5 to 10 membered heteroaryl, 5 to 9 membered heteroaryl, or 5 to 6 membered heteroaryl).

$R^{41.2B}$ is independently oxo, halogen, —$CCl_3$, —$CBr_3$, —$CF_3$, —$C_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{42.2B}$-substituted or unsubstituted alkyl (e.g., $C_1$-$C_8$ alkyl, $C_1$-$C_6$ alkyl, or $C_1$-$C_4$ alkyl), $R^{42.2B}$-substituted or unsubstituted heteroalkyl (e.g., 2 to 8 membered heteroalkyl, 2 to 6 membered heteroalkyl, or 2 to 4 membered heteroalkyl), $R^{42.2B}$-substituted or unsubstituted cycloalkyl (e.g., $C_3$-$C_8$ cycloalkyl, $C_3$-$C_6$ cycloalkyl, or C—$C_6$ cycloalkyl), $R^{42.2B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{42.2B}$-substituted or unsubstituted aryl (e.g., $C_6$-$C_{10}$ aryl, $C_{10}$ aryl, or phenyl), or $R^{42.2B}$-substituted or unsubstituted heteroaryl (e.g., 5 to 10 membered heteroaryl, 5 to 9 membered heteroaryl, or 5 to 6 membered heteroaryl).

In embodiments, $R^{41.2B}$ is $R^{42.2B}$-substituted or unsubstituted alkyl (e.g., $C_1$-$C_8$ alkyl, $C_1$-$C_6$ alkyl, or $C_1$-$C_4$ alkyl). In embodiments, $R^{41.2B}$ is $R^{42.2B}$-substituted alkyl (e.g., $C_1$-$C_8$ alkyl, $C_1$-$C_6$ alkyl, or $C_1$-$C_4$ alkyl). In embodiments, $R^{41.2B}$ is an unsubstituted alkyl (e.g., $C_1$-$C_8$ alkyl, $C_1$-$C_6$ alkyl, or $C_1$-$C_4$ alkyl).

In embodiments, $R^{41.2B}$ is $R^{42.2B}$-substituted or unsubstituted heteroalkyl (e.g., 2 to 8 membered heteroalkyl, 2 to 6 membered heteroalkyl, or 2 to 4 membered heteroalkyl). In embodiments, $R^{41.2B}$ is $R^{42.2B}$-substituted heteroalkyl (e.g., 2 to 8 membered heteroalkyl, 2 to 6 membered heteroalkyl, or 2 to 4 membered heteroalkyl). In embodiments, $R^{41.2B}$ is an unsubstituted heteroalkyl (e.g., 2 to 8 membered heteroalkyl, 2 to 6 membered heteroalkyl, or 2 to 4 membered heteroalkyl).

In embodiments, $R^{41.2B}$ is $R^{42.2B}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{41.2B}$ is $R^{42.2B}$-substituted cycloalkyl (e.g., $C_3$-$C_8$ cycloalkyl, $C_3$-$C_6$ cycloalkyl, or $C_5$-$C_6$ cycloalkyl). In embodiments, $R^{41.2B}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{41.2B}$ is $R^{42.2B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{41.2B}$ is $R^{42.2B}$-substituted heterocycloalkyl (e.g., 3 to 8 membered heterocycloalkyl, 3 to 6 membered heterocycloalkyl, or 5 to 6 membered heterocycloalkyl). In embodiments, $R^{41.2B}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{41.2B}$ is $R^{42.2B}$-substituted or unsubstituted aryl (e.g., $C_6$-$C_{10}$ aryl, $C_{10}$ aryl, or phenyl). In embodiments, $R^{42B}$ is $R^{42.2B}$-substituted aryl (e.g., $C_6$-$C_{10}$ aryl, $C_{10}$ aryl, or phenyl). In embodiments, $R^{41.2B}$ is an unsubstituted aryl (e.g., $C_6$-$C_{10}$ aryl, $C_{10}$ aryl, or phenyl).

In embodiments, $R^{41.2B}$ is $R^{42.2B}$-substituted or unsubstituted heteroaryl (e.g., 5 to 10 membered heteroaryl, 5 to 9 membered heteroaryl, or 5 to 6 membered heteroaryl). In embodiments, $R^{41.2B}$ is $R^{42.2B}$-substituted heteroaryl (e.g., 5 to 10 membered heteroaryl, 5 to 9 membered heteroaryl, or 5 to 6 membered heteroaryl). In embodiments, $R^{41.2B}$ is an unsubstituted heteroaryl (e.g., 5 to 10 membered heteroaryl, 5 to 9 membered heteroaryl, or 5 to 6 membered heteroaryl).

$R^{42.2B}$ is independently oxo, halogen, —CCl₃, —CBr₃, —CF₃, —C₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂C₁, —OCH₂Br, —OCH₂I, —OCH₂F, $R^{43.2B}$-substituted or unsubstituted alkyl (e.g., $C_1$-$C_8$ alkyl, $C_1$-$C_6$ alkyl, or $C_1$-$C_4$ alkyl), $R^{43.2B}$-substituted or unsubstituted heteroalkyl (e.g., 2 to 8 membered heteroalkyl, 2 to 6 membered heteroalkyl, or 2 to 4 membered heteroalkyl), $R^{43.2B}$-substituted or unsubstituted cycloalkyl (e.g., $C_3$-$C_8$ cycloalkyl, $C_3$-$C_6$ cycloalkyl, or C—$C_6$ cycloalkyl), $R^{43.2B}$-substituted or unsubstituted heterocycloalkyl (e.g., 3 to 8 membered heterocycloalkyl, 3 to 6 membered heterocycloalkyl, or 5 to 6 membered heterocycloalkyl), $R^{43.2B}$-substituted or unsubstituted aryl (e.g., $C_6$-$C_{10}$ aryl, $C_{10}$ aryl, or phenyl), or $R^{43.2B}$-substituted or unsubstituted heteroaryl (e.g., 5 to 10 membered heteroaryl, 5 to 9 membered heteroaryl, or 5 to 6 membered heteroaryl).

In embodiments, $R^{42.2B}$ is $R^{43.2B}$-substituted or unsubstituted alkyl (e.g., $C_1$-$C_8$ alkyl, $C_1$-$C_6$ alkyl, or $C_1$-$C_4$ alkyl). In embodiments, $R^{42.2B}$ is $R^{43.2B}$-substituted alkyl (e.g., $C_1$-$C_8$ alkyl, $C_1$-$C_6$ alkyl, or $C_1$-$C_4$ alkyl). In embodiments, $R^{42.2B}$ is an unsubstituted alkyl (e.g., $C_1$-$C_8$ alkyl, $C_1$-$C_6$ alkyl, or $C_1$-$C_4$ alkyl).

In embodiments, $R^{42.2B}$ is $R^{43.2B}$-substituted or unsubstituted heteroalkyl (e.g., 2 to 8 membered heteroalkyl, 2 to 6 membered heteroalkyl, or 2 to 4 membered heteroalkyl). In embodiments, $R^{42.2B}$ is $R^{43.2B}$-substituted heteroalkyl (e.g., 2 to 8 membered heteroalkyl, 2 to 6 membered heteroalkyl, or 2 to 4 membered heteroalkyl). In embodiments, $R^{42.2B}$ is an unsubstituted heteroalkyl (e.g., 2 to 8 membered heteroalkyl, 2 to 6 membered heteroalkyl, or 2 to 4 membered heteroalkyl).

In embodiments, $R^{42.2B}$ is $R^{43.2B}$-substituted or unsubstituted cycloalkyl (e.g., $C_3$-$C_8$ cycloalkyl, $C_3$-$C_6$ cycloalkyl, or C—$C_6$ cycloalkyl). In embodiments, $R^{42.2B}$ is $R^{43.2B}$-substituted cycloalkyl (e.g., $C_3$-$C_8$ cycloalkyl, $C_3$-$C_6$ cycloalkyl, or $C_5$-$C_6$ cycloalkyl). In embodiments, $R^{42.2B}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{42.2B}$ is $R^{43.2B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{42.2B}$ is $R^{43.2B}$-substituted heterocycloalkyl (e.g., 3 to 8 membered heterocycloalkyl, 3 to 6 membered heterocycloalkyl, or 5 to 6 membered heterocycloalkyl). In embodiments, $R^{42.2B}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{42.2B}$ is $R^{43.2B}$-substituted or unsubstituted aryl (e.g., $C_6$-$C_{10}$ aryl, $C_{10}$ aryl, or phenyl). In embodiments, $R^{42.2B}$ is $R^{43.2B}$-substituted aryl (e.g., $C_6$-$C_{10}$ aryl, $C_{10}$ aryl, or phenyl). In embodiments, $R^{42.2B}$ is an unsubstituted aryl (e.g., $C_6$-$C_{10}$ aryl, $C_{10}$ aryl, or phenyl).

In embodiments, $R^{42.2B}$ is $R^{43.2B}$-substituted or unsubstituted heteroaryl (e.g., 5 to 10 membered heteroaryl, 5 to 9 membered heteroaryl, or 5 to 6 membered heteroaryl). In embodiments, $R^{42.2B}$ is $R^{43.2B}$-substituted heteroaryl (e.g., 5 to 10 membered heteroaryl, 5 to 9 membered heteroaryl, or 5 to 6 membered heteroaryl). In embodiments, $R^{42.2B}$ is an unsubstituted heteroaryl (e.g., 5 to 10 membered heteroaryl, 5 to 9 membered heteroaryl, or 5 to 6 membered heteroaryl).

$R^{13}$, $R^{16}$, $R^{19}$, $R^{19.2}$, $R^{19.3}$, $R^{22}$, $R^{25}$, $R^{28}$, $R^{31}$, $R^{34}$, $R^{37}$, $R^4$, $R^{43}$, $R^{43.2B}$, and $R^{47}$ are independently hydrogen, oxo, halogen, —CCl₃, —CBr₃, —CF₃, —C₃, —CN, —OH, —NH₂, —COOH, —CONH₂, —NO₂, —SH, —SO₃H, —SO₄H, —SO₂NH₂, —NHNH₂, —ONH₂, —NHC(O) NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^{11A}$, $R^{11B}$, $R^{11C}$, $R^{11D}$, $R^{14A}$, $R^{14B}$, $R^{14C}$, $R^{14D}$, $R^{17A}$, $R^{17B}$, $R^{17C}$, $R^{17D}$, $R^{17.2A}$, $R^{17.2B}$, $R^{17.2C}$, $R^{17.2D}$, $R^{17.3A}$, $R^{17.3B}$, $R^{17.3C}$, $R^{17.3D}$, $R^{20A}$, $R^{20B}$, $R^{20C}$, $R^{20D}$, $R^{23A}$, $R^{23B}$, $R^{23C}$, $R^{23D}$, $R^{26A}$, $R^{26B}$, $R^{26C}$, $R^{26D}$, $R^{29A}$, $R^{29B}$, $R^{29C}$, $R^{29D}$, $R^{32A}$, $R^{32B}$, $R^{32C}$, $R^{32D}$, $R^{35A}$, $R^{35B}$, $R^{35C}$, $R^{35D}$, $R^{38A}$, $R^{38B}$, $R^{38C}$, $R^{38D}$, $R^{45A}$, $R^{45B}$, $R^{45C}$, and $R^{45D}$ are independently hydrogen, oxo, halogen, —CCl₃, —CBr₃, —CF₃, —C₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{11A}$, $R^{11B}$, $R^{11C}$, $R^{11D}$, $R^{14A}$, $R^{14B}$, $R^{14C}$, $R^{14D}$, $R^{17A}$, $R^{17B}$, $R^{17C}$, $R^{17D}$, $R^{17.2A}$, $R^{17.2B}$, $R^{17.2C}$, $R^{17.2D}$, $R^{17.3A}$, $R^{17.3B}$, $R^{17.3C}$, $R^{17.3D}$, $R^{20A}$, $R^{20B}$, $R^{20C}$, $R^{20D}$, $R^{23A}$, $R^{23B}$, $R^{23C}$, $R^{23D}$, $R^{26A}$, $R^{26B}$, $R^{26C}$, $R^{26D}$, $R^{29A}$, $R^{29B}$, $R^{29C}$, $R^{29D}$, $R^{32A}$, $R^{32B}$, $R^{32C}$, $R^{32D}$, $R^{35A}$, $R^{35B}$, $R^{35C}$, $R^{35D}$, $R^{38A}$, $R^{38B}$, $R^{38C}$, $R^{38D}$, $R^{45A}$, $R^{45B}$, $R^{45C}$, and $R^{45D}$ are independently oxo, halogen, —CCl$_3$, —CBr$_3$, —CF$_3$, —CI$_3$, —CN, —OH, —NH$_2$, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $X^{1.1}$ is —Cl. In embodiments, $X^{1.1}$ is —F. In embodiments, $X^{1.1}$ is —Br. In embodiments, $X^{1.1}$ is —I. In embodiments, $X^{2.1}$ is —Cl. In embodiments, $X^{2.1}$ is —F. In embodiments, $X^{2.1}$ is —Br. In embodiments, $X^{2.1}$ is —I. In embodiments, $X^{3.1}$ is —Cl. In embodiments, $X^{3.1}$ is —F. In embodiments, $X^{3.1}$ is —Br. In embodiments, $X^{3.1}$ is —I. In embodiments, $X^{3.2}$ is —Cl. In embodiments, $X^{3.2}$ is —F. In embodiments, $X^{3.2}$ is —Br. In embodiments, $X^{3.2}$ is —I. In embodiments, $X^{3.3}$ is —Cl. In embodiments, $X^{3.3}$ is —F. In embodiments, $X^{3.3}$ is —Br. In embodiments, $X^{3.3}$ is —I. In embodiments, $X^{4.1}$ is —Cl. In embodiments, $X^{4.1}$ is —F. In embodiments, $X^{4.1}$ is —Br. In embodiments, $X^{4.1}$ is —I. In embodiments, $X^{5.1}$ is —Cl. In embodiments, $X^{5.1}$ is —F. In embodiments, $X^{5.1}$ is —Br. In embodiments, $X^{5.1}$ is —I. In embodiments, $X^{6.1}$ is —Cl. In embodiments, $X^{6.1}$ is —F. In embodiments, $X^{6.1}$ is —Br. In embodiments, $X^{6.1}$ is —I. In embodiments, $X^{7.1}$ is —C$_1$. In embodiments, $X^{7.1}$ is —F. In embodiments, $X^{7.1}$ is —Br. In embodiments, $X^{7.1}$ is —I. In embodiments, $X^{8.1}$ is —Cl. In embodiments, $X^{8.1}$ is —F. In embodiments, $X^{8.1}$ is —Br. In embodiments, $X^{8.1}$ is —I. In embodiments, $X^{9.1}$ is —Cl. In embodiments, $X^{9.1}$ is —F. In embodiments, $X^{9.1}$ is —Br. In embodiments, $X^{9.1}$ is —I. In embodiments, $X^{10.1}$ is —Cl. In embodiments, $X^{10.1}$ is —F. In embodiments, $X^{10.1}$ is —Br. In embodiments, $X^{10.1}$ is —I. In embodiments, $X^{44.1}$ is —Cl. In embodiments, $X^{44.1}$ is —F. In embodiments, $X^{44.1}$ is —Br. In embodiments, $X^{44.1}$ is —I.

In embodiments, $X^{1.1}$ is —Cl, and $X^1$ is N. In embodiments, $X^{1.1}$ is —F, and $X^1$ is N. In embodiments, $X^{1.1}$ is —Br, and $X^1$ is N. In embodiments, $X^{1.1}$ is —I, and $X^1$ is N. In embodiments, $X^{2.1}$ is —Cl, and $X^1$ is N. In embodiments, $X^{2.1}$ is —F, and X is N. In embodiments, $X^{2.1}$ is —Br, and $X^1$ is N. In embodiments, $X^{2.1}$ is —I, and $X^1$ is N. In embodiments, $X^{3.1}$ is —Cl, and $X^1$ is N. In embodiments, $X^{3.1}$ is —F, and X is N. In embodiments, $X^{3.1}$ is —Br, and $X^1$ is N. In embodiments, $X^{3.1}$ is —I, and $X^1$ is N. In embodiments, $X^{4.1}$ is —Cl, and $X^1$ is N. In embodiments, $X^{4.1}$ is —F, and X is N. In embodiments, $X^{4.1}$ is —Br, and $X^1$ is N. In embodiments, $X^{4.1}$ is —I, and $X^1$ is N. In embodiments, $X^{5.1}$ is —Cl, and $X^1$ is N. In embodiments, $X^{5.1}$ is —F, and X is N. In embodiments, $X^{5.1}$ is —Br, and $X^1$ is N. In embodiments, $X^{5.1}$ is —I, and $X^1$ is N. In embodiments, $X^{6.1}$ is —Cl, and $X^1$ is N. In embodiments, $X^{6.1}$ is —F, and $X^1$ is N. In embodiments, $X^{6.1}$ is —Br, and $X^1$ is N. In embodiments, $X^{6.1}$ is —I, and $X^1$ is N. In embodiments, $X^{7.1}$ is —Cl, and $X^1$ is N. In embodiments, $X^{7.1}$ is —F, and $X^1$ is N. In embodiments, $X^{7.1}$ is —Br, and $X^1$ is N. In embodiments, $X^{7.1}$ is —I, and $X^1$ is N. In embodiments, $X^{8.1}$ is —Cl, and $X^1$ is N. In embodiments, $X^{8.1}$ is —F, and $X^1$ is N. In embodiments, $X^{8.1}$ is —Br, and $X^1$ is N. In embodiments, $X^{8.1}$ is —I, and $X^1$ is N. In embodiments, $X^{9.1}$ is —Cl, and $X^1$ is N. In embodiments, $X^{9.1}$ is —F, and $X^1$ is N. In embodiments, $X^{9.1}$ is —Br, and $X^1$ is N. In embodiments, $X^{9.1}$ is —I, and $X^1$ is N. In embodiments, $X^{10.1}$ is —Cl, and $X^1$ is N. In embodiments, $X^{10.1}$ is —F, and $X^1$ is N. In embodiments, $X^{10.1}$ is —Br, and $X^1$ is N. In embodiments, $X^{10.1}$ is —I, and $X^1$ is N.

In embodiments, $X^{1.1}$ is —Cl, and $X^2$ is N. In embodiments, $X^{1.1}$ is —F, and $X^2$ is N. In embodiments, $X^{1.1}$ is —Br, and $X^2$ is N. In embodiments, $X^{1.1}$ is —I, and $X^2$ is N. In embodiments, $X^{2.1}$ is —Cl, and $X^2$ is N. In embodiments, $X^{2.1}$ is —F, and $X^2$ is N. In embodiments, $X^{2.1}$ is —Br, and $X^2$ is N. In embodiments, $X^{2.1}$ is —I, and $X^2$ is N. In embodiments, $X^{3.1}$ is —Cl, and $X^2$ is N. In embodiments, $X^{3.1}$ is —F, and $X^2$ is N. In embodiments, $X^{3.1}$ is —Br, and $X^2$ is N. In embodiments, $X^{3.1}$ is —I, and $X^2$ is N. In embodiments, $X^{4.1}$ is —Cl, and $X^2$ is N. In embodiments, $X^{4.1}$ is —F, and $X^2$ is N. In embodiments, $X^{4.1}$ is —Br, and $X^2$ is N. In embodiments, $X^{4.1}$ is —I, and $X^2$ is N. In embodiments, $X^{5.1}$ is —Cl, and $X^2$ is N. In embodiments, $X^{5.1}$ is —F, and $X^2$ is N. In embodiments, $X^{5.1}$ is —Br, and $X^2$ is N. In embodiments, $X^{5.1}$ is —I, and $X^2$ is N. In embodiments, $X^{6.1}$ is —Cl, and $X^2$ is N. In embodiments, $X^{6.1}$ is —F, and $X^2$ is N. In embodiments, $X^{6.1}$ is —Br, and $X^2$ is N. In embodiments, $X^{6.1}$ is —I, and $X^2$ is N. In embodiments, $X^{7.1}$ is —Cl, and $X^2$ is N. In embodiments, $X^{7.1}$ is —F, and $X^2$ is N. In embodiments, $X^{7.1}$ is —Br, and $X^2$ is N. In embodiments, $X^{7.1}$ is —I, and $X^2$ is N. In embodiments, $X^{8.1}$ is —Cl, and $X^2$ is N. In embodiments, $X^{8.1}$ is —F, and $X^2$ is N. In embodiments, $X^{8.1}$ is —Br, and $X^2$ is N. In embodiments, $X^{8.1}$ is —I, and $X^2$ is N. In embodiments, $X^{9.1}$ is —Cl, and $X^2$ is N. In embodiments, $X^{9.1}$ is —F, and $X^2$ is N. In embodiments, $X^{9.1}$ is —Br, and $X^2$ is N. In embodiments, $X^{9.1}$ is —I, and $X^2$ is N. In embodiments, $X^{10.1}$ is —Cl, and $X^2$ is N. In embodiments, $X^{10.1}$ is —F, and $X^2$ is N. In embodiments, $X^{10.1}$ is —Br, and $X^2$ is N. In embodiments, $X^{10.1}$ is —I, and $X^2$ is N.

In embodiments, $X^{1.1}$ is —Cl, and $X^3$ is N. In embodiments, $X^{1.1}$ is —F, and $X^3$ is N. In embodiments, $X^{1.1}$ is —Br, and $X^3$ is N. In embodiments, $X^{1.1}$ is —I, and $X^3$ is N. In embodiments, $X^{2.1}$ is —Cl, and $X^3$ is N. In embodiments, $X^{2.1}$ is —F, and $X^3$ is N. In embodiments, $X^{2.1}$ is —Br, and $X^3$ is N. In embodiments, $X^{2.1}$ is —I, and $X^3$ is N. In embodiments, $X^{3.1}$ is —Cl, and $X^3$ is N. In embodiments, $X^{3.1}$ is —F, and $X^3$ is N. In embodiments, $X^{3.1}$ is —Br, and $X^3$ is N. In embodiments, $X^{3.1}$ is —I, and $X^3$ is N. In embodiments, $X^{4.1}$ is —Cl, and $X^3$ is N. In embodiments, $X^{4.1}$ is —F, and $X^3$ is N. In embodiments, $X^{4.1}$ is —Br, and $X^3$ is N. In embodiments, $X^{4.1}$ is —I, and $X^3$ is N. In embodiments, $X^{5.1}$ is —Cl, and $X^3$ is N. In embodiments, $X^{5.1}$ is —F, and $X^3$ is N. In embodiments, $X^{5.1}$ is —Br, and $X^3$ is N. In embodiments, $X^{5.1}$ is —I, and $X^3$ is N. In embodiments, $X^{6.1}$ is —Cl, and $X^3$ is N. In embodiments, $X^{6.1}$ is —F, and $X^3$ is N. In embodiments, $X^{6.1}$ is —Br, and $X^3$ is N. In embodiments, $X^{6.1}$ is —I, and $X^3$ is N. In embodiments, $X^{7.1}$ is —Cl, and $X^3$ is N. In embodiments, $X^{7.1}$ is —F, and $X^3$ is N. In embodiments, $X^{7.1}$ is —Br, and $X^3$ is N. In embodiments, $X^{7.1}$ is —I, and $X^3$ is N. In embodiments, $X^{8.1}$ is —Cl, and $X^3$ is N. In embodiments, $X^{8.1}$ is —F, and $X^3$ is N. In embodiments, $X^{8.1}$ is —Br, and $X^3$ is N. In embodiments, $X^{8.1}$ is —I, and $X^3$ is N. In embodiments, $X^{9.1}$ is —Cl, and $X^3$ is N. In embodiments, $X^{9.1}$ is —F, and $X^3$ is N. In embodiments, $X^{9.1}$ is —Br, and $X^3$ is N. In embodiments, $X^{9.1}$ is —I, and $X^3$ is N. In embodiments, $X^{10.1}$ is —Cl, and $X^3$ is N. In embodiments, $X^{10.1}$ is —F, and $X^3$ is N. In embodiments, $X^{10.1}$ is —Br, and $X^3$ is N. In embodiments, $X^{10.1}$ is —I, and $X^3$ is N.

In embodiments, n1 is 0. In embodiments, n1 is 1. In embodiments, n1 is 2. In embodiments, n1 is 3. In embodiments, n1 is 4. In embodiments, n2 is 0. In embodiments, n2 is 1. In embodiments, n2 is 2. In embodiments, n2 is 3. In embodiments, n2 is 4. In embodiments, n3 is 0. In embodiments, n3 is 1. In embodiments, n3 is 2. In embodiments, n3 is 3. In embodiments, n3 is 4. In embodiments, n3.2 is 0. In embodiments, n3.2 is 1. In embodiments, n3.2 is 2. In embodiments, n3.2 is 3. In embodiments, n3.2 is 4. In embodiments, n3.3 is 0. In embodiments, n3.3 is 1. In embodiments, n3.3 is 2. In embodiments, n3.3 is 3. In embodiments, n3.3 is 4. In embodiments, n4 is 0. In embodiments, n4 is 1. In embodiments, n4 is 2. In embodiments, n4 is 3. In embodiments, n4 is 4. In embodiments, n5 is 0. In embodiments, n5 is 1. In embodiments, n5 is 2. In embodiments, n5 is 3. In embodiments, n5 is 4. In embodiments, n6 is 0. In embodiments, n6 is 1. In embodiments, n6 is 2. In embodiments, n6 is 3. In embodiments, n6 is 4. In embodiments, n7 is 0. In embodiments, n7 is 1. In embodiments, n7 is 2. In embodiments, n7 is 3. In embodiments, n7 is 4. In embodiments, n8 is 0. In embodiments, n8 is 1. In embodiments, n8 is 2. In embodiments, n8 is 3. In embodiments, n8 is 4. In embodiments, n8 is 0. In embodiments, n8 is 1. In embodiments, n8 is 2. In embodiments, n8 is 3. In embodiments, n8 is 4. In embodiments, n9 is 0. In embodiments, n9 is 1. In embodiments, n9 is 2. In embodiments, n9 is 3. In embodiments, n9 is 4. In embodiments, n10 is 0. In embodiments, n10 is 1. In embodiments, n10 is 2. In embodiments, n10 is 3. In embodiments, n10 is 4. In embodiments, n44 is 0. In embodiments, n44 is 1. In embodiments, n44 is 2. In embodiments, n44 is 3. In embodiments, n44 is 4.

In embodiments, m1 is 1. In embodiments, m1 is 2. In embodiments, v1 is 1. In embodiments, v is 2. In embodiments, m2 is 1. In embodiments, m2 is 2. In embodiments, v2 is 1. In embodiments, v2 is 2. In embodiments, m3 is 1. In embodiments, m3 is 2. In embodiments, v3 is 1. In embodiments, v3 is 2. In embodiments, m3.2 is 1. In embodiments, m3.2 is 2. In embodiments, v3.2 is 1. In embodiments, v3.2 is 2. In embodiments, m3.3 is 1. In embodiments, m3.3 is 2. In embodiments, v3.3 is 1. In embodiments, v3.3 is 2. In embodiments, m4 is 1. In embodiments, m4 is 2. In embodiments, v4 is 1. In embodiments, v4 is 2. In embodiments, m5 is 1. In embodiments, m5 is 2. In embodiments, v5 is 1. In embodiments, v5 is 2. In embodiments, m6 is 1. In embodiments, m6 is 2. In embodiments, v6 is 1. In embodiments, v6 is 2. In embodiments, m7 is 1. In embodiments, m7 is 2. In embodiments, v7 is 1. In embodiments, v7 is 2. In embodiments, m8 is 1. In embodiments, m8 is 2. In embodiments, v8 is 1. In embodiments, v8 is 2. In embodiments, m9 is 1. In embodiments, m9 is 2. In embodiments, v9 is 1. In embodiments, v9 is 2. In embodiments, m10 is 1. In embodiments, m10 is 2. In embodiments, v10 is 1. In embodiments, v10 is 2. In embodiments, m44 is 1. In embodiments, m44 is 2. In embodiments, v44 is 1. In embodiments, v44 is 2.

In embodiments, z1 is 0. In embodiments, z1 is 1. In embodiments, z1 is 2. In embodiments, z is 3. In embodiments, z1 is 4. In embodiments, z1 is 5.

In embodiments, z2 is 0. In embodiments, z2 is 1. In embodiments, z2 is 2. In embodiments, z2 is 3. In embodiments, z2 is 4. In embodiments, z2 is 5. The symbol z2 is an integer from 0 to 2.

In embodiments, z3 is 0. In embodiments, z3 is 1. In embodiments, z3 is 2. In embodiments, z3 is 3. In embodiments, z3 is 4. In embodiments, z3 is 5. In embodiments, z3 is 6. In embodiments, z3 is 7. In embodiments, z3 is 8. In embodiments, z3 is 9. In embodiments, z3 is 10. In embodiments, z3 is 11. The symbol z3 is an integer from 0 to 4.

In embodiments, z4 is 0. In embodiments, z4 is 1. In embodiments, z4 is 2.

In embodiments, z1 is 2, z2 is 0, z4 is 1, and $R^7$ is hydrogen, substituted or unsubstituted alkyl, substituted or unsubstituted phenyl, —F, —OH, —CH$_2$OH, —(CH$_2$)$_2$OH, —(CH$_2$)$_3$OH, —C(CH$_3$)$_2$OH, —CH$_2$SO$_2$NH$_2$, —(CH$_2$)$_2$SO$_2$NH$_2$, —CH$_2$C(O)NH$_2$, —(CH$_2$)$_2$C(O)NH$_2$, —(CH$_2$)$_3$C(O)NH$_2$, —CH$_2$NHSO$_2$CF$_3$, —(CH$_2$)$_2$NHSO$_2$CF$_3$, —(CH$_2$)$_3$NHSO$_2$CF$_3$, —CH$_2$NHSO$_2$CH$_3$, —(CH$_2$)$_2$NHSO$_2$CH$_3$, —(CH$_2$)$_3$NHSO$_2$CH$_3$, —CH$_2$SO$_2$CH$_3$, —COOH, —(CH$_2$)$_2$SO$_2$CH$_3$, —CH$_2$SO$_2$NH$_2$ or —(CH$_2$)$_2$SO$_2$NH$_2$.

In embodiments, $R^1$ and $R^2$ are independently hydrogen, substituted or unsubstituted alkyl or substituted or unsubstituted heteroalkyl. In embodiments, $R^1$ is independently hydrogen, $R^{11}$-substituted or unsubstituted alkyl or $R^{11}$-substituted or unsubstituted heteroalkyl. In embodiments, $R^2$ is independently hydrogen, $R^{14}$-substituted or unsubstituted alkyl or $R^{14}$-substituted or unsubstituted heteroalkyl. In embodiments, $R^1$ and $R^2$ are hydrogen.

In embodiments, the compound has structural Formula (II):

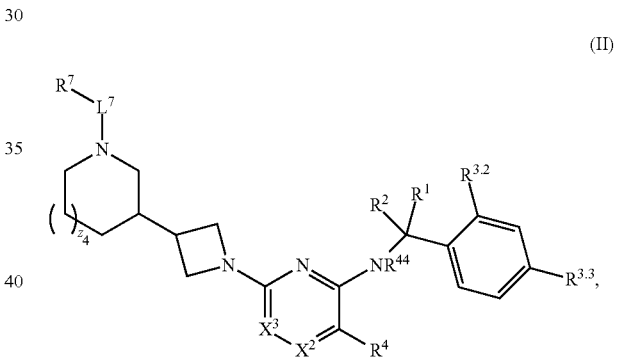

or a pharmaceutically acceptable salt thereof, wherein $R^1$, $R^2$, $R^4$, $X^2$, $X^3$, z4, $L^7$, and $R^7$ as described herein, including embodiments. $R^{3.2}$ and $R^{3.3}$ are independently substituents encompassed by the definitions of $R^3$. In embodiments, $R^{3.2}$ is hydrogen, halogen, —CX$^{3.2}_3$, —CHX$^{3.2}_2$, —CH$_2$X$^{3.2}$, —CN, —N$_3$, —SO$_{n3.2}$R$^{3.2A}$, —SO$_{v3.2}$NR$^{3.2B}$R$^{3.2C}$, —N—NR$^{3.2B}$R$^{3.2C}$, —ONR$^{3.2B}$R$^{3.2C}$, —NHC(O)NHNR$^{3.2B}$R$^{3.2C}$, —NHC(O)NR$^{3.2B}$R$^{3.2C}$, —N(O)$_{m3.2}$, —NR$^{3.2B}$R$^{3.2C}$, —C(O)R$^{3.2D}$, —C(O)OR$^{3.2D}$, —C(O)NR$^{3.2B}$R$^{3.2C}$, —OR$^{3.2A}$, —NR$^{3.2B}$SO$_2$R$^{3.2A}$, —NR$^{3.2B}$C(O)R$^{3.2D}$, —NR$^{3.2B}$C(O)OR$^{3.2D}$, —NR$^{3.2B}$OR$^{3.2D}$, —OCX$^{3.2}_3$, —OCHX$^{3.2}_2$, —OCH$_2$X$^{3.2}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{3.3}$ is hydrogen, halogen, —CX$^{3.3}_3$, —CHX$^{3.3}_2$, —CH$_2$X$^{3.3}$, —CN, —N$_3$, —SO$_{n3.3}$R$^{3.3A}$, —SO$_{v3.3}$NR$^{3.3B}$R$^{3.3C}$, —NNR$^{3.3B}$R$^{3.3C}$, —ONR$^{3.3B}$R$^{3.3C}$, —NHC(O)NHNR$^{3.3B}$R$^{3.3C}$, —NHC(O)NR$^{3.3B}$R$^{3.3C}$, —N(O)$_{m3.3}$, —NR$^{3.3B}$R$^{3.3C}$, —C(O)R$^{3.3D}$, —C(O)OR$^{3.3D}$, —C(O)NR$^{3.3B}$R$^{3.3C}$, —OR$^{3.3A}$, —NR$^{3.3B}$SO$_2$R$^{3.3A}$, —NR$^{3.3B}$C(O)R$^{3.3D}$, —NR$^{3.3B}$C(O)OR$^{3.3D}$, —NR$^{3.3B}$OR$^{3.3D}$, —OCX$^{3.3}_3$, —OCHX$^{3.3}_2$, —OCH$_2$X$^{3.3}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n3.2, and n3.3 are independently an integer from 0 to 4. The symbols m3.2, m3.3, v3.2 and v3.3 are independently 1 or 2. In embodiments, R$^4$ is hydrogen, —CX$^{4.1}_3$, —CN, —C(O)NR$^{4B}$R$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{3.2A}$, R$^{3.2B}$, R$^{3.2C}$, R$^{3.2D}$, R$^{3.3A}$, R$^{3.3B}$, R$^{3.3C}$ and R$^{3.3D}$ are independently hydrogen, halogen, —CF$_3$, —CCl$_3$, —CBr$_3$, —CI$_3$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{32B}$, R$^{32C}$, R$^{3.3B}$ and R$^{3.3C}$ substituents bonded to the same nitrogen atom may optionally be joined to form a substituted or unsubstituted heterocycloalkyl or substituted or unsubstituted heteroaryl; and X$^{3.2}$ and X$^{3.3}$ are independently —Cl, —Br, —I or —F.

In embodiments, the compound has structural Formula (IIa):

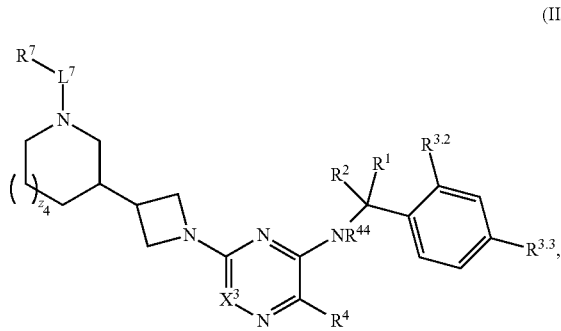

(IIa)

or a pharmaceutically acceptable salt thereof, wherein R$^1$, R$^2$, R$^{3.2}$, R$^{3.3}$, R$^4$, R$^{44}$, X$^3$, z4, L$^7$, and R$^7$ as described herein, including embodiments.

In embodiments, wherein the compound has structural Formula (IIb):

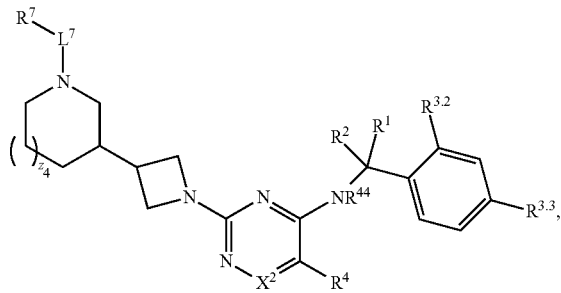

(IIb)

or a pharmaceutically acceptable salt thereof, wherein R$^1$, R$^2$, R$^{3.2}$, R$^{3.3}$, R$^4$, R$^{44}$, X$^2$, z4, L$^7$, and R$^7$ as described herein, including embodiments.

In embodiments, the compound has structural Formula (IIc):

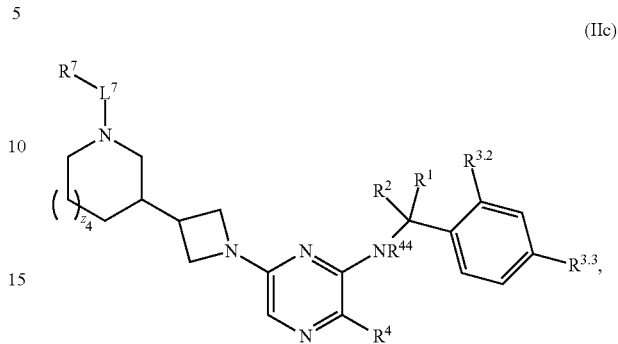

(IIc)

or a pharmaceutically acceptable salt thereof wherein R$^1$, R$^2$, R$^{3.2}$, R$^{3.3}$, R$^4$, R$^{44}$, z4, L$^7$, and R$^7$ as described herein, including embodiments. In embodiments, z4 is 1.

In embodiments, the compound has structural Formula (IIc-1):

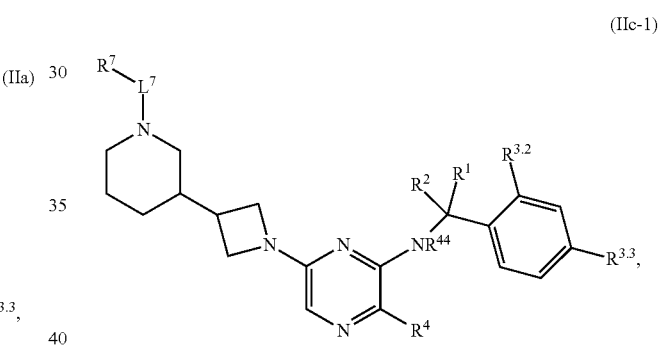

(IIc-1)

or a pharmaceutically acceptable salt thereof wherein R$^1$, R$^2$, R$^{3.2}$, R$^{3.3}$, R$^4$, R$^{44}$, L$^7$, and R$^7$ as described herein, including embodiments.

In embodiments, the compound has structural Formula (IIc-2):

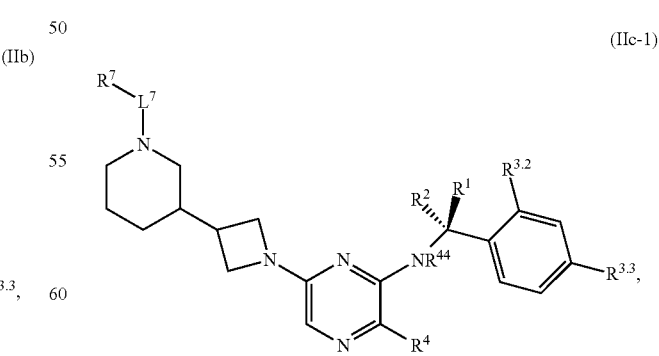

(IIc-1)

or a pharmaceutically acceptable salt thereof wherein R$^1$, R$^2$, R$^{3.2}$, R$^{3.3}$, R$^4$, R$^{44}$, L$^7$, and R$^7$ as described herein, including embodiments.

In embodiments, the compound has structural Formula (IIc-3):

(IIc-2)

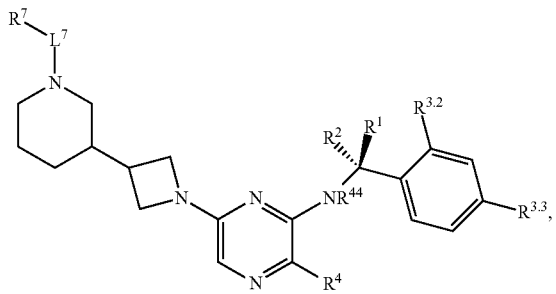

or a pharmaceutically acceptable salt thereof wherein $R^1$, $R^2$, $R^{3.2}$, $R^{3.3}$, $R^4$, $L^7$, and $R^7$ as described herein, including embodiments.

In embodiments, $R^1$ and $R^2$ are independently hydrogen, substituted or unsubstituted alkyl or substituted or unsubstituted heteroalkyl. In embodiments, $R^1$ is hydrogen. In embodiments, $R^2$ is substituted or unsubstituted alkyl. In embodiments, $R^2$ is hydrogen. In embodiments, $R^1$ is substituted or unsubstituted alkyl. In embodiments, $R^4$ is hydrogen, —CN, —C(O)NH$_2$, —CX$^{4.1}$$_3$ or substituted or unsubstituted alkyl. In embodiments, $R^{3.2}$ and $R^{3.3}$ are independently halogen. In embodiments, $R^{3.2}$ and $R^{3.3}$ are independently chlorine. In embodiments, $R^7$ is —OR$^{7A}$, —C(O)R$^{7D}$, —C(O)OR$^{7D}$, —C(O)NR$^{7B}$R$^{7C}$, —SO$_{n7}$R$^{7A}$, —SO$_{v7}$NR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $L^7$ is a bond or substituted or unsubstituted alkylene. In embodiments, $L^7$ is a bond. In embodiments, $L^7$ is a bond; and $R^7$ is hydrogen, substituted or unsubstituted alkyl, phenyl, —(CH$_2$)$_2$OH, —CH$_2$C(CH$_3$)$_2$OH, —(CH$_2$)$_3$OH, —(CH$_2$)$_2$CH(CH$_3$)$_2$OH, —(CH$_2$)$_2$SO$_2$NH$_2$, —(CH$_2$)$_3$SO$_2$NH$_2$, —(CH$_2$)$_2$CONH$_2$, —(CH$_2$)$_3$CONH$_2$—(CH$_2$)$_3$CON(H)Me, —(CH$_2$)$_3$CON(Me)$_2$, —(CH$_2$)$_2$SO$_2$Me, —(CH$_2$)$_3$SO$_2$Me, —CH$_2$CH(OH)Me, —CH$_2$CO$_2$H, —(CH$_2$)$_2$CO$_2$H, —CH(CH$_3$)CH$_2$CO$_2$H, —(CH$_2$)$_3$CO$_2$H, —(CH$_2$)$_2$SO$_2$NHCH$_3$, —(CH$_2$)$_2$SO$_2$N(CH$_3$)$_2$, —(CH$_2$)$_2$SO$_2$—(N-morpholinyl), —(CH$_2$)$_2$NHCOCH$_3$, —(CH$_2$)$_2$NHCOCH$_3$, —(CH$_2$)$_2$NHCOCH(CH$_3$)$_2$, —(CH$_2$)$_2$NHSO$_2$CH$_3$, —(CH$_2$)$_2$NHSO$_2$CF$_3$, —(CH$_2$)$_2$NHSO$_2$NHCH(CH$_3$)$_2$, —CH$_2$CH(CH$_3$)CH$_2$OH (R and S), —CH(CH$_3$)(CH$_2$)$_2$OH, —CH$_2$—(2-imidazoyl), —CH$_2$—(4-imidazoyl), —CH$_2$—(3-pyrazoyl), 4-tetrahydropyranyl, 3-oxetanyl, —(CH$_2$)$_2$NHCO$_2$Me, or —(CH$_2$)$_3$NHCO$_2$Me.

In embodiments, the compound has structural Formula (IId):

(IId)

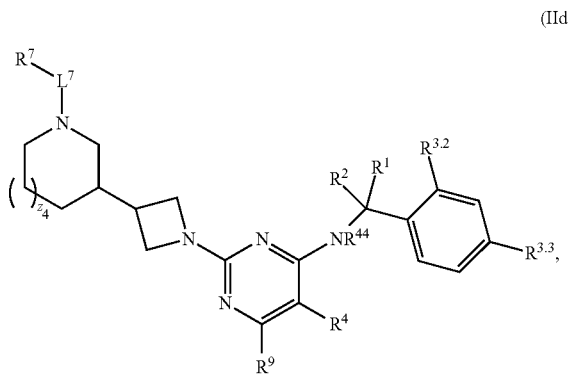

or a pharmaceutically acceptable salt thereof, wherein $R^1$, $R^2$, $R^{3.2}$, $R^{3.3}$, $R^4$, $R^9$, $R^{44}$, z4, $L^7$, and $R^7$ as described herein, including embodiments.

In embodiments, the compound has structural Formula (IId-1):

(IId-1)

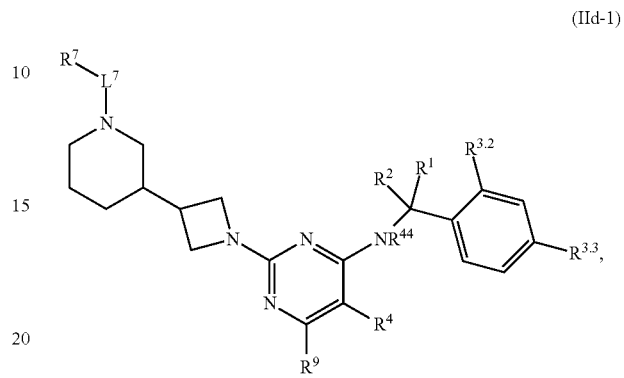

or a pharmaceutically acceptable salt thereof, wherein $R^1$, $R^2$, $R^{3.2}$, $R^{3.3}$, $R^4$, $R^9$, $R^{44}$, z4, $L^7$, and $R^7$ as described herein, including embodiments.

In embodiments, the compound has structural Formula (IId-2):

(IId-2)

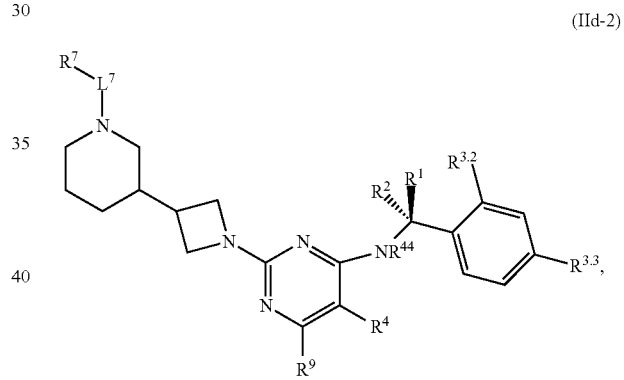

or a pharmaceutically acceptable salt thereof, wherein $R^1$, $R^2$, $R^{3.2}$, $R^{3.3}$, $R^4$, $R^9$, $R^{44}$, z4, $L^7$, and $R^7$ as described herein, including embodiments.

In embodiments, the compound has structural Formula (IId-3):

(IId-3)

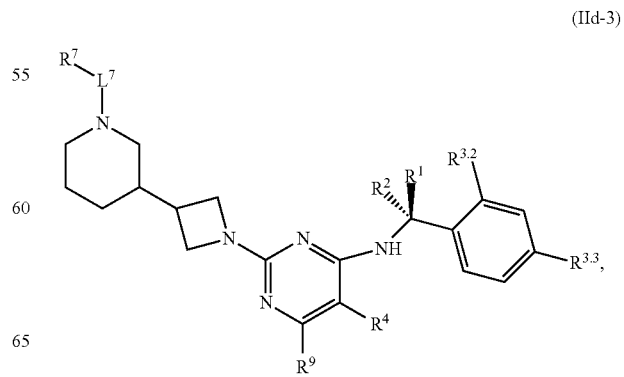

or a pharmaceutically acceptable salt thereof, wherein $R^1$, $R^2$, $R^{3.2}$, $R^{3.3}$, $R^4$, $R^9$, z4, $L^7$, and $R^7$ as described herein, including embodiments.

In embodiments, the compound has structural Formula (IId-4):

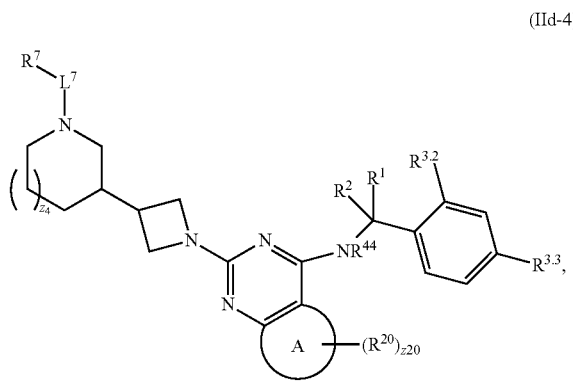

or a pharmaceutically acceptable salt thereof, wherein $R^1$, $R^2$, $R^{3.2}$, $R^{3.3}$, $R^{20}$, $R^{44}$, z4, $L^7$, and $R^7$ as described herein, including embodiments. $R^4$ and $R^9$ are joined to form Ring A. The symbol z20 is an integer from 0 to 12.

In embodiments, the compound has structural Formula (IId-5):

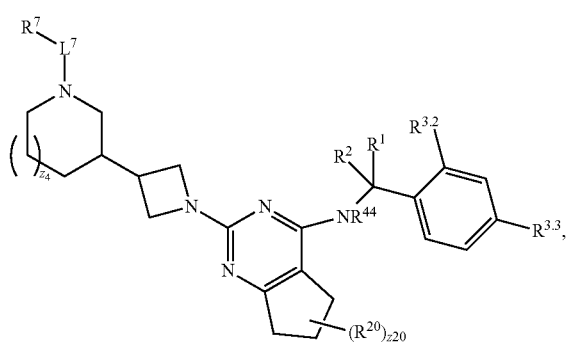

or a pharmaceutically acceptable salt thereof, wherein $R^1$, $R^2$, $R^{3.2}$, $R^{3.3}$, $R^{20}$, $R^{44}$, z4, $L^7$, and $R^7$ as described herein, including embodiments.

In embodiments, the compound has structural Formula (IId-6):

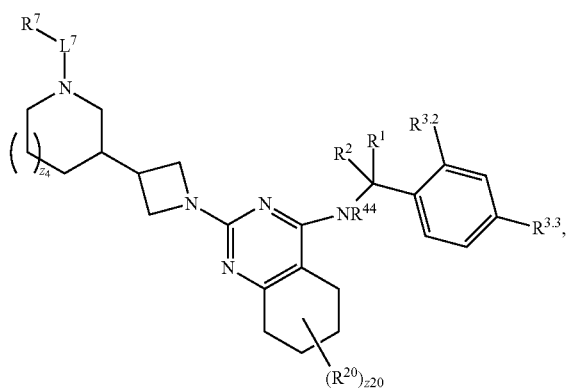

or a pharmaceutically acceptable salt thereof, wherein $R^1$, $R^2$, $R^{3.2}$, $R^{3.3}$, $R^{20}$, $R^{44}$, z4, $L^7$, z20, and $R^7$ as described herein, including embodiments.

In embodiments, the compound has structural Formula (IId-7):

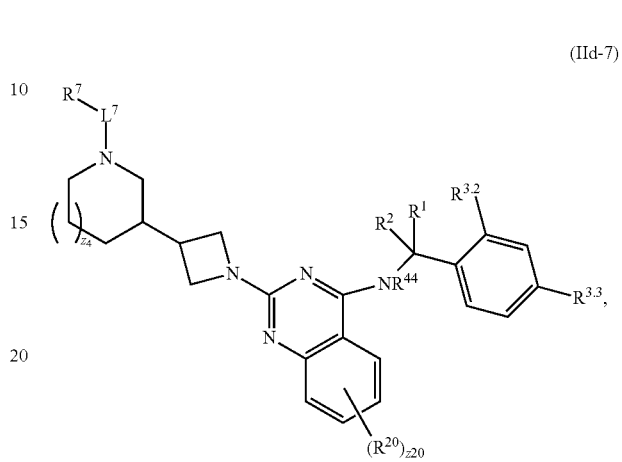

or a pharmaceutically acceptable salt thereof, wherein R, $R^2$, $R^{3.2}$, $R^{3.3}$, $R^{20}$, $R^{44}$, z4, $L^7$, z20, and $R^7$ as described herein, including embodiments.

In embodiments, the compound has structural Formula (IId-8) or (IId-9):

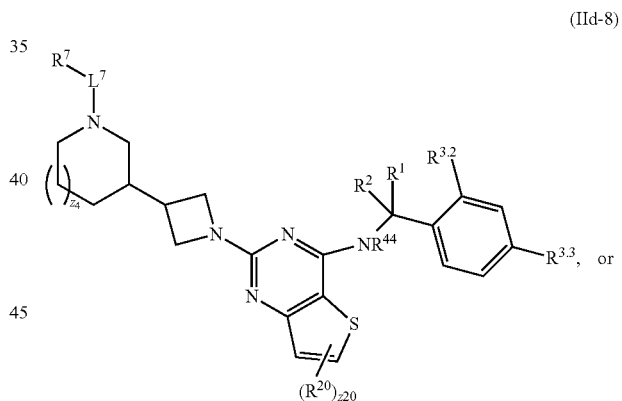

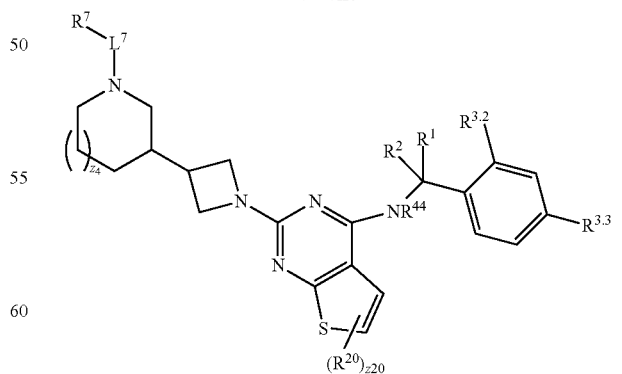

(IId-9), or a pharmaceutically acceptable salt thereof, wherein $R^1$, $R^2$, $R^{3.2}$, $R^{3.3}$, $R^{20}$, $R^{44}$, z4, $L^7$, z20, and $R^7$ as described herein, including embodiments.

In embodiments, z20 is an integer from 0 to 2. In embodiments, z20 is 0. In embodiments, z20 is 1. In embodiments, z20 is 2. In embodiments, z20 is 3. In embodiments, z20 is 4. In embodiments, z20 is 5. In embodiments, z20 is 6. In embodiments, z20 is 7. In embodiments, z20 is 8. In embodiments, z20 is 9. In embodiments, z20 is 10. In embodiments, z20 is 11. In embodiments, z20 is 12.

In embodiments, z4 is 1. In embodiments, $R^1$ and $R^2$ are independently hydrogen, substituted or unsubstituted alkyl or substituted or unsubstituted heteroalkyl. In embodiments, $R^1$ is hydrogen. In embodiments, $R^2$ is substituted or unsubstituted alkyl. In embodiments, $R^2$ is hydrogen. In embodiments, $R^1$ is substituted or unsubstituted alkyl. In embodiments, $R^4$ is hydrogen, —CN, —C(O)NH$_2$, —CX$^{4.1}_3$ or substituted or unsubstituted alkyl. In embodiments, $R^4$ is —CN, —C(O)NH$_2$, —CF$_3$ or —CH$_3$. In embodiments, $R^{3.2}$ and $R^{3.3}$ are independently halogen. In embodiments, $R^{3.2}$ and $R^{3.3}$ are independently chlorine. In embodiments, $R^7$ is —OR$^{7A}$, —C(O)R$^{7D}$, —C(O)OR$^{7D}$, —C(O)NR$^{7B}$R$^{7C}$, —SO$_{n7}$R$^{7A}$, —SO$_7$NR$^{7B}$R$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $L^7$ is a bond or substituted or unsubstituted alkylene. In embodiments, $L^7$ is a bond. In embodiments, $L^7$ is a bond; and $R^7$ is hydrogen, substituted or unsubstituted alkyl, phenyl, —(CH$_2$)$_2$OH, —CH$_2$C(CH$_3$)$_2$OH, —(CH$_2$)$_{30}$H, —(CH$_2$)$_2$CH(CH$_3$)$_2$OH, —(CH$_2$)$_2$SO$_2$NH$_2$, —(CH$_2$)$_3$SO$_2$NH$_2$, —(CH$_2$)$_2$CONH$_2$, —(CH$_2$)$_3$CONH$_2$—(CH$_2$)$_3$CON(H)Me, —(CH$_2$)$_3$CON(Me)$_2$, —(CH$_2$)$_2$SO$_2$Me, —(CH$_2$)$_3$SO$_2$Me, —CH$_2$CH(OH)Me, —CH$_2$CO$_2$H, —(CH$_2$)$_2$CO$_2$H, —CH(CH$_3$)CH$_2$CO$_2$H, —(CH$_2$)$_3$CO$_2$H, —(CH$_2$)$_2$SO$_2$NHCH$_3$, —(CH$_2$)$_2$SO$_2$N(CH$_3$)$_2$, —(CH$_2$)$_2$SO$_2$—(N- morpholinyl), —(CH$_2$)$_2$NHCOCH$_3$, —(CH$_2$)$_3$NHCOCH$_3$, —(CH$_2$)$_2$NHCOCH(CH$_3$)$_2$, —(CH$_2$)$_2$NHSO$_2$CH$_3$, —(CH$_2$)$_2$NHSO$_2$CF$_3$, —(CH$_2$)$_2$NHSO$_2$NHCH(CH$_3$)$_2$, —CH$_2$CH(CH$_3$)CH$_2$OH (R and S), —CH(CH$_3$)(CH$_2$)$_2$OH, —CH$_2$—(2-imidazoyl), —CH$_2$—(4-imidazoyl), —CH$_2$—(3-pyrazoyl), 4-tetrahydropyranyl, 3-oxetanyl, —(CH$_2$)$_2$NHCO$_2$Me, or —(CH$_2$)$_3$NHCO$_2$Me.

In embodiments, the compound has structural Formula (III):

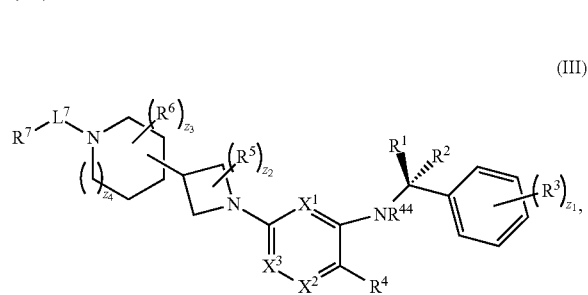

or a pharmaceutically acceptable salt thereof, wherein $R^1$, $R^2$, $R^4$, $R^3$, z1, $X^1$, $X^2$, $X^3$, $R^5$, z2, $R^6$, z3, z4, $L^7$, $R^{44}$ and $R^7$ as described herein, including embodiments. In embodiments, $R^2$ is hydrogen. In embodiments, $R^1$ is hydrogen. In embodiments, $R^1$ is —CH$_3$.

In embodiments, the compound has structural Formula (III-1):

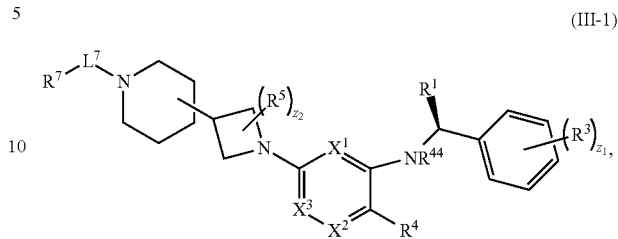

or a pharmaceutically acceptable salt thereof, wherein RU $R^2$, $R^4$, $R^3$, z1, $X^1$, $X^2$, $X^3$, $R^5$, z2, $R^6$, z3, z4, $L^7$, $R^{44}$ and $R^7$ as described herein, including embodiments.

In embodiments, the compound has structural Formula (IV):

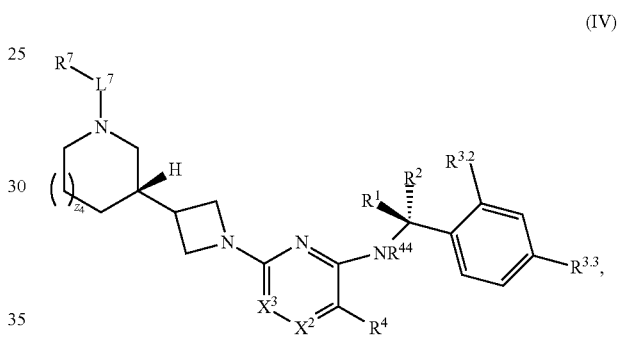

or a pharmaceutically acceptable salt thereof, wherein $R^1$, $R^2$, $R^4$, $R^{3.2}$, $R^{3.3}$, $X^2$, $X^3$, z4, $L^7$, $R^{44}$ and $R^7$ as described herein, including embodiments. In embodiments, $R^2$ is hydrogen. In embodiments, $R^1$ is hydrogen. In embodiments, $R^1$ is —CH$_3$.

In embodiments, the compound has structural Formula (V):

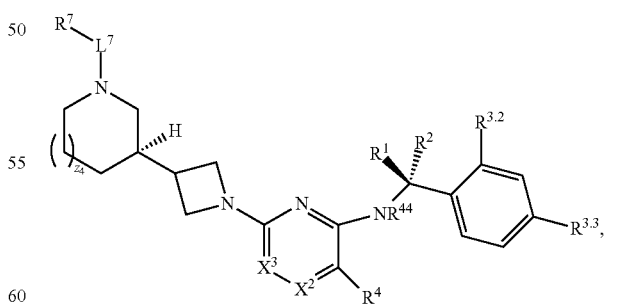

or a pharmaceutically acceptable salt thereof, wherein $R^1$, $R^2$, $R^4$, $R^{3.2}$, $R^{3.3}$, $X^2$, $X^3$, z4, $L^7$, $R^{44}$ and $R^7$ as described herein, including embodiments. In embodiments, $R^2$ is hydrogen. In embodiments, $R^1$ is hydrogen. In embodiments, $R^1$ is —CH$_3$.

In embodiments, the compound has structural Formula (VI):

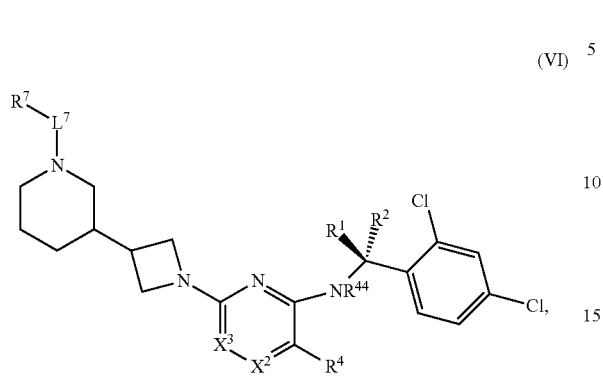

(VI)

or a pharmaceutically acceptable salt thereof, wherein $R^1$, $R^2$, $R^4$, $X^2$, $X^3$, $L^7$, $R^{44}$ and $R^7$ as described herein, including embodiments.

In embodiments, the compound has structural Formula (VII):

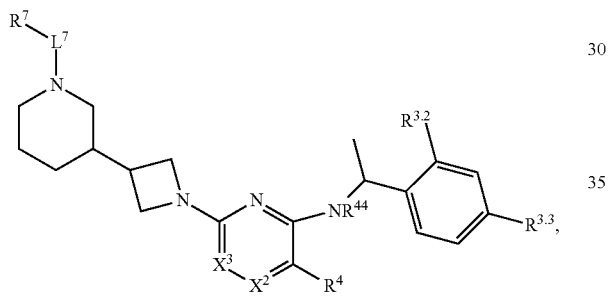

(VII)

or a pharmaceutically acceptable salt thereof, wherein $R^4$, $R^{3.2}$, $R^{3.3}$, $X^2$, $X^3$, $L^7$, $R^{44}$ and $R^7$ as described herein, including embodiments.

In embodiments, the compound has the formula:

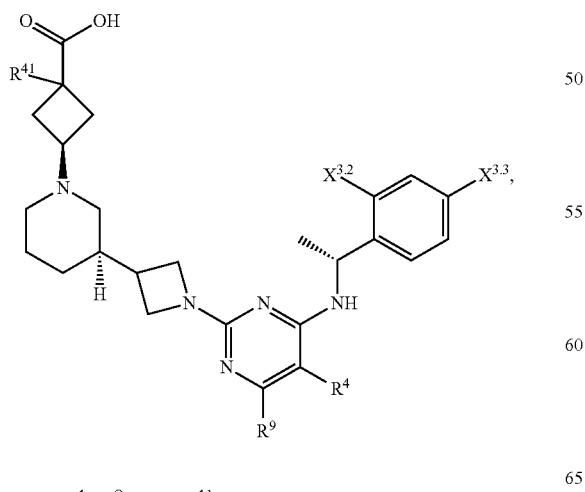

wherein $R^4$, $R^9$, and $R^{41}$ are as described herein, including embodiments. $X^{3.2}$ $X^{3.3}$ are independently halogen.

In embodiments, the compound has the structure:

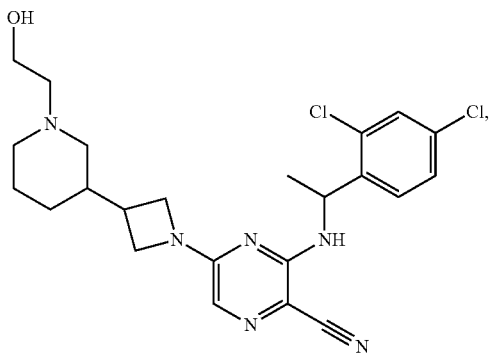

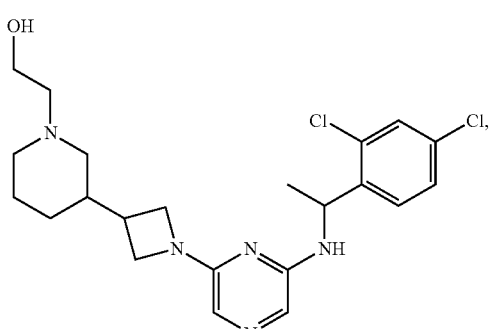

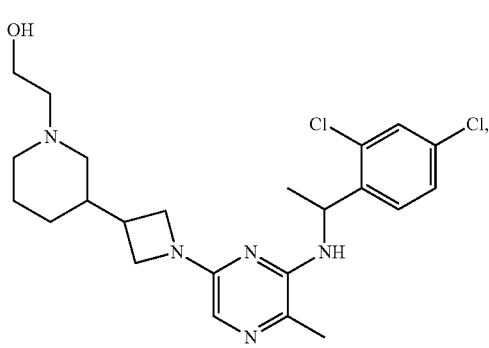

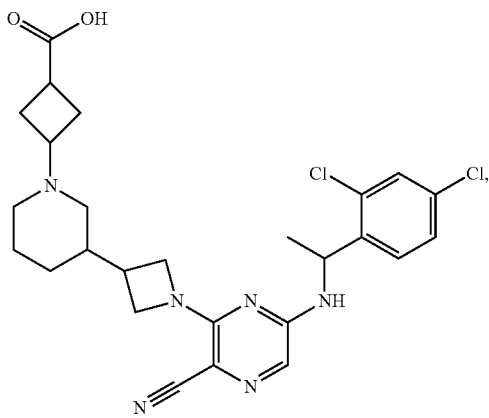

167
-continued
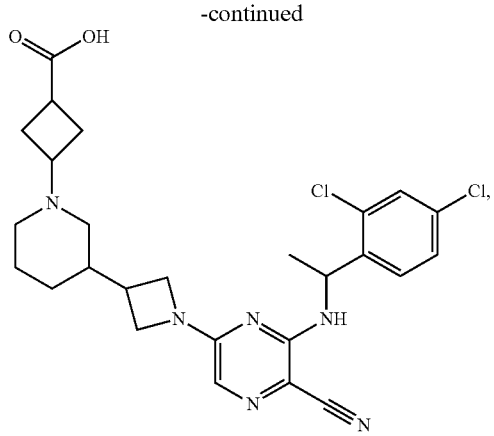
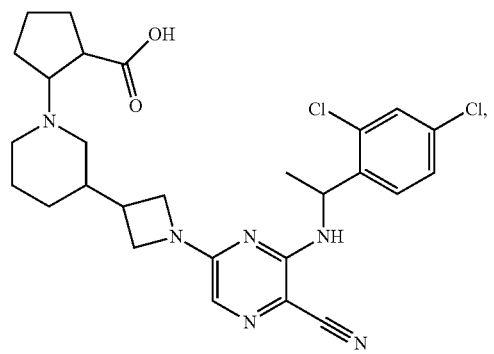
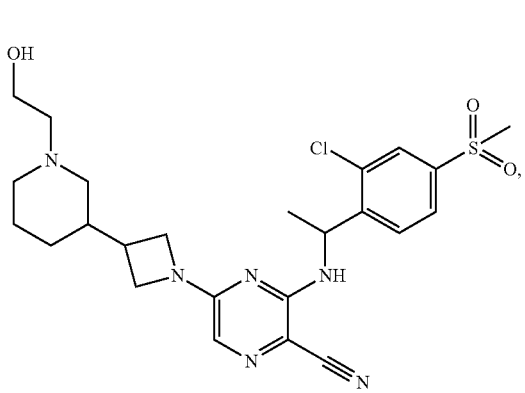
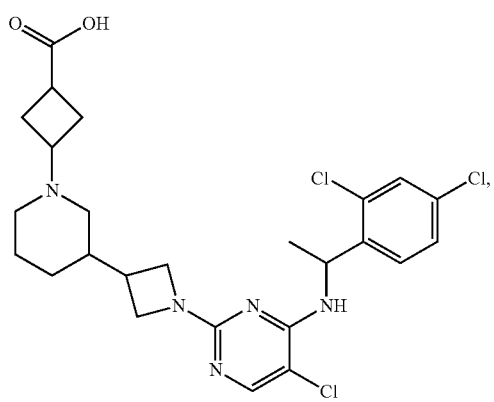
168
-continued
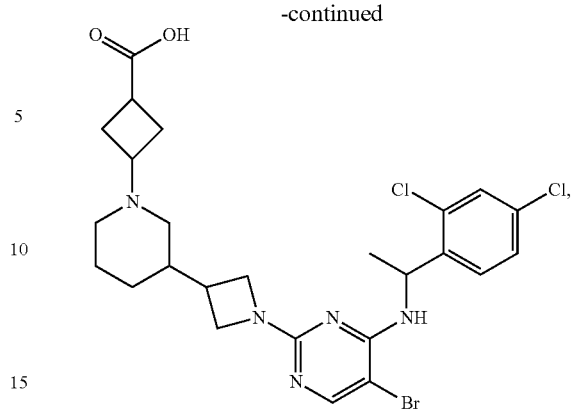
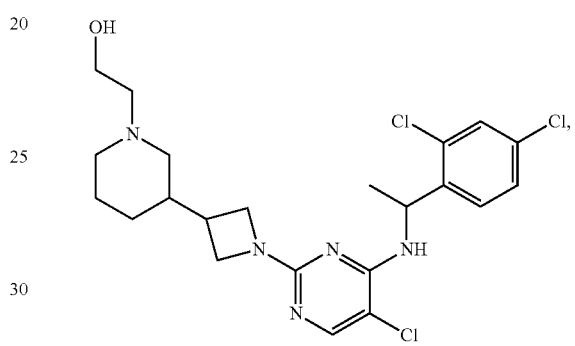
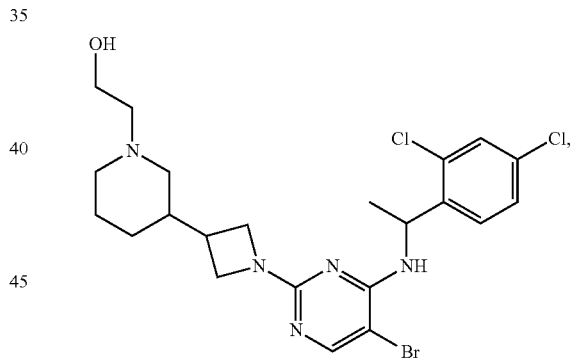
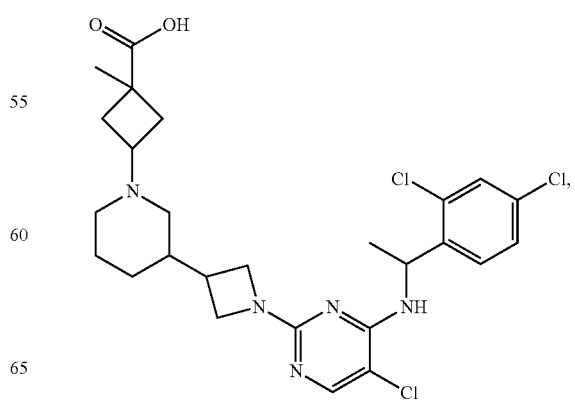

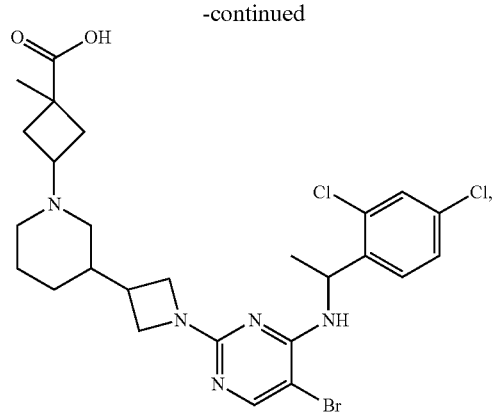
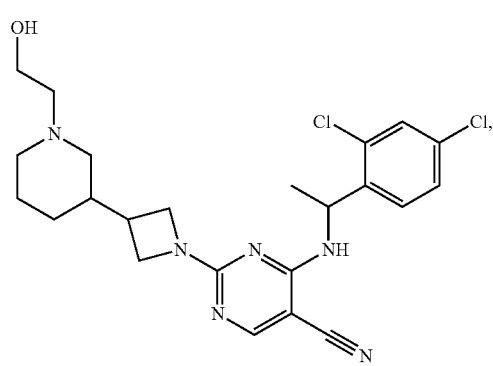
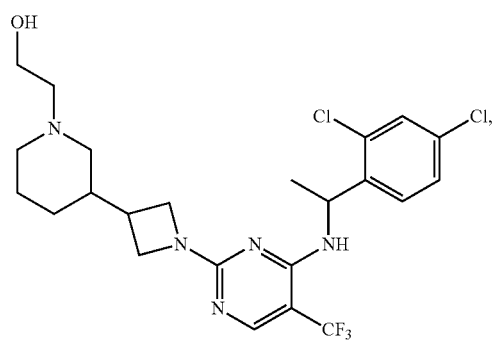
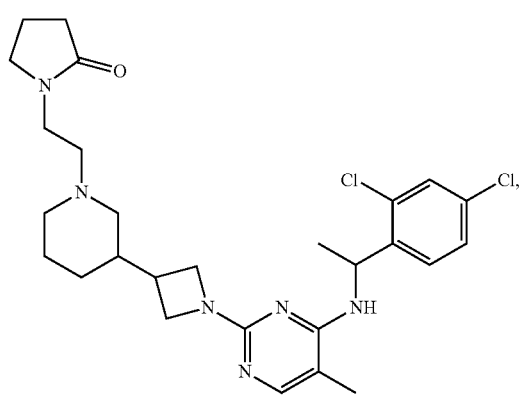
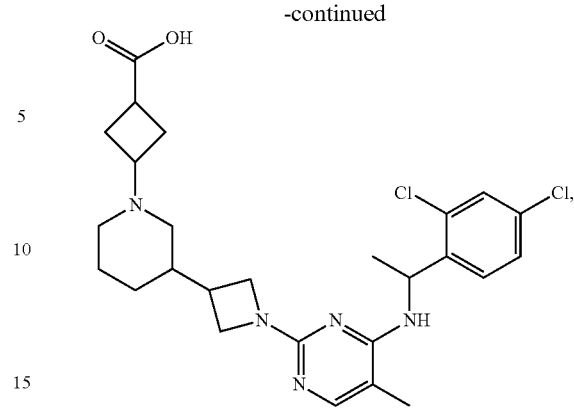
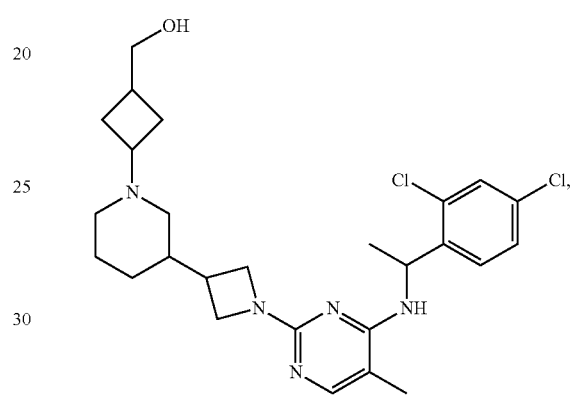
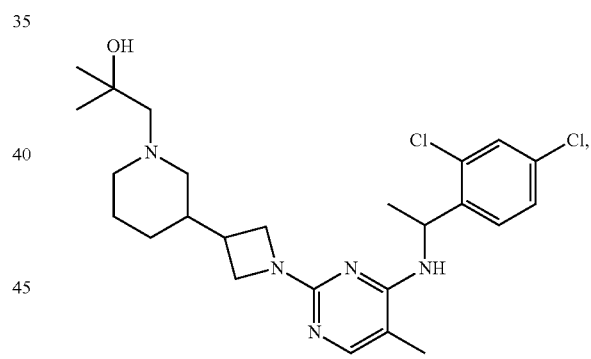
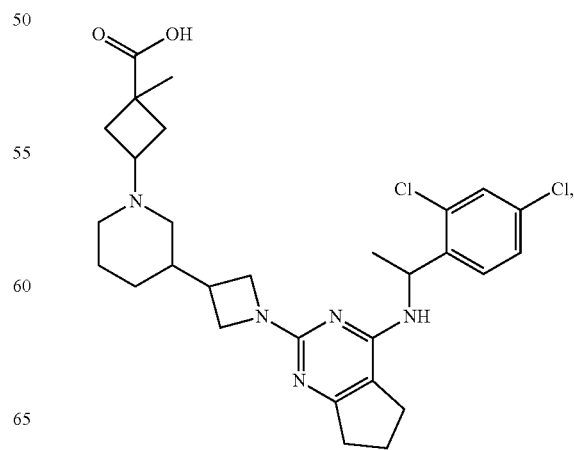

171
-continued
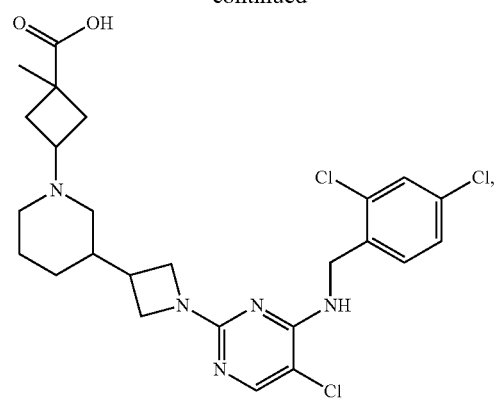
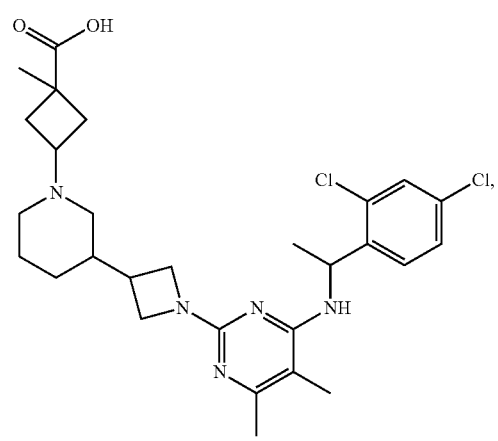
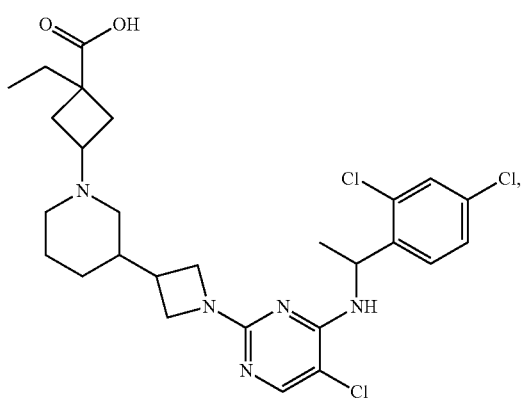
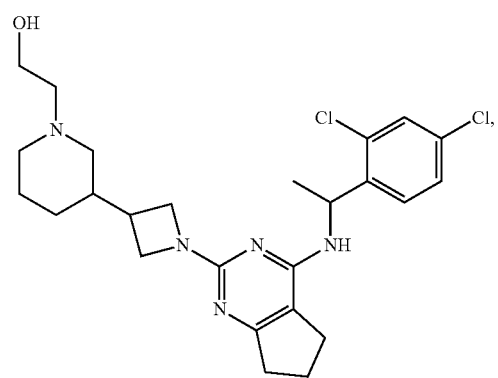
172
-continued
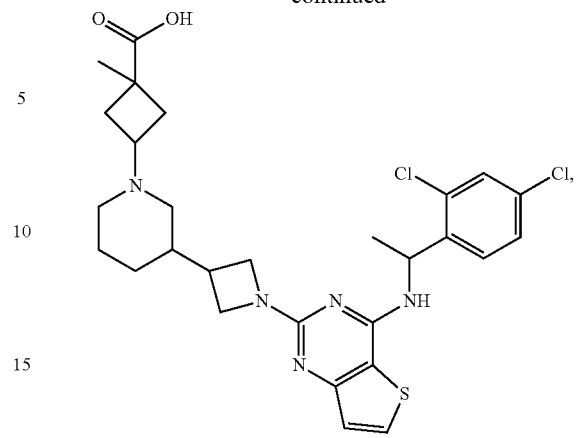
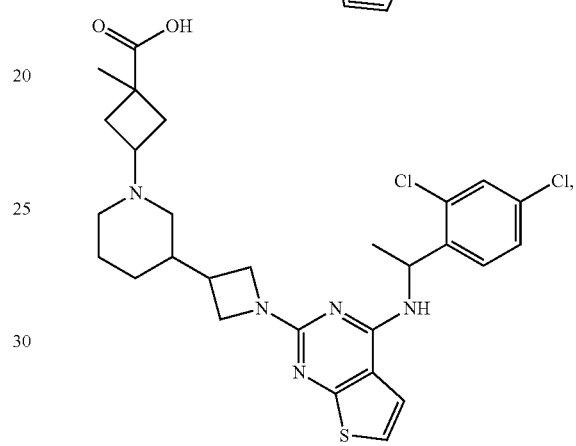
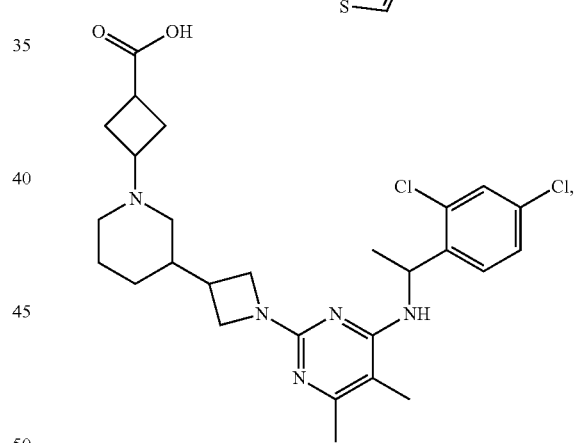
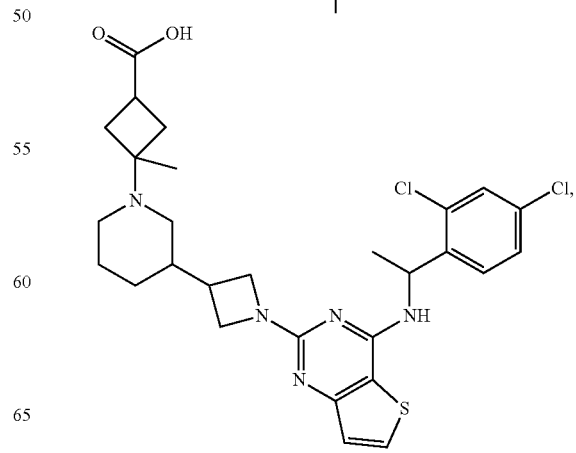

-continued
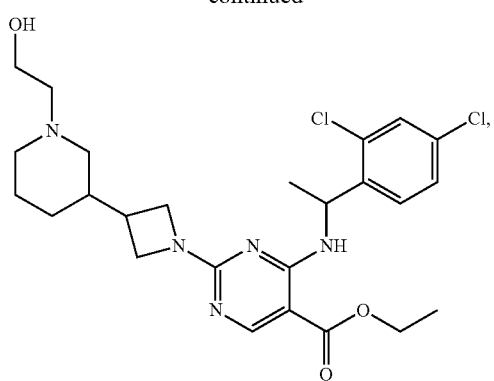
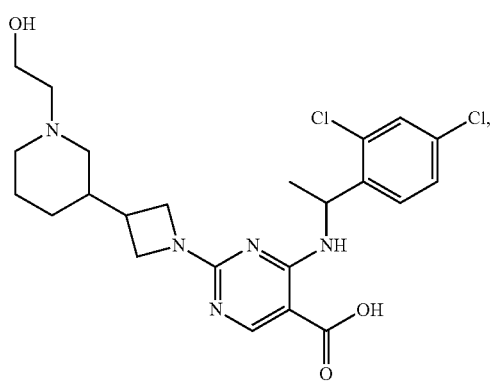
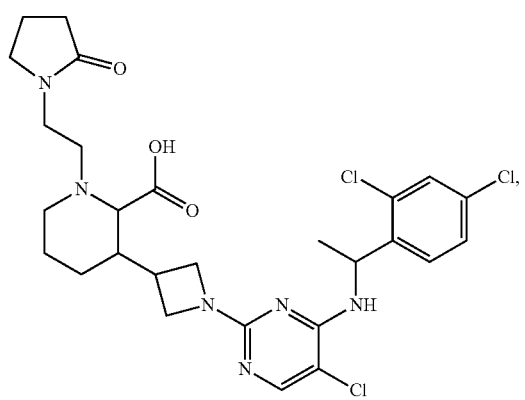
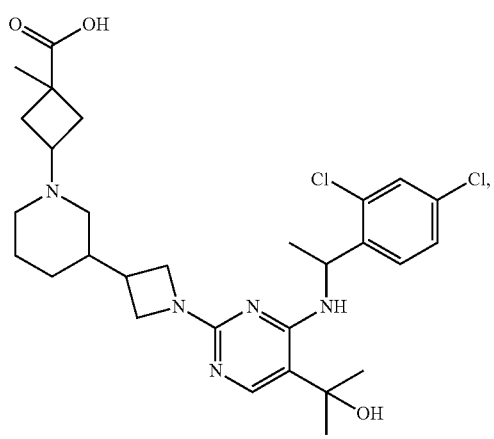
-continued
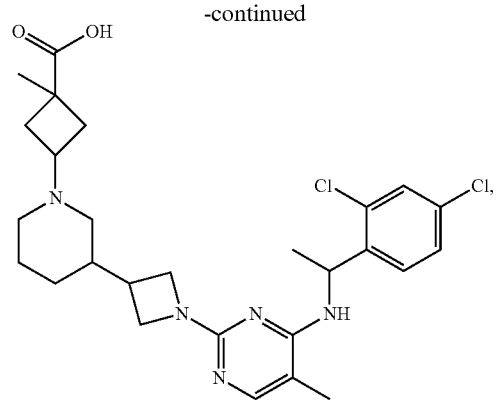
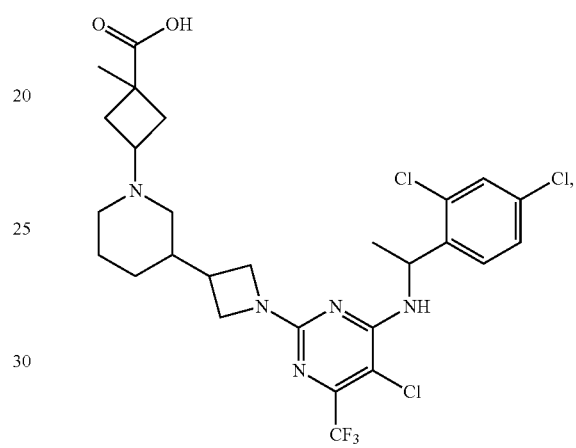
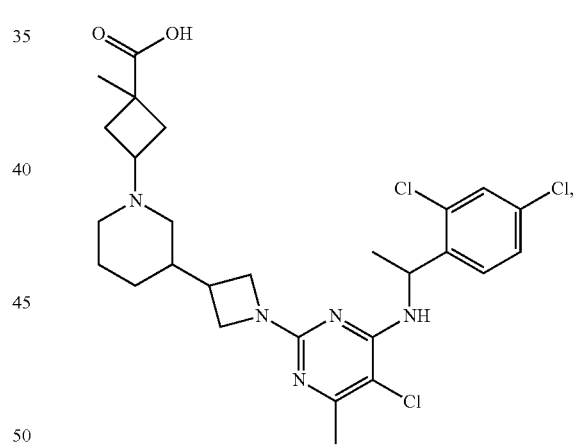
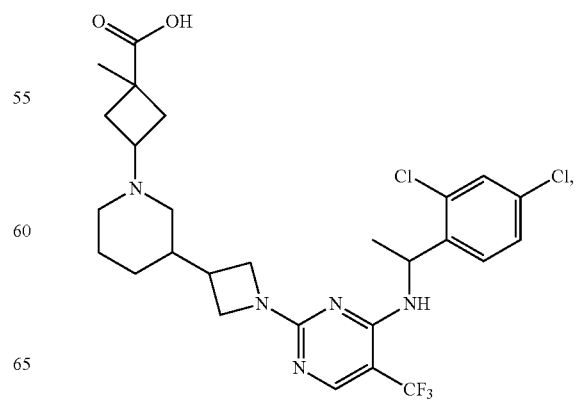

-continued
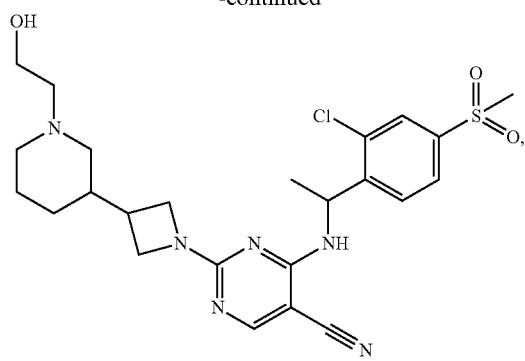
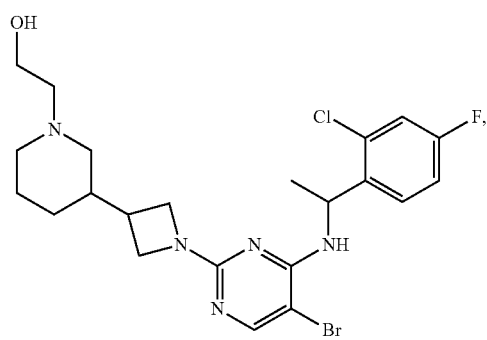
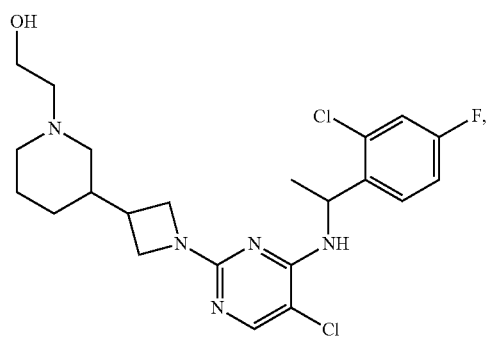
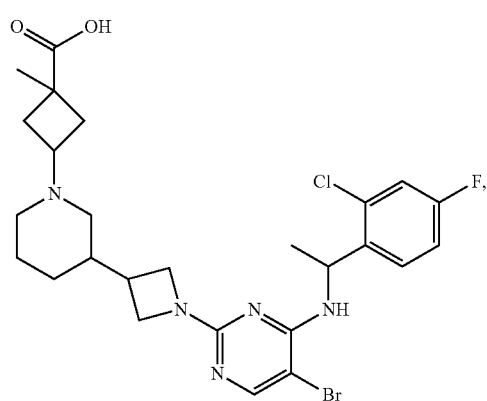
-continued
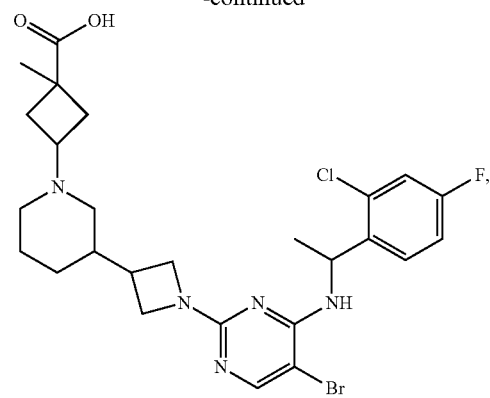
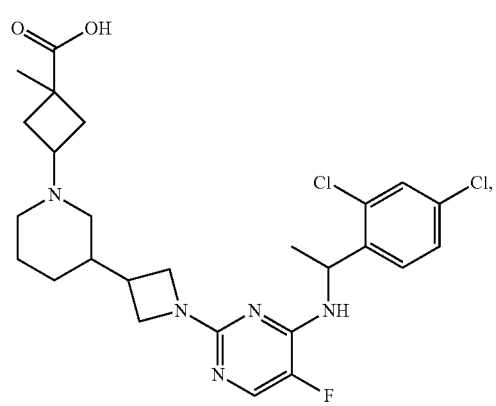
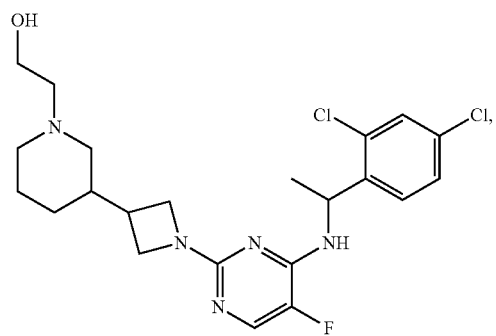
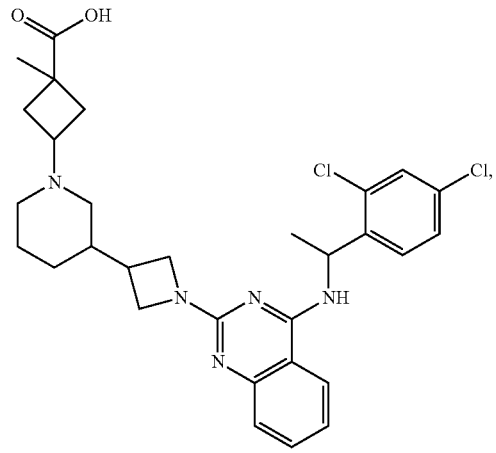

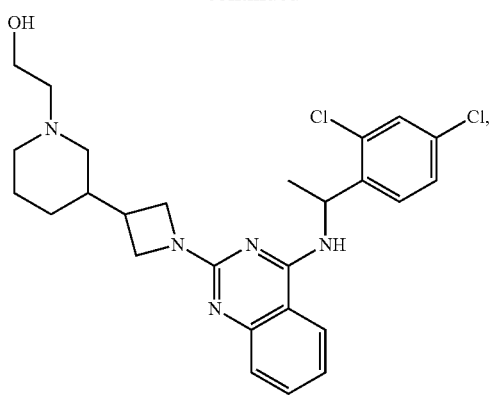
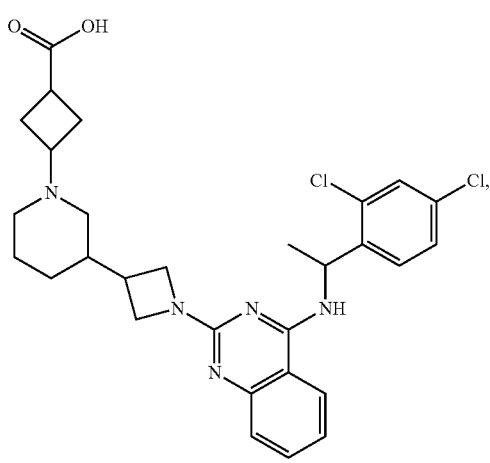
or a pharmaceutically acceptable salt thereof.
In other embodiments, the compound has the structure:
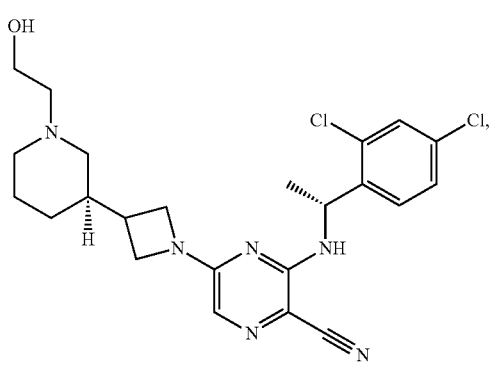
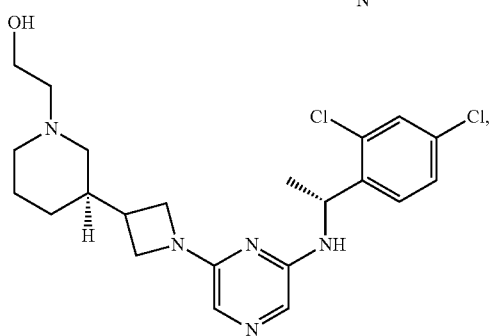
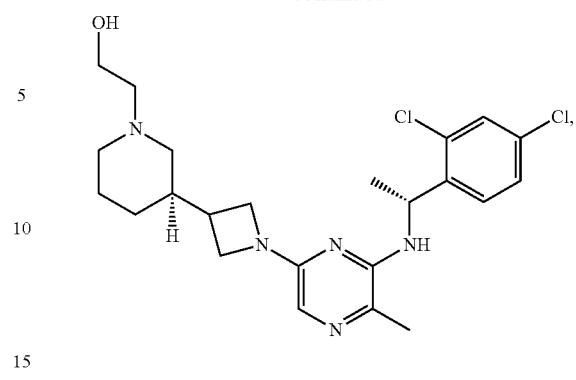
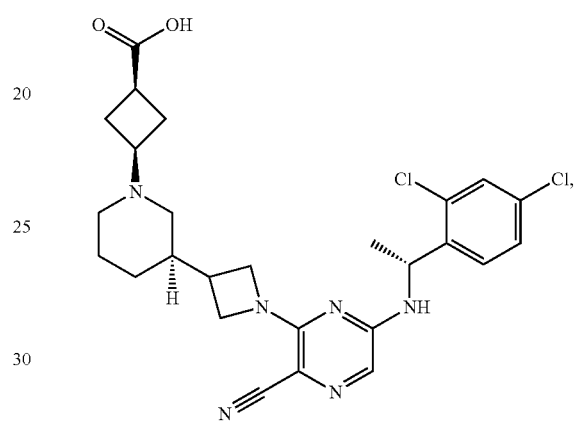
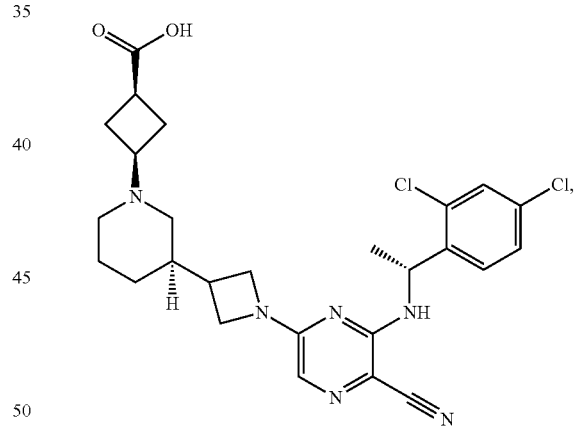
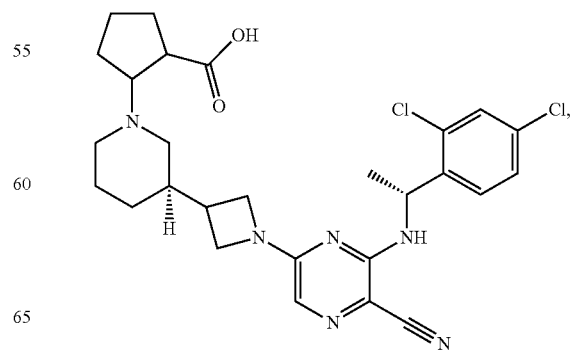

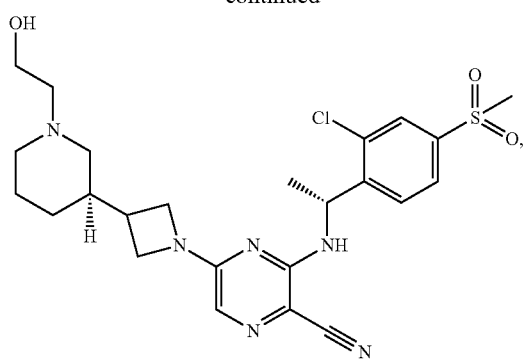
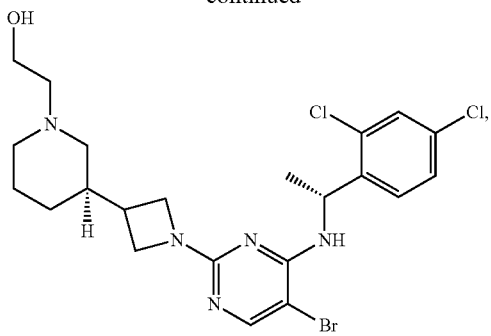
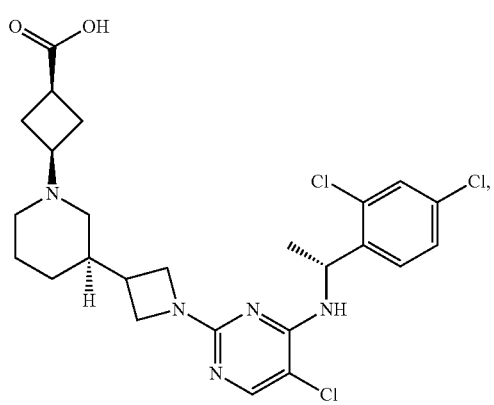
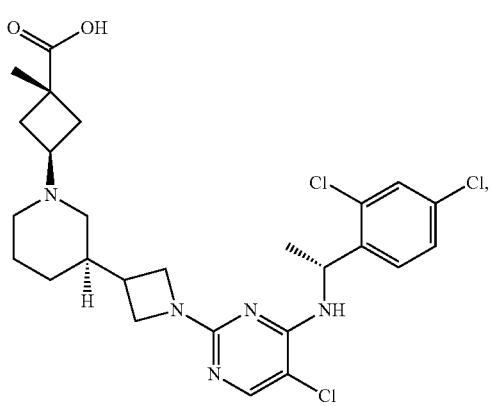
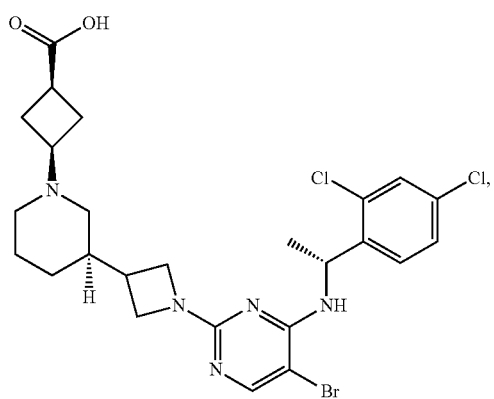
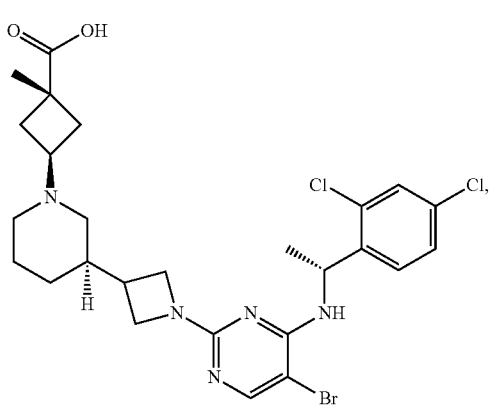
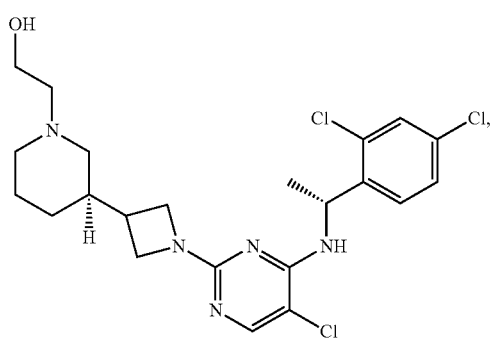
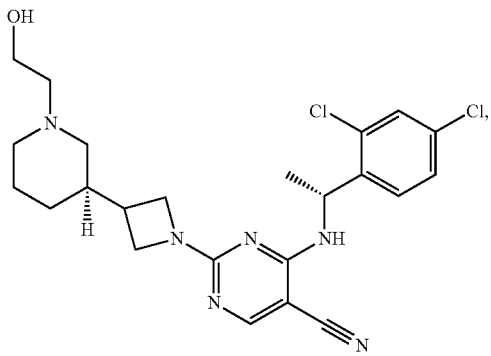

-continued
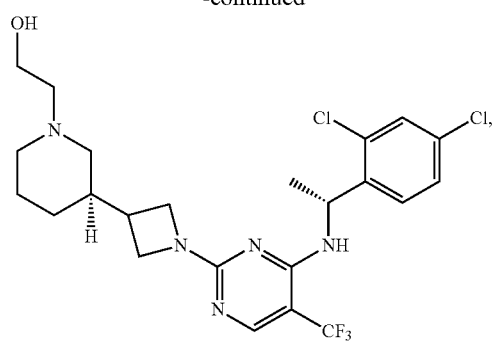
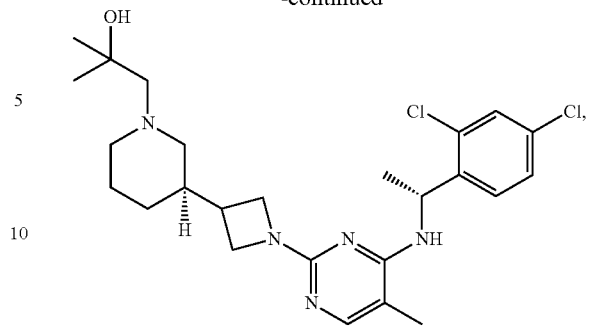
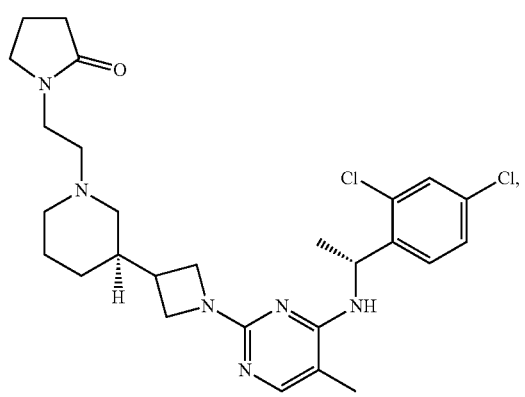
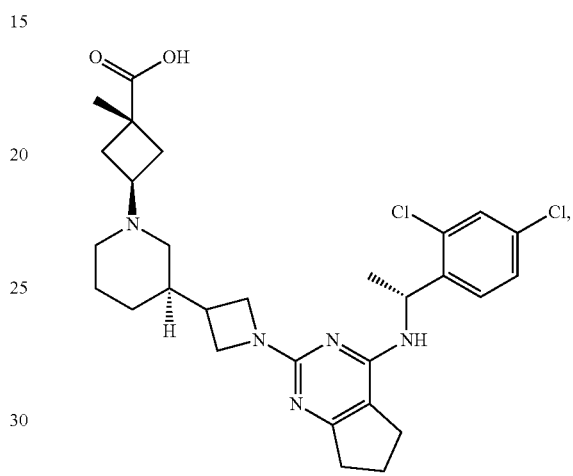
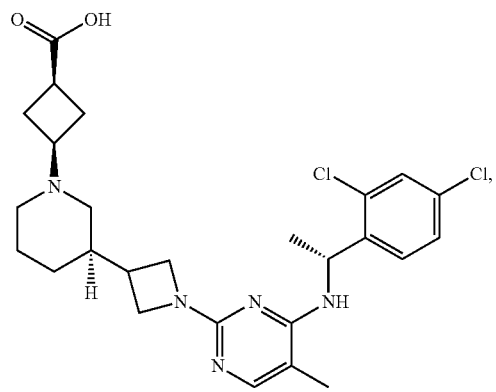
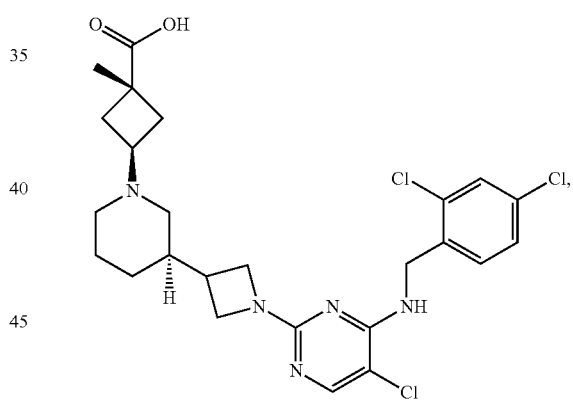
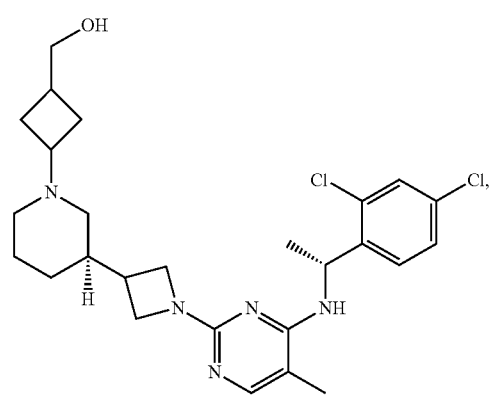
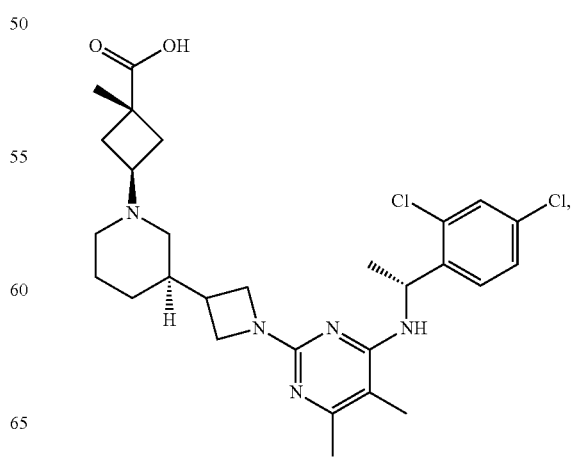

183
-continued
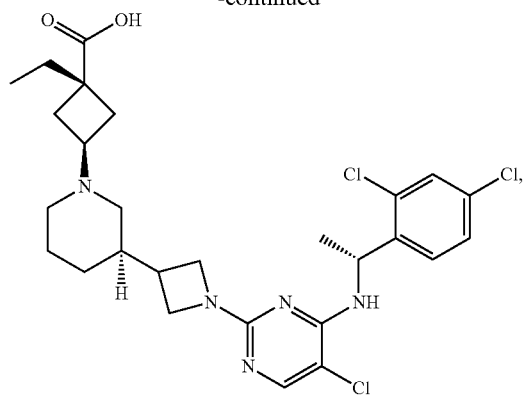
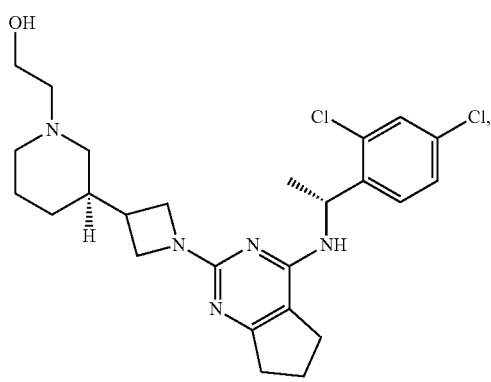
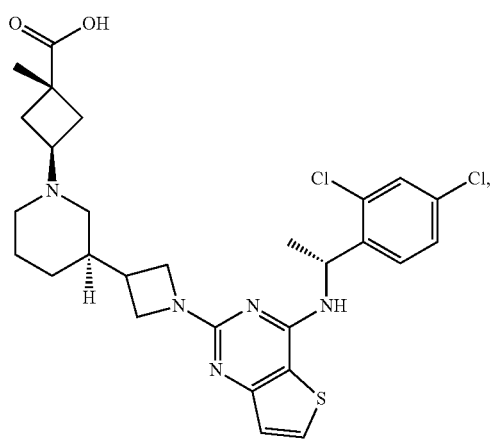
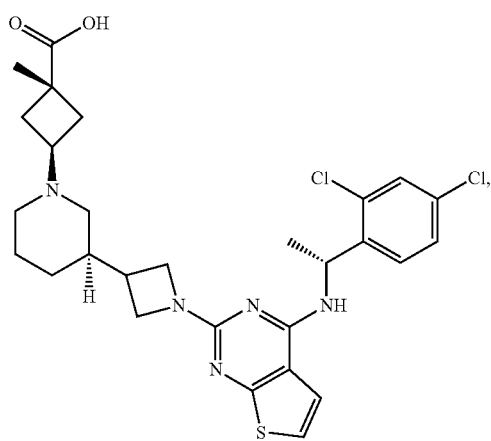
184
-continued
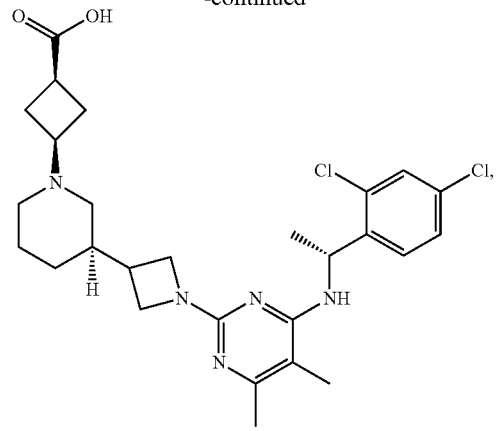
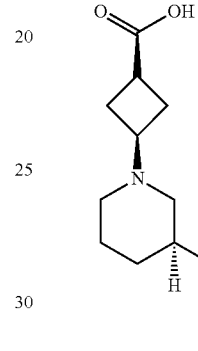
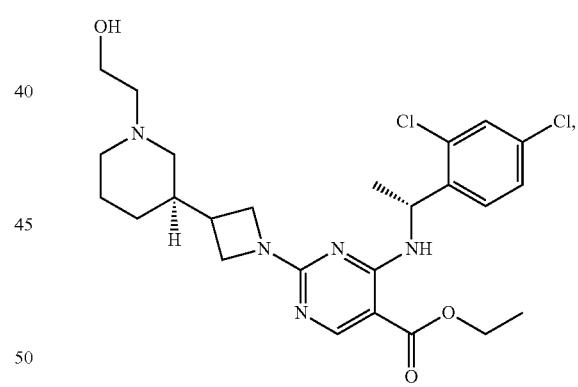
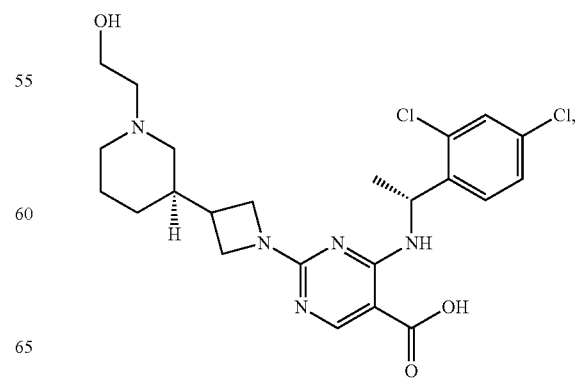

185
-continued
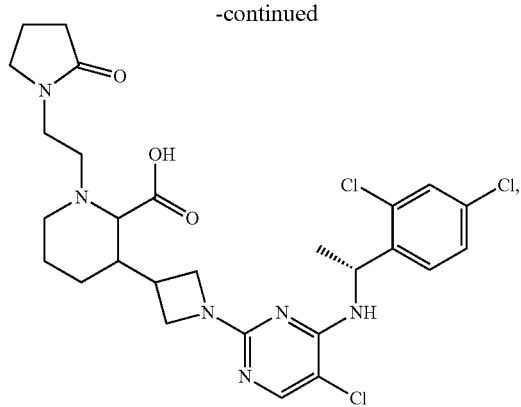
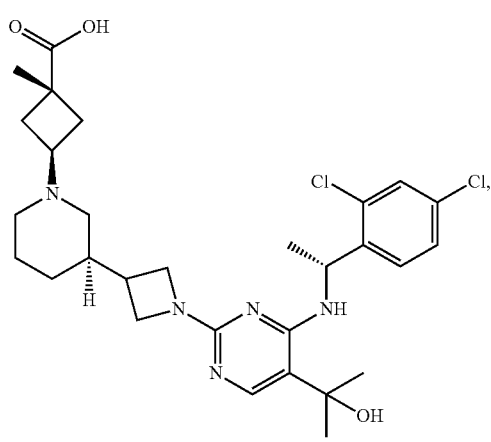
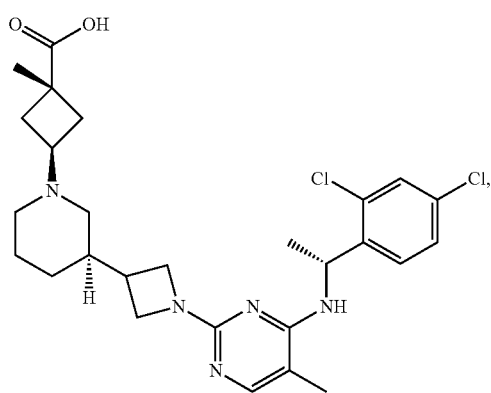
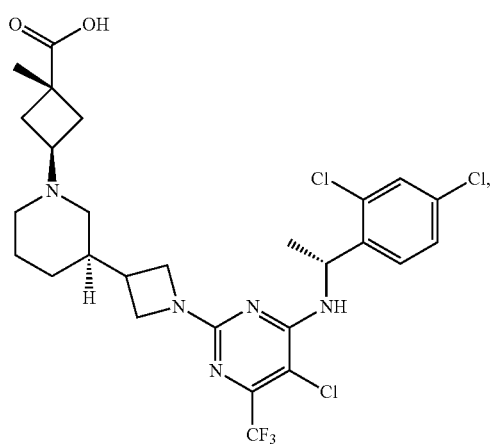
186
-continued
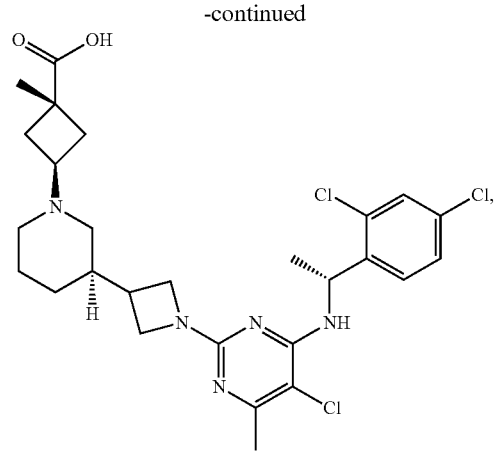
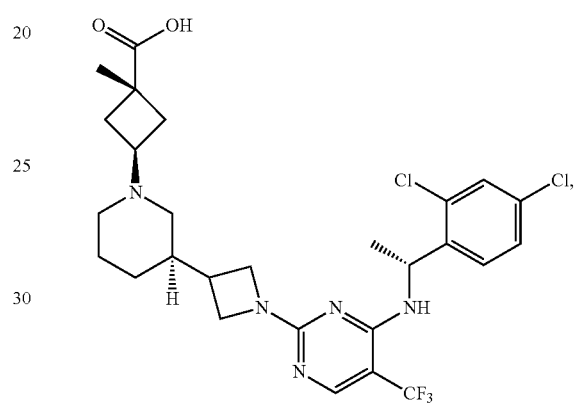
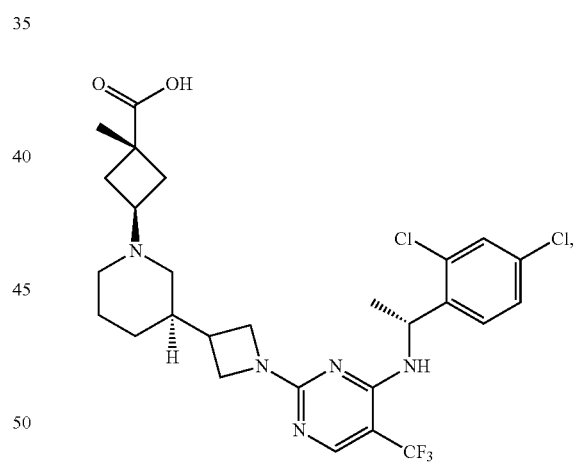
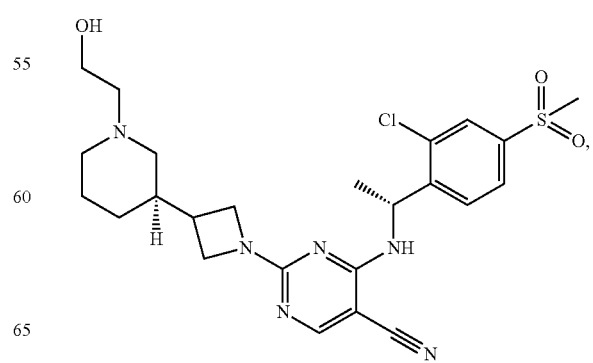

-continued
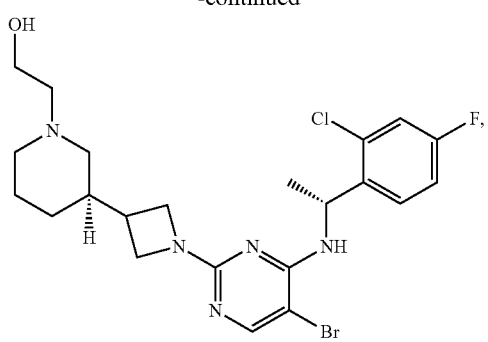
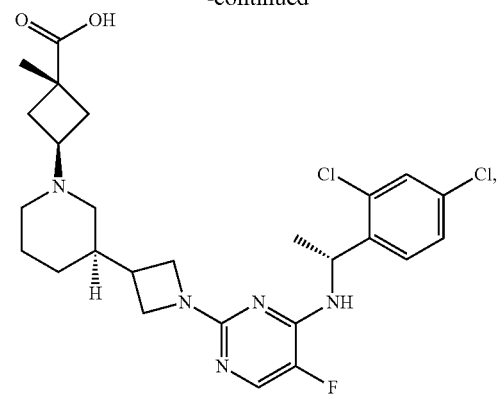
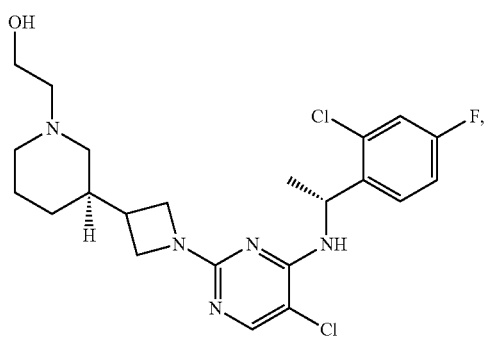
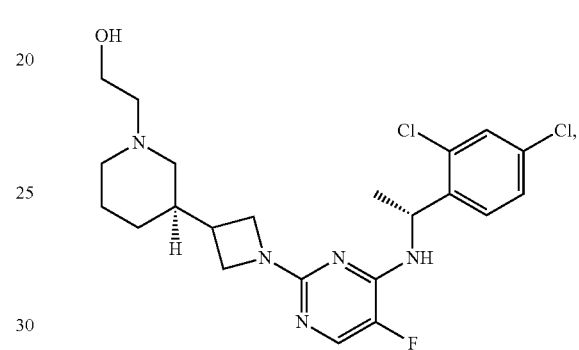
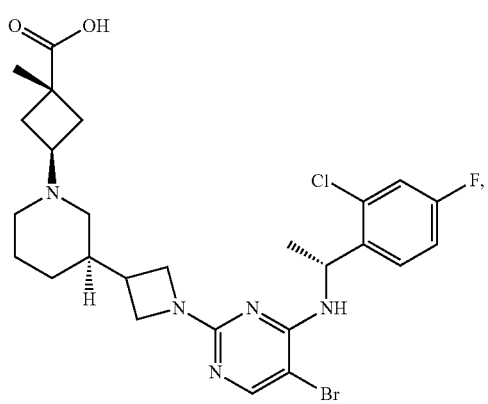
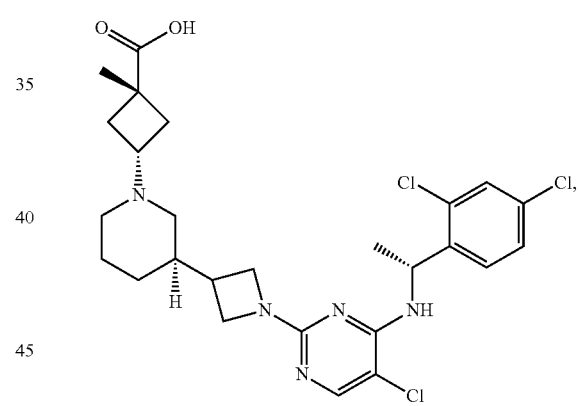
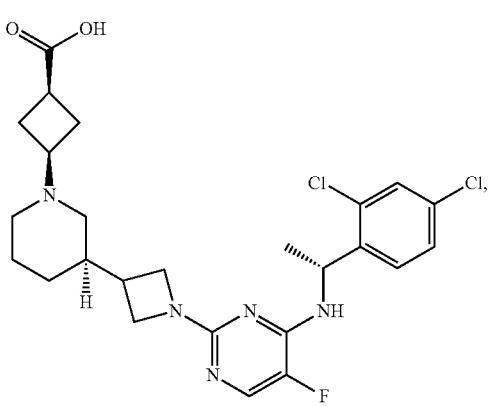
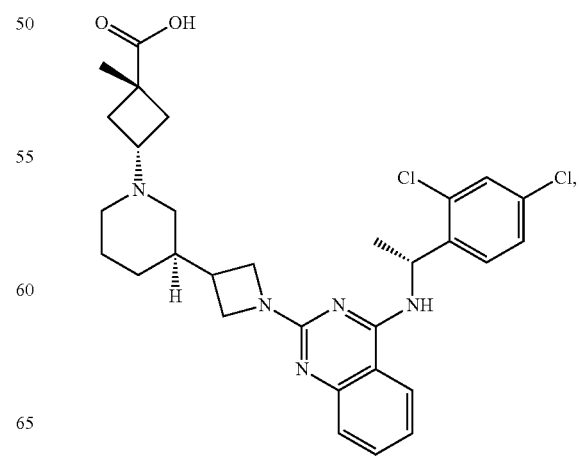

189
-continued
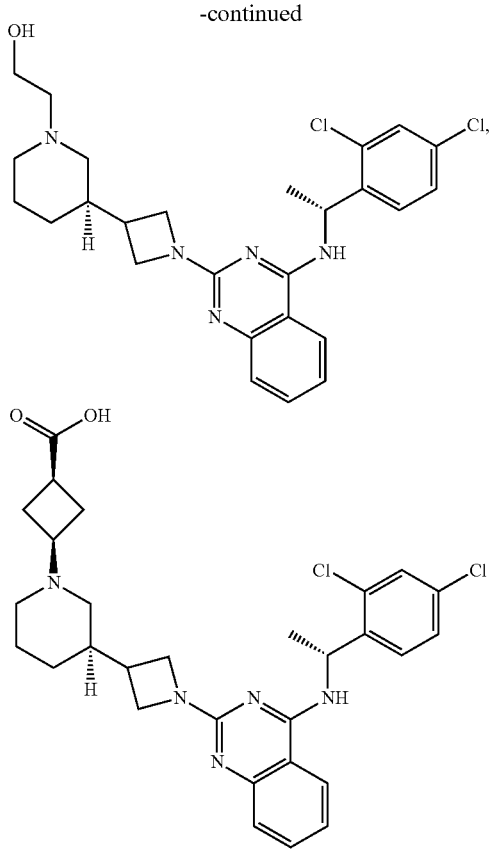
or a pharmaceutically acceptable salt thereof. In other embodiments, the compound has a structure as shown in Table 2, wherein $R^4$ and $R^{44}$ are as described herein, including embodiments:
TABLE 2
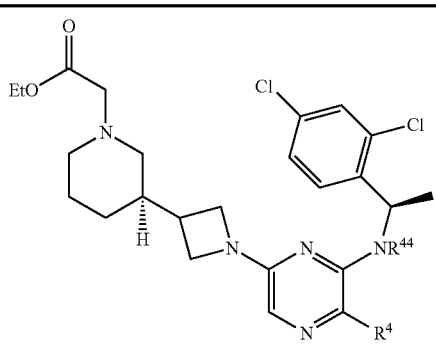
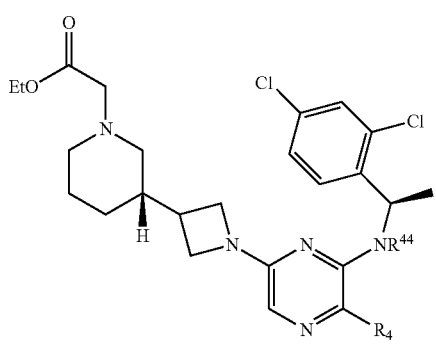
TABLE 2-continued
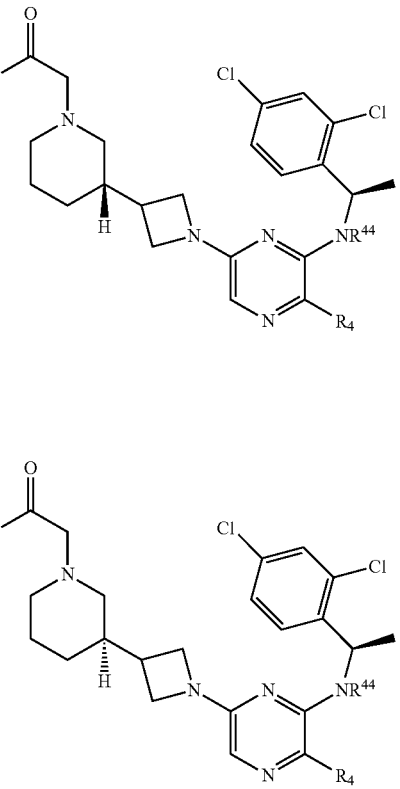
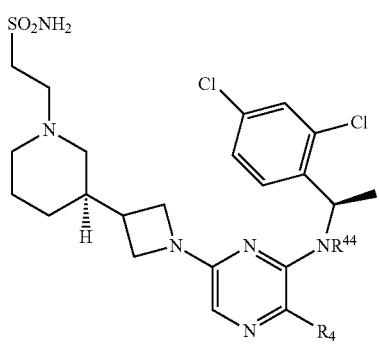
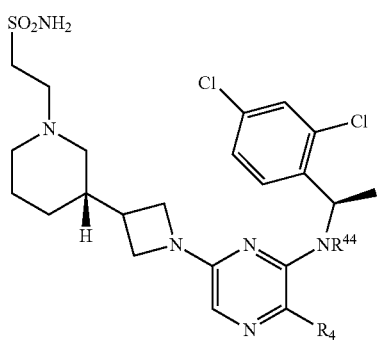

TABLE 2-continued
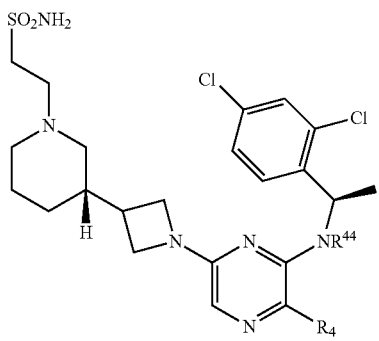
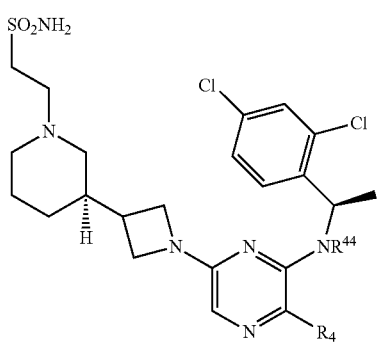
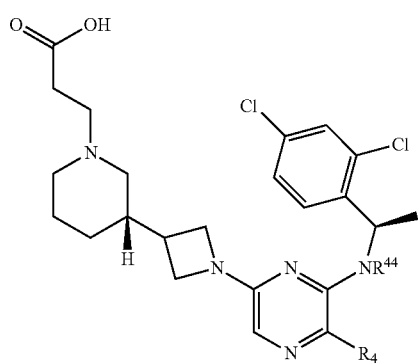
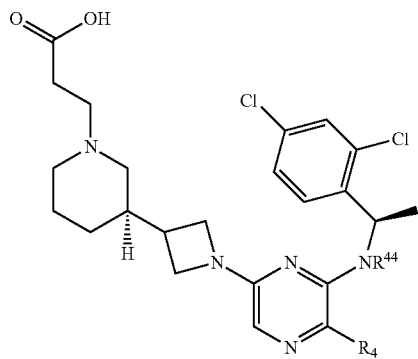
TABLE 2-continued
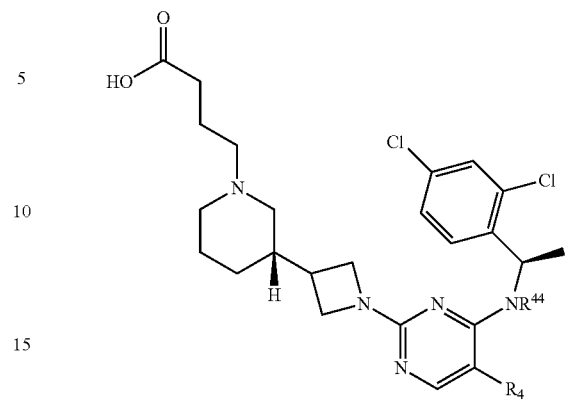
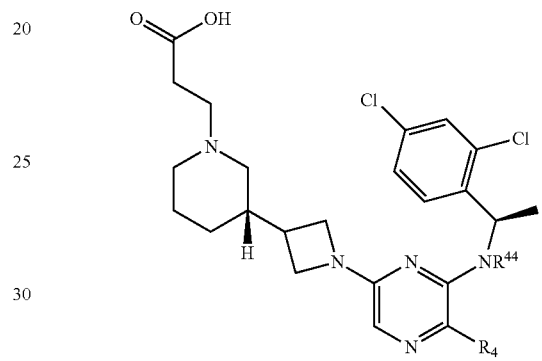
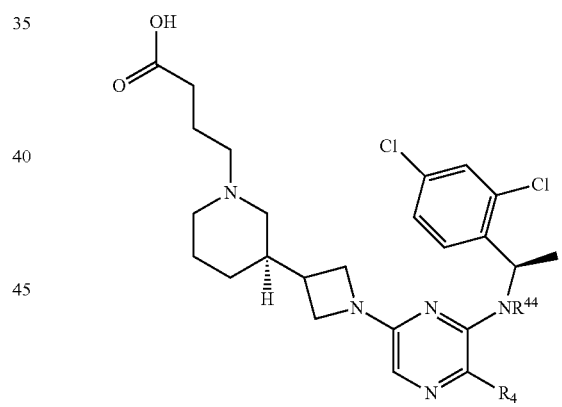
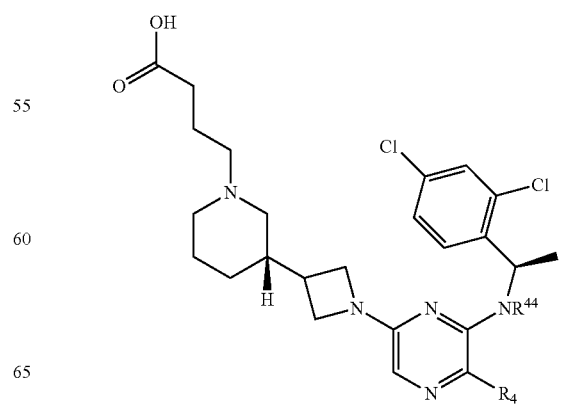

TABLE 2-continued
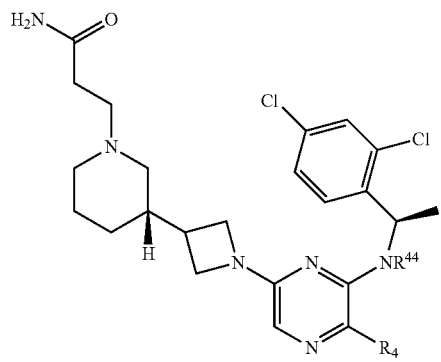
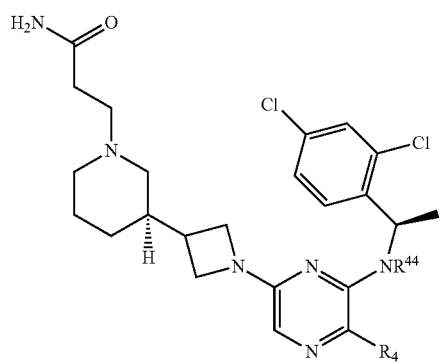
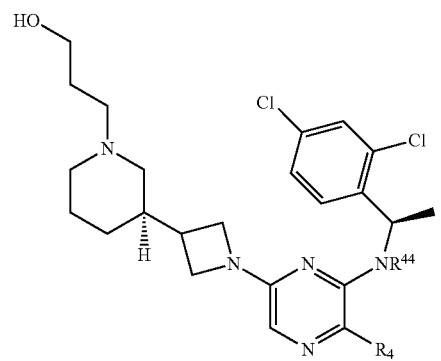
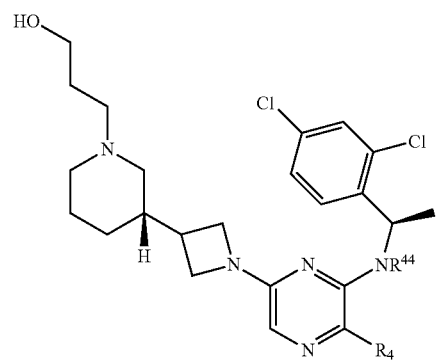
TABLE 2-continued
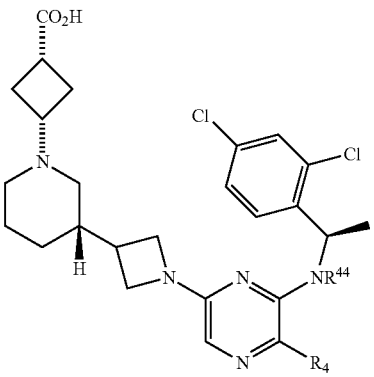
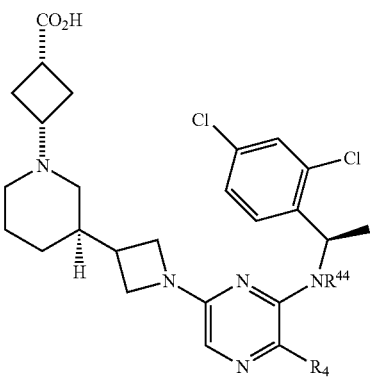
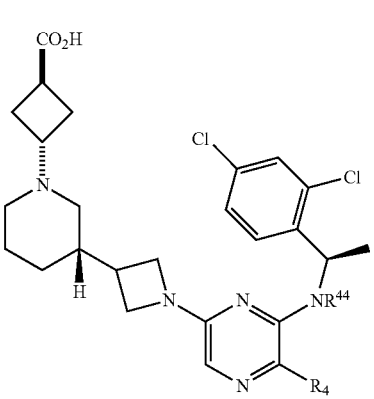
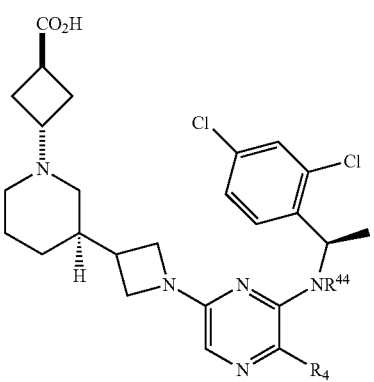

TABLE 2-continued
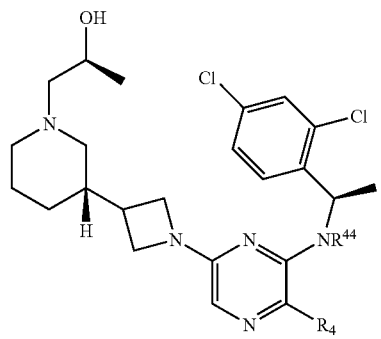
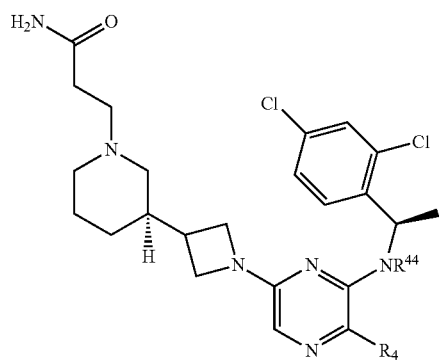
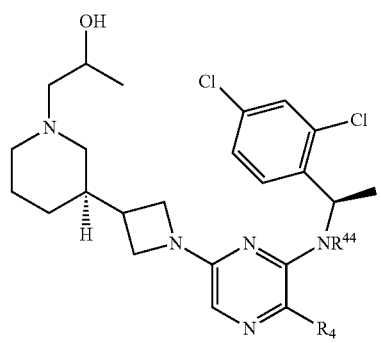
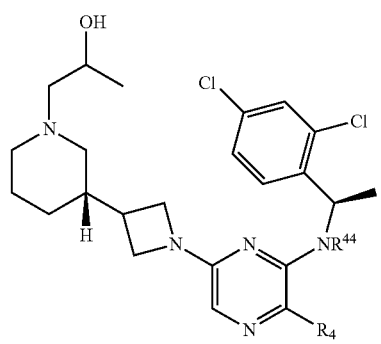
TABLE 2-continued
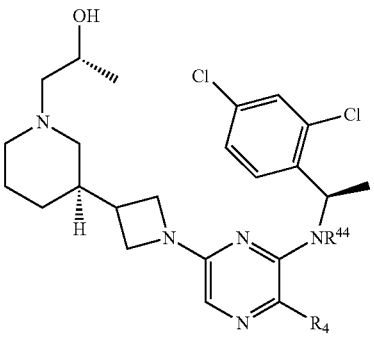
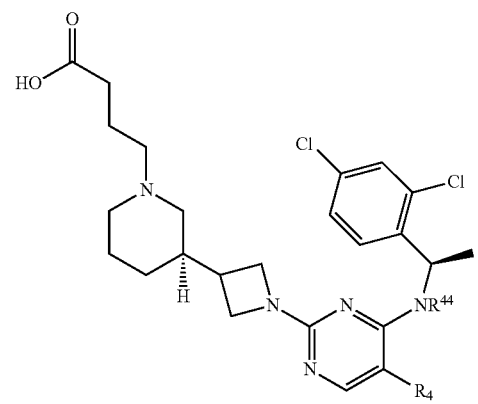
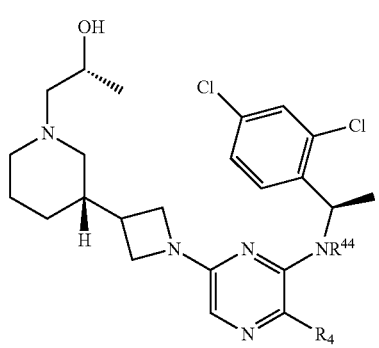
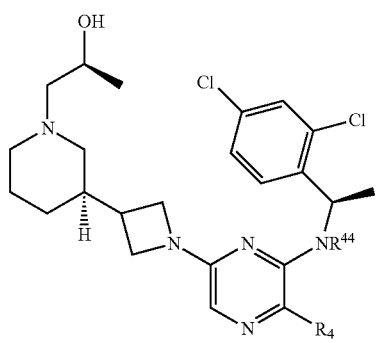

TABLE 2-continued
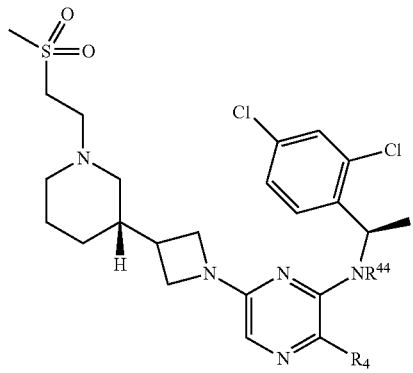
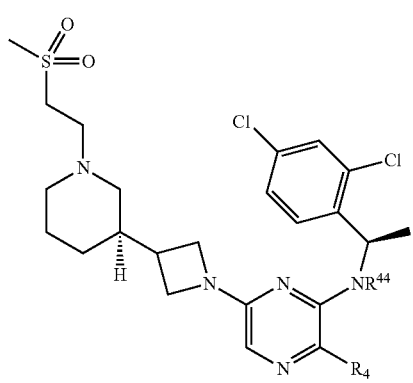
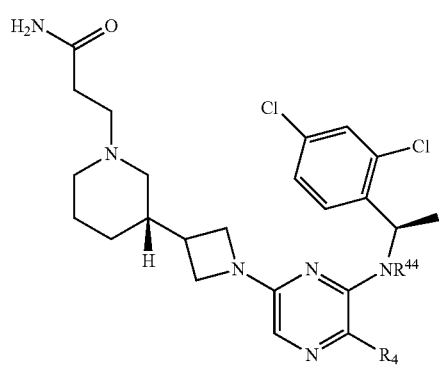
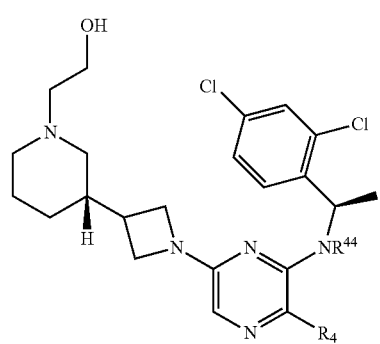
TABLE 2-continued
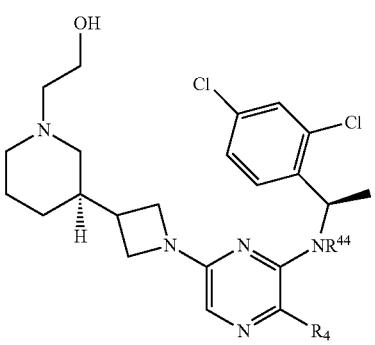
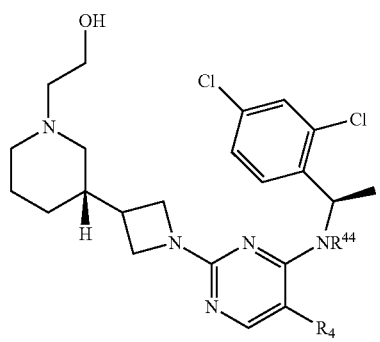
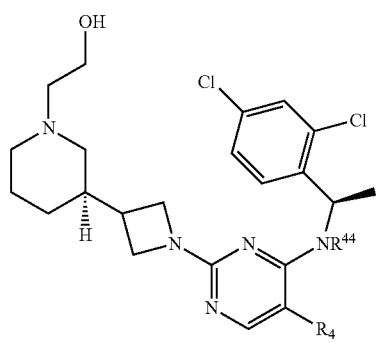
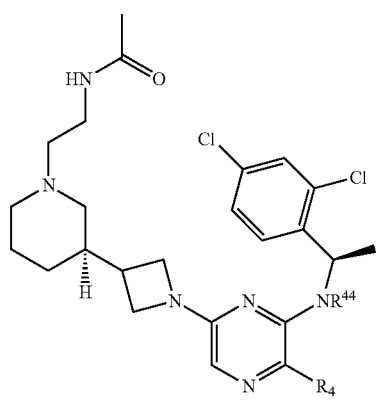

TABLE 2-continued
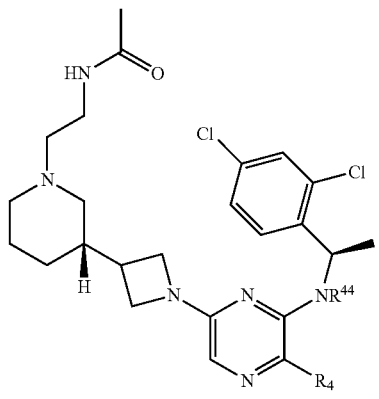
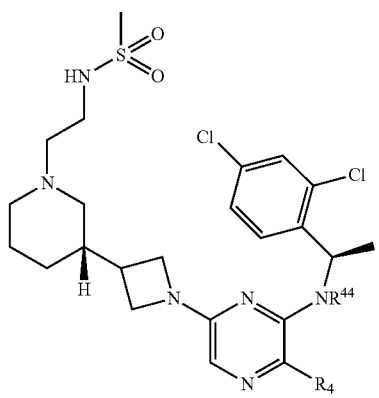
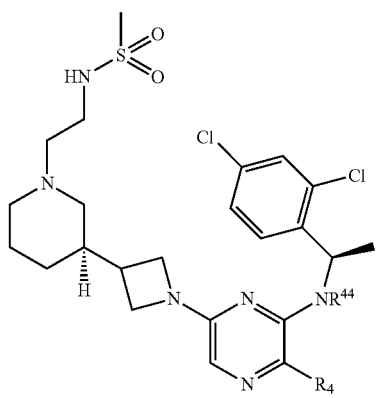
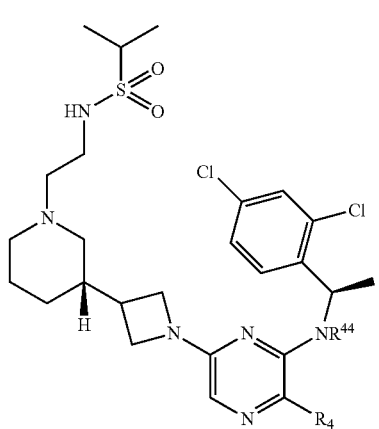
TABLE 2-continued
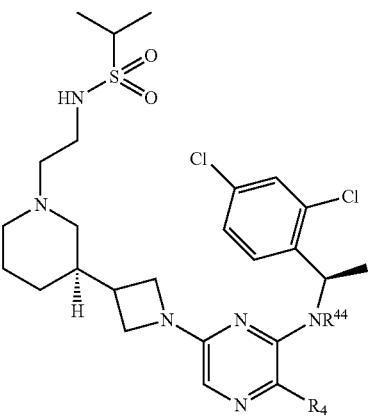
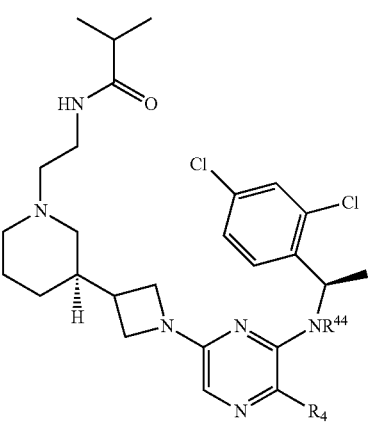
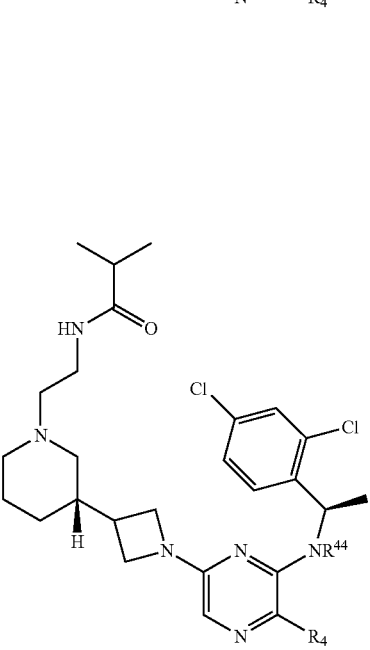

TABLE 2-continued
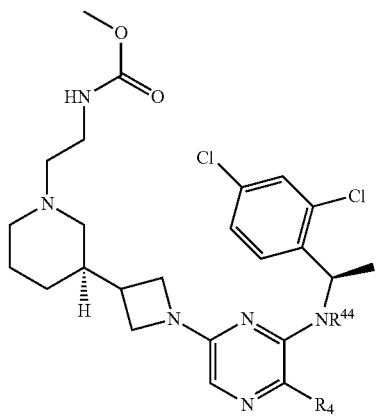
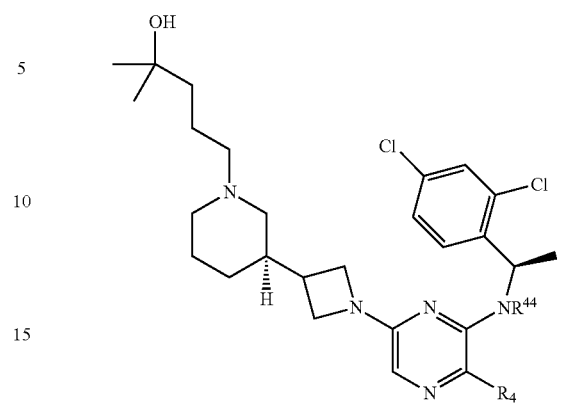
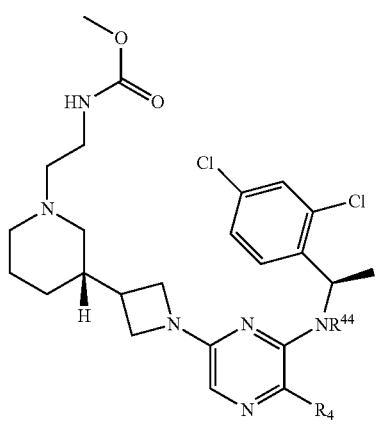
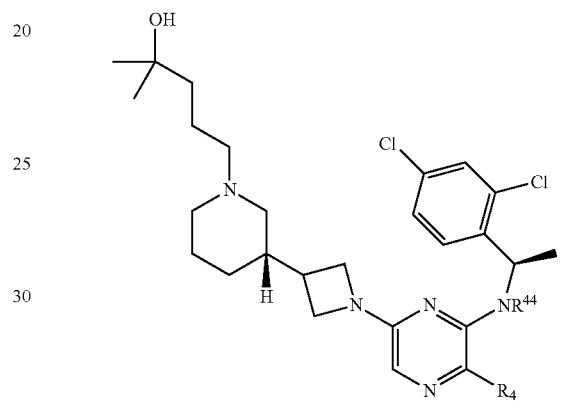
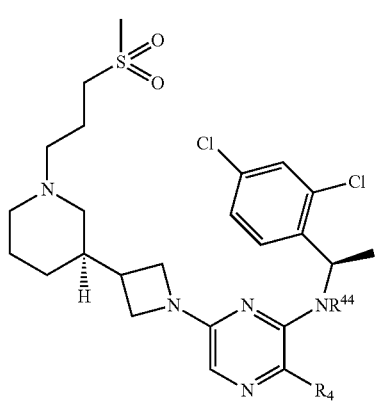
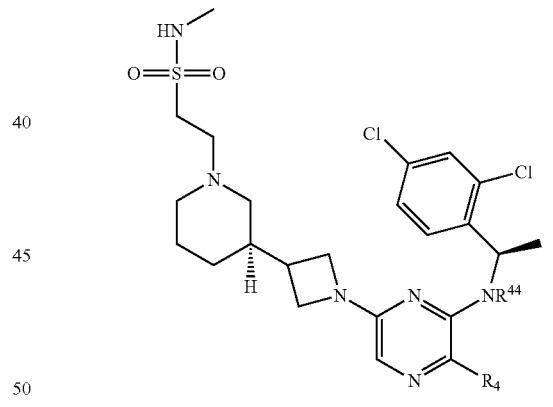
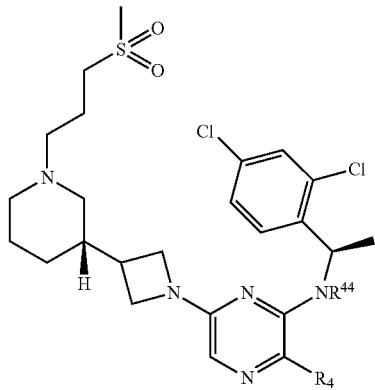
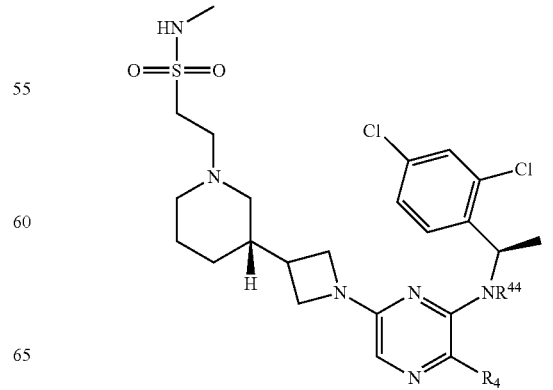

TABLE 2-continued
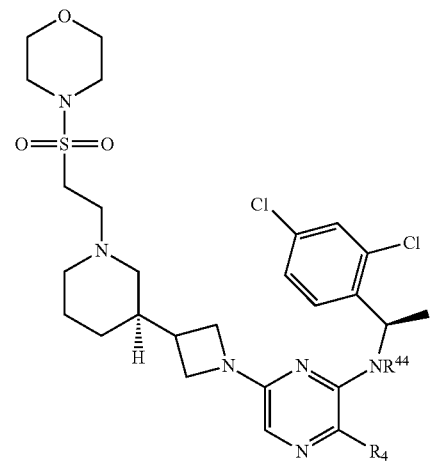
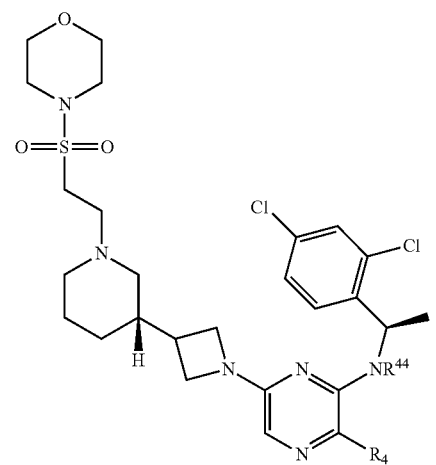
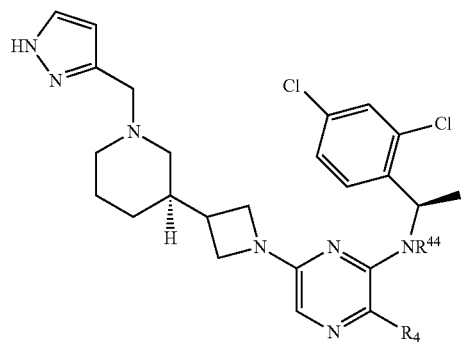
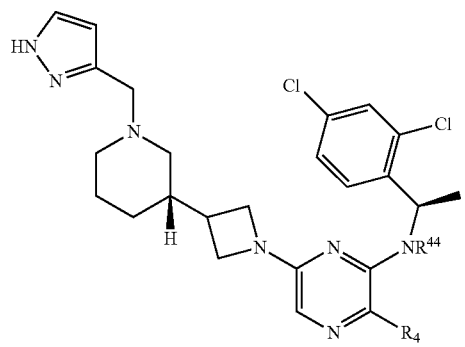
TABLE 2-continued
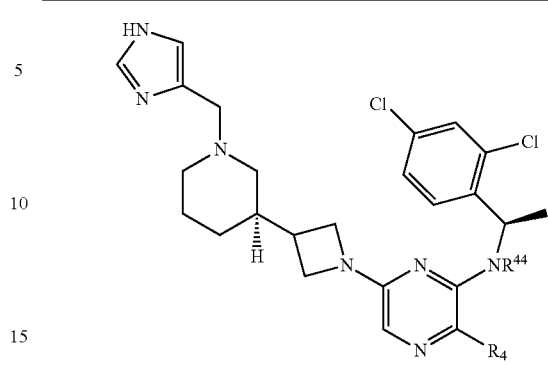
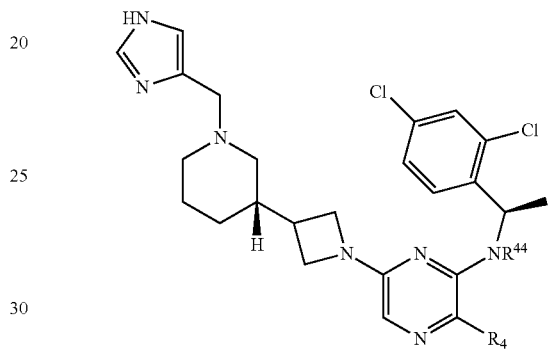
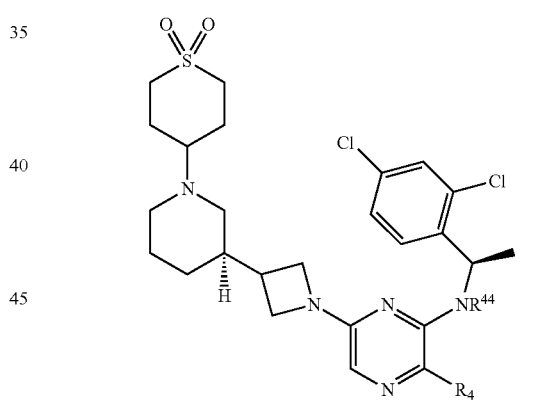
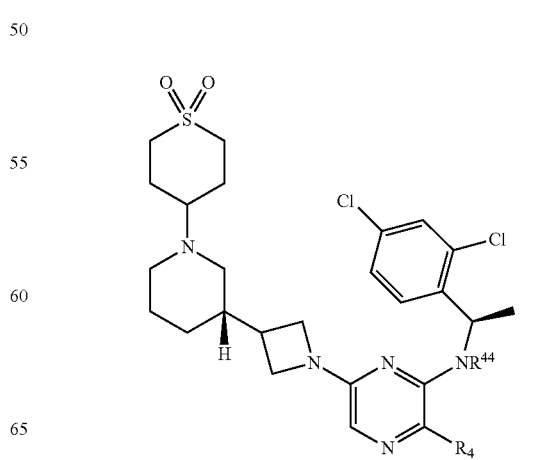

TABLE 2-continued
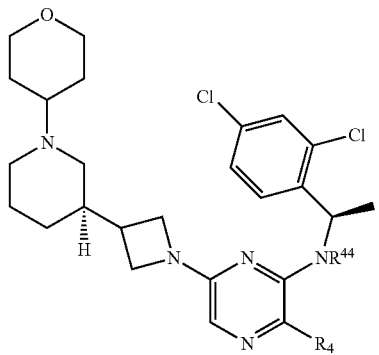
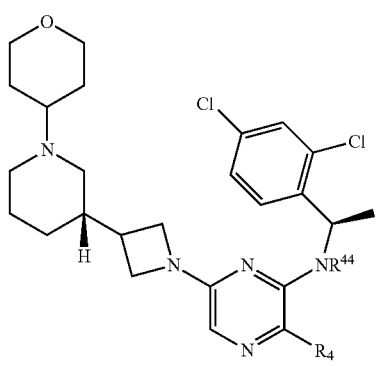
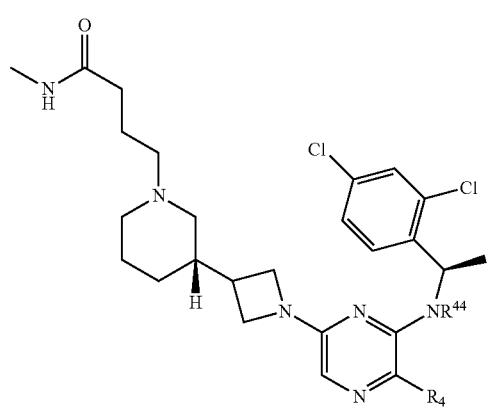
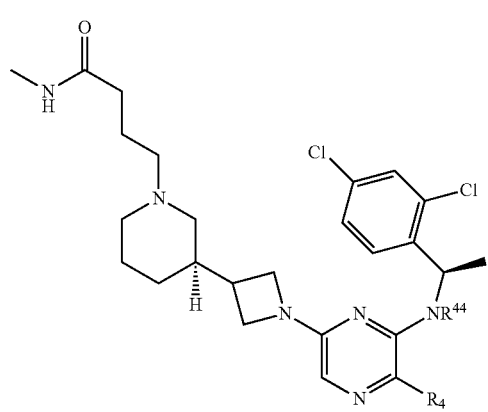
TABLE 2-continued
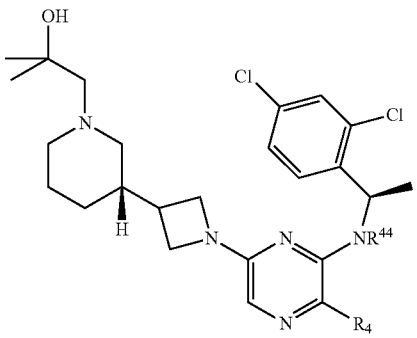
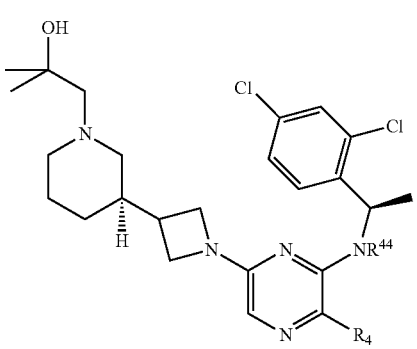
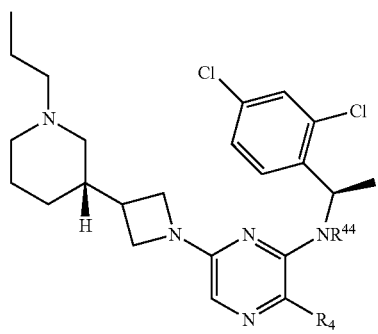
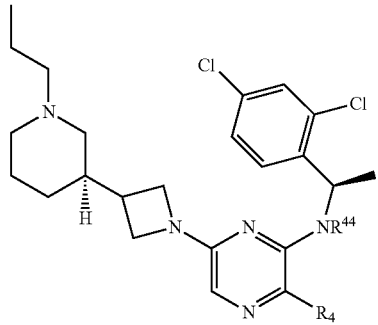

TABLE 2-continued
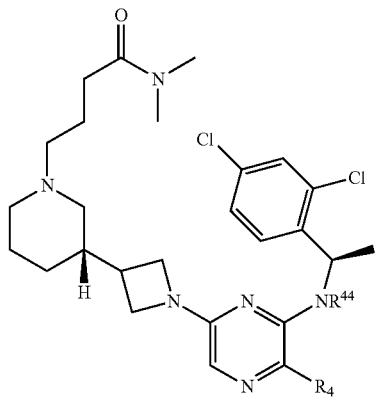
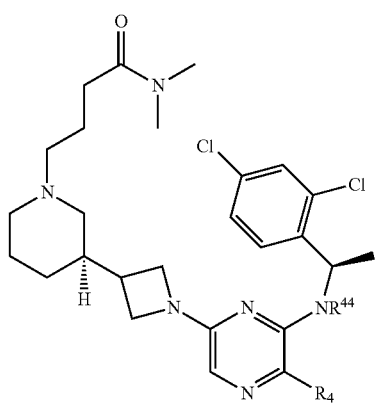
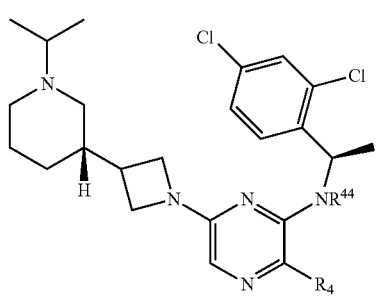
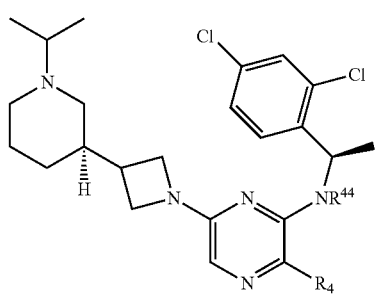
TABLE 2-continued
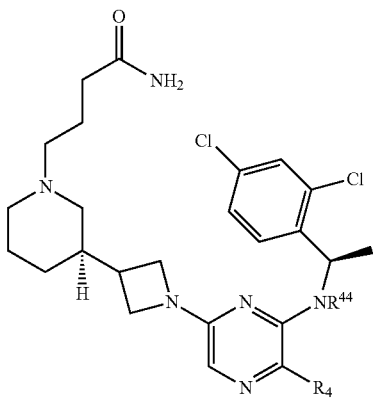
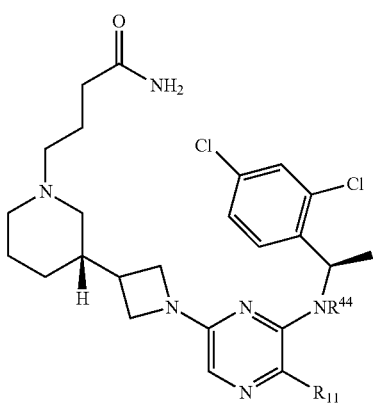
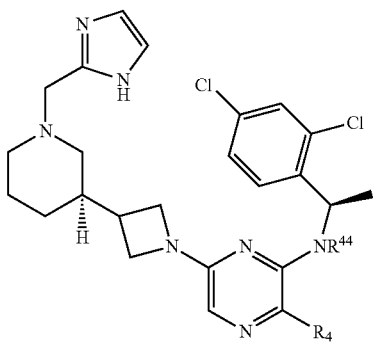
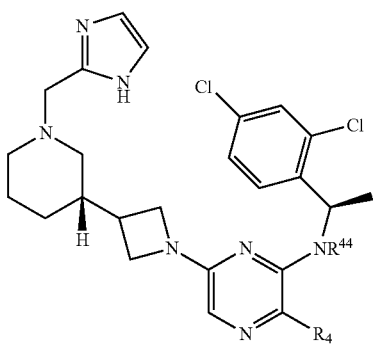

TABLE 2-continued
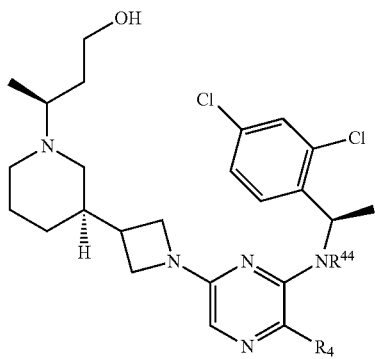
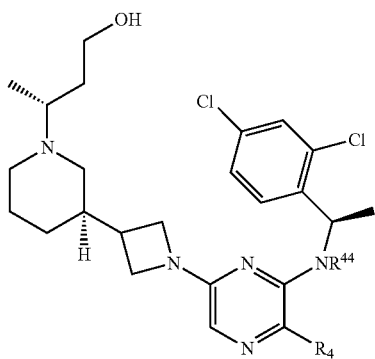
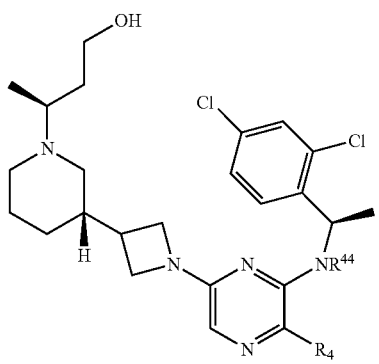
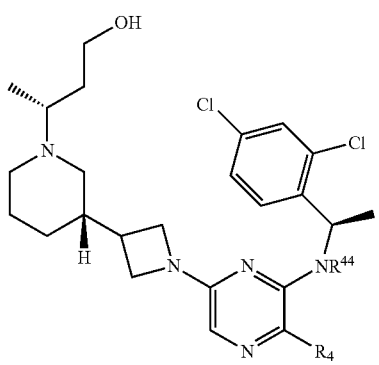
TABLE 2-continued
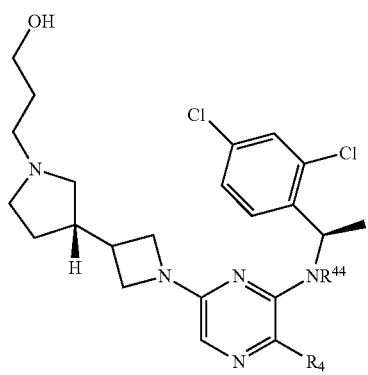
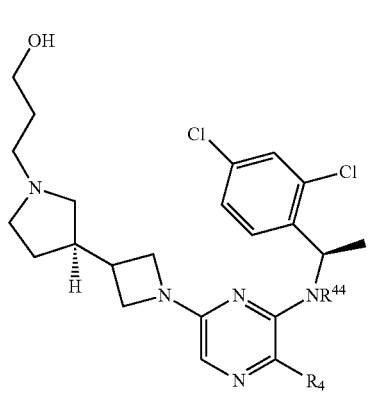
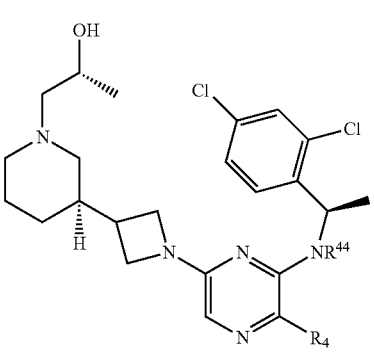
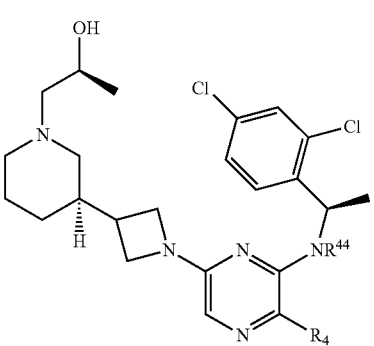

TABLE 2-continued

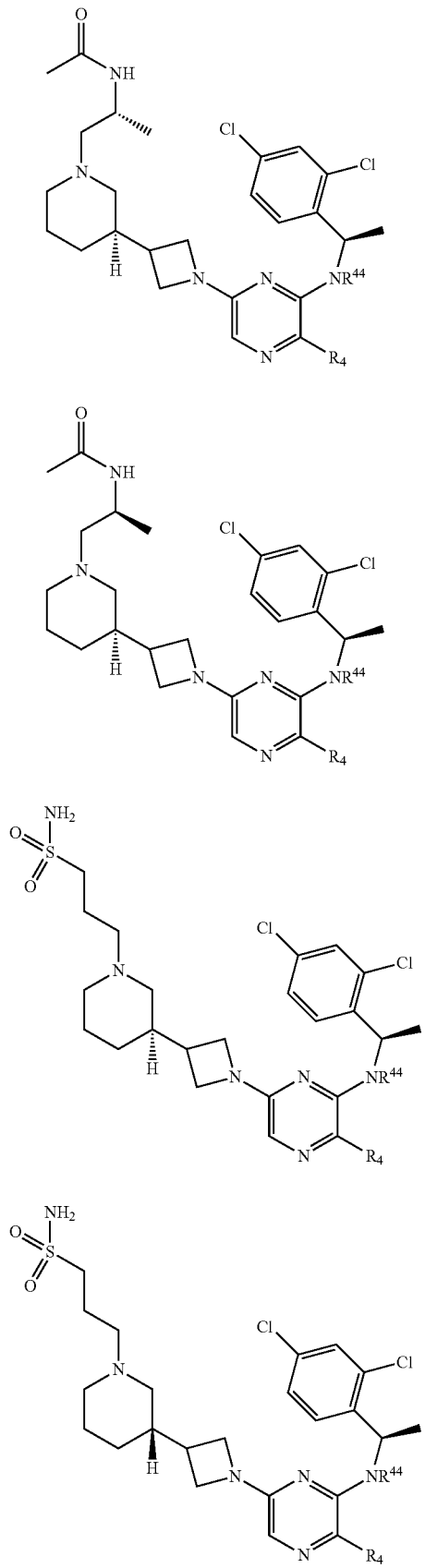

TABLE 2-continued

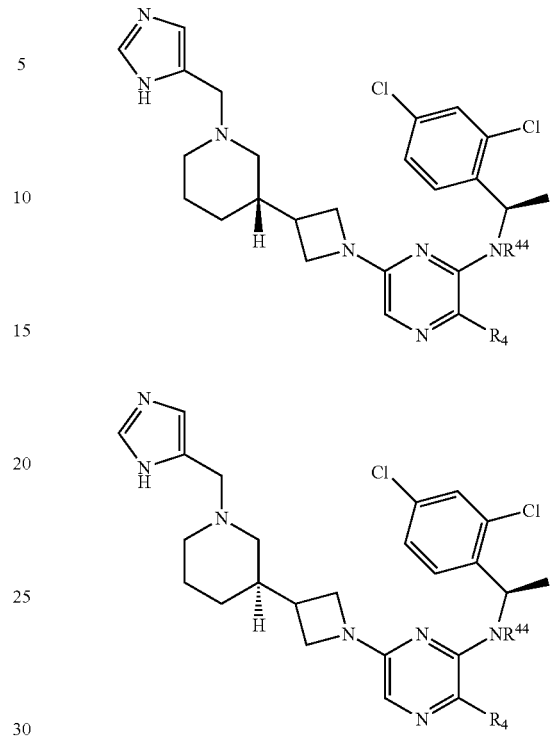

In certain embodiments, the Table 2 compounds have $R^4$ selected from hydrogen, halide, and substituted or unsubstituted alkyl. In embodiments, the Table 2 compounds have $R^{44}$ selected from hydrogen, and substituted or unsubstituted alkyl. In embodiments, the Table 2 compounds have $R^{44}$ as hydrogen and $R^4$ selected from halide, and substituted or unsubstituted $C_{1-4}$ alkyl. In embodiments, the Table 2 compounds have $R^{44}$ as hydrogen and $R^4$ selected from hydrogen, —CN, halogen, —CF$_3$, —COOH, —COOCH$_2$CH$_3$,

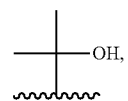

and —CH$_3$.

In embodiments, the compound has the formula:

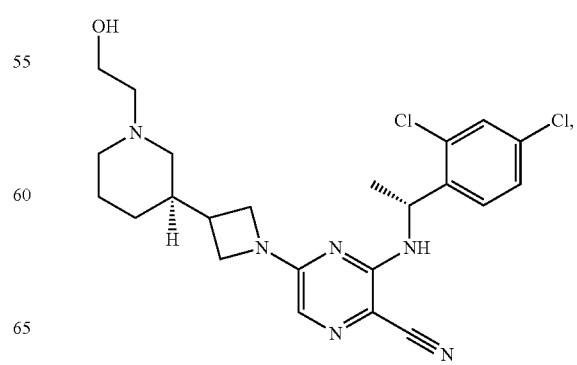

213
-continued
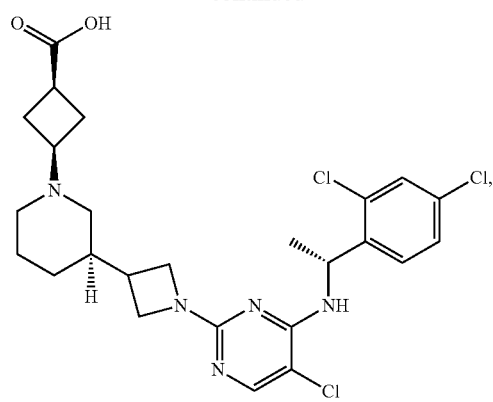
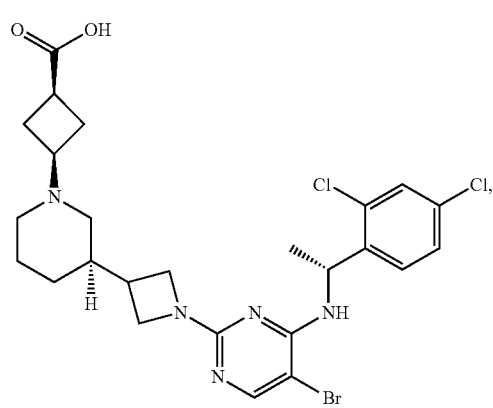
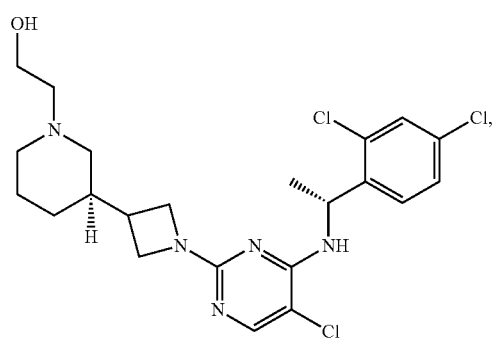
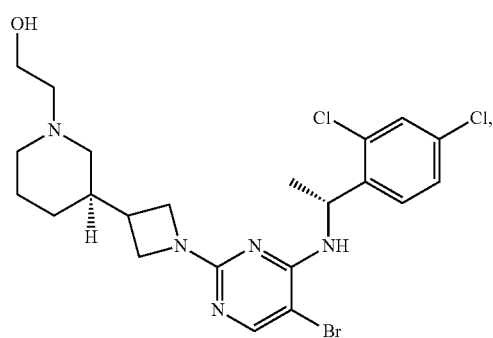
214
-continued
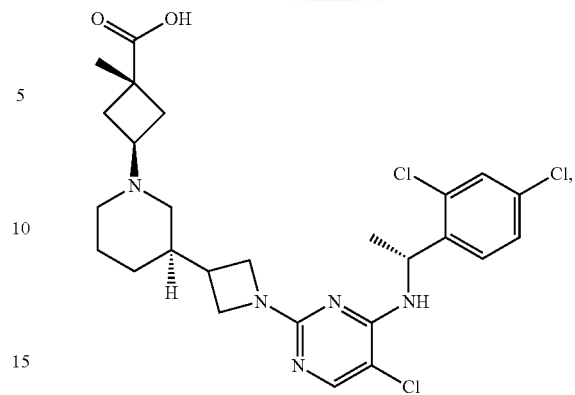
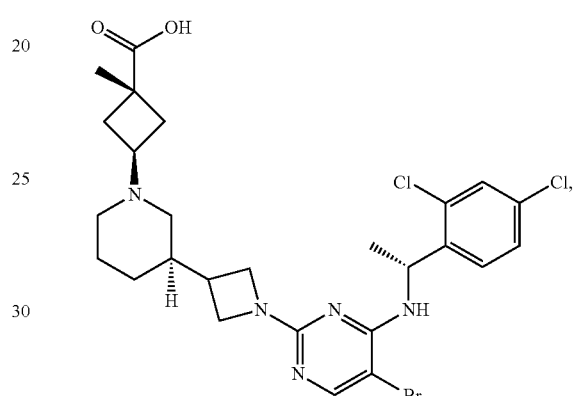
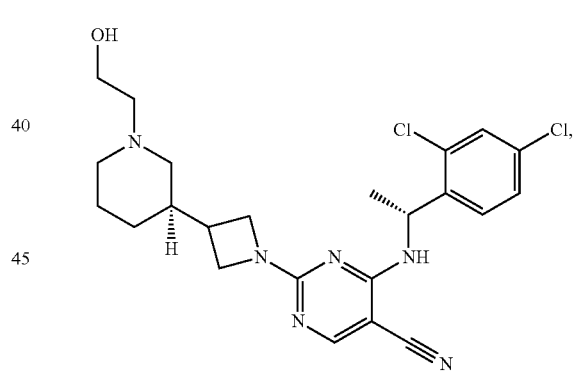
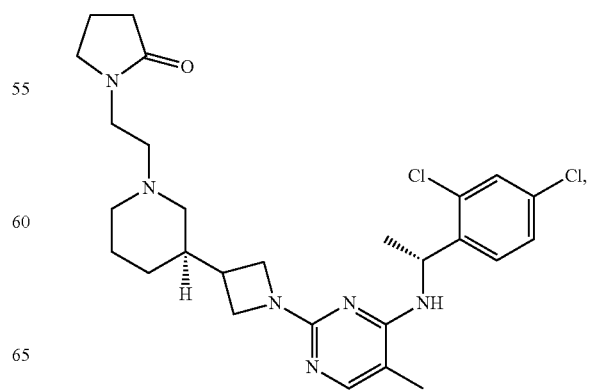

215
-continued
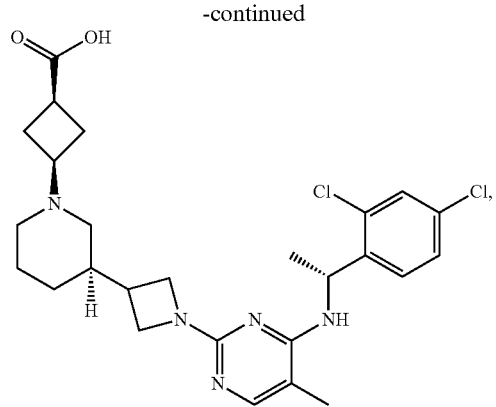
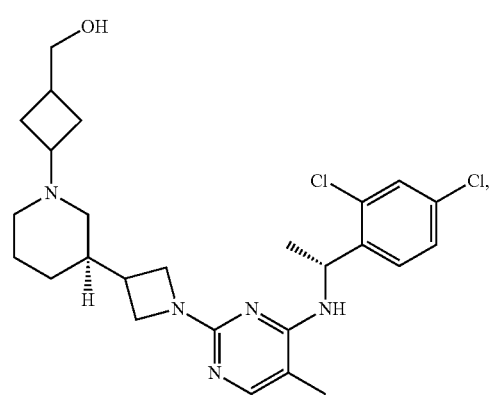
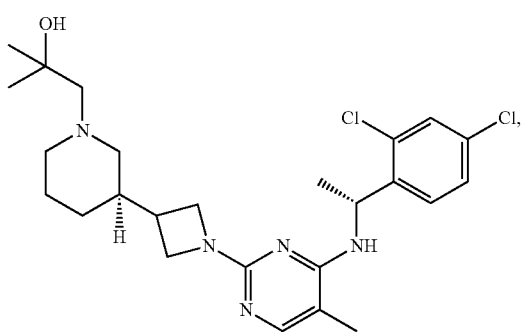
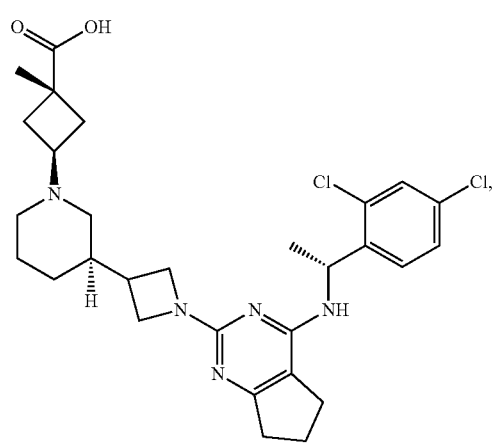
216
-continued
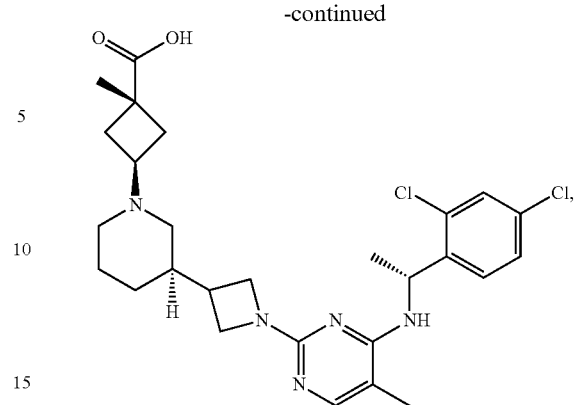
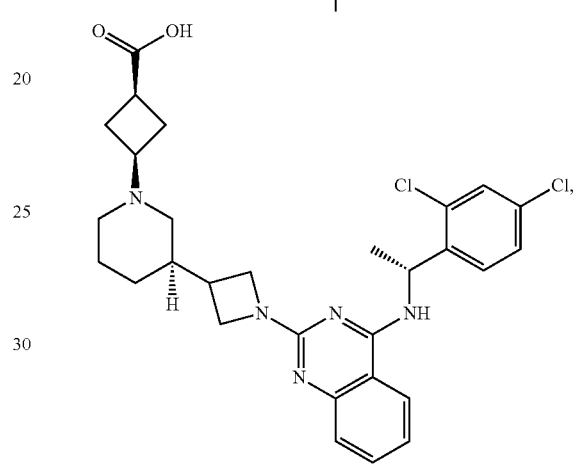
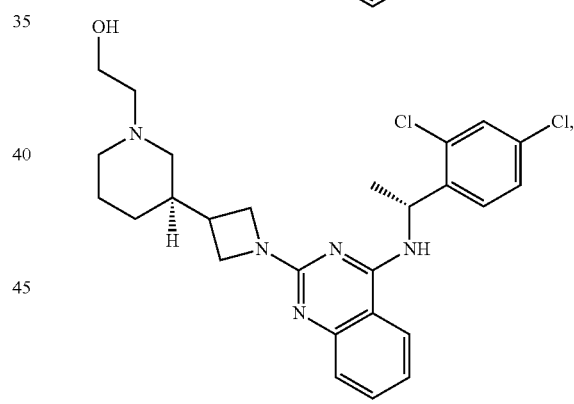
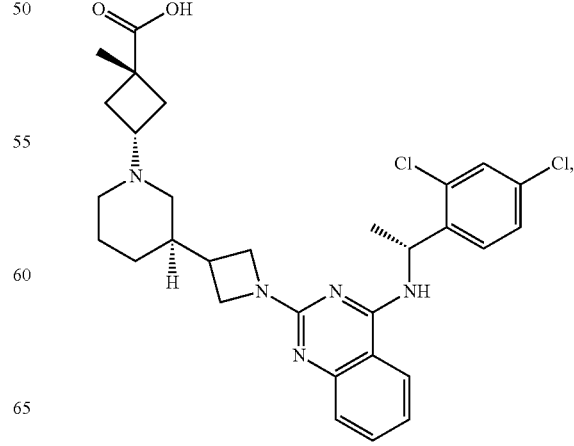

217
-continued
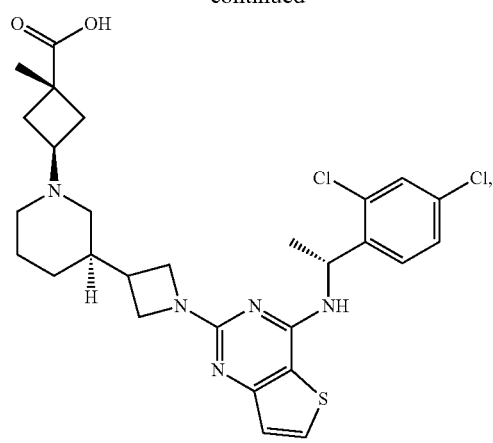
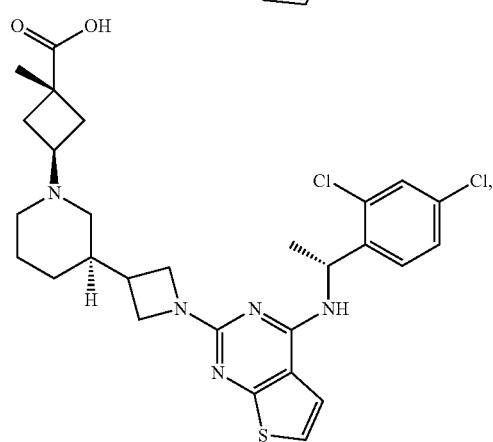
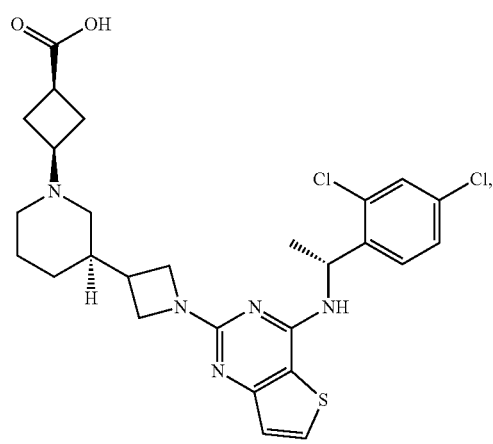
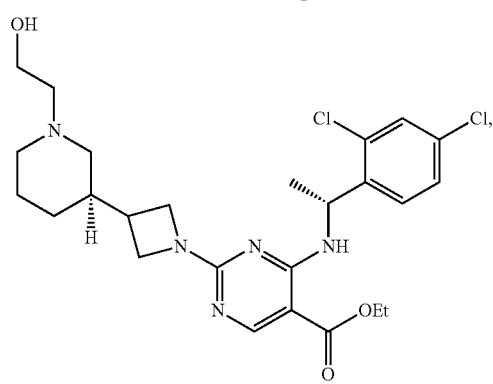
218
-continued
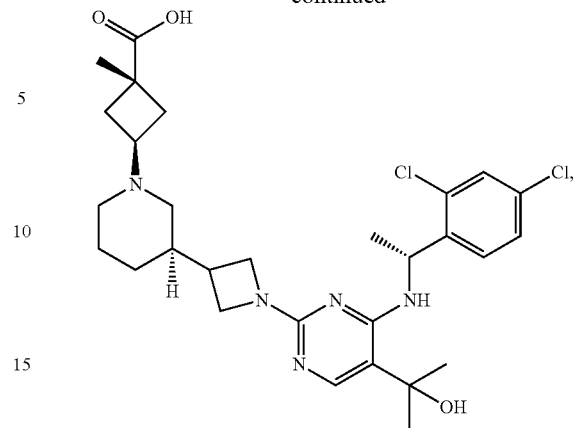
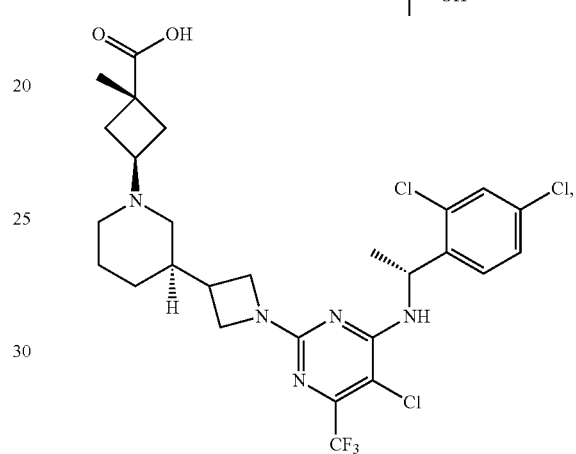
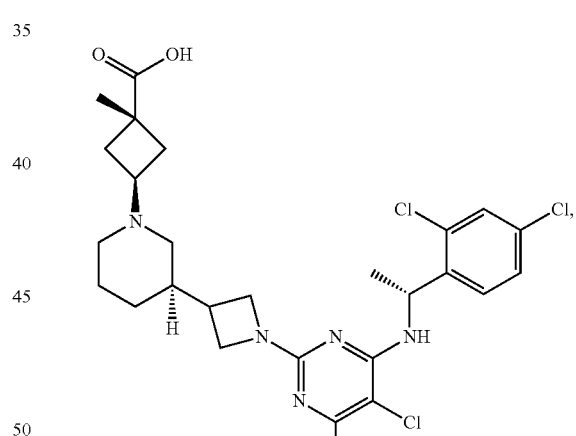
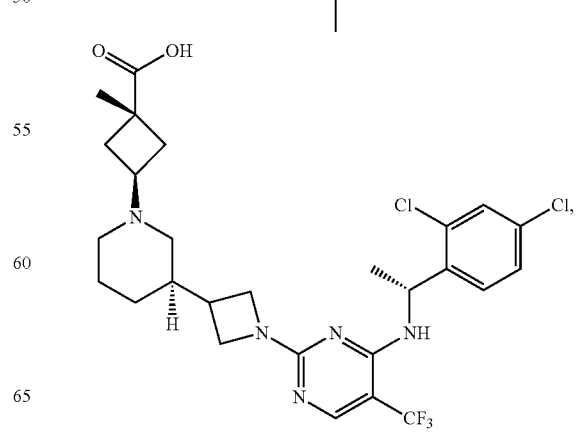

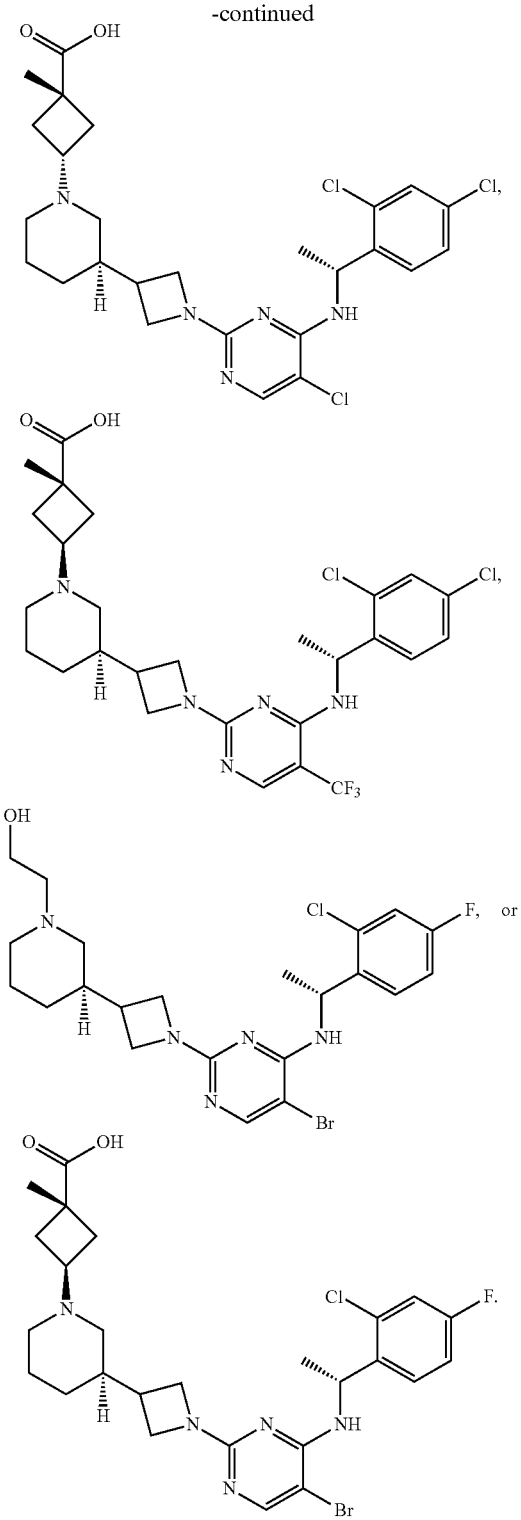

In some embodiments, a compound as described herein may include multiple instances of a substituent (e.g., $R^3$, $R^5$, or $R^6$ and/or other variables). In such embodiments, each variable may optional be different and be appropriately labeled to distinguish each group for greater clarity. For example, where each $R^3$, $R^5$, $R^6$ is different, they may be referred to, for example, as $R^{3.1}$, $R^{3.2}$, $R^{3.3}$, $R^{3.4}$, $R^{3.5}$, $R^{5.1}$, $R^{5.2}$, $R^{5.3}$, $R^{5.4}$, or $R^{6.1}$, $R^{6.2}$, $R^{6.3}$, $R^{6.4}$, $R^{6.5}$, $R^{6.6}$, $R^{6.7}$, $R^{6.8}$, $R^{6.9}$, or $R^{6.10}$, respectively, wherein the definition of $R^3$ is assumed by (independently assigned to) $R^{3.1}$, $R^{3.2}$, $R^{3.3}$, $R^{3.4}$, $R^{3.5}$; $R^5$ is assumed by (independently assigned to) $R^{5.1}$, $R^{5.2}$, $R^{5.3}$, $R^{5.4}$; or $R^6$ is assumed by (independently assigned to) $R^{6.1}$, $R^{6.2}$, $R^{6.3}$, $R^{6.4}$, $R^{6.5}$, $R^{6.6}$, $R^{6.7}$, $R^{6.8}$, $R^{6.9}$, or $R^{6.10}$. The variables used within a definition of $R^3$, $R^5$, or $R^6$, and/or other variables that appear at multiple instances and are different may similarly be appropriately labeled to distinguish each group for greater clarity.

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer. In embodiments, the compound is a compound described herein (e.g., in an aspect, embodiment, example, figure, table, scheme, or claim).

III. Pharmaceutical Compositions

In an aspect is provided a pharmaceutical composition, including a compound as described herein, including embodiments (e.g., structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII)) and a pharmaceutically acceptable excipient.

The compounds described herein (e.g., CCR4 inhibitors) may be in the form of compositions suitable for administration to a subject. In general, such compositions are "pharmaceutical compositions" including a compound (e.g., CCR4 inhibitor(s)) and one or more pharmaceutically acceptable or physiologically acceptable diluents, carriers or excipients. In embodiments, the compound described herein (e.g., CCR4 inhibitor) is present in a therapeutically acceptable amount. The pharmaceutical compositions may be used in the methods described herein. For example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein.

The pharmaceutical compositions containing the active ingredient (e.g., an inhibitor of CCR4 function, compound described herein) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions may include a therapeutically effective amount of a CCR4 inhibitor described herein and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a CCR4 inhibitor (e.g., compound described herein), including implants (e.g., implantable pumps) and catheter systems, slow injection pumps and devices, all of which are well known to the skilled artisan.

Depot injections, which are generally administered subcutaneously or intramuscularly, may also be utilized to release the compound (e.g., CCR4 inhibitor) disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor© EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present invention contemplates the administration of a compound described herein (e.g., CCR4 inhibitor) in the form of suppositories for rectal administration. The suppositories can be prepared by mixing the drug with a suitable non-irritating excipient, which is solid at ordinary temperatures but liquid at the rectal temperature and will therefore melt in the rectum to release the drug. Such materials include, but are not limited to, cocoa butter and polyethylene glycols.

The compounds (e.g., CCR4 inhibitor) described herein may be in the form of any other suitable pharmaceutical composition (e.g., sprays for nasal or inhalation use) currently known or developed in the future.

IV. Methods of Use

In another aspect is provided a method of inhibiting C—C chemokine receptor type 4 (CCR4), the method including contacting CCR4 with a compound as described herein, including embodiments, (e.g., structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII)) or a pharmaceutically acceptable salt thereof.

In an aspect, is provided a method of treating or preventing a disease or disorder mediated by CCR4, including administering to a subject in need thereof a therapeutically effective amount of a compound as described herein, including embodiments, (e.g., structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII)) or a pharmaceutically acceptable salt thereof.

In embodiments, the method includes administering a therapeutically effective amount of a compound as described herein, including embodiments, (e.g., the structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII)) or a pharmaceutically acceptable salt thereof.

In embodiments, the disease or disorder is an immune or inflammatory disease or disorder. In embodiments, the methods of treating an immune or inflammatory disease or disorder disclosed herein further include co-administering an anti-inflammatory agent in combination with a compound described herein (e.g., of structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII), or a pharmaceutically acceptable salt thereof). In embodiments, the anti-inflammatory is thalidomide or a derivative thereof, a retinoid, dithranol or calcipotriol, a non-steroidal anti-inflammatory agent (NSAID), cyclo-oxygenase inhibiting nitric oxide donor (CINOD), glucocorticosteroid, methotrexate, leflunomide, hydroxychloroquine, d-penicillamine, auranofin, analgesic; diacerein, hyaluronic acid derivative or nutritional supplement.

In embodiments, the disease or disorder is traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, transplant rejection, interstitial cystitis, atherosclerosis, or atopic dermatitis.

In embodiments, the disease or disorder is a cardiovascular or metabolic disease or disorder. In embodiments, the methods of treating a cardiovascular or metabolic disease or disorder disclosed herein further include co-administering a cardiovascular agent or a metabolic disorder agent in combination with a compound described herein (e.g., of structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII), or a pharmaceutically acceptable salt thereof). In embodiments, the cardiovascular agent is a calcium channel blocker, a beta-adrenoceptor blocker, an angiotensin-converting enzyme (ACE) inhibitor, an angiotensin-2 receptor antagonist, a lipid lowering agent, a modulator of blood cell morphology, a thrombolytic or an anticoagulant.

In embodiments, the disease or disorder is cancer. In embodiments, the methods of treating cancer disclosed herein further include co-administering a chemotherapeutic agent or anticancer agent in combination with a compound described herein (e.g., of structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII), or a pharmaceutically acceptable salt thereof). In embodiments, the chemotherapeutic agent or anticancer agent is an antiproliferative/antineoplastic drug, an antimetabolite, an antitumour antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5α-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras antisense, an agent used in a gene therapy, an immunotherapeutic agent, or an antibody. In embodiments, the methods of treating cancer disclosed herein further include co-administering a chemotherapeutic agent or anticancer agent in combination with a compound described herein (e.g., of structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII), or a pharmaceutically acceptable salt thereof) and a therapeutically effective amount of at least two of: a CCR4 inhibitor, an inhibitor of the PD-L1/PD-1 pathway, an inhibitor of CTLA-4 or an agonistic antibody of CD137 (4-1BB). In embodiments, the methods of treating cancer disclosed herein further include co-administering a chemotherapeutic agent or anticancer agent in combination with a compound described herein (e.g., of structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII), or a pharmaceutically acceptable salt thereof) and a therapeutically effective amount of at least two of: a CCR4 inhibitor, an immune modulator agent, or an agent from Table 1, or any combination thereof.

In embodiments, the disease or disorder is inflammatory bowel disease. In embodiments, the disease or disorder is rheumatoid arthritis. In embodiments, the disease or disorder is psoriasis. In embodiments, the disease or disorder includes allergy-related disorders (e.g., hypersensitivity and anaphylactic responses); gastrointestinal disorders (e.g., Crohn's disease, ulcerative colitis, ileitis and enteritis); psoriasis and inflammatory dermatoses (e.g., dermatitis, eczema, atopic dermatitis, allergic contact dermatitis, dermatomyositis, urticaria and pruritus); vasculitis; scleroderma; asthma, COPD, and respiratory allergic diseases (e.g., allergic rhinitis and hypersensitivity lung diseases); autoimmune diseases, including arthritis (e.g., rheumatoid and psoriatic), multiple sclerosis, systemic lupus erythematosus, type I diabetes and glomerulonephritis; graft rejection (e.g., allograft rejection); transplant rejection (e.g., solid organ); cancers, such as leukemias, lymphomas and metastatic cancers, particularly solid tumors (e.g., gastric cancers); and other diseases in which inhibition of undesired inflammatory and/or immune responses is desired, such as atherosclerosis, neurodegenerative diseases (e.g., Alzheimer's disease), encephalitis, meningitis, hepatitis, nephritis, sepsis, sarcoidosis, allergic conjunctivitis, otitis, and sinusitis. In particular embodiments, the CCR4-mediated disease, disorder or condition is asthma, COPD, rhinitis, idiopathic pulmonary fibrosis, psoriasis and contact dermatitis. In embodiments the disease or disorder is including pulmonary fibrosis, hepatic inflammation, asthma, atopic dermatitis, cancer (e.g., thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma), or granuloma development.

In embodiments, the method further includes administering a therapeutically effective amount of a compound as described herein, including embodiments (e.g., the structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII)) or a pharmaceutically acceptable salt thereof.

In embodiments, the administration of the compounds disclosed herein for the treatment or prevention of immune-, inflammatory-, or cancer-related diseases, disorders and conditions. Such diseases, disorders and conditions are described in detail elsewhere, as are other maladies that may be treated or prevented with compounds (e.g., CCR4 inhibitor) described herein.

It is frequently beneficial to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity. Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

In embodiments, compounds of the present invention are effective in the treatment and prevention of IBD (e.g., Crohn's disease and ulcerative colitis, both of which are chronic idiopathic diseases that can affect any part of the gastrointestinal tract, and are associated with many untoward effects, and patients with prolonged ulcerative colitis are at an increased risk of developing colon cancer). Current IBD treatments are aimed at controlling inflammatory symptoms, and while certain agents (e.g., corticosteroids, aminosalicylates and standard immunosuppressive agents (e.g., cyclosporine, azathioprine, and methotrexate)) have met with limited success, long-term therapy may cause liver damage (e.g., fibrosis or cirrhosis) and bone marrow suppression, and patients often become refractory to such treatments.

The compounds described herein can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The compounds described herein can also be used to stimulate the immune system of patients suffering from iatrogenically-induced immune suppression, including those who have undergone bone marrow transplants, chemotherapy, or radiotherapy.

In accordance with the present invention, a compound or pharmaceutical salt thereof can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). In embodiments are methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. In embodiments is included reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In some embodiments, the tumor or cancer is colon cancer, ovarian cancer, breast cancer, melanoma, lung cancer, glioblastoma, or leukemia. In particular embodiments, the cancer is gastric cancer. The use of the term(s) cancer-related diseases, disorders and conditions is meant to refer broadly to conditions that are associated, directly or indirectly, with cancer, and includes, e.g., angiogenesis and precancerous conditions such as dysplasia. In embodiments, the cancer is thyroid carcinoma, cholangiocarcinoma, pancreatic cancer, pancreatic adenocarcinoma, skin cutaneous melanoma, colon cancer, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma.

In embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, are methods for treating a proliferative condition, cancer, tumor, or precancerous condition with a compound described herein and at least one additional therapeutic or diagnostic agent, examples of which are set forth elsewhere herein.

In an aspect is provided methods for treating and/or preventing a proliferative condition, cancer, tumor, or precancerous disease, disorder or condition with a compound described herein.

In embodiments drawn to methods of treating cancer, the administration of a therapeutically effective amount of a compound described herein results in a cancer survival rate greater than the cancer survival rate observed by administering either agent alone. In further embodiments drawn to methods of treating cancer, the administration of a therapeutically effective amount of a compound described herein (e.g., CCR4 inhibitor) results in a reduction of tumor size or a slowing of tumor growth greater than reduction of tumor size or tumor growth observed following administration of either agent alone. In embodiments, the methods of treating cancer disclosed herein further include administering a chemotherapeutic agent or anticancer agent in combination with a compound described herein (e.g., of structural Formula (I), (II), (IIa), (IIb), (IIc), (IIc-1), (IIc-2), (IIc-3), (IId), (IId-1), (IId-2), (IId-3), (IId-4), (IId-5), (IId-6), (IId-7), (IId-8), (IId-9), (III), (III-1), (IV), (V), (VI), or (VII)), or a pharmaceutically acceptable salt thereof. In embodiments, the chemotherapeutic agent or anticancer agent is an anti-proliferative/antineoplastic drug, an antimetabolite, an anti-tumour antibiotic, an antimitotic agent, a topoisomerase inhibitor, a cytostatic agent, an oestrogen receptor down regulator, an antiandrogen, a LHRH antagonist or LHRH agonist, a progestogen, an aromatase inhibitor, an inhibitor of 5α-reductase, an agent which inhibits cancer cell invasion, an inhibitor of growth factor function, a farnesyl transferase inhibitor, a tyrosine kinase inhibitor, a serine/threonine kinase inhibitor, an inhibitor of the epidermal growth factor family, an inhibitor of the platelet-derived growth factor family, an inhibitor of the hepatocyte growth factor family; an antiangiogenic agent, a vascular damaging agent, an agent used in antisense therapy, an anti-ras anti-sense, an agent used in a gene therapy, an immunotherapeutic agent, or an antibody. In embodiments, the methods of treating cancer disclosed herein further include co-administering a therapeutically effective amount of at least two of: a CCR4 inhibitor, an inhibitor of the PD-L1/PD-1 pathway, an inhibitor of CTLA-4 or an agonistic antibody of CD137 (4-1BB). In embodiments, the methods of treating cancer disclosed herein further include co-administering a therapeutically effective amount of at least two of: a CCR4 inhibitor, an agent that may be an immune modulator or an agent from Table 1.

Inhibition of CCR4 activity may also represent an important strategy for the treatment or prevention of neurological, neuropsychiatric, neurodegenerative or other diseases, disorders and conditions having some association with the central nervous system, including disorders associated with impairment of cognitive function and/or motor function. Many of these diseases, disorders and conditions comprise an immune and/or inflammatory component. In embodiments, the disease or disorder is Parkinson's disease, extra pyramidal syndrome (EPS), dystonia, akathisia, tardive dyskinesia, restless leg syndrome, epilepsy, periodic limb movement in sleep, attention deficit disorders, depression, anxiety, dementia, Alzheimer's disease, Huntington's disease, multiple sclerosis, cerebral ischemia, hemorrhagic stroke, subarachnoid hemorrhage, or traumatic brain injury.

Embodiments of the present invention contemplate the administration of the compounds described herein to a subject for the treatment or prevention of any other disorder that may benefit from at least some level of CCR4 modulation. Such diseases, disorders and conditions may include, for example, asthma, chronic obstructive pulmonary disease (COPD) including chronic bronchitis and emphysema, idiopathic pulmonary fibrosis, atopic or contact dermatitis, urticaria, allergic rhinitis, nasal polyps, allergic conjunctivitis, thrombosis, reperfusion injury of the myocardium and brain, chronic glomerulonephritis, sepsis, adult respiratory distress syndrome, and pain. Additional diseases, disorders and conditions include allergic bronchopulmonary aspergillosis, allergic fungal sinusitis, severe asthma with fungal sensitization and diseases involving a pathogenic role for fungi including invasion or colonization (such as invasive aspergillosis, aspergilloma or candidiasis).

In embodiments, the disease or disorder includes cardiovascular (e.g., cardiac ischemia), metabolic (e.g., development of insulititis diabetes), hepatic (e.g., hepatic fibrosis, NASH, and NAFLD), ophthalmologic (e.g., diabetic retinopathy), and renal (e.g., renal failure) disorders.

Described herein is the administration of the compounds described herein, and compositions (e.g., pharmaceutical salts, pharmaceutical composition) thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the compounds disclosed herein over a defined period of time. In embodiments, the administration is oral administration.

In an aspect provided are methods for treating and/or preventing certain cardiovascular- and/or metabolic-related diseases, disorders and conditions, as well as disorders associated therewith, with a compound described herein.

The compounds of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the compounds of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the compounds described herein may be administered (e.g., orally) at dosage levels of about 0.01 mg/kg to about 50 mg/kg, or about 1 mg/kg to about 25 mg/kg, of subject body weight per day, one, two, three, four or more times a day, to obtain the desired therapeutic effect.

For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. A pharmaceutically acceptable carrier(s), diluent(s) and/or excipient(s) may be present in an amount of from about 0.1 g to about 2.0 g.

In embodiments, the dosage of the desired compound is contained in a "unit dosage form". The phrase "unit dosage form" refers to physically discrete units, each unit including a predetermined amount of the compound (e.g., CCR4 inhibitor), sufficient to produce the desired effect. It will be appreciated that the parameters of a unit dosage form will depend on the particular agent and the effect to be achieved.

V. Kits

In an aspect, provided herein is a kit including a compound described herein (e.g., a CCR4 inhibitor) or pharmaceutical compositions thereof. The kits may be in the form of a physical structure housing various components, as described below, and may be utilized, for example, in practicing the methods described above.

A kit may include one or more of the compounds disclosed herein (e.g., provided in a sterile container), which may be in the form of a pharmaceutical composition suitable for administration to a subject. The compounds described herein (e.g., CCR4 inhibitors) can be provided in a form that is ready for use (e.g., a tablet or capsule) or in a form requiring, for example, reconstitution or dilution (e.g., a powder) prior to administration. When the compound (e.g., CCR4 inhibitor) is in a form that needs to be reconstituted or diluted by a user, the kit may also include diluents (e.g., sterile water), buffers, pharmaceutically acceptable excipients, and the like, packaged with, or separately from, the compound. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The successful operation of the host defense system is the result of several processes that work together to eliminate foreign pathogens. Coordinated innate and acquired immune responses are required, and many secreted and cell-associated factors have been identified as important mediators coordinating and regulating these two arms of host defense (see, e.g., Ness, T. et al. (2006) J Immunol 177:7531-39).

Chemokines are a family of cytokines that act as chemoattractants to guide leukocyte migration. They are secreted by a wide variety of cells and can be functionally divided into two groups, hemostatic chemokines and inflammatory chemokines. Hemostatic chemokines are constituently produced in certain tissues and control cells of the immune system during processes of immune surveillance, such as directing lymphocytes to the lymph nodes to allow them to screen for invasion of pathogens. Inflammatory chemokines are released from cells in response to a pathological event (e.g., pro-inflammatory stimuli such as IL-1 or viruses). They function primarily as chemoattractants as part of the inflammatory response and serve to guide cells of both the innate and adaptive immune systems to the site of inflammation. [See, e.g., Le, Y. et al. (2004) Cellular & Molec Immuno 1(2):95-104.]

Structurally, there are four subgroups of chemokines, classified according to the spacing of the first two cysteine residues: i) CC chemokines (β-chemokines) have adjacent cysteines; ii) CXC chemokines (α-chemokines) having a single amino acid residue between the first two cysteines; iii) C chemokines (γ-chemokines) have only a single N-terminal cysteine residue; and iv) $CX_3C$ chemokines (δ-chemokines) having three amino acid residues between the first two cysteines. CC chemokines, examples of which include monocyte chemoattractant protein-1 (MCP-1 or CCL2) and CCL5 (RANTES), induce the migration of monocytes and other cell types; at least 27 members have been identified. CXC chemokines (some 17 in number) can be subdivided into two groups, both of which have unique structural and functional features; the CXC chemokines bind to CXC chemokine receptors, of which 7 are known (designated CXCR1-7). Only two members of the C chemokine subgroup have been identified, XCL1 and XCL2 (lymphotactin-α and -β, respectively). Finally, the $CX_3C$ chemokine subgroup has only one member, $CX_3CL1$, which is both secreted and associated with the surface of the cells that express it, resulting in both chemoattractant and adhesion properties. [See Sokol, C. and Luster, A. (2015) Cold Spring Harb Prospect Biol doi: 10.1101/cshperspect.a016303.]

Chemokines bind to specific G protein-coupled receptors ("chemokine receptors"), which are characterized by containing seven transmembrane domains, found on the surface of leukocytes (see Horuk (1994) Trends Pharm. Sci. 15:159-165). Approximately 20 human chemokine receptors have been identified, which are divided into four subgroups depending on the type of chemokine they bind: CXCR bind CXC chemokines; CCR bind CC chemokines; CX3CR1 binds CX3CL1, the sole CXC3 chemokine; and XCR1 binds XCL1 and XCL2, the two XC chemokines. Binding of a chemokine ligand to its cognate receptor triggers the receptor, resulting in dissociation of an intracellular heterotrimeric G-protein complex into Gα and Gβγ subunits. These second messengers play an integral role in the activation of several signaling cascades (e.g., the MAP kinase pathway), resulting in responses that include chemotaxis, inflammatory mediator release, degranulation, and changes in cell shape. Chemokine receptors have been implicated as being important mediators of inflammatory and immunoregulatory disorders and diseases, including asthma and allergic diseases, as well as autoimmune pathologies such as rheumatoid arthritis and atherosclerosis. [See, e.g., Comerford, I. and McColl, S. (2011) Immunol Cell Biol 89:183-84.]

The C—C chemokine receptor type 4 (CCR4), first identified by Power et al. (J. Biol. Chem. 270:19495-500 (1995)), plays a vital role in the progression of a number of inflammation-related and other disorders (Gadhe, CG (February 2015) Mol Biosyst 11(2):618-34). CCR4 is a high affinity receptor for the C—C-type chemokines CCL2 (MCP-1), CCL4 (MIP-1), CCL5 (RANTES), CCL17 (TARC), and CCL22 (MDC). Increased expression of CCR4 and its ligands is associated with the pathogenesis of a diverse array of diseases, including pulmonary fibrosis, hepatic inflammation, granuloma development, certain cancers and diabetes, each of which is characterized by the infiltration of $CCR4^+$ T cells into affected sites. The identification of compounds that modulate CCR4 function provides an opportunity for the development of therapeutic agents for the treatment of a diverse array of diseases and disorders associated with CCR4 activation.

The present invention relates to compounds that inhibit C—C chemokine receptor type 4 (CCR4) activity, and compositions (e.g., pharmaceutical compositions) comprising the compounds. Such compounds, including methods of their synthesis, and compositions are described in detail herein. The present invention also relates to the use of such compounds and compositions for the treatment and/or prevention of diseases, disorders and conditions mediated, in whole or in part, by CCR4.

Many subjects suffer from the debilitating effects of inflammatory- and/or immune-related disorders such as asthma and rheumatoid arthritis. Recently generated data support the role of inhibitors of CCR4 function to modulate such inflammatory- and/or immune-related activity in a therapeutically beneficial manner. In addition, subjects diagnosed with cancer and the number of deaths attributable to cancer continue to rise, both in the US and abroad. Traditional treatment approaches comprising chemotherapy and radiotherapy are generally difficult for the patient to tolerate and become less effective as cancers (e.g., tumors) evolve to circumvent such treatments.

Identification of CCR4 Inhibitors

In embodiments, compounds described herein possess at least one property or characteristic that is of therapeutic relevance. Candidate inhibitors may be identified by using, for example, an art-accepted assay or model. The Example section described assay(s) that were used to determine the CCR4 inhibitory activity of the compounds described herein, as well as assays that could be used to evaluate one or more characteristics of the compounds; the skilled artisan is aware of other procedures, assay formats, and the like that can be employed to generate data and information useful to assess the CCR4 inhibitors described herein.

After identification, candidate inhibitors can be further evaluated by using techniques that provide data regarding characteristics of the inhibitors (e.g., pharmacokinetic parameters). Comparisons of the candidate inhibitors to a reference standard (which may the "best-of-class" of current inhibitors) are indicative of the potential viability of such candidates. CCR4 inhibitors that can serve as reference or benchmark compounds include those shown to demonstrate desired activity and characteristics as described in, for example, US Patent Publn 2012/0015932 and PCT Publication 2013/082490. Other means of analyzing candidate inhibitors will be apparent to the skilled artisan.

Synthesis Details

The following general schemes represent synthetic methods that may be used in the preparation of the compounds described herein, as well as common chemical intermediates generated in the preparation thereof. The skilled artisan will recognize that these schemes are representative only, and that in many instances alternative synthetic means may be employed.

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; g=microgram; mg=milligram; g=gram; kg=kilogram; dl or dL=deciliter; µl or µL=microliter; ml or mL=milliliter; l or L=liter; µM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; psi=pounds per square inch; HPLC=high performance liquid chromatography; BW=body weight; U=unit; ns=not statistically significant; HATU=(1-[Bis(dimethylamino)methylene]-1H-1,2,3-triazolo[4,5-b]pyridinium 3-oxid hexafluorophosphate); TFA=trifluoroacetic acid; MBTE=methyl t-butyl ether; DCM=dichloromethane; PBS=phosphate-buffered saline; IHC=immunohistochemistry; DMSO=dimethylsulfoxide; EtOAc=ethyl acetate; EtOH=ethanol; DMEM=Dulbeco's Modification of Eagle's Medium; EDTA=ethylenediaminetetraacetic acid; Me=methyl; Et=ethyl; S—singlet; D—doublet; dd—doublet of doublet; m—multiplet.

General Synthetic Schemes

General preparation of the aminopyrimidine ($X^2$=C, $X^3$=N) or aminopyrazine ($X^2$=N, $X^3$=C)

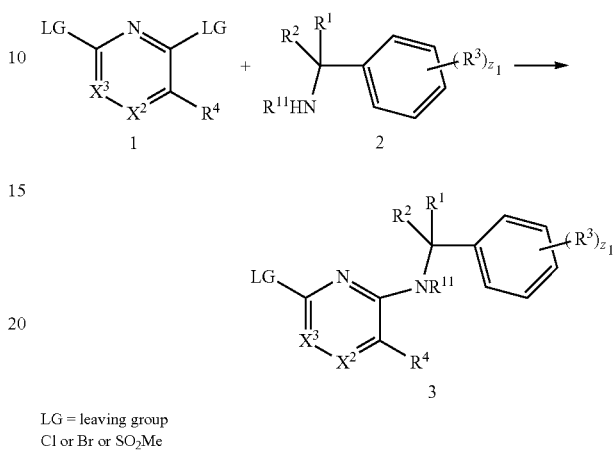

LG = leaving group
Cl or Br or $SO_2Me$

To a solution of compounds of a heterocycle of general structure 1 and benzylic amine 2 in a solution such as acetonitrile or DMF is added a base such as triethyl amine and the reaction is stirred for 12-36 hours at a temperature between room temperature and 120 C. The solvent is removed under reduced pressure and the residue is purified by silica gel chromatography using a mixture of organic solvents that may include hexanes, ethyl acetate or dichloromethane to give target compound 3.

General synthesis of diaminopyrimidine ($X^2$=$CR^9$, $X^3$=N) or diaminopyrazine ($X^2$=N, $X^3$=$CR^{10}$):

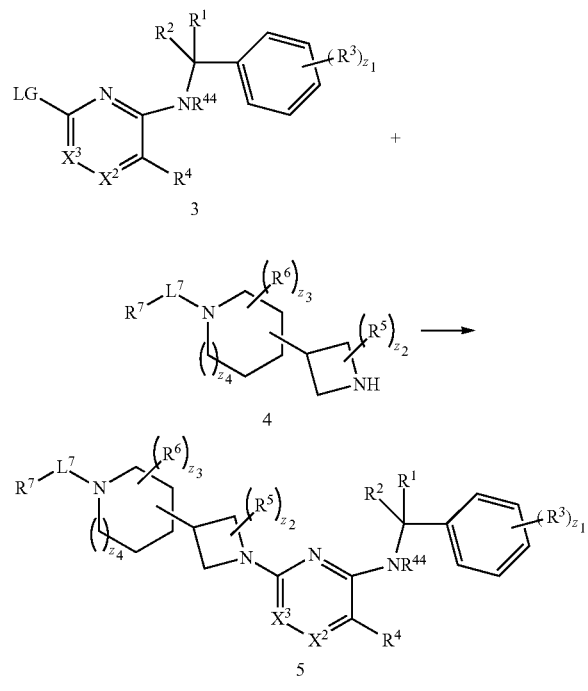

LG = leaving group
Cl or Br or $SO_2Me$

To a solution of an amino heterocyclic compound of a general structure 3 and an azetidine of general structure 4 in an organic solvent such as a DMSO is added a base such as diisopropyl ethyl amine cesium fluoride. The reaction mixture is heated in a seaed tube between approximately 100° C. for 4-24 hours. The reaction mixture is partitioned between water and an organic solvent such as ethyl acetate and the organic layer is dried with sodium sulfate, filtered and concentrated in vacuo. The resulting residue can be purified either by silica gel chromatography using a mixture of solvents that can include hexanes, ethyl aceate, dichloro methane or methanol or by using reversed phase HPLC methods.

Alternatively, a solution of an amino heterocyclic compound of a general structure 3 and an azetidine of general structure 4 in an organic solvent such as a mixture of 1,2-dimethoxyethane and tert-butanol is sarged with argon and is treated with an organometallic catalyst such as $Pd_2dba_3$ a ligand such as BINAP and a base such as potassium tert-butoxide and heated to a temperature of approximately 100° C. to 4-24 hours. The mixture was then cooled to room temperature, filtered through a plug of sand with EtOAc and further with 20% MeOH in dichloromethane and all volatiles were then removed in vacuo. The resulting residue can be purified wither by silica gel chromatography using a mixture of solvents that can include hexanes, ethyl acetate, dichloro methane or methanol or by using reversed phase HPLC methods.

General Synthesis of Azetidine Derivatives:

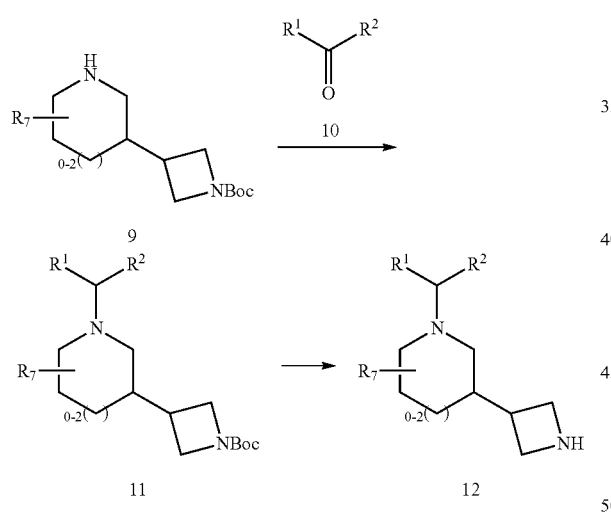

To a solution of the protected ketone of general structure 10 in an organic solvent such as dichloroethane is added amine 9 and an imine reducing agent such as sodium triacetoxyborohydride and the mixture is stirred for between 4 and 18 h. The reaction is treated with a weak aqueous base such as aqueous sodium carbonate and the mixture is extracted with an organic solvent such as ethyl acetate. The organic solvent is separated, treated with a drying agent such as sodium sulfate and the dried solution is evaporated to give amine of general structure 11. The protective group on compound of general structure 11 can be exposed to an acidic organic solution, for example HCl in dioxane or trifluoroacetic acid in DCM or can be removed using catalytic Pd. The mixture is stirred at room temperature for a time between one and 16 h. The reaction mixture can be concentrated or filtered through a celite pad and then concentrated under reduced pressure to give an amine salt of the general structure 12 that can be used in subsequent reactions without further purification.

Alternatively the piperidine 9 can be reacted with an alkyl halide optionally in the presence sodium iodide, in the presence of a base such as sodium carbonate in a solvent such as DMF. After stirring between 4 and 18 h, the reaction is diluted with water, and the mixture is extracted with an organic solvent such as ethyl acetate. The organic solvent is separated, treated with a drying agent such as sodium sulfate and the dried solution is evaporated to give amine of general structure 11. The protective group on compound of general structure 11 can be exposed to an acidic organic solution, for example HCl in dioxane or trifluoroacetic acid in DCM or can be removed using catalytic Pd. The mixture is stirred at room temperature for a time between one and 16 h. The reaction mixture can be concentrated or filtered through a celite pad and then concentrated under reduced pressure to give an amine salt of the general structure 12 that can be used in subsequent reactions without further purification.

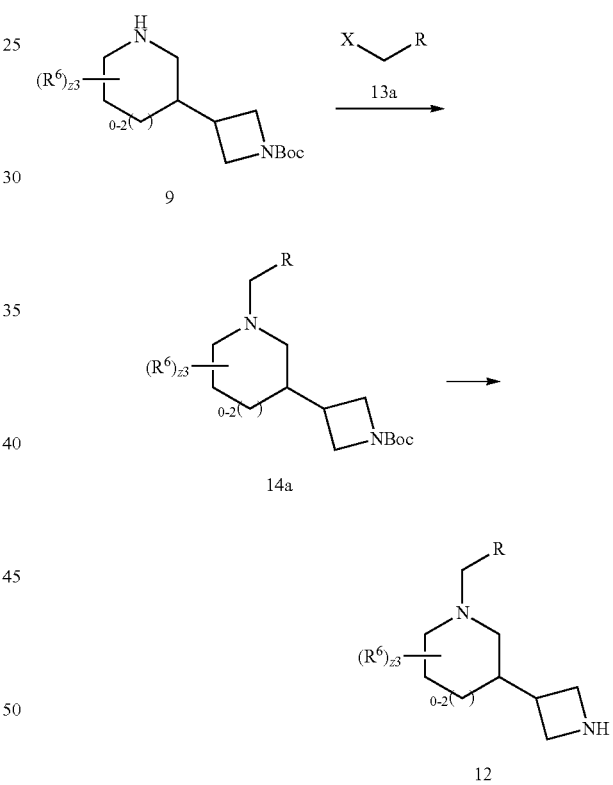

For instances where $R^8$ contains electron withdrawing groups (EWG):

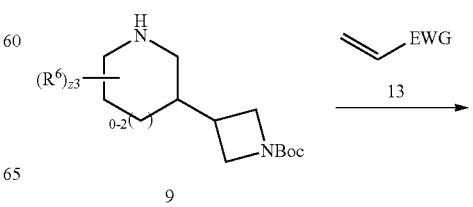

-continued

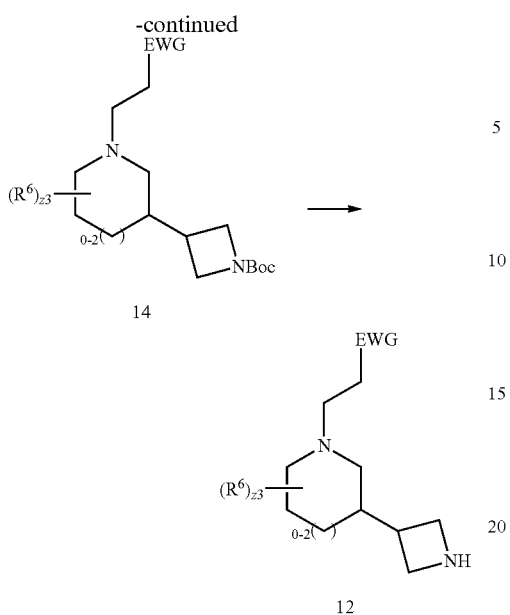

14

12

To a solution of amine of general structure 9 in dry organic solvent such as DCM is added Michael acceptor 13, Reaction mixture was stirred either at room temperature or at 50° C. until complete conversion which can be monitored using TLC or LCMS. Upon completion solvent is removed. The resulting residue can be purified by silica gel chromatography using a mixture of organic solvents for example a mixture of MeOH and DCM to give compounds of the general formula 14. The protective group on compound of general structure 14 can be exposed to an acidic organic solution, for example HCl in dioxane or trifluoroacetic acid in DCM or can be removed using catalytic Pd. The mixture is stirred at room temperature for a time between one and 16 h. The reaction mixture can be concentrated or filtered through a celite pad and then concentrated under reduced pressure to give an amine salt of the general structure 12 that can be used in subsequent reactions without further purification.

General Procedure A: Alkylation of tert-butyl 3-(piperidin-3-yl)azetidine-1-Carboxylate by Reductive Amination

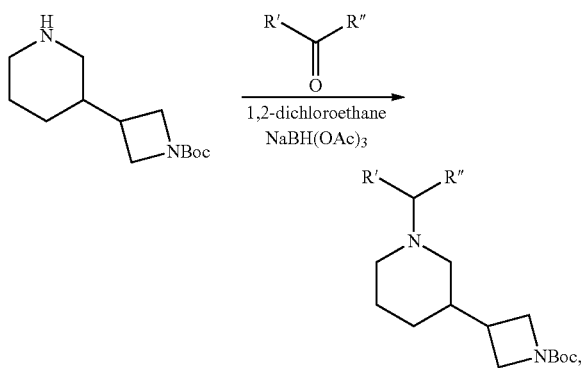

wherein R' and R" are a substituent described herein (e.g., $L^7$-$R^7$)

Commercially available tert-butyl 3-(piperidin-3-yl)azetidine-1-carboxylate (240 mg, 1 mmol) was dissolved in 6 mL of dry 1,2-dichloromethane and carbonyl compound (1 mmol) was added all at once. Mixture was allowed to stir at room temperature for 5 min and then NaBH(OAc)$_3$ (2 mmol) was added and reaction mixture was stirred for 1-18 hrs at room temperature. Conversion was monitored by LCMS. Upon completion, saturated sodium bicarbonate solution was added and the reaction mixture was allowed to stir for additional 30 min. The mixture was extracted 3 times with dichloromethane, combined organic phase was dried over MgSO$_4$, filtered, and the residue was purified on silica using methanol dichloromethane as eluent.

General Procedure B: Alkylation of tert-butyl 3-(piperidin-3-yl)azetidine-1-carboxylate

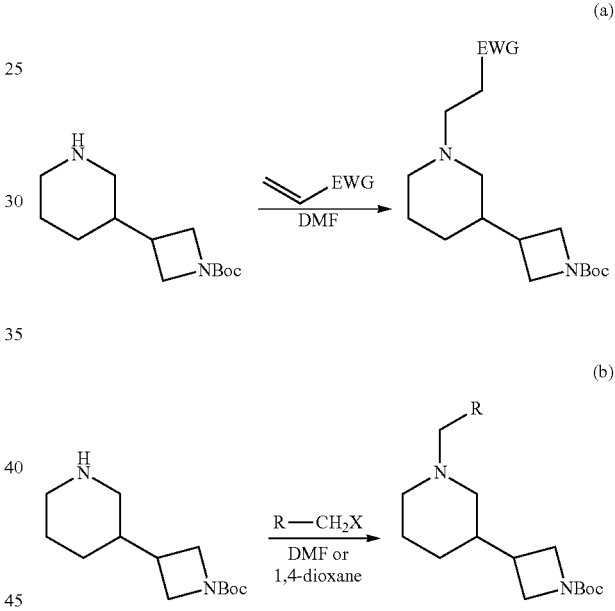

tert-Butyl 3-(piperidin-3-yl)azetidine-1-carboxylate (240 mg, 1 mmol) was dissolved in 5 mL of dry solvent and either (a) Michael acceptor (1 mmol) was added to the solution all at once and reaction mixture was stirred either at room temperature or at 50° C. until complete conversion was achieved (followed by LCMS); upon completion solvent was removed in vacuo and product purified by silica gel chromatography using methanol and dichloromethane as eluent, or (b) 1 mmol of alkyl halide, 10 mol % of sodium iodide, and sodium carbonate (2 mmol) were added to the solution all at once and the reaction mixture was heated to 75° C. under nitrogen atmosphere and monitored by LCMS; upon completion the reaction mixture was diluted with 20 mL of water, extracted 3 times with ethyl acetate, combined organic phase was dried over sodium sulfate, filtered, and concentrated under reduced pressure; the residue was purified on silica using methanol and dichloromethane as the eluent.

General Procedure C: Deprotection of 1-alkyl tert-butyl 3-(piperidin-3-yl)azetidine-1-carboxylate

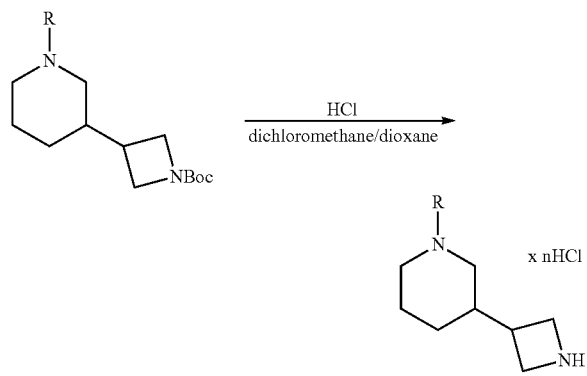

1-Alkyl tert-butyl 3-(piperidin-3-yl)azetidine-1-carboxylate (0.7 mmol) was dissolved in 3 mL of dichloromethane and 2 mL of 4M solution of HCl in 1,4-dioxane was added to it. The resulting mixture was stirred at room temperature until complete conversion was reached (1-3 h). After that solvents were removed in vacuo and residue was dried on high vacuum for 12 h. Product was used in the next step without purification.

General Procedure D: Nucleophilic Aromatic Substitution with 1-alkyl 3-(azetidin-3-yl)piperidine

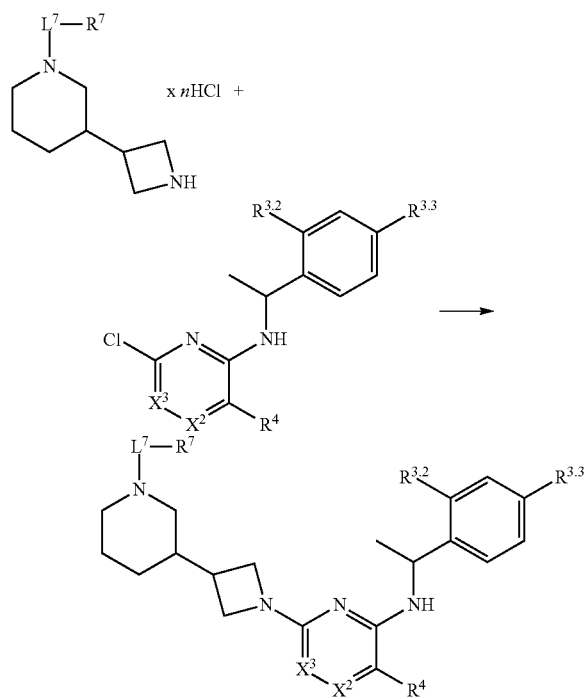

To a solution of an amino-chloro heterocyclic compound and an azetidine in an organic solvent such as a DMSO is added a base such as diisopropyl ethyl amine cesium fluoride. The reaction mixture is heated in a sealed tube between approximately 100° C. for 4-24 hours. The reaction mixture is partitioned between water and an organic solvent such as ethyl acetate and the organic layer is dried with sodium sulfate, filtered and concentrated in vacuo. The resulting residue can be purified either by silica gel chromatography using a mixture of solvents that can include hexanes, ethyl acetate, dichloro methane or methanol or by using reversed phase HPLC methods to give the desired target compound.

Alternatively, a solution of amino-chloro heterocyclic compound and an azetidine in an organic solvent such as a mixture of 1,2-dimethoxyethane and tert-butanol is sarged with argon and is treated with an organometallic catalyst such as $Pd_2dba_3$ a ligand such as BINAP and a base such as potassium tert-butoxide and heated to a temperature of approximately 100° C. to 4-24 hours. The mixture was then cooled to room temperature, filtered through a plug of sand with EtOAc and further with 20% MeOH in dichloromethane and all volatiles were then removed in vacuo. The resulting residue can be purified wither by silica gel chromatography using a mixture of solvents that can include hexanes, ethyl acetate, dichloro methane or methanol or by using reversed phase HPLC methods.

Synthetic Examples

Method A: Preparation of (R)-2-chloro-N-(1-(2,4-dichlorophenyl)ethyl)-5-methylpyrimidin-4-amine

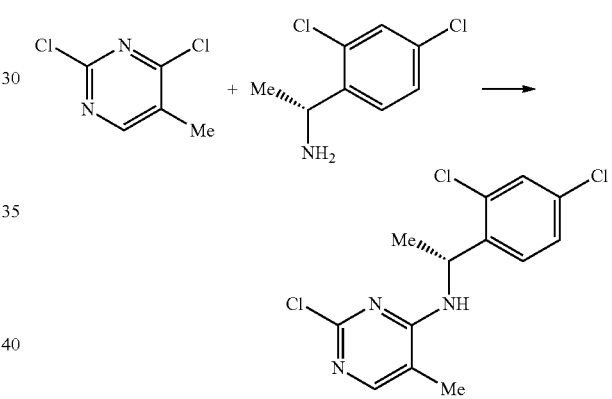

2,4-dichloro-5-methylpyrimidine (2.00 g, 12.3 mmol) was added to a solution of (1R)-1-(2,4-dichlorophenyl)ethanamine (2.33 g, 12.3 mmol) and triethylamine (2.57 mL, 18.4 mmol) in acetonitrile (40.0 mL) and the mixture was stirred at room temperature overnight. The mixture was evaporated then loaded onto silica gel using 5 mL of dichloromethane, and the crude product was purified by flash column chromatography (0-60% EtOAc/hexanes) yielding (R)-2-chloro-N-(1-(2,4-dichlorophenyl)ethyl)-5-methylpyrimidin-4-amine (1.20 g, 31% yield). [M+H] =315.9.

Method B: Preparation of (1R,3r)-3-((R)-3-(1-(tert-butoxycarbonyl)azetidin-3-yl)piperidin-1-yl)-1-methylcyclobutane-1-carboxylic Acid

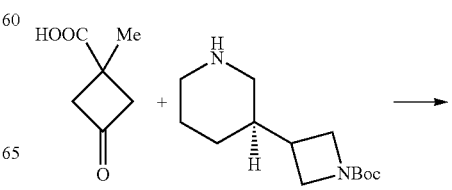

-continued

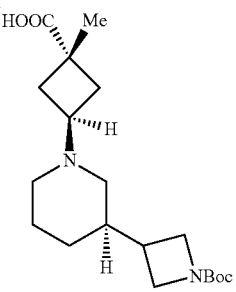

A suspension of 1-methyl-3-oxo-cyclobutanecarboxylic acid (4.48 g, 34.9 mmol), tert-butyl 3-[(3R)-3-piperidyl]azetidine-1-carboxylate (8.00 g, 33.3 mmol), and sodium triacetoxyborohydride (10.00 g, 47.4 mmol) in DCE (200 mL) was placed under a nitrogen atmosphere and cooled to −5° C. To the cooled suspension was added slowly acetic acid (1.90 mL, 33.2 mmol). The reaction was stirred for an additional 5 minutes and then the cooling bath was removed. After the reaction was stirred at room temperature for 5 hours, additional 1-methyl-3-oxo-cyclobutanecarboxylic acid (0.95 g, 2.4 mmol) and sodium triacetoxyborohydride (3.51 g, 16.6 mmol) was added to consume any remaining tert-butyl 3-[(3R)-3-piperidyl]azetidine-1-carboxylate. The reaction was stirred at room temperature for an additional 18 h. The crude material was adsorbed onto silica gel and purified by flash column chromatography (0-20% MeOH in DCM) to obtain a slight mixture of diastereomers which was again purified via flash column chromatography (0-20% MeOH in DCM) to give the desired, more polar isomer (1R,3r)-3-((R)-3-(1-(tert-butoxycarbonyl)azetidin-3-yl)piperidin-1-yl)-1-methylcyclobutane-1-carboxylic acid as white solid (4.20 g, 36% yield). The stereochemistry around the cyclobutane ring has been tentatively assigned as the trans-isomer. [M+H]=353.2.

Method C: Preparation of (1R,3r)-3-((R)-3-(azetidin-3-yl)piperidin-1-yl)-1-methylcyclobutane-1-carboxylic Acid

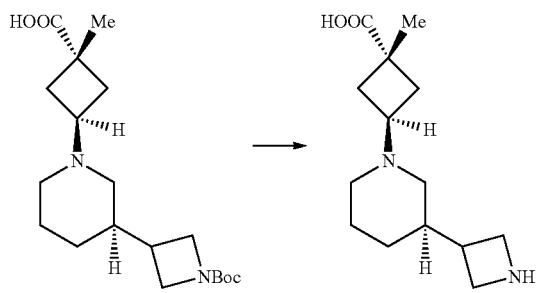 [SMILES: CC(C)(C)OC(=O)N1CC([C@H]2CCCN([C@H]3C[C@](C)(C(=O)O)C3)C2)C1 ; C[C@]1(C(=O)O)C[C@H](N2CCC[C@H](C3CNC3)C2)C1]

To a solution of (1R,3r)-3-((R)-3-(1-(tert-butoxycarbonyl)azetidin-3-yl)piperidin-1-yl)-1-methylcyclobutane-1-carboxylic acid (500 mg, 1.42 mmol) in dichloromethane (10 mL) was added 4N HCl in dioxane (1.77 mL, 7.1 mmol). The solution was stirred at room temperature until no residual starting material was observed by LCMS. The mixture was then rotary evaporated to remove all volatiles and diluted with 20% MeOH in DCM, treated with Amberlyst A26 (hydroxide form), filtered, and evaporated all volatiles to give the free base which was used without further purification.

Method D: Preparation of (1R,3r)-3-((R)-3-(1-(4-(((R)-1-(2,4-dichlorophenyl)ethyl)amino)-5-methylpyrimidin-2-yl)azetidin-3-yl)piperidin-1-yl)-1-methylcyclobutane-1-carboxylic Acid Example 36

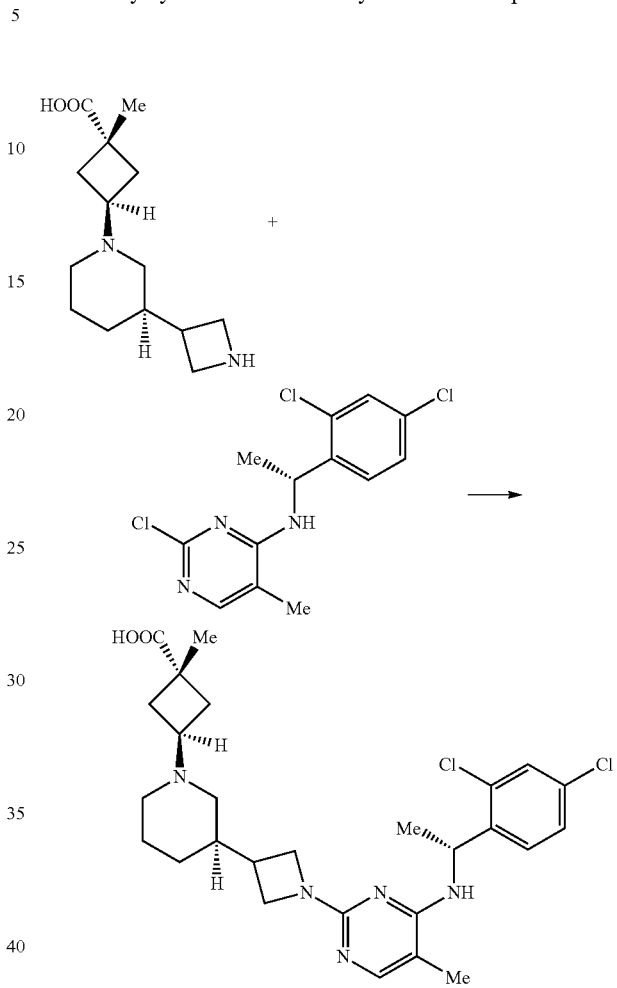

A solution of (1R,3r)-3-((R)-3-(azetidin-3-yl)piperidin-1-yl)-1-methylcyclobutane-1-carboxylic acid (35.0 mg, 0.14 mmol) and (R)-2-chloro-N-(1-(2,4-dichlorophenyl)ethyl)-5-methylpyrimidin-4-amine (53.2 mg, 0.17 mmol) in 1,2-dimethoxyethane:tert-butanol (1 mL:1 mL) was sparged with an argon gas balloon. To this solution at room temperature was added potassium tert-butoxide (24.0 mg (0.21 mmol), BINAP (17.4 mg, 0.028 mmol), and Pd$_2$dba$_3$ (12.8 mg, 0.014 mmol). The mixture was further sparged with argon gas for ten minutes. The balloon was removed, and the vessel was sealed and heated overnight at 100° C. The mixture was then cooled to room temperature, filtered through a plug of sand with EtOAc and further with 20% MeOH in dichloromethane and all volatiles were then removed in vacuo. The mixture was diluted with water:acetonitrile (2 mL:2 mL) and 5 drops of trifluoroacetic acid, filtered through a syringe filter 0.45 µM, and purified via reverse preparative HPLC (0-100% acetonitrile (with 0.1% TFA) in water) to give the desired product (1R,3r)-3-((R)-3-(1-(4-(((R)-1-(2,4-dichlorophenyl)ethyl)amino)-5-methylpyrimidin-2-yl)azetidin-3-yl)piperidin-1-yl)-1-methylcyclobutane-1-carboxylic acid as the trifluoroacetic acid salt (10 mg, 13% yield)

Method E: Preparation of Methyl (1R,3r)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylate

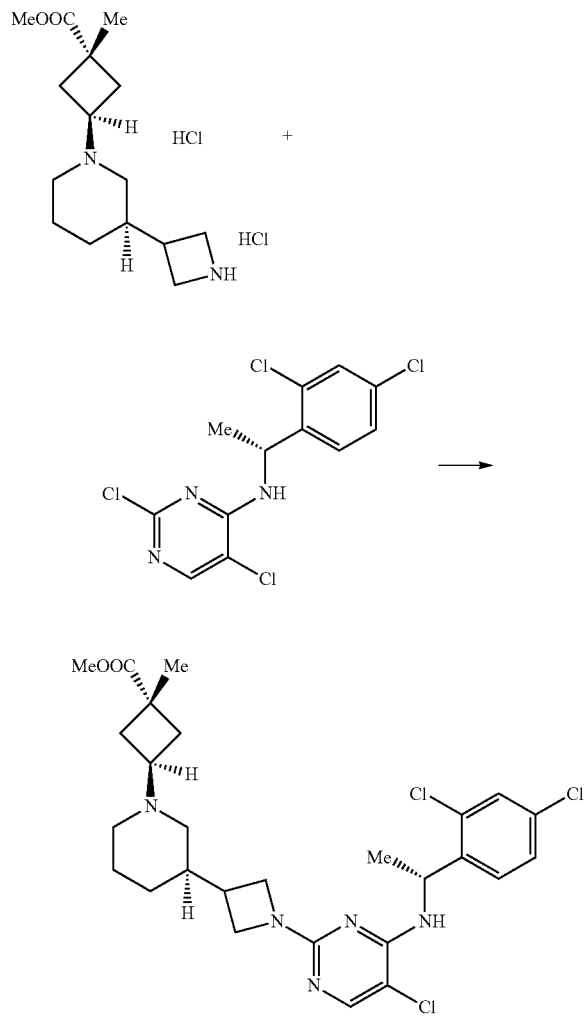 [SMILES: COC(=O)[C@]1(C)C[C@@H](N2CCC[C@H](C3CNC3)C2)C1 ; Cl ; Cl ; C[C@@H](Nc1nc(Cl)ncc1Cl)c1ccc(Cl)cc1Cl ; COC(=O)[C@]1(C)C[C@@H](N2CCC[C@H](C3CN(c4ncc(Cl)c(N[C@H](C)c5ccc(Cl)cc5Cl)n4)C3)C2)C1]

To a vial containing a solution of Methyl (1R,3r)-3-((R)-3-(azetidin-3-yl)piperidin-1-yl)-1-methylcyclobutane-1-carboxylate dihydrochloric acid salt (65.0 mg, 0.19 mmol) (prepared using similar methods to methods B and C) and (R)-2,5-dichloro-N-(1-(2,4-dichlorophenyl)ethyl)pyrimidin-4-amine (70.7 mg, 0.19 mmol) in DMSO (1.26 mL) at r.t. was added N,N-diisopropylethylamine (0.17 mL, 0.964 mmol) and cesium fluoride (29.3 mg, 0.19 mmol). The vial was sealed and heated to 100° C. for 4 hours, cooled to room temperature diluted with water, extracted with EtOAc, dried with sodium sulfate, filtered and concentrated in vacuo. The crude material was adsorbed onto silica gel and purified by flash column chromatography (0-10% MeOH in DCM) to obtain a slight mixture of diastereomers which was again purified by flash column chromatography (0-20% MeOH in DCM) to the desired compound methyl (1R,3r)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylate (37.0 mg, 34% yield). [M+H]=566.

Method F: (1R,3r)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylic Acid Example 12

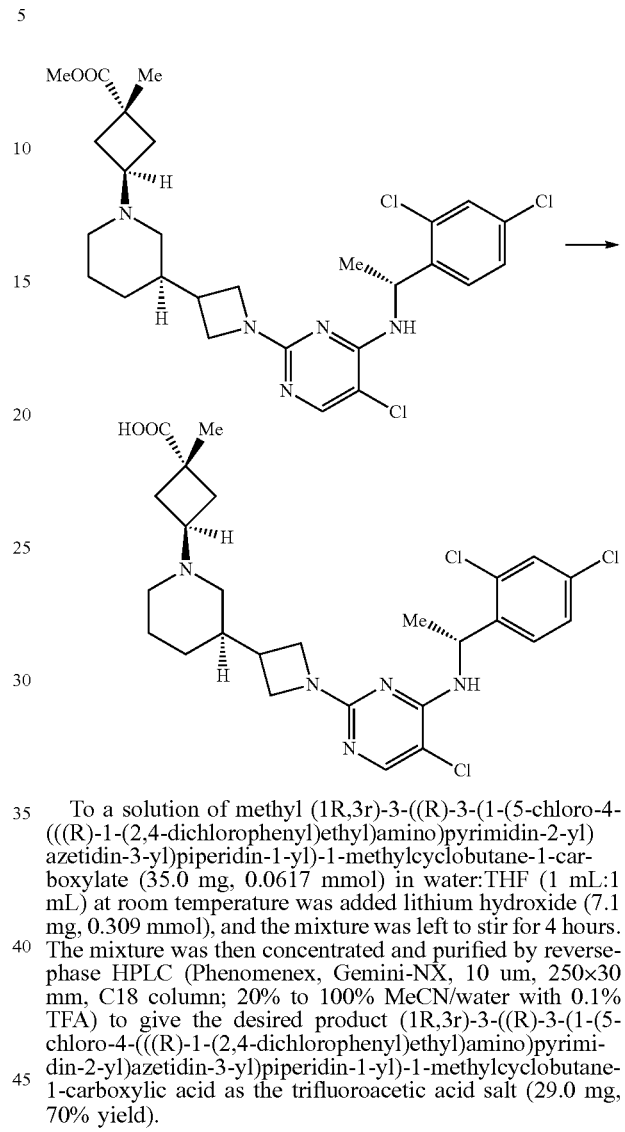

To a solution of methyl (1R,3r)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylate (35.0 mg, 0.0617 mmol) in water:THF (1 mL:1 mL) at room temperature was added lithium hydroxide (7.1 mg, 0.309 mmol), and the mixture was left to stir for 4 hours. The mixture was then concentrated and purified by reverse-phase HPLC (Phenomenex, Gemini-NX, 10 um, 250×30 mm, C18 column; 20% to 100% MeCN/water with 0.1% TFA) to give the desired product (1R,3r)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylic acid as the trifluoroacetic acid salt (29.0 mg, 70% yield).

Compounds Synthesized Using Methods A-F

Example 1

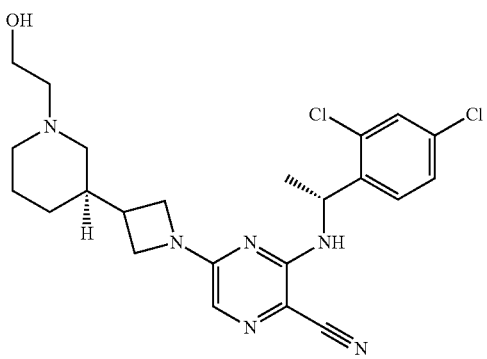 [SMILES: C[C@@H](Nc1nc(N2CC([C@H]3CCCN(CCO)C3)C2)cnc1C#N)c1ccc(Cl)cc1Cl]

3-(((R)-1-(2,4-dichlorophenyl)ethyl)amino)-5-(3-((R)-1-(2-hydroxyethyl)piperidin-3-yl)azetidin-1-yl)pyrazine-2-carbonitrile. H NMR (400 MHz, CDCl₃; benzenesulfonic acid salt) δ 8.85-9.15 (bs, 1H), 7.76-7.72 (m, 2H), 7.51-7.44 (m, 2H), 7.32-7.20 (m, 5H), 7.00 (s, 1H), 6.06-6.00 (m, 1H), 5.44-5.34 (m, 1H), 4.48-4.38 (bm, 1H), 4.04-3.97 (m, 1H), 3.94-3.80 (m, 3H), 3.65-3.53 (m, 2H), 3.47-3.37 (m, 1H), 3.19-3.12 (m, 2H), 2.84-2.72 (m, 1H), 2.50-2.30 (m, 2H), 1.91-1.83 (m, 2H), 1.73-1.65 (m, 1H), 1.49 (m, J=7.1 Hz, 3H), 1.06-0.92 (m, 1H). [M+H] 475.0

Example 2

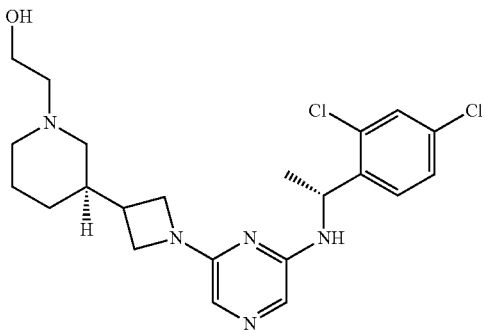 [SMILES: C[C@@H](Nc1cncc(N2CC([C@H]3CCCN(CCO)C3)C2)n1)c1ccc(Cl)cc1Cl]

2-((R)-3-(1-(6-(((R)-1-(2,4-dichlorophenyl)ethyl)amino)pyrazin-2-yl)azetidin-3-yl)piperidin-1-yl)ethan-1-ol. ¹H NMR (400 MHz, CD₃OD; trifluoroacetic acid salt) δ 7.45 (d, J=2.1 Hz, 1H), 7.37 (d, J=8.4 Hz, 1H), 7.27 (dd, J=8.4, 2.1 Hz, 1H), 7.13 (s, 1H), 6.89 (s, 1H), 5.41-5.20 (m, 1H), 4.10 (dd, J=8.6 Hz, 1H), 4.00 (dd, J=8.6 Hz, 1H), 3.94-3.82 (m, 2H), 3.78 (dd, J=9.1, 5.7 Hz, 1H), 3.70-3.55 (m, 2H), 3.52 (d, J=12.3 Hz, 1H), 3.17-2.98 (m, 2H), 2.95-2.82 (m, 1H), 2.74-2.40 (m, 2H), 2.15-1.93 (m, 2H), 1.96-1.81 (m, 1H), 1.74-1.57 (m, 2H), 1.53-1.36 (m, 5H), 1.06-0.94 (m, 3H). [M+H] 450.0.

Example 3

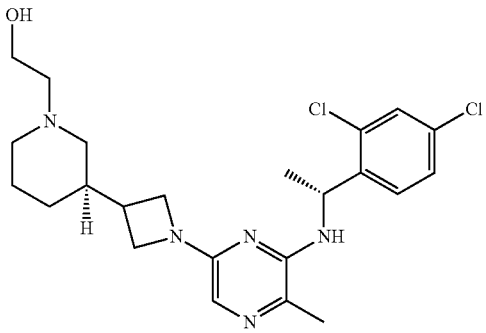 [SMILES: Cc1ncc(N2CC([C@H]3CCCN(CCO)C3)C2)nc1N[C@H](C)c1ccc(Cl)cc1Cl]

2-((R)-3-(1-(6-(((R)-1-(2,4-dichlorophenyl)ethyl)amino)-5-methylpyrazin-2-yl)azetidin-3-yl)piperidin-1-yl)ethan-1-ol. ¹H NMR (400 MHz, CD₃OD; free base) δ 7.42-7.34 (m, 2H), 7.21 (dd, J=8.4, 2.1 Hz, 1H), 7.12 (s, 1H), 5.23-5.14 (m, 1H), 3.98-3.84 (m, 2H), 3.75-3.61 (m, 3H), 3.46-3.40 (m, 1H), 2.95 (d, J=11.5 Hz, 1H), 2.85 (d, J=11.0 Hz, 1H), 2.54 (t, J=6.1 Hz, 2H), 2.33 (dd, J=17.8, 9.3 Hz, 1H), 2.16 (s, 3H), 2.09-1.98 (m, 1H), 1.79-1.51 (m, 5H), 1.43 (d, J=6.9 Hz, 3H), 1.28 (s, 1H), 1.06-0.73 (m, 1H). [M+H] 464.1.

Example 4

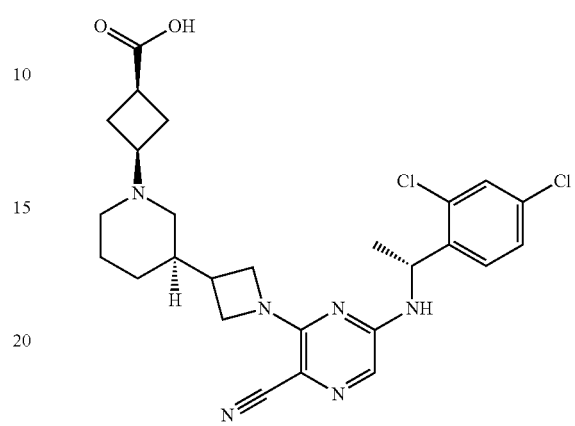

(1S,3s)-3-((R)-3-(1-(3-cyano-6-(((R)-1-(2,4-dichlorophenyl)ethyl)amino)pyrazin-2-yl)azetidin-3-yl)piperidin-1-yl)cyclobutane-1-carboxylic acid. ¹H NMR (400 MHz, CD₃OD; trifluoroacetic acid salt) δ 7.44 (d, J=2.1 Hz, 1H), 7.34 (d, J=8.5 Hz, 1H), 7.32 (s, 1H), 7.27 (dd, J=8.4, 2.1 Hz, 1H), 5.33 (q, J=6.9 Hz, 1H), 4.18 (q, J=9.0 Hz, 2H), 3.93 (dd, J=9.2, 5.8 Hz, 1H), 3.73-3.56 (m, 2H), 3.55-3.42 (m, 1H), 3.03-2.87 (m, 1H), 2.76-2.56 (m, 4H), 2.57-2.33 (m, 4H), 2.06 (d, J=14.5 Hz, 1H), 1.85 (d, J=12.0 Hz, 2H), 1.72 (dd, J=27.0, 13.3 Hz, 1H), 1.48 (d, J=7.0 Hz, 3H), 1.15 (q, J=13.6 Hz, 1H). [M+H] 529.2

Example 5

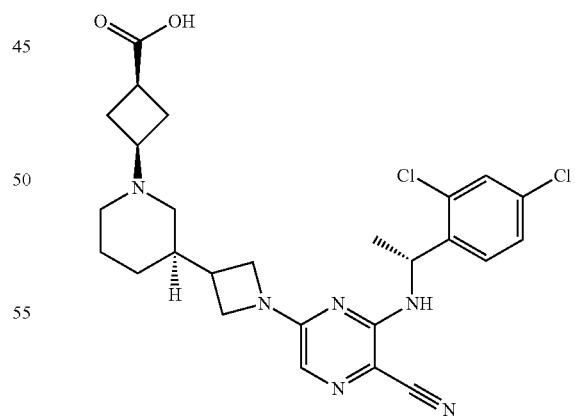

(1S,3s)-3-((R)-3-(1-(5-cyano-6-(((R)-1-(2,4-dichlorophenyl)ethyl)amino)pyrazin-2-yl)azetidin-3-yl)piperidin-1-yl)cyclobutane-1-carboxylic acid. ¹H NMR (400 MHz, CD₃OD; trifluoroacetic acid salt) δ 7.44-7.37 (m, 2H), 7.25 (dd, J=8.4, 2.1 Hz, 1H), 7.03 (s, 1H), 5.43 (q, J=7.0 Hz, 1H), 4.14 (t, J=8.9 Hz, 1H), 4.09-3.93 (m, 1H), 3.90-3.80 (m, 1H), 3.65-3.52 (m, 1H), 3.54-3.45 (m, 1H), 2.95 (p, J=9.1 Hz, 1H), 2.75-2.52 (m, 5H), 2.51-2.35 (m, 3H), 2.04 (d, J=14.8 Hz, 1H), 1.98-1.81 (m, 3H), 1.72 (q, J=14.7, 13.8 Hz, 1H), 1.50 (d, J=7.1 Hz, 3H), 1.14 (q, J=12.5, 12.1 Hz, 1H). [M+H] 529.2

Example 6

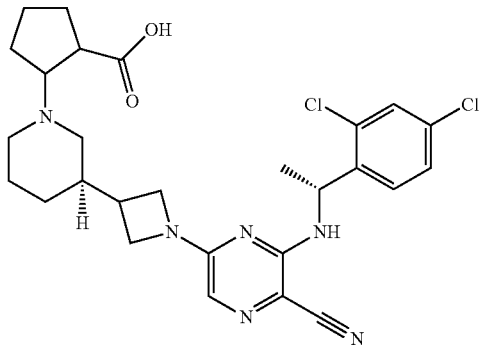 [SMILES: C[C@@H](Nc1nc(N2CC([C@H]3CCCN(C4CCCC4C(=O)O)C3)C2)cnc1C#N)c1ccc(Cl)cc1Cl]

2-((R)-3-(1-(5-cyano-6-(((R)-1-(2,4-dichlorophenyl)ethyl)amino)pyrazin-2-yl)azetidin-3-yl)piperidin-1-yl)cyclopentane-1-carboxylic acid. $^1$H NMR (400 MHz, CD$_3$OD; trifluoroacetic acid salt) δ 7.45-7.37 (m, 2H), 7.25 (d, J=8.4 Hz, 1H), 7.04 (s, 1H), 5.43 (bs, 1H), 4.15 (t, J=8.8 Hz, 1H), 4.10-3.92 (m, 2H), 3.88-3.52 (m, 3H), 3.20-2.43 (m, 4H), 2.33-2.12 (m, 3H), 2.12-1.56 (m, 8H), 1.50 (d, J=6.9 Hz, 3H), 1.15 (bs, 1H). [M+H] 543.2

Example 7

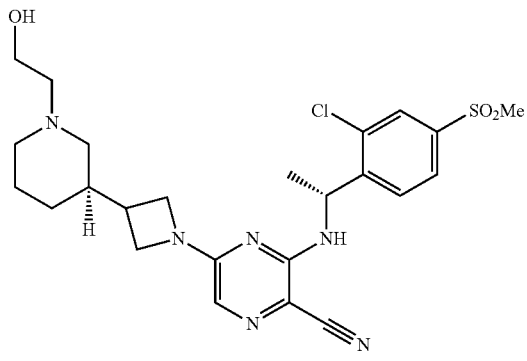 [SMILES: C[C@@H](Nc1nc(N2CC([C@H]3CCCN(CCO)C3)C2)cnc1C#N)c1ccc(S(C)(=O)=O)cc1Cl]

3-(((R)-1-(2-chloro-4-(methylsulfonyl)phenyl)ethyl)amino)-5-(3-((R)-1-(2-hydroxyethyl)piperidin-3-yl)azetidin-1-yl)pyrazine-2-carbonitrile. $^1$H NMR (CD$_3$OD; free base) δ: 7.97 (d, J=1.8 Hz, 1H), 7.82 (dd, J=8.2, 1.8 Hz, 1H), 7.62 (d, J=8.3 Hz, 1H), 7.32 (s, 1H), 5.43 (q, J=7.0 Hz, 1H), 4.19 (t, J=8.6 Hz, 1H), 4.00 (t, J=8.8 Hz, 1H), 3.91-3.84 (m, 1H), 3.74-3.62 (m, 3H), 3.15 (s, 3H), 2.92 (d, J=11.3 Hz, 1H), 2.84 (d, J=7.4 Hz, 1H), 2.60-2.47 (m, 2H), 2.41 (dd, J=14.1, 6.7 Hz, 1H), 2.04 (t, J=11.5 Hz, 1H), 1.77-1.66 (m, 4H), 1.66-1.54 (m, 1H), 1.51 (d, J=7.1 Hz, 3H), 0.88 (q, J=10.6 Hz, 1H). [M+H] 519.0

Example 8

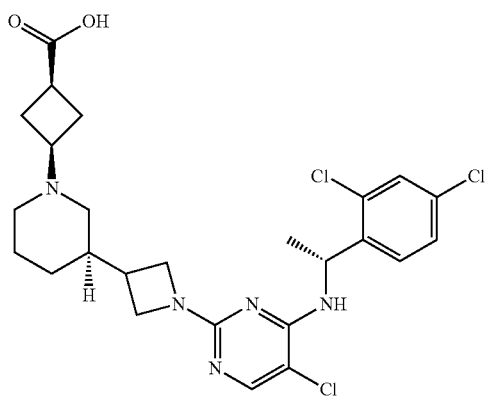 [SMILES: C[C@@H](Nc1nc(N2CC([C@H]3CCCN([C@H]4C[C@@H](C(=O)O)C4)C3)C2)ncc1Cl)c1ccc(Cl)cc1Cl]

(1S,3s)-3-((R)-3-(1-(5-chloro-4-(((R)-1-(2,4-dichlorophenyl)ethyl)amino)pyrimidin-2-yl)azetidin-3-yl)piperidin-1-yl)cyclobutane-1-carboxylic acid. $^1$H NMR (400 MHz, CD$_3$OD; trifluoroacetic acid salt) δ 7.95 (s, 1H), 7.47 (d, J=2.1 Hz, 1H), 7.40 (d, J=8.4 Hz, 1H), 7.31 (dd, J=8.4, 2.1 Hz, 1H), 5.64 (s, 1H), 4.26 (t, J=8.8 Hz, 1H), 4.20-3.94 (m, 3H), 3.59 (p, J=8.4 Hz, 1H), 3.49 (d, J=12.1 Hz, 1H), 3.37-3.16 (m, 1H), 3.14-2.87 (m, 1H), 2.79-2.54 (m, 3H), 2.54-2.36 (m, 4H), 2.14-1.94 (m, 2H), 1.92-1.66 (m, 2H), 1.58 (d, J=7.1 Hz, 3H), 1.14 (q, J=12.9 Hz, 1H). [M+H] 538.2

Example 9

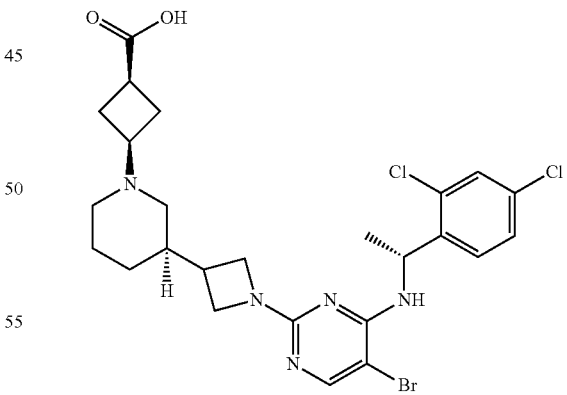

(1S,3s)-3-((R)-3-(1-(5-bromo-4-(((R)-1-(2,4-dichlorophenyl)ethyl)amino)pyrimidin-2-yl)azetidin-3-yl)piperidin-1-yl)cyclobutane-1-carboxylic acid. H NMR (400 MHz, CD$_3$OD; trifluoroacetic acid salt) δ 8.03 (s, 1H), 7.48 (d, J=2.1 Hz, 1H), 7.41 (d, J=8.4 Hz, 1H), 7.32 (dd, J=8.4, 2.2 Hz, 1H), 5.69-5.58 (m, 1H), 4.30-4.21 (m, 1H), 4.20-3.86 (m, 3H), 3.59 (p, J=8.2, 7.5 Hz, 1H), 3.50 (d, J=12.7 Hz, 1H), 3.39-3.22 (m, 1H), 2.95 (p, J=8.8 Hz, 1H), 2.75-2.56 (m, 4H), 2.53-2.37 (m, 3H), 2.11-1.96 (m, 2H), 1.93-1.67 (m, 2H), 1.59 (d, J=7.1 Hz, 3H), 1.15 (q, J=11.3 Hz, 1H). [M+H] 582.1

Example 10

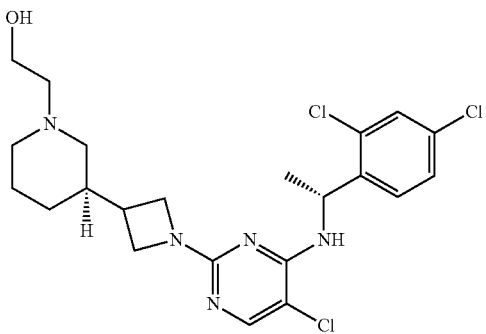

2-((R)-3-(1-(5-chloro-4-(((R)-1-(2,4-dichlorophenyl)ethyl)amino)pyrimidin-2-yl)azetidin-3-yl)piperidin-1-yl)ethan-1-ol. ¹H NMR (400 MHz, CD₃OD; trifluoroacetic acid salt) δ 7.96 (s, 1H), 7.48 (d, J=1.9 Hz, 1H), 7.41 (d, J=8.5 Hz, 1H), 7.32 (dd, J=8.3, 1.8 Hz, 1H), 5.64 (q, J=6.9, 6.3 Hz, 1H), 4.27 (t, J=9.0 Hz, 1H), 4.22-3.80 (m, 4H), 3.65 (d, J=12.5 Hz, 1H), 3.52 (d, J=12.2 Hz, 1H), 3.37-3.20 (m, 3H), 2.92 (t, J=12.7 Hz, 1H), 2.75-2.54 (m, 2H), 2.19-1.95 (m, 2H), 1.95-1.75 (m, 2H), 1.58 (d, J=7.0 Hz, 3H), 1.16 (q, J=14.0, 13.2 Hz, 1H). [M+H] 484.1

Example 11

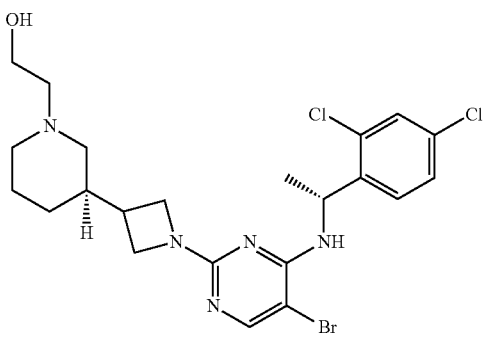 [SMILES: C[C@@H](Nc1nc(N2CC([C@H]3CCCN(CCO)C3)C2)ncc1Cl)c1ccc(Cl)cc1Cl]

2-((R)-3-(1-(5-bromo-4-(((R)-1-(2,4-dichlorophenyl)ethyl)amino)pyrimidin-2-yl)azetidin-3-yl)piperidin-1-yl)ethan-1-ol. ¹H NMR (400 MHz, CD₃OD; trifluoroacetic acid salt) δ 8.03 (s, 1H), 7.47 (d, J=1.9 Hz, 1H), 7.41 (d, J=8.5 Hz, 1H), 7.31 (dd, J=8.5, 1.9 Hz, 1H), 5.63 (q, J=7.2 Hz, 1H), 4.26 (t, J=9.2 Hz, 1H), 4.18-3.94 (m, 2H), 3.94-3.82 (m, 2H), 3.65 (d, J=12.4 Hz, 1H), 3.52 (d, J=11.9 Hz, 1H), 3.38-3.22 (m, 3H), 2.92 (t, J=12.4 Hz, 1H), 2.75-2.53 (m, 2H), 2.23-1.95 (m, 2H), 1.95-1.75 (m, 2H), 1.59 (d, J=7.1 Hz, 3H), 1.15 (q, J=12.9 Hz, 1H). [M+H] 528.1

Example 12

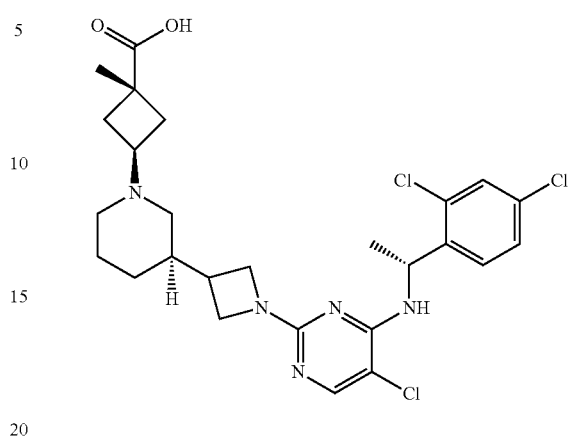

(1R,3r)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylic acid. ¹H NMR (400 MHz, CD₃OD; trifluoroacetic acid salt) δ 8.80 (d, J=6.7 Hz, 1H), 7.96 (s, 1H), 7.48 (d, J=1.9 Hz, 1H), 7.41 (d, J=8.4 Hz, 1H), 7.32 (dd, J=8.4, 1.9 Hz, 1H), 5.65 (s, 1H), 4.25 (t, J=8.8 Hz, 1H), 4.21-3.93 (m, 3H), 3.73 (p, J=8.1 Hz, 1H), 3.49 (d, J=12.1 Hz, 1H), 3.39-3.23 (m, 1H), 2.80 (t, J=10.1 Hz, 2H), 2.68 (t, J=12.6 Hz, 1H), 2.60 (dd, J=15.1, 7.2 Hz, 1H), 2.44 (t, J=12.1 Hz, 1H), 2.28 (t, J=10.3 Hz, 2H), 2.17-1.95 (m, 2H), 1.92-1.68 (m, 2H), 1.59 (d, J=7.1 Hz, 3H), 1.40 (s, 3H), 1.13 (q, J=12.5 Hz, 1H). [M+H] 552.2

Example 13

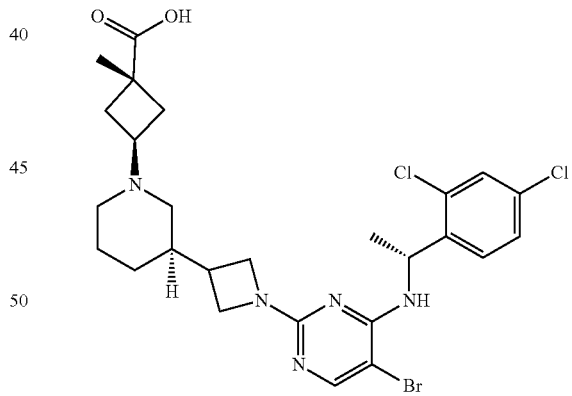

(1R,3r)-3-((R)-3-(1-(5-bromo-4-(((R)-1-(2,4-dichlorophenyl)ethyl)amino)pyrimidin-2-yl)azetidin-3-yl)piperidin-1-yl)-1-methylcyclobutane-1-carboxylic acid. ¹H NMR (400 MHz, CD₃OD; trifluoroacetic acid salt) δ 8.03 (s, 1H), 7.48 (d, J=1.9 Hz, 1H), 7.41 (d, J=8.5 Hz, 1H), 7.32 (dd, J=8.4, 2.0 Hz, 1H), 5.63 (s, 1H), 4.24 (t, J=9.1 Hz, 1H), 4.20-3.91 (m, 3H), 3.73 (p, J=8.6 Hz, 1H), 3.49 (d, J=12.1 Hz, 1H), 3.39-3.23 (m, 1H), 2.80 (t, J=10.1 Hz, 2H), 2.68 (t, J=12.8 Hz, 1H), 2.59 (dd, J=15.5, 7.6 Hz, 1H), 2.44 (t, J=12.1 Hz, 1H), 2.27 (t, J=9.2 Hz, 2H), 2.13-1.96 (m, 2H), 1.93-1.68 (m, 2H), 1.59 (d, J=7.1 Hz, 3H), 1.40 (s, 3H), 1.13 (q, J=11.7 Hz, 1H). [M+H] 596.1

Example 14

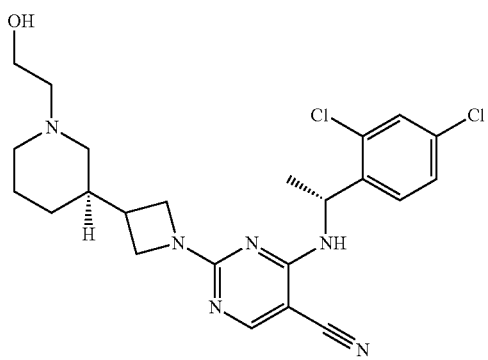

4-(((R)-1-(2,4-dichlorophenyl)ethyl)amino)-2-(3-((R)-1-(2-hydroxyethyl)piperidin-3-yl)azetidin-1-yl)pyrimidine-5-carbonitrile. ¹H NMR (400 MHz, CD₃CN; benzenesulfonic acid salt) δ 9.00-8.80 (bs, 1H), 8.15 (s, 1H), 7.74-7.71 (m, 2H), 7.50-7.50 (m, 2H), 7.33-7.20 (m, 4H), 6.45-6.40 (bm, 1H), 5.55-5.43 (m, 1H), 4.05-3.95 (m, 1H), 3.93-3.83 (m, 2H), 3.75-3.65 (m, 1H), 3.63-3.53 (m, 1H), 3.50-3.37 (m, 1H), 3.28-3.10 (m, 3H), 2.84-2.71 (m, 1H), 2.50-2.00 (bm, 4H), 1.93-1.63 (bm, 4H), 1.49 (d, J=7.1 Hz, 3H), 1.08-0.90 (m, 1H). [M+H] 475.1

Example 15

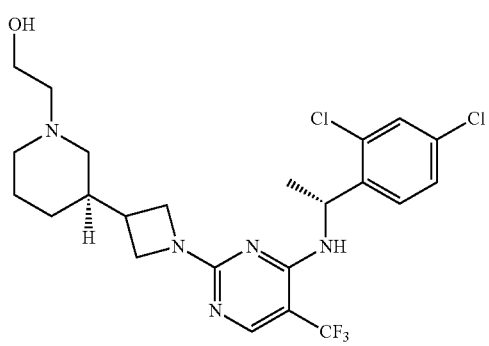 [SMILES: C[C@@H](Nc1nc(N2CC([C@H]3CCCN(CCO)C3)C2)ncc1C(F)(F)F)c1ccc(Cl)cc1Cl]

2-((R)-3-(1-(4-(((R)-1-(2,4-dichlorophenyl)ethyl)amino)-5-(trifluoromethyl)pyrimidin-2-yl)azetidin-3-yl)piperidin-1-yl)ethan-1-ol. ¹H NMR (400 MHz, CD₃CN; benzenesulfonic acid salt) δ 8.08 (s, 1H), 7.76-7.72 (m, 2H), 7.49-7.46 (m, 1H), 7.43-7.40 (m, 1H), 7.30-7.21 (m, 4H), 5.39-5.29 (m, 1H), 4.18-4.08 (m, 1H), 4.00-3.84 (m, 3H), 3.80-3.70 (m, 1H), 3.65-3.35 (m, 3H), 3.20-3.13 (m, 2H), 2.87-2.72 (m, 1H), 2.60-2.14 (m, 6H), 1.96-1.86 (m, 2H), 1.75-1.65 (m, 1H), 1.44 (d, J=7.0 Hz, 3H), 1.14-0.94 (m, 1H). [M+H] 518.1

Example 16

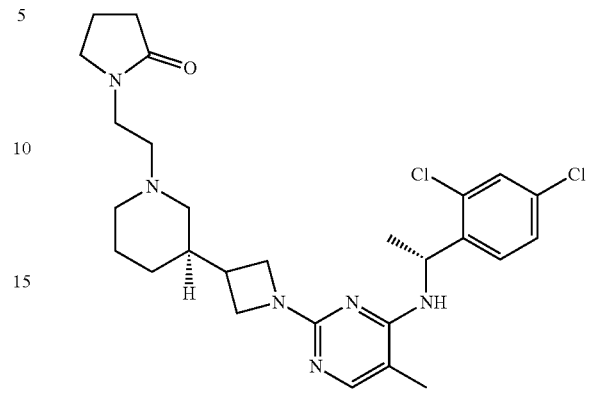

1-(2-((R)-3-(1-(4-(((R)-1-(2,4-dichlorophenyl)ethyl)amino)-5-methylpyrimidin-2-yl)azetidin-3-yl)piperidin-1-yl)ethyl)pyrrolidin-2-one. ¹H NMR (400 MHz, CD₃OD; trifluoroacetic acid salt) δ 8.31 (d, J=6.4 Hz, 1H), 7.54-7.45 (m, 2H), 7.37 (d, J=8.4 Hz, 1H), 7.30 (dd, J=8.4, 2.1 Hz, 1H), 5.72-5.56 (m, 1H), 4.29-4.18 (m, 1H), 4.17-4.04 (m, 1H), 3.97 (s, 1H), 3.88-3.43 (m, 5H), 3.41-3.32 (m, 1H), 2.99-2.85 (m, 1H), 2.66-2.50 (m, 2H), 2.47-2.34 (m, 2H), 2.19-1.92 (m, 6H), 1.92-1.66 (m, 2H), 1.56 (d, J=7.1 Hz, 3H), 1.42-1.21 (m, 1H), 1.22-1.08 (m, 1H). [M+H] 531.3

Example 17

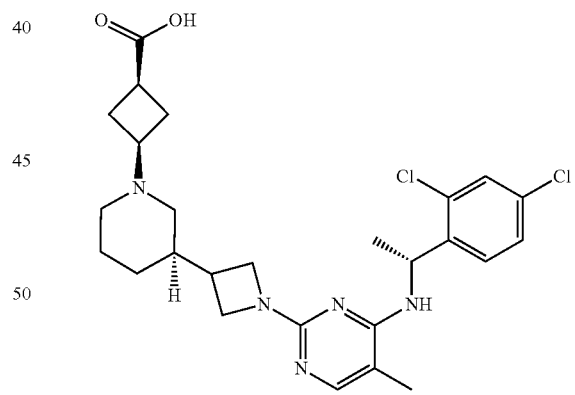

(1S,3s)-3-((R)-3-(1-(4-(((R)-1-(2,4-dichlorophenyl)ethyl)amino)-5-methylpyrimidin-2-yl)azetidin-3-yl)piperidin-1-yl)cyclobutane-1-carboxylic acid. ¹H NMR (400 MHz, CD₃OD; trifluoroacetic acid salt) δ 7.49 (s, 1H), 7.39 (d, J=2.1 Hz, 1H), 7.33 (d, J=8.4 Hz, 1H), 7.22 (dd, J=8.4, 2.1 Hz, 1H), 5.59-5.43 (m, 1H), 3.98-3.86 (m, 1H), 3.85-3.73 (m, 1H), 3.58 (dd, J=8.5, 5.9 Hz, 1H), 2.95-2.77 (m, 2H), 2.44-2.22 (m, 4H), 2.02 (s, 3H), 1.76-1.51 (m, 3H), 1.48 (d, J=7.1 Hz, 3H), 1.38-1.21 (m, 1H), 0.96-0.72 (m, 1H). [M+H] 518.1

Example 18

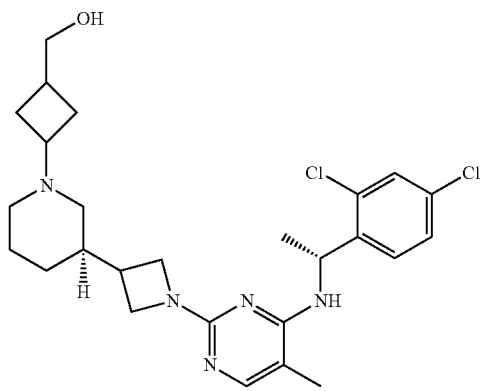 [SMILES: Cc1cnc(N2CC([C@H]3CCCN(C4CC(CO)C4)C3)C2)nc1N[C@H](C)c1ccc(Cl)cc1Cl]

(3-((R)-3-(1-(4-(((R)-1-(2,4-dichlorophenyl)ethyl)amino)-5-methylpyrimidin-2-yl)azetidin-3-yl)piperidin-1-yl)cyclobutyl)methanol. H NMR (400 MHz, CD$_3$OD; free base) δ 7.51 (s, 1H), 7.41 (d, J=2.2 Hz, 1H), 7.34 (d, J=8.4 Hz, 1H), 7.24 (dd, J=8.4, 2.1 Hz, 1H), 4.05-3.93 (m, 1H), 3.95-3.76 (m, 1H), 3.69-3.58 (m, 2H), 3.52 (d, J=5.4 Hz, 1H), 3.45-3.37 (m, 1H), 3.11 (dd, J=31.6, 13.6 Hz, 1H), 2.68 (s, 1H), 2.46-2.05 (m, 1H), 2.04 (s, 3H), 1.96-1.58 (m, 3H), 1.50 (d, J=7.1 Hz, 3H), 1.13-0.93 (m, 1H). [M+H] 504.2

Example 19

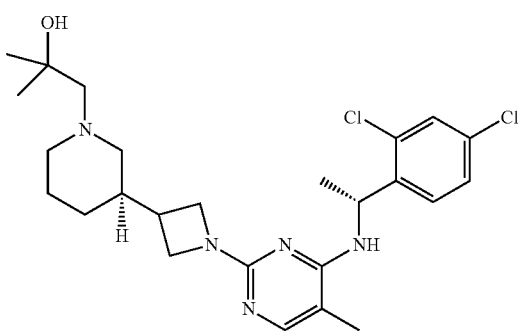 [SMILES: Cc1cnc(N2CC([C@H]3CCCN(CC(C)(C)O)C3)C2)nc1N[C@H](C)c1ccc(Cl)cc1Cl]

1-((R)-3-(1-(4-(((R)-1-(2,4-dichlorophenyl)ethyl)amino)-5-methylpyrimidin-2-yl)azetidin-3-yl)piperidin-1-yl)-2-methylpropan-2-ol. $^1$H NMR (400 MHz, CD$_3$OD; free base) δ 7.49 (s, 1H), 7.39 (d, J=2.1 Hz, 1H), 7.33 (d, J=8.4 Hz, 1H), 7.22 (dd, J=8.4, 2.1 Hz, 1H), 5.52-5.43 (m, 1H), 3.96-3.86 (m, 1H), 3.85-3.73 (m, 1H), 3.58 (dd, J=8.5, 5.9 Hz, 1H), 2.93-2.79 (m, 2H), 2.42-2.22 (m, 4H), 2.02 (s, 3H), 1.73-1.53 (m, 5H), 1.48 (d, J=7.1 Hz, 3H), 1.36-1.22 (m, 1H), 1.17 (s, 6H), 0.95-0.74 (m, 1H). [M+H] 492.2

Example 20

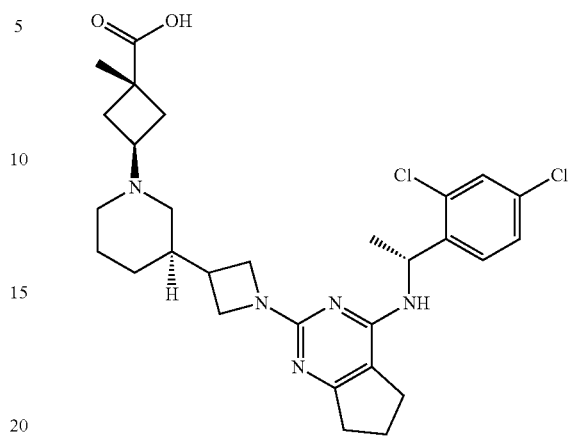

(1R,3r)-3-((R)-3-(1-(4-(((R)-1-(2,4-dichlorophenyl)ethyl)amino)-6,7-dihydro-5H-cyclopenta[d]pyrimidin-2-yl)azetidin-3-yl)piperidin-1-yl)-1-methylcyclobutane-1-carboxylic acid. $^1$H NMR (400 MHz, CD$_3$OD; trifluoroacetic acid salt) δ 7.91 (s, 1H), 7.47 (d, J=2.1 Hz, 1H), 7.36 (d, J=8.5 Hz, 1H), 7.30 (dd, J=8.5, 2.1 Hz, 1H), 6.49-6.34 (m, 1H), 4.40-4.18 (m, 2H), 4.15-4.02 (m, 1H), 3.99-3.84 (m, 1H), 3.83-3.68 (m, 1H), 3.65-3.44 (m, 3H), 2.60-2.22 (m, 2H), 2.16-1.98 (m, 2H), 1.90 (d, J=7.0 Hz, 3H), 1.80-1.43 (m, 4H). [M+H] 558.1

Example 21

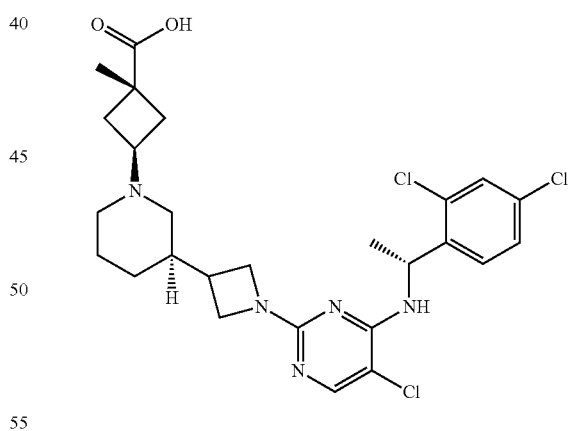

(1R,3r)-3-((R)-3-(1-(5-chloro-4-((2,4-dichlorobenzyl)amino)pyrimidin-2-yl)azetidin-3-yl)piperidin-1-yl)-1-methylcyclobutane-1-carboxylic acid. $^1$H NMR (400 MHz, CD$_3$OD; trifluoroacetic acid salt) δ 7.74 (d, J=4.4 Hz, 1H), 7.26 (d, J=5.0 Hz, 1H), 7.09 (d, J=6.0 Hz, 2H), 4.55-4.49 (m, 3H), 4.04-3.90 (m, 3H), 3.82-3.66 (m, 3H), 3.53-3.42 (m, 1H), 3.25 (d, J=11.9 Hz, 1H), 2.61-2.52 (m, 3H), 2.51-2.32 (m, 3H), 2.26-2.13 (m, 1H), 2.07-1.94 (m, 2H), 1.91-1.72 (m, 2H), 1.67 (d, J=12.8 Hz, 1H), 1.53 (d, J=13.5 Hz, 1H), 1.17 (d, J=5.4 Hz, 3H), 0.98-0.85 (m, 1H). [M+H] 538.1

Example 22

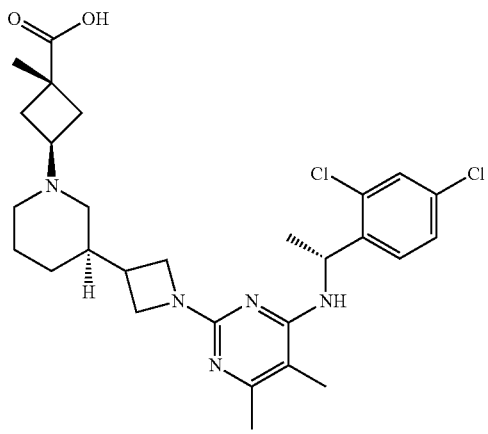 [SMILES: Cc1nc(N2CC([C@H]3CCCN([C@H]4C[C@](C)(C(=O)O)C4)C3)C2)nc(N[C@H](C)c2ccc(Cl)cc2Cl)c1C]

(1R,3r)-3-((R)-3-(1-(4-(((R)-1-(2,4-dichlorophenyl)ethyl)amino)-5,6-dimethylpyrimidin-2-yl)azetidin-3-yl)piperidin-1-yl)-1-methylcyclobutane-1-carboxylic acid. $^1$H NMR (400 MHz, CD$_3$OD; trifluoroacetic acid salt) δ 7.49 (s, 1H), 7.40 (d, J=8.3 Hz, 1H), 7.31 (dd, J=8.4, 2.1 Hz, 1H), 5.45-5.26 (m, 1H), 4.69 (s, 1H), 4.50-3.84 (m, 3H), 3.80-3.64 (m, 1H), 3.49 (d, J=13.4 Hz, 1H), 2.90-2.76 (m, 2H), 2.74-2.62 (m, 1H), 2.55-2.34 (m, 2H), 2.26 (s, 3H), 2.23-2.18 (m, 1H), 2.03 (s, 3H), 1.94-1.60 (m, 2H), 1.51 (d, J=7.0 Hz, 3H), 1.45-1.34 (m, 3H), 1.21-1.01 (m, 1H). [M+H] 546.3

Example 23

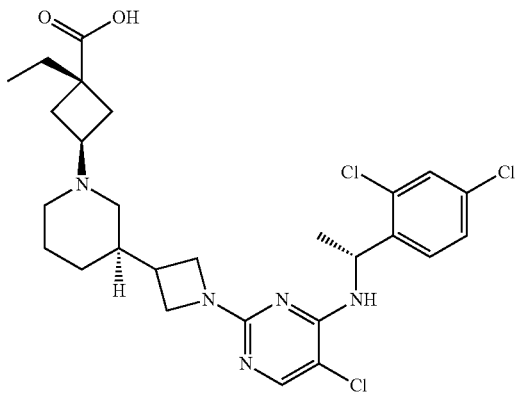 [SMILES: CC[C@]1(C(=O)O)C[C@H](N2CCC[C@H](C3CN(c4ncc(Cl)c(N[C@H](C)c5ccc(Cl)cc5Cl)n4)C3)C2)C1]

(1R,3s)-3-((R)-3-(1-(5-chloro-4-(((R)-1-(2,4-dichlorophenyl)ethyl)amino)pyrimidin-2-yl)azetidin-3-yl)piperidin-1-yl)-1-ethylcyclobutane-1-carboxylic acid. $^1$H NMR (400 MHz, CD$_3$OD; trifluoroacetic acid salt) δ 8.78 (d, J=6.7 Hz, 1H), 7.96 (d, J=1.4 Hz, 1H), 7.49 (d, J=2.1 Hz, 1H), 7.41 (d, J=8.4 Hz, 1H), 7.32 (dd, J=8.4, 2.1 Hz, 1H), 5.70-5.58 (m, 1H), 4.32-3.80 (m, 3H), 3.73-3.57 (m, 1H), 3.50 (d, J=12.8 Hz, 1H), 2.83-2.52 (m, 1H), 2.50-2.31 (m, 2H), 2.27-2.14 (m, 1H), 2.08-1.93 (m, 2H), 1.91-1.64 (m, 2H), 1.59 (d, J=7.1 Hz, 3H), 1.23-1.07 (m, 1H), 1.00-0.75 (m, 3H). [M+H] 566.0

Example 24

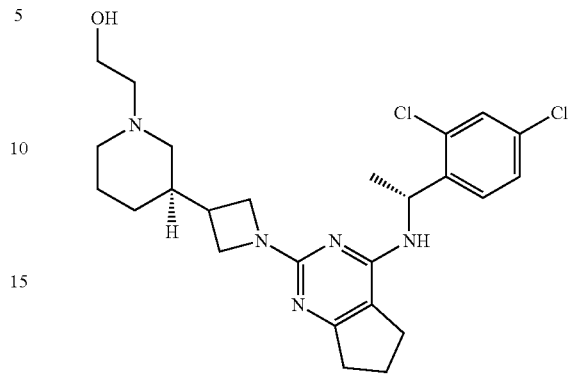

2-((R)-3-(1-(4-(((R)-1-(2,4-dichlorophenyl)ethyl)amino)-6,7-dihydro-5H-cyclopenta[d]pyrimidin-2-yl)azetidin-3-yl)piperidin-1-yl)ethan-1-ol. $^1$H NMR (400 MHz, CD$_3$OD; trifluoroacetic acid salt) δ 7.47 (dd, J=15.8, 2.1 Hz, 1H), 7.40 (d, J=8.4 Hz, 1H), 7.31 (dt, J=8.4, 2.0 Hz, 1H), 5.47-5.34 (m, 1H), 4.61-4.42 (m, 1H), 4.35-4.25 (m, 1H), 4.23-4.16 (m, 1H), 4.00 (d, J=7.0 Hz, 1H), 3.93-3.81 (m, 2H), 3.65 (d, J=12.4 Hz, 1H), 3.60-3.42 (m, 1H), 3.28-3.19 (m, 1H), 3.01-2.76 (m, 5H), 2.74-2.45 (m, 2H), 2.23-1.72 (m, 6H), 1.55-1.43 (m, 3H), 1.37 (dd, J=6.7, 3.4 Hz, 1H), 1.23-1.05 (m, 1H). [M+H] 490.2

Example 25

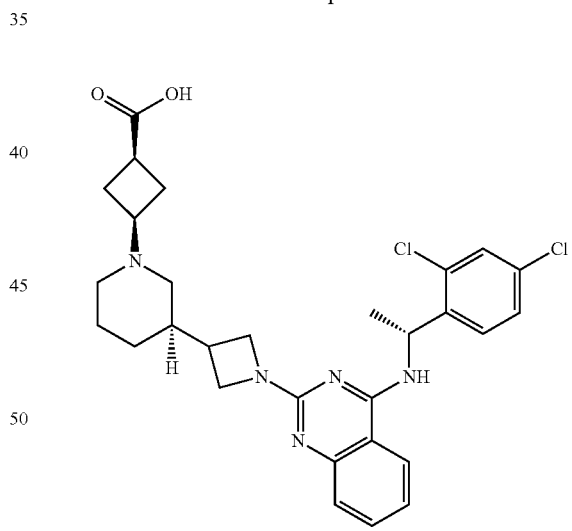

(1S,3s)-3-((R)-3-(1-(4-(((R)-1-(2,4-dichlorophenyl)ethyl)amino)quinazolin-2-yl)azetidin-3-yl)piperidin-1-yl)cyclobutane-1-carboxylic acid. $^1$H NMR (400 MHz, CD$_3$OD; trifluoroacetic acid salt) δ 9.42 (d, J=6.2 Hz, 1H), 8.36 (dd, J=8.3, 1.2 Hz, 1H), 7.80 (ddd, J=8.5, 7.2, 1.3 Hz, 1H), 7.56-7.38 (m, 4H), 7.29 (dd, J=8.4, 2.1 Hz, 1H), 5.90-5.60 (m, 1H), 4.36 (t, J=9.1 Hz, 1H), 4.27-3.93 (m, 2H), 3.78-3.54 (m, 1H), 3.56-3.44 (m, 1H), 3.44-3.33 (m, 1H), 3.03-2.89 (m, 1H), 2.77-2.57 (m, 5H), 2.57-2.38 (m, 3H), 2.19-1.96 (m, 1H), 1.95-1.71 (m, 3H), 1.65 (d, J=7.1 Hz, 3H), 1.26-1.01 (m, 1H). [M+H] 554.0

Example 26

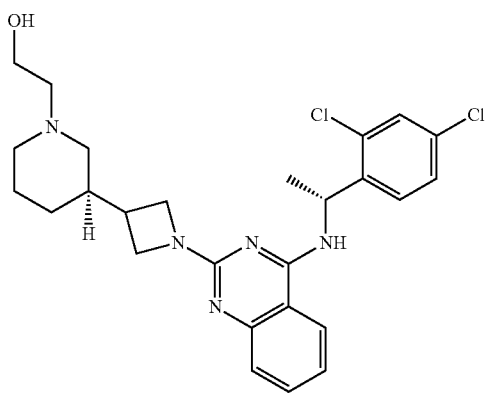 [SMILES: C[C@@H](Nc1nc(N2CC([C@H]3CCCN(CCO)C3)C2)nc2ccccc12)c1ccc(Cl)cc1Cl]

2-((R)-3-(1-(4-(((R)-1-(2,4-dichlorophenyl)ethyl)amino)quinazolin-2-yl)azetidin-3-yl)piperidin-1-yl)ethan-1-ol. ¹H NMR (400 MHz, CD₃OD; trifluoroacetic acid salt) δ 9.43 (d, J=6.2 Hz, 1H), 8.36 (dd, J=8.2, 1.1 Hz, 1H), 7.81 (ddd, J=8.4, 7.2, 1.2 Hz, 1H), 7.53-7.39 (m, 4H), 7.30 (dd, J=8.4, 2.1 Hz, 1H), 5.88-5.66 (m, 1H), 4.38 (t, J=9.1 Hz, 1H), 4.23-4.01 (m, 2H), 3.90 (d, J=5.3 Hz, 2H), 3.77-3.43 (m, 3H), 3.29-3.18 (m, 2H), 3.02-2.86 (m, 1H), 2.82-2.56 (m, 2H), 2.31-1.97 (m, 2H), 1.86 (d, J=15.1 Hz, 2H), 1.65 (d, J=7.0 Hz, 3H), 1.26-1.10 (m, 1H). [M+H] 500.0

Example 27

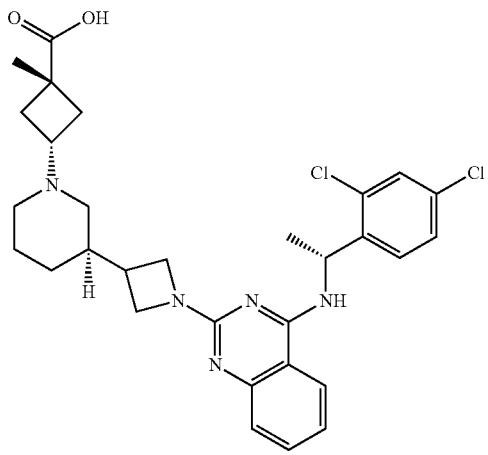 [SMILES: C[C@@H](Nc1nc(N2CC([C@H]3CCCN([C@H]4C[C@@](C)(C(=O)O)C4)C3)C2)nc2ccccc12)c1ccc(Cl)cc1Cl]

(1S,3s)-3-((R)-3-(1-(4-(((R)-1-(2,4-dichlorophenyl)amino)quinazolin-2-yl)azetidin-3-yl)piperidin-1-yl)-1-methylcyclobutane-1-carboxylic acid. ¹H NMR (400 MHz, CD₃OD; trifluoroacetic acid salt) δ 9.41 (d, J=6.1 Hz, 1H), 8.36 (d, J=8.2 Hz, 1H), 7.87-7.74 (m, 1H), 7.57-7.37 (m, 4H), 7.30 (dd, J=8.4, 2.1 Hz, 1H), 5.91-5.61 (m, 1H), 4.36 (t, J=9.1 Hz, 1H), 4.25-3.91 (m, 2H), 3.83-3.56 (m, 2H), 3.55-3.44 (m, 1H), 3.43-3.20 (m, 2H), 2.88-2.75 (m, 2H), 2.75-2.56 (m, 2H), 2.53-2.39 (m, 1H), 2.37-2.22 (m, 2H), 2.10-1.97 (m, 1H), 1.96-1.71 (m, 2H), 1.65 (d, J=6.9 Hz, 3H), 1.40 (s, 3H), 1.25-1.03 (m, 1H). [M+H] 568.0

Example 28

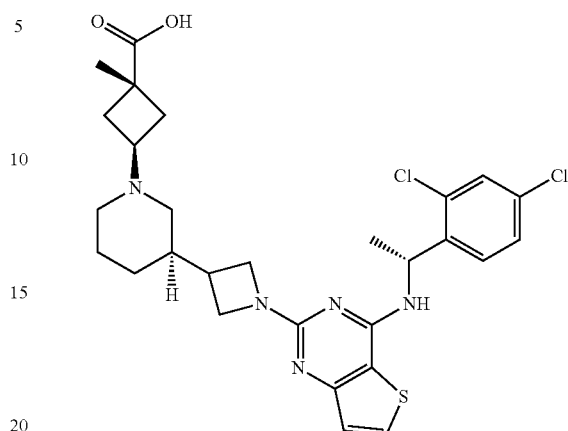

(1R,3r)-3-((R)-3-(1-(4-(((R)-1-(2,4-dichlorophenyl)ethyl)amino)thieno[3,2-d]pyrimidin-2-yl)azetidin-3-yl)piperidin-1-yl)-1-methylcyclobutane-1-carboxylic acid. ¹H NMR (400 MHz, CD₃OD; trifluoroacetic acid salt) δ 9.48 (d, J=6.2 Hz, 1H), 8.14 (d, J=5.4 Hz, 1H), 7.50 (d, J=2.1 Hz, 1H), 7.40 (d, J=8.4 Hz, 1H), 7.31 (dd, J=8.4, 2.1 Hz, 1H), 7.18 (d, J=5.4 Hz, 1H), 5.79-5.64 (m, 1H), 4.35-4.24 (m, 1H), 4.25-4.12 (m, 1H), 4.11-3.98 (m, 1H), 3.82-3.63 (m, 1H), 3.50 (d, J=12.2 Hz, 1H), 2.89-2.76 (m, 2H), 2.75-2.57 (m, 1H), 2.51-2.41 (m, 1H), 2.31-2.20 (m, 2H), 2.10-1.96 (m, 2H), 1.96-1.70 (m, 1H), 1.60 (d, J=7.1 Hz, 3H), 1.41 (s, 3H), 1.24-1.05 (m, 1H). [M+H] 574.2

Example 29

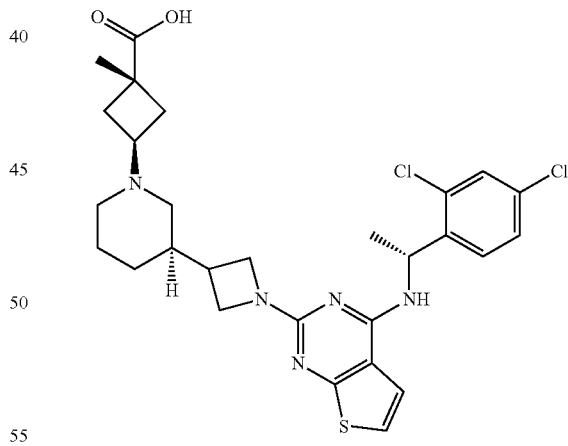

(1R,3r)-3-((R)-3-(1-(4-(((R)-1-(2,4-dichlorophenyl)ethyl)amino)thieno[2,3-d]pyrimidin-2-yl)azetidin-3-yl)piperidin-1-yl)-1-methylcyclobutane-1-carboxylic acid. ¹H NMR (400 MHz, CD₃OD; trifluoroacetic acid salt) δ 7.64 (d, J=5.8 Hz, 1H), 7.50 (d, J=2.1 Hz, 1H), 7.41 (d, J=8.4 Hz, 1H), 7.36-7.27 (m, 2H), 5.78-5.63 (m, 1H), 4.36-4.22 (m, 1H), 4.24-4.13 (m, 1H), 4.10-4.00 (m, 1H), 3.94-3.62 (m, 2H), 3.55-3.43 (m, 1H), 2.88-2.76 (m, 2H), 2.75-2.56 (m, 2H), 2.51-2.40 (m, 1H), 2.31-2.18 (m, 2H), 2.11-1.97 (m, 2H), 1.95-1.68 (m, 2H), 1.61 (d, J=7.0 Hz, 3H), 1.41 (s, 3H), 1.22-1.07 (m, 1H). [M+H] 574.2

Example 30

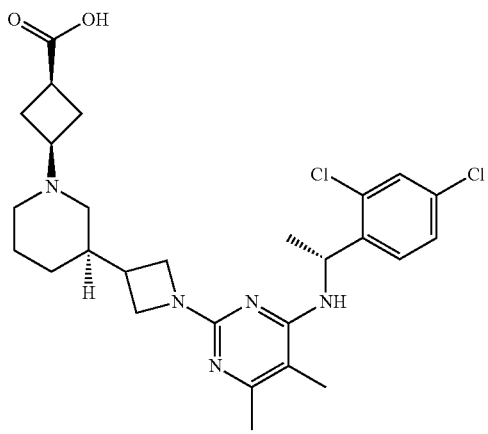 [SMILES: Cc1nc(N2CC([C@H]3CCCN([C@H]4C[C@@H](C(=O)O)C4)C3)C2)nc(N[C@H](C)c2ccc(Cl)cc2Cl)c1C]

(1S,3s)-3-((R)-3-(1-(4-(((R)-1-(2,4-dichlorophenyl)ethyl)amino)-5,6-dimethylpyrimidin-2-yl)azetidin-3-yl)piperidin-1-yl)cyclobutane-1-carboxylic acid. $^1$H NMR (400 MHz, CD$_3$OD; trifluoroacetic acid salt) δ 7.48 (s, 1H), 7.40 (d, J=8.3 Hz, 1H), 7.31 (dd, J=8.4, 2.1 Hz, 1H), 5.44-5.29 (m, 1H), 4.76-4.62 (m, 1H), 4.55-4.17 (m, 2H), 3.98 (d, J=46.2 Hz, 1H), 3.69-3.55 (m, 1H), 3.51 (d, J=13.7 Hz, 1H), 3.06-2.83 (m, 1H), 2.77-2.54 (m, 3H), 2.55-2.32 (m, 4H), 2.08-1.95 (m, 4H), 1.93-1.64 (m, 2H), 1.50 (d, J=7.0 Hz, 3H), 1.21-1.01 (m, 1H). [M+H] 532.3

Example 31

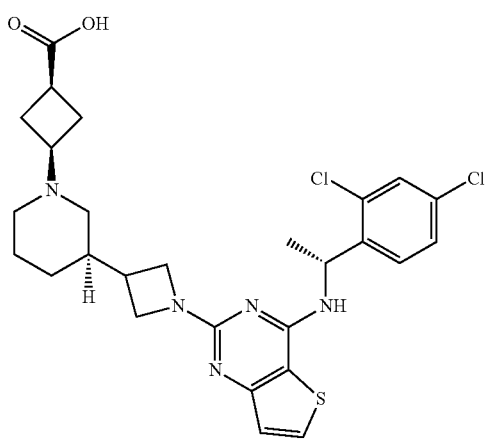 [SMILES: C[C@@H](Nc1nc(N2CC([C@H]3CCCN([C@H]4C[C@@H](C(=O)O)C4)C3)C2)nc2ccsc12)c1ccc(Cl)cc1Cl]

(1S,3s)-3-((R)-3-(1-(4-(((R)-1-(2,4-dichlorophenyl)ethyl)amino)thieno[3,2-d]pyrimidin-2-yl)azetidin-3-yl)piperidin-1-yl)cyclobutane-1-carboxylic acid. $^1$H NMR (400 MHz, CD$_3$OD; trifluoroacetic acid salt) δ 8.14 (d, J=5.4 Hz, 1H), 7.50 (d, J=2.1 Hz, 1H), 7.40 (d, J=8.4 Hz, 1H), 7.31 (dd, J=8.4, 2.1 Hz, 1H), 7.18 (d, J=5.4 Hz, 1H), 5.78-5.68 (m, 1H), 4.36-4.28 (m, 1H), 4.25-4.10 (m, 1H), 4.05 (s, 1H), 3.67-3.56 (m, 1H), 3.56-3.45 (m, 1H), 3.03-2.88 (m, 1H), 2.77-2.58 (m, 4H), 2.56-2.37 (m, 3H), 2.10-1.66 (m, 3H), 1.60 (d, J=7.1 Hz, 3H), 1.35-1.06 (m, 1H). [M+H] 560.2

Example 32

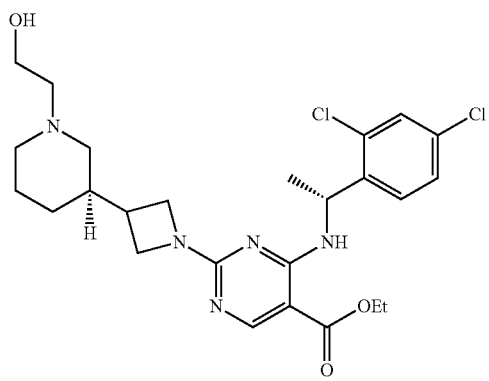

ethyl 4-(((R)-1-(2,4-dichlorophenyl)ethyl)amino)-2-(3-((R)-1-(2-hydroxyethyl)piperidin-3-yl)azetidin-1-yl)pyrimidine-5-carboxylate. $^1$H NMR (400 MHz, CD$_3$OD; trifluoroacetic acid salt) δ 9.39 (s, 1H), 8.44 (s, 1H), 7.49 (s, 1H), 7.40 (d, J=8.4 Hz, 1H), 7.32 (dd, J=8.4, 2.1 Hz, 1H), 5.68-5.54 (m, 1H), 4.46-4.26 (m, 4H), 4.15-3.95 (m, 2H), 3.93-3.83 (m, 2H), 3.65 (d, J=12.2 Hz, 1H), 3.59-3.43 (m, 1H), 2.99-2.80 (m, 1H), 2.65 (s, 1H), 2.20-1.96 (m, 2H), 1.94-1.75 (m, 2H), 1.59 (d, J=7.0 Hz, 3H), 1.38 (t, J=7.1 Hz, 3H), 1.16 (d, J=13.1 Hz, 1H). [M+H] 522.2

Example 33

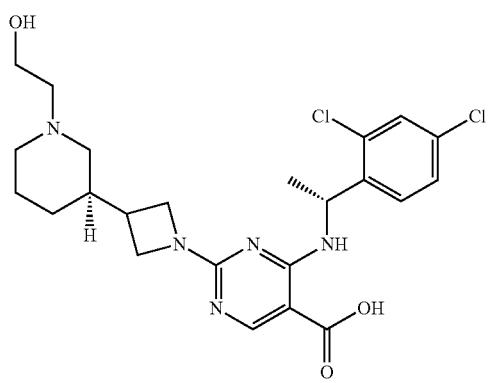 [SMILES: CCOC(=O)c1cnc(N2CC([C@H]3CCCN(CCO)C3)C2)nc1N[C@H](C)c1ccc(Cl)cc1Cl]

4-(((R)-1-(2,4-dichlorophenyl)ethyl)amino)-2-(3-((R)-1-(2-hydroxyethyl)piperidin-3-yl)azetidin-1-yl)pyrimidine-5-carboxylic acid. $^1$H NMR (400 MHz, CD$_3$OD; trifluoroacetic acid salt) δ 9.65 (s, 1H), 8.42 (s, 1H), 7.49 (s, 1H), 7.39 (d, J=8.4 Hz, 1H), 7.32 (dd, J=8.4, 2.1 Hz, 1H), 5.67-5.47 (m, 1H), 4.44-4.13 (m, 2H), 4.13-3.95 (m, 2H), 3.97-3.84 (m, 2H), 3.65 (d, J=12.5 Hz, 1H), 3.59-3.42 (m, 1H), 2.98-2.85 (m, 1H), 2.76-2.52 (m, 2H), 2.26-1.93 (m, 2H), 1.97-1.76 (m, 2H), 1.59 (d, J=7.0 Hz, 3H), 1.17 (d, J=13.2 Hz, 1H). [M+H] 494.2

Example 34

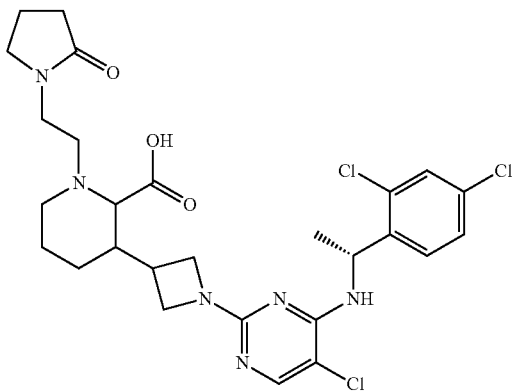 [SMILES: C[C@@H](Nc1nc(N2CC(C3CCCN(CCN4CCCC4=O)C3C(=O)O)C2)ncc1Cl)c1ccc(Cl)cc1Cl]

3-(1-(5-chloro-4-(((R)-1-(2,4-dichlorophenyl)ethyl)amino)pyrimidin-2-yl)azetidin-3-yl)-1-(2-(2-oxopyrrolidin-1-yl)ethyl)piperidine-2-carboxylic acid. $^1$H NMR (400 MHz, CD$_3$OD; trifluoroacetic acid salt) δ 8.78 (d, J=7.1 Hz, 1H), 7.96 (s, 1H), 7.57-7.45 (m, 1H), 7.41 (dd, J=8.6, 3.0 Hz, 1H), 7.32 (dd, J=8.4, 2.1 Hz, 1H), 5.73-5.59 (m, 1H), 4.56-4.40 (m, 1H), 4.34-3.79 (m, 4H), 3.79-3.57 (m, 1H), 3.57-3.37 (m, 4H), 2.98-2.73 (m, 1H), 2.52-2.30 (m, 3H), 2.16-2.01 (m, 2H), 2.01-1.92 (m, OH), 1.91-1.79 (m, OH), 1.76-1.61 (m, 1H), 1.59 (d, J=7.0 Hz, 3H), 1.53-1.22 (m, 1H). [M+H] 595.2

Example 35

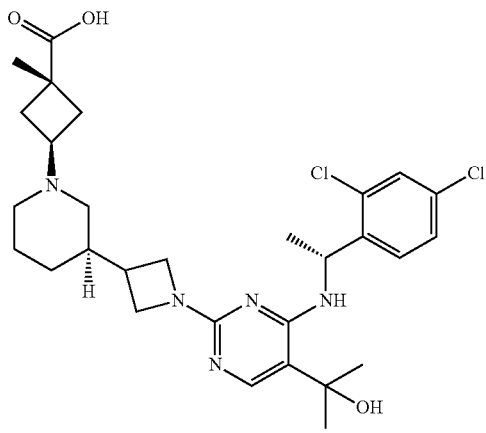 [SMILES: C[C@@H](Nc1nc(N2CC([C@H]3CCCN([C@H]4C[C@](C)(C(=O)O)C4)C3)C2)ncc1C(C)(C)O)c1ccc(Cl)cc1Cl]

(1R,3r)-3-((R)-3-(1-(4-(((R)-1-(2,4-dichlorophenyl)ethyl)amino)-5-(2-hydroxypropan-2-yl)pyrimidin-2-yl)azetidin-3-yl)piperidin-1-yl)-1-methylcyclobutane-1-carboxylic acid. $^1$H NMR (400 MHz, CD$_3$OD; trifluoroacetic acid salt) δ 7.57-7.44 (m, 2H), 7.41-7.27 (m, 2H), 5.65-5.53 (m, 1H), 4.34-4.19 (m, 1H), 4.19-4.05 (m, 1H), 4.03-3.92 (m, 1H), 3.82-3.69 (m, 1H), 3.50 (d, J=13.0 Hz, 1H), 2.87-2.76 (m, 2H), 2.77-2.51 (m, 1H), 2.54-2.37 (m, 1H), 2.30-2.15 (m, 2H), 2.12-1.96 (m, 1H), 1.82 (dd, J=46.9, 14.3 Hz, 1H), 1.66-1.52 (m, 8H), 1.42 (s, 3H), 1.22-1.08 (m, 1H). [M+H] 576.2

Example 36

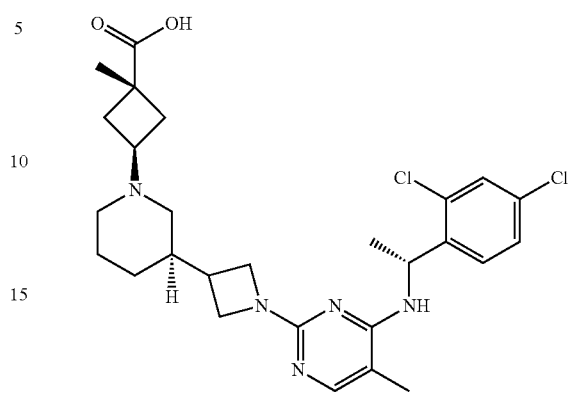

(1R,3r)-3-((R)-3-(1-(4-(((R)-1-(2,4-dichlorophenyl)ethyl)amino)-5-methylpyrimidin-2-yl)azetidin-3-yl)piperidin-1-yl)-1-methylcyclobutane-1-carboxylic acid. 1H NMR $^1$H NMR (400 MHz, CD$_3$CN; trifluoroacetic acid salt) 7.48 (d, J=2.1 Hz, 1H), 7.43-7.37 (m, 2H), 7.30 (dd, J=8.4, 2.1 Hz, 1H), 7.07 (d, J=6.3 Hz, 1H), 5.56-5.48 (m, 1H), 4.17-4.11 (m, 1H), 3.91-3.85 (m, 1H), 3.60-3.49 (m, 1H), 3.42-3.35 (m, 1H), 3.30-3.22 (m, 2H), 2.74-2.64 (m, 2H), 2.55-2.30 (m, 4H), 2.25-2.17 (m, 1H), 2.15-2.06 (m, 1H), 2.03 (s, 3H), 1.90-1.86 (m, 1H), 1.83-1.69 (m, 2H), 1.55 (d, J=7.1 Hz, 3H), 1.39-1.27 (m, 4H), 1.08-0.96 (m, 1H). [M+H] 532.1

Example 37

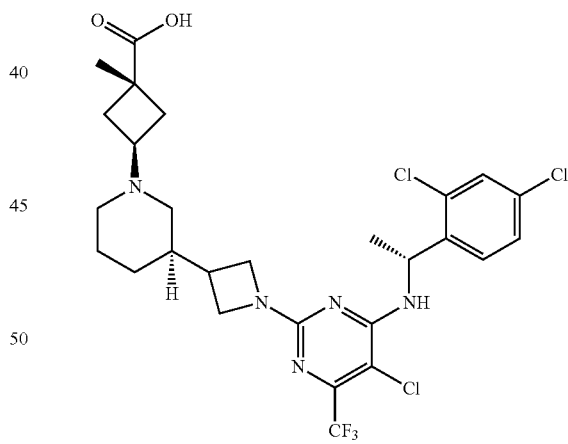

(1R,3r)-3-((R)-3-(1-(5-chloro-4-(((R)-1-(2,4-dichlorophenyl)ethyl)amino)-6-(trifluoromethyl)pyrimidin-2-yl)azetidin-3-yl)piperidin-1-yl)-1-methylcyclobutane-1-carboxylic acid. $^1$H NMR (400 MHz, CD$_3$CN; trifluoroacetic acid salt) δ 9.83 (s, 1H), 7.50-7.47 (m, 1H), 7.42-7.38 (m, 1H), 7.33-7.28 (m, 1H), 6.64 (d, J=6.3 Hz, 1H), 5.53-5.42 (m, 1H), 4.01 (t, J=8.8 Hz, 1H), 3.89 (s, 1H), 3.78-3.68 (m, 1H), 3.67-3.54 (m, 1H), 3.44-3.36 (m, 1H), 3.31-3.26 (m, 1H), 2.79-2.65 (m, 3H), 2.61-2.48 (m, 1H), 2.44-2.20 (m, 4H), 1.94-1.90 (m, 1H), 1.86-1.69 (m, 2H), 1.54 (d, J=7.1 Hz, 3H), 1.46-1.40 (m, 1H), 1.37 (s, 3H), 1.10-0.97 (m, 1H). [M+H] 620.0

Example 38

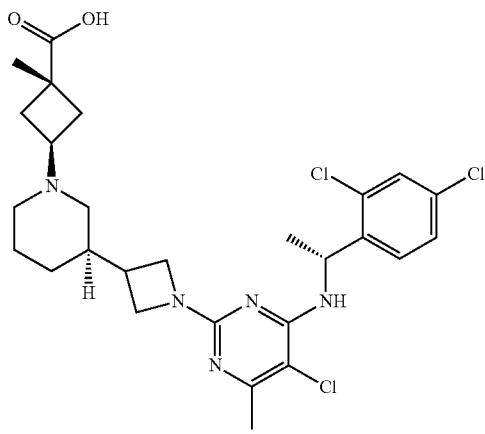 [SMILES: Cc1nc(N2CC([C@H]3CCCN([C@H]4C[C@](C)(C(=O)O)C4)C3)C2)nc(N[C@H](C)c2ccc(Cl)cc2Cl)c1Cl]

(1R,3r)-3-((R)-3-(1-(5-chloro-4-(((R)-1-(2,4-dichlorophenyl)ethyl)amino)-6-methylpyrimidin-2-yl)azetidin-3-yl)piperidin-1-yl)-1-methylcyclobutane-1-carboxylic acid. $^1$H NMR (400 MHz, CD$_3$CN; trifluoroacetic acid salt) δ 11.58 (s, 1H), 7.51 (d, J=2.1 Hz, 1H), 7.41 (d, J=8.4 Hz, 1H), 7.34 (dd, J=8.4, 2.1 Hz, 1H), 7.31 (d, J=6.4 Hz, 1H), 5.58-5.48 (m, 1H), 4.26-4.17 (m, 1H), 4.01-3.95 (m, 1H), 3.62-3.53 (m, 1H), 3.45-3.37 (m, 1H), 3.33-3.26 (m, 1H), 2.77-2.65 (m, 2H), 2.59-2.42 (m, 3H), 2.39 (s, 3H), 2.28-2.06 (m, 2H), 1.95-1.91 (m, 2H), 1.84-1.73 (m, 3H), 1.58 (d, J=7.1 Hz, 3H), 1.40-1.36 (m, 1H), 1.35 (s, 3H), 1.11-0.96 (m, 1H). [M+H] 566.0

Example 39

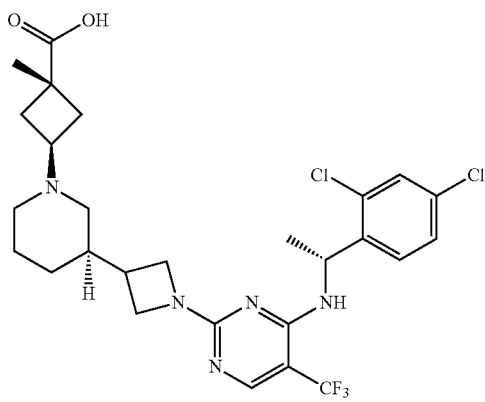 [SMILES: C[C@@H](Nc1nc(N2CC([C@H]3CCCN([C@H]4C[C@](C)(C(=O)O)C4)C3)C2)ncc1C(F)(F)F)c1ccc(Cl)cc1Cl]

(1R,3r)-3-((R)-3-(1-(4-(((R)-1-(2,4-dichlorophenyl)ethyl)amino)-5-(trifluoromethyl)pyrimidin-2-yl)azetidin-3-yl)piperidin-1-yl)-1-methylcyclobutane-1-carboxylic acid. $^1$H NMR (400 MHz, CD$_3$CN; trifluoroacetic acid salt) δ 10.51 (s, 1H), 8.22-8.17 (m, 1H), 7.53-7.49 (m, 1H), 7.54-7.32 (m, 2H), 7.09 (d, J=6.4 Hz, 1H), 5.70-5.55 (m, 1H), 4.31-4.17 (m, 2H), 4.11-3.93 (m, 2H), 3.69-3.49 (m, 2H), 3.46-3.35 (m, 1H), 3.34-3.21 (m, 1H), 2.81-2.65 (m, 2H), 2.62-2.48 (m, 2H), 2.48-2.19 (m, 4H), 1.87-1.67 (m, 2H), 1.59 (d, J=7.1 Hz, 3H), 1.40 (s, 3H), 1.15-0.97 (m, 1H). [M+H] 586.0

Example 40

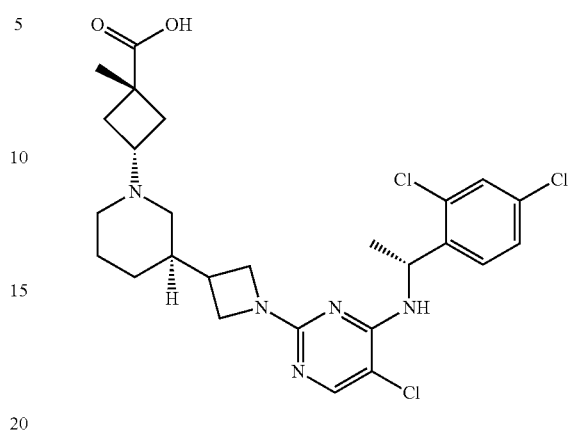

(1S,3s)-3-((R)-3-(1-(5-chloro-4-(((R)-1-(2,4-dichlorophenyl)ethyl)amino)pyrimidin-2-yl)azetidin-3-yl)piperidin-1-yl)-1-methylcyclobutane-1-carboxylic acid. $^1$H NMR (400 MHz, CD$_3$OD; trifluoroacetic acid salt) δ 8.78 (d, J=6.7 Hz, 1H), 7.96 (s, 1H), 7.48 (t, J=1.9 Hz, 1H), 7.41 (dd, J=8.4, 1.7 Hz, 1H), 7.32 (dt, J=8.5, 1.9 Hz, 1H), 5.72-5.56 (m, 1H), 4.33-4.21 (m, 1H), 4.20-3.85 (m, 3H), 3.78-3.64 (m, 1H), 3.54-3.43 (m, 1H), 2.77-2.55 (m, 5H), 2.45 (t, J=12.2 Hz, 1H), 2.36-2.22 (m, 2H), 2.12-1.94 (m, 2H), 1.93-1.68 (m, 2H), 1.59 (d, J=7.1 Hz, 3H), 1.45 (s, 3H), 1.23-1.06 (m, 1H). [M+H] 552.0

Example 41

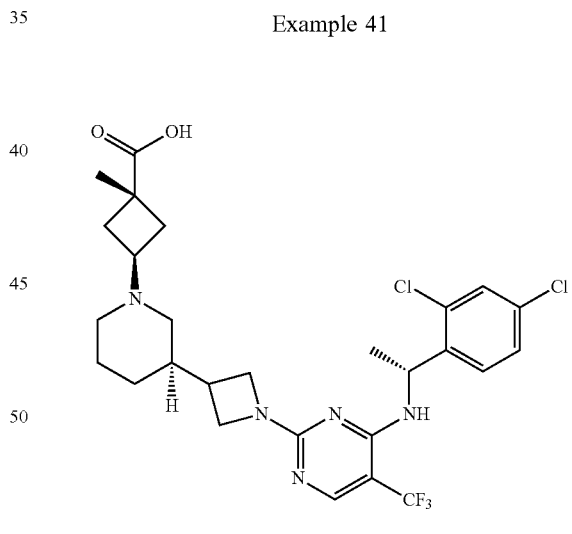

(1R,3r)-3-((R)-3-(1-(5-cyclopropyl-4-(((R)-1-(2,4-dichlorophenyl)ethyl)amino)pyrimidin-2-yl)azetidin-3-yl)piperidin-1-yl)-1-methylcyclobutane-1-carboxylic acid. $^1$H NMR (400 MHz, CD$_3$CN; trifluoroacetic acid salt) δ 11.50 (s, 1H), 7.49 (d, J=2.1 Hz, 1H), 7.44-7.38 (m, 2H), 7.32 (dd, J=8.4, 2.2 Hz, 1H), 7.28 (d, J=6.5 Hz, 1H), 5.60-5.49 (m, 1H), 4.21-4.09 (m, 2H), 3.97-3.87 (m, 2H), 3.62-3.48 (m, 2H), 3.45-3.23 (m, 2H), 2.75-2.65 (m, 2H), 2.55-2.32 (m, 4H), 2.27-2.04 (m, 2H), 1.93-1.84 (m, 1H), 1.85-1.72 (m, 2H), 1.58 (d, J=7.1 Hz, 3H), 1.32 (s, 3H), 1.08-0.94 (m, 3H), 0.61-0.50 (m, 2H). [M+H] 558.1

Example 42

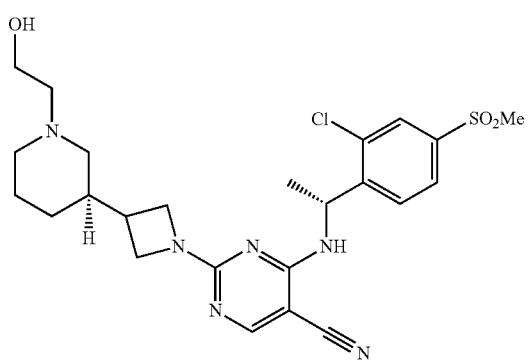 [SMILES: C[C@@H](Nc1nc(N2CC([C@H]3CCCN(CCO)C3)C2)ncc1C#N)c1ccc(S(C)(=O)=O)cc1Cl]

4-(((R)-1-(2-chloro-4-(methylsulfonyl)phenyl)ethyl)amino)-2-(3-((R)-1-(2-hydroxyethyl)piperidin-3-yl)azetidin-1-yl)pyrimidine-5-carbonitrile. $^1$H NMR (400 MHz, CD$_3$OD; trifluoroacetic acid salt) δ 8.25 (s, 1H), 8.02 (s, 1H), 7.85 (dd, J=8.2, 1.9 Hz, 1H), 7.67 (d, J=8.2 Hz, 1H), 5.68-5.49 (m, 1H), 4.13 (t, J=9.1 Hz, 2H), 3.88 (d, J=18.8 Hz, 4H), 3.65 (d, J=12.2 Hz, 1H), 3.27-3.21 (m, 2H), 3.17 (s, 3H), 2.91 (td, J=12.8, 3.1 Hz, 1H), 2.70-2.56 (m, 1H), 2.11-1.69 (m, 4H), 1.58 (d, J=7.1 Hz, 3H), 1.23-1.03 (m, 1H). [M+H] 519.0

Example 43

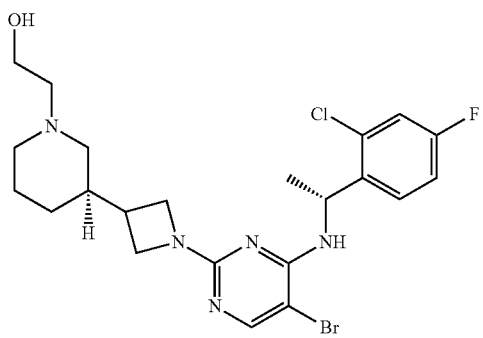 [SMILES: C[C@@H](Nc1nc(N2CC([C@H]3CCCN(CCO)C3)C2)ncc1Br)c1ccc(F)cc1Cl]

2-((R)-3-(1-(5-bromo-4-(((R)-1-(2-chloro-4-fluorophenyl)ethyl)amino)pyrimidin-2-yl)azetidin-3-yl)piperidin-1-yl)ethan-1-ol. $^1$H NMR (400 MHz, CD$_3$OD; trifluoroacetic acid salt) δ: 7.90 (s, 1H), 7.43 (dd, J=8.7, 6.1 Hz, 1H), 7.21 (dd, J=8.6, 2.6 Hz, 1H), 7.05 (td, J=8.4, 2.6 Hz, 1H), 5.58 (q, J=7.1 Hz, 1H), 4.12 (t, J=8.7 Hz, 1H), 4.00 (t, J=9.3 Hz, 1H), 3.89 (t, J=5.1 Hz, 2H), 3.84-3.74 (m, 1H), 3.65 (d, J=12.1 Hz, 2H), 3.51 (d, J=12.3 Hz, 1H), 3.24 (q, J=4.8 Hz, 2H), 2.91 (td, J=14.3, 13.4, 3.0 Hz, 1H), 2.66 (t, J=12.1 Hz, 1H), 2.48 (h, J=8.0 Hz, 1H), 2.03 (d, J=14.2 Hz, 2H), 1.97-1.65 (m, 3H), 1.54 (d, J=7.1 Hz, 3H), 1.23-1.05 (m, 1H). [M+H] 512.1

Example 44

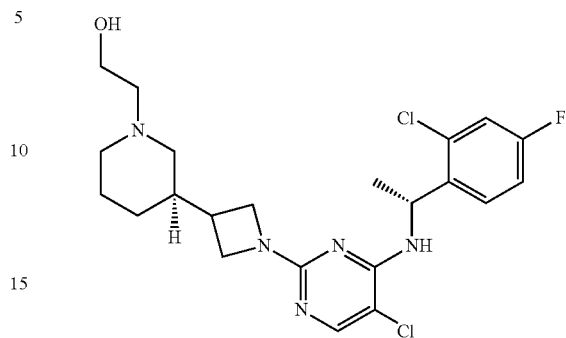

2-((R)-3-(1-(5-chloro-4-(((R)-1-(2-chloro-4-fluorophenyl)ethyl)amino)pyrimidin-2-yl)azetidin-3-yl)piperidin-1-yl)ethan-1-ol. $^1$H NMR (400 MHz, CD$_3$OD; trifluoroacetic acid salt) δ: 7.96 (s, 1H), 7.46 (dd, J=8.8, 5.9 Hz, 1H), 7.25 (dd, J=8.7, 2.6 Hz, 1H), 7.09 (td, J=8.4, 2.7 Hz, 1H), 5.68 (q, J=7.1 Hz, 1H), 4.37-4.25 (m, 1H), 4.22-4.12 (m, 1H), 3.99 (s, 1H), 3.90 (t, J=5.1 Hz, 3H), 3.66 (d, J=12.4 Hz, 1H), 3.53 (d, J=12.5 Hz, 1H), 3.28-3.22 (m, 2H), 2.92 (td, J=12.8, 3.1 Hz, 1H), 2.74-2.55 (m, 2H), 2.11 (dd, J=15.7, 8.2 Hz, 1H), 2.03 (d, J=15.5 Hz, 1H), 1.86 (t, J=14.7 Hz, 2H), 1.59 (d, J=7.1 Hz, 3H), 1.25-1.08 (m, 1H). [M+H] 468.0

Example 45

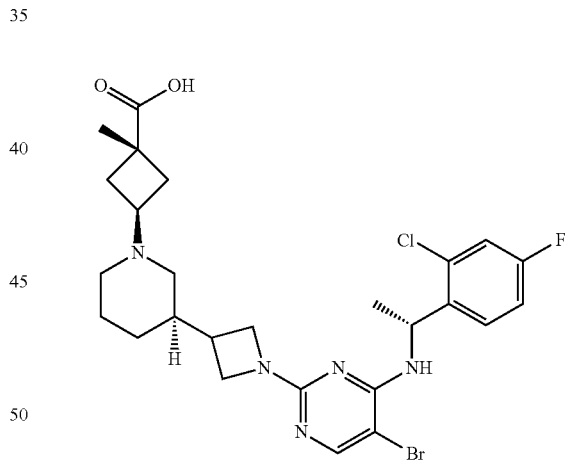

(1R,3r)-3-((R)-3-(1-(5-bromo-4-(((R)-1-(2-chloro-4-fluorophenyl)ethyl)amino)pyrimidin-2-yl)azetidin-3-yl)piperidin-1-yl)-1-methylcyclobutane-1-carboxylic acid. $^1$H NMR (400 MHz, CD$_3$OD; trifluoroacetic acid salt) δ: 8.02 (s, 1H), 7.47 (dd, J=8.7, 5.9 Hz, 1H), 7.25 (dd, J=8.6, 2.7 Hz, 1H), 7.13-7.04 (m, 1H), 5.67 (q, J=7.0 Hz, 1H), 4.25 (t, J=8.9 Hz, 1H), 4.14 (s, 1H), 4.00 (s, 1H), 3.75 (q, J=8.4 Hz, 1H), 3.56-3.44 (m, 1H), 2.92-2.76 (m, 2H), 2.71 (d, J=12.7 Hz, 1H), 2.60 (dd, J=15.5, 7.5 Hz, 1H), 2.45 (t, J=12.1 Hz, 1H), 2.34-2.17 (m, 2H), 2.04 (d, J=14.9 Hz, 2H), 1.82 (dd, J=39.0, 13.6 Hz, 2H), 1.59 (d, J=7.1 Hz, 3H), 1.42 (s, 3H), 1.15 (q, J=12.4 Hz, 1H). [M+H] 580.0

Example 46

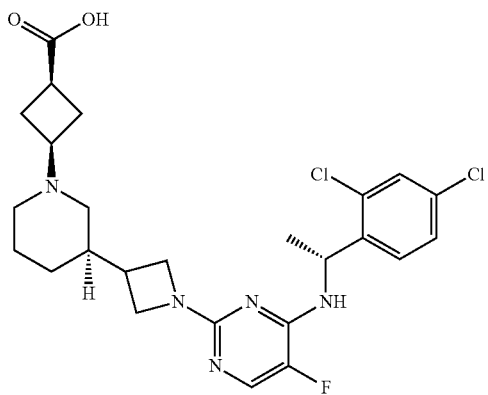

(1S,3s)-3-((R)-3-(1-(4-(((R)-1-(2,4-dichlorophenyl)ethyl)amino)-5-fluoropyrimidin-2-yl)azetidin-3-yl)piperidin-1-yl)cyclobutane-1-carboxylic acid. H NMR (400 MHz, CD$_3$OD; trifluoroacetic acid salt) δ 10.83-10.57 (br s, 1H), 7.96 (br s, 1H), 7.79 (d, J=5.3 Hz, 1H), 7.51 (d, J=2.0 Hz, 1H), 7.44 (d, J=8.4 Hz, 1H), 7.35 (dd, J=8.4, 1.9 Hz, 1H), 5.59-5.50 (m, 1H), 4.18 (t, J=8.9 Hz, 1H), 4.12-4.00 (m, 1H), 3.94 (d, J=5.5 Hz, 1H), 3.81-3.62 (m, 1H), 3.43 (d, J=9.4 Hz, 2H), 3.32 (d, J=11.9 Hz, 1H), 2.95-2.82 (m, 1H), 2.62-2.46 (m, 6H), 2.26 (t, J=11.7 Hz, 1H), 2.13 (d, J=9.5 Hz, 1H), 1.58 (d, J=7.0 Hz, 3H), 1.12-0.99 (m, 1H). [M+H]522.0

Example 47

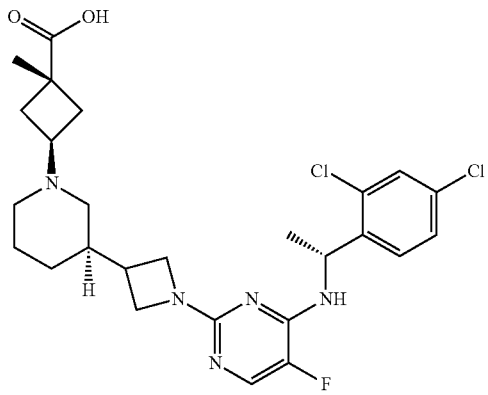 [SMILES: C[C@@H](Nc1nc(N2CC([C@H]3CCCN([C@H]4C[C@](C)(C(=O)O)C4)C3)C2)ncc1F)c1ccc(Cl)cc1Cl]

(1R,3r)-3-((R)-3-(1-(4-(((R)-1-(2,4-dichlorophenyl)ethyl)amino)-5-fluoropyrimidin-2-yl)azetidin-3-yl)piperidin-1-yl)-1-methylcyclobutane-1-carboxylic acid. $^1$H NMR (400 MHz, CD$_3$CN; trifluoroacetic acid salt) δ 11.30 (s, 1H), 7.79 (d, J=5.2 Hz, 1H), 7.51 (s, 1H), 7.43 (d, J=8.5 Hz, 1H), 7.35 (d, J=8.5 Hz, 1H), 5.58-5.49 (m, 1H), 4.17 (t, J=9.1 Hz, 1H), 4.11-4.00 (m, 1H), 3.92 (s, 1H), 3.87-3.67 (m, 1H), 3.57 (d, J=7.6 Hz, 1H), 3.41 (d, J=12.8 Hz, 1H), 3.29 (d, J=10.7 Hz, 1H), 2.72 (d, J=11.4 Hz, 2H), 2.58-2.46 (m, 2H), 2.45-2.31 (m, 2H), 2.28-2.08 (m, 2H), 1.92 (s, 1H), 1.84-1.71 (m, J=12.3 Hz, 2H), 1.57 (d, J=7.1 Hz, 3H), 1.35 (s, 3H), 1.04 (q, J=13.2 Hz, 1H). [M+H] 536.0

Example 48

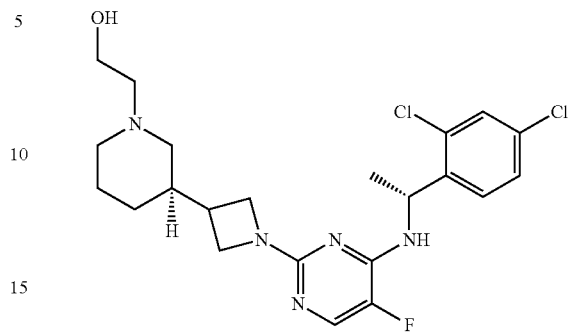

2-((R)-3-(1-(4-(((R)-1-(2,4-dichlorophenyl)ethyl)amino)-5-fluoropyrimidin-2-yl)azetidin-3-yl)piperidin-1-yl)ethan-1-ol. $^1$H NMR (400 MHz, CD$_3$CN; trifluoroacetic acid salt) δ 9.26 (br s, 1H), 7.78 (d, J=5.2 Hz, 1H), 7.52 (d, J=2.1 Hz, 1H), 7.44 (d, J=8.4 Hz, 1H), 7.36 (dd, J=8.4, 2.2 Hz, 1H), 5.58-5.50 (m, 1H), 4.20 (t, J=9.1 Hz, 1H), 4.12-4.02 (m, 1H), 3.90 (dd, J=8.3, 6.0 Hz, 1H), 3.85 (s, 2H), 3.60 (d, J=12.9 Hz, 1H), 3.47 (d, J=12.2 Hz, 1H), 3.16 (s, 2H), 2.81 (t, J=13.3 Hz, 1H), 2.70 (s, 1H), 2.57-2.47 (m, 2H), 2.20-2.07 (m, 2H), 1.90-1.77 (m, 2H), 1.57 (d, J=7.1 Hz, 3H), 1.15-1.02 (m, J=16.3 Hz, 1H). [M+H] 468.0

Calcium Flux Assay. Compounds were evaluated in a calcium flux assay substantially performed as follows. Chem5-hCCR4 cells (EMD Millipore, Hayward, Calif.; HTS009C) were cultured under standard conditions and frozen in aliquots of 10×106 cells/mL. The day prior to compound testing, a vial was rapidly thawed and pipetted into 20 mL media (DMEM+10% FBS+1% Pen-Strep+1% L-glutamine). Cells were harvested by centrifugation and re-suspended in fresh culture medium. 25 μL of cell suspension was seeded into 384-well plates (Corning, Tewksbury, Mass.; CellBind with black wall/clear bottom). The plates were centrifuged at 300 g for 10 seconds and incubated overnight at 37° C. and 5% CO2. The day of compound testing, media was removed from the plates and 25 μL serum free media was added to each well. Plates were returned to the incubator for 2 h. 25 μL assay buffer (Hank's balanced salt solution+20 mM HEPES pH 7.4) containing FLIPR Calcium 6 dye (Molecular Devices, Sunnyvale, Calif.; #R$^{8.191}$) and probenecid (2.5 mM) was added to each well and incubated at 37° C. and 5% CO2 for 2 h. Compounds in DMSO were added to the plates using an HP D300e digital dispenser, and all wells were normalized to contain 0.25 μL (0.5%) DMSO. Plates were incubated for 1 hour at 37° C. and 5% CO2. CCL22 (Peprotech; Rockyhill, N.J.) was diluted in assay buffer containing 0.1% BSA to 7.5 nM (corresponding to 5×EC80 of 1.5 nM).

Assay plates and working solution of CCL22 were transferred to the FlexStation plate reader (Molecular Devices) at 37° C. for 5 min of equilibration. Fluorescence recordings at 485 excitation/525 emission were performed at 2.5 second intervals. At t=16 seconds, 12.5 μL of CCL22 solution was added to each well and reads continued for 30 seconds at 2.5 second intervals. The minimum fluorescence (Fmin) was calculated by averaging the reads prior to ligand addition and the change in fluorescence (ΔF) was calculated by subtracting the Fmin from the average of the reads following ligand addition. The response ΔF/Fmin was plotted as a function of the compound concentration and the IC50 values were determined by non-linear regression analysis using a 4-parameter fit in either PRISM software (GraphPad; La Jolla, Calif.) or Dotmatics Browser.

Using the calcium flux assay described herein, the activity for compounds described herein was determined.

The potency levels are set forth in Table 3, wherein $IC_{50}$: A<0.1 µM; B=0.1-0.5 µM; and C>0.5 µM.

TABLE 3

| Example Number | Potency |
| --- | --- |
| 1 | A |
| 2 | B |
| 3 | C |
| 4 | C |
| 5 | B |
| 6 | B |
| 7 | C |
| 8 | A |
| 9 | A |
| 10 | A |
| 11 | A |
| 12 | A |
| 13 | A |
| 14 | A |
| 15 | C |
| 16 | A |
| 17 | A |
| 18 | A |
| 19 | A |
| 20 | A |
| 21 | C |
| 22 | A |
| 23 | B |

TABLE 3-continued

| Example Number | Potency |
| --- | --- |
| 24 | B |
| 25 | A |
| 26 | A |
| 27 | A |
| 28 | A |
| 29 | A |
| 30 | B |
| 31 | A |
| 32 | A |
| 33 | C |
| 34 | B |
| 35 | A |
| 36 | B |
| 37 | A |
| 38 | A |
| 39 | A |
| 40 | A |
| 41 | A |
| 42 | C |
| 43 | A |
| 44 | B |
| 45 | A |
| 46 | C |
| 47 | B |
| 48 | B |

Examples 49 to 53 are shown in Table 4.

The compounds disclosed in Table 4 below were synthesized using the methods previously described herein, particularly those methods used in the synthesis of the compounds of Examples 1-7 herein. The $IC_{50}$ potencies for these compounds were also measured as described earlier herein.

TABLE 4

| Ex. No. | Chemical Structure | Chemical Name | Potency |
| --- | --- | --- | --- |
| 49 | 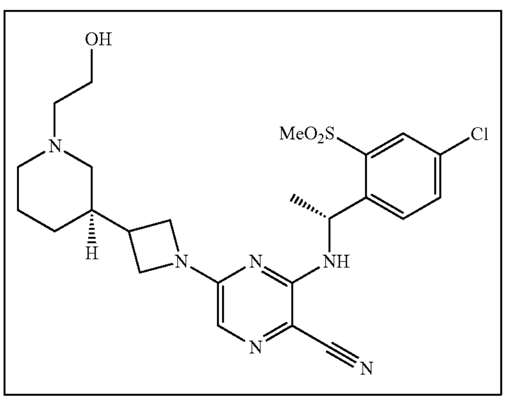 [SMILES: C[C@@H](Nc1nc(N2CC([C@H]3CCCN(CCO)C3)C2)cnc1C#N)c1ccc(Cl)cc1S(C)(=O)=O] | 3-[[(1R)-1-(4-chloro-2-methylsulfonyl-phenyl)ethyl]amino]-5-[3-[(3R)-1-(2-hydroxyethyl)-3-piperidyl]azetidin-1-yl]pyrazine-2-carbonitrile; 2,2,2-trifluoroacetic acid | C |
| 50 | 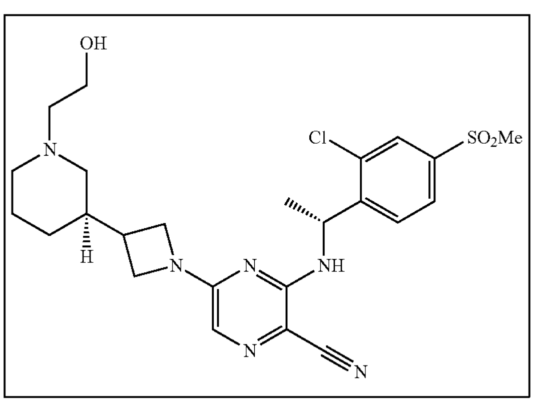 [SMILES: C[C@@H](Nc1nc(N2CC([C@H]3CCCN(CCO)C3)C2)cnc1C#N)c1ccc(S(C)(=O)=O)cc1Cl] | 5-[[(1R)-1-(2-chloro-4-methylsulfonyl-phenyl)ethyl]amino]-3-[3-[(3R)-1-(2-hydroxyethyl)-3-piperidyl]azetidin-1-yl]pyrazine-2-carbonitrile | C |

TABLE 4-continued

| Ex. No. | Chemical Structure | Chemical Name | Potency |
|---|---|---|---|
| 51 | 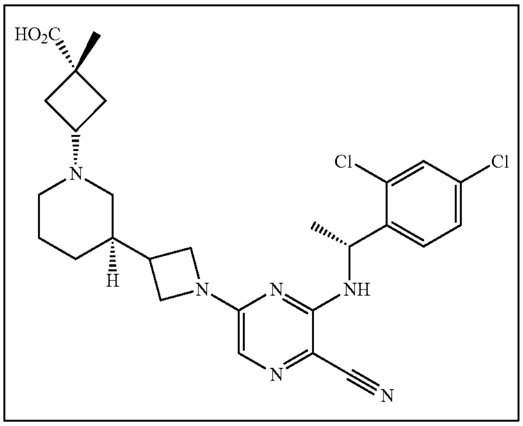 | 3-[(1S,3R)-3-[1-[5-cyano-6-[[(1R)-1-(2,4-dichlorophenyl)ethyl]amino]pyrazin-2-yl]azetidin-3-yl]-1-piperidyl]-1-methyl-cyclobutanecarboxylic acid; 2,2,2-trifluoroacetic acid | C |
| 52 | 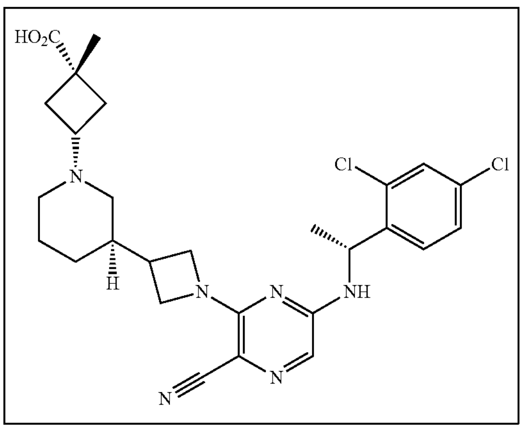 | 3-[(1S,3R)-3-[1-[3-cyano-6-[[(1R)-1-(2,4-dichlorophenyl)ethyl]amino]pyrazin-2-yl]azetidin-3-yl]-1-piperidyl]-1-methyl-cyclobutanecarboxylic acid; 2,2,2-trifluoroacetic acid | C |
| 53 | 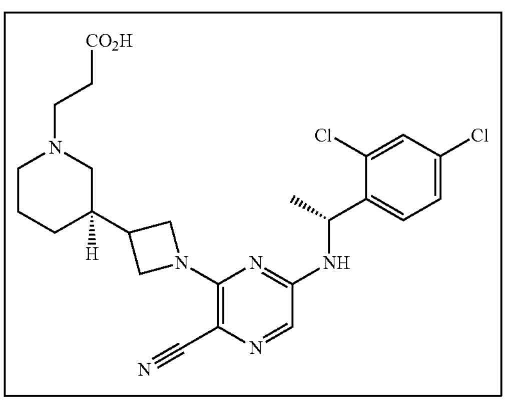 [SMILES: C[C@@H](Nc1cnc(C#N)c(N2CC([C@H]3CCCN(CCC(=O)O)C3)C2)n1)c1ccc(Cl)cc1Cl] | 3-(3-(1-(3-cyano-6-(((R)-1-(2,4-dichlorophenyl)ethyl)amino)pyrazin-2-yl)azetidin-3-yl)piperidin-1-yl)propanoic acid | C |

Examples 54 to 95 are shown in Table 5.

The compounds disclosed in Table 5 below were synthesized using the methods previously described herein, particularly those methods used in the synthesis of the compounds of Examples 8-48 herein. The $IC_{50}$ potencies for these compounds were also measured as described earlier herein.

TABLE 5

| Ex. No. | Chemical Structure | Chemical Name | Potency |
|---|---|---|---|
| 54 | 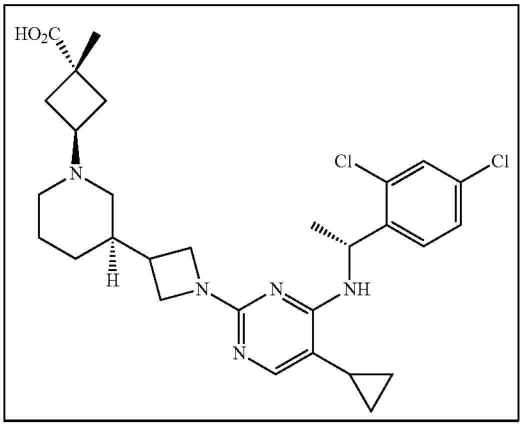 [SMILES: C[C@@H](Nc1nc(N2CC([C@H]3CCCN([C@H]4C[C@](C)(C(=O)O)C4)C3)C2)ncc1C1CC1)c1ccc(Cl)cc1Cl] | 3-[(3R)-3-[1-[5-cyclopropyl-4-[[(1R)-1-(2,4-dichlorophenyl)ethyl]amino]pyrimidin-2-yl]azetidin-3-yl]-1-piperidyl]-1-methyl-cyclobutanecarboxylic acid | A |
| 55 | 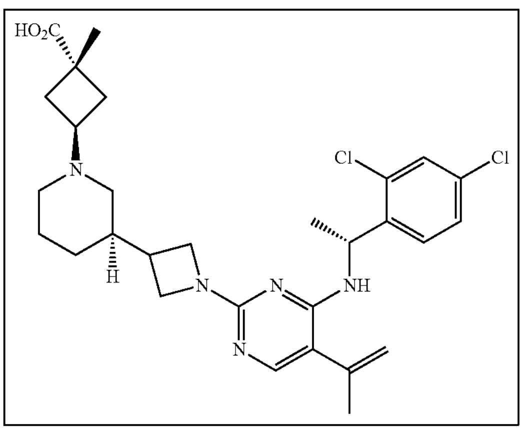 [SMILES: C=C(C)c1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[7-[(1R)-1-(2,4-dichlorophenyl)ethyl]-5-methyl-5,6-dihydropyrrolo[2,3-d]pyrimidin-2-yl]azetidin-3-yl]-1-piperidyl]-1-methyl-cyclobutanecarboxylic acid; 2,2,2-trifluoroacetic acid | A |
| 56 | 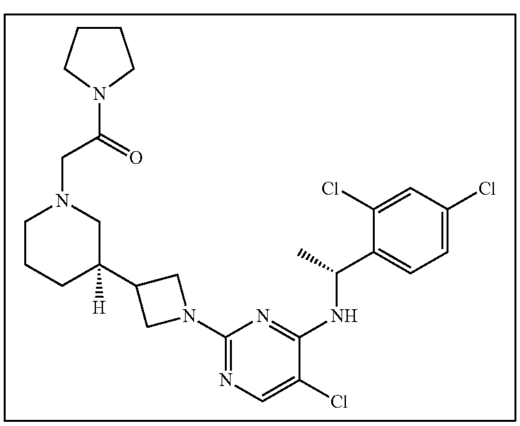 [SMILES: C[C@@H](Nc1nc(N2CC([C@H]3CCCN(CC(=O)N4CCCC4)C3)C2)ncc1Cl)c1ccc(Cl)cc1Cl] | 2-[(3R)-3-[1-[5-chloro-4-[[(1R)-1-(2,4-dichlorophenyl)ethyl]amino]pyrimidin-2-yl]azetidin-3-yl]-1-piperidyl]-1-pyrrolidin-1-yl-ethanone; 2,2,2-trifluoroacetic acid | B |

TABLE 5-continued

| Ex. No. | Chemical Structure | Chemical Name | Potency |
|---|---|---|---|
| 57 | 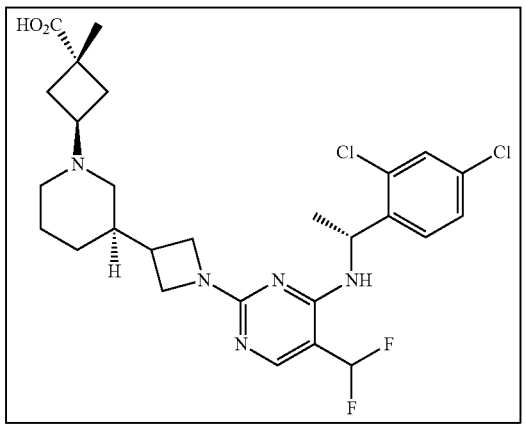 [SMILES: C[C@@H](Nc1nc(N2CC([C@H]3CCCN([C@H]4C[C@](C)(C(=O)O)C4)C3)C2)ncc1C(F)F)c1ccc(Cl)cc1Cl] | 3-[(3R)-3-[1-[2-[[(1R)-1-(2,4-dichlorophenyl)ethyl]amino]-5-(difluoromethyl)pyrimidin-4-yl]azetidin-3-yl]-1-piperidyl]-1-methyl-cyclobutanecarboxylic acid; 2,2,2-trifluoroacetic acid | A |
| 58 | 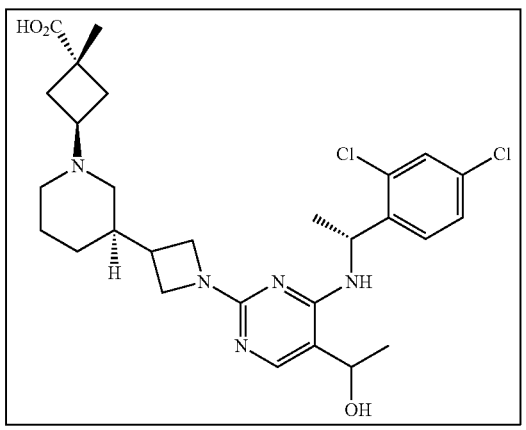 [SMILES: CC(O)c1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[4-[[(1R)-1-(2,4-dichlorophenyl)ethyl]amino]-5-(1-hydroxyethyl)pyrimidin-2-yl]azetidin-3-yl]-1-piperidyl]-1-methyl-cyclobutanecarboxylic acid; 2,2,2-trifluoroacetic acid | A |
| 59 | 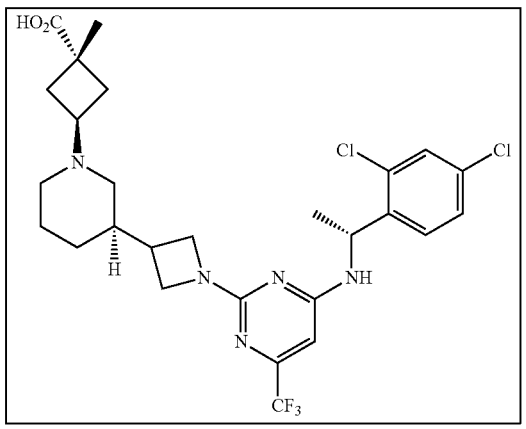 [SMILES: C[C@@H](Nc1cc(C(F)(F)F)nc(N2CC([C@H]3CCCN([C@H]4C[C@](C)(C(=O)O)C4)C3)C2)n1)c1ccc(Cl)cc1Cl] | 3-[(1R)-3-[1-[4-[[(1R)-1-(2,4-dichlorophenyl)ethyl]amino]-6-(trifluoromethyl)pyrimidin-2-yl]azetidin-3-yl]-1-piperidyl]-1-methyl-cyclobutanecarboxylic acid | B |

TABLE 5-continued

| Ex. No. | Chemical Structure | Chemical Name | Potency |
|---|---|---|---|
| 60 | 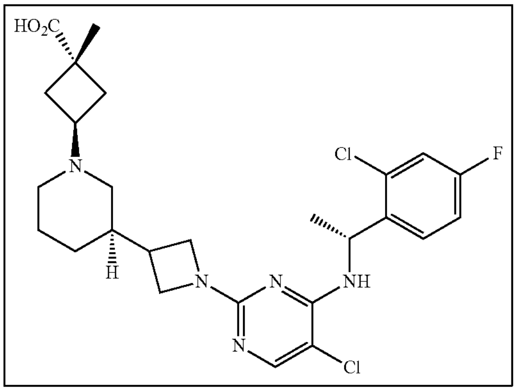 [SMILES: C[C@@H](Nc1nc(N2CC([C@H]3CCCN([C@H]4C[C@](C)(C(=O)O)C4)C3)C2)ncc1Cl)c1ccc(F)cc1Cl] | 3-[(3R)-3-[3-[5-chloro-4-[[(1R)-1-(2-chloro-4-fluoro-phenyl)ethyl]amino]pyrimidin-2-yl]cyclobutyl]-1-piperidyl]-1-methyl-cyclobutanecarboxylic acid; 2,2,2-trifluoroacetic acid | A |
| 61 | 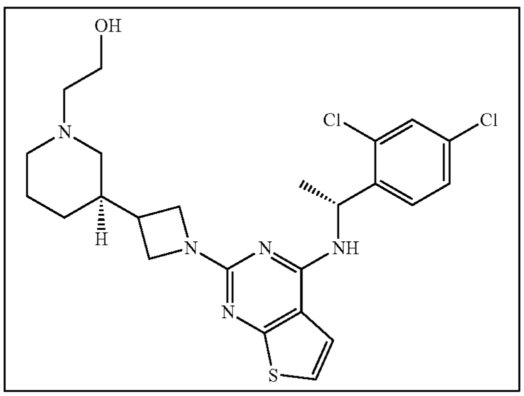 [SMILES: C[C@@H](Nc1nc(N2CC([C@H]3CCCN(CCO)C3)C2)nc2sccc12)c1ccc(Cl)cc1Cl] | 2-[(3R)-3-[1-[4-[[(1R)-1-(2,4-dichlorophenyl)ethyl]amino]thieno[2,3-d]pyrimidin-2-yl]azetidin-3-yl]-1-piperidyl]ethanol; 2,2,2-trifluoroacetic acid | A |
| 62 | 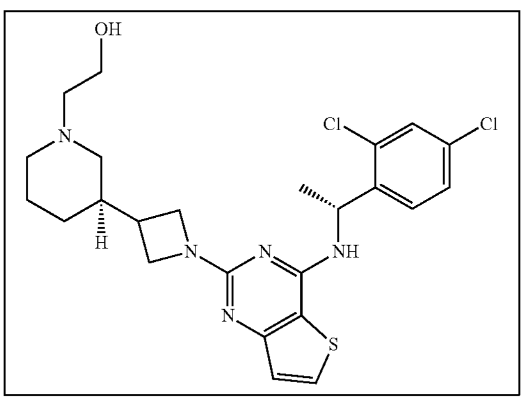 [SMILES: C[C@@H](Nc1nc(N2CC([C@H]3CCCN(CCO)C3)C2)nc2ccsc12)c1ccc(Cl)cc1Cl] | 2-[(3R)-3-[1-[4-[[(1R)-1-(2,4-dichlorophenyl)ethyl]amino]thieno[3,2-d]pyrimidin-2-yl]azetidin-3-yl]-1-piperidyl]ethanol; 2,2,2-trifluoroacetic acid | A |
| 63 | 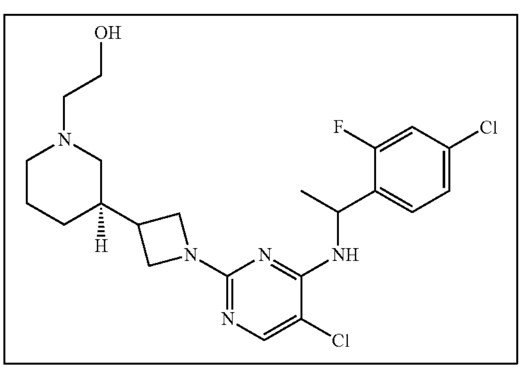 [SMILES: CC(Nc1nc(N2CC([C@H]3CCCN(CCO)C3)C2)ncc1Cl)c1ccc(Cl)cc1F] | 2-[(3R)-3-[1-[5-chloro-4-[1-(4-chloro-2-fluoro-phenyl)ethylamino]pyrimidin-2-yl]azetidin-3-yl]-1-piperidyl]ethanol; 2,2,2-trifluoroacetic acid | A |

TABLE 5-continued

| Ex. No. | Chemical Structure | Chemical Name | Potency |
|---|---|---|---|
| 64 | 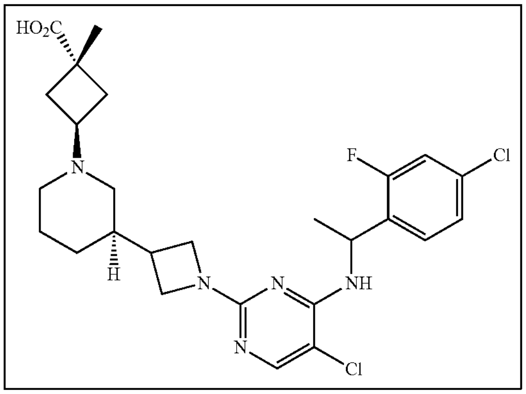 [SMILES: CC(Nc1nc(N2CC([C@H]3CCCN([C@H]4C[C@](C)(C(=O)O)C4)C3)C2)ncc1Cl)c1ccc(Cl)cc1F] | 3-[(3R)-3-[3-[5-chloro-4-[1-(4-chloro-2-fluoro-phenyl)ethylamino]pyrimidin-2-yl]cyclobutyl]-1-piperidyl]-1-methyl-cyclobutanecarboxylic acid; 2,2,2-trifluoroacetic acid | A |
| 65 | 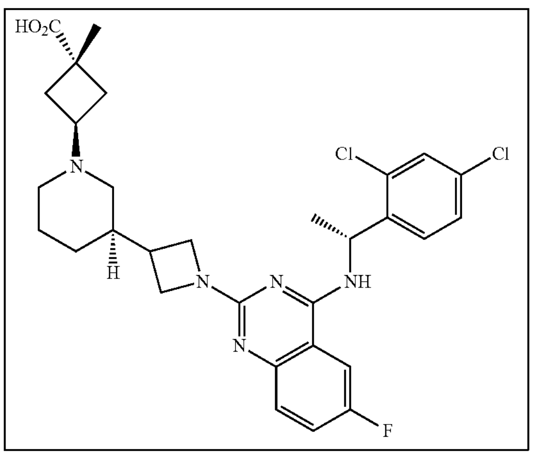 [SMILES: C[C@@H](Nc1nc(N2CC([C@H]3CCCN([C@H]4C[C@](C)(C(=O)O)C4)C3)C2)nc2ccc(F)cc12)c1ccc(Cl)cc1Cl] | 3-[(1R,3R)-3-[1-[4-[[(1R)-1-(2,4-dichlorophenyl)ethyl]amino]-6-fluoro-quinazolin-2-yl]azetidin-3-yl]-1-piperidyl]-1-methyl-cyclobutanecarboxylic acid; 2,2,2-trifluoroacetic acid | A |
| 66 | 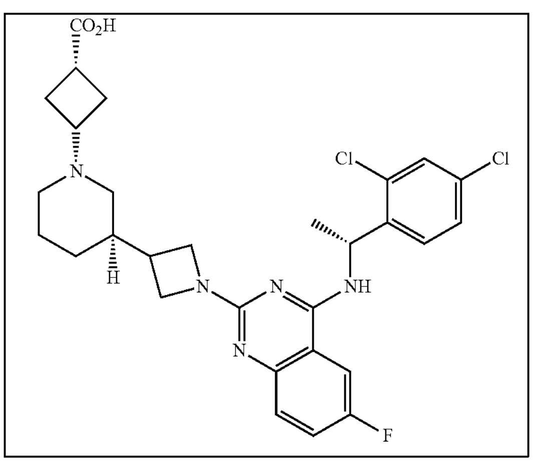 | 3-[(1S,3R)-3-[1-[4-[[(1R)-1-(2,4-dichlorophenyl)ethyl]amino]-6-fluoro-quinazolin-2-yl]azetidin-3-yl]-1-piperidyl]cyclobutanecarboxylic acid; 2,2,2-trifluoroacetic acid | A |

TABLE 5-continued

| Ex. No. | Chemical Structure | Chemical Name | Potency |
|---|---|---|---|
| 67 | 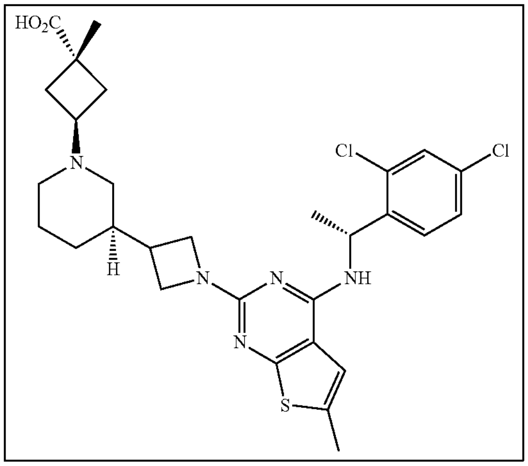 [SMILES: Cc1cc2c(N[C@H](C)c3ccc(Cl)cc3Cl)nc(N3CC([C@H]4CCCN([C@H]5C[C@](C)(C(=O)O)C5)C4)C3)nc2s1] | 3-[(3R)-3-[1-[4-[[(1R)-1-(2,4-dichlorophenyl)ethyl]amino]-6-methyl-thieno[2,3-d]pyrimidin-2-yl]azetidin-3-yl]-1-piperidyl]-1-methyl-cyclobutanecarboxylic acid; 2,2,2-trifluoroacetic acid | A |
| 68 | 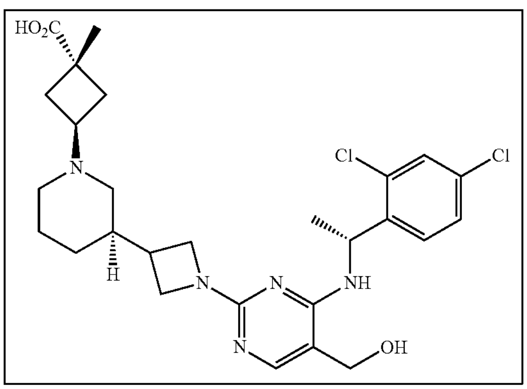 [SMILES: C[C@@H](Nc1nc(N2CC([C@H]3CCCN([C@H]4C[C@](C)(C(=O)O)C4)C3)C2)ncc1CO)c1ccc(Cl)cc1Cl] | 3-[(3R)-3-[1-[4-[[(1R)-1-(2,4-dichlorophenyl)ethyl]amino]-5-(hydroxymethyl)pyrimidin-2-yl]azetidin-3-yl]-1-piperidyl]-1-methyl-cyclobutanecarboxylic acid | A |
| 69 | 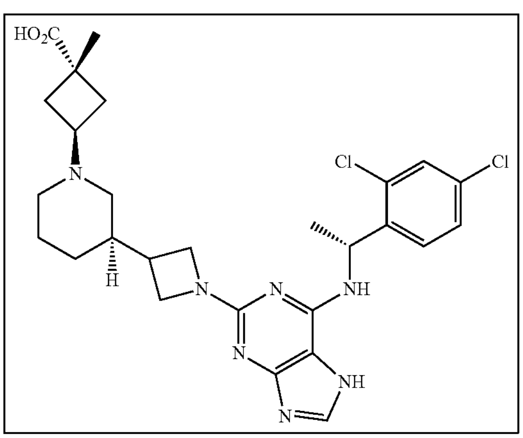 [SMILES: C[C@@H](Nc1nc(N2CC([C@H]3CCCN([C@H]4C[C@](C)(C(=O)O)C4)C3)C2)nc2nc[nH]c12)c1ccc(Cl)cc1Cl] | 3-[(3R)-3-[1-[6-[[(1R)-1-(2,4-dichlorophenyl)ethyl]amino]-7H-purin-2-yl]azetidin-3-yl]-1-piperidyl]-1-methyl-cyclobutanecarboxylic acid; 2,2,2-trifluoroacetic acid | B |

TABLE 5-continued

| Ex. No. | Chemical Structure | Chemical Name | Potency |
|---|---|---|---|
| 70 | 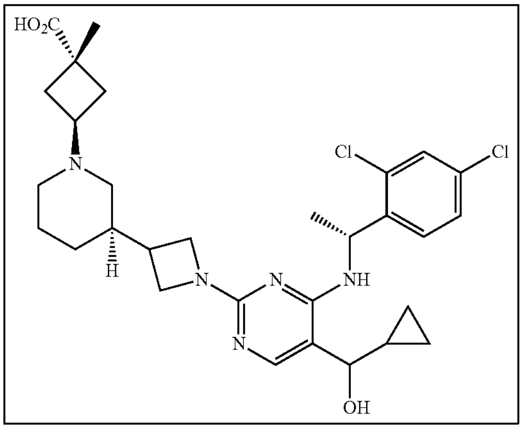 [SMILES: C[C@@H](Nc1nc(N2CC([C@H]3CCCN([C@H]4C[C@](C)(C(=O)O)C4)C3)C2)ncc1C(O)C1CC1)c1ccc(Cl)cc1Cl] | 3-[(3R)-3-[1-[5-[cyclopropyl(hydroxy)methyl]-4-[[(1R)-1-(2,4-dichlorophenyl)ethyl]amino]pyrimidin-2-yl]azetidin-3-yl]-1-piperidyl]-1-methyl-cyclobutanecarboxylic acid; 2,2,2-trifluoroacetic acid | A |
| 71 | 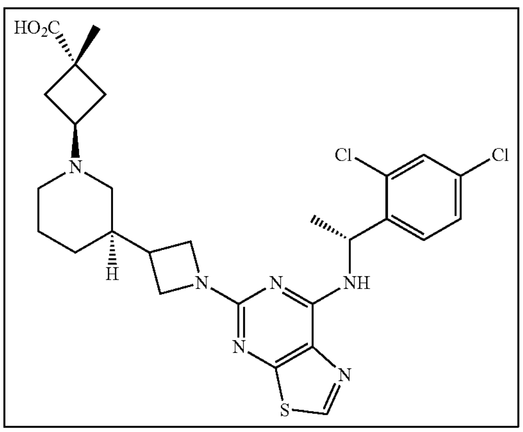 [SMILES: C[C@@H](Nc1nc(N2CC([C@H]3CCCN([C@H]4C[C@](C)(C(=O)O)C4)C3)C2)nc2scnc12)c1ccc(Cl)cc1Cl] | 3-[(3R)-3-[1-[7-[[(1R)-1-(2,4-dichlorophenyl)ethyl]amino]thiazolo[5,4-d]pyrimidin-5-yl]azetidin-3-yl]-1-piperidyl]-1-methyl-cyclobutanecarboxylic acid; 2,2,2-trifluoroacetic acid | A |
| 72 | 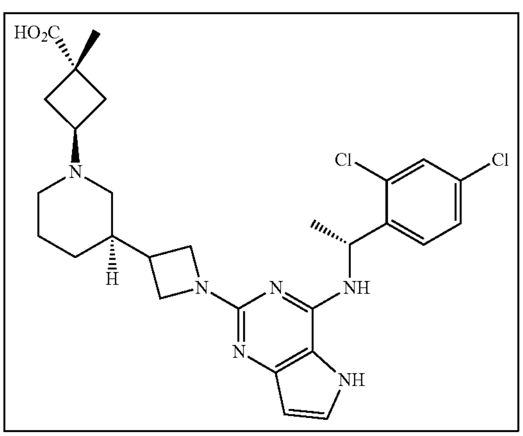 [SMILES: C[C@@H](Nc1nc(N2CC([C@H]3CCCN([C@H]4C[C@](C)(C(=O)O)C4)C3)C2)nc2cc[nH]c12)c1ccc(Cl)cc1Cl] | 3-[(3R)-3-[1-[4-[[(1R)-1-(2,4-dichlorophenyl)ethyl]amino]-5H-pyrrolo[3,2-d]pyrimidin-2-yl]azetidin-3-yl]-1-piperidyl]-1-methyl-cyclobutanecarboxylic acid; 2,2,2-trifluoroacetic acid | A |

TABLE 5-continued

| Ex. No. | Chemical Structure | Chemical Name | Potency |
|---|---|---|---|
| 73 | 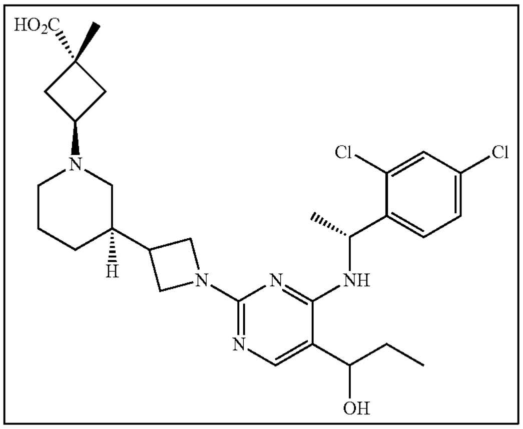 [SMILES: CCC(O)c1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[4-[[(1R)-1-(2,4-dichlorophenyl)ethyl]amino]-5-(1-hydroxypropyl)pyrimidin-2-yl]azetidin-3-yl]-1-piperidyl]-1-methyl-cyclobutanecarboxylic acid; 2,2,2-trifluoroacetic acid | A |
| 74 | 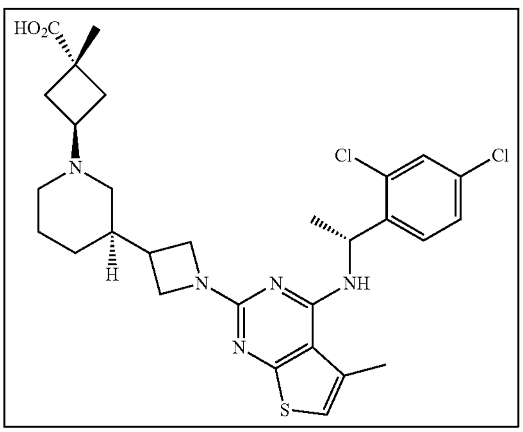 [SMILES: Cc1csc2nc(N3CC([C@H]4CCCN([C@H]5C[C@](C)(C(=O)O)C5)C4)C3)nc(N[C@H](C)c3ccc(Cl)cc3Cl)c12] | 3-[(3R)-3-[1-[4-[[(1R)-1-(2,4-dichlorophenyl)ethyl]amino]-5-methyl-thieno[2,3-d]pyrimidin-2-yl]azetidin-3-yl]-1-piperidyl]-1-methyl-cyclobutanecarboxylic acid; 2,2,2-trifluoroacetic acid | A |
| 75 | 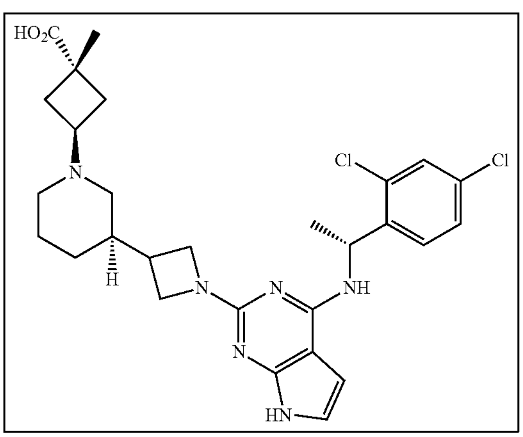 [SMILES: C[C@@H](Nc1nc(N2CC([C@H]3CCCN([C@H]4C[C@](C)(C(=O)O)C4)C3)C2)nc2[nH]ccc12)c1ccc(Cl)cc1Cl] | 3-[(3R)-3-[1-[4-[[(1R)-1-(2,4-dichlorophenyl)ethyl]amino]-7H-pyrrolo[2,3-d]pyrimidin-2-yl]azetidin-3-yl]-1-piperidyl]-1-methyl-cyclobutanecarboxylic acid; 2,2,2-trifluoroacetic acid | A |

TABLE 5-continued

| Ex. No. | Chemical Structure | Chemical Name | Potency |
|---|---|---|---|
| 76 | 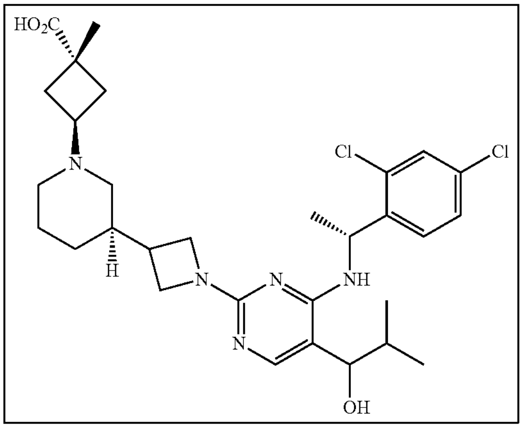 [SMILES: CC(C)C(O)c1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[4-[[(1R)-1-(2,4-dichlorophenyl)ethyl]amino]-5-(1-hydroxy-2-methyl-propyl)pyrimidin-2-yl]azetidin-3-yl]-1-piperidyl]-1-methyl-cyclobutanecarboxylic acid; 2,2,2-trifluoroacetic acid | A |
| 77 | 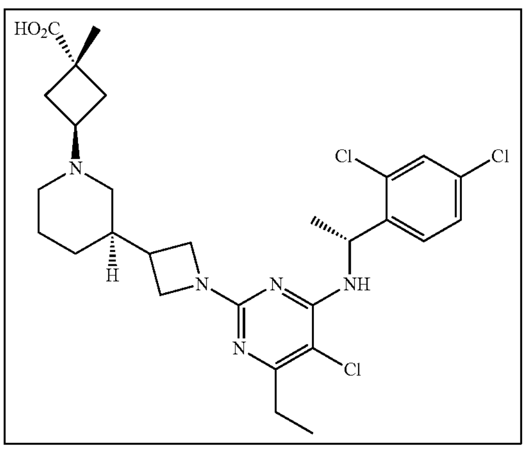 [SMILES: CCc1nc(N2CC([C@H]3CCCN([C@H]4C[C@](C)(C(=O)O)C4)C3)C2)nc(N[C@H](C)c2ccc(Cl)cc2Cl)c1Cl] | 3-[(3R)-3-[1-[5-chloro-4-[[(1R)-1-(2,4-dichlorophenyl)ethyl]amino]-6-ethyl-pyrimidin-2-yl]azetidin-3-yl]-1-piperidyl]-1-methyl-cyclobutanecarboxylic acid; 2,2,2-trifluoroacetic acid | A |
| 78 | 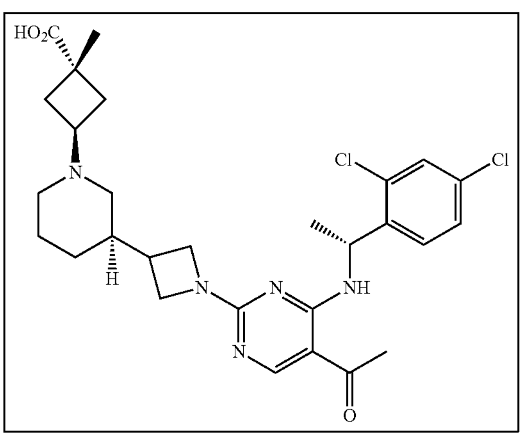 [SMILES: CC(=O)c1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[5-acetyl-4-[[(1R)-1-(2,4-dichlorophenyl)ethyl]amino]pyrimidin-2-yl]azetidin-3-yl]-1-piperidyl]-1-methyl-cyclobutanecarboxylic acid; 2,2,2-trifluoroacetic acid | A |

TABLE 5-continued

| Ex. No. | Chemical Structure | Chemical Name | Potency |
|---|---|---|---|
| 79 | 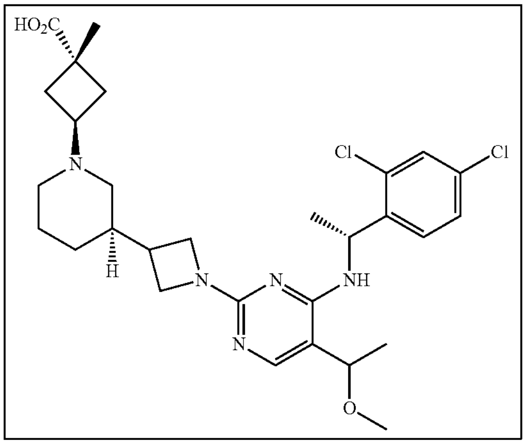 [SMILES: COC(C)c1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[4-[[(1R)-1-(2,4-dichlorophenyl)ethyl]amino]-5-(1-methoxyethyl)pyrimidin-2-yl]azetidin-3-yl]-1-piperidyl]-1-methyl-cyclobutanecarboxylic acid; 2,2,2-trifluoroacetic acid | A |
| 80 | 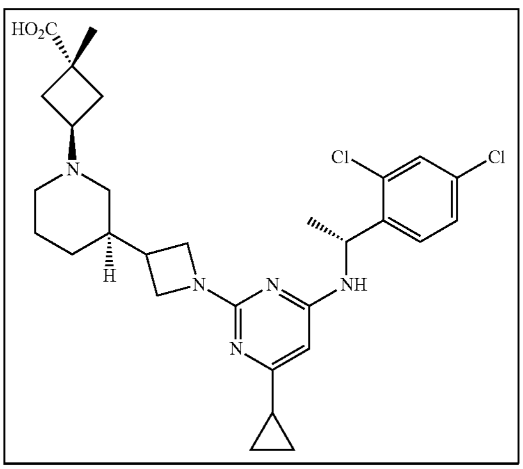 [SMILES: C[C@@H](Nc1cc(C2CC2)nc(N2CC([C@H]3CCCN([C@H]4C[C@](C)(C(=O)O)C4)C3)C2)n1)c1ccc(Cl)cc1Cl] | 3-[(3R)-3-[1-[4-cyclopropyl-6-[[(1R)-1-(2,4-dichlorophenyl)ethyl]amino]pyrimidin-2-yl]azetidin-3-yl]-1-piperidyl]-1-methyl-cyclobutanecarboxylic acid; 2,2,2-trifluoroacetic acid | A |
| 81 | 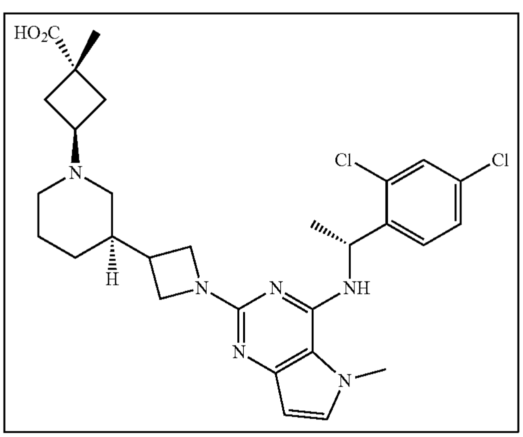 [SMILES: C[C@@H](Nc1nc(N2CC([C@H]3CCCN([C@H]4C[C@](C)(C(=O)O)C4)C3)C2)nc2ccn(C)c12)c1ccc(Cl)cc1Cl] | 3-[(3R)-3-[1-[4-[[(1R)-1-(2,4-dichlorophenyl)ethyl]amino]-5-methyl-pyrrolo[3,2-d]pyrimidin-2-yl]azetidin-3-yl]-1-piperidyl]-1-methyl-cyclobutanecarboxylic acid; 2,2,2-trifluoroacetic acid | A |

TABLE 5-continued

| Ex. No. | Chemical Structure | Chemical Name | Potency |
|---|---|---|---|
| 82 | 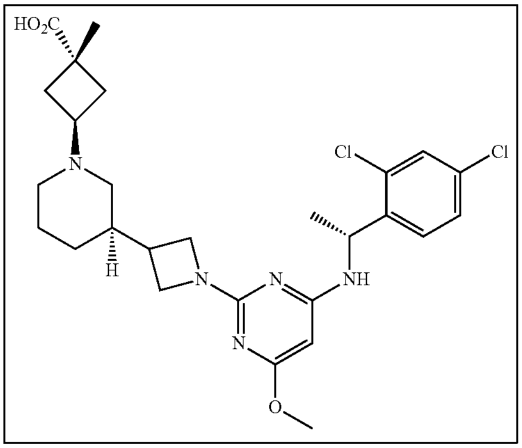 [SMILES: COc1cc(N[C@H](C)c2ccc(Cl)cc2Cl)nc(N2CC([C@H]3CCCN([C@H]4C[C@](C)(C(=O)O)C4)C3)C2)n1] | 3-[(3R)-3-[1-[4-[[(1R)-1-(2,4-dichlorophenyl)ethyl]amino]-6-rnethoxy-pyrimidin-2-yl]azetidin-3-yl]-1-piperidyl]-1-methyl-cyclobutanecarboxylic acid; 2,2,2-trifluoroacetic acid | C |
| 83 | 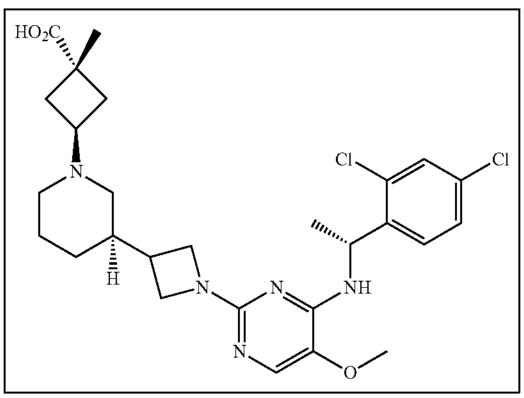 [SMILES: COc1cnc(N2CC([C@H]3CCCN([C@H]4C[C@](C)(C(=O)O)C4)C3)C2)nc1N[C@H](C)c1ccc(Cl)cc1Cl] | 3-[(3R)-3-[1-[4-[[(1R)-1-(2,4-dichlorophenyl)ethyl]amino]-5-methoxy-pyrimidin-2-yl]azetidin-3-yl]-1-piperidyl]-1-methyl-cyclobutanecarboxylic acid; 2,2,2-trifluoroacetic acid | A |
| 84 | 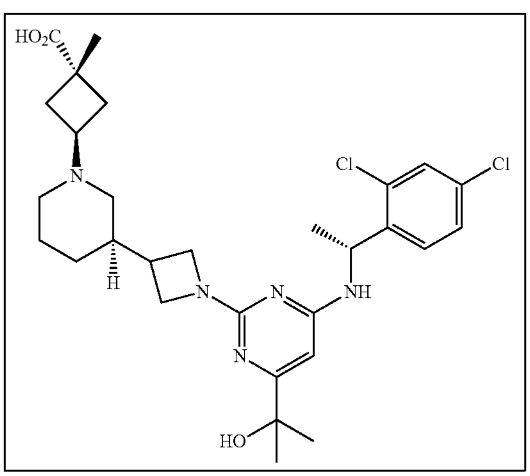 [SMILES: C[C@@H](Nc1cc(C(C)(C)O)nc(N2CC([C@H]3CCCN([C@H]4C[C@](C)(C(=O)O)C4)C3)C2)n1)c1ccc(Cl)cc1Cl] | 3-[(3R)-3-[1-[5-chloro-4-[[(1R)-1-(2,4-dichlorophenyl)ethyl]amino]-6-(1-hydroxy-1-methyl-ethyl)pyrimidin-2-yl]azetidin-3-yl]-1-piperidyl]-1-methyl-cyclobutanecarboxylic acid; 2,2,2-trifluoroacetic acid | A |

TABLE 5-continued

| Ex. No. | Chemical Structure | Chemical Name | Potency |
|---|---|---|---|
| 85 | 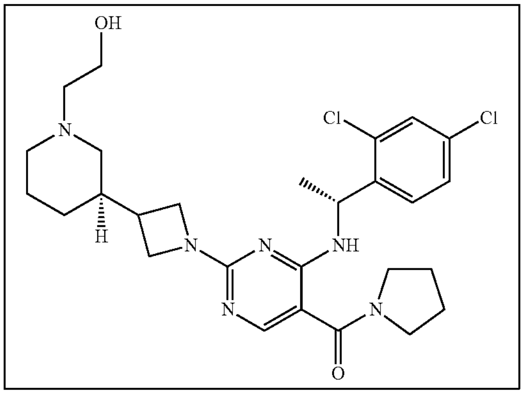 [SMILES: C[C@@H](Nc1nc(N2CC([C@H]3CCCN(CCO)C3)C2)ncc1C(=O)N1CCCC1)c1ccc(Cl)cc1Cl] | [4-[[(1R)-1-(2,4-dichlorophenyl)ethyl]amino]-2-[3-[(3R)-1-(2-hydroxyethyl)-3-piperidyl]azetidin-1-yl]pyrimidin-5-yl]-pyrrolidin-1-yl-methanone; 2,2,2-trifluoroacetic acid | B |
| 86 | 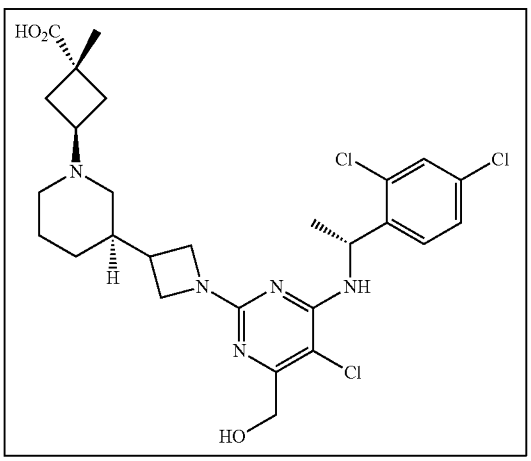 [SMILES: C[C@@H](Nc1nc(N2CC([C@H]3CCCN([C@H]4C[C@](C)(C(=O)O)C4)C3)C2)nc(CO)c1Cl)c1ccc(Cl)cc1Cl] | 3-[(3R)-3-[1-[5-chloro-4-[[(1R)-1-(2,4-dichlorophenyl)ethyl]amino]-6-(hydroxymethyl)pyrimidin-2-yl]azetidin-3-yl]-1-piperidyl]-1-methyl-cyclobutanecarboxylic acid; 2,2,2-trifluoroacetic acid | A |
| 87 | 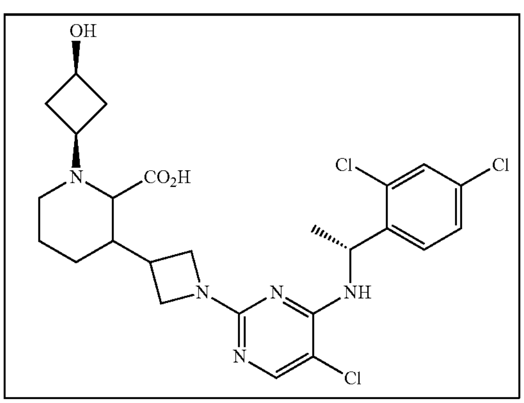 [SMILES: C[C@@H](Nc1nc(N2CC(C3CCCN([C@H]4C[C@@H](O)C4)C3C(=O)O)C2)ncc1Cl)c1ccc(Cl)cc1Cl] | 3-[1-[5-chloro-4-[[(1R)-1-(2,4-dichlorophenyl)ethyl]amino]pyrimidin-2-yl]azetidin-3-yl]-1-(3-hydroxycyclobutyl)piperidine-2-carboxylic acid; 2,2,2-trifluoroacetic acid | A |

TABLE 5-continued

| Ex. No. | Chemical Structure | Chemical Name | Potency |
|---|---|---|---|
| 88 | 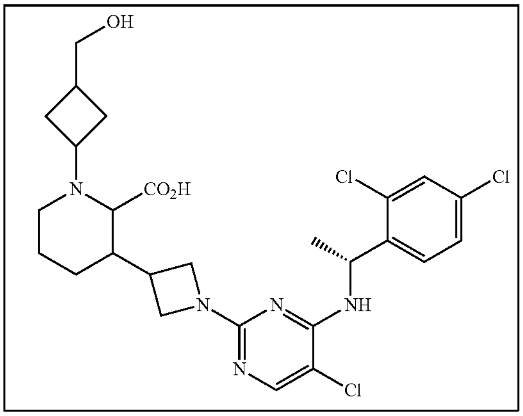 [SMILES: C[C@@H](Nc1nc(N2CC(C3CCCN(C4CC(CO)C4)C3C(=O)O)C2)ncc1Cl)c1ccc(Cl)cc1Cl] | 3-[1-[5-chloro-4-[[(1R)-1-(2,4-dichlorophenyl)ethyl]amino]pyrimidin-2-yl]azetidin-3-yl]-1-[3-(hydroxymethyl)cyclobutyl]piperidine-2-carboxylic acid; 2,2,2-trifluoroacetic acid | A |
| 89 | 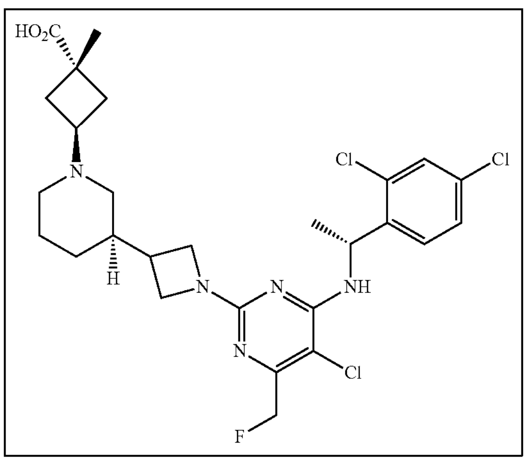 [SMILES: C[C@@H](Nc1nc(N2CC([C@H]3CCCN([C@H]4C[C@](C)(C(=O)O)C4)C3)C2)nc(CF)c1Cl)c1ccc(Cl)cc1Cl] | 3-[(3R)-3-[1-[5-chloro-4-[[(1R)-1-(2,4-dichlorophenyl)ethyl]amino]-6-(fluoromethyl)pyrimidin-2-yl]azetidin-3-yl]-1-piperidyl]-1-methyl-cyclobutanecarboxylic acid; 2,2,2-trifluoroacetic acid | A |
| 90 | 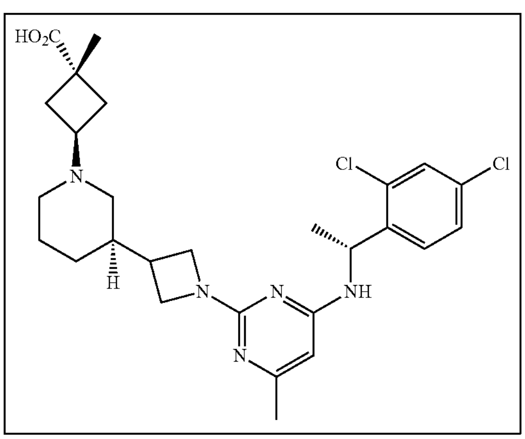 [SMILES: Cc1cc(N[C@H](C)c2ccc(Cl)cc2Cl)nc(N2CC([C@H]3CCCN([C@H]4C[C@](C)(C(=O)O)C4)C3)C2)n1] | 3-[(3R)-3-[1-[4-[[(1R)-1-(2,4-dichlorophenyl)ethyl]amino]-6-methyl-pyrimidin-2-yl]azetidin-3-yl]-1-piperidyl]-1-methyl-cyclobutanecarboxylic acid; 2,2,2-trifluoroacetic acid | A |

TABLE 5-continued

| Ex. No. | Chemical Structure | Chemical Name | Potency |
|---|---|---|---|
| 91 | 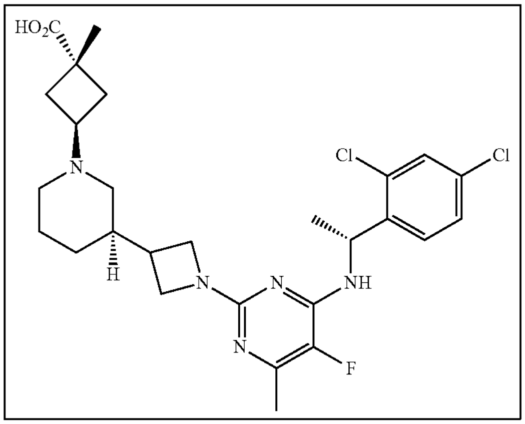 [SMILES: Cc1nc(N2CC([C@H]3CCCN([C@H]4C[C@](C)(C(=O)O)C4)C3)C2)nc(N[C@H](C)c2ccc(Cl)cc2Cl)c1F] | 3-[(3R)-3-[1-[4-[[(1R)-1-(2,4-dichlorophenyl)ethyl]amino]-5-fluoro-6-methyl-pyrimidin-2-yl]azetidin-3-yl]-1-piperidyl]-1-methyl-cyclobutanecarboxylic acid; 2,2,2-trifluoroacetic acid | A |
| 92 | 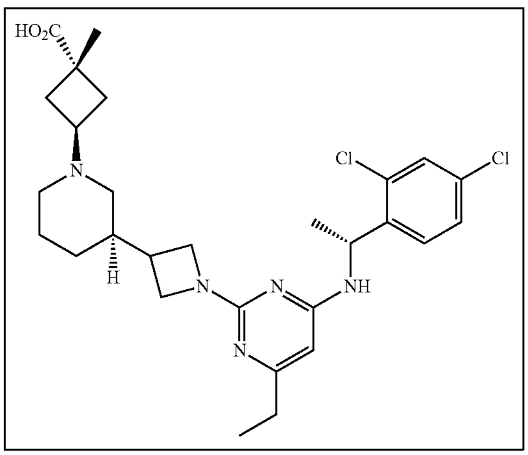 [SMILES: CCc1cc(N[C@H](C)c2ccc(Cl)cc2Cl)nc(N2CC([C@H]3CCCN([C@H]4C[C@](C)(C(=O)O)C4)C3)C2)n1] | 3-[(3R)-3-[1-[4-[[(1R)-1-(2,4-dichlorophenyl)ethyl]amino]-6-ethyl-pyrimidin-2-yl]azetidin-3-yl]-1-piperidyl]-1-methyl-cyclobutanecarboxylic acid; 2,2,2-trifluoroacetic acid | A |
| 93 | 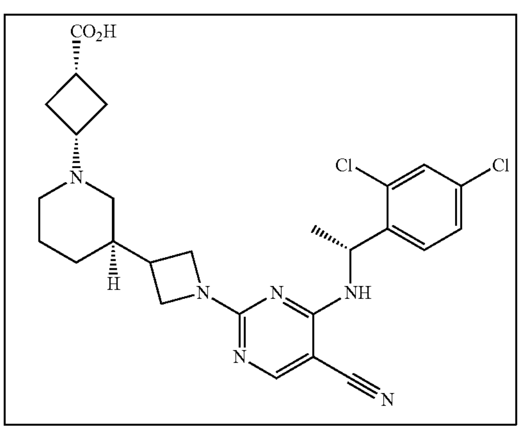 [SMILES: C[C@@H](Nc1nc(N2CC([C@H]3CCCN([C@H]4C[C@@H](C(=O)O)C4)C3)C2)ncc1C#N)c1ccc(Cl)cc1Cl] | 3-[(3R)-3-[1-[5-cyano-4-[[(1R)-1-(2,4-dichlorophenyl)ethyl]amino]pyrimidin-2-yl]azetidin-3-yl]-1-piperidyl]cyclobutanecarboxylic acid | B |

TABLE 5-continued

| Ex. No. | Chemical Structure | Chemical Name | Potency |
|---|---|---|---|
| 94 | 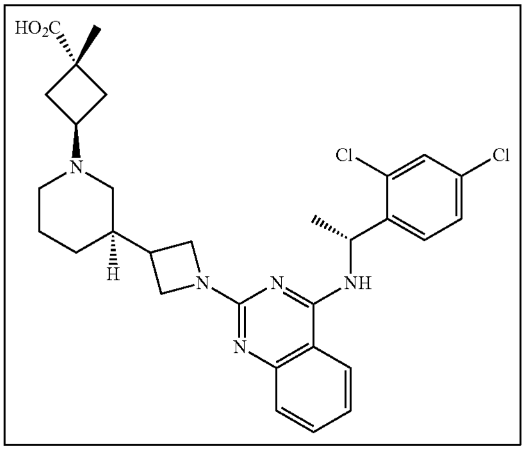 [SMILES: C[C@@H](Nc1nc(N2CC([C@H]3CCCN([C@H]4C[C@](C)(C(=O)O)C4)C3)C2)nc2ccccc12)c1ccc(Cl)cc1Cl] | 3-[(1R,3R)-3-[1-[4-[[(1R)-1-(2,4-dichlorophenyl)ethyl]amino]quinazolin-2-yl]azetidin-3-yl]-1-piperidyl]-1-methyl-cyclobutanecarboxylic acid; 2,2,2-trifluoroacetic acid | A |
| 95 | 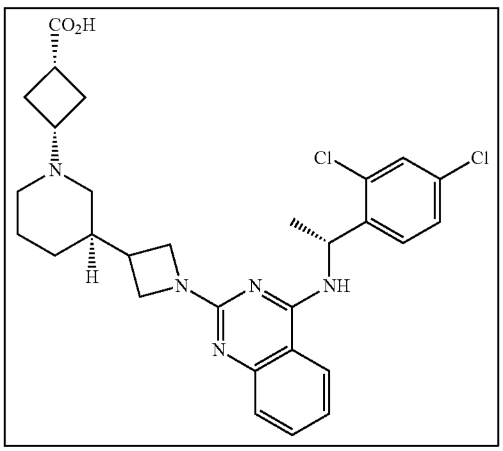 [SMILES: C[C@@H](Nc1nc(N2CC([C@H]3CCCN([C@H]4C[C@@H](C(=O)O)C4)C3)C2)nc2ccccc12)c1ccc(Cl)cc1Cl] | 3-[(1S,3R)-3-[1-[4-[[(1R)-1-(2,4-dichlorophenyl)ethyl]amino]quinazolin-2-yl]azetidin-3-yl]-1-piperidyl]cyclobutanecarboxylic acid; 2,2,2-trifluoroacetic acid | A |

Potent and Selective C—C Motif Chemokine Receptor (CCR4) Antagonists Potentiate Anti-Tumor Immune Responses by Inhibiting Regulatory T Cells ($T_{reg}$)

Naturally occurring suppressive $CD4^+$ $Foxp3^+$ $T_{reg}$ are essential for immune tolerance. Although $T_{reg}$-mediated suppression of effector cells is important to control inflammatory responses and prevent autoimmune diseases, the presence of $T_{reg}$ in the tumor microenvironment (TME) has been shown to dampen anti-tumor immune responses. Human $T_{reg}$ express CCR4, the receptor for the chemokines CCL17 and CCL22. These chemokines are produced by tumor cells or tumor-associated macrophages and dendritic cells, as well as by effector T cells ($T_{eff}$). Preclinical and clinical data in various cancer types supports a role for CCR4-mediated recruitment and accumulation of $T_{reg}$ in the TME which can be associated with poor prognosis. Further, recent longitudinal studies in patients receiving IO agents demonstrate an influx of $T_{reg}$ in responding patients which may dampen optimal anti-tumor responses. Therefore, CCR4 is an ideal target to selectively block $T_{reg}$ recruitment into the TME.

Multiple structurally unique series of selective small molecule antagonists of CCR4 have been developed. These antagonists have cellular potencies in multiple assays (including in a functional chemotaxis assay with primary human $T_{reg}$ in 100% serum) in the low double-digit nM range. Representative compounds are selective against other chemokine receptors, GPCRs and ion channels, including the hERG channel, and lack inhibition of common human CYP450 enzymes. Moreover, compounds have excellent in vitro and in vivo ADME properties, consistent with convenient oral dosing. In preclinical syngeneic tumor models, our CCR4 antagonists block $T_{reg}$ migration and support expansion of activated $T_{eff}$. In contrast to the non-selective approach of depleting anti-CCR4 antibodies, our compounds reduce $T_{reg}$ in the tumor, but not in peripheral tissues such as blood, spleen or skin. In preclinical efficacy studies, CCR4 antagonists potentiate the anti-tumor effects of various checkpoint inhibitors and immune stimulators such as anti-PD-L1 and anti-CD137 antibodies. Enhanced tumor growth inhibition and increases in the percentage of tumor free mice when these agents are combined with CCR4 antagonists, without any gross toxicity, was observed.

Chemotaxis Assays.

Generally speaking, chemotaxis assays may be performed using 5 μm filterplates (Neuroprobe) with the chemoattractant (MDC, TARC, or SDF) placed in the lower chamber, and a cell suspension of 100,000 CEM cells in the upper chamber. The assays may be incubated 1-2 h at 37° C., and the number of cells in the lower chamber quantified by the CyQUANT assay (Molecular Probes).

The following serum chemotaxis assay was used to determine the extent to which the compounds of the present invention block cellular migration mediated through CCR4. The assay was performed using the ChemoTX (Gaithersburg, Md.) migration system with a 5 μm pore size polycarbonate trach-etch (PCTE) membrane. CCRF-CEM cells which express CCR4 were collected by centrifugation at 400×g at room temperature, then suspended at 2 million cells/mL in human serum. Compounds (or an equivalent volume of solvent (DMSO)) were then added to the cell/serum mixture at a final DMSO concentration of 0.25% (v/v), followed by a 30-minute compound pre-incubation period. Separately, recombinant human MDC was diluted to 0.9 nM in 1×HBSS with 0.1% BSA, and 29 μL of diluted MDC was placed in the lower wells of the ChemoTX plate. The polycarbonate (or PCTE) membrane (5 μm pore size) was placed onto the plate, and 50 μL of the cell/compound mixture was transferred into each well of the membrane. The plates were incubated at 37° C. for 60 minutes, after which the polycarbonate membranes were removed, and 10 μL of the DNA-intercalating agent CyQUANT was added to the lower wells. The amount of fluorescence, corresponding to the number of migrated cells, was measured using an Envision plate reader (PerkinElmer; Waltham, Mass.)

Detection of radiolabeled TARC and/or MDC binding to CCR4—Protocol A. Source plates of chemical libraries may be obtained from commercial vendors and may contain individual compounds at 5 mg/mL in DMSO. From these, multiple compound plates containing 10 compounds in each well may be prepared and then diluted in 20% DMSO to a concentration of 50 μg/mL. An aliquot of 20 μL of each mixture may be put into the test plates and stored frozen until use.

A CCR4—expressing stable transfectant cell line may be prepared using current standard molecular biological methods. The CCR4 transfectants may be cultured in IMDM-5% FBS, and harvested when the concentration is between 0.5-1.0×10$^6$ cells/mL. The cells may be centrifuged and resuspended in assay buffer (20 mM HEPES, pH 7.1, 140 mM NaCl, 1 mM CaCl$_2$, 5 mM MgCl$_2$, and with 0.2% BSA) to a concentration of 5.6×10$^6$ cells/mL. To establish the screening assays, 0.09 mL of cells may be added to the assay plates containing the compounds (yielding a final compound concentration of 1-5 μg/mL each (2-10 μM)), and then 0.09 mL of $^{125}$I-TARC or $^{125}$I-MDC diluted in assay buffer (final concentration 50 μM, with ~30,000 cpm per well) may be added. The plates may then be sealed and incubated for approximately 3 hrs at 4° C. on a shaker platform. The assay plates may be harvested using Packard filter plates, pre-soaked in 0.3% PEI (polyethyleneimine) solution, on a Packard vacuum cell harvester. Scintillation fluid (50 μL) was added to all wells and the plates may be sealed and counted in a Top Count scintillation counter. Control wells containing either diluent only (for total counts) or excess MDC or TARC (1 μg/mL, for non-specific binding) may be used to calculate the percent of total inhibition for each set of compounds. IC$_{50}$ values are those concentrations required to reduce the binding of labeled MDC or TARC to the receptor by 50%.

Detection of radiolabeled TARC and/or MDC binding to CCR4—Protocol B. $^{125}$I labelled TARC and MDC are available from commercial sources (e.g., Perkin Elmer Life Sciences). All buffers and materials are available from commercial sources (e.g., Sigma).

To measure binding of $^{125}$I-TARC or $^{125}$I-MDC to cells expressing CCR4 (e.g., CEM cells (e.g., ATCC HB-12624)), the $^{125}$I-TARC or $^{125}$I-MDC is diluted to a concentration of approximately 200 μM in a buffered saline solution (e.g., RPMI supplemented with 0.5% BSA), and added to an equal volume of a suspension of cells (e.g., CEM cells at 5×10$^6$ cells/mL). The resulting mixture is incubated for a period of time (e.g., 2 hrs), and the unbound $^{125}$I-TARC or $^{125}$I-MDC is separated from the cells by filtration, e.g., by passage through GF/B filter plate (Packard Biosciences) pre-treated with 0.3% polyethyleneimine (Sigma), using a Packard Filtermate 96 (Packard Biosciences). The amount of $^{125}$I-TARC or $^{125}$I-MDC retained with the cells on the filterplate is measured by adding a small amount of scintillation fluid (e.g., 50 μL of Microscint-20 Packard Biosciences)), and reading scintillation on appropriate detection equipment, e.g., a Packard TopCount 383 (Packard Biosciences).

Non-specific binding of $^{125}$I-TARC or $^{125}$I-MDC can be estimated by measuring the amount of $^{125}$I-TARC or $^{125}$I-MDC retained with the cells on the filterplate when the assay is performed in the presence of a large excess of unlabeled TARC or MDC. Inhibition of $^{125}$I-TARC or $^{125}$I-MDC binding to CCR4 is defined as a decrease in the retention of $^{125}$I-TARC or $^{125}$I-MDC to the cells on the filterplate.

Calcium Mobilization Assay.

Calcium mobilization experiments may be performed by labeling the human T-cell line CEM with NDO-1 dye (45 min at room temperature), washing with PBS, and re-suspending into flux buffer (HBSS with 1% FBS). For each experiment, 1×10$^6$ cells may be incubated at 37° C. in the cuvette of a PTI spectrometer, and the ratio of 410/490 nm emission plotted over time (typically 2-3 minutes), with compounds added at 5 seconds, followed by MDC, TARC or other chemokines.

Production of TNFα.

The present invention contemplates the use of a murine model of TNFα production by LPS stimulation. A CCR4 antagonistic compound(s) may be suspended in a medium, orally administered to a mouse (male, C57BL/6), and after 0.5 hour LPS (055:B5, Sigma) peritoneally administered to the mouse at a dose of 60 mg/kg. To the control groups, only the medium may be administered. Sixty min after LPS treatment, heparin-added blood collection may be conducted from the abdominal vena cava under ether anesthesia, and centrifuged (12,000 rpm) at 4° C. for 3 min to provide plasma (which may be stored at −80° C. before use). TNFα in the plasma may be quantified using an ELISA kit (R&D systems; Minneapolis, Minn.).

Efficacy of CCR4 Antagonists for Therapeutic Indications. Septic Shock.

A representative procedure for evaluating the efficacy of CCR4 antagonists for treatment of septic shock is described herein. An animal model of endotoxic shock may be induced by injecting mice with LPS. Three groups (15 mice per group) may be treated with an i.p. injection of an LPS dose that produces 90% mortality in mice. One group of mice may also receive PBS and Tween 0.5% i.p. 30 min before LPS administration. A second group of mice may also receive different doses of the CCR4 antagonist(s) given either i.p., IV, SC, IM, PO or via any other mode of administration 30 min before, or concurrently with, LPS administration. A third group of mice may serve as a positive control and consist of mice treated with either mouse IL-10 i.p. or anti-TNF antibodies i.p. 30 min before LPS administration. Mice are monitored for death for 72 h following the LPS injection.

Asthma.

Representative procedures for evaluating the efficacy of CCR4 antagonists for treatment of asthma are as described herein. Procedure A: An animal model of asthma may be induced by sensitizing mice to an experimental antigen (e.g. OVA) by standard immunization techniques, and subsequently introducing that same antigen into the mice's lungs by aerosolization. Three groups of mice (10 mice per group) may be actively sensitized on Day 0 by a single i.p. injection with 100 µg OVA in PBS, along with an IgE-selective adjuvant (e.g. aluminum hydroxide). Eleven days' post-sensitization, at the peak of their IgE response, the mice may be placed in a Plexiglas chamber and challenged with aerosolized OVA (1%) for 30 min using the ultrasonic nebulizer (e.g., DeVilbliss; Ingersoll Rand; Dublin, IE). One group of mice may additionally receive PBS and Tween 0.5% i.p. at the initial sensitization, and at different dosing schedules thereafter, up until the aerosolized OVA challenge. A second group of mice may receive different doses of the CCR4 antagonist(s) given either i.p., IV, SC, IM, PO or via any other mode of administration at the initial sensitization, and at different dosing schedules thereafter, up until the aerosolized OVA challenge. A third group of mice, serving as a positive control, may be treated with either mouse IL-10 i.p., anti-IL-4 antibodies i.p., or anti-IL5 antibodies i.p. at the initial sensitization, and at different dosing schedules thereafter, up until the aerosolized OVA challenge.

Following the aerosolized OVA challenge, mice may be analyzed at different time points for pulmonary function, cellular infiltrates in bronchoalveolar lavage (BAL), histological examination of lungs, and measurement of serum OVA-specific IgE titers.

Procedure B.

Ovalbumin (OVA, 0.2 mg/mL) and Alum (8 mg/mL) prepared in physiological saline may be intraperitoneally administered (500 µL) to mice (male, $C_{57B}L/6$) on Day 1 (test starting day) and Day 8 (1 week thereafter), to sensitize the mice. On Days 15 to 21, mice may be placed in an inhalation chamber (W: 240 mm x L: 240 mm x H: 120 mm), and a 2% OVA solution may be sprayed with an ultrasonic wave-type nebulizer (NE-U12; Omron, San Ramon, Calif.) for 20 min to conduct induction. A CCR4 antagonist(s) may be suspended in a medium and administered orally at 30 min before OVA sensitization on Day 8 and at 30 min before OVA induction on Days 15 to 21. For a control group, only the medium may be administered. Three h post-OVA inhalation on Day 21, the mice may be exsanguinated, catheter tubes inserted into their trachea, and lungs washed with heparin-containing physiological saline (10 U/mL) to provide a bronchoalveolar lavage fluid (BALF). Leukocyte number in BALF may be counted using hemocyte counter (SF-3000; Sysmex, Kobe, JP).

Dermatitis.

Representative procedures for evaluating the efficacy of CCR4 antagonists for treatment of dermatitis are as described herein. Mouse DTH Model. Mice (male, Balb/c) may be shaved on the abdomen with hair clippers, and to the abdomen may be applied ethanol solution (100 µL) of 7% (w/v) 2,4,6-trinitrochlrobenzene (TNCB), to sensitize the mice. Seven days' post-sensitization, a 1% (w/v) TNCB solution in olive oil (20 µL) may be applied to the auricle of the mice (both sides of the right ear), to conduct induction. A CCR4 antagonist(s) may be dissolved in a medium, applied to both sides of the right ear (20 µL) 2 h before applying TNCB. To the control groups, only the medium may be applied. Immediately following compound(s) administration and 24 h after TNCB application, the thickness of the mice auricles may be measured with Dialthickness gauge (Ozaki Seisakusho, JP), which may be used as indicator for efficacy in mouse DTH model.

Dermatitis Model to which Hapten is Applied.

To the auricle (both sides of the right ear) of the mice (male, Balb/c), 1% (w/v) TNCB solution (acetone:olive oil=4:1) (20 µL) may be applied to conduct first sensitization. Seven days' post-sensitization, 1% (w/v) TNCB (acetone:olive oil=4:1) (20 µL) may be applied to the auricle of the mice, to conduct induction (Day 0); this procedure may be repeated on Days 2, 4, 6, 8, 10, 12, 14 and 16. A CCR4 antagonist(s) may be dissolved in a medium, and applied to both sides of the right ear (20 µL) two h before applying TNCB. To the control groups, medium only may be applied. Immediately following compound(s) administration and 24 h post-TNCB application, the thickness of the mice auricles may be measured with Dialthickness gauge, which may be used as an indicator of efficacy in mouse dermatitis model to which hapten is continuously applied.

Infection.

A representative procedure for evaluating the efficacy of CCR4 antagonists for augmenting protective immunity against viruses, bacteria and parasites is as described herein. Protective immunity to microbial pathogens is frequently mediated by Th1 regulatory T cells. Because CCR4 antagonists are believed to be inhibitors of Th2 regulatory cells, they may alter the cross-regulation that normally exists between Th1 and Th2 cells and potentiate Th1 cells, thereby augmenting protection against infectious disease.

Three groups of mice (15 mice per group) may be infected with the intracellular parasite *Leishmania major* (*L. major*) by injecting *L. major* promastigotes SC into their left hind footpads. Four weeks after infection, the mice may be challenged with either *Leishmania* freeze-thawed antigen, or PBS as a negative control, in the contra-lateral footpad. One group of mice may also receive PBS and Tween 0.5% i.p. at the initial sensitization, and at different dosing schedules thereafter, up until the *Leishmania* antigen challenge. A second group of mice may receive different doses of the CCR4 antagonist(s) given either i.p., IV, SC, IM, PO or via any other mode of administration at the initial sensitization, and at different dosing schedules thereafter, up until the *Leishmania* antigen challenge. A third group of mice, serving as positive control, may consist of mice treated with either IL-12, anti-IL-4 antibodies i.p., or anti-IL-5 antibodies i.p. at the initial sensitization, and at different dosing schedules thereafter, up until the *Leishmania* antigen challenge.

Over the next 48 h, footpad swelling, caused by a Delayed-Type Hypersensitivity reaction to the *Leishmania* antigen challenge, may be monitored with a metric caliper. The response of draining lymph node T cells to *Leishmania* antigen stimulation in vitro may also be measured, both at the level of proliferation, cytokine production, and other phenotypic criteria.

Rheumatoid Arthritis.

Rheumatoid Arthritis (RA), which is generally characterized by chronic inflammation in the membrane lining (the synovium) of the joints, affects approximately 1% of the U.S. population, or 2.1 million people in the U.S. Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL (etanercept), REMICADE (infliximab), HUMIRA (adalimumab) and KINERET (anakinra). Though some of these agents relieve symptoms, inhibit progression of structural damage, and improve physical function in particular patient populations, there is still a need for alternative agents with improved efficacy, complementary mechanisms of action, and fewer/less severe adverse effects.

A representative procedure for evaluating the efficacy of CCR4 antagonists for treatment of rheumatoid arthritis is as described herein. An animal model of rheumatoid arthritis may be induced in rodents by injecting them with type II collagen in selected adjuvants. Three rodent groups, each consisting of 15 genetically-susceptible mice or rats, may be injected SC or intra-dermally with type II collagen emulsified in Complete Freund's Adjuvant at days 0 and 21. One group of rodents may additionally receive PBS and Tween 0.5% i.p. at the initial sensitization, and at different dosing schedules thereafter. A second group of rodents may receive different doses of the CCR4 antagonist(s) given either i.p., IV, SC, IM, PO or via any other mode of administration at the initial sensitization, and at different dosing schedules thereafter. A third group, serving as positive control, may consist of rodents treated with either mouse IL-10 i.p., or anti-TNF antibodies i.p. at the initial sensitization, and at different dosing schedules thereafter.

Animals may be monitored from weeks 3 until 8 for the development of swollen joints or paws, and graded on a standard disease-severity scale. Disease severity may be confirmed by histological analysis of joints.

Systemic Lupus Erythematosus.

A representative procedure for evaluating the efficacy of CCR4 antagonists for treatment of Systemic Lupus Erythematosus (SLE) is as described herein. Female NZB/W F1 mice spontaneously develop an SLE-like pathology commencing at 6 months of age that is characterized by proteinuria, serum autoantibodies, glomerulonephritis, and eventually death.

Three groups of NZB/W mice, each comprising 20 mice per group, may be evaluated. One group of mice may receive PBS and Tween 0.5% i.p. soon after weaning, and thereafter at varying dosing schedules. A second group of mice may receive different doses of the CCR4 antagonist(s) given either i.p., IV, SC, IM, PO or via any other mode of administration soon after weaning, and thereafter at varying dosing schedules. A third group of mice, serving as positive control, may comprise mice treated with anti-IL-10 antibodies given soon after weaning, and thereafter at varying dosing schedules. Disease development may be monitored in terms of eventual mortality, kidney histology, serum autoantibody levels, and proteinuria.

Cancer-Related Malignancy.

A representative procedure for evaluating the efficacy of CCR4 antagonists for treatment of cancer is as described herein. Mice homozygous for the severe combined immune deficiency spontaneous mutation $Prkdc^{scid}$(SCID mice), are characterized by an absence of functional T cells and B cells, lymphopenia, hypogammaglobulinemia, and a normal hematopoietic microenvironment. Additional mouse genetic backgrounds can result in lack of natural killer cells (in NOD-SCID); while the addition of mutations in IL2 receptor gamma chain results in loss of much cytokine signaling resulting in highly immune-deficient mice (NSG). Immunodeficient mice (SCID mice, NOD-SCID mice, NSG or other) can be engrafted with a human immune system following transplant of PBMCs, CD34+ hematopoietic stem cells, or isolated immune effector populations. These humanized mice may be transplanted cultured established human tumor cell lines (xenograft) or with primary human tumor cells to create a patient derived xenograft (PDX). Additionally, normal mouse strains may be transplanted with a variety of well-characterized mouse tumor lines, including the thymoma EL4 cell line, which have been transfected with OVA to allow easy evaluation of tumor-specific antigen responses following vaccination with OVA. Three groups of mice from any of these tumor models may be tested for CCR4 antagonist efficacy. One group receives PBS and Tween 0.5% i.p. soon after tumor transplant, and thereafter at varying dosing schedules. A second group receives different doses of the CCR4 antagonist(s) given either i.p., IV, SC, IM, PO or via any other mode of administration following tumor transplant, and thereafter at varying dosing schedules. A third group, serving as positive control, may comprise mice treated with either anti-IL-4 antibodies, anti-IFNγ antibodies, IL-4, or TNF, given i.p. soon after tumor transplant, and thereafter at varying dosing schedules. A second group receives different doses of the CCR4 antagonist(s) given either i.p., IV, SC, IM, PO or via any other mode of administration following tumor transplant, and thereafter at varying dosing schedules. A third group, serving as positive control, may comprise mice treated with either anti-IL-4 antibodies, anti-IFNγ antibodies, IL-4, or TNF, given i.p. soon after tumor transplant, and thereafter at varying dosing schedules.

Efficacy may be monitored via tumor growth versus regression. In the case of the OVA-transfected EL4 thymoma model, cytolytic OVA-specific responses may be measured by stimulating draining lymph node cells with OVA in vitro, and measuring antigen-specific cytotoxicity at various times, such as 72 h.

Allograft Transplantation Models.

Allograft mouse tumor systems, also known as syngeneic models, may be used to evaluate the compounds of the present invention. In contrast to conventional xenograft models, which often lack relevance due to the animals' immunocompromised status, the host immune system is normal in syngeneic models, which may more closely represent the native tumor micro-environment. Because they retain intact immune systems, syngeneic mouse models are particularly relevant for studies of immunologically-based targeted therapies, that modulate the immune system's ability to seek out and destroy cancer cells. For example, the MC38 model of colorectal cancer can be used to explore the activity of treatment with a CCR4 inhibitor. Treatment with the CCR4 inhibitor and/or other agents may be initiated prior to, along with, or after MC38 cancer cells have been implanted or injected into recipient mice. Mice are then divided or randomized into treatment groups, each containing multiple mice, and the impact of treatment can be measured. Endpoints for anti-tumor responses include the absence or presence of a tumor, it's size, time to a size (including any detection at all) or time to regression, long term regression, or other accepted endpoints. Additional endpoints of activity include, for example, a characterization of the immune cell populations in and around the tumor or systemically or markers of immune cell responses (e.g. cytokine levels).

Syngeneic models consist of tumor tissues derived from the same genetic background as a given mouse strain. Cancerous cells or solid tumors may be transplanted into a host mouse. Because the cancer tissues and the recipient share ancestry, the transplant is not rejected by the host's immune system. Tissues may then be monitored for changes such as growth or shrinkage, metastasis, and survival rate. Therapeutic interventions may be performed and the results assessed to understand the treatment potentials.

A discussion of syngeneic models and other tumor models for efficacy determinations is set forth in Teicher, B A, (October 2006) Mol Cancer Ther 5:2435. Multiple syngeneic tumor models with well-characterized responses to known immune checkpoint inhibitors (e.g., anti-PDL-1, anti-PD-1 and anti-CTLA-4) are commercially available (e.g., GenScript (Piscataway, N.H.) and Charles River Labs (Wilmington, Mass.)).

Psoriasis.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-αinhibitors (also used in the treatment of rheumatoid arthritis (RA)), including ENBREL (etanercept), REMICADE (infliximab) and HUMIRA (adalimumab)), and T-cell inhibitors such as AMEVIVE (alefacept) and RAPTIVA (efalizumab). Though several of these agents are effective to some extent in certain patient populations, none have been shown to effectively treat all patients.

A representative procedure for evaluating the efficacy of CCR4 antagonists for treatment of psoriasis is as described herein. A rodent model of psoriasis may be generated by intravenously transferring a population of purified T cells (e.g., CD45Rbhi T cells) obtained from the spleens of BALB/c mice into immunodeficient recipient CB 17 scid/scid mice. Mice develop signs of redness, swelling, and skin lesions resembling those of human psoriasis in their ears, feet and tail by 8 weeks after transfer. Three groups of mice, each comprising 10-15 CB.17 scid/scid mice, may be injected with purified CD45Rbhi T cells. One group of mice may additionally receive PBS and Tween 0.5% i.p. at the initial cell transfer, and at different dosing schedules thereafter. A second group of mice may receive different doses of the CCR4 antagonist(s) given either i.p., IV, SC, IM, PO or via any other mode of administration at the initial cell transfer, and at different dosing schedules thereafter. A third group of mice, serving as positive control, may consist of mice treated with antibodies to either IL-12, IL-4, IFNγ, or TNF, or with cytokine IL-10 at the initial cell transfer, and at different dosing schedules thereafter. Animals may be monitored for development of psoriatic-like lesions for 3 months after cell transfer.

Inflammatory Bowel Disease.

Several murine models of IBD (e.g., Crohn's disease and ulcerative colitis) have been developed. Some of the models occur in genetically engineered transgenic mice that have been depleted of certain cytokine genes (e.g., IL-10 or IL-2) by homologous recombination. A particular murine model of IBD is obtained by transferring highly purified populations of CD4+T lymphocytes bearing the surface marker phenotype cd45rb hi into SCID mice.

Representative procedures for evaluating the efficacy of CCR4 antagonists for treatment of inflammatory bowel disease comprise three groups of mice from any of the aforementioned models. One group of mice may receive PBS and Tween 0.5% i.p. soon after weaning in the case of the spontaneous models in transgenic mice, or at the time of cell transfer into SCID mice and varying dosings thereafter for the cell transfer model. A second group of mice may receive different doses of the CCR4 antagonist(s) given either i.p., IV, SC, IM, PO or via any other mode of administration soon after weaning in the case of the spontaneous models in transgenic mice, or at the time of cell transfer into SCID mice and varying dosings thereafter for the cell transfer model. A third group of mice, serving as positive control, may comprise mice treated with antibodies to either IFNγ or TNF, or with the cytokine IL-10 soon after weaning in the case of the spontaneous models in transgenic mice, or at the time of cell transfer into SCID mice and varying dosings thereafter for the cell transfer model. Mice may be evaluated for 6-8 weeks for disease development, monitored initially for weight loss and/or prolapsed rectum, and subsequently for histological evaluation of their colons and intestinal tracts.

Example 96. The Effect of 2-((R)-3-(1-(1-((R)-1-(2, 4-Dichlorophenyl)ethyl)-3-(cyano)-1H-pyrazolo[3,4-b]pyrazin-6-yl)azetidin-3-yl)piperidin-1-yl)ethan-1-ol and (1R,3r)-3-((R)-3-(1-(5-chloro-4-(((R)-1-(2,4-dichlorophenyl)ethyl)amino)-6-methylpyrimidin-2-yl)azetidin-3-yl)piperidin-1-yl)-1-methylcyclobutane-1-carboxylic Acid on the Level of Lung Eosinophilia in a Murine Model of Ovalbumin-Induced Pulmonary Inflammation A study was performed to investigate the effects of daily oral administration of the compound 2-((R)-3-(1-(1-((R)-1-(2,4-Dichlorophenyl)ethyl)-3-(cyano)-1H-pyrazolo[3,4-b]pyrazin-6-yl)azetidin-3-yl)piperidin-1-yl)ethan-1-ol (FLX-A-12) (disclosed in US Patent Publication 2018-0072740 published Mar. 15, 2018) and the compound (1R,3r)-3-((R)-3-(1-(5-chloro-4-(((R)-1-(2,4-dichlorophenyl)ethyl)amino)-6-methylpyrimidin-2-yl)azetidin-3-yl)piperidin-1-yl)-1-methylcyclobutane-1-carboxylic acid (FLX-B-10) (disclosed in Example 38 herein) on the level of lung eosinophilia in a murine model of ovalbumin-induced pulmonary inflammation. An automated system of haematological cellular analysis (DASIT Sysmex XT-2000iV) was used to perform total and differential cell counts and assess the degree of ovalbumin challenge-induced pulmonary eosinophilia. FLX-A-12 and FLX-B-10 were administered daily for five days at the doses of 50 and 30-100 mg/kg respectively, and eosinophilic inflammation was measured 24 hours after the last ovalbumin challenge. Dexamethasone was included as a positive reference substance (3 mg/kg p.o. daily). On days 20-23 inclusive, mice received vehicle (30% PG in water), reference compound (Dexamethasone, 3 mg/kg) and test compounds (FLX-A-12 at 50 mg/kg and FLX-B-10 at 30 and 100 mg/kg), 1 hr prior ovalbumin challenge via the p.o. route. In addition, the test compounds (FLX-A-12 and FLX-B-10) were dosed on day 19 24 hr prior to the dosing on day 20.

FLX-A-12 was formulated at the concentration of 5 mg/mL (corresponding to the dose of 50 mg/kg in a dose volume of 10 mL/kg) in 30% PG in water. The doses of FLX-B-10 (30 and 100 mg/kg) were prepared by dissolving 3 and 10 mg/ml of the compound respectively in 30% PG in water at a dose volume of 10 ml/kg. The dose of Dexamethasone (3 mg/kg) was prepared by dissolving 0.3 mg/mL of the compound in 30% PG in water at a dose volume of 10 ml/kg.

The effects of FLX-A-12 and FLX-B-10 were assessed in the ovalbumin mouse model of pulmonary inflammation. The study was performed in female Balb/c mice, and included the following 6 treatment groups (n=10/group): (i) Vehicle group: challenged with saline and dosed with compound Vehicle, 1 hr before challenge; (ii) OVA/Vehicle group (control): challenged with ovalbumin and dosed with compound Vehicle, 1 hr before challenge; (iii) OVA/FLX-A-12 50 mg/kg (p.o.): challenged with ovalbumin and dosed with FLX-A-12, 1 hr before challenge; (iv) OVA/FLX-B-10 30 mg/kg (p.o.): challenged with ovalbumin and dosed with FLX-B-10, 1 hr before challenge; (v) OVA/FLX-B-10 100 mg/kg (p.o.): challenged with ovalbumin and dosed with FLX-B-10, 1 hr before challenge; and (vi) Dexamethasone 3 mg/kg (p.o.) group: challenged with ovalbumin and dosed with Dexamethasone, 1 hr before challenge.

The eosinophilic inflammation induced by ovalbumin-challenge (i.n.) was measured as cell count increase in bronchoalveolar lavage fluid (BALF) using an automated system of haematological cellular analysis (DASIT Sysmex XT-2000iV) at 24 hours after the last OVA-challenge. The effects of the test compounds were evaluated as ability to decrease the eosinophilic inflammation with respect to the OVA group.

For antigen sensitization, on day 1, animals received 10 µg of OVA in 2 mg of Aluminium hydroxide hydrate ($AlOH_3$) at a dose volume of 200 µl per mouse subcutaneously (s.c.). On day 14, all animals got a second (boost) s.c. injection with the same dose of Alum/OVA as above.

On days 20-23 inclusive, mice received vehicle, 30% PG in water, reference compound (Dexamethasone 3 mg/kg) and test compounds (FLX-A-12 at 50 mg/kg and FLX-B-10 at 30 and 100 mg/kg), 1 hr prior OVA challenge via the p.o. route. In addition, test compounds (FLX-A-12 and FLX-B-10) were dosed on day 19, 24 hr prior to the dosing on day 20. All compounds were administered at a dose volume of 10 ml/kg. Dose volumes were calculated based on individual animal weight. Following the p.o. treatments on days 20-23 inclusive, all animals was anaesthetised and intranasally dosed with 50 µl of Saline or 50 µg of OVA in 50 µl of saline. 24 hours following the final challenge on day 23, animals were sacrificed by anaesthetic overdose (inhalation of 4-4.5% Isoflurane/O2, 2l/m and i.p. of Thiopental Na 300 mg/kg). A blood sample was obtained from descending vena cava, placed in an EDTA-coated microtainer and centrifuged at 3000 g for 10 minutes at 4° C. to separate the plasma. The plasma was stored at −80° C. prior to analysis.

Whole lungs were taken for histological analysis. The lungs were inflated using a syringe with 0.6 ml of 10% phosphate buffered formalin (PBF). Following that, the lungs were stored in 10% PBF at room temperature for 24 hr. Subsequently, the lungs were lavaged three times with 0.4 mL of PBS solution. The BALF was kept on ice for a short time period. The recovered fluid was centrifuged at 400 g at 4° C. for 5 minutes. An aliquot of BALF supernatant (~250 µl) was stored at −80° C. for subsequent analysis of mediator levels (IL-4/5/13, CCL17 and CCL22). The quantification of IL-4/5/13, CCL17 and CCL22 was performed using a mouse magnetic bead-based immunoassay (Mouse Cytokine/Chemokine Magnetic Bead Panel and Panel II) according to the instructions provided in the kit with some minor modifications. BALF samples were used undiluted. Plate fluorescence was read with a Luminex (Bio-Plex 100 System). Cell pellets were suspended in 0.5 mL of PBS, and cells (lymphocytes and eosinophils) were counted by an automated system of haematological cellular analysis (DASIT Sysmex XT-2000iV).

Figure 2:
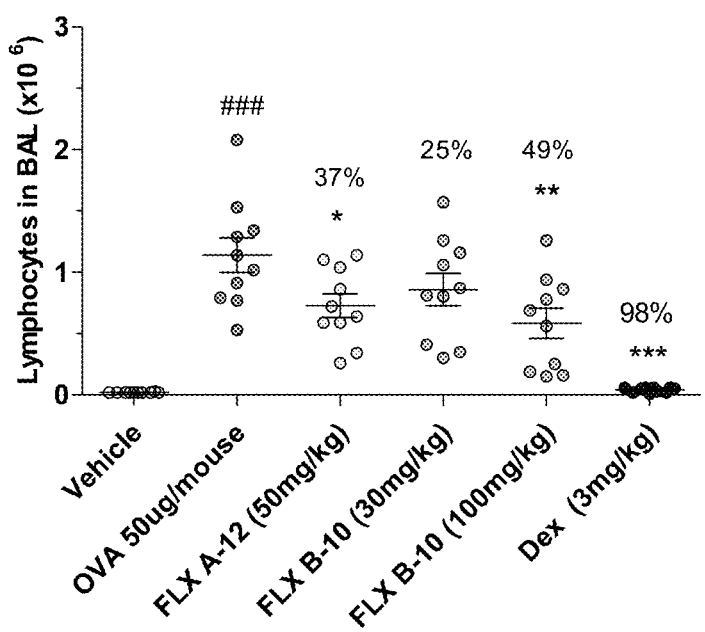
FIG. 2 depicts a graph of lymphocyte cell counts in bronchoalveolar lavage fluid.

The ability of test compounds to inhibit the eosinophilic inflammation induced by ovalbumin was measured by cell counts in BALF using an automated system of haematological cellular analysis (DASIT Sysmex XT-2000iV) at 24 hours after last ovalbumin challenge. Data were expressed as mean±sem for each treatment group. Differences between treated groups with respect to the vehicle group were analysed as by a one way ANOVA followed by Dunnett's Multiple Comparison Test. $P<0.05$ was accepted as statistically significant. The effect of test compounds on the eosinophilic inflammation was expressed as percentage inhibition of the control response for each treatment group. Results of the effect of ovalbumin-challenge (50 µg/mouse) in development of allergic asthma are reported in FIGS. 1 and 2. In the OVA group, the cell count increased at 24 hours after ovalbumin-challenge, with respect to Vehicle group. Treatment with Dexamethasone (3 mg/kg, p.o.) caused a reduction in the eosinophilic cell count at 24 hours after challenge, which was statistically significant. The percentage of reduction was 92%. Dexamethasone confirmed its anti-inflammatory profile in this model. Results of the effect of FLX-A-12 (50 mg/kg, p.o.) in the Ovalbumin-induced asthma model are reported in FIGS. 1 and 2. Treatment with FLX-B-10 (30 and 100 mg/kg) resulted in statistically significant reduction of eosinophilic inflammation only at 100 mg/kg with respect to the OVA group.

Figure 3:
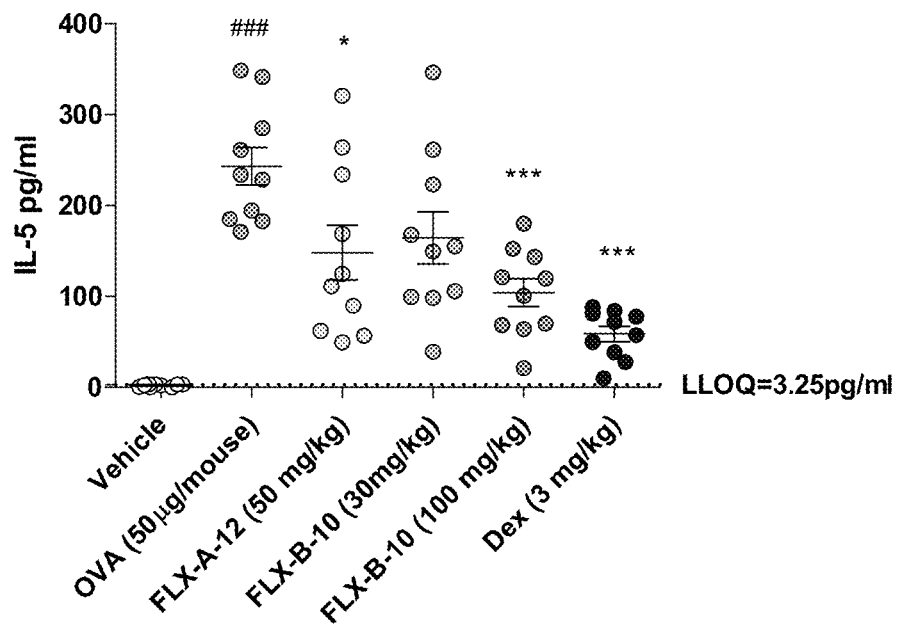
FIG. 3 depicts a graph of the concentration of the inflammatory mediator IL-5 in bronchoalveolar lavage fluid.
Figure 4:
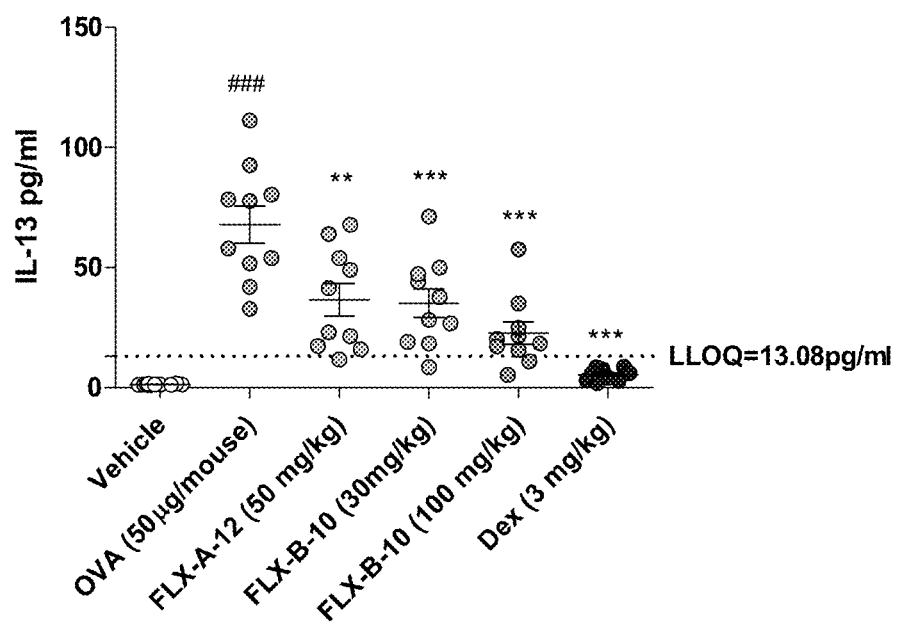
FIG. 4 depicts a graph of the concentration of the inflammatory mediator IL-13 in bronchoalveolar lavage fluid.
Figure 5:
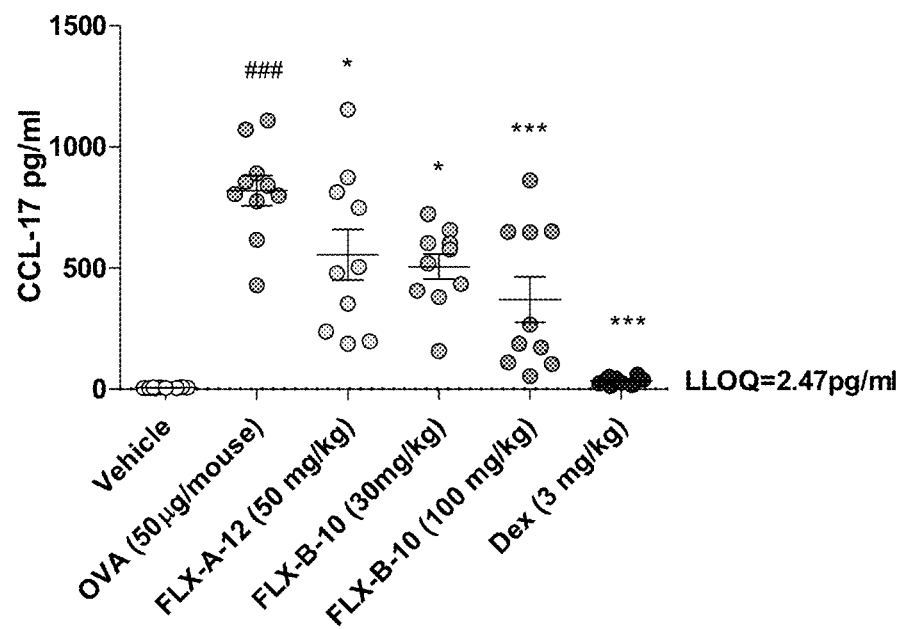
FIG. 5 depicts a graph of the concentration of the inflammatory mediator CCL-17 in bronchoalveolar lavage fluid.
Figure 6:
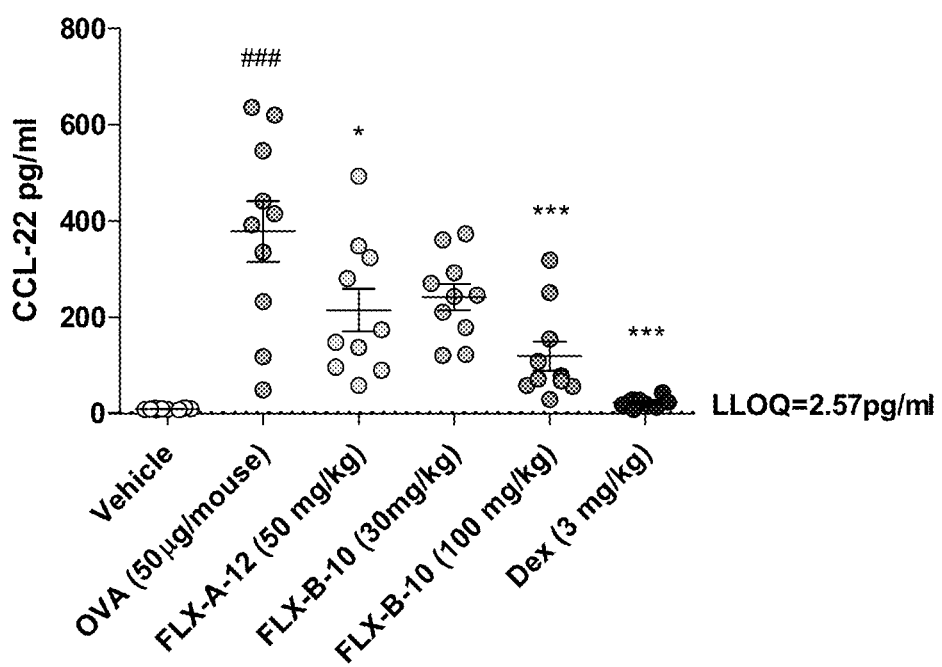
FIG. 6 is a graph of the concentration of the inflammatory mediator CCL-22 in bronchoalveolar lavage fluid.

Inflammatory mediator analysis revealed that IL-5, IL-13, CCL-17 and CCL-22 were significantly reduced in the presence of test and reference compounds. IL-5 levels were significantly reduced in the presence of FLX-A-12 at 50 mg/kg, FLX-B-10 at 100 mg/kg, and Dexamethasone (FIG. 3). IL-13 was significantly reduced in all conditions when compared to OVA. A dose-dependent decrease was observed in FLX-B-10 treatment groups (FIG. 4). Also, CCL-17 was significantly reduced in all conditions (FIG. 5), while CCL-22 was significantly reduced in all conditions, except for FLX-B-10 at 30 mg/kg. A dose-dependent decrease was observed in FLX-B-10 treatment groups (FIG. 6).

Example 97. Inhibition of Treg Trafficking into Inflamed Ear Tissue by CCR4 Antagonist in a Delayed-Type Hypersensitivity (DTH) Model The Delayed Type Hypersensitivity (DTH) is an in vivo model of inflammation driven by cell-mediated immunity (Th2 response). Th2 infiltration into tissues is dependent on chemokines and chemokine receptors and Th2 express high levels of the CCR4 chemokine receptor. The DTH reaction is divided into 2 phases, the sensitization phase (initial immunization with a specific antigen) and the efferent or challenge phase. The CCR4 antagonist is tested at multiple doses (10, 30 or 100 mg/kg), to determine the effect on phenotypic parameters in this model.

Study Design: Mice are sensitized topically with a 50 uL solution of oxazolone (1% (w/v)) in absolute ethanol on their shaved abdomens. Seven days after sensitization, mice are challenged with 20 uL of 0.5% oxazolone applied to the right ear. 50 uL of solvent alone is applied to the left ear. For prophylactic dosing, vehicle (1% HPMC), 10 mg/kg dexamethasone or the test CCR4 antagonist compound at multiple doses (10, 30 and 100 mg/kg) is administered either subcutaneously or by oral gavage once a day (QD) or twice a day (BID). Twenty-four hours after challenge, ear swelling is quantified using a caliper and the net increase in thickness of the right ear (oxazolone-treated) compared with the left ear (vehicle control).

A dose-dependent decrease of ear swelling in CCR4 antagonist-treated animals is observed compared to the vehicle groups. Animals that are dosed subcutaneously (QD) with 100 mg/kg of CCR4 antagonist compound show a stronger inhibition of ear swelling when compared to animals that are dosed orally with 100 mg/kg (BID) and is comparable to the dexamethasone (10 mg/kg QD) dosed group.

In an oxazolone-induced mouse DTH model, dosing with a CCR4 antagonist significantly reduces ear swelling. This data suggests that recruitment of inflammatory CCR4+ T cells is significantly blocked by the CCR4 antagonist.

Although the invention has been described with reference to the above examples, it will be understood that modifications and variations are encompassed within the spirit and scope of the invention. Accordingly, the invention is limited only by the following claims.

What is claimed is:
1. A method of treating or preventing inflammation in a subject in need thereof comprising administering to said subject a therapeutically effective amount of a compound of structural Formula (IIb):

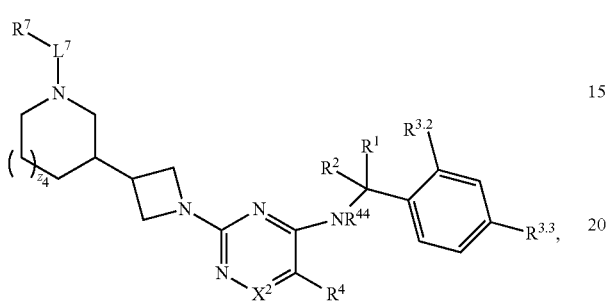

(IIb)

or a pharmaceutically acceptable salt thereof, wherein:
$X^2$ is $CR^9$;
n1, n2, n3.2, n3.3, n4, n7, and n9, are independently an integer from 0 to 4;
m1, m2, m3.2, m3.3, m4, m7, m9, v1, v2, v3.2, v3.3, v4, v7, and v9, v10, and are independently 1 or 2;
z4 is 1;
$L^7$ is a bond, —O—, —S—, —$NR^{7.2B}$—, —C(O)—, —C(O)O—, —S(O)—, —S(O)$_2$—, $R^{41}$-substituted or unsubstituted $C_1$-$C_8$ alkylene or $R^{41}$-substituted or unsubstituted $C_3$-$C_8$ cycloalkylene;
$R^{41}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{42}$-substituted or unsubstituted $C_1$-$C_8$ alkyl, $R^{42}$-substituted or unsubstituted 2 to 8 membered heteroalkyl, $R^{42}$-substituted or unsubstituted $C_3$-$C_8$ cycloalkyl, $R^{42}$-substituted or unsubstituted 3 to 8 membered heterocycloalkyl, $R^{42}$-substituted or unsubstituted $C_6$-$C_{10}$ aryl, or $R^{42}$-substituted or unsubstituted 5 to 6 membered heteroaryl;
$R^{42}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{43}$-substituted or unsubstituted $C_1$-$C_8$ alkyl, $R^{43}$-substituted or unsubstituted 2 to 8 membered heteroalkyl, $R^{4}$-substituted or unsubstituted $C_3$-$C_8$ cycloalkyl, $R^{43}$-substituted or unsubstituted 3 to 8 membered heterocycloalkyl, $R^{43}$-substituted or unsubstituted $C_6$-$C_{10}$ aryl, or $R^{43}$-substituted or unsubstituted 5 to 6 membered heteroaryl;
$R^{43}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;
$R^1$ is hydrogen, halogen, —$CX^{1.1}{}_3$, —$CHX^{1.1}{}_2$, —$CH_2X^{1.1}$, —CN, —$N_3$, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}{}_3$, —$OCHX^{1.1}{}_2$, —$OCH_2X^{1.1}$, $R^{11}$-substituted or unsubstituted $C_1$-$C_8$ alkyl, $R^{11}$-substituted or unsubstituted 2 to 8 membered heteroalkyl, $R^{11}$-substituted or unsubstituted $C_3$-$C_8$ cycloalkyl, $R^{11}$-substituted or unsubstituted 3 to 8 membered heterocycloalkyl, $R^{11}$-substituted or unsubstituted $C_6$-$C_{10}$ aryl, or $R^{11}$-substituted or unsubstituted 5 to 6 membered heteroaryl;
$R^{11}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{12}$-substituted or unsubstituted $C_1$-$C_8$ alkyl, $R^{12}$-substituted or unsubstituted 2 to 8 membered heteroalkyl, $R^{12}$-substituted or unsubstituted $C_3$-$C_8$ cycloalkyl, $R^{12}$-substituted or unsubstituted 3 to 8 membered heterocycloalkyl, $R^{12}$-substituted or unsubstituted $C_6$-$C_{10}$ aryl, or $R^{12}$-substituted or unsubstituted 5 to 6 membered heteroaryl;
$R^{12}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{13}$-substituted or unsubstituted $C_1$-$C_8$ alkyl, $R^{13}$-substituted or unsubstituted 2 to 8 membered heteroalkyl, $R^{13}$-substituted or unsubstituted $C_3$-$C_8$ cycloalkyl, $R^{13}$-substituted or unsubstituted 3 to 8 membered heterocycloalkyl, $R^{13}$-substituted or unsubstituted $C_6$-$C_{10}$ aryl, or $R^{13}$-substituted or unsubstituted 5 to 6 membered heteroaryl;
$R^{13}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^2$ is hydrogen, halogen, $-CX^{2.1}_3$, $-CHX^{2.1}_2$, $-CH_2X^{2.1}$, $-CN$, $-N_3$, $-SO_{n2}R^{2A}$, $-SO_{v2}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m2}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, $-OCH_2X^{2.1}$, $R^{14}$-substituted or unsubstituted $C_1$-$C_8$ alkyl, $R^{14}$-substituted or unsubstituted 2 to 8 membered heteroalkyl, $R^{14}$-substituted or unsubstituted $C_3$-$C_8$ cycloalkyl, $R^{14}$-substituted or unsubstituted 3 to 8 membered heterocycloalkyl, $R^{14}$-substituted or unsubstituted $C_6$-$C_{10}$ aryl, or $R^{14}$-substituted or unsubstituted 5 to 6 membered heteroaryl;

$R^{14}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{15}$-substituted or unsubstituted $C_1$-$C_8$ alkyl, $R^{15}$-substituted or unsubstituted 2 to 8 membered heteroalkyl, $R^{15}$-substituted or unsubstituted $C_3$-$C_8$ cycloalkyl, $R^{15}$-substituted or unsubstituted 3 to 8 membered heterocycloalkyl, $R^{15}$-substituted or unsubstituted $C_6$-$C_{10}$ aryl, or $R^{15}$-substituted or unsubstituted 5 to 6 membered heteroaryl;

$R^{15}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{16}$-substituted or unsubstituted $C_1$-$C_8$ alkyl, $R^{16}$-substituted or unsubstituted 2 to 8 membered heteroalkyl, $R^{16}$-substituted or unsubstituted $C_3$-$C_8$ cycloalkyl, $R^{16}$-substituted or unsubstituted 3 to 8 membered heterocycloalkyl, $R^{16}$-substituted or unsubstituted $C_6$-$C_{10}$ aryl, or $R^{16}$-substituted or unsubstituted 5 to 6 membered heteroaryl;

$R^{16}$ is independently hydrogen, oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^{3.2}$ is hydrogen, halogen or $-SO_{n3.2}R^{3.2A}$;

$R^{3.3}$ is hydrogen, halogen, or $-SO_{n3.2}R^{3.3A}$;

$R^4$ is hydrogen, halogen, $-CX^{4.1}_3$, $-CHX^{4.1}_2$, $-CH_2X^{4.1}$, $-CN$, $-N_3$, $-SO_{n4}R^{4A}$, $-SO_{v4}NR^{4B}R^{4C}$, $-NHNR^{4B}R^{4C}$, $-ONR^{4B}R^{4C}$, $-NHC(O)NHNR^{4B}R^{4C}$, $-NHC(O)NR^{4B}R^{4C}$, $-N(O)_{m4}$, $-NR^{4B}R^{4C}$, $-C(O)R^{4D}$, $-C(O)OR^{4D}$, $-C(O)NR^{4B}R^{4C}$, $-OR^{4A}$, $-NR^{4B}SO_2R^{4A}$, $-NR^{4B}C(O)R^{4D}$, $-NR^{4B}C(O)OR^{4D}$, $-NR^{4B}OR^{4D}$, $-OCX^{4.1}_3$, $-OCHX^{4.1}_2$, $-OCH_2X^{4.1}$, $R^{20}$-substituted or unsubstituted $C_1$-$C_8$ alkyl, $R^{20}$-substituted or unsubstituted 2 to 8 membered heteroalkyl, $R^{20}$-substituted or unsubstituted $C_3$-$C_8$ cycloalkyl, $R^{20}$-substituted or unsubstituted 3 to 8 membered heterocycloalkyl, $R^{20}$-substituted or unsubstituted $C_6$-$C_{10}$ aryl, or $R^{20}$-substituted or unsubstituted 5 to 6 membered heteroaryl;

$R^{20}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{21}$-substituted or unsubstituted $C_1$-$C_8$ alkyl, $R^{21}$-substituted or unsubstituted 2 to 8 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted $C_6$-$C_{10}$ aryl, or $R^{21}$-substituted or unsubstituted 5 to 6 membered heteroaryl;

$R^{21}$ is independently oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $R^{22}$-substituted or unsubstituted $C_1$-$C_8$ alkyl, $R^{22}$-substituted or unsubstituted 2 to 8 membered heteroalkyl, $R^{22}$-substituted or unsubstituted $C_3$-$C_8$ cycloalkyl, $R^{22}$-substituted or unsubstituted 3 to 8 membered heterocycloalkyl, $R^{22}$-substituted or unsubstituted $C_6$-$C_{10}$ aryl, or $R^{22}$-substituted or unsubstituted 5 to 6 membered heteroaryl;

$R^{22}$ is independently hydrogen, oxo, halogen, $-CCl_3$, $-CBr_3$, $-CF_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^7$ is hydrogen, halogen, $-CX^{7.1}_3$, $-CHX^{7.1}_2$, $-CH_2X^{7.1}$, $-CN$, $-N_3$, $-SO_{n7}R^{7A}$, $-SO_{v7}NR^{7B}R^{7C}$, $-NHNR^{7B}R^{7C}$, $-ONR^{7B}R^{7C}$, $-NHC(O)NHNR^{7B}R^{7C}$, $-NHC(O)NR^{7B}R^{7C}$, $-N(O)_{m7}$, $-NR^{7B}R^{7C}$, $-C(O)R^{7D}$, $-C(O)OR^{7D}$, $-C(O)NR^{7B}R^{7C}$, $-OR^{7A}$, $-NR^{7B}SO_2R^{7A}$, $-NR^{7B}C(O)R^{7D}$, $-NR^{7B}C(O)OR^{7D}$, $-NR^{7B}OR^{7D}$, $-OCX^{7.1}_3$, $-OCHX^{7.1}_2$, $-OCH_2X^{7.1}$, $R^{29}$-substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 8 membered heterocycloalkyl, $R^{29}$-substituted or unsubstituted $C_6$-$C_{10}$ aryl, or $R^{29}$-substituted or unsubstituted 5 to 6 membered heteroaryl;

$R^{29}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{30}$-substituted or unsubstituted $C_1$-$C_8$ alkyl, $R^{30}$-substituted or unsubstituted 2 to 8 membered heteroalkyl, $R^{30}$-substituted or unsubstituted $C_3$-$C_8$ cycloalkyl, $R^{30}$-substituted or unsubstituted 3 to 8 membered heterocycloalkyl, $R^{30}$-substituted or unsubstituted $C_6$-$C_{10}$ aryl, or $R^{30}$-substituted or unsubstituted 5 to 6 membered heteroaryl;

$R^{30}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I—OCH$_2$F, $R^{31}$-substituted or unsubstituted C1-$C_8$ alkyl, $R^{31}$-substituted or unsubstituted 2 to 8 membered heteroalkyl, $R^{31}$-substituted or unsubstituted $C_3$-$C_8$ cycloalkyl, $R^{31}$-substituted or unsubstituted 3 to 8 membered heterocycloalkyl, $R^{31}$-substituted or unsubstituted $C_6$-$C_{10}$ aryl, or $R^{31}$-substituted or unsubstituted 5 to 6 membered heteroaryl;

$R^{31}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^9$ is hydrogen, halogen, —CX$^{9.1}$$_3$, —CHX$^{9.1}$$_2$, —CH$_2$X$^{9.1}$, —CN, —N$_3$, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}$$_3$, —OCHX$^{9.1}$$_2$, —OCH$_2$X$^{9.1}$, $R^{35}$-substituted or unsubstituted $C_1$-$C_8$ alkyl, $R^{35}$-substituted or unsubstituted 2 to 8 membered heteroalkyl, $R^{35}$-substituted or unsubstituted $C_3$-$C_8$ cycloalkyl, $R^{35}$-substituted or unsubstituted 3 to 8 membered heterocycloalkyl, $R^{35}$-substituted or unsubstituted aryl, or $R^{35}$-substituted or unsubstituted 5 to 6 membered heteroaryl;

$R^{35}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{36}$-substituted or unsubstituted $C_1$-$C_8$ alkyl, $R^{36}$-substituted or unsubstituted 2 to 8 membered heteroalkyl, $R^{36}$-substituted or unsubstituted $C_3$-$C_8$ cycloalkyl, $R^{36}$-substituted or unsubstituted 3 to 8 membered heterocycloalkyl, $R^{36}$-substituted or unsubstituted $C_6$-$C_{10}$ aryl, or $R^{36}$-substituted or unsubstituted 5 to 6 membered heteroaryl;

$R^{36}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{37}$-substituted or unsubstituted $C_1$-$C_8$ alkyl, $R^{37}$-substituted or unsubstituted 2 to 8 membered heteroalkyl, $R^{37}$-substituted or unsubstituted $C_3$-$C_8$ cycloalkyl, $R^{37}$-substituted or unsubstituted 3 to 8 membered heterocycloalkyl, $R^{37}$-substituted or unsubstituted $C_6$-$C_{10}$ aryl, or $R^{37}$-substituted or unsubstituted 5 to 6 membered heteroaryl;

$R^{37}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^{44}$ is hydrogen;

$R^{1A}$, $R^{1B}$, $R^{1C}$, $R^{1D}$, and $R^{7.2B}$ are independently hydrogen, halogen, —CF$_3$, —CCl$_3$, —CBr$_3$, —CI$_3$, —COOH, —CONH$_2$, $R^{11}$-substituted or unsubstituted $C_1$-$C_8$ alkyl, $R^{11}$-substituted or unsubstituted 2 to 8 membered heteroalkyl, $R^{11}$-substituted or unsubstituted C3-$C_8$ cycloalkyl, $R^{11}$-substituted or unsubstituted 3 to 8 membered heterocycloalkyl, $R^{11}$-substituted or unsubstituted $C_6$-$C_{10}$ aryl, or $R^{11}$-substituted or unsubstituted 5 to 6 membered heteroaryl; $R^{1B}$ and $R^{1C}$ substituents bonded to the same nitrogen atom may optionally be joined to form a $R^{11}$-substituted or unsubstituted 3 to 8 membered heterocycloalkyl or $R^{11}$-substituted or unsubstituted 5 to 6 membered heteroaryl;

$R^{2A}$, $R^{2B}$, $R^{2C}$, and $R^{2D}$ are independently hydrogen, halogen, —CF$_3$, —CCl$_3$, —CBr$_3$, —CI$_3$, —COOH, —CONH$_2$, $R^{14}$-substituted or unsubstituted $C_1$-$C_8$ alkyl, $R^{14}$-substituted or unsubstituted 2 to 8 membered heteroalkyl, $R^{14}$-substituted or unsubstituted $C_3$-$C_8$ cycloalkyl, $R^{14}$-substituted or unsubstituted 3 to 8 membered heterocycloalkyl, $R^{14}$-substituted or unsubstituted $C_6$-$C_{10}$ aryl, or $R^{14}$-substituted or unsubstituted 5 to 6 membered heteroaryl; $R^{2B}$ and $R^{2C}$ substituents bonded to the same nitrogen atom may optionally be joined to form a $R^{14}$-substituted or unsubstituted 3 to 8 membered heterocycloalkyl or $R^{14}$-substituted or unsubstituted 5 to 6 membered heteroaryl;

$R^{4A}$, $R^{4B}$, $R^{4C}$, and $R^{4D}$ are independently hydrogen, halogen, —CF$_3$, —CCl$_3$, —CBr$_3$, —CI$_3$, —COOH, —CONH₂, R²⁰-substituted or unsubstituted C₁-C₈ alkyl, R²⁰-substituted or unsubstituted 2 to 8 membered heteroalkyl, R²⁰-substituted or unsubstituted C₃-C₈ cycloalkyl, R²⁰-substituted or unsubstituted 3 to 8 membered heterocycloalkyl, R²⁰-substituted or unsubstituted C₆-C₁₀ aryl, or R²⁰-substituted or unsubstituted 5 to 10 membered heteroaryl; R⁴ᴮ and R⁴ᶜ substituents bonded to the same nitrogen atom may optionally be joined to form a R²⁰-substituted or unsubstituted 3 to 8 membered heterocycloalkyl or R²⁰-substituted or unsubstituted 5 to 6 membered heteroaryl;

R⁷ᴬ, R⁷ᴮ, R⁷ᶜ, and R⁷ᴰ are independently hydrogen, halogen, —CF₃, —CCl₃, —CBr₃, —CI₃, —COOH, —CONH₂, R²⁹-substituted or unsubstituted C₁-C₈ alkyl, R²⁹-substituted or unsubstituted 2 to 8 membered heteroalkyl, R²⁹-substituted or unsubstituted C₃-C₈ cycloalkyl, R²⁹-substituted or unsubstituted 3 to 8 membered heterocycloalkyl, R²⁹-substituted or unsubstituted C₆-C₁₀ aryl, or R²⁹-substituted or unsubstituted 5 to 6 membered heteroaryl; R⁷ᴮ and R⁷ᶜ substituents bonded to the same nitrogen atom may optionally be joined to form a R²⁹ substituted or unsubstituted 3 to 8 membered heterocycloalkyl or R²⁹-substituted or unsubstituted 5 to 6 membered heteroaryl;

R⁹ᴬ, R⁹ᴮ, R⁹ᶜ, and R⁹ᴰ are independently hydrogen, halogen, —CF₃, —CCl₃, —CBr₃, —CI₃, —COOH, —CONH₂, R³⁵-substituted or unsubstituted C₁-C₈ alkyl, R³⁵-substituted or unsubstituted 2 to 8 membered heteroalkyl, R³⁵-substituted or unsubstituted C₃-C₈ cycloalkyl, R³⁵-substituted or unsubstituted 3 to 8 membered heterocycloalkyl, R³⁵-substituted or unsubstituted C₆-C₁₀ aryl, or R³⁵-substituted or unsubstituted 5 to 6 membered heteroaryl: R⁹ᴮ and R⁹ᶜ substituents bonded to the same nitrogen atom may optionally be joined to form a R³⁵-substituted or unsubstituted 3 to 8 membered heterocycloalkyl or R³⁵-substituted or unsubstituted 5 to 6 membered heteroaryl; and X$^{1.1}$, X$^{2.1}$, X$^{4.1}$, X$^{7.1}$, and X$^{9.1}$, are independently —Cl, —Br, —I or —F;

wherein:
each substituted or unsubstituted 2 to 8 membered heteroalkyl contains at least one carbon atom and at least one heteroatom;
each substituted or unsubstituted 3 to 8 membered heterocycloalkyl contains at least one carbon atom and at least one heteroatom;
each substituted or unsubstituted 5 to 6 membered heteroaryl contains at least one carbon atom and at least one heteroatom; and
each heteroatom is selected from oxygen (O), nitrogen (N), sulfur (S), phosphorus (P), and silicon (Si).

2. A method of inhibiting C—C chemokine receptor type 4 (CCR4), comprising contacting CCR4 with a compound of structural Formula (IIb):

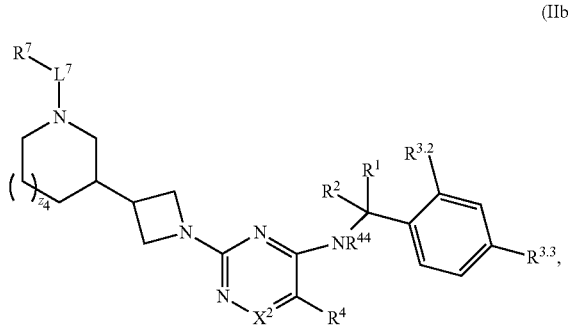

(IIb)

or a pharmaceutically acceptable salt thereof, wherein:
X² is CR⁹;
n1, n2, 3.2, n3.3, n4, n7, and n9, are independently an integer from 0 to 4;
m1, m2, m3.2, m3.3, m4, m7, m9, v1, v2, v3.2, v3.3, v4, v7, and v9, v10, and are independently 1 or 2;
z1 is an integer from 0 to 5;
z4 is 1;
L⁷ is a bond, —O—, —S—, —NR$^{7.2B}$—, —C(O)—, —C(O)O—, —S(O)—, —S(O)₂—, R⁴¹-substituted or unsubstituted C₁-C₈ alkylene or R⁴¹-substituted or unsubstituted C₃-C₈ cycloalkylene;

R⁴¹ is independently oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, R⁴²-substituted or unsubstituted C₁-C₈ alkyl, R⁴²-substituted or unsubstituted 2 to 8 membered heteroalkyl, R⁴²-substituted or unsubstituted C₃-C₈ cycloalkyl, R⁴²-substituted or unsubstituted 3 to 8 membered heterocycloalkyl, R⁴²-substituted or unsubstituted C₆-C₁₀ aryl, or R⁴²-substituted or unsubstituted 5 to 6 membered heteroaryl;

R⁴² is independently oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, R⁴³-substituted or unsubstituted C₁-C₈ alkyl, R⁴³-substituted or unsubstituted 2 to 8 membered heteroalkyl, R⁴-substituted or unsubstituted C₃-C₈ cycloalkyl, R⁴³-substituted or unsubstituted 3 to 8 membered heterocycloalkyl, R⁴³-substituted or unsubstituted C₆-C₁₀ aryl, or R⁴³-substituted or unsubstituted 5 to 6 membered heteroaryl;

R⁴³ is independently hydrogen, oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, unsubstituted C₁-C₈ alkyl, unsubstituted 2 to 8 membered heteroalkyl, unsubstituted C₃-C₈ cycloalkyl, unsubstituted 3 to 8 membered heterocycloalkyl, unsubstituted C₆-C₁₀ aryl, or unsubstituted 5 to 6 membered heteroaryl;

R¹ is hydrogen, halogen, —CX$^{1.1}$₃, —CHX$^{1.1}$₂, —CH₂X$^{1.1}$, —CN, —N₃, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO₂R$^{1A}$, —NR$^{1B}$C(O)R$^{1D}$, —NR$^{1B}$C(O)OR$^{1D}$, —NR$^{1B}$OR$^{1D}$, —OCX$^{1.1}$₃, —OCHX$^{1.1}$₂, —OCH₂X$^{1.1}$, R¹¹-substituted or unsubstituted C₁-C₈ alkyl, R¹¹-substituted or unsubstituted 2 to 8 membered heteroalkyl, R¹¹-substituted or unsubstituted C₃-C₈ cycloalkyl, R¹¹-substituted or unsubstituted 3 to 8 membered heterocycloalkyl, $R^{11}$-substituted or unsubstituted $C_6$-$C_{10}$ aryl, or $R^{11}$-substituted or unsubstituted 5 to 6 membered heteroaryl;

$R^{11}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{12}$-substituted or unsubstituted $C_1$-$C_8$ alkyl, $R^{12}$-substituted or unsubstituted 2 to 8 membered heteroalkyl, $R^{12}$-substituted or unsubstituted $C_3$-$C_8$ cycloalkyl, $R^{12}$-substituted or unsubstituted 3 to 8 membered heterocycloalkyl, $R^{12}$-substituted or unsubstituted $C_6$-$C_{10}$ aryl, or $R^{12}$-substituted or unsubstituted 5 to 6 membered heteroaryl;

$R^{12}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{13}$-substituted or unsubstituted $C_1$-$C_8$ alkyl, $R^{13}$-substituted or unsubstituted 2 to 8 membered heteroalkyl, $R^{13}$-substituted or unsubstituted $C_3$-$C_8$ cycloalkyl, $R^{13}$-substituted or unsubstituted 3 to 8 membered heterocycloalkyl, $R^{13}$-substituted or unsubstituted $C_6$-$C_{10}$ aryl, or $R^{13}$-substituted or unsubstituted 5 to 6 membered heteroaryl;

$R^{13}$ is independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^2$ is hydrogen, halogen, —$CX^{2.1}_3$, —$CHX^{2.1}_2$, —$CH_2X^{2.1}$, —CN, —$N_3$, —$SO_{n2}R^{2A}$, —$SO_{v2}NR^{2B}R^{2C}$, —$NNR^{2B}R^{2C}$, —$ONR^{2B}R^{2C}$, —NHC(O)$NHNR^{2B}R^{2C}$, —NHC(O)$NR^{2B}R^{2C}$, —N(O)$_{m2}$, —$NR^{2B}R^{2C}$, —C(O)$R^{2D}$, —C(O)O$R^{2D}$, —C(O)$NR^{2B}R^{2C}$, —$OR^{2A}$, —$NR^{2B}SO_2R^{2A}$, —$NR^{2B}C(O)R^{2D}$, —$NR^{2B}C(O)OR^{2D}$, —$NR^{2B}OR^{2D}$, —$OCX^{2.1}_3$, —$OCHX^{2.1}_2$, —$OCH_2X^{2.1}$, $R^{14}$-substituted or unsubstituted $C_1$-$C_8$ alkyl, $R^{14}$-substituted or unsubstituted 2 to 8 membered heteroalkyl, $R^{14}$-substituted or unsubstituted $C_3$-$C_8$ cycloalkyl, $R^{14}$-substituted or unsubstituted 3 to 8 membered heterocycloalkyl, $R^{14}$-substituted or unsubstituted $C_6$-$C_{10}$ aryl, or $R^{14}$-substituted or unsubstituted 5 to 6 membered heteroaryl;

$R^{14}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{15}$-substituted or unsubstituted $C_1$-$C_8$ alkyl, $R^{15}$-substituted or unsubstituted 2 to 8 membered heteroalkyl, $R^{15}$-substituted or unsubstituted $C_3$-$C_8$ cycloalkyl, $R^{15}$-substituted or unsubstituted 3 to 8 membered heterocycloalkyl, $R^{15}$-substituted or unsubstituted $C_6$-$C_{10}$ aryl, or $R^{15}$-substituted or unsubstituted 5 to 6 membered heteroaryl;

$R^{15}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{16}$-substituted or unsubstituted $C_1$-$C_8$ alkyl, $R^{16}$-substituted or unsubstituted 2 to 8 membered heteroalkyl, $R^{16}$-substituted or unsubstituted $C_3$-$C_8$ cycloalkyl, $R^{16}$-substituted or unsubstituted 3 to 8 membered heterocycloalkyl, $R^{16}$-substituted or unsubstituted $C_6$-$C_{10}$ aryl, or $R^{16}$-substituted or unsubstituted 5 to 6 membered heteroaryl;

$R^{16}$ is independently hydrogen, oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^{3.2}$ is hydrogen, halogen or —$SO_{n3.2}R^{3.2A}$;

$R^{3.3}$ is hydrogen, halogen, or —$SO_{n3.2}R^{3.3A}$;

$R^4$ is hydrogen, halogen, —$CX^{4.1}_3$, —$CHX^{4.1}_2$, —$CH_2X^{4.1}$, —CN, —$N_3$, —$SO_{n4}R^{4A}$, —$SO_{v4}NR^{4B}R^{4C}$, —$NHNR^{4B}R^{4C}$, —$ONR^{4B}R^{4C}$, —NHC(O)$NHNR^{4B}R^{4C}$, —NHC(O)$NR^{4B}R^{4C}$, —N(O)$_{m4}$, —$NR^{4B}R^{4C}$, —C(O)$R^{4D}$, —C(O)O$R^{4D}$, —C(O)$NR^{4B}R^{4C}$, —$OR^{4A}$, —$NR^{4B}SO_2R^{4A}$, —$NR^{4B}C(O)R^{4D}$, —$NR^{4B}C(O)OR^{4D}$, —$NR^{4B}OR^{4D}$, —$OCX^{4.1}_3$, —$OCHX^{4.1}_2$, —$OCH_2X^{4.1}$, $R^{20}$-substituted or unsubstituted $C_1$-$C_8$ alkyl, $R^{20}$-substituted or unsubstituted 2 to 8 membered heteroalkyl, $R^{20}$-substituted or unsubstituted $C_3$-$C_8$ cycloalkyl, $R^{20}$-substituted or unsubstituted 3 to 8 membered heterocycloalkyl, $R^{20}$-substituted or unsubstituted $C_6$-$C_{10}$ aryl, or $R^{20}$-substituted or unsubstituted 5 to 6 membered heteroaryl;

$R^{20}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, $R^{21}$-substituted or unsubstituted $C_1$-$C_8$ alkyl, $R^{21}$-substituted or unsubstituted 2 to 8 membered heteroalkyl, $R^{21}$-substituted or unsubstituted $C_3$-$C_8$ cycloalkyl, $R^{21}$-substituted or unsubstituted 3 to 8 membered heterocycloalkyl, $R^{21}$-substituted or unsubstituted $C_6$-$C_{10}$ aryl, or $R^{21}$-substituted or unsubstituted 5 to 6 membered heteroaryl;

$R^{21}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{22}$-substituted or unsubstituted $C_1$-$C_8$ alkyl, $R^{22}$-substituted or unsubstituted 2 to 8 membered heteroalkyl, $R^{22}$-substituted or unsubstituted $C_3$-$C_8$ cycloalkyl, $R^{22}$-substituted or unsubstituted 3 to 8 membered heterocycloalkyl, $R^{22}$-substituted or unsubstituted $C_6$-$C_{10}$ aryl, or $R^{22}$-substituted or unsubstituted 5 to 6 membered heteroaryl;

$R^{22}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^7$ is hydrogen, halogen, —CX$^{7.1}_3$, —CHX$^{7.1}_2$, —CH$_2$X$^{7.1}$, —CN, —N$_3$, —SO$_{n7}$R$^{7A}$, —SO$_{v7}$NR$^{7B}$R$^{7C}$, —NHNR$^{7B}$R$^{7C}$, —ONR$^{7B}$R$^{7C}$, —NHC(O)NHNR$^{7B}$R$^{7C}$, —NHC(O)NR$^{7B}$R$^{7C}$, —N(O)$_{m7}$, —NR$^{7B}$R$^{7C}$, —C(O)R$^{7D}$, —C(O)OR$^{7D}$, —C(O)NR$^{7B}$R$^{7C}$, —OR$^{7A}$, —NR$^{7B}$SO$_2$R$^{7A}$, —NR$^{7B}$C(O)R$^{7D}$, —NR$^{7B}$C(O)OR$^{7D}$, —NR$^{7B}$OR$^{7D}$, —OCX$^{7.1}_3$, —OCHX$^{7.1}_2$, —OCH$_2$X$^{7.1}$, $R^{29}$-substituted or unsubstituted $C_1$-$C_8$ alkyl, $R^{29}$-substituted or unsubstituted 2 to 8 membered heteroalkyl, $R^{29}$-substituted or unsubstituted $C_3$-$C_8$ cycloalkyl, $R^{29}$-substituted or unsubstituted 3 to 8 membered heterocycloalkyl, $R^{29}$-substituted or unsubstituted $C_6$-$C_{10}$ aryl, or $R^{29}$-substituted or unsubstituted 5 to 6 membered heteroaryl;

$R^{29}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{30}$-substituted or unsubstituted $C_1$-$C_8$ alkyl, $R^{30}$-substituted or unsubstituted 2 to 8 membered heteroalkyl, $R^{30}$-substituted or unsubstituted $C_3$-$C_8$ cycloalkyl, $R^{30}$-substituted or unsubstituted 3 to 8 membered heterocycloalkyl, $R^{30}$-substituted or unsubstituted $C_6$-$C_{10}$ aryl, or $R^{30}$-substituted or unsubstituted 5 to 6 membered heteroaryl;

$R^{30}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{31}$-substituted or unsubstituted C1-$C_8$ alkyl, $R^{31}$-substituted or unsubstituted 2 to 8 membered heteroalkyl, $R^{31}$-substituted or unsubstituted $C_3$-$C_8$ cycloalkyl, $R^{31}$-substituted or unsubstituted 3 to 8 membered heterocycloalkyl, $R^{31}$-substituted or unsubstituted $C_6$-$C_{10}$ aryl, or $R^{31}$-substituted or unsubstituted 5 to 6 membered heteroaryl;

$R^{31}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_8$ alkyl, unsubstituted 2 to 8 membered heteroalkyl, unsubstituted $C_3$-$C_8$ cycloalkyl, unsubstituted 3 to 8 membered heterocycloalkyl, unsubstituted $C_6$-$C_{10}$ aryl, or unsubstituted 5 to 6 membered heteroaryl;

$R^9$ is hydrogen, halogen, —CX$^{9.1}_3$, —CHX$^{9.1}_2$, —CH$_2$X$^{9.1}$, —CN, —N$_3$, —SO$_{n9}$R$^{9A}$, —SO$_{v9}$NR$^{9B}$R$^{9C}$, —NHNR$^{9B}$R$^{9C}$, —ONR$^{9B}$R$^{9C}$, —NHC(O)NHNR$^{9B}$R$^{9C}$, —NHC(O)NR$^{9B}$R$^{9C}$, —N(O)$_{m9}$, —NR$^{9B}$R$^{9C}$, —C(O)R$^{9D}$, —C(O)OR$^{9D}$, —C(O)NR$^{9B}$R$^{9C}$, —OR$^{9A}$, —NR$^{9B}$SO$_2$R$^{9A}$, —NR$^{9B}$C(O)R$^{9D}$, —NR$^{9B}$C(O)OR$^{9D}$, —NR$^{9B}$OR$^{9D}$, —OCX$^{9.1}_3$, —OCHX$^{9.1}_2$, —OCH$_2$X$^{9.1}$, $R^{35}$-substituted or unsubstituted $C_1$-$C_8$ alkyl, $R^{35}$-substituted or unsubstituted 2 to 8 membered heteroalkyl, $R^{35}$-substituted or unsubstituted $C_3$-$C_8$ cycloalkyl, $R^{35}$-substituted or unsubstituted 3 to 8 membered heterocycloalkyl, $R^{35}$-substituted or unsubstituted aryl, or $R^{35}$-substituted or unsubstituted 5 to 6 membered heteroaryl;

$R^{35}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{36}$-substituted or unsubstituted $C_1$-$C_8$ alkyl, $R^{36}$-substituted or unsubstituted 2 to 8 membered heteroalkyl, $R^{36}$-substituted or unsubstituted $C_3$-$C_8$ cycloalkyl, $R^{36}$-substituted or unsubstituted 3 to 8 membered heterocycloalkyl, $R^{36}$-substituted or unsubstituted $C_6$-$C_{10}$ aryl, or $R^{36}$-substituted or unsubstituted 5 to 6 membered heteroaryl;

$R^{36}$ is independently oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, $R^{37}$-substituted or unsubstituted $C_1$-$C_8$ alkyl, $R^{37}$-substituted or unsubstituted 2 to 8 membered heteroalkyl, $R^{37}$-substituted or unsubstituted $C_3$-$C_8$ cycloalkyl, $R^{37}$-substituted or unsubstituted 3 to 8 membered heterocycloalkyl, $R^{37}$-substituted or unsubstituted $C_6$-$C_{10}$ aryl, or $R^{37}$-substituted or unsubstituted 5 to 6 membered heteroaryl;

R$^{37}$ is independently hydrogen, oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted C$_1$-C$_8$ alkyl, unsubstituted 2 to 8 membered heteroalkyl, unsubstituted C$_3$-C$_8$ cycloalkyl, unsubstituted 3 to 8 membered heterocycloalkyl, unsubstituted C$_6$-C$_{10}$ aryl, or unsubstituted 5 to 6 membered heteroaryl;

R$^{44}$ is hydrogen;

R$^{1A}$, R$^{1B}$, R$^{1C}$, R$^{1D}$, and R$^{7.2B}$ are independently hydrogen, halogen, —CF$_3$, —CCl$_3$, —CBr$_3$, —CI$_3$, —COOH, —CONH$_2$, R$^{11}$-substituted or unsubstituted C$_1$-C$_8$ alkyl, R$^{11}$-substituted or unsubstituted 2 to 8 membered heteroalkyl, R$^{11}$-substituted or unsubstituted C3-C$_8$ cycloalkyl, R$^{11}$-substituted or unsubstituted 3 to 8 membered heterocycloalkyl, R$^{11}$-substituted or unsubstituted C$_6$-C$_{10}$ aryl, or R$^{11}$-substituted or unsubstituted 5 to 6 membered heteroaryl; R$^{1B}$ and R$^{1C}$ substituents bonded to the same nitrogen atom may optionally be joined to form a R$^{11}$-substituted or unsubstituted 3 to 8 membered heterocycloalkyl or R$^{11}$-substituted or unsubstituted 5 to 6 membered heteroaryl;

R$^{2A}$, R$^{2B}$, R$^{2C}$, and R$^{2D}$ are independently hydrogen, halogen, —CF$_3$, —CCl$_3$, —CBr$_3$, —CI$_3$, —COOH, —CONH$_2$, R$^{14}$-substituted or unsubstituted C$_1$-C$_8$ alkyl, R$^{14}$-substituted or unsubstituted 2 to 8 membered heteroalkyl, R$^{14}$-substituted or unsubstituted C$_3$-C$_8$ cycloalkyl, R$^{14}$-substituted or unsubstituted 3 to 8 membered heterocycloalkyl, R$^{14}$-substituted or unsubstituted C$_6$-C$_{10}$ aryl, or R$^{14}$-substituted or unsubstituted 5 to 6 membered heteroaryl; R$^{2B}$ and R$^{2C}$ substituents bonded to the same nitrogen atom may optionally be joined to form a R$^{14}$-substituted or unsubstituted 3 to 8 membered heterocycloalkyl or R$^{14}$-substituted or unsubstituted 5 to 6 membered heteroaryl;

R$^{4A}$, R$^{4B}$, R$^{4C}$, and R$^{4D}$ are independently hydrogen, halogen, —CF$_3$, —CCl$_3$, —CBr$_3$, —CI$_3$, —COOH, —CONH$_2$, R$^{20}$-substituted or unsubstituted C$_1$-C$_8$ alkyl, R$^{20}$-substituted or unsubstituted 2 to 8 membered heteroalkyl, R$^{20}$-substituted or unsubstituted C$_3$-C$_8$ cycloalkyl, R$^{20}$-substituted or unsubstituted 3 to 8 membered heterocycloalkyl, R$^{20}$-substituted or unsubstituted C$_6$-C$_{10}$ aryl, or R$^{20}$-substituted or unsubstituted 5 to 10 membered heteroaryl; R$^{4B}$ and R$^{4C}$ substituents bonded to the same nitrogen atom may optionally be joined to form a R$^{20}$-substituted or unsubstituted 3 to 8 membered heterocycloalkyl or R$^{20}$-substituted or unsubstituted 5 to 6 membered heteroaryl;

R$^{7A}$, R$^{7B}$, R$^{7C}$, and R$^{7D}$ are independently hydrogen, halogen, —CF$_3$, —CCl$_3$, —CBr$_3$, —CI$_3$, —COOH, —CONH$_2$, R$^{29}$-substituted or unsubstituted C$_1$-C$_8$ alkyl, R$^{29}$-substituted or unsubstituted 2 to 8 membered heteroalkyl, R$^{29}$-substituted or unsubstituted C$_3$-C$_8$ cycloalkyl, R$^{29}$-substituted or unsubstituted 3 to 8 membered heterocycloalkyl, R$^{29}$-substituted or unsubstituted C$_6$-C$_{10}$ aryl, or R$^{29}$-substituted or unsubstituted 5 to 6 membered heteroaryl; R$^{7B}$ and R$^{7C}$ substituents bonded to the same nitrogen atom may optionally be joined to form a R$^{29}$ substituted or unsubstituted 3 to 8 membered heterocycloalkyl or R$^{29}$-substituted or unsubstituted 5 to 6 membered heteroaryl;

R$^{9A}$, R$^{9B}$, R$^{9C}$, and R$^{9D}$ are independently hydrogen, halogen, —CF$_3$, —CCl$_3$, —CBr$_3$, —CI$_3$, —COOH, —CONH$_2$, R$^{35}$-substituted or unsubstituted C$_1$-C$_8$ alkyl, R$^{35}$-substituted or unsubstituted 2 to 8 membered heteroalkyl, R$^{35}$-substituted or unsubstituted C$_3$-C$_8$ cycloalkyl, R$^{35}$-substituted or unsubstituted 3 to 8 membered heterocycloalkyl, R$^{35}$-substituted or unsubstituted C$_6$-C$_{10}$ aryl, or R$^{35}$-substituted or unsubstituted 5 to 6 membered heteroaryl; R$^{9B}$ and R$^{9C}$ substituents bonded to the same nitrogen atom may optionally be joined to form a R$^{35}$-substituted or unsubstituted 3 to 8 membered heterocycloalkyl or R$^{35}$-substituted or unsubstituted 5 to 6 membered heteroaryl; and X$^{1.1}$, X$^{2.1}$, X$^{4.1}$, X$^{7.1}$, and X$^{9.1}$, are independently —Cl, —Br, —I or —F wherein:

each substituted or unsubstituted 2 to 8 membered heteroalkyl contains at least one carbon atom and at least one heteroatom;

each substituted or unsubstituted 3 to 8 membered heterocycloalkyl contains at least one carbon atom and at least one heteroatom;

each substituted or unsubstituted 5 to 6 membered heteroaryl contains at least one carbon atom and at least one heteroatom; and each heteroatom is selected from oxygen (O), nitrogen (N), sulfur (S), phosphorus (P), and silicon (Si).

3. The method of claim 1, further comprising co-administering an anti-inflammatory agent to the subject.

4. The method of claim 3, wherein the anti-inflammatory agent is a thalidomide derivative, a retinoid, a non-steroidal anti-inflammatory agent (NSAID), a cyclo-oxygenase inhibiting nitric oxide donor (CINOD), a glucocorticosteroid, an analgesic, a hyaluronic acid derivative, or a nutritional supplement.

5. The method of claim 1, wherein the inflammation is asthma, urticaria, rhinitis or dermatitis.

6. The method of claim 5, wherein the inflammation is allergic asthma, autoimmune urticaria, allergic rhinitis or contact dermatitis.

7. The method of claim 4, wherein the anti-inflammatory agent is thalidomide, dithranol, calcipotriol, methotrexate, leflunomide, hydroxychloroquine, d-penicillamine, auranofin, or diacerein.

8. The method of claim 1, comprising administering a therapeutically effective amount of a pharmaceutical composition comprising the compound of formula (IIb), or a pharmaceutically acceptable salt thereof, and a pharmaceutically acceptable carrier.

9. The method of claim 1 or 2, wherein the compound has the formula:

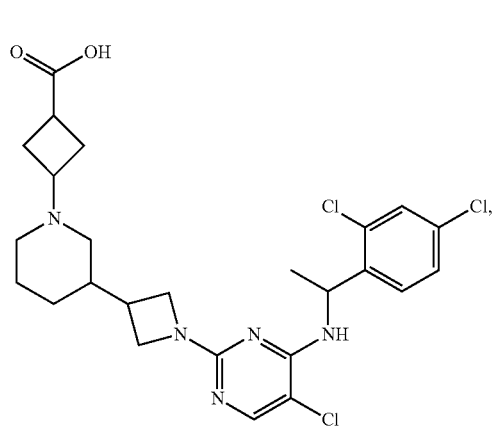 [SMILES: CC(Nc1nc(N2CC(C3CCCN(C4CC(C(=O)O)C4)C3)C2)ncc1Cl)c1ccc(Cl)cc1Cl]

or a pharmaceutically acceptable salt thereof.

10. The method of claim 1 or 2, wherein the compound has the formula:

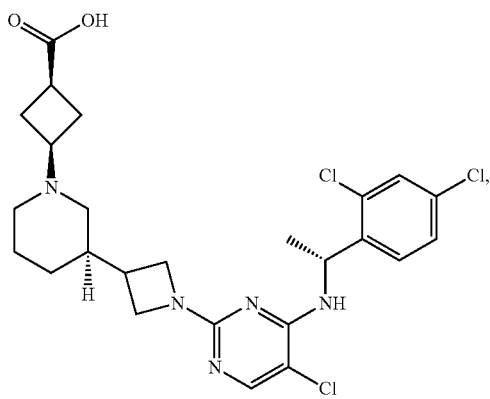 [SMILES: C[C@@H](Nc1nc(N2CC([C@H]3CCCN([C@H]4C[C@@H](C(=O)O)C4)C3)C2)ncc1Cl)c1ccc(Cl)cc1Cl]

or a pharmaceutically acceptable salt thereof.

11. The method of claim 1 or 2, wherein the compound has the formula:

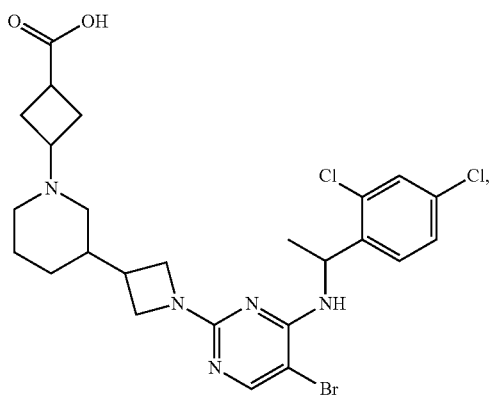

or a pharmaceutically acceptable salt thereof.

12. The method of claim 1 or 2, wherein the compound has the formula:

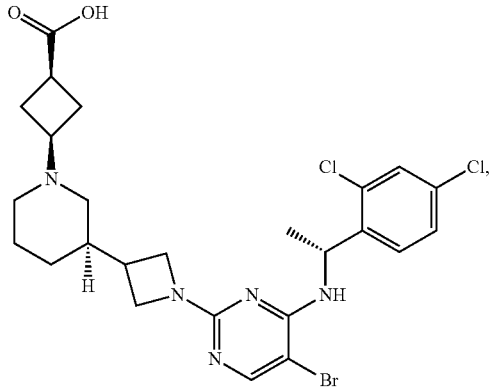 [SMILES: C[C@@H](Nc1nc(N2CC([C@H]3CCCN([C@H]4C[C@@H](C(=O)O)C4)C3)C2)ncc1Br)c1ccc(Cl)cc1Cl]

or a pharmaceutically acceptable salt thereof.

13. The method of claim 1 or 2, wherein the compound has the formula:

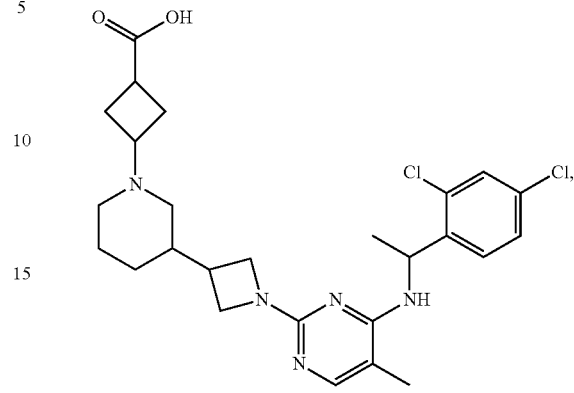

or a pharmaceutically acceptable salt thereof.

14. The method of claim 1 or 2, wherein the compound has the formula:

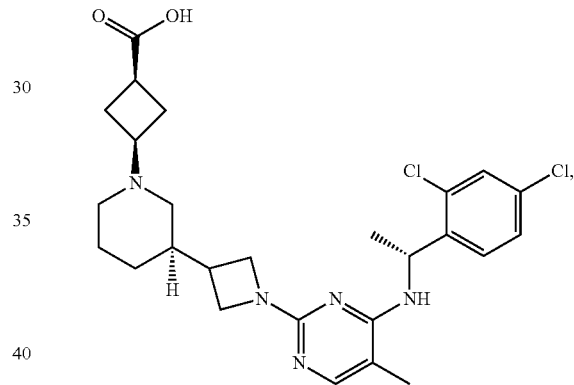

a pharmaceutically acceptable salt thereof.

15. The method of claim 1 or 2, wherein the compound has the formula:

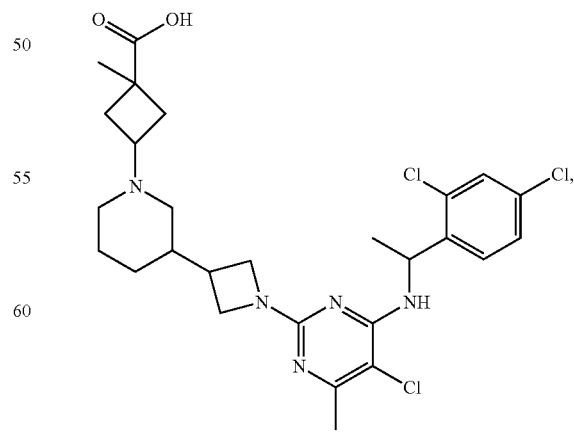

a pharmaceutically acceptable salt thereof.

16. The method of claim 1 or 2, wherein the compound has the formula:

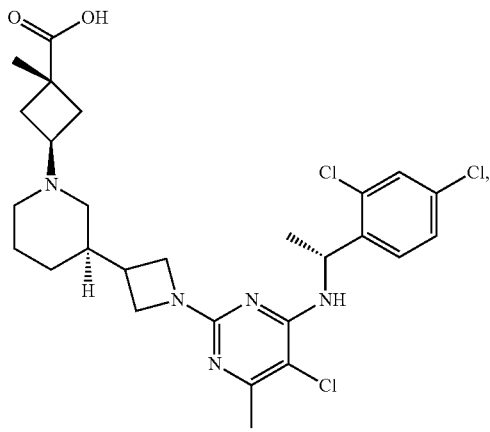 [SMILES: Cc1nc(N2CC([C@H]3CCCN([C@H]4C[C@](C)(C(=O)O)C4)C3)C2)nc(N[C@H](C)c2ccc(Cl)cc2Cl)c1Cl]

or a pharmaceutically acceptable salt thereof.

17. The method of claim 1 or 2, wherein the compound has the formula:

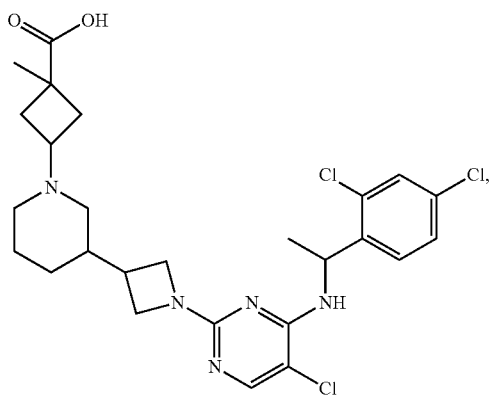 [SMILES: CC(Nc1nc(N2CC(C3CCCN(C4CC(C)(C(=O)O)C4)C3)C2)ncc1Cl)c1ccc(Cl)cc1Cl]

or a pharmaceutically acceptable salt thereof.

18. The method of claim 1 or 2, wherein the compound has the formula:

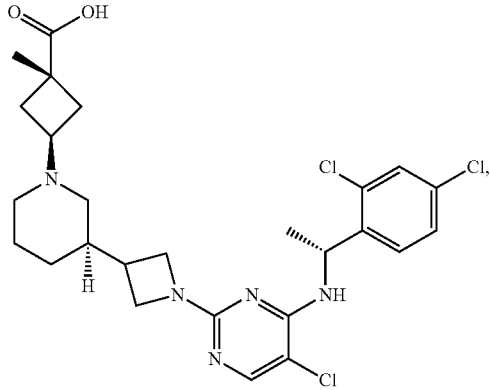 [SMILES: C[C@@H](Nc1nc(N2CC([C@H]3CCCN([C@H]4C[C@](C)(C(=O)O)C4)C3)C2)ncc1Cl)c1ccc(Cl)cc1Cl]

or a pharmaceutically acceptable salt thereof.

19. The method of claim 1 or 2, wherein the compound has the formula:

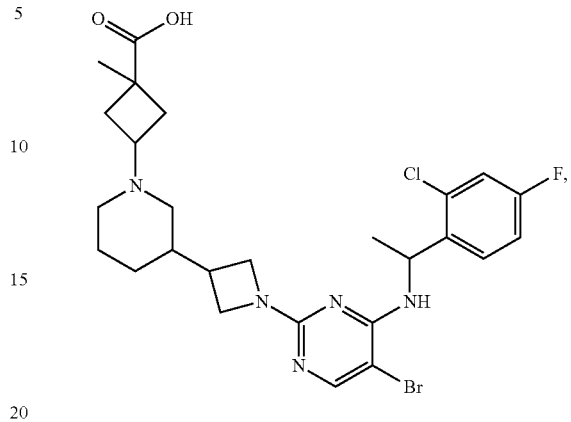

or a pharmaceutically acceptable salt thereof.

20. The method of claim 1 or 2, wherein the compound has the formula:

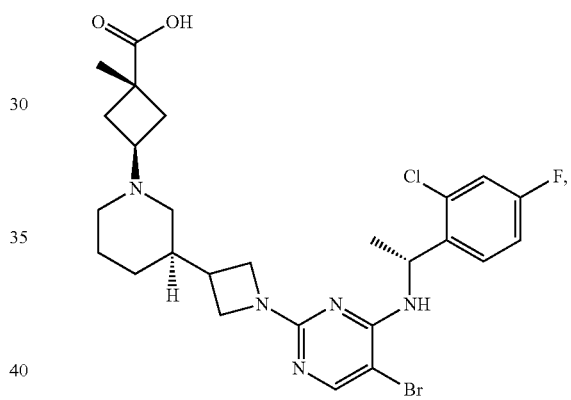

or a pharmaceutically acceptable salt thereof.

21. The method of claim 1 or 2, wherein the compound has the formula:

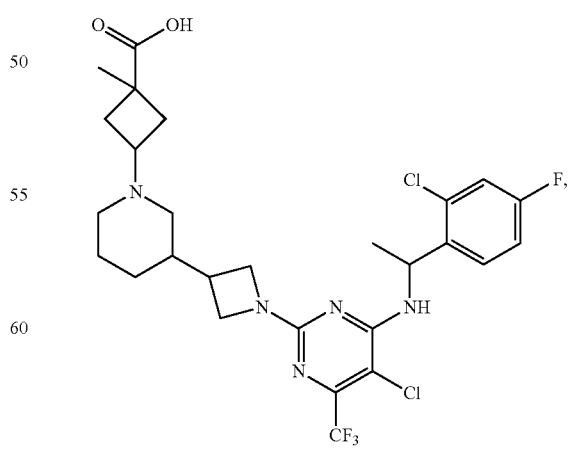

or a pharmaceutically acceptable salt thereof.

22. The method of claim 1 or 2, wherein the compound has the formula:

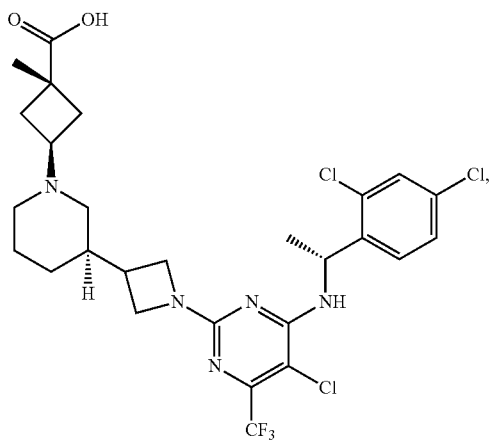 [SMILES: C[C@@H](Nc1nc(N2CC([C@H]3CCCN([C@H]4C[C@](C)(C(=O)O)C4)C3)C2)nc(C(F)(F)F)c1Cl)c1ccc(Cl)cc1Cl]

or a pharmaceutically acceptable salt thereof.

23. The method of claim 1 or 2, wherein the compound has the formula:

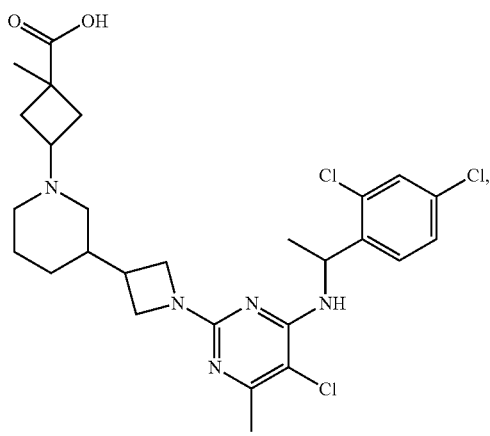 [SMILES: Cc1nc(N2CC(C3CCCN(C4CC(C)(C(=O)O)C4)C3)C2)nc(NC(C)c2ccc(Cl)cc2Cl)c1Cl]

or a pharmaceutically acceptable salt thereof.

24. The method of claim 1 or 2, wherein the compound has the formula:

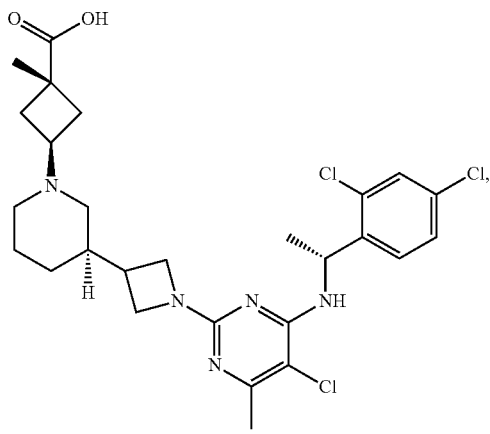 [SMILES: Cc1nc(N2CC([C@H]3CCCN([C@H]4C[C@](C)(C(=O)O)C4)C3)C2)nc(N[C@H](C)c2ccc(Cl)cc2Cl)c1Cl]

or a pharmaceutically acceptable salt thereof.

25. The method of claim 1 or 2, wherein the compound has the formula:

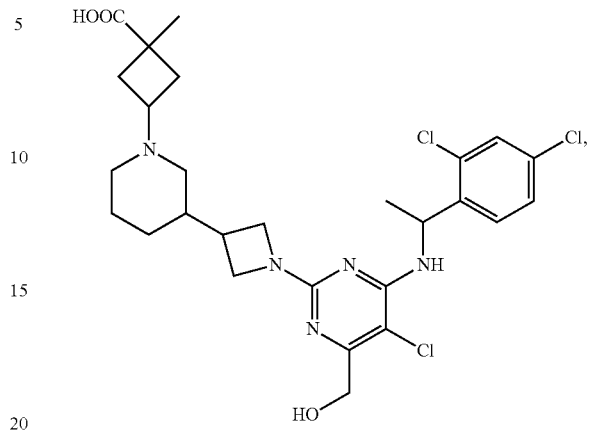

or a pharmaceutically acceptable salt thereof.

26. The method of claim 1 or 2, wherein the compound has the formula:

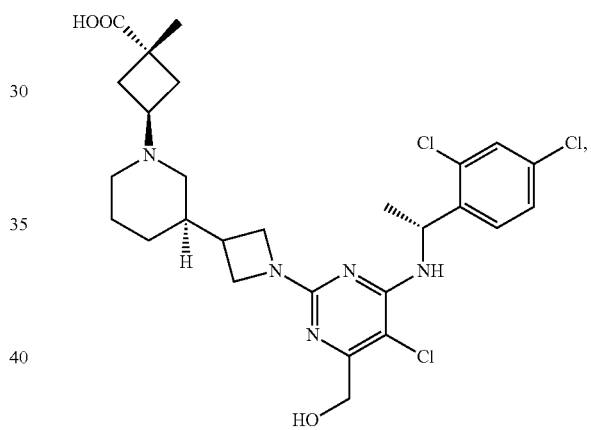

or a pharmaceutically acceptable salt thereof.

27. The method of claim 1 or 2, wherein the compound has the formula:

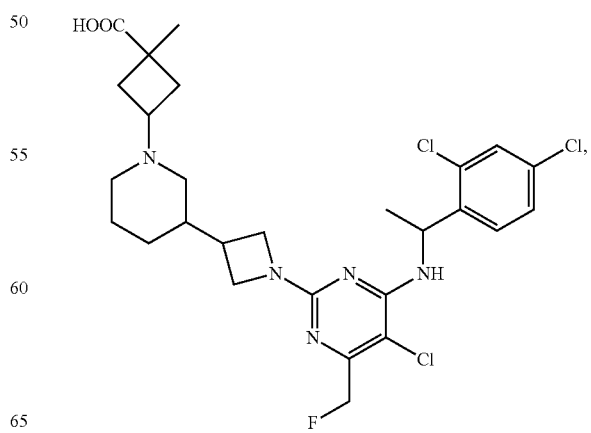

or a pharmaceutically acceptable salt thereof.

28. The method of claim 1 or 2, wherein the compound has the formula:
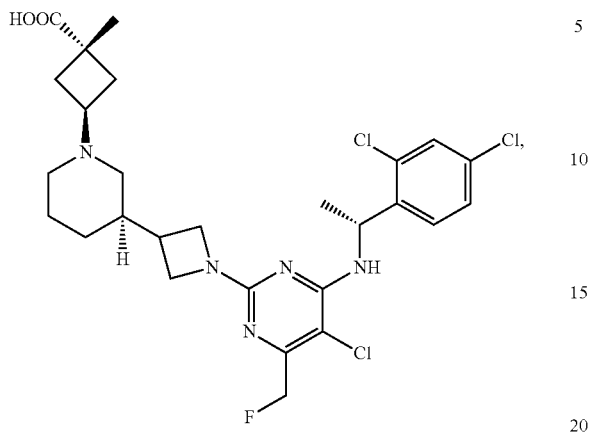
or a pharmaceutically acceptable salt thereof.